US006335170B1

(12) United States Patent
Orntoft

(10) Patent No.: US 6,335,170 B1
(45) Date of Patent: *Jan. 1, 2002

(54) GENE EXPRESSION IN BLADDER TUMORS

(76) Inventor: Torben F. Orntoft, Helgesvej 19, DK 8230 Aabyhoj (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/510,643

(22) Filed: Feb. 22, 2000

Related U.S. Application Data

(60) Provisional application No. 60/121,124, filed on Feb. 22, 1999.

(51) Int. Cl.$^7$ .......................... C12Q 1/68; C12P 19/34; C07H 21/02
(52) U.S. Cl. ..................... 435/6; 435/91.1; 435/91.2; 536/23.1; 536/24.3; 536/24.31; 536/24.33
(58) Field of Search ..................... 435/6, 91.1, 91.2; 536/23.1, 24.3, 24.31, 24.33

(56) References Cited

U.S. PATENT DOCUMENTS

| 5,677,125 A | * | 10/1997 | Holt et al. | ...................... 435/6 |
| 5,700,637 A | | 12/1997 | Southern | ........................ 435/6 |

FOREIGN PATENT DOCUMENTS

| DE | 198 18 619 A1 | 10/1999 |
| WO | 89/10977 | 11/1989 |
| WO | 96/30389 | 10/1996 |
| WO | 97/16206 | 5/1997 |
| WO | 97/28446 | 8/1997 |
| WO | 98/53319 | 11/1998 |
| WO | 99/47674 | 9/1999 |

OTHER PUBLICATIONS

Liebert et al, "Identification of new biomarkers for bladder cancer using the differential display reverse transcriptase polymerase chain reaction", Proc. Am. Assn. Cancer Res. 38:287, Abstract 1928, Mar. 1997.*

Liebert et al, "Novel molecular markers fof bladder cancer revealed by differential display reverse transcriptase polymerase chain reaction", J. Urol. 159(5 suppl.) 286, Abstract 1101, May 1998.*

Peter S. Nelson, et al., "An Expressed–Sequence–Tag Database of the Human Prostate: Sequence Analysis of 1168 cDNA Clones", Genomics 47, pp. 12–25, 1998.

David B. Krizman, et al., "Construction of a Representative cDNA Library from Prostatic Intraepithelial Neoplasia", Cancer Research 56, pp. 5380–5383, Dec. 1, 1996.

Victoria Hawkins, et al., "PEDB: The Prostate Expression Database", Nucleic Acids Research, vol. 27,No. 1, pp. 240–208, 1999.

Lin Zhang, et al., "Gene Expression Profiles in Normal and Cancer Cells", Science, vol. 276,pp. 1268–1272, May 23, 1997.

Torben F. Orntoft, et al., "Molecular Alterations in Bladder Cancer", United Editorial, XP–000971351, Nov. 11, 1997.

Margaret A. Knowles, et al., Molecular Genetics of Bladder Cancer: Pathways of Development and Progression, Cancer Surveys, vol. 31, pp. 49–76, 1998.

* cited by examiner

Primary Examiner—Jeffrey Fredman
(74) Attorney, Agent, or Firm—Banner & Witcoff, Ltd.

(57) ABSTRACT

Methods for analyzing tumor cells, particularly bladder tumor cells employ gene expression analysis of samples. Gene expression patterns are formed and compared to reference patterns. Alternatively gene expression patterns are manipulated to exclude genes which are expressed in contaminating cell populations. Another alternative employs subtraction of the expression of genes which are expressed in contaminating cell types. These methods provide improved accuracy as well as alternative basis for analysis from diagnostic and prognostic tools currently available.

21 Claims, 15 Drawing Sheets

FIG. 6A 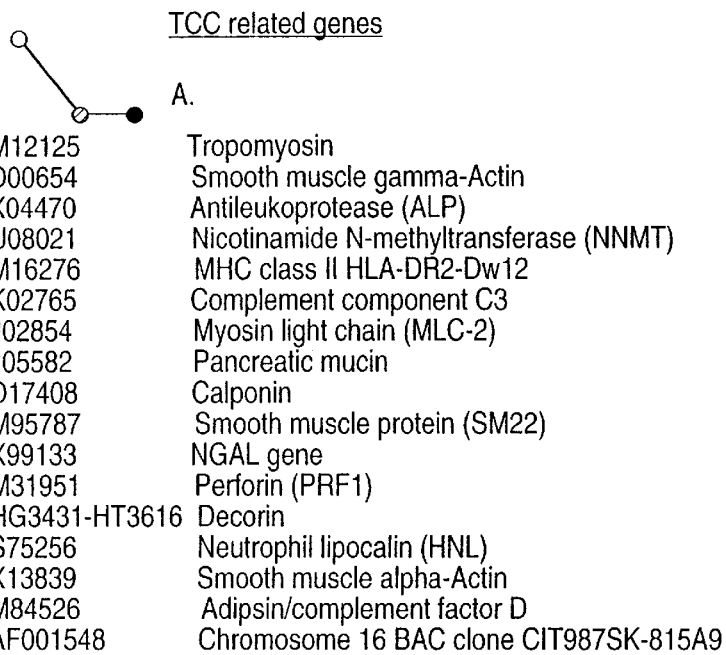

TCC related genes

A.

| | |
|---|---|
| M12125 | Tropomyosin |
| D00654 | Smooth muscle gamma-Actin |
| X04470 | Antileukoprotease (ALP) |
| U08021 | Nicotinamide N-methyltransferase (NNMT) |
| M16276 | MHC class II HLA-DR2-Dw12 |
| K02765 | Complement component C3 |
| J02854 | Myosin light chain (MLC-2) |
| J05582 | Pancreatic mucin |
| D17408 | Calponin |
| M95787 | Smooth muscle protein (SM22) |
| X99133 | NGAL gene |
| M31951 | Perforin (PRF1) |
| HG3431-HT3616 | Decorin |
| S75256 | Neutrophil lipocalin (HNL) |
| X13839 | Smooth muscle alpha-Actin |
| M84526 | Adipsin/complement factor D |
| AF001548 | Chromosome 16 BAC clone CIT987SK-815A9 |

FIG. 6B 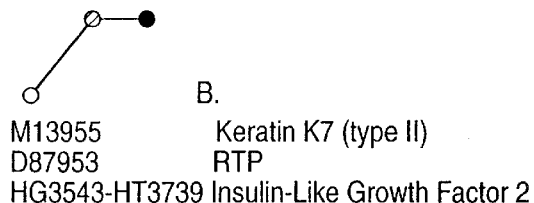

B.

| | |
|---|---|
| M13955 | Keratin K7 (type II) |
| D87953 | RTP |
| HG3543-HT3739 | Insulin-Like Growth Factor 2 |

FIG. 6C 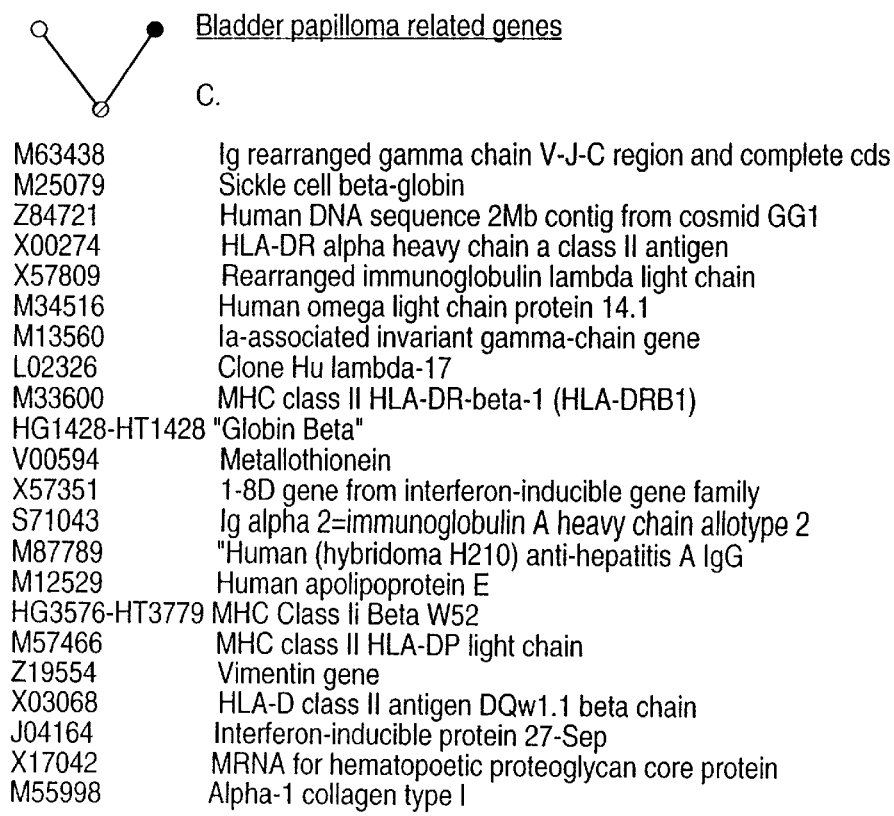

Bladder papilloma related genes

C.

| | |
|---|---|
| M63438 | Ig rearranged gamma chain V-J-C region and complete cds |
| M25079 | Sickle cell beta-globin |
| Z84721 | Human DNA sequence 2Mb contig from cosmid GG1 |
| X00274 | HLA-DR alpha heavy chain a class II antigen |
| X57809 | Rearranged immunoglobulin lambda light chain |
| M34516 | Human omega light chain protein 14.1 |
| M13560 | Ia-associated invariant gamma-chain gene |
| L02326 | Clone Hu lambda-17 |
| M33600 | MHC class II HLA-DR-beta-1 (HLA-DRB1) |
| HG1428-HT1428 | "Globin Beta" |
| V00594 | Metallothionein |
| X57351 | 1-8D gene from interferon-inducible gene family |
| S71043 | Ig alpha 2=immunoglobulin A heavy chain allotype 2 |
| M87789 | "Human (hybridoma H210) anti-hepatitis A IgG |
| M12529 | Human apolipoprotein E |
| HG3576-HT3779 | MHC Class Ii Beta W52 |
| M57466 | MHC class II HLA-DP light chain |
| Z19554 | Vimentin gene |
| X03068 | HLA-D class II antigen DQw1.1 beta chain |
| J04164 | Interferon-inducible protein 27-Sep |
| X17042 | MRNA for hematopoetic proteoglycan core protein |
| M55998 | Alpha-1 collagen type I |

FIG. 6D

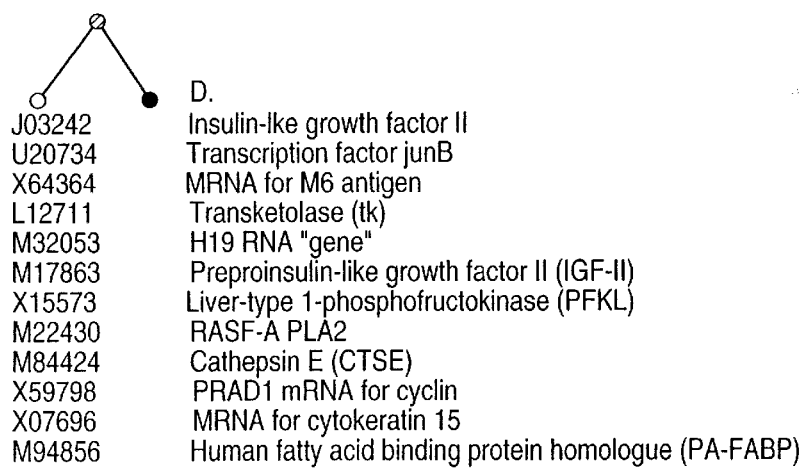

D.
| | |
|---|---|
| J03242 | Insulin-lke growth factor II |
| U20734 | Transcription factor junB |
| X64364 | MRNA for M6 antigen |
| L12711 | Transketolase (tk) |
| M32053 | H19 RNA "gene" |
| M17863 | Preproinsulin-like growth factor II (IGF-II) |
| X15573 | Liver-type 1-phosphofructokinase (PFKL) |
| M22430 | RASF-A PLA2 |
| M84424 | Cathepsin E (CTSE) |
| X59798 | PRAD1 mRNA for cyclin |
| X07696 | MRNA for cytokeratin 15 |
| M94856 | Human fatty acid binding protein homologue (PA-FABP) |

Invasive TCC related genes

FIG. 6E

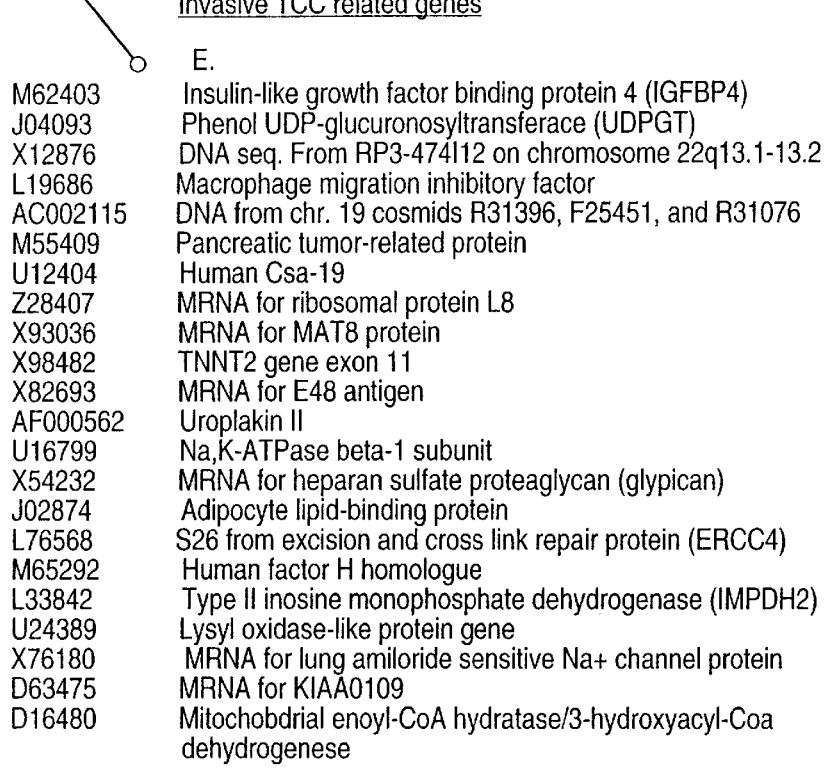

E.
| | |
|---|---|
| M62403 | Insulin-like growth factor binding protein 4 (IGFBP4) |
| J04093 | Phenol UDP-glucuronosyltransferace (UDPGT) |
| X12876 | DNA seq. From RP3-474I12 on chromosome 22q13.1-13.2 |
| L19686 | Macrophage migration inhibitory factor |
| AC002115 | DNA from chr. 19 cosmids R31396, F25451, and R31076 |
| M55409 | Pancreatic tumor-related protein |
| U12404 | Human Csa-19 |
| Z28407 | MRNA for ribosomal protein L8 |
| X93036 | MRNA for MAT8 protein |
| X98482 | TNNT2 gene exon 11 |
| X82693 | MRNA for E48 antigen |
| AF000562 | Uroplakin II |
| U16799 | Na,K-ATPase beta-1 subunit |
| X54232 | MRNA for heparan sulfate proteaglycan (glypican) |
| J02874 | Adipocyte lipid-binding protein |
| L76568 | S26 from excision and cross link repair protein (ERCC4) |
| M65292 | Human factor H homologue |
| L33842 | Type II inosine monophosphate dehydrogenase (IMPDH2) |
| U24389 | Lysyl oxidase-like protein gene |
| X76180 | MRNA for lung amiloride sensitive Na+ channel protein |
| D63475 | MRNA for KIAA0109 |
| D16480 | Mitochobdrial enoyl-CoA hydratase/3-hydroxyacyl-Coa dehydrogenese |

FIG. 6F

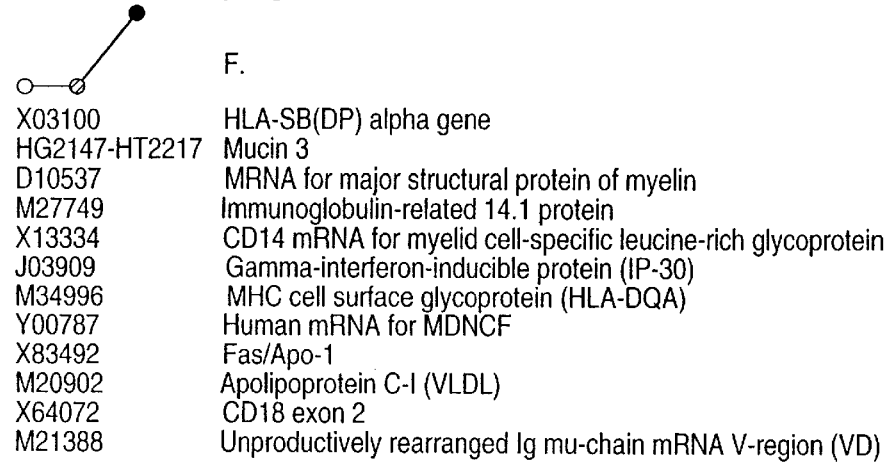

F.
| | |
|---|---|
| X03100 | HLA-SB(DP) alpha gene |
| HG2147-HT2217 | Mucin 3 |
| D10537 | MRNA for major structural protein of myelin |
| M27749 | Immunoglobulin-related 14.1 protein |
| X13334 | CD14 mRNA for myelid cell-specific leucine-rich glycoprotein |
| J03909 | Gamma-interferon-inducible protein (IP-30) |
| M34996 | MHC cell surface glycoprotein (HLA-DQA) |
| Y00787 | Human mRNA for MDNCF |
| X83492 | Fas/Apo-1 |
| M20902 | Apolipoprotein C-I (VLDL) |
| X64072 | CD18 exon 2 |
| M21388 | Unproductively rearranged Ig mu-chain mRNA V-region (VD) |

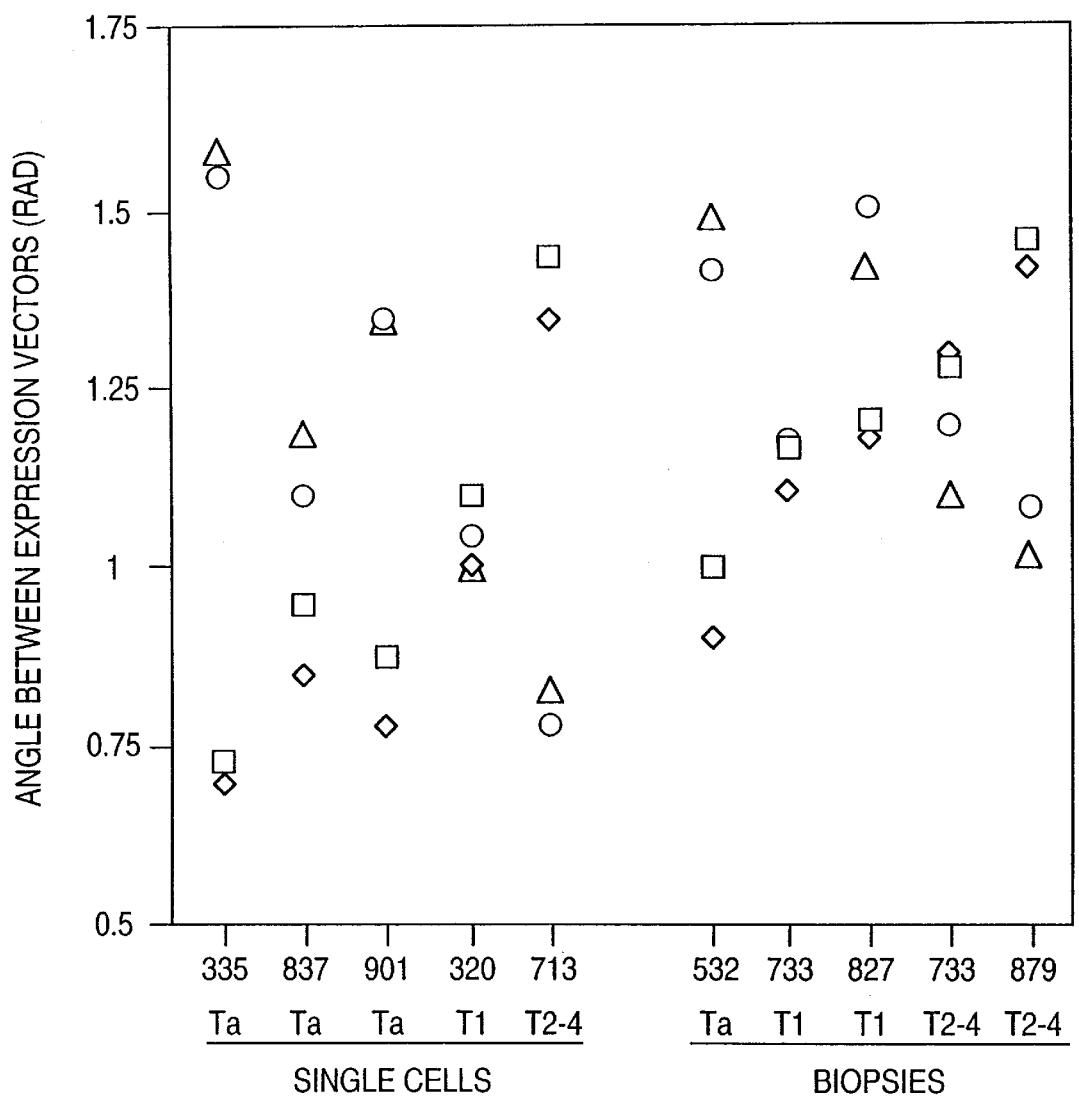

GENE EXPRESSION IN BLADDER TUMORS

This application claims the benefit of U.S. Provisional Application No. 60/121,124, filed Feb. 22, 1999, which is hereby incorporated by reference in its entirety.

TECHNICAL FIELD OF THE INVENTION

This invention is related to the field of cancer diagnosis and treatment. In particular it is related to the use of gene expression to categorize and detect tumors.

BACKGROUND OF THE INVENTION

The building of large databases containing human genome sequences is the basis for studies of gene expressions in various tissues during normal physiological and pathologic conditions. Constantly (constitutively) expressed sequences as well as sequences whose expression is altered during disease processes are important for our understanding of cellular properties, and for the identification of candidate genes for future therapeutic intervention. As the number of known genes and ESTs build up in the databases, array-based simultaneous screening of thousands of genes is necessary to obtain a profile of transcriptional behaviour, and to identify key genes that, either alone or in combination with other genes, control various aspects of cellular life. One cellular behaviour that has been a mystery for many years is the malignant behaviour of cancer cells. We now know that, for example, defects in DNA repair can lead to cancer, but the cancer-creating mechanism in heterozygous individuals is still largely unknown, as is the malignant cell's ability to repeat cell cycles, to avoid apoptosis, to escape the immune system, to invade and metastasize, and to escape therapy. There are hints and indications in these areas and excellent progress has been made, but the myriad of genes interacting with each other in a highly complex multidimensional network is making the road to insight long and contorted.

Similar appearing tumors—morphologically, histochemically, microscopically—can be profoundly different. They can have different invasive and metastasizing properties, as well as respond differently to therapy. There is a thus a need in the art for methods which distinguish tumors and tissues on different bases than are currently in use in the clinic.

SUMMARY OF THE INVENTION

It is an object of the present invention to provide a method of determining an expression pattern of a cell sample independent of the proportion of submucosal, smooth muscle, or connective tissue cells present.

It is another object of the present invention to provide a method of determining an expression pattern of a cell sample.

It is an object of the present invention to provide a method for determining an expression pattern of a urothelium or bladder cancer cell.

Another object of the invention is to provide a method of detecting an invasive tumor in a patient.

Another object of the invention is to provide a method to diagnose a bladder cancer.

Another object of the invention is to provide a method to predict outcome or prescribe treatment of a bladder tumor.

Another object of the invention is to provide a method to determine grade or stage of a bladder tumor.

Still another object of the invention is to provide a method of identifying a tissue sample as urothelial.

Yet another object of the invention provides a method of determining an expression pattern of a bladder tissue sample independent of the proportion of submucosal, muscle, and connective tissue cells present.

These and other objects of the invention are achieved by providing one or more of the embodiments described below. In one embodiment a method is provided of determining an expression pattern of a cell sample independent of the proportion of submucosal, smooth muscle, or connective tissue cells present. Expression is determined of one or more genes in a sample comprising cells. The one or more genes exclude genes which are expressed in the submucosal, muscle, and connective tissue. A pattern of expression is formed for the sample which is independent of the proportion of submucosal, muscle, and connective tissue cells in the sample.

In another aspect of the invention a method of determining an expression pattern of a cell sample is provided. Expression is determined of one or more genes in a sample comprising cells. A first pattern of expression is thereby formed for the sample. Genes which are expressed in submucosal, smooth muscle, or connective tissue cells are removed from the first pattern of expression, forming a second pattern of expression which is independent of the proportion of submucosal, smooth muscle, or connective tissue cells in the sample.

Another embodiment of the invention provides a method for determining an expression pattern of a urothelium or bladder cancer cell. Expression is determined of one or more genes in a sample comprising urothelium or bladder cancer cells; the expression determined forms a first pattern of expression. A second pattern of expression which was formed using the one or more genes and a sample comprising predominantly submucosal, smooth muscle, or connective tissue cells, is subtracted from the first pattern of expression, forming a third pattern of expression. The third pattern of expression reflects expression of the urothelium or bladder cancer cells independent of the proportion of submucosal, smooth muscle, or connective tissue cells present in the sample.

In another embodiment of the invention a method is provided of detecting an invasive tumor in a patient. A marker is detected in a sample of a body fluid. The body fluid is selected from the group consisting of blood, plasma, serum, urine, ascites fluid, pleural fluid, spinal fluid, sputum, and mucous secretions. The marker is an mRNA or protein expression product of a gene which is more prevalent in submucosal, smooth muscle, or connective tissue than in the body fluid. An increased amount of the marker in the body fluid indicates a tumor which has become invasive in the patient.

In another aspect of the invention a method is provided for diagnosing a bladder cancer. A first pattern of expression is determined of one or more genes in a bladder tissue sample suspected of being neoplastic. The first pattern of expression is compared to a second and third reference pattern of expression. The second pattern is of the one or more genes in normal urothelium and the third pattern is of the one or more genes in bladder cancer. A first pattern of expression which is found to be more similar to the third pattern than the second indicates neoplasia of the bladder tissue sample.

According to yet another aspect of the invention a method is provided for predicting outcome or prescribing treatment of a bladder tumor. A first pattern of expression is determined of one or more genes in a bladder tumor sample. The first pattern is compared to one or more reference patterns of expression determined for bladder tumors at a grade between I and IV. The reference pattern which shares maximum similarity with the first pattern is identified. The outcome or treatment appropriate for the grade of tumor of the reference pattern with the maximum similarity is assigned to the bladder tumor sample.

In another embodiment of the invention a method is provided for determining grade of a bladder tumor. A first pattern of expression is determined of one or more genes in a bladder tumor sample. The first pattern is compared to one or more reference patterns of expression determined for bladder tumors at a grade between I and IV. The reference pattern which shares maximum similarity with the first pattern is identified. The grade of the reference pattern with the maximum similarity is assigned to the bladder tumor sample.

Yet another embodiment of the invention provides a method to determine stage of a bladder tumor. A first pattern of expression is determined of one or more genes in a bladder tumor sample. The first pattern is compared to one or more reference patterns of expression determined for bladder tumors at different stages. The reference pattern which shares maximum similarity with the first pattern is identified. The stage of the reference pattern with the maximum similarity is assigned to the bladder tumor sample.

In still another embodiment of the invention a method is provided for identifying a tissue sample as urothelial. A first pattern of expression is determined of one or more genes in a tissue sample. The first pattern of expression is compared to a second pattern of expression obtained from normal urothelial cells. Similarity between the first and second patterns identifies the tissue sample is urothelial in its origin.

Another aspect of the invention is a method to identify a set of genes useful for diagnosing, predicting outcome, or prescribing treatment of a bladder cancer. A first pattern of expression is determined of one or more genes in a first bladder tissue sample. A second pattern of expression is determined of the one or more genes in a second bladder tissue sample. The first bladder tissue sample is a normal urothelium sample or an earlier stage or lower grade of bladder tumor than the second bladder tissue sample. The first pattern of expression is compared to the second pattern of expression to identify a first set of genes whose expression is increased or decreased in the second bladder tissue sample relative to the first bladder tissue sample. Those genes which are expressed in submucosal, smooth muscle or connective tissue are removed from the first set of genes to produce a second set of genes. Expression of the second set of genes can be used for diagnosing, predicting outcome, or prescribing treatment of a bladder cancer.

According to yet another aspect of the invention a method is provided for determining an expression pattern of a bladder tissue sample independent of the proportion of submucosal, smooth muscle, or connective tissue cells present. A single-cell suspension of disaggregated bladder tumor cells is isolated from a bladder tissue sample comprising bladder cells, submucosal cells, smooth muscle cells, or connective tissue cells. The expression of one or more genes in the single-cell suspension is determined. A pattern of expression is thus formed for the sample which is independent of the proportion of submucosal, smooth muscle, or connective tissue cells in the bladder tissue sample.

According to still another aspect of the invention a method is provided for screening compounds to identify candidate therapeutic agents for treating bladder cancer. Bladder tumor cells are contacted with a test compound. Gene expression of one or more genes is determined in the bladder tumor cells which have been contacted with the test compound. The one or more genes are ones whose expression changes during the development of a bladder cancer. A test compound is identified as a candidate therapeutic agent if it causes gene expression of at least one of the one or more genes to change to a level which is characteristic of an earlier stage of cancer progression.

The present invention thus provides the art with numerous methods for molecularly assessing bladder cells. The methods aid the art in diagnosing, identifying, classifying, treating, detecting, and treating tumors of the bladder.

BRIEF DESCRIPTION OF THE DRAWINGS AND TABLES

This application file contains at least one drawing executed in color. Copies of this patent application publication with color drawing(s) will be provided by the Office upon request and payment of the necessary fee.

All genes scored as present on two chips (approximately 9000 genes) were compared. Increased genes were compared to increased genes and decreased genes to decreased genes, on two separate chips, followed by plotting of the numerical difference of the medians. A TaGrII tumor compared to the TaGrII pool, and the TaGrII pool to T2GrIV pool (1, 2, 3, 4); T2GrIII to T2GrIII pool, and T2GrIII pool to T2GrIV pool (5, 6, 7, 8); T2GrIV to T2GrIV pool, and T2GrIV pool to TaGrII pool (9, 10, 11, 12). Paired T-test of medians showed a borderline significant difference, with pool vs. pool scoring highest (P-value of 0.07).

Figure 3:
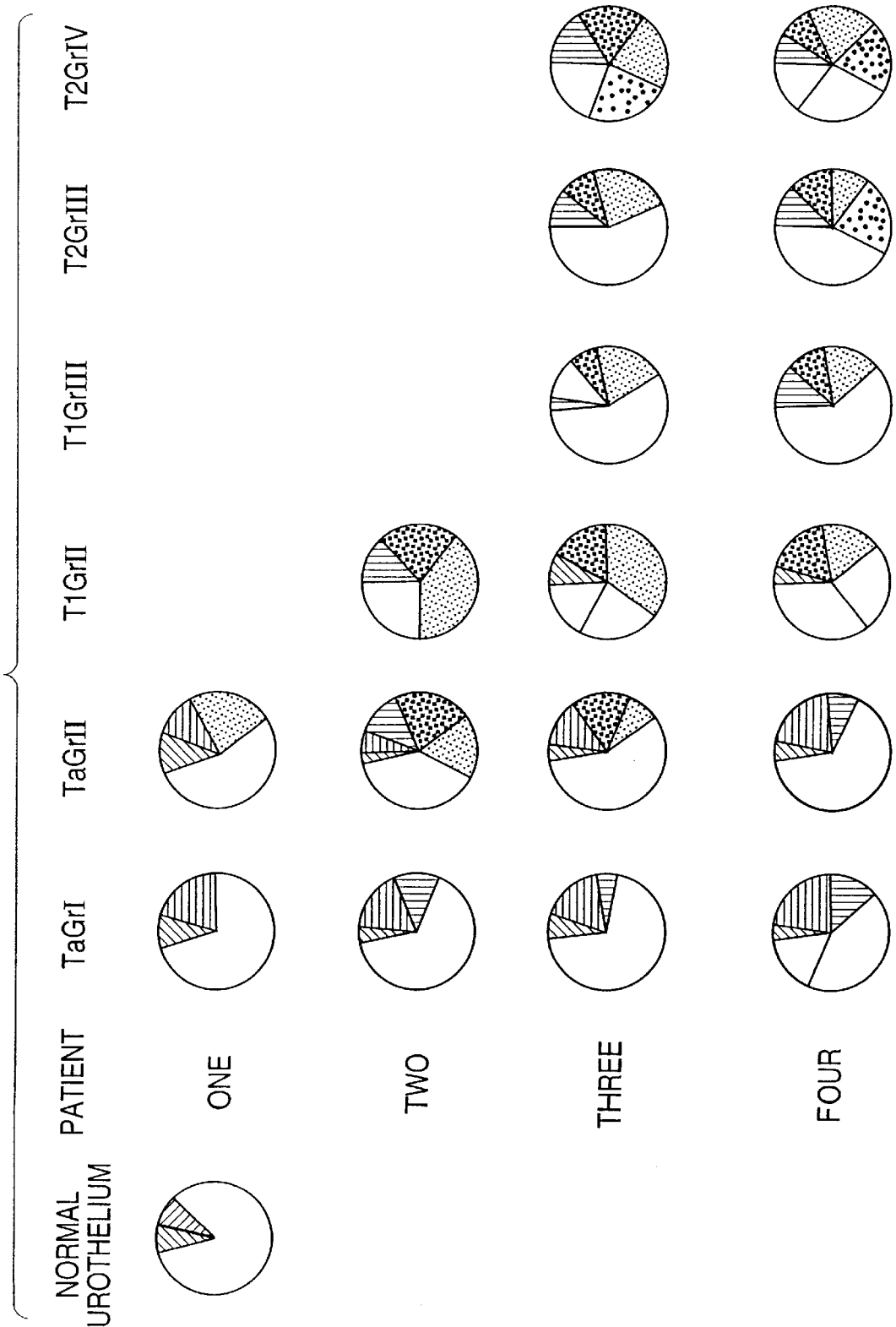

FIG. 3 shows progression of a bladder cancer from normal urothelium to invasive grade IV tumor. The expression patterns change during the progression, with a great variation in pattern from stage to stage, but also within a stage and even within tumors having the same stage and grade of atypia.

FIG. 4 shows the correlation between transcript levels from genes expressed in at least one sample.

Figure 4A:
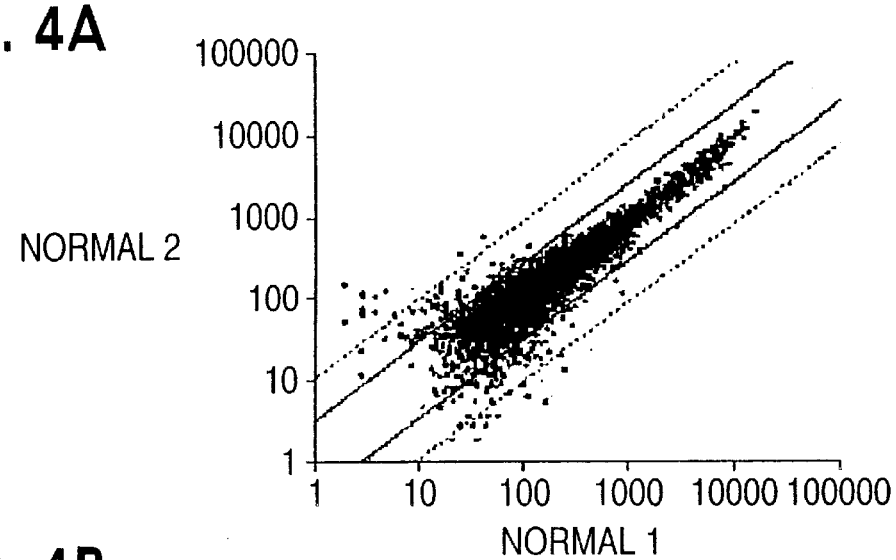

FIG. 4A demonstrates the repeatability of microarray expression analysis. Duplicate determinations on a normal sample are compared.

Figure 4B:
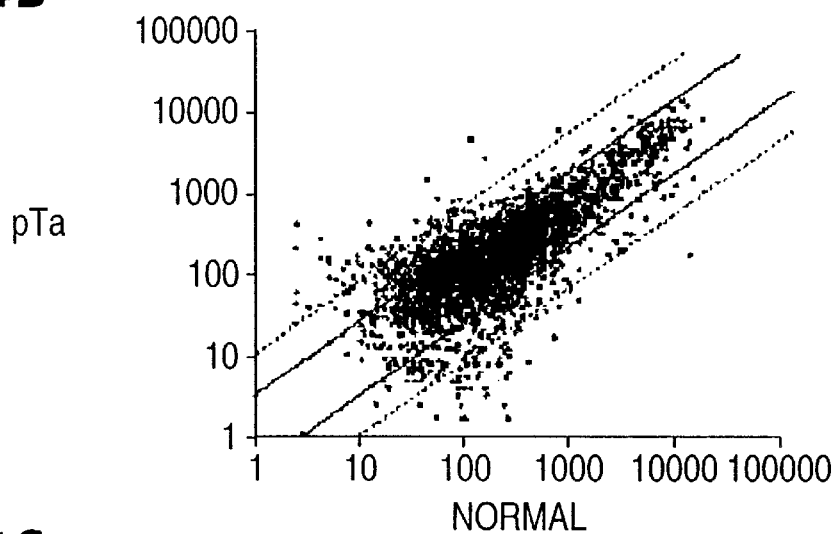
Figure 4C:
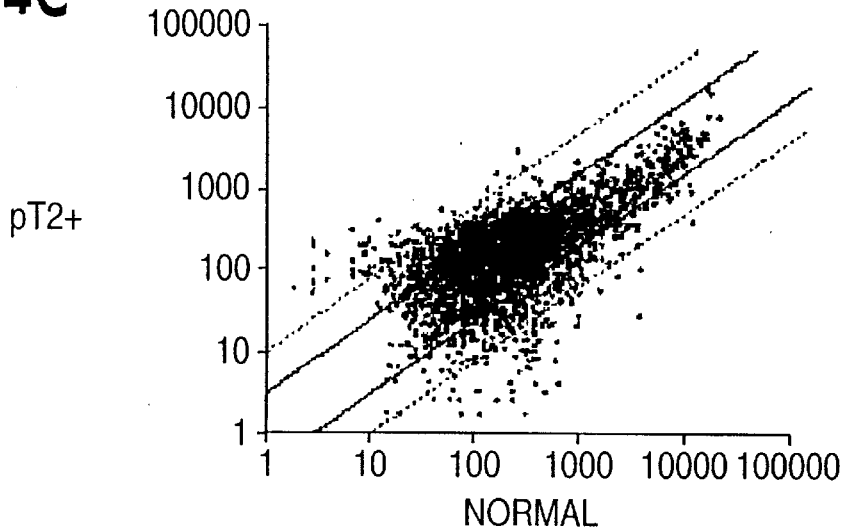
Figure 5A:
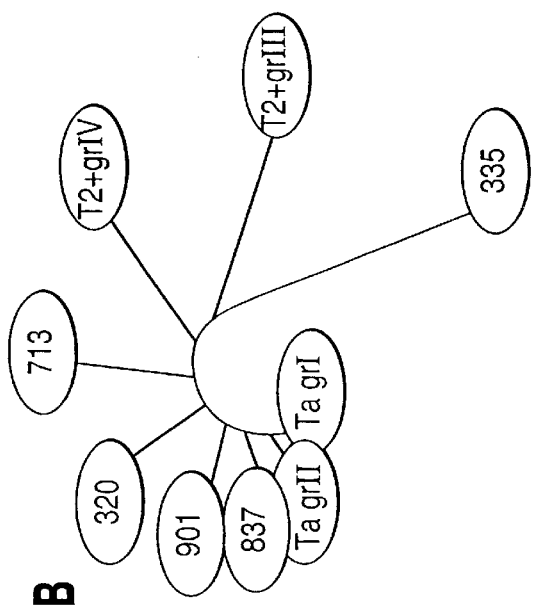
Figure 5B:
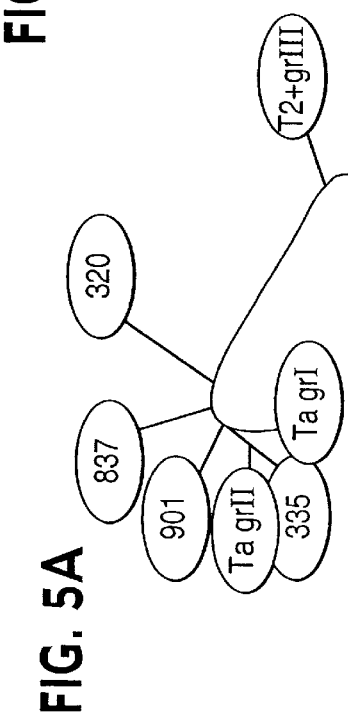
Figure 5C:
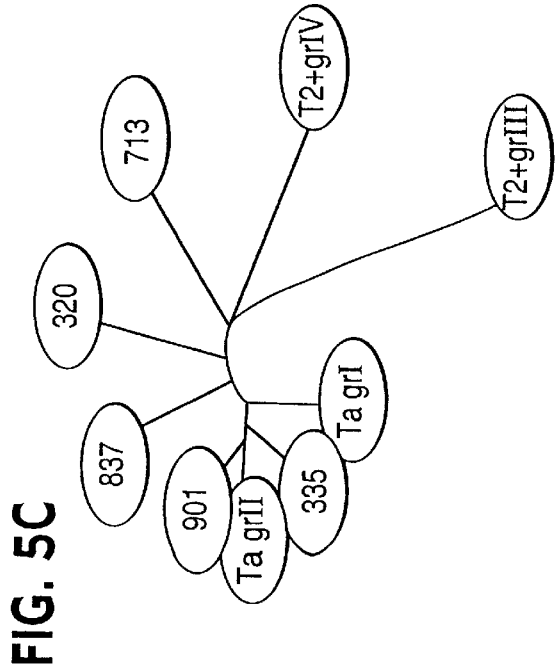
Figure 5D:
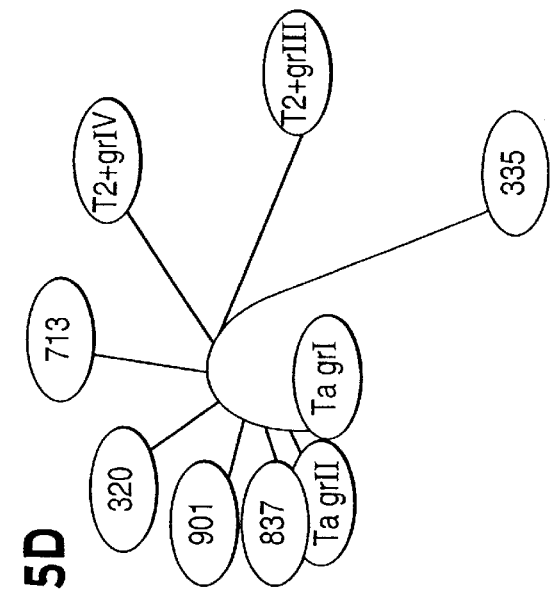
Figure 7A:
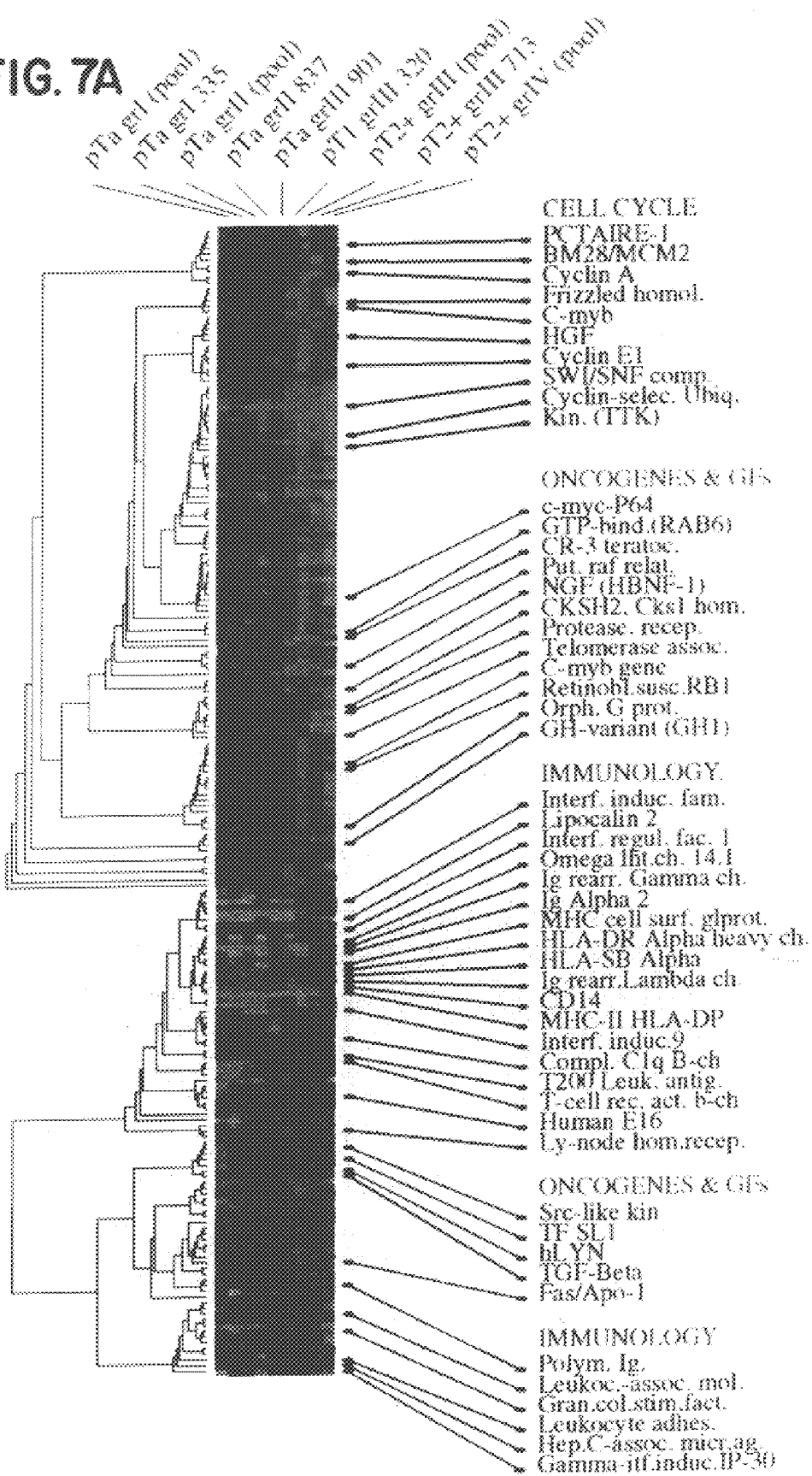
Figure 7B:
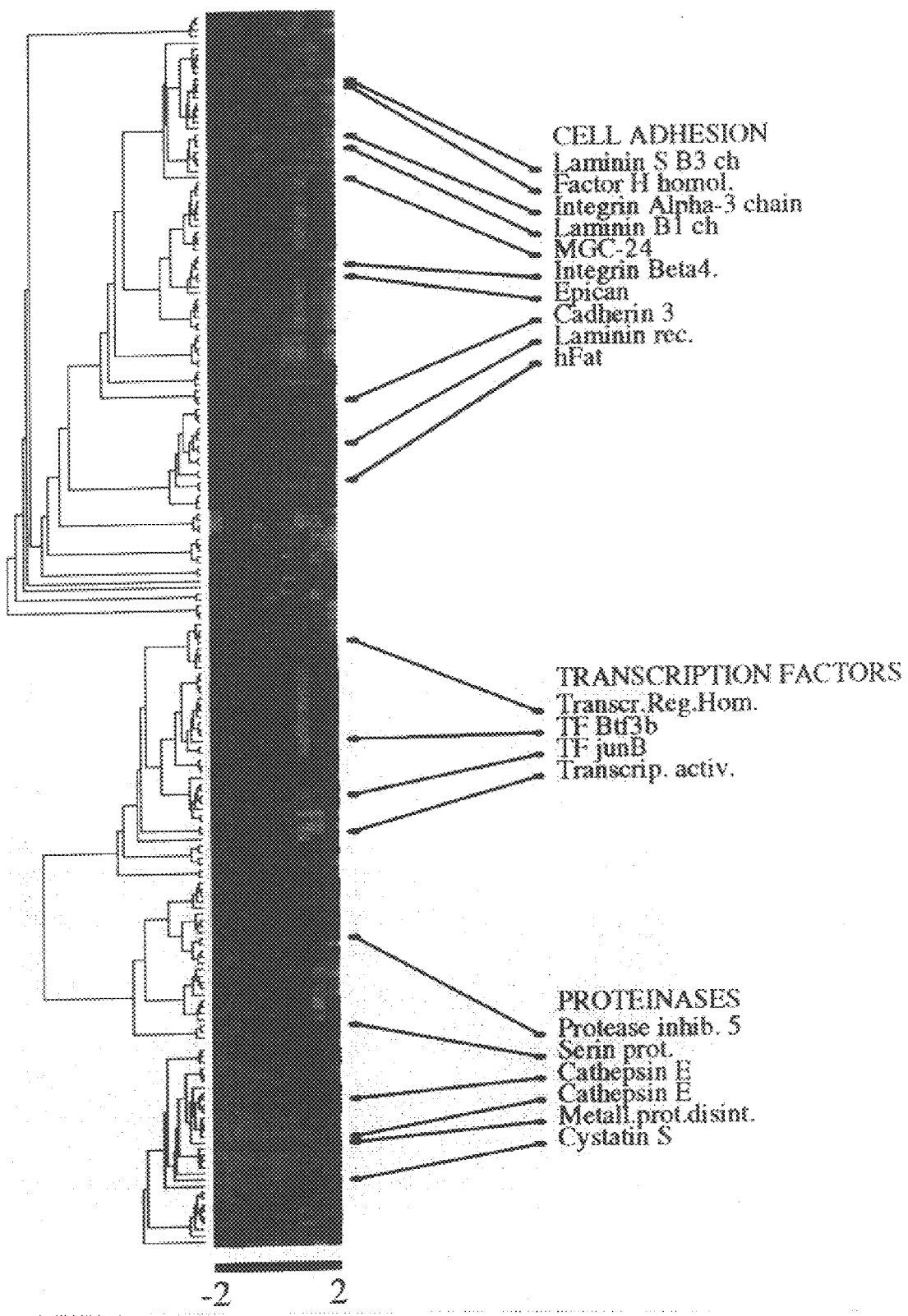
Figure 7C:
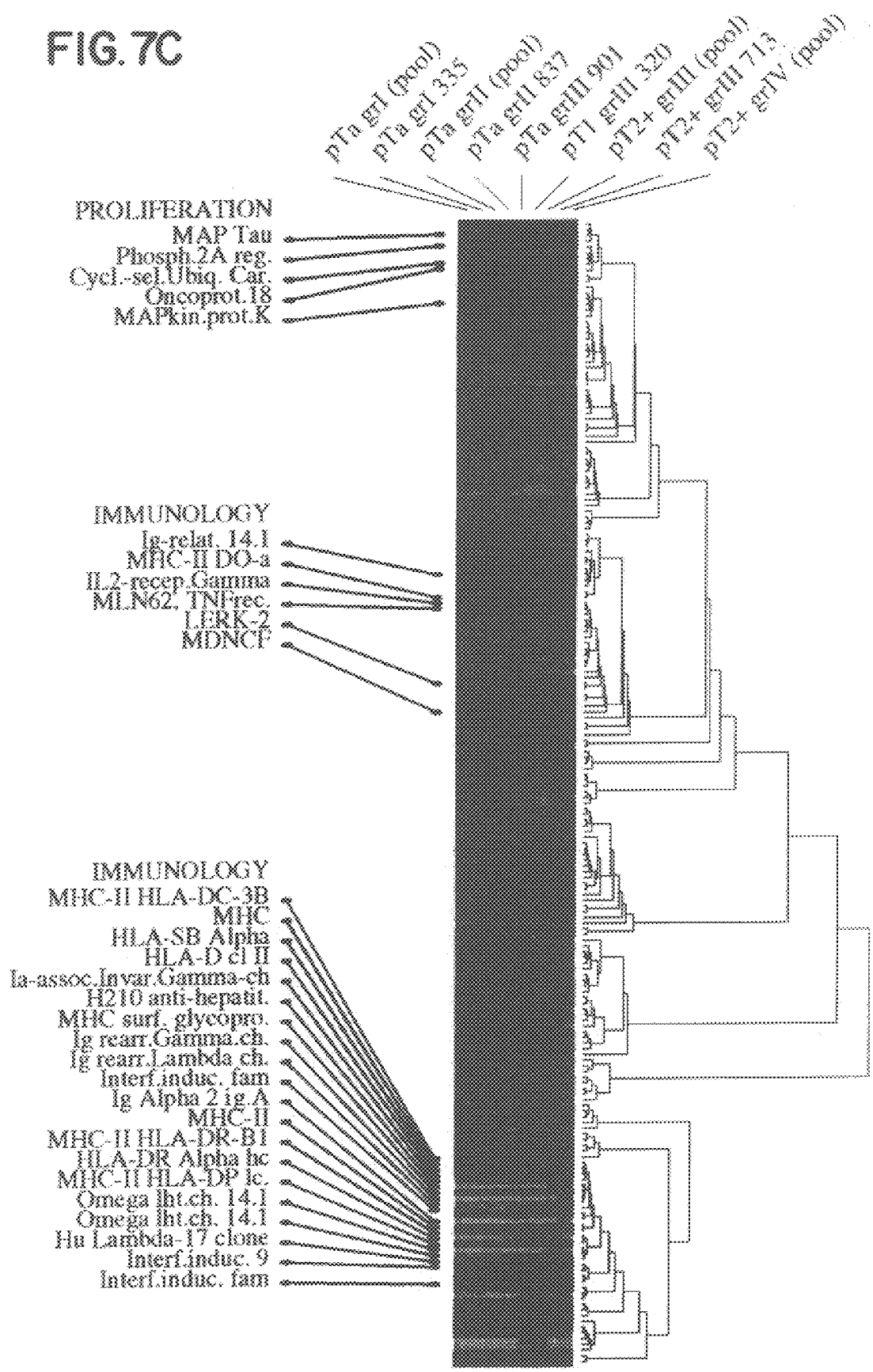
Figure 7D:
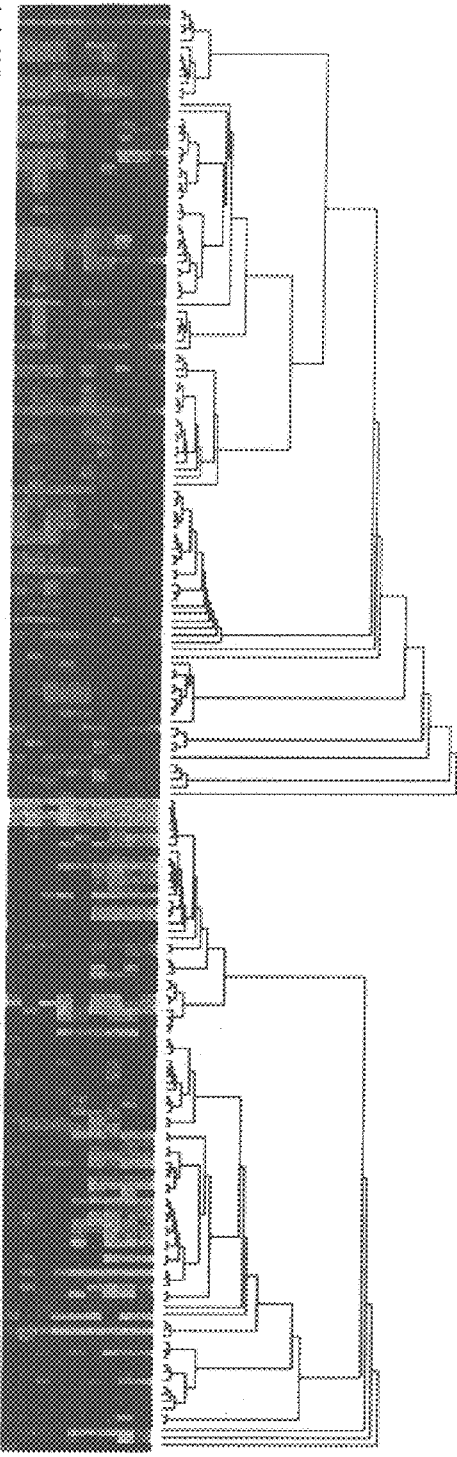

FIG. 4B is a plot of a pTa tumor vs. the normal pool. FIG. 4C is a plot of an invasive pT2 tumor versus the normal pool. The vast majority of transcripts are present at similar levels in both normal and tumor tissue.

FIG. 5 shows dendrograms of tissues based on different clustering methods. Clustering was either based on log-fold change in expression level of genes (FIGS. 5A, 5C), or the absolute difference (FIGS. 5B, 5D), comparing tumor to a pool of normal samples. Genes used for clustering were either those 10% of the genes that covaried best with progression (A, B), or all 4076 genes that were scored as present in at least one sample (C, D).

FIGS. 6A through 6F show how the pattern of expression changes during progression of bladder cancer based on levels of transcripts in pools of normal biopsies, superficial pTa tumors grade II, and invasive pT2+grade IV tumors. The curve at the top left portion of each subfigure shows the direction of change in gene expression based on pools of normal urothelium (open circle), superficial pTa tumor (gray circle) and invasive pT2+ tumor (black circle). Fold change in gene expression level was calculated on a probe-to-probe basis using 20 probes per gene and eliminating the highest and lowest outliers (olympic scoring). It is noteworthy that reduced expression is the most common event.

FIG. 7 shows a cluster diagram of 9 bladder tumors representing the progression of bladder cancer. Each column represents a tumor preparation, and each row a gene. The diagrams show clustering based on log-fold change from normal urothelium (left diagram) and based on absolute difference from normal urothelium (right diagram). A decreased expression is displayed as shades of cyan, an increased expression as shades of yellow, and no change as black.

The dendrograms at each side show the relation between the different genes. In the middle, distinct functional clusters are identified and members of the clusters are annotated in brief (for full length ID of all genes in the diagram and Genbank numbers see www.mdl.dk/supplementary data). In an effort to identify those genes most indicative of cancer progression a weighting scheme was used to select the 400 genes that covaried best with the different stages of bladder cancer. Gene clustering was based on normalized Euclidean distance (vector angle) calculated between genes or gene cluster centers.

FIG. 8 shows the vector angle between pools and individual single cell preparations or biopsies. The numbers refer to patient samples and the stage of each is indicated. Pools are identified as follows: squares, Ta grade I pool; diamonds, Ta grade II pool; circles, T2–4 grade III pool; triangles, T2–4 grade IV pool. The lowest angle for each sample determines the whether the sample is classified as a superficial (Ta or T1) or muscle-invasive tumor (T1–T4).

Figure 9:
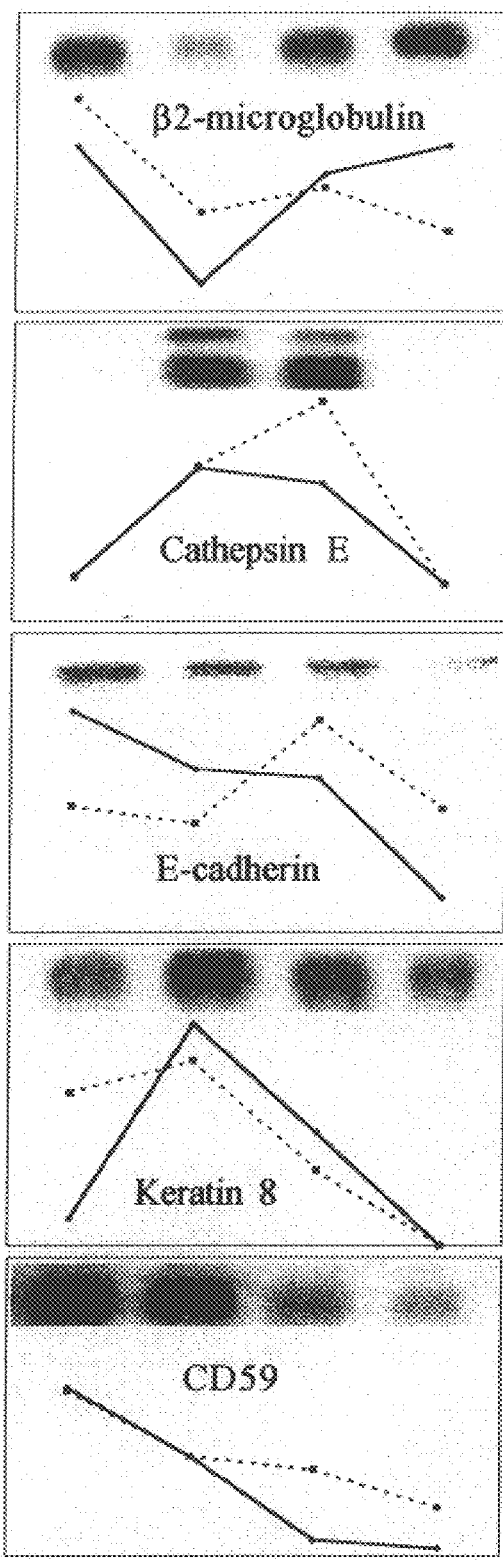

FIG. 9 shows a comparison of Northern blots and oligonucleotide arrays. The samples analyzed were normal pool (Norm), superficial pTaGrI tumor (335), minimally invasive pT1 grade III (901), and invasive pT2 grade III (713). The Northern blots were scanned by densitometry and plotted (solid lines) together with a plot of the level detected on the arrays (dotted lines). The levels of expression ranged from 3–6,000 units (beta-2 microglobulin) to 100–600 units (E-cadherin). The level of transcripts detected was similar with both methods.

Figure 10:
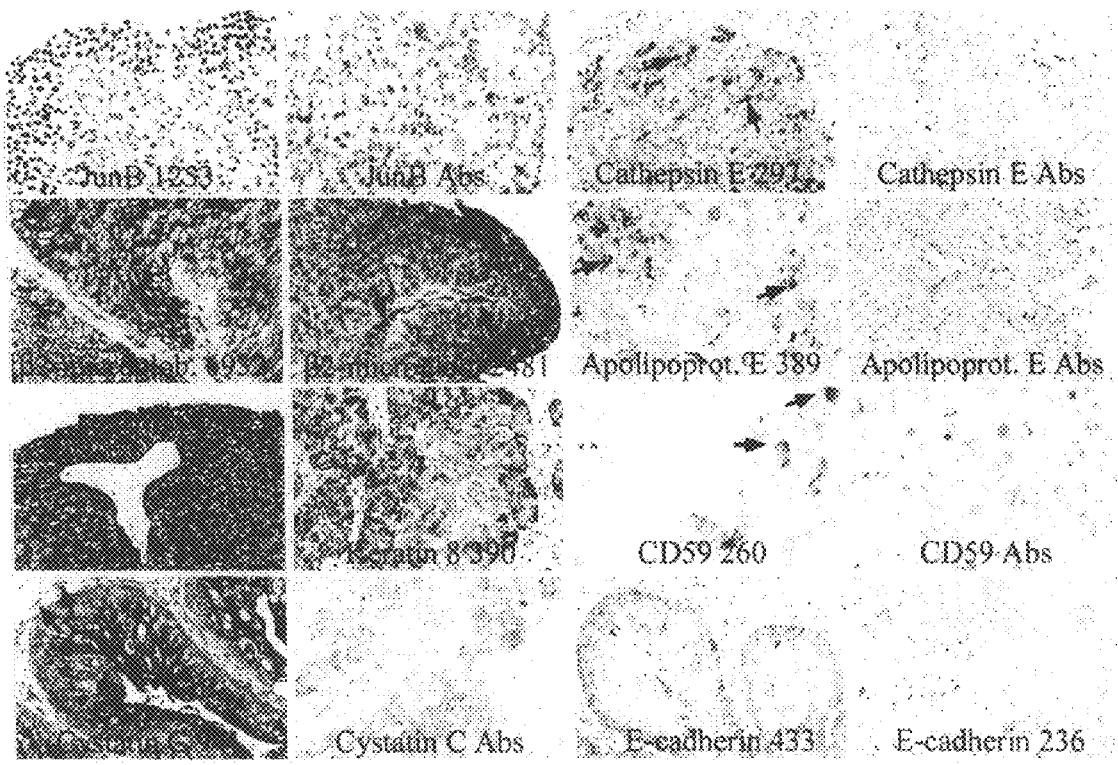

FIG. 10 shows immunohistochemical staining of the tissue sections used for expression analysis. On each section the protein examined is indicated and the level measured on the oligonucleotide array. Arrows indicate stained urothelial cells in cathepsin E (297 arbitrary units), ApoE (389 units), and CD59 (260 units) stainings, and stained stromal cells or leukocytes in beta2-microglobulin (2481 units) and cystatin C (941 units).

Figure 11:
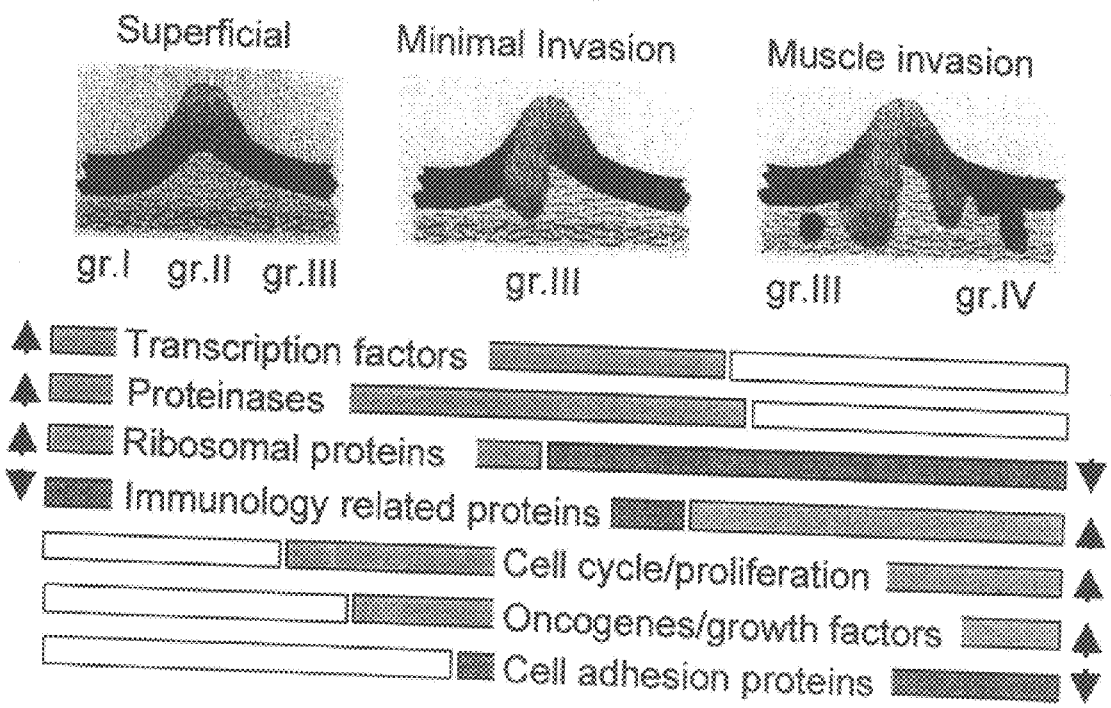

FIG. 11 presents a model of gene expression events during the progression of bladder cancer. The top of the figure shows the stages of bladder cancer, and the lower part shows the sequence of transcriptional events. The color cyan identifies reduced expression, yellow increased expression (also indicated by arrows). The figure is based on data from cluster analysis, and combines the different cluster methods.

Table 1 shows genes which were highly expressed in bladder wall. Expression is shown in "connective tissue" which includes muscle and submucosal cells, a TaGr III, a T$_2$Gr III, and a T$_2$Gr IV bladder tumor. Genes above the 90$^{th}$ percentile are grouped according to the purported function of the protein.

Table 2A shows high intensity genes in bladder wall compared to single cell solutions and biopsies of tumors.

Table 2B shows expression of genes related to bladder wall.

Table 3 shows the number of genes that are expressed as in the tumor-pool to which the tumor belongs, or altered as in a tumor pool of higher or lower stage or grade.

Tables 4A and 4B show genes whose expression signals a higher stage or grade.

Table 5 shows the cumulative data on the number of genes whose expression levels are changed at least 3-fold, at least 5-fold and at least 7-fold between Normal, Ta (superficial) and stages T2–4. For example the first row indicates that 9 genes are increased at least 3 fold going from Normal to Superficial and from Superficial to T2–4.

Table 6 (enclosure 1) shows gene expression (both the log-fold and absolute (average) difference) in normal submucosa and connective tissue. The column that shows average differences (AvgDiff) identifies the level of expression of the gene. Genes marked with a "P" are expressed in the tissue. Proteins and mRNAs of the identified genes can be used as markers for the presence of cancer or invasive disease when present or increased in a body fluid.

Table 7 (enclosure 2) shows gene expression in normal human urinary bladder mucosa (urothelium). Identified genes' can be used to identify a unknown cell as being of urothelial origin. This is useful in cell culture as well as in diagnosis of metastasis or analysis of cells in urine.

Table 8 (enclosure 3) shows gene expression in bladder cancer from different stages of the disease. Genes identified as being up and/or down regulated at least two fold during the change from normal urothelium via superficial disease to invasive cancer can be used for staging, grading, prognosis, prescription. An intensity value of 21 or greater indicates expression of the gene.

Table 9 lists the top 200 positively covarying and the top 200 negatively covarying genes with respect to the progression of bladder cancer, as identified by cluster analysis. The results are presented for cluster analysis performed using both the log-fold and absolute difference methods.

Table 10 summarizes the results of the immunolocalization of proteins whose expression varies during bladder cancer progression.

Several of the tables described above contain lists which include both genes and expressed sequence tags (ESTs). Reference to the "genes" of a table shall be understood to include the gene containing the EST.

DETAILED DESCRIPTION OF THE INVENTION

It is a discovery of the present inventor that characteristic patterns of expression of genes can be used to characterize different types of tissue. Thus, for example, gene expression patterns can be used to characterize stages and grades of bladder tumors. Similarly, gene expression patterns can be used to distinguish cells having a bladder origin from other cells. Moreover, gene expression of cells which routinely contaminate bladder tumor biopsies has been identified, and such gene expression can be removed or subtracted from patterns obtained from bladder biopsies. Further, the gene expression patterns of single-cell solutions of bladder tumor cells have been found to be far freer of interfering expression of contaminating muscle, submucosal, and connective tissue cells than biopsy samples.

Working with human tumor material requires biopsies, and working with RNA requires freshly frozen or immediately processed biopsies. Biopsies inevitably contain many different cell types in addition to cancer cells, such as cells present in blood, connective and muscle tissue, endothelium etc. In the case of DNA studies, microdissection or laser capture are methods of choice, however, the time-dependent degradation of RNA makes it difficult to perform manipulation of the tissue for more than a few minutes. Furthermore, studies of expressed sequences may be difficult on the few cells obtained via microdissection or laser capture, as these may have an expression pattern that deviates from the predominant pattern in a tumor due to intra-tumoral heterogeneity.

High-density expression arrays were used to evaluate the impact of bladder wall components in bladder tumor biopsies, and tested preparation of single cell solutions as a means of eliminating the contaminants. The results of these evaluations permitted the design of methods of evaluating bladder samples without the interfering background noise caused by ubiquitous contaminating submucosal, muscle, and connective tissue cells.

The evaluating assays of the invention may be of any type. While high-density expression arrays can be used, other techniques are also contemplated. These include other techniques for assaying for specific mRNA species, including RT-PCR and Northern Blotting, as well as techniques for assaying for particular protein products, such as ELISA. Western Blotting, and enzyme assays. Gene expression patterns according to the present invention are determined by measuring a gene product of a particular gene, including mRNA and protein. A pattern may be for one or more genes.

Using the results provided in the accompanying figures and tables, a gene is indicated as being expressed if an intensity value of greater than or equal to 21 is shown. Conversely, an intensity value of less than 21 indicates that the gene is not expressed above background levels. Comparison of an expression pattern to another may score a change from expressed to non-expressed, or the reverse. Alternatively, changes in intensity of expression may be scored, either increases or decreases. Any statistically significant change can be used. Typically changes which are greater than 2-fold are suitable. Changes which are greater than 3-fold or 5-fold are highly significant.

A pattern of characteristic expression of just one gene can be useful in characterizing a cell type source or a stage of disease. However, more genes may be usefully analyzed. Useful patterns include expression of at least one, two, three, five, ten, fifteen, twenty, twenty-five, fifty, seventy-five, or one hundred informative genes. As used herein, the phrase "stage-specific reference pattern" refers to a pattern of gene expression characteristic of a given stage of progression in a bladder tumor. A stage-specific reference pattern can include one or more genes listed in Table 4 and/or one or more genes listed in Table 8 and/or one or more genes listed in Table 9 and/or one or more genes listed in FIG. 6.

RNA or protein can be isolated and assayed from a test sample using any techniques known in the art. They can, for example, be isolated from fresh or frozen biopsy, from formalin-fixed tissue, from body fluids, such as blood, plasma, serum, urine, or sputum.

Stage of a bladder tumor indicates how deeply the tumor has penetrated. Superficial tumors are termed Ta, and $T_{1-4}$ are used to describe increasing degrees of penetration into the muscle. The grade of a bladder tumor is expressed on a scale of I–IV (1–4). The grade reflects the cytological appearance of the cells. Grade I cells are almost normal. Grade II cells are slightly deviant. Grade III cells are clearly abnormal. And Grade IV cells are highly abnormal.

As used herein, the reference to genes which are expressed in "submucosal, smooth muscle, or connective tissue" or patterns of expression in "other cell types" can include the expression of one or more of the genes listed in Table 1 and/or one or more of the genes listed in Table 6. The term "connective tissue cell" includes any stromal cell such as fibroblasts, macrophages, mast cells, granulocytes, etc. The data provided herein of expression for submucosal, smooth muscle, and connective tissue can be used in at least three ways to improve the quality of data for a tested sample. The genes identified in the data as expressed can be excluded from the testing altogether or tested but eliminated from the analysis. Alternatively, the intensity of expression of the genes expressed in the submucosal, smooth muscle, and/or connective tissue can be subtracted from the intensity of expression determined for the test tissue.

Patterns can be compared manually (by a person) or by a computer or other machine. An algorithm can be used to detect similarities and differences. The algorithm may score and compare, for example, the genes which are expressed and the genes which are not expressed. Alternatively, the algorithm may look for changes in intensity of expression of a particular gene and score changes in intensity between two samples. A variety of such algorithms are known in the art. Similarities may be determined on the basis of genes which are expressed in both samples and genes which are not expressed in both samples or on the basis of genes whose intensity of expression are numerically similar. Differences are considered significant when they are greater than 2-fold, 3-fold or 5-fold from the base value. Alternatively, a mathematical approach can be used to conclude whether differences in the gene expression exhibited by different samples is significant (see, e.g., Golub et al., Science 286, 531 (1999). One approach to determine whether a sample is more similar to or has maximum similarity with a given condition (e.g., a particular grade or stage of tumor progression) is to compare the Euclidean distances (see Golub et al. and Example 6) between the sample and one or more pools representing different conditions for comparison; the pool with the smallest vector angle is then chosen as the most similar to the test sample among the pools compared.

The data collected and disclosed here as "connective tissue" is presumed to contain both smooth muscle and submucosal gene expression as well. Thus it represents the composite expression of those cell types which can typically contaminate a bladder tumor biopsy.

Genes identified as changing in various stages or grades of bladder cancer can be used as markers for drug screening. Thus by treating bladder cancer cells with test compounds or extracts, and monitoring the expression of genes identified as changing in the progression of bladder cancers, one can identify compounds or extracts which change expression of genes to a pattern which is of an earlier stage/grade or even of normal urothelium. As used herein, the reference to expression of genes in "normal urothelium" or "normal urothelial cells" can include one or more genes listed in Table 7.

As demonstrated below, pools of tumors of a similar stage or grade, particularly bladder tumors, can be made and the expression of the pool evaluated. The expression data of the pool can be used to define a stage or grade of tumor. The use of the pool minimizes the variations found from individual tumor to individual tumor of the same grade or stage. The expression data of the pool can then be used as a comparator to which individual tumor samples are compared, in an effort to categorize, prognosticate, and prescribe the tumor samples. The methods described herein for classifying the stage or grade of a tumor can be combined with sequence analysis of genes whose expression is altered compared to normal tissue in the individual patient. In particular, mutations in key genes such as tumor suppressor genes can help to refine the application of the gene expression results to diagnosis and prognosis.

As used herein, the reference to expression of "genes in bladder cancer" or "genes in a bladder tumor" can include one or more genes listed in Table 4 and/or one or more of the genes listed in Table 8 and/or one or more genes listed in Table 9.

The above disclosure generally describes the present invention. A more complete understanding can be obtained by reference to the following specific examples which are provided herein for purposes of illustration only, and are not intended to limit the scope of the invention.

EXAMPLE 1

Quantification of Gene Expression Using Microarrays

Material

Bladder tumor biopsies were sampled from patients after informed consent was obtained, and after removal of the necessary amount of tissue for routine pathological examination. Tumors examined were 335 (stage pTa gradeI), 837 (pTa GrII), 901 (pTa GrIII), 320 (pT1 GrIII), 713 (pT2 GrIII). RNA from six different tumors of the same stage and grade was combined to form each pool. Four such pools were prepared (pTa GrI pool, pTa GrII pool, pT2+GrIII pool, and pT2+GrIV pool). Normal bladder mucosa biopsies from 36 patients with prostatic hyperplasia or incontinence were pooled (as RNA) to obtain a normal urothelial reference. Single cell solutions were made by disintegrating biopsies on ice with a scalpel and a syringe followed by filtering through a 50 micron filter.

Preparation of mRNA

Total RNA was isolated using the RNAzol B RNA isolation method (WAK-Chemie Medical GMBH). Poly (A)+ RNA was isolated by an oligo-dT selection step (Oligotex mRNA kit from Qiagen).

Preparation of cRNA

One µg mRNA was used as starting material for the cDNA preparation. The first and second strand cDNA synthesis was performed using the SuperScript Choice System (Life Technologies) according to the manufacturer's instructions, except that an oligo-dT primer containing a T7 RNA polymerase promoter site was used. Labeled cRNA was prepared using the MEGAscrip In Vitro Transcription kit (Ambion). Biotin labeled CTP and UTP (Enzo) was used in the reaction together with unlabeled NTP's. Following the IVT reaction, the unincorporated nucleotides were removed using RNeasy columns (Qiagen).

Array Hybridization and Scanning

Ten µg of cRNA was fragmented at 94° C. for 35 min. in a fragmentation buffer containing 40 mM Tris-acetate pH 8.1, 100 mM KOAc, 30 mM MgOAc. Prior to hybridization, the fragmented cRNA in a 6×SSPE-T hybridization buffer (1M NaCl, 10 mM Tris pH 7.6, 0.005% Triton) was heated to 95° C. for 5 min and subsequently to 40° C. for 5 min before loading onto an Affymetrix probe array cartridge (HuGeneF1 set array, part No. V900160). The probe array was then incubated for 16 h at 40° C. at constant rotation (60 rpm). The washing and staining procedure was performed in the Affymetrix Fluidics Station. The probe array was exposed to 10 washes in 6×SSPE-T at 25° C. followed by 4 washes in 0.5×SSPE-T at 50° C. The biotinylated cRNA was stained with a streptavidin-phycoerythrin conjugate, 10 µg/ml (Molecular Probes, Eugene, Oreg.) in 6×SSPE-T for 30 min at 25° C. followed by 10 washes in 6×SSPE-T at 25° C. The probe arrays were scanned at 560 nm using a confocal laser scanning microscope with an argon ion laser as the excitation source (made for Affymetrix by Molecular Dynamics). The readings from the quantitative scanning were analyzed by the Affymetrix Gene Expression Analysis Software.

Normalization of Data

Figure 1:
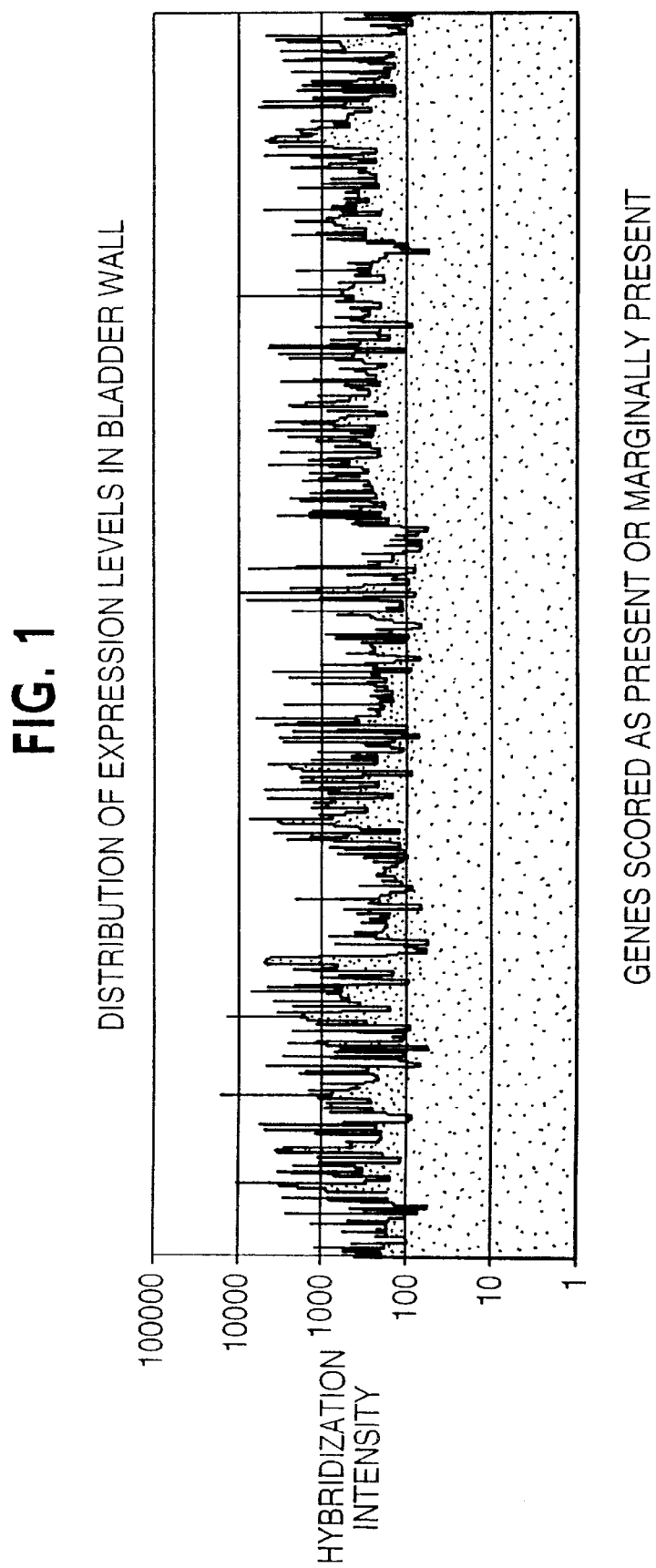
FIG. 1 shows a distribution of expression levels in bladder wall tissue expressed in arbitrary units. Only genes scored as present or marginally present are shown.

To compare samples, normalization of the data was necessary. For that purpose we compared scaling to total GAPDH intensity (sum of 3', middle, 5' probe sets) of 7000 units with scaling to a total chip intensity (global scaling) of 281850 units (averaging 150 units per probe set). Both gave similar results with scaling factors that differed less than ten percent in a set of experiments. Based on this we chose the global scaling for all experiments. The variation in hybridization intensity following global scaling in biopsies from the bladder wall is shown in FIG. 1.

EXAMPLE 2

Interference of Bladder Wall Components on Expression Profiling of Bladder Tumor Biopsies Biopsies contain epithelial cells that most often are the targets for the studies (e.g., in the identification and characterization of carcinoma cells), and in addition many other cells that contaminate the epithelial cell fraction to a varying extent. The contaminants include histiocytes, endothelial cells, leukocytes, nerve cells, muscle cells etc. Microdissection is the method of choice for DNA examination, but in case of expression studies this procedure is difficult due to RNA degradation during the procedure. Our approach has been to gently remove the epithelium and monitor the expression in the remaining submucosa and underlying connective tissue (the bladder wall). Genes expressed at high or low levels in the bladder wall should be interrogated when performing expression monitoring of the urothelium and urothelial tumors. A similar approach could be used for studies of epithelia in other organs.

We gently scraped off some of the normal urothelium lining the bladder lumen from bladders removed at cystectomy for bladder cancer. Then biopsies were taken from the denuded submucosa and connective tissue, reaching approximately 5 mm into the bladder wall, and immediately disintegrated in guanidinium isothiocyanate. Total RNA was extracted from four different cystectomy specimens, pooled, and poly(A)+ mRNA was prepared from the pool followed by conversion to double-stranded cDNA and in vitro transcription into cRNA containing biotin-labeled CTP and UTP.

The labeled sample was hybridized to a set of 4 arrays containing 7074 probe sets for human genes. A total of 1491 of the examined genes (21.1%) were scored as present, and 120 (1.7%) as present but rare. The percentile distribution of the expression intensity was (90%, 1308; 75%, 383; 50%, 163; 25%, 85; 10%, 47). Genes above the $90^{th}$ percentile (Table 1) were grouped according to the purported function of the protein (Table 1, first column). Many of the highly expressed genes belong to a group of genes that encode proteins involved in transcription and translation, probably reflecting that these genes generally are highly expressed in the various cell types present in the bladder wall, and corresponding to recent data on yeast. Structural proteins such as keratins and proline rich proteins are highly expressed whereas collagen genes are only medium expressed. Extremely high expression is shown by the cystic fibrosis antigen gene, the S100 calcium binding protein, the cystatin B and the cytokeratin 13 genes that are all above 10,000 units.

To evaluate the influence of bladder wall tissue in urothelial tumor biopsies, we monitored the expression level in 3 biopsies from transitional cell carcinomas (one superficially invasive (#733-2) and two muscle invasive (#733-1 and #879-1). The expression intensity in the tumor biopsies of genes that are highly expressed in bladder wall are listed in Table 1. Many genes are expressed to the same magnitude in the tumor biopsies as in bladder wall, 82 genes (5%) were present at a level above 1308 in all samples, and above the 75% percentile of the bladder wall sample intensity (383 units) 210 genes were expressed in all three biopsies as well as in bladder wall. Genes that were not expressed in bladder wall but present in the urothelial biopsies amounted to 196.

Genes that are expressed and genes that are not expressed in bladder wall can both interfere with the interpretation of the expression in a biopsy, and should be interrogated when interpreting expression intensities in urothelial tumor biopsies, as the bladder wall component of a biopsy varies in amount from biopsy to biopsy.

It is remarkable how similarly many genes belonging to the groups encoding metabolically active proteins, transcription and translation related proteins, mitochondrial and nucleoproteins, are expressed in the different samples (Table 1). It seems reasonable to expect that it is incompatible with cellular function to stray from a narrow interval regarding these genes. Although some of the examined cells are malignant of atypia grade IV, which is a severe morphological deviation from normal, the key cellular fuinctions are obviously still under strict control.

Twenty six genes were expressed at an intensity above 1308 in bladder wall and more than five times lower in tumor biopsies. These genes, marked with bold (Table 1), include keratins (7 genes) encoding proteins like keratins type II, 4, and 6. Another prominent group are the genes encoding proline-rich proteins (5 genes). These gene expressions can be used to monitor the amount of bladder wall present in a given biopsy of tumors. The tumor biopsy 879-1 obviously has a larger bladder wall component than the other biopsies, as it contains keratin 13 and several other highly expressed bladder wall mRNAs at a low level, but higher than the other specimens (Table 1).

An interesting result was the S100 calcium binding protein A7 gene transcript that was highly expressed in bladder wall and totally absent from the other biopsies (also absent from a number of other examined tumor biopsies from bladder). As all samples were collected with the same procedures, it indicates that this expression is either individual and occurred by chance in the patients from whom we removed the bladder wall biopsies, or, more likely, that the presence of urothelial RNAases degrade this transcript very fast.

Bladder tumors have a reduced intercellular cohesion, and easily disintegrate into single cell solutions. To eliminate bladder wall cells from the urothelial tumor cells, five tumors were disintegrated into single cell solutions before extraction of RNA, and compared to three tumors where RNA was extracted from the biopsy directly. We expected that this disintegration procedure might lead to an enrichment of tumor cells and loss of connective tissue cells. Examination of genes highly expressed in bladder wall (Table 2A), showed a similar expression in single cell solutions of bladder tumor cells compared to biopsies. However, the level was much lower than seen in the bladder wall and raised the question whether the expressed RNAs originate from the bladder wall or from the urothelial cells.

To answer this question we examined the expression of genes expected to be present in bladder wall (Table 2B). Some of these genes were expressed in the bladder tumor samples, and probably indicate the presence of bladder wall components in these. It was striking that the single cell solutions contained much lower expression levels of these genes compared to the biopsies ($p<0.004$). Although the number of examined tumors was small this indicates that preparation of single cell solutions may reduce the presence of bladder wall cells in the samples. The absence of keratin 8 in the bladder wall sample demonstrated that this sample was devoid of urothelial cells (Table 2B).

The genes known to be related to the bladder wall components, showed a variable level throughout the samples. Some genes like myosin light chain 2 gene, fibroblast tropomyosin gene and alpha-1 collagen type IV gene, were generally more expressed in the tumor samples than the other genes (Table 2B). We hypothesize that this may reflect that there is a differential expression of genes in the connective tissue component that inevitably is included in a tumor biopsy, an expression that may deviate from the one found in the bladder wall further away from the tumor. An example of this differential expression in bladder wall was the presence of transcript from the myosin light chain gene in the tumor samples but not in the bladder wall biopsies (Table 2B).

In tumors many important events take place in the non-epithelial compartment. Tumors need a connective tissue support, they need blood vessels, they interact with the immune system and have intercellular signaling with various sorts of other cells in a complicated way that has not yet been clarified in detail. Gene expression originating from the non-epithelial compartment contributes to the expression profile of a tumor, and might be of great importance in relation to the clinical outcome and therapeutic response of the tumor.

EXAMPLE 3

Expression Profiling of Tumor Pools to Assess Individual Tumor Heterogeneity

We expected tumors from the same pathology stage and grade to have a more similar gene expression than tumors from different stages and grades. This was the case; however, these differences were not striking, and there were exceptions. Based on this we hypothesized that, a given tumor scored by a pathologist at light microscopy to be similar to another one may actually represent tumors with a remarkably different gene expression. The reason for this could be that tumors do not progress from a well defined stage to another well defined stage, but rather that a continuous change is taking place at the expression level—which is then only partly reflected by morphology.

We tested this hypothesis by examining the expression which differed between a pool of tumors from a given stage and a single tumor, to see whether the differentially expressed genes were linked to a certain stage or whether they were a random deviation. It was evident that tumor expression that deviates from the pool systematically have expressions belonging to either a lower or a higher stage, or both, or unique expressions not seen in the pool (FIG. 3). The low stage Ta tumor had 43 genes whose expressions were increased or decreased similar to the ones seen in a Stage 2 grade IV tumor pool, and only three expressions that were altered in the opposite direction of stage 2 grade IV. The stage 2 grade IV tumor had 33 genes whose expression was either increased or decreased similar to the ones seen in the Ta superficial tumor pool, and only 8 genes altered in the opposite direction. In the T2 grade III tumor, gene expressions that were increased or decreased similar to the superficial or the grade IV invasive pool could be found. Furthermore some gene expressions were only low in this grade III tumor, and higher in both superficial and grade IV tumor pools. The clinical information on the examined single tumors (Table 3) paralleled the expression findings as the intermediate grade III tumor was the first muscle invasive tumor in a patient who had had a superficial tumor five months earlier. It seems that this tumor has not reached the level of malignancy as seen in the other invasive tumor. The latter was of grade IV, and was a big solid tumor with muscle invasion at first visit. The superficial Ta tumor was the fifth recurrence and was followed by two new recurrences 64 and 159 days later—also of superficial nature.

The genes that were identified in lower stage and grade tumors and shown to be similar to the expression in high stage tumors are listed in Tables 4A and 4B. These genes may "signal" a higher stage or grade, or represent a transition from low stage or grade to high stage or grade. To aid in avoiding interpreting bladder wall expression as tumor cell-specific expression, the expression level in bladder wall is listed in Tables 4A and 4B. Two columns are shown which simulate an increase in bladder wall content to 20% and 50% of the sample. These columns were obtained by adding a 20% or 50% contribution from the "bladder wall" column to the appropriate remaining percentage contribution (80% or 50%) from the TaGrII Pool column. Single tumor expression level (column labeled "Ta single tumor") was interrogated in this context. Expression levels which are unlikely to be due to bladder wall contamination are shown in bold; other expressions are shown in regular font. We believe this procedure is useful and leads to reliable conclusions.

These genes form a complex group of genes with highly different functions. It is not totally unexpected that mucin synthesis is changed, nor that cytokeratin 15 is decreased when moving from Ta and to higher stage. The gene expressions which signal a higher grade of atypia in already invasive grade III tumors are, among others, immunology related genes. This may indicate that the more atypical cells are either surrounded by inflammatory cells, or that the tumor cells start synthesizing these proteins. Further investigation is needed to elucidate this point, and these proteins will be an interesting parameter to follow in relation to clinical course in the future. The strong up-regulation of cathepsin B may indicate an increased proteolytic attack against the connective tissue.

The cause of the changed expression is unknown and could be either a transcriptional regulation or secondary to gain or loss of chromosome material. Both mechanisms are known to occur in cancer cells.

EXAMPLE 4

Change of Transcript Level During the Progression of Bladder Cancer

Biopsies from human bladder tumors were analyzed as single tumors or as pools of tumors representing the different stages in the progression of the bladder cancer disease. We used a total of 5 single tumors and 4 tumor pools, each pool made by combining six tumors. To generate a normal reference material, we pooled biopsies from normal bladder mucosa from 35 volunteers. The biopsies were disintegrated into single cell solutions immediately after removal, filtered and snap frozen in guanidinium isothiocyanate. From the cell solutions RNA was extracted, reverse transcribed to cDNA and the cDNA transcribed into labelled cRNA, that was incubated on the chip cartridges followed by scanning and scaling to a global chip intensity amounting to 150 units per probe set. The scaling made it possible to compare individual experiments to each other. To verify the reproducibility, double determinations were made in selected cases and showed a good correlation (FIG. 4A).

We compared gene expression at three different steps in the progression of bladder cancer to each other by the use of the normal pool as a reference. A scatter plot of the noninvasive pTa grade one tumor and the invasive highly abnormal grade four pT2+ tumor showed a minor subfraction of the gene transcripts to deviate much from those in the normal urothelium. The large majority of transcripts were within a narrow range in both tumors and normal urothelium (FIGS. 4B, C). The number of deviating genes was higher in the most abnormal tumor.

We then analyzed transcripts that showed alterations larger than five-fold, when comparing three different pools representing the transition from normal urothelium to superficial tumor, and further on to invasive transitional cell carcinomas (TCC). The method applied consisted in a probe-to-probe comparison (20 probes per gene) based on the software GeneChip® Analysis Suite 3.1 from Affymetrix, Inc. Increased levels indicate that the transcript is either upregulated at the stated level or turned on de novo reaching a given fold above the background level. Decreased levels in a similar way indicate reduction or loss of transcript. Alterations of a single transcript during the progression of the bladder cancer disease can follow several different pathways (FIG. 6). Some of the transcript changes reflect the transition from normal cells to tumor cells, and are grouped as TCC related genes (FIGS. 6A, B). A distinct feature of group A was the presence of 6 smooth muscle related genes. Others are altered only in superficial tumors, not in invasive tumors, and are grouped as Bladder papilloma related genes (FIGS. 6C, D). Group C, with down-regulated genes, contained 15 immunology-related genes. Group D contained a variety of genes encoding proteins with different functions. Finally some genes only showed an alteration in invasive tumors and are grouped as Invasive TCC related genes (FIGS. 6E, F). The genes in group E encoded functionally unrelated proteins, whereas group F contained 5 immunology-related genes. Thus, it seemed possible to define groups of genes whose expression level is associated with the stage of bladder tumors.

EXAMPLE 5

Cluster Analysis

The level of a gene transcript during disease progression can be thought of as a pattern that can be correlated to patterns of other gene transcripts. If the expression of one gene is very similar to the expression of another gene in several samples they are a correlated pair of genes. This pair of genes can then be correlated to other genes with a similar transcriptional behavior in the set of tissues examined, and together these constitute a gene cluster. In the next step the relation between clusters is established and a dendrogram of genes is formed, in which strongly correlating gene clusters are near each other. The principles are described in Eisen et al., Proc. Natl. Acad. Sci. USA 95, 14863 (1998). Briefly, each gene vector was placed in its own cluster, where the cluster prototype was set to the gene vector. All pair-wise vector angles between cluster prototypes were calculated. The smallest vector angle was identified, and those clusters were merged as a weighted average of the two prototypes (and also a weighted average of all the gene vectors each prototype represented). The vector angles were then updated between the newly merged clusters and the merger process was repeated. The final clusters are displayed in the order in which they were merged.

Exactly the same procedure used to cluster genes can be used to cluster the tissue samples, showing the relation between the different tissues based on their gene expression. We based clustering analysis on either the 4067 transcripts being scored as present in at least one of the samples, or based on those 400 transcripts (see Table 9) that covaried best with a weighting scheme adding increasing values to increasing stages.

The scaled AvgDif measures as calculated by the Affymetrix software were extracted for the normal pool and each of the graded tissues. Only the 4067genes with an AbsCall of P (present) in at least one of the tissues were considered. All AvgDif measures below 20 were set to 20. For each tissue and each gene, the AvgDif from the normal pool was either subtracted, to define the "absolute difference," or divided and natural logarithm applied to define the "log-fold" relative measure. The relative expression measures for each tissue (log-fold or absolute difference) were used to cluster tissues by a hierarchical method using the Euclidean distance between tissues. Tissue dendrograms were constructed with the PHYLIP program using clustering order and distances. A weighting scheme (see Example 6) for the seven observed stages and grades of cancer was used to select 200 positively covarying and 200 negatively covarying genes with respect to progression. The same hierarchical method and a normalized Euclidean distance (vector angle) were used to cluster the top 400 positively and negatively covarying genes for both relative expression measures. Gene dendrograms were constructed by the same method as for the tissue dendrograms.

Tissue Clusters

Different algorithms based on either fold change or absolute differences in transcript levels across the different samples were applied to all transcripts or only those covarying with a progression scale. Both methods were able to cluster the tissues according to the tumor's or tumor pools stage and grade of atypia in a meaningful way (FIG. 5). The two noninvasive and the two invasive pools each clustered very closely together both using the fold change and the absolute difference, indicating a close genetic relation between these, and indicating that one effect of pooling samples is a reduction of the variation in gene expression. The single tumor preparations showed a more varied distribution but still reflected the stage of the tumor. In the log-fold dendrograms (FIGS. 5A, C) the superficial tumors 335, 837 and 901 cluster close to the superficial pools, but the pTa grade III tumor 901 seems closer to the superficial pools than the pTa grade II tumor 837. This may either be due to the variation in histopathological grading or due to the tumors having different genetic properties. The minimally invasive pT1 grade III tumor 320 is correctly placed in between the muscle invasive and the superficial tumors, and the muscle invasive tumor 713 is placed very close to the pools of pT2+ tumors. Tumor 713 seemed to be closer to the pT2+grade IV than Grade III pool although it was histopathologically scored as grade III. In the absolute difference dendrogram (FIGS. 5B, D) the superficial tumors 837 and 901 are closely related to the superficial pools, the pT1 superficially invasive tumor is less related and finally the invasive tumor 713 located closest to the invasive pools. An exception was the superficial tumor pTa grade I, 335-6 that deviated from all other tumors. Whether this tumor has unique properties is unknown, however it did not deviate from the expected location in the dendrograms based on fold change.

The dendrograms show that the clustering algorithms work very well, that the dataset obtained from the oligonucleotide arrays reflect the biological properties of the tumors, and that objective information on a tumor's stage and grade can be obtained from mathematical analysis of gene expression data. Furthermore, it is seen that when ranking based on covariance to the progression is used to extract the top 10% covarying genes, these have a dendrogram that is almost identical to the one based on 4067 genes. We therefore used the ranking procedure when analyzing gene clusters.

Gene Clusters

The data obtained from cluster analysis are presented as colored images in which genes with similar expression patterns are clustered next to each other on the vertical axis and the samples according to stage and grade on the horizontal axis (FIG. 7). The color of each cell in the tabular image represents the ratio between the sample expression of the gene in question and the expression in normal urothelium. The color saturation is directly proportional to the magnitude of the measured expression ratio, cyan indicating the lowest ratio, yellow indicating the highest ratio. Black indicates a ratio of one, a similar level of expression in tumor as in normal urothelium. The two different clustering methods, log-fold and absolute difference gave completely different clusters across the set of samples (FIG. 7).

In the log-fold based cluster analysis, the top 200 positively covarying genes can be divided into five different clusters containing functionally related genes (FIG. 7, left upper column). The cluster shown at the top contains genes related to cell proliferation such as cyclins A and E, PCTAIRE-1, and SWI/SNF. The next cluster mainly contains oncogenes and growth factors. Genes in both these clusters are expressed at a level close to that seen in normal urothelium in superficial tumors (black) and increase during disease progression (yellow). The two clusters at the lower part show a reduced expression level in the superficial tumors compared to normal (cyan) and then an increase above the normal urothelial level in invasive tumors (shades of yellow). These clusters contain a set of immunologically related genes, like different MHC's and immunoglobulins, cancer related genes like src-like kinase and Fas/Apo-1, and finally another immunologically related cluster at the bottom.

The 200 negatively covarying genes (FIG. 7, left lower column) could be divided into three different clusters based on log-fold change and function of the genes. The upper cluster contains genes related to cell adhesion like laminins, integrins and P-cadherin (FIG. 7, left lower column). They all show a reduced level of expression in the invasive tumors as evidenced by the cyan coloring to the right. The small middle cluster contains four genes related to transcription, and finally the lowest cluster in the figure contains five proteinases, like cathepsin E (two different probe sets for the same gene) and metalloproteinase as well as a protease inhibitor. The lower clusters are characterized by an increase in level in superficial tumors (yellow) followed by a reduction to a level below normal urothelium in invasive tumors.

In the absolute difference based cluster analysis the top 200 covarying genes that showed a positive covariance contained only few clusters having a functional relation. The upper cluster (FIG. 7, right upper column) contained five genes related to cell proliferation like the microtubule-associated protein and oncoprotein 18/stathmin. The next cluster was a set of immunology related genes like MHC and LERK-2. Both these clusters showed an increased expression level in invasive tumors compared to normal urothelium. The cluster at the lower end of the figure showed a reduced level in superficial tumors and a return to normal or increased level in invasive tumors. This cluster contained many immunology-related genes like MHC, HLA and immunoglobulin genes. Finally, for genes that showed a negative covariance based on absolute difference (FIG. 7, right lower column), this was mainly due to clustering of ribosomal genes. A very tight cluster in the middle of the graph show ribosomes that are upregulated in expression in superficial tumors and downregulated or unaltered in invasive tumors. The middle ribosomal cluster is generally expressed at a lower level than in normal urothelium, whereas the cluster at the bottom of the figure is similar to the one in the middle. Other genes that seemed to cluster were a small tight cluster of immunology related genes, and two tumor inhibitors, TGF-beta superfamily protein and Sui 1 in the uppermost cluster.

Thus, a pattern of altered gene transcription occurs during the progression of bladder cancer that involves a number of genes belonging to functionally different gene families. Cluster analysis identified many biologically relevant genes, and in that aspect was superior to the probe-by-probe comparison described above.

EXAMPLE 6

Classification of Tumor Progression Stage Based on Expression Analysis

We built a classifier that accurately identifies the stage of progression of a bladder tumor by comparing the expression of 400 selected genes (listed in Table 9) in a sample of the tumor with pool data for muscle-invasive and non-muscle invasive bladder tumors. The classifier calculated the angle between the vector resulting from the log-fold changes in expression of the pool and the vector resulting from the log-fold changes of the same genes in a single tumor or tissue biopsy sample.

A set of 400 genes that covary with the disease progression was selected from the approximately 4000 genes by constructing a vector based on a weighting scheme which designated the least invasive tumors (Ta, grade I) as 1 and the most invasive (T2, grade IV) as 8. Intermediate values were Ta, grade II=2; Ta, grade III=3; T1=5; and T2, grade III=7. Thus, the vector for the nine samples and pools was (1,1,2,2,3,5,7,7,8). The covariance between this vector and any gene expression vector out of the 4000 genes was:

$$c(X, Y) = \sum_{i=1}^{n} (x_i - \text{mean}(X))(y_i - \text{mean}(Y))/(n-1)$$

The 400 top covarying genes (200 positively covarying and 200 negatively covarying) were selected for the classifier and for the cluster analysis. The cluster analysis was then carried out as described by Eisen et al., Proc. Natl. Acad. Sci. USA 95, 14863 (1998) (see Example 5).

The classifier was based on a modification of the method described by Golub et al., Science 286, 531 (1999). Briefly, each sample or pool was represented as a vector whose coordinates represent the log-fold changes. The Euclidean distance (vector angle) between the two vectors (one from the sample to be classified and one from either the non-invasive pool or the invasive pool used for classification) was then calculated as:

$$A(X,Y) = a\cos(dp(X,Y)/(\text{len}(X) \times \text{len}(Y)))$$

where $$dp(X, Y) = \sum_{i=1}^{n} (x_i \times y_i)$$

and $$\text{len}(X) = \text{sqrt}\left(\sum_{i=1}^{n} x^2\right)$$

After the sample had been compared in this way to each pool, invasive and non-invasive, the pool which differed from the sample by the smaller angle was determined to be the class of the sample.

Samples from ten bladder tumors were assigned by the classifier, and the results are shown in FIG. 8. The classifier was able to correctly call the presence or absence of muscle invasion in all ten samples examined (7 non-muscle invasive, 3 muscle invasive), based on categorizations made by a pathologist. To cross-validate the classification methodology, two non-invasive (Ta) and two invasive (T2) pools were compared with tumors from each of 10 patients. Since two pools were available for each stage, four possible combinations (classifier sets) of one Ta pool and one T2 pool were tested. The classification rate was calculated as the number of tumors correctly identified times 10. The results for each of the four classifier sets were averaged to obtain the data shown in FIG. 8.

EXAMPLE 7

Confirmation of Microarray Expression Analysis by Northern Blotting

In order to confirm the array data, Northern blotting was performed on the same samples of RNA as used for array hybridization. A standardized amount of RNA was run in each lane, followed by blotting with a labelled RNA probe, and quantitation of the band obtained (FIG. 9).

Total RNA, 0.5–4 µg per lane, was separated in 1.5% agarose-formaldehyde gels, transferred onto Zeta-Probe® nylon membrane (Bio-Rad) by positive pressure (Posiblotter, Stratagene) and immobilized by baking for 20 min at 120° C. The filters were hybridized with digoxygenin-labelled (DIG) RNA transcribed from 600–1000 bp PCR products containing a T7 promotor incorporated via the antisense primers. Filters were hybridized with 10 ng probe per ml of ultrahyb™ hybridisations solution at 68° C. for 16 h and washed to a stringency of 0.1×SSC at 68° C. Specific hybridization was detected by reacting the membrane with monoclonal anti-DIG antibodies conjugated with alkaline phosphatase, incubating with ECF chemifluorescence substrate (AmershamPharmacia) and scanning on a Storm 840 (Molecular Dynamics). The hybridization signals were quantified with ImageQuant 5.0 software.

As can be seen from the plots, the oligonucleotide array and the Northern blot gave similar results with the different probes, both in genes expressed at a high level (beta2-microglobulin), and those expressed at a very low level (CD59).

EXAMPLE 8

Immunohistochemical Localization of Expressed Proteins

The biopsy samples used to study gene expression in bladder tumors contain cells other than urothelial cells, although the amount of other cells should be limited due to the use of single cell solutions. We therefore used immunostaining of tissue sections from the single tumors examined to determine which cells expressed the protein encoded by the transcript in question. We used the transcript levels to select a group of proteins supposed to show variation from sample to sample, making possible a rough correlation between level of protein detected and intensity of the transcript on the microarray.

Four μm sections were cut from paraffin-embedded tissue blocks, mounted, and deparaffinized by incubation at 80° C. for 10 min, followed by immersion in heated oil at 60° C. for 10 min (Estisol 312, Estichem A/S, Denmark) and rehydration. Antigen retrieval was achieved in TEG (Tris-EDTA-Glycerol) buffer using microwaves at 900 W. The tissue sections cooled in the buffer for 15 min before a brief rinse in tap water. Endogenous peroxidase activity was blocked by incubating the sections with 1% $H_2O_2$ for 20 min, followed by three rinses in tap water, 1 min each. The sections were then soaked in PBS buffer for 2 min. The next steps were modified from the descriptions given by Oncogene Science Inc., in the Mouse Immunohistochemistry Detection System, XHCO1 (UniTect, Uniondale, N.Y., USA). Briefly, the tissue sections were incubated overnight at 4° C. with primary antibody (against beta-2 microglobulin (Dako), cytokeratin 8, cystatin-C (both from Europa,US), junB, CD59, E-cadherin, apo-E, cathepsin E, vimentin, IGFII (all from Santa Cruz), followed by three rinses in PBS buffer for 5 min each. Afterwards, the sections were incubated with biotinylated secondary antibody for 30 min, rinsed three times with PBS buffer and subsequently incubated with ABC (avidin-biotinlylated horseradish peroxidase complex) for 30 min, followed by three rinses in PBS buffer. Staining was performed by incubation with AEC (3-amino-ethylcarbazole) for 10 min. The tissue sections were counter stained with Mayers hematoxylin, washed in tap water for 5 min. and mounted with glycerol-gelatin. Positive and negative controls were included in each staining round with all antibodies.

We found several of the proteins to be expressed not only by urothelial cells but also by leukocytes, endothelial cells or histiocytes (Table 10, FIG. 10). Of the examined proteins only keratin 8 and ApoE were confined to urothelium; the other proteins were also present in other cell types. Based on the assumption that transcript and protein originates from the same cell, this clearly indicates that conclusions on the origin of the transcripts requires a histological examination, or other verification procedure. The amount of stroma in a biopsy, the vascularization (amount of endothelial cells), the level of leukocyte infiltration, and the grade of atypia of the urothelial cells were all parameters that seemed to influence the level of a given transcript.

The level of protein identified by immunostaining, disregarding the cell type expressing the protein, correlated well with the transcript level measured on the microarray (FIG. 10). However, no attempt was made to quantitate the immunostaining due to the often large heterogeneity in staining across the sections.

TABLE 1

| Gene name Structural proteins | Description | Con. Tissue Bladder Wall | #733-2 $T_1$ gII | #733-1 $T_2$ gIII | #879-1 $T_2$ gIV |
|---|---|---|---|---|---|
| X07695_at | Human mRNA for cytokeratin 4 C-terminal region | 7458 | 37 | 78 | 87 |
| L42601_t_at | Homo sapiens karatin 6 isoform K5c (KRT6C) gene | 5155 | 183 | 126 | 389 |
| L42583_t_at | Homo sapiens keratin 6 isoform K6a (KRT6A) gene | 4939 | 125 | 155 | 388 |
| V015158_t_at | Human messenger fragment encoding cytoskeletal keralin (type II), mRNA from cultured epidermal ce | 4779 | 140 | 175 | 364 |
| X00351_t_at | Human mRNA for beta-actin | 4186 | 2876 | 1199 | 1322 |
| M10277_s_at | "Human cytoplasmic beta-actin""gene,""complete cds" | 3788 | 3321 | 3768 | 1830 |
| HG2815-HT4023_s_at | "Myosin," Light "Chain," "Alkali," Smooth Muscle" (Gb:U02629),"Muscle," Att Splice | 3415 | 3458 | 4176 | 2003 |
| HG2815-HT293f_at | "Myosin," "Light""Chain," "Alkali,""Smooth Muscle""(Gb:U02629,""Non-Muscle," "Alt. Splice 2" | 2265 | 3687 | 4146 | 2018 |
| X57683_at | H. sapiens mRNA for keratin 4 fgb=X57683/intype=RNA | 2126 | 126 | 160 | 193 |
| L42611_f_at | "Homo sapiens keratin 6 isoform K6a (KRT6E)" "mRNA" "complete cds" | 1946 | 301 | 226 | 224 |
| HG2815-HT2931_s_at | "Myosin,""Light" "Chain," "Alkali,""Smooth Muscle""(Gb:U0629), " "Non-Muscle," "Alt. Splice 2" | 1926 | 1594 | 2811 | 1178 |
| M85787_at | Human 22kDa smooth muscle protein (Sm22) "mRNA," complete cds | 1735 | 68 | 318 | 2326 |
| M55998_at | "Human alpha-t collagen type I""gene,""3' end" | 1610 | 425 | 4219 | 1874 |
| M21389_at | Human keratin type II(58 kD) "mRNA," complete cds | 1572 | 20 | 20 | 611 |
| X13839_at | Human mRNA for vascular smooth muscle alpha-actin | 1405 | 20 | 329 | 1164 |
| Metabolic-catabolic- and anabolic enzyme | | | | | |
| U46692_ma1_at | Human cystatin B, complete cds. | 10030 | 859 | 463 | 1687 |
| X01677_f_at | "Human liver mRNA for glyceraldehyde-3-phosphate dehydrogenase""(G3PD,"" EC 1.2.1.12)" | 3234 | 3018 | 3046 | 1664 |
| D78361_at | Human mRNA for ornithine decarboxylase "antizyme," ORF 1 and ORF 2 | 2518 | 2151 | 2373 | 4422 |
| U49689_ma1_at | Human ubiquitin gene, complete cds. | 2053 | 2902 | 2621 | 3237 |
| M86400_at | Human phospholipase A2 "mRNA," complete cds | 1653 | 1320 | 1048 | 1051 |
| M24485_s_at | "Homo sapiens (clone pHGST-pl) glutathione S-translerase pi(GSTP1)""gene.""complete cds" | 1522 | 2457 | 1493 | 544 |

TABLE 1-continued

| Gene name<br>Structural proteins | Description | Con.<br>Tissue<br>Bladder<br>Wall | #733-2<br>$T_1$ gII | #733-1<br>$T_2$ gIII | #879-1<br>$T_2$ gIV |
|---|---|---|---|---|---|
| M26880_at | Human ubiquitin "mRNA," complete cds | 1508 | 599 | 906 | 1072 |
| M63138_at | Human cathepsin D (catD) gene | 1489 | 695 | 1131 | 1990 |
| X77584_at | H. sapiens mRNA for ATL-derived factor/thiredoxin | 1470 | 815 | 713 | 568 |
| X02152_at | Human mRNA for lactate dehydrogenase-A "(LDH-A)," EC 1.1.1.27) | 1432 | 1478 | 491 | 1173 |
| M27891_at | Human cystalin C (CST3) gene | 1363 | 1028 | 730 | 2233 |
| X58997_ma1_at | Human UbA52 gene coding for ubiquitin-52 amino acid fusion protein. | 1308 | 1414 | 1296 | 1637 |
| Proteins related to transcription and translation | | | | | |
| Z12962_at | H. sapiens mRNA for homologue to yeast ribosomal protein L41 | 7468 | 9785 | 8449 | 8798 |
| K69150_at | L06432 H. sapiens mRNA for ribosomal protein S18. | 6256 | 6392 | 4994 | 2859 |
| L06499_at | "Homo sapiens ribosomal protein L37a(RPL37A) "mRNA," complete cds | 8064 | 5841 | 6648 | 4138 |
| L04483_s_at | "Human ribosomal S21(RPS21)""mRNA,""complete cds" | 5832 | 10817 | 9082 | 2846 |
| D23660_at | Human mRNA for ribosomal "protein," complete cds | 5345 | 4337 | 4331 | 5096 |
| J04617_s_at | "Human elongation factor EF-1-alpha""gene,"complete cds" | 4935 | 8965 | 7517 | 2180 |
| X17208_at | Human mRNA for LLRep3 | 4926 | 9042 | 8931 | 4029 |
| U14969_at | Human ribosomal protein S29 "mRNA," complete cds | 4539 | 4956 | 3427 | 4979 |
| M80854_at | Human ribosomal protein S16 "mRNA," complete cds | 4473 | 5801 | 5019 | 4247 |
| HG2873-HT3017_at | Ribosomal Protein L30 Homolog | 4372 | 8912 | 7949 | 4102 |
| M81757_at | H. sapiens S19 ribosomal protein "mRNA,"complete cds | 4369 | 6727 | 4087 | 4311 |
| U14973_at | Human ribosomal protein S29 "mRNA," complete cds | 4281 | 5175 | 4134 | 4410 |
| HG3364-HT3541_at | Ribosomal Protein L37 | 4242 | 7295 | 4338 | 3574 |
| X03689_s_at | Human mRNA fragment for elongation factor TU (N-terminus)./gb=<br>X03689/ntype=RNA | 4223 | 6855 | 4191 | 1506 |
| X56932_at | H. sapiens mRNA for 23kD highly basic protein | 4210 | 6461 | 5730 | 5089 |
| X60622_at | H. sapiens mRNA for ORF | 3963 | 4047 | 3534 | 3591 |
| U14970_at | Human ribosomal protein S5 "mRNA," complete cds | 3928 | 4473 | 2410 | 2569 |
| U14968_at | Human ribosomal protein L27a "mRNA," complete cds | 3885 | 3772 | 3079 | 4104 |
| X03342_at | Human mRNA for ribosomal protein L32 | 3818 | 5824 | 4184 | 3384 |
| X67247_rna1_at | H. sapiens rpS8 gene for ribosomal protein S8. | 3725 | 3928 | 2702 | 3155 |
| U14972_at | Human ribosomal protein S10 "mRNA," complete cds | 3695 | 6292 | 2894 | 2903 |
| M17885_at | Human acidic ribosomal phosphoprotein P0 "mRNA." complete cds | 3690 | 4911 | 4728 | 5335 |
| HG1800-HT1823_at | Ribosomal Protein S20 | 3582 | 3599 | 5808 | 4271 |
| M17886_at | Human acidic ribosmoal phosphoprotein P1 "mRNA," complete cds | 3488 | 3036 | 3138 | 2648 |
| X06617_at | Human mRNA for ribosomal protein S11 | 3387 | 4561 | 4705 | 3744 |
| X15940_at | Human mRNA for ribosomal protein L31 | 3375 | 6960 | 5371 | 3528 |
| U12485_at | Human ribosomal protein L35 "mRNA," complete cds | 3327 | 5675 | 2106 | 3004 |
| M18000_at | Human ribosomal protein S17 "gene," complete cds | 3315 | 6115 | 4537 | 2410 |
| X63527_at | H. sapiens mRNA for ribosmal protein L19 | 3282 | 5746 | 4830 | 1832 |
| M13934_cds2_at | Human ribosomal protein S14 gene, complete cds. | 3281 | 3512 | 1927 | 2578 |
| M64716_at | Human ribosomal S25 "mRNA," complete cds | 3228 | 2527 | 2087 | 3181 |
| M14199_s_at | "Human laminin receptor (2H5 epitope) "mRNA,""5' and" | 3222 | 8316 | 6902 | 1912 |
| L08505_at | Human ribosomal protein L12 "mRNA," complete cds | 3024 | 4981 | 3541 | 2787 |
| X73480_at | H. sapiens mRNA ribosomal protein L3 | 2949 | 2230 | 1849 | 2458 |
| X62691_at | H. sapiens mRNA for ribosomal protein (homologous to yeast S24) | 2885 | 3540 | 3732 | 1534 |
| U14971_at | Human ribosomal protein S9 "mRNA," complete cds | 2645 | 1907 | 1361 | 2603 |
| M77232_rna1_at | Human ribosmoal protein S6 gene, complete cds and flanking regions. | 2616 | 1948 | 1982 | 2470 |
| X79234_at | H. sapiens mRNA for ribosomal protein L11 | 2502 | 2298 | 2164 | 2290 |
| U09853_at | Human ribosomal protein L9 "mRNA," complete cds | 2506 | 2840 | 2851 | 1911 |
| X55954_at | Human mRNA for HL23 ribosomal protein homologue | 2495 | 5371 | 3501 | 2661 |
| Z26876_at | H. sapiens for ribosomal protein L38 | 2490 | 4036 | 2416 | 2159 |
| M32053_at | Human H19RNA "gene," complete cds (spliced in slice) | 2486 | 6187 | 2945 | 320 |
| L38941_at | Homo sapiens ribosomal protein L34 (RPL34) "mRNA," complete cds | 2460 | 4226 | 2950 | 2004 |
| X28407_at | H. sapiens mRNA for ribosomal protein LB | 2386 | 2775 | 1342 | 1797 |
| Z49148_s_at | H. sapiens mRNA for ribosomal protein L29 | 2303 | 4080 | 2201 | 1028 |
| X64707_at | H. sapiens BBC1 mRNA | 2268 | 2402 | 2224 | 2230 |
| M31520_rna1_s_at | Human ribosomal protein S24 mRNA | 2242 | 8267 | 4925 | 1409 |
| D14530_at | Human homolog of yeast ribosomal protein "S28," complete cds | 2193 | 2112 | 1861 | 945 |
| HG821-HT821_at | Ribosomal Protein S13 | 2159 | 1967 | 1440 | 1700 |
| M30872_at | "Human ribosomal protein L7a (surf 3) large subunit "mRNA," complete cds." | 2150 | 6168 | 2380 | 1000 |
| U58682_at | Human ribosomal protein S28 "mRNA," complete cds | 2129 | 3034 | 1970 | 1929 |
| X89391_at | H. sapiens mRNA for ribosomal protein L6 | 2094 | 2796 | 2790 | 1187 |
| HG33-HT33_at | Ribosomal protein S4 | 2077 | 1656 | 1078 | 1277 |
| A8002533_at | Human mRNA for "Chp1," complete cds | 2083 | 2155 | 1707 | 3217 |
| M55409_s_at | "Human pancreatic tumor-related protein""mRNA,""3' end" | 1992 | 4159 | 1919 | 815 |
| L19527_at | Homo sapiens ribosomal protein L27 (RPL27)"mRNA," complete cds | 1991 | 3103 | 2261 | 2052 |
| HG4319-HT4589_at | Ribosomal Protein L5 | 1960 | 2281 | 1600 | 1370 |
| X5377_at | Human L23 mRNA for putative ribosomal protein | 1915 | 3100 | 2330 | 1075 |
| M31520_at | Human ribosomal protein S24 mRNA | 1876 | 2419 | 2367 | 1416 |
| HG513-HT613_at | Ribosomal Protein S12 | 1873 | 2156 | 2000 | 1145 |
| X55715_at | Human Hums3 mRNA for 40S ribosomal protein s3 | 1744 | 2569 | 2109 | 843 |
| D79205_at | Human mRNA ribosomal protein "L39" complete cds | 1639 | 2212 | 1743 | 1565 |
| X51345_at | Human jun-B mRNA for JUN-B protein | 1446 | 160 | 330 | 721 |
| D87735_at | Human mRNA for ribosomal protein "L14," complete cds | 1439 | 1998 | 1506 | 1306 |
| X57959_at | H. sapiens mRNA for ribosomal protein L7 | 1426 | 1798 | 1880 | 508 |
| HG384-HT386_at | Ribosomal Protein L26 | 1409 | 2496 | 1347 | 923 |

TABLE 1-continued

| Gene name<br>Structural proteins | Description | Con.<br>Tissue<br>Bladder<br>Wall | #733-2<br>$T_1$ gII | #733-1<br>$T_2$ gIII | #879-1<br>$T_2$ gIV |
|---|---|---|---|---|---|
| L11568_at | *Homo sapiens* ribosomal protein L18 (RPL18) "mRNA" complete cds | 1399 | 1876 | 1204 | 1144 |
| HG4542-HT4947_at | Ribosomal Protein L10 | 1378 | 3325 | 1729 | 1566 |
| L26247_at | *Homo sapiens* su1so1 "mRNA," complete cds | 1375 | 1912 | 1521 | 1099 |
| X52966_at | Human mRNA for ribosomal protein L35a | 1361 | 1280 | 910 | 1415 |
| Proteins involved in posttransitional modification | | | | | |
| Z23090_at | *H. sapiens* mRNA for 28 xDa heat shock protein | 9509 | 20 | 939 | 5099 |
| S79522_at | ubiquitin carboxyl extension protein "human," "mRNA," 540 nt] | 3161 | 8899 | 5541 | 2883 |
| U12404_at | Human Csa-19 "mRNA" complete cds | 2522 | 2390 | 1894 | 1684 |
| X68277_at | *H. sapiens* CL 100 mRNA for protein tyrosine phosphatase | 1972 | 71 | 165 | 343 |
| X52851_rna1_at | Human cyclophilin gene for cytophilin (EC 5.2.1 8) | 1727 | 1798 | 2284 | 1278 |
| Cell membrane protiens | | | | | |
| D00017_at | Human lipocortin II mRNA | 2387 | 1068 | 1191 | 2553 |
| M33580_at | Human 26-kDa cell surface protein TAPA-1 "mRNA," complete cds | 1423 | 1013 | 1244 | 1902 |
| Secreted proteins/hormones/growth factor related proteins | | | | | |
| M17733_at | Human thymosin beta-4 "mRNA," complete cds | 2774 | 3792 | 4130 | 6117 |
| Proteins related to immunology | | | | | |
| M63438_s_at | "Human Ig rearranged chain""mRNA.""V-J-C region and complete cds" | 4579 | 20 | 5638 | 9005 |
| J00105_s_at | "Human beta-2-microglobulin gene""mRNA,""3' end" | 3664 | 2764 | 6031 | 2841 |
| M87789_s_at | "Human (hybridoma H210) anti-hepatits A IgG variable""region,""constant" "region," complementan | 3447 | 20 | 3373 | 11685 |
| M24194_at | Human MHC protein homologous to chicken B complex protein "mRNA," complete cds | 3378 | 2880 | 1904 | 2591 |
| D49624_s_at | Human HLA-B null allele mRNA | 2821 | 1098 | 1449 | 2381 |
| X00274_at | Human gene for HLA-DR alpha heavy chain a class II antigen (immune response gene) of the major) | 2780 | 429 | 2264 | 3208 |
| S82297_at | "beta 2-microglobulin (11bo deleted between nucleotides 98–99)""(human,""colon cancer cell line"H | 2360 | 1125 | 3442 | 3974 |
| M34516_at | Human omega light chain protein 14.1(Ig lambda chain related) gene | 2235 | 137 | 1422 | 9736 |
| M84528_at | Human adipsin/complement factor D "mRNA," complete cds | 1875 | 20 | 145 | 544 |
| S71043_rna1_s_at | Ig alpha 2-immunoglobulin A heavy chain allotype 2 (constant "region," germ , line) "[human," peripher | 1473 | 54 | 723 | 4064 |
| M57710_at | Human IgE-binding protein (epsilon-BP) "mRNA," complete cds | 1449 | 1184 | 1215 | 1058 |
| Nucleoproteins | | | | | |
| M84711_at | Human v-fos transformation effector protein "(Fla-1)," mRNA complete cds | 3851 | 3581 | 2842 | 3234 |
| U43901_rna1_s_at | Human 37 kD laminin receptor precursor/p40 ribosome assocaited protein "gene," complete cds | 2812 | 6390 | 5353 | 1838 |
| D13413_rna1_s_at | Human mRNA for tumor-associated 120 kDa nuclear protein "p120," partial cds(carboxyl terminus) | 2851 | 4033 | 5077 | 1310 |
| M32405_at | Human homologue of rat insulinoma gene "(rig)," exons 4-Jan | 2005 | 1973 | 1418 | 2298 |
| M11353_at | Human H3.3 histone class C "mRNA," complete cds | 1697 | 1683 | 3281 | 1581 |
| M23613_at | Human nucleophoamin "mRNA," complete cds | 1448 | 1117 | 1338 | 1175 |
| J03827_at | Y box binding protein-1 (YB-1) mRNA | 1439 | 1139 | 1225 | 1493 |
| Mitochondrial proteins | | | | | |
| M70759_at | *H. sapiens* mitochondrial 16S rRNA gene (partial)/gb=Z70759/type=RNA | 7648 | 3970 | 5895 | 5823 |
| X15341_at | Human COX Via-L mRNA for cytochrome c oxidase liver subunit Via (EC 1.9.3.1) | 1338 | 1580 | 1649 | 1405 |
| Other proteins | | | | | |
| M28311_s_at | Human cyctic fibrosis antigen mRNA complete cds | 15733 | 1713 | 381 | 1298 |
| M66757_s_at | S100 Calcium binding protein A7 | 10368 | 20 | 20 | 20 |
| L05187_at | "*Homo sapiens* small proline-rich protein 1 (SPRR1A)"gene," complete cds" | 6544 | 64 | 104 | 152 |
| L10343_at | Huma alafin "gene," complete cds | 5388 | 20 | 39 | 310 |
| D88422_at | Human DNA for crystallin A | 5167 | 52 | 114 | 171 |
| HG3214-HT3391_at | Metallopanstimulin 1 | 4966 | 9358 | 4730 | 3894 |
| M21005_at | Human migration inhibitory factor-related protein 8 (MRP8) "gene," complete cds | 4930 | 20 | 20 | 319 |
| X16064_at | Human mRNA for translationally controlled tumor protein | 4572 | 3538 | 3980 | 3366 |
| L05188_f_at | "*Homo sapiens* small proline-rich protein 2 (SPRR28) "gene," complete cds" | 4465 | 59 | 20 | 20 |
| M19888_at | "Human small proline rich protein (sprl) "mRNA," clone 128" | 4441 | 20 | 20 | 20 |
| X53085_f_at | Human SPR2-1 gene for small proline rich protein (exon 2) | 4285 | 117 | 33 | 40 |
| X98482_r_at | *H. sapiens* TNNT2 gene exon 11/gb=X98482/type=DNA/annot=mRNA | 3885 | 3603 | 2730 | 1274 |
| HG3549-HT3751_at | Wilm'S Tumor-Related protein | 3843 | 3170 | 2728 | 4068 |
| M20030_f_at | "Human small proline rich protein (sprtl) "mRNA," clone 930" | 3809 | 20 | 28 | 20 |
| X76223_s_at | *H. sapiens* MAL gene exon 1 (and joined CDS). | 3490 | 20 | 20 | 20 |
| X05908_at | Human mRNA for lipocotin | 3217 | 182 | 283 | 333 |
| M1147_at | Human feritin L chain "mRNA," complete cds | 3172 | 7843 | 6176 | 4656 |
| X57348_s_at | *H. sapiens* mRNA (clone 9112) | 3031 | 20 | 52 | 384 |
| V00594_s_at | Human mRNA for metallothione from cadmium-treated cells | 2805 | 1553 | 1408 | 2414 |
| U08155_s_at | Human chromosome Ig substomeric sequence D1S553./gb=U06155/type=DNA/annot=CDS | 2575 | 7538 | 6245 | 1682 |
| M94856_at | Human fatty acid binding protein homologue (PA-FABP) "mRNA," complete cds | 2525 | 166 | 375 | 332 |
| Y07755_at | *H. sapiens* S100A2 "gene," exon "1," 2 and 3 | 2378 | 27 | 47 | 2971 |
| U78027_rna3_at | *Homo sapiens* Bruton's tyrosine kinase (BTK), alpha-D-galactosidase A (GLA), L44-like ribosomal prc | 2156 | 3154 | 2439 | 1379 |
| D38583_at | Human mRNA for "calgizzanin," complete cds | 2101 | 1427 | 1223 | 1336 |
| X57351_s_at | Human 1-8D gene from interferon-inducible gene family | 1945 | 1342 | 2890 | 2932 |
| M38591_at | *Homo sapiens* cellular ligand of annexin II(p11) "mRNA," complete cds | 1819 | 2870 | 1179 | 825 |

TABLE 1-continued

| Gene name Structural proteins | Description | Con. Tissue Bladder Wall | #733-2 $T_1$ gII | #733-1 $T_2$ gIII | #879-1 $T_2$ gIV |
|---|---|---|---|---|---|
| L20941_at | Human ferritin heavy chain "mRNA," complete cds | 1771 | 2131 | 1519 | 1778 |
| M97815_at | Human retinoic acid-binding protein II(CRABP-II) gene | 1655 | 123 | 245 | 549 |
| X53296_s_at | H. sapiens mRNA for IRAP | 1652 | 79 | 66 | 62 |
| X04470_s_at | Human mRNA for antileukoprotease (ALP) from cervix uteri | 1525 | 20 | 20 | 451 |
| X67951_at | H. sapiens mRNA for proliferation-associated gene (pag) | 1472 | 1380 | 1439 | 1450 |
| HG4069-HT4339_s_at | Monocyte Chemotactic Protein 1 | 1416 | 213 | 360 | 149 |
| V07909_at | H. sapiens mRNA for Progression Associated Protein | 1399 | 21 | 26 | 50 |
| J04152_rna1_s_at | M1S1 gene extracted from Human gastriointestinal tumor-associated antigen GA733-1 protein "gene." | 1311 | 325 | 557 | 911 |
| S81914_at | IEX-1=radiation-inducible immediate-early gene "(human," "placents," "mRNA "Pertail," 1223 nt) | 1310 | 188 | 190 | 202 |

TABLE 2A

Bladder wall compared to single cell solutions and biopsies of tumors

| | | Biopsy | Single cell solutions | | | | | Biopsies | | |
|---|---|---|---|---|---|---|---|---|---|---|
| Gene name | Gene product | Bladder wall | Ta GrI | Ta GrII | Ta GrIII | T1 GrIII | T2 GrIII | T1 GrIII | T2 GrIII | T2 GrIV |
| L05188_f_at | Homo sapiens small proline-rich protein 2 (SPRR2B) "gene," complete cds | 4465 | — | — | — | — | — | — | — | — |
| L10343_at | Huma elafin "gene," complete cds | 5388 | — | — | — | — | — | — | — | 310 |
| L42583_f_at | Homo sapiens keratin 6 isoform K6a (KRT6A) gene | 4939 | 384 | 348 | — | 426 | 389 | — | — | 388 |
| L42601_f_at | Homo sapiens keratin 6 isoform K6c (KRT6C) gene | 5155 | 475 | 391 | — | 544 | — | — | — | 389 |
| M19888_at | Human small proline rich protein (sprI) "mRNA," clone 128 | 4441 | — | 160 | — | — | — | — | — | — |
| M2030_f_at | Human small proline rich protein (sprII) "mRNA," clone 930 | 3809 | — | — | — | — | — | — | — | — |
| M21005_at | Human migration inhibitory factor-related protein 8(MRP8) "gene." complete cds | 4930 | — | — | — | — | — | — | — | 319 |
| M21389_at | Human keratin type II (58 kD) "mRNA," complete cds | 1572 | — | — | — | — | — | — | — | 611 |
| S81914_at | IEX-1=radiation-inducible immediate early gene | 1310 | — | — | — | — | — | 188 | — | — |
| V01516_f_at | Human messenger fragment encoding cytoskeletal keratin (type II). | 4779 | 452 | 300 | 346 | 478 | — | — | — | 516 |
| X07695_at | Human mRNA for cytokeratin 4 C-terminal region | 7458 | — | — | — | — | — | — | 78 | — |
| X53065_f_at | Human SPR2-1 gene for small proline rich protein (exon 2) | 4285 | — | — | 178 | — | — | — | — | — |
| X67683_at | H. sapiens mRNA for keratin 4/gb=X67683/ntype=RNA | 2126 | — | 223 | — | 154 | — | 126 | 160 | 193 |
| X68277_at | H. sapiens CL 100 mRNA for protein tyrosine phosphatase | 1972 | 87 | 78 | 81 | 119 | — | 71 | 165 | 343 |
| Y07909_at | H. sapiens mRNA for Progression Associated Protein | 1399 | — | 76 | — | 114 | — | — | — | 71 |

TABLE 2B

Expression of genes related to bladder wall

| | | | Single cell solutions | | | | | Biopsies | | | |
|---|---|---|---|---|---|---|---|---|---|---|---|
| Gene name | Gene product | Bladder wall | Ta GrI | Ta GrII | Ta GrIII | T1 GrIII | T2 GrIII | Mean | T1 GrIII | T2 GrIII | T2 GrIV | Mean |
| Z19554_s_at | H. sapiens vimentin gene | 1186 | — | — | — | 422 | 204 | 125 | 334 | 853 | 674 | 620 |
| J02854_at | Human 20-kDa myosin light chain(MLC-2) | 412 | — | — | — | — | — | 0 | — | — | 615 | 205 |
| M21812_at | Human (clone PWHLC2-24) myosin light chain 2 | 175 | — | 433 | — | — | 690 | 225 | 374 | 427 | 410 | 404 |
| U48959_at | Human myosin light chain kinase (MLCK) | 621 | — | — | — | — | — | 0 | — | — | 617 | 206 |
| X05276_at | Human mRNA for fibroblast tropomyosin TM30 (pl) | 642 | 261 | 313 | 294 | 245 | 139 | 250 | 178 | 283 | 214 | 225 |
| Z24727_at | H. sapiens tropomyosin isoform | 464 | 55 | 76 | 98 | 56 | 59 | 69 | 365 | 468 | 607 | 480 |
| M12125_at | "Human fibroblast muscle-type tropomyosin" | 586 | — | — | — | — | — | 0 | — | — | 426 | 142 |
| M19267_s_at | "Human tropomyosin" | 284 | — | 90 | — | 207 | — | 59 | 492 | 313 | 198 | 334 |
| M6391_rna1_at | Human desmin gene, complete cds. | 392 | — | 192 | — | — | 38 | — | — | 905 | 302 | |
| M26576_cds2_at | Human alpha-1 collagen type IV gene, exon 52. | 207 | — | — | — | — | 0 | — | — | 290 | 97 | |
| | Sum of expressed units | 4969 | 316 | 1104 | 392 | 930 | 1092 | 767 | 1743 | 2344 | 4956 | 3014 |
| X74929_s_at | H. sapiens KRT8 mRNA for keratin 8 | — | 5006 | 2266 | 3494 | 2434 | 2450 | 3130 | 2074 | 1423 | 390 | 1296 |

TABLE 3

Number of genes, out of 3400 genes examined, that are expressed as in the tumor-pool to which the tumor belongs, or altered as in a tumor pool of higher or lower stage or grade

| Clinical data on tumor | 5th superficial recurrence Grade II | First invasive tumor Grade III | Primary tumor, large solid muscle invasive Grade IV |
|---|---|---|---|
| Expression like tumor pool | 770 genes | 516 genes | 625 genes |
| Unique to tumor | 58 | 75 | 93 |
| Increased expression similar to invasive Grade IV pool | 24 | 47 | — |
| Decreased expression similar to invasive Grade IV pool | 19 | 22 | — |
| Increased or decreased similar to Grade II | — | 45 | 33 |

The lines in bold list genes that signal a higher stage or grade.

TABLE 4A

Gene expression that signal a higher grade or stage

| Gene name | Gene product | TaGrII Pool | Ta Single Tumor | T2GrIV Pool | Deviation* | Bladder wall | 20% Wall** | 50% Wall |
|---|---|---|---|---|---|---|---|---|
| HG2147-HT2217r_at | Mucin "3," intestinal (Gb:M56-405) | 0 | 330 | 541 | On | 0 | 0 | 0 |
| HG880-HT880_at | Human mucin 6, gastric (single repeat clone)-human (fragment), partial CDS | 0 | 425 | 493 | On | 0 | 0 | 0 |
| Y00787_s_at | Human mRNA for MDNCF (monocyte-derived neutrophil chemotactic factor) | 0 | 327 | 393 | On | 224 | 44.8 | 112 |
| M21388_r_at | Human unproductively rearranged Ig mu-chain mRNA V-region (VD), 5′ end, clone mu-3A1A | 0 | 284 | 215 | On | 0 | 0 | 0 |
| X83492_at | H. sapiens mRNA for Fas/Apo-1 (clone pCRTM11-Fasdelta(4,7)) | 0 | 236 | 367 | On | 0 | 0 | 0 |
| X07696_at | Human mRNA for cytokeratin 15 | 328 | 0 | 0 | Off | 0 | 282.4 | 164 |
| J05036_s_at | Human cathepsin E "mRNA," complete cds | 1145 | 302 | 0 | Decreased | 0 | 916 | 572.5 |
| M84424_at | Human cathepsin E (CTSE) gene | 413 | 98 | 0 | Decreased | 0 | 330.4 | 206.5 |
| U20734_s_at | Human transcription factor junB (junB) "gene," 5′ region and complete cds | 1250 | 324 | 0 | Decreased | 1069 | 1213.8 | 1159.5 |
| X59798_at | Human PRAD1 mRNA for cyclin | 436 | 0 | 0 | Off | 63 | 361.4 | 249.5 |
| L35263_at | Human CSaids binding protein (CSBP1) "mRNA," complete cds | 162 | 0 | 0 | Off | 0 | 129.6 | 81 |
| M17863_s_at | Human preproinsulin-like growth factor II (IGF-II) variant "mRNA," complete cds | 1663 | 489 | 0 | Decreased | 0 | 1330.4 | 831.5 |
| M62403_s_at | Human insulin-like growth factor binding protein 4 (IGFBP4) "mRNA," complete cds | 968 | 245 | 0 | Decreased | 337 | 841.8 | 652.5 |
| M34376_s_at | Homo sapiens (clone lambda MSP131) beta-microseminoprotein (MSP) gene | 280 | 0 | 0 | Off | 0 | 224 | 140 |
| U22178_s_at | Human prostatic secretory protein 57 "mRNA," complete cds. /gb=U22178/ntype=RNA | 89 | 0 | 0 | Off | 0 | 71.2 | 44.5 |
| U69263_at | Human matrillin-2 precursor "mRNA," complete cds | 116 | 0 | 0 | Off | 152 | 123.2 | 134 |
| U72649_at | Human BTG2 (BTG2) "mRNA," complete cds | 886 | 274 | 289 | Decreased | 244 | 757.6 | 565 |
| U81006_at | Human p76 "mRNA," complete cds | 193 | 0 | 0 | Off | 76 | 169.6 | 134.5 |
| U90916_at | Human clone 23815 mRNA sequence | 250 | 0 | 0 | Off | 31 | 206.2 | 140.5 |
| X63578_rna1_at | H. sapiens gene for parvalbumin. | 176 | 0 | 0 | Off | 0 | 140.8 | 88 |
| X76180_at | H. sapiens mRNA for lung amiloride sensitive Na+ channel | 263 | 0 | 0 | Off | 255 | 253.4 | 254 |
| X87159_at | H. sapiens mRNA for beta subunit of epithelial amiloride-sensitive sodium channel | 188 | 0 | 0 | Off | 0 | 150.4 | 94 |
| Y00264_at | Human mRNA for amyloid A4 precursor of Alzheimer's disease | 295 | 0 | 0 | Off | 183 | 272.6 | 239 |
| Z79693_s_at | H. sapiens mRNA for protein-tyrosine phosphatase NC-PTPCOM1 | 196 | 0 | 0 | Off | 0 | 156.8 | 98 |

Only genes scored as present are shown.
*Deviation describes aberration from pool.
**20% and 50% describes expected units of expression if tumor pool was added 20% or 50% bladder wall components.
Genes in bold do not need interrogation of bladder wall contribution, Off, genes that are turned off. On, genes that are turned on.

TABLE 4B

| Gene Name | Gene Product | T2GrIII Pool | 2GrIII Single tumo | T2GrIV Pool | Grade III po | Bladder wall | 20% Wall** | 50% Wall |
|---|---|---|---|---|---|---|---|---|
| X73501_at | H. sapiens gene for cytokeratin 20 | 0 | 152 | 102 | On | 0 | 0 | 0 |
| X03689_s_at | Human mRNA fragment for elongation factor TU (N-terminus). /gb=X03689/ntype=RNA | 0 | 1845 | 2092 | On | 4233 | 846.6 | 2116.5 |
| X04347_s_at | Human liver mRNA fragment DNA binding protein UPI homologus (C-terminus) | 0 | 1324 | 836 | On | 911 | 182.2 | 455.6 |
| M21142_cds2_s_at | guanine nucleotide-binding protein G-s-alpha-3 gene extracted from Human guanine nucleotide-binding protein alpha-subunit gene (G-s-alpha) | 0 | 1106 | 839 | On | 782 | 156.4 | 391 |
| J00105_s_at | Human beta-2 microglobulin gene "mRNA," 3' end | 1137 | 5199 | 4892 | Increased | 3684 | 1642.4 | 2400.5 |
| S82297_at | beta 2-microglobulin (111bp deleted between nucleotides 98-99) "{human}," colon cancer cell line "HCT"; mRNA "Mutant," 416 nt] | 618 | 4908 | 3909 | Increased | 2360 | 966.4 | 1489 |
| M34516_at | Human omega light chain protein 14.1 (Ig lambda chain related) gene | 0 | 4689 | 6258 | On | 2235 | 447 | 1117.5 |
| L02326_f_at | Homo sapiens (clone Hu lambda-17) lambda-like "gene," complete cds | 0 | 373 | 734 | On | 0 | 0 | 0 |
| M63438_s_at | Human Ig rearranged gamma chain "mRNA," V-J-C region and complete cds | 0 | 1402 | 7075 | On | 4579 | 915.8 | 2289.5 |
| M87789_s_at | Human (hybridoma H210) anti-hepatitis A IgG variable "region, " constant "region," complementary-determining regions "mRNA," complete cds | 0 | 2420 | 4769 | On | 3447 | 689.4 | 1723.5 |
| S71043_rna1_s_at | Ig alpha 2=immunoglobulin A heavy chain allotype 2 (constant "region," germ line) "[human,"peripheral blood "neutrophils," "Genomic," 1799 nt] | 0 | 1175 | 2609 | On | 1473 | 294.6 | 736.5 |
| M14483_rna1_s_at | PTMA gene extracted from Human prothymosin alpha "mRNA," comlete cds | 0 | 1410 | 948 | On | 641 | 128.2 | 320.5 |
| M16652_at | Human pancreatic elastase IIA mRNA, complete cds | 0 | 405 | 222 | On | 201 | 40.2 | 100.5 |
| M61832_s_at | Human S-adenosylhomocysteine hydrolase (AHCY) "mRNA," complete cds | 0 | 233 | 129 | On | 71 | 14.2 | 35.5 |
| M93651_at | Human set "gene," complete cds | 0 | 284 | 213 | On | 159 | 31.8 | 79.5 |
| Z12671_rna1_at | hnrnp a1 protein gene extracted from Human gene for heterogeneous nuclear ribonucleoprotein (hnRNP) core protein A1 | 0 | 716 | 384 | On | 694 | 118.8 | 297 |
| X15183_at | Human mRNA for 90-kDa heat-shock protein | 586 | 1891 | 1790 | Increased | 919 | 662.6 | 752.5 |
| Y-0614_at | H. sapiens mRNA for CRN1 protein | 0 | 171 | 135 | On | 72 | 14.4 | 36 |
| Z49148_s_at | H. sapiens mRNA for ribosomal protein L29 | 616 | 2589 | 1801 | Increased | 2303 | 953.4 | 1459.5 |
| Z48501_s_at | H. sapiens mRNA for polyadenylate binding protein II. /gb=Z48501/ntype=RNA | 560 | 1988 | 2633 | Increased | 1263 | 700.6 | 911.5 |
| HG3076-HT3238_s_at | Heterogeneous Nuclear Ribonucleoprotein "K," Alt. Splice 1 | 0 | 433 | 247 | On | 239 | 47.8 | 119.5 |
| M36430_s_at | Human transduction beta-1 subunit "mRNA," 3' end | 0 | 508 | 265 | On | 118 | 23.6 | 59 |
| HG417-HT417_s_at | Cathepsin B | 0 | 2797 | 1783 | On | 1172 | 234.4 | 586 |
| J02683_s_at | Human ADP/ATP carrier protein "mRNA," complete cds | 0 | 301 | 408 | On | 337 | 67.4 | 168.5 |
| J04046_at | Human calmodulin "mRNA," complete cds | 0 | 425 | 348 | On | 0 | 0 | 0 |
| M26311_s_at | Human cystic fibrosis antigen mRNA, complete cds | 0 | 2359 | 1413 | On | 15733 | 3146.6 | 7866.5 |
| X13546_rna1_at | Human HMG-17 gene for non-histone chromosomal protein HMG-17. | 208 | 740 | 1126 | Increased | 222 | 210.8 | 215 |
| X64229_at | H. sapiens dek mRNA | 0 | 198 | 268 | On | 50 | 10 | 25 |

TABLE 4B-continued

Gene expression that signal a higher grade or stage

| Gene Name | Gene Product | T2GrIII Pool | 2GrIII Single tumo | T2GrIV Pool | Grade III po | Bladder wall | 20% Wall** | 50% Wall |
|---|---|---|---|---|---|---|---|---|
| X67325_at | *H. sapiens* p27 mRNA | 0 | 368 | 893 | On | 0 | 0 | 0 |
| L00205_at | Human K6b (epidermal "keratin," type II) gene | 80 | 0 | 0 | Off | 154 | 94.8 | 117 |
| D10922_s_at | Human mRNA for FMLP-related receptor (HM63) | 495 | 0 | 0 | Off | 26 | 401.2 | 260.5 |
| D55643_s_at | Human spleen PABL (pseudoautosomal boundary-like sequence) "mRNA," clone Sp2./gb=D55643/ntype=RNA | 384 | 0 | 0 | Off | 0 | 291.2 | 182 |
| L11672_at | Human Kruppel related zinc finger protein (HTF10) "mRNA," complete cds | 3690 | 1770 | 1219 | Decreased | 370 | 3026 | 2030 |
| M19878_at | *Homo sapiens* calbindin 27 gene, exons 1 and 2, and Alu repet | 365 | 0 | 0 | Off | 0 | 292 | 182.5 |
| Z35402_rma1_s_at | *H. sapiens* gene encoding "E-cadherin," exon 3 and joined CDS | 762 | 236 | 242 | Decreased | 159 | 641.4 | 460.5 |
| M26665_at | Human histatin 2 (HIS2) mRNA, complete, cds | 210 | 0 | 0 | Off | 0 | 168 | 105 |
| M96233_s_—at | Human glutathione transferase class mu number 4 (GSTM4) "gene," complete cds | 12518 | 0 | 0 | Off | 0 | 10014.4 | 6259 |
| U31215_s_at | Human metabotropic glutamate receptor 1 alpha (mGluR1alpha) "mRNA," complete cds | 317 | 0 | 0 | Off | 0 | 263.8 | 158.6 |
| U33838_at | Human NF-kappa-B p65delta3 "mRNA," spliced transcript lacking exons 6 and "7," partial cds./gb=U33838/ntype=RNA | 478 | 0 | 0 | Off | 57 | 393.8 | 267.5 |
| U79295_at | Human clone 23961 mRNA sequence | 164 | 0 | 0 | Off | 0 | 131.2 | 82 |
| U79304_at | Human clone 23909 "mRNA," partial cds. | 99 | 0 | 0 | Off | 0 | 79.2 | 49.5 |
| X79200_at | *H. sapiens* mRNA for SYT-SSX, synovial sarcoma translocation junction | 844 | 0 | 0 | Off | 0 | 675.2 | 422 |
| X80763_s_at | *H. sapiens* gene for 5-HT2c receptor | 689 | 0 | 0 | Off | 124 | 576 | 406.6 |
| H90846_at | *H. sapiens* mRNA for mixed lineage kinase 2 | 2099 | 801 | 604 | Decreased | 0 | 1679.2 | 1049.5 |
| HG880-HT880_at | Human mucin 6, gastric (single repeat clone) -human (fragment), partial CDS | 1793 | 0 | 493 | decreased | 0 | 1434.4 | 896.5 |
| L06797_s_at | Human (clone L5) orphan G protein-coupled receptor "mRNA," complete cds | 589 | 0 | 150 | Decreased | 109 | 493 | 349 |
| M27749_r_at | Human immunoglobulin-related 14.1 protein "mRNA," complete cds | 1119 | 0 | 0 | Off | 0 | 895.2 | 559.6 |
| M29336_at | Human MHC class II DO-alpha mRNA, partial cds | 1043 | 0 | 217 | Decreased | 0 | 234.4 | 521.5 |
| X66087_at | *H. sapiens a-myb mRNA* | 293 | 0 | 0 | Off | 0 | 234.4 | 146.5 |
| X95632_s_at | *H. sapiens* mRNA for Arg protein tyrosine kinases-binding protein | 261 | 0 | 0 | Off | 0 | 208.8 | 130.5 |

Only genes scored as present are shown.
*Deviation describes aberration from pool.
**20% and 50% describes expected units of expression if tumor pool was added 20% or 50% bladder wall components. Genes in bold do not interrogation of balbder wall contribution. Off, genes that are turned off. On, genes that are turned on.

TABLE 5

| Expression pattern | | | | | >=3 fold ch. | >=5 fold ch. | >=7 fold ch. |
|---|---|---|---|---|---|---|---|
| N | ↑ | Ta | ↑ | T2-4 | 9 V | 0 | 0 |
| N | ↑ | Ta | → | T2-4 | 233 V | 76 | 34 |
| N | ↑ | Ta | ↓ | T2-4 | 164 V | 51 | 23 |
| N | → | Ta | ↑ | T2-4 | 612 V | 262 | 141 |
| N | → | Ta | → | T2-4 | 5407 V | 6455 | 6768 |
| N | → | Ta | ↓ | T2-4 | 264 V | 92 | 41 |
| N | ↓ | Ta | ↑ | T2-4 | 175 V | 49 | 20 |
| N | ↓ | Ta | → | T2-4 | 206 V | 87 | 45 |
| N | ↓ | Ta | ↓ | T2-4 | 2 V | 0 | 0 |

Connective tissue A

| Gene Name | Positiv | Negati | Pairs | Pairs U | Pairs I | Pos Fracti | Log Avg | PM E:MM E: | Pos/Neg | Avg Diff | Abs Call |
|---|---|---|---|---|---|---|---|---|---|---|---|
| hum_alu_at | 68 | 0 | 69 | 69 | 67 | 0.99 | 6.27 | 4 | 0 Inf | 10744 | P |
| L06499_at | 19 | 0 | 20 | 20 | 18 | 0.95 | 7.03 | 3 | 0 Inf | 6064 | P |
| AFFX-HUMGAPDH/M33197_3_ | 18 | 0 | 20 | 20 | 18 | 0.90 | 5.85 | 1 | 0 Inf | 5588 | P |
| L10343_at | 19 | 0 | 20 | 20 | 18 | 0.95 | 6.38 | 2 | 0 Inf | 5388 | P |
| D23660_at | 19 | 0 | 20 | 20 | 18 | 0.95 | 7.89 | 3 | 0 Inf | 5345 | P |
| AFFX-HSAC07/X00351_M_at | 20 | 0 | 20 | 20 | 18 | 1.00 | 6.41 | 0 | 0 Inf | 5185 | P |
| D88422_at | 18 | 0 | 20 | 20 | 18 | 0.90 | 7.09 | 5 | 0 Inf | 5167 | P |
| HG3214-HT3391_at | 19 | 0 | 20 | 20 | 18 | 0.95 | 6.77 | 3 | 0 Inf | 4966 | P |
| M2100_0at | 10 | 3 | 20 | 20 | 18 | 0.50 | 1.87 | 0 | 0 3.3 | 4930 | P |
| HG2873-HT3017_at | 19 | 0 | 20 | 20 | 18 | 0.95 | 7.24 | 4 | 0 Inf | 4372 | P |
| HG3364-HT3541_at | 19 | 0 | 20 | 20 | 18 | 0.95 | 7.09 | 4 | 0 Inf | 4242 | P |
| HG3549-HT3751_at | 20 | 0 | 20 | 20 | 18 | 1.00 | 6.49 | 2 | 0 Inf | 3843 | P |
| M17885_at | 20 | 0 | 20 | 20 | 18 | 1.00 | 6.88 | 2 | 0 Inf | 3690 | P |
| AFFX-HSAC07/X00351_5_at | 17 | 0 | 20 | 20 | 18 | 0.85 | 5.46 | 0 | 0 Inf | 3657 | P |
| HG1800-HT1823_at | 18 | 0 | 20 | 20 | 18 | 0.90 | 4.94 | 1 | 0 Inf | 3582 | P |
| M17886_at | 17 | 1 | 20 | 20 | 18 | 0.85 | 4.70 | 0 | 0 17.0 | 3488 | P |
| AFFX-HUMGAPDH/M33197_M_ | 18 | 0 | 20 | 20 | 18 | 0.90 | 5.29 | 0 | 0 Inf | 3413 | P |
| M18000_at | 20 | 0 | 20 | 20 | 18 | 1.00 | 7.06 | 4 | 0 Inf | 3315 | P |
| M13934_cds2_at | 17 | 0 | 20 | 20 | 18 | 0.85 | 5.00 | 1 | 0 Inf | 3281 | P |
| AFFX-HSAC07/X00351_3_at | 18 | 1 | 20 | 20 | 18 | 0.90 | 5.15 | 0 | 0 18.0 | 3211 | P |
| M11147_at | 17 | 0 | 20 | 20 | 18 | 0.85 | 6.32 | 2 | 0 Inf | 3172 | P |
| L06505_at | 14 | 0 | 20 | 20 | 18 | 0.70 | 4.09 | 0 | 0 Inf | 3024 | P |
| AFFX-CreX-3_at | 20 | 0 | 20 | 20 | 17 | 1.00 | 6.01 | 1 | 0 Inf | 3008 | P |
| M17733_at | 18 | 1 | 20 | 20 | 18 | 0.90 | 6.09 | 1 | 0 18.0 | 2774 | P |
| D78361_at | 17 | 1 | 20 | 20 | 18 | 0.85 | 4.91 | 0 | 0 17.0 | 2518 | P |
| L38941_at | 20 | 0 | 20 | 20 | 18 | 1.00 | 6.50 | 1 | 0 Inf | 2460 | P |
| D00D17_at | 18 | 0 | 20 | 20 | 18 | 0.90 | 4.24 | 0 | 0 Inf | 2387 | P |
| AFFX-CreX-5_at | 19 | 0 | 20 | 20 | 18 | 0.95 | 5.22 | 0 | 0 Inf | 2382 | P |
| D14530_at | 19 | 0 | 20 | 20 | 18 | 0.95 | 6.56 | 2 | 0 Inf | 2193 | P |
| HG821-HT821_at | 18 | 0 | 20 | 20 | 18 | 0.90 | 5.13 | 0 | 0 Inf | 2159 | P |
| D38583_at | 17 | 2 | 20 | 20 | 18 | 0.85 | 4.82 | 0 | 0 8.5 | 2101 | P |
| HG33-HT33_at | 18 | 0 | 20 | 20 | 18 | 0.90 | 5.87 | 1 | 0 Inf | 2077 | P |
| L19527_at | 19 | 0 | 20 | 20 | 18 | 0.95 | 4.69 | 1 | 0 Inf | 1991 | P |
| HG4319-HT4589_at | 18 | 0 | 20 | 20 | 18 | 0.90 | 5.82 | 0 | 0 Inf | 1960 | P |
| AFFX-HUMGAPDH/M33197_5_ | 17 | 0 | 20 | 20 | 17 | 0.85 | 5.57 | 2 | 0 Inf | 1939 | P |
| HG613-HT613_at | 18 | 0 | 20 | 20 | 17 | 0.90 | 5.59 | 1 | 0 Inf | 1873 | P |
| L20941_at | 13 | 1 | 20 | 20 | 18 | 0.65 | 3.44 | 2 | 0 13.0 | 1771 | P |
| M11353_at | 15 | 2 | 20 | 20 | 18 | 0.75 | 5.61 | 4 | 0 7.5 | 1697 | P |
| D79205_at | 20 | 0 | 20 | 20 | 18 | 1.00 | 6.59 | 1 | 0 Inf | 1639 | P |
| AFFX-BioDn-3_at | 12 | 2 | 20 | 20 | 17 | 0.60 | 2.53 | 0 | 0 6.0 | 1598 | P |
| M21389_at | 15 | 0 | 20 | 20 | 18 | 0.75 | 3.40 | 0 | 0 Inf | 1572 | P |
| D87735_at | 17 | 0 | 20 | 20 | 18 | 0.85 | 4.85 | 1 | 0 Inf | 1439 | P |
| J03827_at | 14 | 1 | 20 | 20 | 18 | 0.70 | 3.89 | 2 | 0 14.0 | 1439 | P |
| HG384-HT384_at | 12 | 0 | 20 | 20 | 18 | 0.60 | 4.02 | 3 | 0 Inf | 1409 | P |
| L11566_at | 15 | 0 | 20 | 20 | 18 | 0.75 | 3.76 | 0 | 0 Inf | 1399 | P |
| HG4542-HT4947_at | 12 | 1 | 20 | 20 | 18 | 0.60 | 4.06 | 0 | 0 12.0 | 1378 | P |
| L26247_at | 18 | 1 | 20 | 20 | 18 | 0.90 | 5.33 | 2 | 0 18.0 | 1375 | P |
| D00654_at | 19 | 0 | 20 | 20 | 18 | 0.95 | 4.77 | 0 | 0 Inf | 1245 | P |
| J00124_at | 15 | 1 | 20 | 20 | 18 | 0.75 | 3.91 | 1 | 0 15.0 | 1210 | P |
| D45370_at | 14 | 1 | 20 | 20 | 17 | 0.70 | 2.56 | 0 | 0 14.0 | 1127 | P |
| HG2279-HT2375_at | 13 | 0 | 20 | 20 | 18 | 0.65 | 3.07 | 0 | 0 Inf | 1112 | P |
| M19283_at | 17 | 2 | 20 | 20 | 18 | 0.85 | 3.74 | 2 | 1 8.5 | 1086 | P |
| HG311-HT311_at | 18 | 0 | 20 | 20 | 17 | 0.90 | 5.26 | 1 | 0 Inf | 1067 | P |
| M13903_at | 13 | 0 | 20 | 20 | 18 | 0.65 | 2.57 | 0 | 0 Inf | 1000 | P |
| D14710_at | 13 | 0 | 20 | 20 | 18 | 0.65 | 2.65 | 0 | 0 Inf | 980 | P |
| HG2788-HT2896_at | 16 | 0 | 20 | 20 | 18 | 0.80 | 3.13 | 0 | 0 Inf | 973 | P |

-continued

Connective tissue A

| Gene Name | Positiv | Negati | Pairs | Pairs U | Pairs I | Pos Fracti | Log Avg | PM E:MM E: | Pos/Neg | Avg Diff | Abs Call |
|---|---|---|---|---|---|---|---|---|---|---|---|
| AC002115_cdsl_at | 11 | 0 | 20 | 20 | 18 | 0.55 | 2.71 | 0 | 0 Inf | 941 | P |
| D85429_at | 12 | 0 | 20 | 20 | 18 | 0.60 | 3.21 | 0 | 0 Inf | 917 | P |
| J03592_at | 16 | 0 | 20 | 20 | 18 | 0.80 | 3.50 | 0 | 0 Inf | 905 | P |
| D50840_at | 19 | 0 | 20 | 20 | 18 | 0.95 | 5.59 | 4 | 0 Inf | 851 | P |
| D26068_at | 16 | 1 | 20 | 20 | 18 | 0.80 | 3.30 | 0 | 1 16.0 | 821 | P |
| J03191_at | 18 | 1 | 20 | 20 | 18 | 0.90 | 4.33 | 0 | 0 18.0 | 799 | P |
| HG1153-HT11S3_at | 9 | 0 | 20 | 20 | 18 | 0.45 | 2.17 | 0 | 0 Inf | 772 | P |
| L24203_at | 13 | 2 | 20 | 20 | 18 | 0.65 | 3.15 | 1 | 0 6.5 | 762 | P |
| D13748_at | 11 | 0 | 20 | 20 | 17 | 0.55 | 2.04 | 0 | 0 Inf | 744 | P |
| M19483_at | 13 | 0 | 20 | 20 | 18 | 0.65 | 3.28 | 0 | 0 Inf | 683 | P |
| D16217_at | 12 | 0 | 20 | 20 | 18 | 0.60 | 2.35 | 0 | 0 Inf | 681 | P |
| M15661_at | 14 | 0 | 20 | 20 | 18 | 0.70 | 3.49 | 0 | 0 Inf | 653 | P |
| HG987-HT987_at | 13 | 2 | 20 | 20 | 18 | 0.65 | 3.18 | 1 | 0 6.5 | 640 | P |
| D21261_at | 7 | 0 | 20 | 20 | 18 | 0.35 | 1.71 | 0 | 0 Inf | 623 | P |
| AB001325_at | 9 | 0 | 20 | 20 | 18 | 0.45 | 1.47 | 0 | 0 Inf | 621 | P |
| L19686_rna1_at | 9 | 2 | 20 | 20 | 18 | 0.45 | 2.22 | 0 | 0 4.5 | 612 | P |
| D13118_at | 11 | 0 | 20 | 20 | 18 | 0.55 | 2.52 | 0 | 0 Inf | 611 | P |
| D29012_at | 11 | 1 | 20 | 20 | 18 | 0.55 | 2.02 | 0 | 0 11.0 | 600 | P |
| L09604_at | 10 | 0 | 20 | 20 | 18 | 0.50 | 2.05 | 0 | 0 Inf | 588 | P |
| M14200_rna1_at | 10 | 0 | 20 | 20 | 18 | 0.50 | 1.94 | 0 | 0 Inf | 584 | P |
| L08666_at | 14 | 0 | 20 | 20 | 18 | 0.70 | 3.59 | 2 | 0 Inf | 581 | P |
| D31883_at | 12 | 1 | 20 | 20 | 18 | 0.60 | 2.66 | 0 | 0 12.0 | 587 | P |
| D16562_at | 15 | 1 | 20 | 20 | 18 | 0.75 | 3.68 | 0 | 0 15.0 | 564 | P |
| D89667_at | 12 | 0 | 20 | 20 | 18 | 0.60 | 3.01 | 0 | 0 Inf | 561 | P |
| J04823_rna1_at | 13 | 1 | 20 | 20 | 18 | 0.65 | 2.14 | 0 | 0 13.0 | 559 | P |
| D85815_at | 11 | 2 | 20 | 20 | 18 | 0.55 | 2.36 | 0 | 0 5.5 | 558 | P |
| D11428_at | 12 | 1 | 20 | 20 | 18 | 0.60 | 2.29 | 0 | 0 12.0 | 557 | P |
| D28308_at | 12 | 1 | 20 | 20 | 18 | 0.60 | 1.97 | 0 | 0 12.0 | 554 | P |
| D28124_at | 10 | 0 | 20 | 20 | 18 | 0.50 | 1.83 | 0 | 0 Inf | 552 | P |
| J04456_at | 14 | 1 | 20 | 20 | 18 | 0.70 | 2.87 | 0 | 0 14.0 | 549 | P |
| J04173_at | 15 | 0 | 20 | 20 | 18 | 0.75 | 2.67 | 0 | 0 Inf | 546 | P |
| D87953_at | 16 | 0 | 20 | 20 | 18 | 0.80 | 3.30 | 0 | 0 Inf | 539 | P |
| L19437_at | 9 | 0 | 20 | 20 | 18 | 0.45 | 1.87 | 0 | 0 Inf | 532 | P |
| J04988_at | 11 | 0 | 20 | 20 | 18 | 0.55 | 2.79 | 0 | 0 Inf | 527 | P |
| L38486_at | 9 | 0 | 20 | 20 | 18 | 0.45 | 1.79 | 0 | 0 Inf | 505 | P |
| D87292_at | 9 | 0 | 20 | 20 | 18 | 0.45 | 1.46 | 0 | 0 Inf | 500 | P |
| J02874_at | 14 | 0 | 20 | 20 | 18 | 0.70 | 3.27 | 0 | 0 Inf | 499 | P |
| M19961_at | 10 | 1 | 20 | 20 | 18 | 0.50 | 2.07 | 1 | 0 10.0 | 485 | P |
| D00632_at | 14 | 0 | 20 | 20 | 18 | 0.70 | 2.36 | 0 | 0 Inf | 484 | P |
| D38047_at | 13 | 0 | 20 | 20 | 18 | 0.65 | 2.50 | 0 | 0 Inf | 481 | P |
| HG662-HT662_at | 13 | 3 | 20 | 20 | 18 | 0.65 | 2.27 | 0 | 0 4.3 | 475 | P |
| D14520_at | 9 | 1 | 20 | 20 | 18 | 0.45 | 1.54 | 0 | 0 9.0 | 457 | P |
| K02765_at | 13 | 1 | 20 | 20 | 18 | 0.65 | 1.66 | 0 | 0 13.0 | 455 | P |
| AFFX-BioDn-5_at | 11 | 1 | 20 | 20 | 18 | 0.55 | 1.60 | 0 | 0 11.0 | 450 | P |
| HG174-HT174_at | 11 | 0 | 20 | 20 | 18 | 0.55 | 2.00 | 0 | 0 Inf | 433 | P |
| M16279_at | 10 | 0 | 20 | 20 | 17 | 0.50 | 1.73 | 0 | 0 Inf | 418 | P |
| D23862_at | 9 | 0 | 20 | 20 | 18 | 0.45 | 1.53 | 0 | 0 Inf | 417 | P |
| J02854_at | 10 | 1 | 20 | 20 | 17 | 0.50 | 2.07 | 0 | 0 10.0 | 412 | P |
| M18728_at | 13 | 3 | 20 | 20 | 18 | 0.65 | 2.45 | 1 | 0 4.3 | 412 | P |
| HG3494-HT3688_at | 8 | 1 | 20 | 20 | 17 | 0.40 | 1.35 | 0 | 0 8.0 | 410 | P |
| J04080_at | 13 | 1 | 20 | 20 | 18 | 0.65 | 3.09 | 0 | 0 13.0 | 407 | P |
| D38548_at | 7 | 0 | 20 | 20 | 18 | 0.35 | 1.52 | 0 | 0 Inf | 404 | P |
| D86479_at | 8 | 0 | 20 | 20 | 18 | 0.40 | 1.57 | 0 | 0 Inf | 404 | P |
| D31846_at | 8 | 1 | 20 | 20 | 18 | 0.40 | 1.35 | 0 | 0 8.0 | 402 | P |
| D63874_at | 9 | 0 | 20 | 20 | 18 | 0.45 | 2.26 | 0 | 0 Inf | 398 | P |
| D14812_at | 9 | 0 | 20 | 20 | 18 | 0.45 | 1.51 | 0 | 0 Inf | 396 | P |
| J03040_at | 8 | 0 | 20 | 20 | 18 | 0.40 | 2.06 | 0 | 0 Inf | 393 | P |
| AFFX-HSAC07/X00351_3_st | 12 | 0 | 20 | 20 | 17 | 0.60 | 2.80 | 0 | 0 Inf | 392 | P |
| L27943_at | 8 | 0 | 20 | 20 | 17 | 0.40 | 1.47 | 0 | 0 Inf | 392 | P |
| D30655_at | 13 | 3 | 20 | 20 | 18 | 0.65 | 3.06 | 0 | 0 4.3 | 391 | P |
| J02902_at | 7 | 1 | 20 | 20 | 18 | 0.35 | 1.95 | 0 | 0 7.0 | 391 | P |
| L12168_at | 10 | 0 | 20 | 20 | 18 | 0.50 | 2.54 | 0 | 0 Inf | 390 | P |
| L10284_at | 14 | 0 | 20 | 20 | 18 | 0.70 | 3.39 | 0 | 0 Inf | 388 | P |
| D26599_at | 10 | 1 | 20 | 20 | 18 | 0.50 | 1.87 | 0 | 0 10.0 | 387 | P |
| L76200_at | 11 | 1 | 20 | 20 | 18 | 0.55 | 1.89 | 0 | 0 11.0 | 384 | P |
| J03459_at | 9 | 3 | 20 | 20 | 18 | 0.45 | 1.61 | 1 | 0 3.0 | 381 | P |
| D90209_at | 14 | 0 | 20 | 20 | 17 | 0.70 | 3.34 | 0 | 0 Inf | 380 | P |
| D25274_at | 14 | 2 | 20 | 20 | 17 | 0.70 | 2.26 | 0 | 0 7.0 | 378 | P |
| D26598_at | 10 | 0 | 20 | 20 | 18 | 0.50 | 1.86 | 0 | 0 Inf | 359 | P |
| L19605_at | 10 | 0 | 20 | 20 | 17 | 0.50 | 1.66 | 0 | 0 Inf | 336 | P |
| AFFX-BioC-5_at | 10 | 1 | 20 | 20 | 18 | 0.50 | 1.64 | 0 | 0 10.0 | 333 | P |
| D78151_at | 10 | 0 | 20 | 20 | 18 | 0.50 | 1.81 | 0 | 0 Inf | 319 | P |
| AJ000480_at | 8 | 1 | 20 | 20 | 18 | 0.40 | 1.70 | 0 | 0 8.0 | 314 | P |
| D23673_at | 11 | 2 | 20 | 20 | 17 | 0.55 | 1.79 | 0 | 0 5.5 | 312 | P |
| L11370_at | 10 | 0 | 20 | 20 | 18 | 0.50 | 1.98 | 0 | 0 Inf | 311 | P |

-continued

Connective tissue A

| Gene Name | Positiv | Negati | Pairs | Pairs U | Pairs I | Pos Fracti | Log Avg | PM E:MM E: | Pos/Neg | Avg Diff | Abs Call |
|---|---|---|---|---|---|---|---|---|---|---|---|
| D00761_at | 10 | 0 | 20 | 20 | 18 | 0.50 | 1.77 | 0 | 0 Inf | 310 | P |
| L49169_at | 10 | 0 | 20 | 20 | 18 | 0.50 | 1.99 | 1 | 0 Inf | 306 | P |
| D83779_at | 9 | 1 | 20 | 20 | 17 | 0.45 | 1.49 | 1 | 0 9.0 | 304 | P |
| D28416_at | 7 | 1 | 20 | 20 | 18 | 0.35 | 2.07 | 1 | 0 7.0 | 301 | P |
| D25218_at | 13 | 2 | 20 | 20 | 18 | 0.65 | 2.88 | 2 | 0 6.5 | 300 | P |
| D45248_at | 8 | 0 | 20 | 20 | 18 | 0.40 | 1.62 | 0 | 0 Inf | 300 | P |
| J04611_at | 7 | 1 | 20 | 20 | 18 | 0.35 | 1.48 | 0 | 0 7.0 | 295 | P |
| D63475_at | 12 | 1 | 20 | 20 | 18 | 0.60 | 1.95 | 0 | 0 12.0 | 290 | P |
| L13391_at | 12 | 0 | 20 | 20 | 18 | 0.60 | 3.00 | 0 | 0 Inf | 288 | P |
| L25080_at | 11 | 0 | 20 | 20 | 18 | 0.55 | 1.47 | 0 | 0 Inf | 284 | P |
| HG1862-HT1897_at | 10 | 2 | 20 | 20 | 18 | 0.50 | 1.72 | 0 | 0 5.0 | 281 | P |
| AJ001421_at | 7 | 0 | 20 | 20 | 18 | 0.35 | 1.05 | 0 | 0 Inf | 276 | P |
| K03195_at | 14 | 1 | 20 | 20 | 18 | 0.70 | 3.33 | 3 | 0 14.0 | 274 | P |
| L07633_at | 12 | 1 | 20 | 20 | 17 | 0.60 | 2.38 | 0 | 0 12.0 | 270 | P |
| D38048_at | 10 | 0 | 20 | 20 | 18 | 0.50 | 2.40 | 0 | 0 Inf | 264 | P |
| L08246_at | 10 | 2 | 20 | 20 | 18 | 0.50 | 1.76 | 1 | 0 5.0 | 260 | P |
| AF005775_at | 9 | 0 | 20 | 20 | 18 | 0.45 | 1.64 | 0 | 0 Inf | 253 | P |
| D50310_at | 9 | 1 | 20 | 20 | 18 | 0.45 | 1.79 | 0 | 0 9.0 | 247 | P |
| HG1112-HT1112_at | 11 | 1 | 20 | 20 | 18 | 0.55 | 1.83 | 0 | 0 11.0 | 244 | P |
| L11285_at | 9 | 2 | 20 | 20 | 18 | 0.45 | 1.67 | 0 | 0 4.5 | 244 | P |
| D14689_at | 8 | 2 | 20 | 20 | 18 | 0.40 | 1.35 | 0 | 0 4.0 | 242 | P |
| D55654_at | 10 | 1 | 20 | 20 | 18 | 0.50 | 2.28 | 0 | 0 10.0 | 242 | P |
| D28423_at | 9 | 1 | 20 | 20 | 17 | 0.45 | 2.26 | 0 | 0 9.0 | 241 | P |
| D31765_at | 8 | 1 | 20 | 20 | 18 | 0.40 | 2.07 | 1 | 0 8.0 | 240 | P |
| HG2855-HT2995_at | 8 | 2 | 20 | 20 | 18 | 0.40 | 1.95 | 0 | 0 4.0 | 240 | P |
| M14058_at | 10 | 1 | 20 | 20 | 18 | 0.50 | 2.37 | 0 | 0 10.0 | 240 | P |
| D49400_at | 9 | 2 | 20 | 20 | 17 | 0.45 | 1.66 | 1 | 1 4.5 | 239 | P |
| D87258_at | 8 | 1 | 20 | 20 | 18 | 0.40 | 1.46 | 0 | 0 8.0 | 238 | P |
| D26129_at | 7 | 0 | 20 | 20 | 17 | 0.35 | 1.17 | 0 | 0 Inf | 237 | P |
| L32977_at | 13 | 1 | 20 | 20 | 18 | 0.65 | 2.73 | 0 | 0 13.0 | 237 | P |
| D31767_at | 8 | 2 | 20 | 20 | 17 | 0.40 | 1.33 | 0 | 0 4.0 | 236 | P |
| D61380_at | 10 | 2 | 20 | 20 | 18 | 0.50 | 1.67 | 0 | 0 5.0 | 231 | P |
| D13988_at | 10 | 0 | 20 | 20 | 18 | 0.50 | 1.33 | 0 | 0 Inf | 228 | P |
| AFFX-BioC-3_at | 7 | 0 | 20 | 20 | 18 | 0.35 | 1.42 | 0 | 0 Inf | 226 | P |
| L76191_at | 8 | 1 | 20 | 20 | 18 | 0.40 | 2.28 | 1 | 0 8.0 | 225 | P |
| D42123_at | 9 | 1 | 20 | 20 | 18 | 0.45 | 1.20 | 0 | 0 9.0 | 223 | P |
| D11094_at | 8 | 2 | 20 | 20 | 18 | 0.40 | 1.19 | 0 | 0 4.0 | 222 | P |
| L25085_at | 7 | 0 | 20 | 20 | 18 | 0.35 | 1.77 | 0 | 0 Inf | 222 | P |
| D29643_at | 12 | 2 | 20 | 20 | 18 | 0.60 | 1.88 | 0 | 0 6.0 | 221 | P |
| L11373_at | 8 | 2 | 20 | 20 | 18 | 0.40 | 1.34 | 0 | 0 4.0 | 214 | P |
| D17525_at | 7 | 1 | 20 | 20 | 18 | 0.35 | 1.43 | 0 | 0 7.0 | 211 | P |
| D21260_at | 7 | 0 | 20 | 20 | 18 | 0.35 | 1.14 | 0 | 0 Inf | 211 | P |
| D28364_at | 13 | 0 | 20 | 20 | 18 | 0.65 | 2.59 | 1 | 0 Inf | 209 | P |
| D63878_at | 9 | 2 | 20 | 20 | 18 | 0.45 | 1.28 | 0 | 1 4.5 | 206 | P |
| D78134_at | 7 | 1 | 20 | 20 | 18 | 0.35 | 1.18 | 0 | 0 7.0 | 203 | P |
| D38549_at | 7 | 1 | 20 | 20 | 18 | 0.35 | 1.69 | 2 | 1 7.0 | 201 | P |
| M14016_at | 9 | 1 | 20 | 20 | 18 | 0.45 | 1.96 | 0 | 0 9.0 | 201 | P |
| D21853_at | 9. | 1 | 20 | 20 | 18 | 0.45 | 1.84 | 0 | 0 9.0 | 199 | P |
| L40401_at | 8 | 0 | 20 | 20 | 18 | 0.40 | 1.82 | 0 | 0 Inf | 197 | P |
| D63476_at | 9 | 2 | 20 | 20 | 18 | 0.45 | 1.42 | 0 | 0 4.5 | 195 | P |
| L40027_at | 8 | 0 | 20 | 20 | 18 | 0.40 | 1.93 | 1 | 0 Inf | 193 | P |
| D00762_at | 10 | 0 | 20 | 20 | 18 | 0.50 | 2.12 | 0 | 0 Inf | 188 | P |
| D17400_at | 9 | 2 | 20 | 20 | 18 | 0.45 | 1.50 | 0 | 0 4.5 | 187 | P |
| L03532_at | 11 | 3 | 20 | 20 | 18 | 0.55 | 1.71 | 0 | 0 3.7 | 187 | P |
| L08488_at | 12 | 1 | 20 | 20 | 17 | 0.60 | 3.01 | 1 | 0 12.0 | 187 | P |
| HG3995-HT4265_at | 8 | 1 | 20 | 20 | 18 | 0.40 | 1.14 | 0 | 0 8.0 | 186 | P |
| M11717_rna1_at | 13 | 2 | 20 | 20 | 18 | 0.65 | 3.65 | 2 | 0 6.5 | 186 | P |
| D13370_at | 9 | 1 | 20 | 20 | 17 | 0.45 | 1.75 | 0 | 0 9.0 | 185 | P |
| HG1116-HT1116_at | 8 | 0 | 20 | 20 | 18 | 0.40 | 1.46 | 0 | 0 Inf | 184 | P |
| K03515_at | 8 | 2 | 20 | 20 | 18 | 0.40 | 1.32 | 0 | 0 4.0 | 183 | P |
| D17516_at | 7 | 0 | 20 | 20 | 17 | 0.35 | 1.45 | 0 | 0 Inf | 177 | P |
| HG4272-HT4542_at | 7 | 1 | 20 | 20 | 18 | 0.35 | 1.97 | 1 | 0 7.0 | 177 | P |
| D28137_at | 9 | 3 | 20 | 20 | 18 | 0.45 | 1.55 | 0 | 0 3.0 | 176 | P |
| L22009_at | 8 | 2 | 20 | 20 | 18 | 0.40 | 1.35 | 0 | 0 4.0 | 175 | P |
| D44466_at | 12 | 1 | 20 | 20 | 18 | 0.60 | 2.09 | 1 | 0 12.0 | 173 | P |
| L29277_at | 8 | 0 | 20 | 20 | 17 | 0.40 | 1.41 | 0 | 0 Inf | 173 | P |
| L00352_at | 7 | 1 | 20 | 20 | 18 | 0.35 | 1.98 | 1 | 0 7.0 | 169 | P |
| L34587_at | 7 | 1 | 20 | 20 | 18 | 0.35 | 1.46 | 0 | 0 7.0 | 169 | P |
| L37042_at | 9 | 0 | 20 | 20 | 18 | 0.45 | 1.42 | 0 | 0 Inf | 169 | P |
| D86966_at | 8 | 2 | 20 | 20 | 18 | 0.40 | 1.35 | 0 | 0 4.0 | 168 | P |
| D15050_at | 11 | 0 | 20 | 20 | 17 | 0.55 | 1.77 | 0 | 0 Inf | 166 | P |
| L10838_at | 8 | 0 | 20 | 20 | 18 | 0.40 | 1.16 | 0 | 0 Inf | 166 | P |
| D14043_at | 10 | 1 | 20 | 20 | 18 | 0.50 | 1.73 | 0 | 0 10.0 | 159 | P |
| D87071_at | 8 | 2 | 20 | 20 | 17 | 0.40 | 1.12 | 0 | 0 4.0 | 157 | P |
| D42043_at | 11 | 2 | 20 | 20 | 18 | 0.55 | 2.07 | 0 | 0 5.5 | 155 | P |

-continued

Connective tissue A

| Gene Name | Positiv | Negati | Pairs | Pairs U | Pairs I | Pos Fracti | Log Avg | PM E:MM E: | Pos/Neg | Avg Diff | Abs Call |
|---|---|---|---|---|---|---|---|---|---|---|---|
| L38932_at | 9 | 0 | 20 | 20 | 18 | 0.45 | 1.29 | 0 | 0 Inf | 152 | P |
| D90276_at | 9 | 1 | 20 | 20 | 18 | 0.45 | 1.85 | 1 | 0 9.0 | 148 | P |
| M13450_at | 13 | 3 | 20 | 20 | 18 | 0.65 | 2.36 | 0 | 0 4.3 | 148 | P |
| M11726_at | 9 | 2 | 20 | 20 | 18 | 0.45 | 1.35 | 0 | 0 4.5 | 147 | P |
| L41690_at | 9 | 2 | 20 | 20 | 18 | 0.45 | 1.90 | 0 | 0 4.5 | 146 | P |
| D43950_at | 7 | 0 | 20 | 20 | 18 | 0.35 | 1.52 | 0 | 0 Inf | 145 | P |
| D63851_at | 8 | 2 | 20 | 20 | 18 | 0.40 | 1.12 | 0 | 0 4.0 | 143 | P |
| L19314_at | 7 | 0 | 20 | 20 | 17 | 0.35 | 1.64 | 0 | 0 Inf | 143 | P |
| L41668_rna1_at | 8 | 0 | 20 | 20 | 17 | 0.40 | 1.39 | 0 | 0 Inf | 142 | P |
| 083004_at | 9 | 1 | 20 | 20 | 17 | 0.45 | 1.87 | 0 | 1 9.0 | 141 | P |
| K02574_at | 9 | 1 | 20 | 20 | 18 | 0.45 | 1.80 | 1 | 0 9.0 | 138 | P |
| M13792_at | 10 | 2 | 20 | 20 | 18 | 0.50 | 2.18 | 0 | 0 5.0 | 138 | P |
| HG2415-HT2511_at | 10 | 2 | 20 | 20 | 18 | 0.50 | 1.29 | 0 | 0 5.0 | 135 | P |
| L20773_at | 8 | 2 | 20 | 20 | 18 | 0.40 | 1.39 | 0 | 1 4.0 | 134 | P |
| D10923_at | 8 | 1 | 20 | 20 | 18 | 0.40 | 1.66 | 0 | 0 8.0 | 132 | P |
| M12759_at | 10 | 2 | 20 | 20 | 18 | 0.50 | 1.70 | 1 | 0 5.0 | 131 | P |
| M16038_at | 7 | 0 | 20 | 20 | 18 | 0.35 | 1.77 | 0 | 0 Inf | 131 | P |
| D86963_at | 8 | 1 | 20 | 20 | 18 | 0.40 | 1.52 | 0 | 0 8.0 | 128 | P |
| J05249_at | 10 | 0 | 20 | 20 | 17 | 0.50 | 2.26 | 0 | 0 Inf | 128 | P |
| D90084_at | 7 | 1 | 20 | 20 | 18 | 0.35 | 1.11 | 0 | 0 7.0 | 124 | P |
| AF007875_at | 8 | 1 | 20 | 20 | 18 | 0.40 | 1.33 | 0 | 0 8.0 | 123 | P |
| D00726_at | 7 | 0 | 20 | 20 | 18 | 0.35 | 1.62 | 0 | 0 Inf | 123 | P |
| J05243_at | 9 | 0 | 20 | 20 | 18 | 0.45 | 1.62 | 0 | 0 Inf | 122 | P |
| L13761_rna1_at | 7 | 0 | 20 | 20 | 18 | 0.35 | 1.52 | 0 | 0 Inf | 119 | P |
| L38951_at | 10 | 0 | 20 | 20 | 18 | 0.50 | 1.86 | 0 | 0 Inf | 119 | P |
| M18533_at | 12 | 2 | 20 | 20 | 18 | 0.60 | 3.76 | 4 | 0 6.0 | 119 | P |
| J04605_at | 7 | 1 | 20 | 20 | 18 | 0.35 | 1.22 | 0 | 0 7.0 | 117 | P |
| D38553_at | 7 | 0 | 20 | 20 | 18 | 0.35 | 1.48 | 0 | 0 Inf | 116 | P |
| L36531_at | 7 | 2 | 20 | 20 | 18 | 0.35 | 1.46 | 1 | 0 3.5 | 116 | P |
| L14837_at | 9 | 2 | 20 | 20 | 18 | 0.45 | 2.20 | 2 | 0 4.5 | 113 | P |
| HG4102-HT4372_at | 7 | 1 | 20 | 20 | 18 | 0.35 | 1.12 | 0 | 0 7.0 | 109 | P |
| L40395_at | 8 | 2 | 20 | 20 | 18 | 0.40 | 1.38 | 0 | 0 4.0 | 107 | P |
| D30756_at | 8 | 1 | 20 | 20 | 18 | 0.40 | 2.06 | 2 | 0 8.0 | 106 | P |
| L47738_at | 8 | 0 | 20 | 20 | 17 | 0.40 | 0.90 | 0 | 0 Inf | 105 | P |
| D13641_at | 9 | 1 | 20 | 20 | 18 | 0.45 | 1.05 | 0 | 0 9.0 | 104 | P |
| D45399_at | 9 | 3 | 20 | 20 | 18 | 0.45 | 1.65 | 0 | 0 3.0 | 104 | P |
| L27706_at | 12 | 2 | 20 | 20 | 18 | 0.60 | 1.93 | 0 | 0 6.0 | 104 | P |
| D50683_at | 9 | 3 | 20 | 20 | 18 | 0.45 | 1.47 | 0 | 0 3.0 | 100 | P |
| HG2167-HT2237_at | 9 | 1 | 20 | 20 | 18 | 0.45 | 1.19 | 0 | 0 9.0 | 99 | P |
| D29641_at | 7 | 1 | 20 | 20 | 18 | 0.35 | 1.43 | 0 | 0 7.0 | 98 | P |
| L13977_at | 7 | 1 | 20 | 20 | 18 | 0.35 | 1.58 | 1 | 0 7.0 | 97 | P |
| L34600_at | 7 | 0 | 20 | 20 | 18 | 0.35 | 1.05 | 0 | 0 Inf | 95 | P |
| D12053_at | 8 | 1 | 20 | 20 | 18 | 0.40 | 1.47 | 0 | 0 8.0 | 94 | P |
| M14123_xpt2_at | 9 | 3 | 20 | 20 | 18 | 0.45 | 1.36 | 1 | 0 3.0 | 93 | P |
| 014658_at | 7 | 1 | 20 | 20 | 18 | 0.35 | 0.92 | 0 | 0 7.0 | 92 | P |
| L27841_at | 8 | 2 | 20 | 20 | 18 | 0.40 | 1.00 | 0 | 0 4.0 | 92 | P |
| AF010193_at | 7 | 1 | 20 | 20 | 18 | 0.35 | 1.07 | 0 | 0 7.0 | 91 | P |
| D50926_at | 11 | 2 | 20 | 20 | 18 | 0.55 | 1.24 | 0 | 0 5.5 | 90 | P |
| M11321_at | 10 | 1 | 20 | 20 | 18 | 0.50 | 1.35 | 0 | 0 10.0 | 90 | P |
| HG1102-HT1102_at | 7 | 1 | 20 | 20 | 18 | 0.35 | 1.68 | 1 | 0 7.0 | 89 | P |
| L40393_at | 12 | 2 | 20 | 20 | 17 | 0.60 | 2.43 | 0 | 0 6.0 | 89 | P |
| D80003_at | 9 | 1 | 20 | 20 | 18 | 0.45 | 1.59 | 1 | 0 9.0 | 86 | P |
| M14219_at | 10 | 1 | 20 | 20 | 18 | 0.50 | 1.99 | 1 | 0 10.0 | 86 | P |
| M14539_at | 7 | 0 | 20 | 20 | 18 | 0.35 | 0.98 | 0 | 0 Inf | 86 | P |
| M13699_at | 9 | 3 | 20 | 20 | 18 | 0.45 | 2.24 | 1 | 0 3.0 | 85 | P |
| L19711_at | 8 | 0 | 20 | 20 | 18 | 0.40 | 1.67 | 0 | 0 Inf | 84 | P |
| L76703_at | 9 | 2 | 20 | 20 | 18 | 0.45 | 2.08 | 1 | 0 4.5 | 84 | P |
| D63390_at | 10 | 1 | 20 | 20 | 18 | 0.50 | 2.52 | 2 | 0 10.0 | 82 | P |
| HGB31-HT831_at | 9 | 2 | 20 | 20 | 18 | 0.45 | 1.31 | 1 | 0 4.5 | 78 | P |
| D21255_at | 9 | 1 | 20 | 20 | 18 | 0.45 | 1.63 | 1 | 0 9.0 | 77 | P |
| D78129_at | 9 | 3 | 20 | 20 | 18 | 0.45 | 1.60 | 1 | 0 3.0 | 77 | P |
| L48513_at | 13 | 3 | 20 | 20 | 18 | 0.65 | 1.87 | 1 | 1 4.3 | 77 | P |
| M14636_at | 9 | 3 | 20 | 20 | 18 | 0.45 | 1.62 | 1 | 2 3.0 | 73 | P |
| M15796_at | 7 | 2 | 20 | 20 | 18 | 0.35 | 1.66 | 0 | 0 3.5 | 73 | P |
| HG1103-HT1103_at | 9 | 2 | 20 | 20 | 18 | 0.45 | 1.51 | 1 | 0 4.5 | 71 | P |
| L35240_at | 7 | 1 | 20 | 20 | 18 | 0.35 | 1.02 | 0 | 0 7.0 | 67 | P |
| L77886_at | 9 | 3 | 20 | 20 | 17 | 0.45 | 2.27 | 2 | 0 3.0 | 59 | P |
| D14659_at | 9 | 3 | 20 | 20 | 18 | 0.45 | 1.61 | 1 | 0 3.0 | 54 | P |
| J04156_at | 8 | 2 | 20 | 20 | 18 | 0.40 | 1.23 | 1 | 0 4.0 | 54 | P |
| D87457_at | 8 | 2 | 20 | 20 | 18 | 0.40 | 2.72 | 4 | 0 4.0 | 48 | P |
| L20321_at | 7 | 1 | 20 | 20 | 18 | 0.35 | 0.92 | 1 | 0 7.0 | 32 | P |
| L20814_at | 9 | 3 | 20 | 20 | 18 | 0.45 | 1.61 | 1 | 1 3.0 | 28 | P |

| | | | | | Connective tissue B | | | | | |
|---|---|---|---|---|---|---|---|---|---|---|
| Gene Nam | Positive | Negative | Pairs | Pairs Used | Pairs InAv | Pos Fracti | Log Avg | PM Exces:MM Exces | Pos/Neg | Avg Diff | Abs Call |
| hum__alu_a | 69 | 0 | 69 | 69 | 67 | 1.00 | 7.19 | 12 | 0 Inf | 12502 | P |
| U46692_rn | 19 | 0 | 20 | 20 | 18 | 0.95 | 7.15 | 3 | 0 Inf | 10030 | P |
| AFFX-HUM | 18 | 0 | 20 | 20 | 18 | 0.90 | 6.05 | 0 | 0 Inf | 5799 | P |
| AFFX-HSA | 20 | 0 | 20 | 20 | 18 | 1.00 | 6.50 | 0 | 0 Inf | 5422 | P |
| 14969_at | 20 | 0 | 20 | 20 | 18 | 1.00 | 6.79 | 0 | 0 Inf | 4539 | P |
| M60854_at | 19 | 1 | 20 | 20 | 18 | 0.95 | 6.50 | 2 | 0 19.0 | 4473 | P |
| AFFX-Cre> | 19 | 0 | 20 | 20 | 18 | 0.95 | 7.67 | 3 | 0 Inf | 4430 | P |
| M81757_at | 18 | 0 | 20 | 20 | 18 | 0.90 | 6.62 | 2 | 0 Inf | 4369 | P |
| U14973_at | 19 | 0 | 20 | 20 | 18 | 0.95 | 6.06 | 1 | 0 Inf | 4281 | P |
| AFFX-HSA | 19 | 0 | 20 | 20 | 18 | 0.95 | 6.11 | 1 | 0 Inf | 4114 | P |
| U14970_at | 19 | 0 | 20 | 20 | 18 | 0.95 | 6.15 | 2 | 0 Inf | 3928 | P |
| U14968_at | 18 | 0 | 20 | 20 | 18 | 0.90 | 7.18 | 3 | 0 Inf | 3885 | P |
| U14972_at | 17 | 0 | 20 | 20 | 18 | 0.85 | 5.60 | 2 | 0 Inf | 3695 | P |
| M84711_at | 17 | 1 | 20 | 20 | 18 | 0.85 | 7.59 | 5 | 1 17.0 | 3651 | P |
| AFFX-HUM | 17 | 0 | 20 | 20 | 18 | 0.85 | 5.08 | 0 | 0 Inf | 3483 | P |
| M24194_at | 19 | 0 | 20 | 20 | 18 | 0.95 | 5.69 | 0 | 0 Inf | 3378 | P |
| U12465_at | 19 | 0 | 20 | 20 | 18 | 0.95 | 6.01 | 0 | 0 Inf | 3327 | P |
| M64716_at | 17 | 2 | 20 | 20 | 18 | 0.85 | 5.15 | 3 | 0 8.5 | 3228 | P |
| S79522_at | 19 | 0 | 20 | 20 | 18 | 0.95 | 6.42 | 4 | 0 Inf | 3161 | P |
| AFFX-Cre> | 19 | 0 | 20 | 20 | 18 | 0.95 | 6.86 | 1 | 0 Inf | 2966 | P |
| AFFX-HSA | 18 | 0 | 20 | 20 | 17 | 0.90 | 5.87 | 0 | 0 Inf | 2793 | P |
| AFFX-HUM | 17 | 0 | 20 | 20 | 18 | 0.85 | 5.95 | 4 | 0 Inf | 2690 | P |
| U14971_at | 18 | 0 | 20 | 20 | 18 | 0.90 | 5.27 | 1 | 0 Inf | 2645 | P |
| M77232_rr | 20 | 0 | 20 | 20 | 18 | 1.00 | 7.99 | 6 | 0 Inf | 2616 | P |
| M94856_at | 18 | 0 | 20 | 20 | 18 | 0.90 | 8.28 | 10 | 0 Inf | 2525 | P |
| U12404_at | 20 | 0 | 20 | 20 | 18 | 1.00 | 6.67 | 2 | 0 Inf | 2522 | P |
| U09953_at | 18 | 1 | 20 | 20 | 18 | 0.90 | 6.77 | 3 | 0 18.0 | 2506 | P |
| M32053_at | 20 | 0 | 20 | 20 | 18 | 1.00 | 6.29 | 0 | 0 Inf | 2486 | P |
| U58682_at | 15 | 1 | 20 | 20 | 18 | 0.75 | 4.14 | 1 | 0 15.0 | 2129 | P |
| U49869_rn | 18 | 0 | 20 | 20 | 17 | 0.90 | 5.83 | 2 | 0 Inf | 2053 | P |
| M32405_at | 13 | 2 | 20 | 20 | 17 | 0.65 | 3.40 | 1 | 0 6.5 | 2005 | P |
| M31520_at | 20 | 0 | 20 | 20 | 18 | 1.00 | 6.23 | 4 | 0 Inf | 1876 | P |
| M84526_at | 14 | 1 | 20 | 20 | 18 | 0.70 | 3.38 | 0 | 0 14.0 | 1875 | P |
| M38591_at | 19 | 0 | 20 | 20 | 18 | 0.95 | 6.10 | 3 | 0 Inf | 1819 | P |
| M95787_at | 17 | 0 | 20 | 20 | 18 | 0.85 | 4.53 | 1 | 0 Inf | 1735 | P |
| M97815_at | 17 | 0 | 20 | 20 | 18 | 0.85 | 4.05 | 0 | 0 Inf | 1655 | P |
| M86400_at | 18 | 0 | 20 | 20 | 18 | 0.90 | 5.75 | 3 | 0 Inf | 1653 | P |
| AFFX-BioD | 16 | 2 | 20 | 20 | 17 | 0.80 | 3.26 | 0 | 0 8.0 | 1555 | P |
| M26880_at | 16 | 0 | 20 | 20 | 18 | 0.80 | 7.17 | 9 | 0 Inf | 1506 | P |
| M63138_at | 12 | 1 | 20 | 20 | 18 | 0.60 | 2.92 | 0 | 0 12.0 | 1489 | P |
| M57710_at | 18 | 1 | 20 | 20 | 18 | 0.90 | 6.45 | 2 | 1 18.0 | 1449 | P |
| M23613_at | 17 | 1 | 20 | 20 | 18 | 0.85 | 5.57 | 4 | 0 17.0 | 1448 | P |
| M33680_at | 15 | 0 | 20 | 20 | 18 | 0.75 | 3.69 | 1 | 0 Inf | 1423 | P |
| M27891_at | 14 | 0 | 20 | 20 | 18 | 0.70 | 3.55 | 0 | 0 Inf | 1363 | P |
| S81914_at | 18 | 0 | 20 | 20 | 18 | 0.90 | 5.75 | 1 | 0 Inf | 1310 | P |
| U25789_at | 16 | 0 | 20 | 20 | 18 | 0.80 | 5.97 | 2 | 0 Inf | 1265 | P |
| M74542_at | 14 | 1 | 20 | 20 | 18 | 0.70 | 3.88 | 0 | 0 14.0 | 1233 | P |
| M38690_at | 15 | 1 | 20 | 20 | 18 | 0.75 | 3.97 | 0 | 0 15.0 | 1172 | P |
| S65738_at | 16 | 1 | 20 | 20 | 18 | 0.80 | 5.75 | 0 | 0 16.0 | 1151 | P |
| M34182_at | 7 | 2 | 20 | 20 | 18 | 0.35 | 1.43 | 0 | 0 3.5 | 924 | P |
| M92934_at | 16 | 1 | 20 | 20 | 18 | 0.80 | 4.82 | 0 | 0 16.0 | 898 | P |
| M63379_at | 16 | 0 | 20 | 20 | 18 | 0.80 | 3.59 | 0 | 0 Inf | 891 | P |
| M60047_at | 17 | 0 | 20 | 20 | 18 | 0.85 | 4.42 | 1 | 0 Inf | 847 | P |
| U17077_at | 15 | 0 | 20 | 20 | 18 | 0.75 | 3.94 | 1 | 0 Inf | 841 | P |
| M76378_at | 13 | 0 | 20 | 20 | 18 | 0.65 | 4.01 | 0 | 0 Inf | 839 | P |
| M93056_at | 14 | 0 | 20 | 20 | 18 | 0.70 | 4.58 | 1 | 0 Inf | 834 | P |
| U15008_at | 15 | 0 | 20 | 20 | 17 | 0.75 | 3.48 | 1 | 0 Inf | 816 | P |
| M84332_at | 12 | 1 | 20 | 20 | 18 | 0.60 | 2.32 | 0 | 0 12.0 | 767 | P |
| M69043_at | 14 | 1 | 20 | 20 | 18 | 0.70 | 4.12 | 1 | 0 14.0 | 748 | P |
| U32944_at | 15 | 1 | 20 | 20 | 17 | 0.75 | 4.21 | 2 | 0 15.0 | 743 | P |
| M55593_at | 12 | 1 | 20 | 20 | 18 | 0.60 | 2.46 | 0 | 0 12.0 | 739 | P |
| U09813_at | 15 | 0 | 20 | 20 | 18 | 0.75 | 4.39 | 0 | 0 Inf | 715 | P |
| M98447_rr | 10 | 0 | 20 | 20 | 18 | 0.50 | 2.31 | 0 | 0 Inf | 705 | P |

-continued

Connective tissue B

| Gene Nam | Positive | Negative | Pairs | Pairs Used | Pairs InAv | Pos Fracti | Log Avg | PM Exces:MM Exces | Pos/Neg | Avg Diff | Abs Call |
|---|---|---|---|---|---|---|---|---|---|---|---|
| U41635_at | 13 | 0 | 20 | 20 | 18 | 0.65 | 1.97 | 0 | 0 Inf | 702 | P |
| U51478_at | 15 | 1 | 20 | 20 | 18 | 0.75 | 4.39 | 0 | 0 15.0 | 691 | P |
| M86849_a | 13 | 1 | 20 | 20 | 18 | 0.65 | 4.24 | 1 | 0 13.0 | 675 | P |
| U04313_at | 14 | 0 | 20 | 20 | 18 | 0.70 | 3.59 | 0 | 0 Inf | 667 | P |
| U48959_at | 14 | 1 | 20 | 20 | 18 | 0.70 | 3.07 | 1 | 0 14.0 | 621 | P |
| U46751_at | 13 | 1 | 20 | 20 | 18 | 0.65 | 3.61 | 0 | 0 13.0 | 619 | P |
| S77356_at | 12 | 2 | 20 | 20 | 18 | 0.60 | 3.32 | 1 | 0 6.0 | 579 | P |
| M23254_at | 15 | 1 | 20 | 20 | 18 | 0.75 | 3.68 | 0 | 0 15.0 | 574 | P |
| U44839_at | 9 | 2 | 20 | 20 | 18 | 0.45 | 1.35 | 0 | 0 4.5 | 566 | P |
| M62982_at | 13 | 2 | 20 | 20 | 18 | 0.65 | 3.06 | 0 | 0 6.5 | 561 | P |
| M88468_at | 8 | 2 | 20 | 20 | 18 | 0.40 | 0.98 | 0 | 0 4.0 | 538 | P |
| U21128_at | 11 | 3 | 20 | 20 | 18 | 0.55 | 3.45 | 2 | 0 3.7 | 510 | P |
| U50523_at | 12 | 2 | 20 | 20 | 18 | 0.60 | 2.95 | 0 | 0 6.0 | 510 | P |
| U30255_at | 11 | 0 | 20 | 20 | 17 | 0.55 | 2.64 | 0 | 0 Inf | 503 | P |
| M60858_rr | 16 | 0 | 20 | 20 | 18 | 0.80 | 3.50 | 1 | 0 Inf | 501 | P |
| U37690_at | 10 | 0 | 20 | 20 | 18 | 0.50 | 2.08 | 0 | 0 Inf | 499 | P |
| S45630_at | 11 | 0 | 20 | 20 | 18 | 0.55 | 1.96 | 0 | 0 Inf | 495 | P |
| M98539_at | 13 | 2 | 20 | 20 | 18 | 0.65 | 2.84 | 0 | 0 6.5 | 489 | P |
| S75463_at | 10 | 1 | 20 | 20 | 18 | 0.50 | 1.71 | 0 | 0 10.0 | 484 | P |
| M29540_at | 15 | 2 | 20 | 20 | 18 | 0.75 | 3.86 | 0 | 0 7.5 | 483 | P |
| M80563_al | 13 | 0 | 20 | 20 | 18 | 0.65 | 2.43 | 0 | 0 Inf | 482 | P |
| M22538_al | 13 | 0 | 20 | 20 | 18 | 0.65 | 2.32 | 0 | 0 Inf | 468 | P |
| M75126_al | 11 | 0 | 20 | 20 | 18 | 0.55 | 2.14 | 0 | 0 Inf | 444 | P |
| U56637_at | 12 | 0 | 20 | 20 | 18 | 0.60 | 2.95 | 0 | 0 Inf | 442 | P |
| U46499_at | 14 | 1 | 20 | 20 | 17 | 0.70 | 3.14 | 0 | 0 14.0 | 437 | P |
| U12779_at | 7 | 0 | 20 | 20 | 18 | 0.35 | 1.00 | 0 | 0 Inf | 434 | P |
| U51004_at | 13 | 1 | 20 | 20 | 18 | 0.65 | 2.57 | 0 | 0 13.0 | 433 | P |
| U11861_at | 8 | 1 | 20 | 20 | 18 | 0.40 | 1.49 | 0 | 0 8.0 | 432 | P |
| U03057_at | 12 | 0 | 20 | 20 | 17 | 0.60 | 2.03 | 0 | 0 Inf | 430 | P |
| M96739_al | 7 | 1 | 20 | 20 | 18 | 0.35 | 1.37 | 0 | 0 7.0 | 429 | P |
| M22760_at | 13 | 0 | 20 | 20 | 18 | 0.65 | 3.54 | 0 | 0 Inf | 426 | P |
| U62962_at | 8 | 0 | 20 | 20 | 18 | 0.40 | 1.65 | 0 | 0 Inf | 410 | P |
| AFFX-BioD | 12 | 2 | 20 | 20 | 18 | 0.60 | 1.72 | 0 | 0 6.0 | 400 | P |
| S73591_at | 13 | 2 | 20 | 20 | 18 | 0.65 | 2.35 | 0 | 0 6.5 | 400 | P |
| M63391_rr | 8 | 1 | 20 | 20 | 18 | 0.40 | 1.61 | 0 | 0 8.0 | 392 | P |
| M88338_at | 11 | 2 | 20 | 20 | 18 | 0.55 | 1.48 | 0 | 0 5.5 | 391 | P |
| M76482_at | 14 | 3 | 20 | 20 | 18 | 0.70 | 2.79 | 0 | 0 4.7 | 389 | P |
| M22382_at | 13 | 0 | 20 | 20 | 18 | 0.65 | 2.59 | 0 | 0 Inf | 382 | P |
| M22490_at | 8 | 1 | 20 | 20 | 18 | 0.40 | 1.47 | 0 | 0 8.0 | 377 | P |
| M57567_at | 9 | 1 | 20 | 20 | 18 | 0.45 | 1.77 | 0 | 0 9.0 | 377 | P |
| U15932_at | 14 | 1 | 20 | 20 | 18 | 0.70 | 3.10 | 0 | 1 14.0 | 375 | P |
| AFFX-HSA | 12 | 0 | 20 | 20 | 17 | 0.60 | 2.29 | 0 | 0 Inf | 374 | P |
| S74017_at | 15 | 2 | 20 | 20 | 18 | 0.75 | 2.72 | 0 | 0 7.5 | 372 | P |
| M74491_at | 12 | 0 | 20 | 20 | 18 | 0.60 | 2.09 | 0 | 0 Inf | 363 | P |
| U37519_at | 11 | 1 | 20 | 20 | 18 | 0.55 | 2.22 | 0 | 0 11.0 | 358 | P |
| M29064_at | 15 | 1 | 20 | 20 | 18 | 0.75 | 3.51 | 1 | 1 15.0 | 353 | P |
| M62402_at | 9 | 0 | 20 | 20 | 18 | 0.45 | 1.99 | 0 | 0 Inf | 350 | P |
| U29953_rn | 12 | 0 | 20 | 20 | 18 | 0.60 | 2.67 | 0 | 0 Inf | 349 | P |
| U46025_at | 11 | 0 | 20 | 20 | 18 | 0.55 | 1.97 | 0 | 0 Inf | 349 | P |
| U46570_at | 9 | 1 | 20 | 20 | 18 | 0.45 | 1.53 | 0 | 0 9.0 | 347 | P |
| S73149_at | 8 | 0 | 20 | 20 | 18 | 0.40 | 1.20 | 0 | 0 Inf | 346 | P |
| U33821_at | 10 | 1 | 20 | 20 | 18 | 0.50 | 1.94 | 0 | 0 10.0 | 346 | P |
| U09117_at | 8 | 2 | 20 | 20 | 18 | 0.40 | 1.33 | 0 | 0 4.0 | 344 | P |
| AFFX-BioC | 15 | 2 | 20 | 20 | 18 | 0.75 | 2.38 | 0 | 0 7.5 | 340 | P |
| M37104_at | 17 | 0 | 20 | 20 | 18 | 0.85 | 3.43 | 2 | 0 Inf | 338 | P |
| M59815_at | 10 | 2 | 20 | 20 | 17 | 0.50 | 2.14 | 0 | 0 5.0 | 337 | P |
| M75099_at | 9 | 1 | 20 | 20 | 18 | 0.45 | 1.69 | 0 | 0 9.0 | 331 | P |
| 07857_at | 17 | 1 | 20 | 20 | 17 | 0.85 | 3.44 | 0 | 0 17.0 | 330 | P |
| M28209_at | 13 | 0 | 20 | 20 | 18 | 0.65 | 2.74 | 0 | 0 Inf | 321 | P |
| U02020_at | 15 | 2 | 20 | 20 | 18 | 0.75 | 3.40 | 0 | 0 7.5 | 315 | P |
| M31525_at | 10 | 3 | 20 | 20 | 18 | 0.50 | 1.92 | 0 | 0 3.3 | 314 | P |
| M60278_at | 9 | 2 | 20 | 20 | 18 | 0.45 | 2.06 | 0 | 0 4.5 | 308 | P |
| M83751_at | 13 | 0 | 20 | 20 | 18 | 0.65 | 2.21 | 0 | 0 Inf | 307 | P |
| M63167_at | 10 | 1 | 20 | 20 | 17 | 0.50 | 1.51 | 0 | 0 10.0 | 306 | P |
| U15085_at | 13 | 0 | 20 | 20 | 18 | 0.65 | 2.34 | 0 | 0 Inf | 306 | P |
| M55621_at | 12 | 0 | 20 | 20 | 17 | 0.60 | 2.65 | 0 | 0 Inf | 304 | P |
| S72487_at | 8 | 0 | 20 | 20 | 18 | 0.40 | 1.71 | 0 | 0 Inf | 301 | P |
| U00968_at | 10 | 0 | 20 | 20 | 18 | 0.50 | 1.12 | 0 | 0 Inf | 301 | P |
| M94630_at | 9 | 2 | 20 | 20 | 18 | 0.45 | 1.31 | 1 | 0 4.5 | 290 | P |
| M59465_at | 11 | 2 | 20 | 20 | 18 | 0.55 | 2.68 | 2 | 0 5.5 | 289 | P |
| M37583_at | 13 | 1 | 20 | 20 | 18 | 0.65 | 3.67 | 1 | 0 13.0 | 288 | P |
| M84349_at | 11 | 1 | 20 | 20 | 17 | 0.55 | 2.58 | 0 | 0 11.0 | 286 | P |
| M99701_at | 13 | 1 | 20 | 20 | 18 | 0.65 | 2.72 | 1 | 0 13.0 | 282 | P |
| U37122_at | 10 | 1 | 20 | 20 | 17 | 0.50 | 1.95 | 1 | 0 10.0 | 282 | P |
| U57342_at | 7 | 0 | 20 | 20 | 18 | 0.35 | 1.06 | 0 | 0 Inf | 281 | P |

-continued

Connective tissue B

| Gene Nam | Positive | Negative | Pairs | Pairs Used | Pairs InAv | Pos Fracti | Log Avg | PM Exces:MM Exces | Pos/Neg | Avg Diff | Abs Call |
|---|---|---|---|---|---|---|---|---|---|---|---|
| M34079_at | 9 | 3 | 20 | 20 | 17 | 0.45 | 1.53 | 0 | 0 3.0 | 280 | P |
| S68616_at | 8 | 2 | 20 | 20 | 18 | 0.40 | 1.35 | 0 | 0 4.0 | 279 | P |
| M69006_at | 14 | 2 | 20 | 20 | 17 | 0.70 | 3.20 | 0 | 0 7.0 | 276 | P |
| M88279_at | 11 | 0 | 20 | 20 | 18 | 0.55 | 2.06 | 0 | 0 Inf | 276 | P |
| M31013_at | 12 | 2 | 20 | 20 | 18 | 0.60 | 2.13 | 0 | 0 6.0 | 274 | P |
| M94345_at | 11 | 1 | 20 | 20 | 18 | 0.55 | 1.77 | 0 | 0 11.0 | 274 | P |
| U37689_at | 8 | 0 | 20 | 20 | 18 | 0.40 | 1.35 | 0 | 0 Inf | 269 | P |
| U41515_at | 11 | 1 | 20 | 20 | 18 | 0.55 | 2.31 | 0 | 0 11.0 | 269 | P |
| M37984_rr | 8 | 2 | 20 | 20 | 18 | 0.40 | 1.43 | 0 | 0 4.0 | 267 | P |
| M88458_at | 12 | 0 | 20 | 20 | 18 | 0.60 | 1.93 | 0 | 0 Inf | 265 | P |
| U02570_at | 11 | 1 | 20 | 20 | 18 | 0.55 | 2.26 | 1 | 0 11.0 | 263 | P |
| M68864_at | 9 | 1 | 20 | 20 | 18 | 0.45 | 2.10 | 0 | 0 9.0 | 260 | P |
| M31994_at | 11 | 1 | 20 | 20 | 18 | 0.55 | 2.60 | 0 | 0 11.0 | 257 | P |
| M35878_at | 10 | 2 | 20 | 20 | 18 | 0.50 | 1.55 | 0 | 1 5.0 | 255 | P |
| U62015_at | 8 | 0 | 20 | 20 | 18 | 0.40 | 1.58 | 0 | 0 Inf | 253 | P |
| U44755_at | 7 | 1 | 20 | 20 | 18 | 0.35 | 1.45 | 0 | 0 7.0 | 250 | P |
| M80244_at | 9 | 1 | 20 | 20 | 17 | 0.45 | 1.50 | 0 | 0 9.0 | 249 | P |
| U02493_at | 9 | 1 | 20 | 20 | 18 | 0.45 | 2.04 | 0 | 0 9.0 | 247 | P |
| M29696_at | 8 | 1 | 20 | 20 | 18 | 0.40 | 1.21 | 0 | 0 8.0 | 246 | P |
| M73720_at | 12 | 0 | 20 | 20 | 17 | 0.60 | 2.59 | 0 | 0 Inf | 246 | P |
| U09579_at | 9 | 2 | 20 | 20 | 18 | 0.45 | 2.07 | 1 | 0 4.5 | 242 | P |
| M92303_at | 7 | 2 | 20 | 20 | 18 | 0.35 | 1.41 | 0 | 0 3.5 | 240 | P |
| U20285_at | 7 | 1 | 20 | 20 | 18 | 0.35 | 1.80 | 0 | 0 7.0 | 240 | P |
| U50733_at | 9 | 1 | 20 | 20 | 18 | 0.45 | 1.83 | 0 | 0 9.0 | 239 | P |
| M29536_at | 13 | 2 | 20 | 20 | 18 | 0.65 | 2.11 | 0 | 0 6.5 | 238 | P |
| M63483_at | 11 | 3 | 20 | 20 | 18 | 0.55 | 1.75 | 0 | 0 3.7 | 238 | P |
| M83186_at | 10 | 3 | 20 | 20 | 18 | 0.50 | 1.87 | 0 | 0 3.3 | 238 | P |
| U40391_at | 9 | 1 | 20 | 20 | 18 | 0.45 | 1.50 | 0 | 0 9.0 | 237 | P |
| M86667_at | 13 | 0 | 20 | 20 | 18 | 0.65 | 3.08 | 1 | 0 Inf | 233 | P |
| S53911_at | 11 | 2 | 20 | 20 | 17 | 0.55 | 1.84 | 0 | 0 5.5 | 233 | P |
| AFFX-BioC | 10 | 1 | 20 | 20 | 18 | 0.50 | 1.81 | 0 | 0 10.0 | 232 | P |
| M33308_at | 13 | 0 | 20 | 20 | 18 | 0.65 | 3.20 | 1 | 0 Inf | 231 | P |
| 583364_at | 9 | 1 | 20 | 20 | 18 | 0.45 | 2.20 | 0 | 0 9.0 | 231 | P |
| U06863_at | 7 | 0 | 20 | 20 | 18 | 0.35 | 1.14 | 0 | 0 Inf | 230 | P |
| M37033_at | 11 | 3 | 20 | 20 | 18 | 0.55 | 1.97 | 1 | 0 3.7 | 229 | P |
| U21931_at | 9 | 2 | 20 | 20 | 18 | 0.45 | 1.55 | 0 | 0 4.5 | 229 | P |
| M36341_at | 13 | 1 | 20 | 20 | 17 | 0.65 | 2.63 | 0 | 0 13.0 | 225 | P |
| M55040_at | 8 | 2 | 20 | 20 | 18 | 0.40 | 1.18 | 0 | 0 4.0 | 225 | P |
| M80254_at | 8 | 1 | 20 | 20 | 18 | 0.40 | 1.69 | 0 | 0 8.0 | 223 | P |
| M57763_at | 7 | 2 | 20 | 20 | 18 | 0.35 | 1.35 | 0 | 0 3.5 | 222 | P |
| 33088_at | 8 | 2 | 20 | 20 | 18 | 0.40 | 1.71 | 0 | 0 4.0 | 221 | P |
| M33336_at | 16 | 1 | 20 | 20 | 18 | 0.80 | 2.70 | 0 | 0 16.0 | 217 | P |
| M58028_at | 9 | 1 | 20 | 20 | 18 | 0.45 | 1.46 | 0 | 0 9.0 | 213 | P |
| M63573_at | 11 | 2 | 20 | 20 | 18 | 0.55 | 2.70 | 0 | 0 5.5 | 213 | P |
| M63541_at | 11 | 2 | 20 | 20 | 18 | 0.55 | 1.87 | 0 | 0 5.5 | 213 | P |
| U24105_at | 9 | 0 | 20 | 20 | 18 | 0.45 | 1.86 | 0 | 0 Inf | 212 | P |
| M64992_at | 10 | 1 | 20 | 20 | 17 | 0.50 | 2.15 | 1 | 0 10.0 | 210 | P |
| U38846_at | 12 | 1 | 20 | 20 | 18 | 0.60 | 1.89 | 0 | 0 12.0 | 209 | P |
| U40282_at | 11 | 3 | 20 | 20 | 18 | 0.55 | 1.59 | 0 | 0 3.7 | 208 | P |
| M26576_at | 7 | 2 | 20 | 20 | 18 | 0.35 | 1.40 | 0 | 0 3.5 | 207 | P |
| S77812_at | 9 | 2 | 20 | 20 | 18 | 0.45 | 1.80 | 0 | 0 4.5 | 206 | P |
| U30825_at | 10 | 2 | 20 | 20 | 17 | 0.50 | 2.18 | 0 | 0 5.0 | 206 | P |
| M33552_at | 9 | 1 | 20 | 20 | 18 | 0.45 | 1.19 | 0 | 0 9.0 | 205 | P |
| U52112_rn | 9 | 1 | 20 | 20 | 18 | 0.45 | 1.97 | 1 | 0 9.0 | 205 | P |
| M58603_at | 12 | 2 | 20 | 20 | 17 | 0.60 | 2.77 | 2 | 0 6.0 | 202 | P |
| S82240_at | 12 | 1 | 20 | 20 | 18 | 0.60 | 3.55 | 2 | 0 12.0 | 201 | P |
| M86528_at | 7 | 1 | 20 | 20 | 18 | 0.35 | 1.20 | 0 | 0 7.0 | 200 | P |
| M22632_at | 9 | 1 | 20 | 20 | 18 | 0.45 | 1.38 | 0 | 0 9.0 | 199 | P |
| M81601_at | 11 | 2 | 20 | 20 | 18 | 0.55 | 1.77 | 0 | 0 5.5 | 199 | P |
| M94556_at | 12 | 1 | 20 | 20 | 18 | 0.60 | 2.15 | 0 | 0 12.0 | 199 | P |
| M37435_at | 7 | 1 | 20 | 20 | 18 | 0.35 | 1.74 | 0 | 0 7.0 | 197 | P |
| M64098_at | 11 | 2 | 20 | 20 | 18 | 0.55 | 2.31 | 0 | 0 5.5 | 197 | P |
| U20998_at | 8 | 2 | 20 | 20 | 18 | 0.40 | 2.68 | 1 | 0 4.0 | 196 | P |
| U36764_at | 14 | 1 | 20 | 20 | 17 | 0.70 | 3.29 | 0 | 0 14.0 | 196 | P |
| U12255_at | 8 | 1 | 20 | 20 | 18 | 0.40 | 1.73 | 0 | 0 8.0 | 195 | P |
| U54778_at | 8 | 1 | 20 | 20 | 18 | 0.40 | 1.23 | 0 | 0 8.0 | 195 | P |
| M69039_at | 14 | 2 | 20 | 20 | 17 | 0.70 | 2.86 | 0 | 0 7.0 | 194 | P |
| M24902_at | 11 | 0 | 20 | 20 | 18 | 0.55 | 2.34 | 0 | 0 Inf | 193 | P |
| U52100_at | 12 | 0 | 20 | 20 | 18 | 0.60 | 2.09 | 0 | 0 Inf | 192 | P |
| U03100_at | 12 | 3 | 20 | 20 | 18 | 0.60 | 2.40 | 0 | 0 4.0 | 189 | P |
| M64347_at | 10 | 2 | 20 | 20 | 18 | 0.50 | 1.08 | 0 | 0 5.0 | 186 | P |
| M81780_at | 7 | 0 | 20 | 20 | 18 | 0.35 | 1.01 | 0 | 0 Inf | 186 | P |
| M29877_at | 10 | 1 | 20 | 20 | 18 | 0.50 | 1.51 | 0 | 1 10.0 | 181 | P |
| M62831_at | 9 | 0 | 20 | 20 | 18 | 0.45 | 1.63 | 0 | 0 Inf | 180 | P |
| U49785_at | 12 | 0 | 20 | 20 | 18 | 0.60 | 1.76 | 1 | 0 Inf | 178 | P |

-continued

Connective tissue B

| Gene Nam | Positive | Negative | Pairs | Pairs Used | Pairs InAv | Pos Fracti | Log Avg | PM Exces:MM Exces | Pos/Neg | Avg Diff | Abs Call |
|---|---|---|---|---|---|---|---|---|---|---|---|
| M31627_at | 12 | 2 | 20 | 20 | 18 | 0.60 | 1.96 | 0 | 0 6.0 | 177 | P |
| U07424_at | 10 | 3 | 20 | 20 | 18 | 0.50 | 1.50 | 0 | 0 3.3 | 177 | P |
| M89473_at | 8 | 2 | 20 | 20 | 18 | 0.40 | 1.03 | 0 | 0 4.0 | 174 | P |
| U52101_at | 7 | 1 | 20 | 20 | 18 | 0.35 | 1.22 | 0 | 0 7.0 | 174 | P |
| U16127_at | 8 | 2 | 20 | 20 | 18 | 0.40 | 1.73 | 0 | 0 4.0 | 173 | P |
| U03688_at | 10 | 2 | 20 | 20 | 18 | 0.50 | 2.96 | 0 | 0 5.0 | 172 | P |
| U57877_at | 8 | 2 | 20 | 20 | 18 | 0.40 | 1.10 | 0 | 0 4.0 | 169 | P |
| M23114_at | 14 | 1 | 20 | 20 | 17 | 0.70 | 2.87 | 1 | 0 14.0 | 167 | P |
| M73547_at | 10 | 3 | 20 | 20 | 18 | 0.50 | 1.38 | 0 | 0 3.3 | 165 | P |
| U21049_at | 7 | 0 | 20 | 20 | 18 | 0.35 | 0.95 | 0 | 0 Inf | 165 | P |
| S67325_at | 8 | 1 | 20 | 20 | 18 | 0.40 | 1.24 | 0 | 0 8.0 | 163 | P |
| U18009_at | 10 | 2 | 20 | 20 | 18 | 0.50 | 1.86 | 0 | 0 5.0 | 163 | P |
| U50330_at | 8 | 1 | 20 | 20 | 18 | 0.40 | 1.22 | 0 | 0 8.0 | 163 | P |
| U51678_at | 12 | 2 | 20 | 20 | 18 | 0.60 | 1.84 | 0 | 0 6.0 | 160 | P |
| U24166_at | 12 | 1 | 20 | 20 | 18 | 0.60 | 2.02 | 0 | 0 12.0 | 158 | P |
| U34962_at | 10 | 2 | 20 | 20 | 18 | 0.50 | 1.26 | 0 | 0 5.0 | 152 | P |
| M57399_at | 9 | 3 | 20 | 20 | 18 | 0.45 | 1.33 | 0 | 0 3.0 | 150 | P |
| U53476_at | 7 | 1 | 20 | 20 | 18 | 0.35 | 1.13 | 0 | 0 7.0 | 150 | P |
| M24470_at | 8 | 1 | 20 | 20 | 17 | 0.40 | 1.20 | 0 | 0 8.0 | 148 | P |
| M29927_at | 8 | 0 | 20 | 20 | 17 | 0.40 | 1.33 | 0 | 0 Inf | 147 | P |
| U51711_at | 9 | 1 | 20 | 20 | 17 | 0.45 | 1.67 | 0 | 0 9.0 | 146 | P |
| M34057_at | 10 | 3 | 20 | 20 | 18 | 0.50 | 2.37 | 1 | 0 3.3 | 145 | P |
| U43286_at | 10 | 3 | 20 | 20 | 18 | 0.50 | 1.61 | 0 | 1 3.3 | 143 | P |
| U53445_at | 14 | 1 | 20 | 20 | 17 | 0.70 | 3.30 | 1 | 0 14.0 | 143 | P |
| 365583_rn | 9 | 3 | 20 | 20 | 18 | 0.45 | 1.46 | 1 | 0 3.0 | 141 | P |
| M86546_at | 10 | 1 | 20 | 20 | 17 | 0.50 | 1.83 | 1 | 0 10.0 | 140 | P |
| U31384_at | 9 | 1 | 20 | 20 | 18 | 0.45 | 1.49 | 0 | 0 9.0 | 139 | P |
| M63175_at | 8 | 2 | 20 | 20 | 18 | 0.40 | 1.46 | 0 | 0 4.0 | 138 | P |
| M93283_at | 10 | 2 | 20 | 20 | 17 | 0.50 | 1.39 | 0 | 0 5.0 | 138 | P |
| U30888_at | 8 | 2 | 20 | 20 | 18 | 0.40 | 1.54 | 0 | 0 4.0 | 138 | P |
| U47101_at | 9 | 0 | 20 | 20 | 18 | 0.45 | 1.92 | 0 | 0 Inf | 138 | P |
| M97287_at | 8 | 2 | 20 | 20 | 18 | 0.40 | 1.29 | 1 | 2 4.0 | 137 | P |
| AFFX-M27 | 9 | 0 | 20 | 20 | 18 | 0.45 | 2.11 | 0 | 0 Inf | 136 | P |
| U51240_at | 7 | 1 | 20 | 20 | 18 | 0.35 | 1.11 | 0 | 0 7.0 | 136 | P |
| U49070_at | 8 | 0 | 20 | 20 | 18 | 0.40 | 1.08 | 0 | 0 Inf | 135 | P |
| M33195_at | 9 | 1 | 20 | 20 | 18 | 0.45 | 1.29 | 0 | 0 9.0 | 133 | P |
| M59830_at | 11 | 3 | 20 | 20 | 18 | 0.55 | 1.45 | 1 | 0 3.7 | 133 | P |
| U07802_at | 10 | 2 | 20 | 20 | 17 | 0.50 | 1.85 | 0 | 0 5.0 | 133 | P |
| U39317_at | 7 | 2 | 20 | 20 | 18 | 0.35 | 2.00 | 1 | 0 3.5 | 132 | P |
| U61374_at | 9 | 1 | 20 | 20 | 18 | 0.45 | 1.43 | 0 | 0 9.0 | 132 | P |
| M98776_rr | 9 | 1 | 20 | 20 | 18 | 0.45 | 1.12 | 0 | 0 9.0 | 130 | P |
| M22877_at | 14 | 1 | 20 | 20 | 17 | 0.70 | 2.26 | 1 | 0 14.0 | 129 | P |
| M91036_rr | 7 | 1 | 20 | 20 | 18 | 0.35 | 0.98 | 0 | 0 7.0 | 128 | P |
| S77763_at | 9 | 2 | 20 | 20 | 18 | 0.45 | 1.34 | 0 | 0 4.5 | 126 | P |
| U58334_at | 7 | 0 | 20 | 20 | 17 | 0.35 | 0.92 | 0 | 0 Inf | 125 | P |
| M64929_at | 10 | 1 | 20 | 20 | 18 | 0.50 | 2.14 | 1 | 0 10.0 | 124 | P |
| S72008_at | 10 | 0 | 20 | 20 | 17 | 0.50 | 2.43 | 1 | 0 Inf | 124 | P |
| M35416_at | 9 | 3 | 20 | 20 | 18 | 0.45 | 1.39 | 0 | 0 3.0 | 122 | P |
| M37721_at | 12 | 3 | 20 | 20 | 18 | 0.60 | 2.38 | 1 | 0 4.0 | 122 | P |
| M55671_at | 8 | 1 | 20 | 20 | 18 | 0.40 | 1.97 | 1 | 0 8.0 | 122 | P |
| M27492_at | 9 | 1 | 20 | 20 | 18 | 0.45 | 1.71 | 1 | 0 9.0 | 121 | P |
| U52969_at | 7 | 1 | 20 | 20 | 18 | 0.35 | 1.15 | 0 | 0 7.0 | 118 | P |
| M55542_at | 13 | 2 | 20 | 20 | 18 | 0.65 | 3.06 | 3 | 0 6.5 | 117 | P |
| S81419_at | 8 | 1 | 20 | 20 | 18 | 0.40 | 1.23 | 0 | 0 8.0 | 117 | P |
| U01147_at | 8 | 1 | 20 | 20 | 18 | 0.40 | 1.42 | 0 | 0 8.0 | 116 | P |
| U10439_at | 8 | 1 | 20 | 20 | 18 | 0.40 | 1.89 | 0 | 0 8.0 | 116 | P |
| M59916_at | 8 | 2 | 20 | 20 | 18 | 0.40 | 1.19 | 0 | 0 4.0 | 115 | P |
| U24152_at | 8 | 2 | 20 | 20 | 18 | 0.40 | 1.26 | 0 | 0 4.0 | 115 | P |
| M74524_at | 7 | 0 | 20 | 20 | 18 | 0.35 | 2.07 | 1 | 0 Inf | 114 | P |
| M83738_at | 8 | 2 | 20 | 20 | 18 | 0.40 | 1.98 | 1 | 0 4.0 | 114 | P |
| S43646_at | 7 | 2 | 20 | 20 | 18 | 0.35 | 1.31 | 0 | 0 3.5 | 114 | P |
| U00952_at | 9 | 2 | 20 | 20 | 18 | 0.45 | 1.64 | 1 | 0 4.5 | 114 | P |
| U09770_at | 8 | 1 | 20 | 20 | 17 | 0.40 | 1.08 | 0 | 0 8.0 | 114 | P |
| U15782_at | 7 | 1 | 20 | 20 | 18 | 0.35 | 1.66 | 0 | 0 7.0 | 114 | P |
| U40369_rn | 9 | 1 | 20 | 20 | 18 | 0.45 | 1.88 | 1 | 0 9.0 | 113 | P |
| M23197_at | 9 | 0 | 20 | 20 | 18 | 0.45 | 1.35 | 0 | 0 Inf | 111 | P |
| U14193_at | 8 | 2 | 20 | 20 | 17 | 0.40 | 1.13 | 0 | 0 4.0 | 109 | P |
| U37518_at | 7 | 2 | 20 | 20 | 18 | 0.35 | 1.69 | 0 | 0 3.5 | 109 | P |
| U02082_at | 11 | 0 | 20 | 20 | 18 | 0.55 | 1.54 | 0 | 0 Inf | 108 | P |
| U47742_at | 9 | 2 | 20 | 20 | 18 | 0.45 | 1.57 | 1 | 0 4.5 | 108 | P |
| U50553_at | 8 | 0 | 20 | 20 | 18 | 0.40 | 1.20 | 0 | 0 Inf | 108 | P |
| M64925_at | 9 | 1 | 20 | 20 | 18 | 0.45 | 2.12 | 0 | 0 9.0 | 106 | P |
| U29171_at | 8 | 1 | 20 | 20 | 17 | 0.40 | 1.16 | 0 | 0 8.0 | 104 | P |
| M63603_a | 10 | 2 | 20 | 20 | 18 | 0.50 | 1.51 | 0 | 1 5.0 | 103 | P |
| U07358_at | 9 | 2 | 20 | 20 | 18 | 0.45 | 1.51 | 1 | 0 4.5 | 103 | P |

-continued

Connective tissue B

| Gene Nam | Positive | Negative | Pairs | Pairs Used | Pairs InAv | Pos Fracti | Log Avg | PM Exces:MM Exces | Pos/Neg | Avg Diff | Abs Call |
|---|---|---|---|---|---|---|---|---|---|---|---|
| U16031_at | 9 | 3 | 20 | 20 | 18 | 0.45 | 1.50 | 1 | 0 3.0 | 103 | P |
| S83366_cc | 9 | 2 | 20 | 20 | 18 | 0.45 | 1.76 | 0 | 0 4.5 | 101 | P |
| M80482_at | 7 | 1 | 20 | 20 | 18 | 0.35 | 1.34 | 0 | 0 7.0 | 100 | P |
| M96803_at | 7 | 1 | 20 | 20 | 18 | 0.35 | 1.49 | 1 | 0 7.0 | 99 | P |
| S77415_at | 9 | 2 | 20 | 20 | 18 | 0.45 | 2.53 | 2 | 0 4.5 | 96 | P |
| M30894_at | 8 | 0 | 20 | 20 | 18 | 0.40 | 1.47 | 0 | 0 Inf | 95 | P |
| S71018_at | 7 | 0 | 20 | 20 | 18 | 0.35 | 1.12 | 0 | 0 Inf | 95 | P |
| U13695_at | 11 | 0 | 20 | 20 | 18 | 0.55 | 2.52 | 0 | 0 Inf | 95 | P |
| U39400_at | 10 | 3 | 20 | 20 | 18 | 0.50 | 1.61 | 0 | 0 3.3 | 95 | P |
| M77698_at | 9 | 3 | 20 | 20 | 18 | 0.45 | 1.45 | 1 | 0 3.0 | 94 | P |
| U37251_at | 10 | 1 | 20 | 20 | 18 | 0.50 | 2.32 | 1 | 0 10.0 | 92 | P |
| M90696_at | 10 | 2 | 20 | 20 | 18 | 0.50 | 1.61 | 1 | 0 5.0 | 91 | P |
| U28386_at | 9 | 3 | 20 | 20 | 18 | 0.45 | 1.71 | 3 | 1 3.0 | 89 | P |
| U08989_at | 9 | 0 | 20 | 20 | 18 | 0.45 | 2.73 | 2 | 0 Inf | 88 | P |
| S67156_at | 8 | 0 | 20 | 20 | 18 | 0.40 | 1.84 | 0 | 0 Inf | 86 | P |
| U28686_at | 9 | 1 | 20 | 20 | 18 | 0.45 | 1.70 | 0 | 1 9.0 | 85 | P |
| U35048_at | 10 | 1 | 20 | 20 | 17 | 0.50 | 2.17 | 1 | 0 10.0 | 83 | P |
| M30269_at | 7 | 2 | 20 | 20 | 18 | 0.35 | 2.00 | 2 | 0 3.5 | 82 | P |
| M34309_at | 9 | 3 | 20 | 20 | 18 | 0.45 | 1.72 | 1 | 0 3.0 | 82 | P |
| M37197_at | 10 | 2 | 20 | 20 | 18 | 0.50 | 1.60 | 0 | 0 5.0 | 82 | P |
| U45976_at | 11 | 1 | 20 | 20 | 18 | 0.55 | 2.70 | 0 | 0 11.0 | 80 | P |
| S80562_at | 9 | 2 | 20 | 20 | 18 | 0.45 | 2.06 | 1 | 1 4.5 | 77 | P |
| U33818_at | 9 | 1 | 20 | 20 | 18 | 0.45 | 0.99 | 0 | 1 9.0 | 77 | P |
| M22995_at | 9 | 0 | 20 | 20 | 18 | 0.45 | 1.52 | 0 | 0 Inf | 76 | P |
| U14747_at | 8 | 2 | 20 | 20 | 18 | 0.40 | 1.09 | 0 | 0 4.0 | 76 | P |
| M81118_at | 9 | 3 | 20 | 20 | 18 | 0.45 | 1.52 | 2 | 1 3.0 | 75 | P |
| M28983_at | 7 | 2 | 20 | 20 | 18 | 0.35 | 1.30 | 1 | 0 3.5 | 74 | P |
| M65217_at | 9 | 3 | 20 | 20 | 18 | 0.45 | 2.24 | 2 | 0 3.0 | 72 | P |
| M37825_at | 10 | 3 | 20 | 20 | 18 | 0.50 | 1.50 | 0 | 0 3.3 | 70 | P |
| M54992_at | 10 | 3 | 20 | 20 | 18 | 0.50 | 1.38 | 0 | 0 3.3 | 70 | P |
| U10117_at | 9 | 3 | 20 | 20 | 18 | 0.45 | 1.52 | 1 | 0 3.0 | 70 | P |
| U12471_cc | 7 | 2 | 20 | 20 | 18 | 0.35 | 1.55 | 0 | 0 3.5 | 70 | P |
| U18242_at | 9 | 2 | 20 | 20 | 18 | 0.45 | 2.09 | 0 | 0 4.5 | 70 | P |
| U26032_at | 9 | 3 | 20 | 20 | 18 | 0.45 | 1.63 | 1 | 0 3.0 | 70 | P |
| M32886_at | 10 | 2 | 20 | 20 | 17 | 0.50 | 0.94 | 0 | 0 5.0 | 66 | P |
| U18291_at | 9 | 2 | 20 | 20 | 18 | 0.45 | 2.25 | 0 | 0 4.5 | 66 | P |
| S76965_at | 8 | 2 | 20 | 20 | 18 | 0.40 | 1.70 | 2 | 0 4.0 | 65 | P |
| U23070_at | 9 | 3 | 20 | 20 | 18 | 0.45 | 1.44 | 2 | 0 3.0 | 65 | P |
| M81379_at | 7 | 1 | 20 | 20 | 18 | 0.35 | 1.05 | 0 | 0 7.0 | 63 | P |
| U49436_at | 10 | 2 | 20 | 20 | 18 | 0.50 | 2.41 | 2 | 0 5.0 | 63 | P |
| M25393_at | 9 | 3 | 20 | 20 | 18 | 0.45 | 1.61 | 1 | 1 3.0 | 62 | P |
| M88579_at | 9 | 3 | 20 | 20 | 18 | 0.45 | 1.74 | 2 | 0 3.0 | 62 | P |
| M62397_at | 9 | 2 | 20 | 20 | 18 | 0.45 | 1.92 | 1 | 0 4.5 | 60 | P |
| M63823_at | 7 | 2 | 20 | 20 | 18 | 0.35 | 1.40 | 0 | 0 3.5 | 57 | P |
| U23942_at | 7 | 0 | 20 | 20 | 18 | 0.35 | 1.40 | 0 | 0 Inf | 56 | P |
| U18062_at | 8 | 1 | 20 | 20 | 18 | 0.40 | 1.83 | 1 | 0 8.0 | 50 | P |
| S67798_at | 8 | 2 | 20 | 20 | 18 | 0.40 | 1.33 | 0 | 0 4.0 | 49 | P |
| M74093_at | 8 | 2 | 20 | 20 | 18 | 0.40 | 1.09 | 0 | 0 4.0 | 48 | P |
| U00951_at | 8 | 2 | 20 | 20 | 18 | 0.40 | 1.61 | 1 | 0 4.0 | 47 | P |
| U50939_at | 7 | 2 | 20 | 20 | 18 | 0.35 | 1.47 | 1 | 0 3.5 | 46 | P |
| U24576_at | 8 | 2 | 20 | 20 | 18 | 0.40 | 2.15 | 1 | 0 4.0 | 42 | P |
| U07151_at | 8 | 2 | 20 | 20 | 18 | 0.40 | 1.14 | 0 | 0 4.0 | 40 | P |
| U38810_at | 8 | 1 | 20 | 20 | 18 | 0.40 | 1.37 | 1 | 0 8.0 | 40 | P |
| U13948_at | 9 | 2 | 20 | 20 | 18 | 0.45 | 1.61 | 1 | 0 4.5 | 37 | P |
| S78569_at | 7 | 1 | 20 | 20 | 18 | 0.35 | 0.99 | 0 | 0 7.0 | 35 | P |
| U28833_at | 7 | 1 | 20 | 20 | 18 | 0.35 | 1.04 | 0 | 1 7.0 | 33 | P |
| U29615_at | 8 | 2 | 20 | 20 | 18 | 0.40 | 1.05 | 0 | 0 4.0 | 33 | P |
| M81882_at | 8 | 2 | 20 | 20 | 18 | 0.40 | 1.65 | 1 | 0 4.0 | 31 | P |
| U57452_at | 7 | 1 | 20 | 20 | 18 | 0.35 | 0.96 | 0 | 0 7.0 | 29 | P |

Connective tissue C

| Gene Name | Posit | Negat | Pairs | Pairs | Pairs In | Pos Fracti | Log Avg | PM Ex MM Excess | Pos/Neg | Avg Diff | Abs Call |
|---|---|---|---|---|---|---|---|---|---|---|---|
| Z23090_at | 20 | 0 | 20 | 20 | 18 | 1.00 | 6.28 | 1 | 0 Inf | 9609 | P |
| Z70759_at | 20 | 0 | 20 | 20 | 18 | 1.00 | 8.75 | 11 | 0 Inf | 7648 | P |
| Z12962_at | 18 | 0 | 20 | 20 | 18 | 0.90 | 6.95 | 3 | 0 Inf | 7468 | P |
| X07695_at | 20 | 0 | 20 | 20 | 18 | 1.00 | 6.77 | 2 | 0 Inf | 7458 | P |
| hum_alu_at | 69 | 0 | 69 | 69 | 67 | 1.00 | 7.07 | 11 | 0 Inf | 7071 | P |

-continued

Connective tissue C

| Gene Name | Posit | Negat | Pairs | Pairs | Pairs In | Pos Fracti | Log Avg | PM Ex MM Excess | Pos/Neg | Avg Diff | Abs Call |
|---|---|---|---|---|---|---|---|---|---|---|---|
| X69150_at | 19 | 0 | 20 | 20 | 18 | 0.95 | 7.89 | 8 | 0 Inf | 6256 | P |
| X17206_at | 20 | 0 | 20 | 20 | 18 | 1.00 | 7.81 | 8 | 0 Inf | 4928 | P |
| X16064_at | 19 | 0 | 20 | 20 | 18 | 0.95 | 8.14 | 6 | 0 Inf | 4572 | P |
| X56932_at | 20 | 0 | 20 | 20 | 18 | 1.00 | 7.69 | 5 | 0 Inf | 4210 | P |
| AFFX-HUMGAPDH/M33197_3_at | 20 | 0 | 20 | 20 | 18 | 1.00 | 7.15 | 2 | 0 Inf | 4188 | P |
| AFFX-HSAC07/X00351_M_at | 20 | 0 | 20 | 20 | 18 | 1.00 | 6.52 | 1 | 0 Inf | 3970 | P |
| X80822_at | 19 | 0 | 20 | 20 | 18 | 0.95 | 6.50 | 1 | 0 Inf | 3963 | P |
| X03342_at | 20 | 0 | 20 | 20 | 18 | 1.00 | 7.76 | 5 | 0 Inf | 3818 | P |
| X67247_ma1_at | 20 | 0 | 20 | 20 | 18 | 1.00 | 8.34 | 6 | 0 Inf | 3725 | P |
| X06617_at | 20 | 0 | 20 | 20 | 18 | 1.00 | 6.38 | 2 | 0 Inf | 3387 | P |
| X15940_at | 19 | 0 | 20 | 20 | 18 | 0.95 | 7.29 | 5 | 0 Inf | 3375 | P |
| X63527_at | 19 | 0 | 20 | 20 | 18 | 0.95 | 7.71 | 7 | 0 Inf | 3282 | P |
| X05908_at | 19 | 0 | 20 | 20 | 18 | 0.95 | 8.70 | 8 | 0 Inf | 3217 | P |
| AFFX-CreX-3_at | 19 | 0 | 20 | 20 | 18 | 0.95 | 8.12 | 6 | 0 Inf | 3155 | P |
| AFFX-HSAC07/X00351_3_at | 20 | 0 | 20 | 20 | 18 | 1.00 | 6.57 | 2 | 0 Inf | 2994 | P |
| X73460_at | 19 | 0 | 20 | 20 | 18 | 0.95 | 6.62 | 3 | 0 Inf | 2949 | P |
| X62691_at | 20 | 0 | 20 | 20 | 18 | 1.00 | 7.33 | 4 | 0 Inf | 2885 | P |
| AFFX-HSAC07/X00351_5_at | 19 | 0 | 20 | 20 | 18 | 0.95 | 6.46 | 1 | 0 Inf | 2782 | P |
| X00274_at | 20 | 0 | 20 | 20 | 18 | 1.00 | 7.97 | 8 | 0 Inf | 2780 | P |
| AFFX-HUMGAPDH/M33197_M_at | 18 | 0 | 20 | 20 | 18 | 0.90 | 5.92 | 0 | 0 Inf | 2639 | P |
| X79234_at | 20 | 0 | 20 | 20 | 18 | 1.00 | 8.10 | 4 | 0 Inf | 2602 | P |
| X55954_at | 20 | 0 | 20 | 20 | 18 | 1.00 | 7.53 | 6 | 0 Inf | 2495 | P |
| Z26876_at | 20 | 0 | 20 | 20 | 18 | 1.00 | 7.65 | 6 | 0 Inf | 2490 | P |
| Z28407_at | 17 | 0 | 20 | 20 | 18 | 0.85 | 5.59 | 1 | 0 Inf | 2386 | P |
| Y07755_at | 19 | 0 | 20 | 20 | 18 | 0.95 | 7.10 | 2 | 0 Inf | 2378 | P |
| X64707_at | 19 | 0 | 20 | 20 | 18 | 0.95 | 5.87 | 2 | 0 Inf | 2268 | P |
| AFFX-CreX-5_at | 19 | 0 | 20 | 20 | 18 | 0.95 | 7.77 | 3 | 0 Inf | 2185 | P |
| U78027_ma3_at | 18 | 2 | 20 | 20 | 18 | 0.90 | 7.38 | 6 | 0 9.0 | 2156 | P |
| X67683_at | 19 | 0 | 20 | 20 | 18 | 0.95 | 5.62 | 1 | 0 Inf | 2126 | P |
| AFFX-HUMGAPDH/M33197_5_at | 19 | 0 | 20 | 20 | 18 | 0.95 | 7.18 | 6 | 0 Inf | 2120 | P |
| X69391_at | 19 | 0 | 20 | 20 | 18 | 0.95 | 7.24 | 4 | 0 Inf | 2094 | P |
| A6002533_at | 18 | 0 | 20 | 20 | 18 | 0.90 | 5.92 | 0 | 0 Inf | 2063 | P |
| X68277_at | 19 | 0 | 20 | 20 | 18 | 0.95 | 8.28 | 7 | 0 Inf | 1972 | P |
| X53777_at | 18 | 1 | 20 | 20 | 18 | 0.90 | 7.13 | 6 | 0 18.0 | 1915 | P |
| X55715_at | 20 | 0 | 20 | 20 | 18 | 1.00 | 7.32 | 2 | 0 Inf | 1744 | P |
| X52851_rna1_at | 20 | 0 | 20 | 20 | 18 | 1.00 | 6.55 | 3 | 0 Inf | 1727 | P |
| X67951_at | 20 | 0 | 20 | 20 | 18 | 1.00 | 6.97 | 2 | 0 Inf | 1472 | P |
| X77584_at | 19 | 0 | 20 | 20 | 18 | 0.95 | 7.09 | 3 | 0 Inf | 1470 | P |
| X02152_at | 18 | 0 | 20 | 20 | 18 | 0.90 | 6.79 | 2 | 0 Inf | 1432 | P |
| X57959_at | 19 | 0 | 20 | 20 | 18 | 0.95 | 7.24 | 3 | 0 Inf | 1426 | P |
| X13839_at | 18 | 0 | 20 | 20 | 18 | 0.90 | 6.61 | 3 | 0 Inf | 1405 | P |
| AFFX-BioDn-3_at | 17 | 2 | 20 | 20 | 18 | 0.85 | 4.13 | 0 | 0 8.5 | 1401 | P |
| X52966_at | 17 | 1 | 20 | 20 | 18 | 0.85 | 6.56 | 5 | 0 17.0 | 1361 | P |
| X15341_at | 20 | 0 | 20 | 20 | 18 | 1.00 | 6.91 | 6 | 0 Inf | 1338 | P |
| X56997_ma1_at | 17 | 0 | 20 | 20 | 18 | 0.85 | 5.20 | 2 | 0 Inf | 1308 | P |
| X80909_at | 18 | 0 | 20 | 20 | 18 | 0.90 | 7.15 | 4 | 0 Inf | 1203 | P |
| X60489_at | 19 | 0 | 20 | 20 | 18 | 0.95 | 6.91 | 4 | 0 Inf | 1169 | P |
| X12447_at | 15 | 0 | 20 | 20 | 18 | 0.75 | 3.29 | 1 | 0 Inf | 1127 | P |
| Z25749_ma1_at | 18 | 1 | 20 | 20 | 18 | 0.90 | 5.26 | 0 | 0 18.0 | 1122 | P |
| X51466_at | 16 | 0 | 20 | 20 | 18 | 0.80 | 5.14 | 1 | 0 Inf | 1116 | P |
| X53331_at | 18 | 0 | 20 | 20 | 18 | 0.90 | 6.29 | 1 | 0 Inf | 1079 | P |
| Z19574_ma1_at | 19 | 0 | 20 | 20 | 18 | 0.95 | 5.04 | 0 | 0 Inf | 1069 | P |
| X82693_at | 19 | 0 | 20 | 20 | 18 | 0.95 | 4.56 | 0 | 0 Inf | 1046 | P |
| X95404_at | 15 | 0 | 20 | 20 | 18 | 0.75 | 4.66 | 1 | 0 Inf | 960 | P |
| AF001548_ma1_at | 17 | 0 | 20 | 20 | 18 | 0.85 | 5.12 | 1 | 0 Inf | 950 | P |
| X15183_at | 17 | 1 | 20 | 20 | 18 | 0.85 | 6.82 | 2 | 0 17.0 | 919 | P |
| U94586_at | 20 | 0 | 20 | 20 | 17 | 1.00 | 8.01 | 6 | 0 Inf | 876 | P |
| X16560_at | 17 | 0 | 20 | 20 | 18 | 0.85 | 6.16 | 3 | 0 Inf | 858 | P |
| U65932_at | 19 | 0 | 20 | 20 | 18 | 0.95 | 5.61 | 0 | 0 Inf | 853 | P |
| X07696_at | 17 | 0 | 20 | 20 | 18 | 0.85 | 5.66 | 1 | 0 Inf | 777 | P |
| X15822_at | 18 | 0 | 20 | 20 | 18 | 0.90 | 5.06 | 3 | 0 Inf | 760 | P |
| V00572_at | 20 | 0 | 20 | 20 | 18 | 1.00 | 6.57 | 2 | 0 Inf | 758 | P |
| X04412_at | 17 | 1 | 20 | 20 | 18 | 0.85 | 4.49 | 1 | 0 17.0 | 746 | P |
| X93036_at | 16 | 0 | 20 | 20 | 17 | 0.80 | 4.59 | 1 | 0 Inf | 730 | P |
| Y00433_at | 17 | 0 | 20 | 20 | 18 | 0.85 | 4.30 | 0 | 0 Inf | 708 | P |
| X65614_at | 18 | 0 | 20 | 20 | 18 | 0.90 | 5.02 | 1 | 0 Inf | 687 | P |
| U90915_at | 18 | 1 | 20 | 20 | 18 | 0.90 | 5.53 | 3 | 0 18.0 | 684 | P |
| X16832_at | 16 | 0 | 20 | 20 | 18 | 0.80 | 4.30 | 0 | 0 Inf | 661 | P |
| X05276_at | 19 | 0 | 20 | 20 | 18 | 0.95 | 4.58 | 0 | 0 Inf | 642 | P |
| AFFX-HSAC07/X00351_3_st | 18 | 0 | 20 | 20 | 18 | 0.90 | 4.98 | 0 | 0 Inf | 630 | P |
| U73824_at | 19 | 0 | 20 | 20 | 18 | 0.95 | 6.59 | 3 | 0 Inf | 586 | P |
| V01512_ma1_at | 19 | 0 | 20 | 20 | 18 | 0.95 | 6.39 | 2 | 0 Inf | 574 | P |
| U93205_at | 18 | 0 | 20 | 20 | 18 | 0.90 | 3.74 | 0 | 0 Inf | 570 | P |
| X13238_at | 17 | 1 | 20 | 20 | 18 | 0.85 | 5.69 | 1 | 0 17.0 | 563 | P |

-continued

Connective tissue C

| Gene Name | Posit | Negat | Pairs | Pairs | Pairs In | Pos Fracti | Log Avg | PM Ex MM Excess | Pos/Neg | Avg Diff | Abs Call |
|---|---|---|---|---|---|---|---|---|---|---|---|
| X56494_at | 14 | 1 | 20 | 20 | 18 | 0.70 | 3.58 | 1 | 0 14.0 | 563 | P |
| X07979_at | 18 | 1 | 20 | 20 | 17 | 0.90 | 5.96 | 2 | 0 18.0 | 543 | P |
| X86693_at | 16 | 0 | 20 | 20 | 18 | 0.80 | 5.33 | 2 | 0 Inf | 533 | P |
| Z48950_at | 17 | 0 | 20 | 20 | 18 | 0.85 | 4.43 | 0 | 0 Inf | 527 | P |
| X02317_at | 19 | 0 | 20 | 20 | 18 | 0.95 | 5.45 | 0 | 0 Inf | 509 | P |
| X59834_at | 17 | 1 | 20 | 20 | 18 | 0.85 | 5.44 | 0 | 0 17.0 | 482 | P |
| Z24727_at | 17 | 0 | 20 | 20 | 18 | 0.85 | 5.17 | 2 | 0 Inf | 464 | P |
| X56468_at | 18 | 0 | 20 | 20 | 18 | 0.90 | 5.18 | 1 | 0 Inf | 462 | P |
| X03100_cds2_at | 14 | 0 | 20 | 20 | 18 | 0.70 | 3.38 | 1 | 0 Inf | 457 | P |
| Y00503_at | 18 | 0 | 20 | 20 | 18 | 0.90 | 4.44 | 0 | 0 Inf | 452 | P |
| U67171_at | 12 | 0 | 20 | 20 | 18 | 0.60 | 2.64 | 0 | 0 Inf | 440 | P |
| U78095_at | 16 | 1 | 20 | 20 | 17 | 0.80 | 3.28 | 0 | 0 16.0 | 435 | P |
| X15880_at | 10 | 1 | 20 | 20 | 18 | 0.50 | 3.09 | 0 | 0 10.0 | 429 | P |
| X69550_at | 13 | 1 | 20 | 20 | 18 | 0.65 | 2.30 | 0 | 0 13.0 | 420 | P |
| X62654_ma1_at | 17 | 1 | 20 | 20 | 17 | 0.85 | 3.73 | 1 | 0 17.0 | 404 | P |
| X67698_at | 17 | 0 | 20 | 20 | 18 | 0.85 | 3.49 | 0 | 0 Inf | 401 | P |
| U72511_at | 15 | 0 | 20 | 20 | 18 | 0.75 | 3.49 | 1 | 0 Inf | 383 | P |
| X04106_at | 13 | 2 | 20 | 20 | 18 | 0.65 | 2.50 | 0 | 0 6.5 | 383 | P |
| X68314_at | 14 | 0 | 20 | 20 | 18 | 0.70 | 3.09 | 0 | 0 Inf | 380 | P |
| X51521_at | 19 | 1 | 20 | 20 | 18 | 0.95 | 4.60 | 1 | 0 19.0 | 376 | P |
| X60036_at | 17 | 0 | 20 | 20 | 18 | 0.85 | 4.60 | 0 | 0 Inf | 376 | P |
| U79294_at | 15 | 1 | 20 | 20 | 18 | 0.75 | 3.95 | 2 | 0 15.0 | 370 | P |
| X59892_at | 12 | 1 | 20 | 20 | 18 | 0.60 | 2.57 | 0 | 0 12.0 | 366 | P |
| U70370_at | 12 | 2 | 20 | 20 | 18 | 0.60 | 2.66 | 1 | 0 6.0 | 361 | P |
| X91504_at | 11 | 1 | 20 | 20 | 18 | 0.55 | 1.54 | 0 | 0 11.0 | 360 | P |
| U73843_at | 13 | 1 | 20 | 20 | 18 | 0.65 | 3.39 | 1 | 0 13.0 | 356 | P |
| L20688_at | 13 | 0 | 20 | 20 | 18 | 0.65 | 2.63 | 0 | 0 Inf | 356 | P |
| X16662_at | 14 | 2 | 20 | 20 | 18 | 0.70 | 3.64 | 1 | 0 7.0 | 355 | P |
| X54304_at | 15 | 0 | 20 | 20 | 18 | 0.75 | 3.90 | 0 | 0 Inf | 350 | P |
| Y00764_at | 17 | 1 | 20 | 20 | 18 | 0.85 | 5.54 | 2 | 0 17.0 | 347 | P |
| Z29505_at | 18 | 0 | 20 | 20 | 18 | 0.90 | 4.62 | 0 | 0 Inf | 345 | P |
| U90878_at | 16 | 1 | 20 | 20 | 18 | 0.80 | 5.35 | 0 | 0 16.0 | 335 | P |
| Z21507_at | 15 | 1 | 20 | 20 | 18 | 0.75 | 4.26 | 0 | 0 15.0 | 335 | P |
| Z32765_at | 11 | 1 | 20 | 20 | 18 | 0.55 | 2.00 | 0 | 0 11.0 | 330 | P |
| X60221_at | 17 | 1 | 20 | 20 | 18 | 0.85 | 5.00 | 0 | 0 17.0 | 329 | P |
| X62320_at | 10 | 0 | 20 | 20 | 18 | 0.50 | 2.31 | 0 | 0 Inf | 327 | P |
| X83218_at | 17 | 0 | 20 | 20 | 18 | 0.85 | 5.26 | 0 | 0 Inf | 322 | P |
| X52003_at | 9 | 2 | 20 | 20 | 18 | 0.45 | 2.33 | 0 | 0 4.5 | 321 | P |
| X15882_at | 11 | 2 | 20 | 20 | 18 | 0.55 | 1.84 | 0 | 0 5.5 | 314 | P |
| X17042_at | 16 | 0 | 20 | 20 | 17 | 0.80 | 5.83 | 3 | 0 Inf | 314 | P |
| X78136_at | 15 | 1 | 20 | 20 | 18 | 0.75 | 4.66 | 0 | 0 15.0 | 309 | P |
| Y00486_ma1_at | 8 | 0 | 20 | 20 | 18 | 0.40 | 1.74 | 0 | 0 Inf | 307 | P |
| X13794_ma1_at | 16 | 1 | 20 | 20 | 18 | 0.80 | 4.91 | 1 | 0 16.0 | 300 | P |
| U70735_at | 17 | 0 | 20 | 20 | 18 | 0.85 | 3.57 | 0 | 0 Inf | 298 | P |
| X71973_at | 12 | 1 | 20 | 20 | 18 | 0.60 | 2.30 | 0 | 0 12.0 | 297 | P |
| U78521_at | 9 | 0 | 20 | 20 | 18 | 0.45 | 1.26 | 0 | 0 Inf | 296 | P |
| U94855_at | 18 | 0 | 20 | 20 | 18 | 0.90 | 4.74 | 0 | 0 Inf | 293 | P |
| D29805_at | 11 | 3 | 20 | 20 | 18 | 0.55 | 2.57 | 1 | 0 3.7 | 291 | P |
| X75861_at | 16 | 1 | 20 | 20 | 18 | 0.80 | 4.65 | 1 | 0 16.0 | 290 | P |
| AFFX-BioDn-5_at | 13 | 0 | 20 | 20 | 18 | 0.65 | 3.14 | 0 | 0 Inf | 288 | P |
| U77604_at | 13 | 1 | 20 | 20 | 18 | 0.65 | 2.79 | 0 | 0 13.0 | 286 | P |
| X90858_at | 15 | 2 | 20 | 20 | 18 | 0.75 | 3.54 | 0 | 0 7.5 | 285 | P |
| X86809_at | 11 | 1 | 20 | 20 | 18 | 0.55 | 1.89 | 0 | 0 11.0 | 283 | P |
| X80692_at | 14 | 0 | 20 | 20 | 18 | 0.70 | 3.84 | 0 | 0 Inf | 276 | P |
| U72512_at | 7 | 0 | 20 | 20 | 17 | 0.35 | 1.41 | 0 | 0 Inf | 272 | P |
| X55733_at | 14 | 0 | 20 | 20 | 18 | 0.70 | 3.92 | 2 | 0 Inf | 272 | P |
| Y00281_at | 14 | 2 | 20 | 20 | 18 | 0.70 | 3.22 | 0 | 0 7.0 | 272 | P |
| U90313_at | 17 | 0 | 20 | 20 | 18 | 0.85 | 3.76 | 0 | 0 Inf | 270 | P |
| X81817_at | 15 | 2 | 20 | 20 | 18 | 0.75 | 3.43 | 1 | 0 7.5 | 266 | P |
| Z48199_at | 10 | 1 | 20 | 20 | 18 | 0.50 | 1.74 | 0 | 0 10.0 | 263 | P |
| U77594_at | 10 | 0 | 20 | 20 | 18 | 0.50 | 2.03 | 0 | 0 Inf | 262 | P |
| X75593_at | 10 | 2 | 20 | 20 | 18 | 0.50 | 2.92 | 1 | 0 5.0 | 260 | P |
| Z14244_at | 18 | 0 | 20 | 20 | 17 | 0.90 | 6.43 | 5 | 0 Inf | 260 | P |
| X91247_at | 18 | 1 | 20 | 20 | 18 | 0.90 | 4.44 | 0 | 0 18.0 | 258 | P |
| X06985_at | 11 | 1 | 20 | 20 | 18 | 0.55 | 2.03 | 1 | 0 11.0 | 257 | P |
| X76180_at | 12 | 1 | 20 | 20 | 18 | 0.60 | 2.72 | 0 | 0 12.0 | 255 | P |
| X76717_at | 10 | 1 | 20 | 20 | 18 | 0.50 | 2.26 | 0 | 0 10.0 | 251 | P |
| U65785_at | 11 | 0 | 20 | 20 | 18 | 0.55 | 1.75 | 0 | 0 Inf | 249 | P |
| X91257_at | 13 | 0 | 20 | 20 | 18 | 0.65 | 3.06 | 0 | 0 Inf | 249 | P |
| X87838_at | 16 | 0 | 20 | 20 | 18 | 0.80 | 4.72 | 1 | 0 Inf | 248 | P |
| X75252_at | 12 | 1 | 20 | 20 | 18 | 0.60 | 3.02 | 0 | 0 12.0 | 247 | P |
| X97074_at | 12 | 0 | 20 | 20 | 18 | 0.60 | 2.12 | 0 | 0 Inf | 247 | P |
| X16135_at | 14 | 2 | 20 | 20 | 18 | 0.70 | 3.23 | 0 | 0 7.0 | 242 | P |
| X99688_at | 9 | 1 | 20 | 20 | 18 | 0.45 | 1.72 | 0 | 0 9.0 | 242 | P |

-continued

Connective tissue C

| Gene Name | Posit | Negat | Pairs | Pairs | Pairs In | Pos Fracti | Log Avg | PM Ex MM Excess | Pos/Neg | Avg Diff | Abs Call |
|---|---|---|---|---|---|---|---|---|---|---|---|
| U84569_at | 13 | 2 | 20 | 20 | 17 | 0.65 | 1.94 | 0 | 0 6.5 | 241 | P |
| X13444_at | 9 | 0 | 20 | 20 | 18 | 0.45 | 1.61 | 0 | 0 Inf | 241 | P |
| U70732_ma1_at | 9 | 2 | 20 | 20 | 18 | 0.45 | 1.35 | 0 | 0 4.5 | 240 | P |
| X71428_at | 11 | 1 | 20 | 20 | 18 | 0.55 | 2.25 | 0 | 0 11.0 | 240 | P |
| U83115_at | 13 | 0 | 20 | 20 | 18 | 0.65 | 3.05 | 1 | 0 Inf | 239 | P |
| X82434_at | 11 | 0 | 20 | 20 | 18 | 0.55 | 1.84 | 0 | 0 Inf | 237 | P |
| X59417_at | 14 | 2 | 20 | 20 | 18 | 0.70 | 2.91 | 1 | 1 7.0 | 231 | P |
| X57346_at | 13 | 1 | 20 | 20 | 17 | 0.65 | 3.80 | 0 | 0 13.0 | 230 | P |
| X85785_ma1_at | 9 | 0 | 20 | 20 | 18 | 0.45 | 1.61 | 0 | 0 Inf | 229 | P |
| X13546_ma1_at | 15 | 0 | 20 | 20 | 17 | 0.75 | 2.97 | 0 | 0 Inf | 222 | P |
| X52730_ma1_at | 8 | 0 | 20 | 20 | 18 | 0.40 | 1.24 | 0 | 0 Inf | 222 | P |
| X74104_at | 15 | 1 | 20 | 20 | 18 | 0.75 | 4.00 | 1 | 0 15.0 | 222 | P |
| U66879_at | 9 | 2 | 20 | 20 | 17 | 0.45 | 2.00 | 0 | 0 4.5 | 221 | P |
| Z27113_at | 11 | 1 | 20 | 20 | 18 | 0.55 | 2.14 | 0 | 0 11.0 | 221 | P |
| U66059_cds7_at | 10 | 1 | 20 | 20 | 18 | 0.50 | 1.73 | 0 | 0 10.0 | 220 | P |
| D13146_cds1_at | 7 | 0 | 20 | 20 | 18 | 0.35 | 1.70 | 0 | 0 Inf | 218 | P |
| AFFX-BioC-5_at | 16 | 0 | 20 | 20 | 18 | 0.80 | 3.02 | 0 | 0 Inf | 217 | P |
| X69910_at | 15 | 1 | 20 | 20 | 18 | 0.75 | 3.67 | 0 | 0 15.0 | 217 | P |
| U78678_at | 9 | 1 | 20 | 20 | 18 | 0.45 | 1.58 | 0 | 0 9.0 | 215 | P |
| X76013_at | 11 | 1 | 20 | 20 | 18 | 0.55 | 2.70 | 0 | 0 11.0 | 215 | P |
| U70867_at | 9 | 1 | 20 | 20 | 18 | 0.45 | 1.44 | 0 | 0 9.0 | 212 | P |
| X69433_at | 9 | 1 | 20 | 20 | 18 | 0.45 | 2.12 | 0 | 0 9.0 | 212 | P |
| X96924_ma1_at | 7 | 1 | 20 | 20 | 18 | 0.35 | 1.37 | 0 | 0 7.0 | 212 | P |
| U77827_at | 9 | 0 | 20 | 20 | 18 | 0.45 | 1.98 | 1 | 0 Inf | 209 | P |
| X69908_rna1_at | 9 | 2 | 20 | 20 | 18 | 0.45 | 2.00 | 1 | 0 4.5 | 209 | P |
| X80200_at | 10 | 1 | 20 | 20 | 17 | 0.50 | 2.04 | 0 | 0 10.0 | 208 | P |
| Z11793_at | 15 | 1 | 20 | 20 | 18 | 0.75 | 4.49 | 4 | 0 15.0 | 208 | P |
| U81556_at | 12 | 2 | 20 | 20 | 18 | 0.60 | 2.25 | 0 | 0 6.0 | 207 | P |
| U67963_at | 9 | 1 | 20 | 20 | 18 | 0.45 | 2.10 | 0 | 0 9.0 | 206 | P |
| X99585_at | 14 | 1 | 20 | 20 | 18 | 0.70 | 4.48 | 1 | 0 14.0 | 206 | P |
| U68566_at | 10 | 2 | 20 | 20 | 18 | 0.50 | 1.94 | 0 | 0 5.0 | 204 | P |
| U77396_at | 8 | 0 | 20 | 20 | 18 | 0.40 | 1.53 | 0 | 0 Inf | 201 | P |
| U88629_at | 12 | 1 | 20 | 20 | 18 | 0.60 | 3.30 | 0 | 0 12.0 | 199 | P |
| X02612_at | 12 | 1 | 20 | 20 | 18 | 0.60 | 2.99 | 0 | 0 12.0 | 199 | P |
| X15187_at | 14 | 1 | 20 | 20 | 18 | 0.70 | 3.68 | 0 | 0 14.0 | 199 | P |
| Y00282_at | 14 | 0 | 20 | 20 | 18 | 0.70 | 3.70 | 1 | 0 Inf | 199 | P |
| U85611_at | 11 | 1 | 20 | 20 | 18 | 0.55 | 2.16 | 0 | 0 11.0 | 192 | P |
| X72964_at | 12 | 0 | 20 | 20 | 18 | 0.60 | 2.74 | 0 | 0 Inf | 192 | P |
| U73379_at | 12 | 0 | 20 | 20 | 17 | 0.60 | 1.94 | 0 | 0 Inf | 191 | P |
| X56253_rna1_at | 12 | 1 | 20 | 20 | 18 | 0.60 | 2.65 | 1 | 0 12.0 | 191 | P |
| X64559_at | 10 | 1 | 20 | 20 | 18 | 0.50 | 1.50 | 0 | 0 10.0 | 190 | P |
| U86529_at | 7 | 0 | 20 | 20 | 18 | 0.35 | 1.56 | 0 | 0 Inf | 189 | P |
| X04366_at | 11 | 1 | 20 | 20 | 18 | 0.55 | 2.47 | 0 | 0 11.0 | 188 | P |
| X52947_at | 14 | 0 | 20 | 20 | 18 | 0.70 | 5.43 | 2 | 0 Inf | 188 | P |
| U70663_at | 8 | 0 | 20 | 20 | 18 | 0.40 | 1.58 | 0 | 0 Inf | 187 | P |
| X89750_at | 19 | 0 | 20 | 20 | 18 | 0.95 | 4.23 | 0 | 0 Inf | 186 | P |
| Y08976_at | 9 | 1 | 20 | 20 | 18 | 0.45 | 1.58 | 0 | 0 9.0 | 185 | P |
| X69699_at | 7 | 0 | 20 | 20 | 18 | 0.35 | 1.59 | 0 | 0 Inf | 183 | P |
| X01388_at | 7 | 1 | 20 | 20 | 18 | 0.35 | 1.02 | 0 | 0 7.0 | 182 | P |
| U70063_at | 9 | 3 | 20 | 20 | 18 | 0.45 | 2.13 | 0 | 0 3.0 | 176 | P |
| U72517_at | 10 | 2 | 20 | 20 | 18 | 0.50 | 1.55 | 0 | 0 5.0 | 175 | P |
| X76228_at | 11 | 1 | 20 | 20 | 18 | 0.55 | 2.50 | 0 | 0 11.0 | 175 | P |
| X78549_at | 13 | 0 | 20 | 20 | 17 | 0.65 | 1.73 | 1 | 0 Inf | 175 | P |
| Z14000_at | 7 | 0 | 20 | 20 | 18 | 0.35 | 1.05 | 0 | 0 Inf | 174 | P |
| 9254_at | 13 | 1 | 20 | 20 | 18 | 0.65 | 4.22 | 0 | 0 13.0 | 165 | P |
| 62078_at | 9 | 0 | 20 | 20 | 18 | 0.45 | 1.84 | 0 | 0 Inf | 165 | P |
| U94585_at | 10 | 3 | 20 | 20 | 18 | 0.50 | 1.40 | 0 | 0 3.3 | 163 | P |
| U72066_at | 11 | 1 | 20 | 20 | 18 | 0.55 | 1.50 | 0 | 0 11.0 | 162 | P |
| U88964_at | 9 | 1 | 20 | 20 | 18 | 0.45 | 2.60 | 0 | 0 9.0 | 161 | P |
| U70660_at | 9 | 1 | 20 | 20 | 18 | 0.45 | 1.35 | 0 | 0 9.0 | 160 | P |
| X52541_at | 16 | 0 | 20 | 20 | 17 | 0.80 | 3.99 | 2 | 0 Inf | 160 | P |
| X95586_at | 16 | 0 | 20 | 20 | 18 | 0.80 | 3.20 | 0 | 0 Inf | 160 | P |
| X71129_at | 10 | 1 | 20 | 20 | 17 | 0.50 | 1.89 | 1 | 0 10.0 | 159 | P |
| X53416_at | 8 | 0 | 20 | 20 | 18 | 0.40 | 1.65 | 0 | 0 Inf | 158 | P |
| X12794_at | 8 | 1 | 20 | 20 | 18 | 0.40 | 1.58 | 0 | 0 8.0 | 157 | P |
| X61970_at | 13 | 0 | 20 | 20 | 18 | 0.65 | 3.44 | 0 | 0 Inf | 157 | P |
| Z37986_at | 9 | 1 | 20 | 20 | 18 | 0.45 | 1.61 | 0 | 0 9.0 | 157 | P |
| J04182_at | 12 | 1 | 20 | 20 | 18 | 0.60 | 2.60 | 0 | 0 12.0 | 157 | P |
| AFFX-BioC-3_at | 11 | 1 | 20 | 20 | 18 | 0.55 | 2.12 | 0 | 0 11.0 | 156 | P |
| X14787_at | 12 | 2 | 20 | 20 | 18 | 0.60 | 4.02 | 0 | 1 6.0 | 155 | P |
| X62535_at | 10 | 0 | 20 | 20 | 18 | 0.50 | 2.78 | 1 | 0 Inf | 155 | P |
| X85373_at | 11 | 0 | 20 | 20 | 18 | 0.55 | 2.75 | 1 | 0 Inf | 155 | P |
| X96484_at | 10 | 1 | 20 | 20 | 18 | 0.50 | 1.71 | 0 | 0 10.0 | 154 | P |
| X98311_at | 9 | 0 | 20 | 20 | 18 | 0.45 | 1.80 | 0 | 0 Inf | 154 | P |

-continued

Connective tissue C

| Gene Name | Posit | Negat | Pairs | Pairs | Pairs In | Pos Fracti | Log Avg | PM Ex MM Excess | Pos/Neg | Avg Diff | Abs Call |
|---|---|---|---|---|---|---|---|---|---|---|---|
| L00205_at | 12 | 0 | 20 | 20 | 18 | 0.60 | 2.47 | 0 | 0 Inf | 154 | P |
| X16316_at | 10 | 2 | 20 | 20 | 18 | 0.50 | 1.87 | 0 | 0 5.0 | 153 | P |
| U69263_at | 14 | 1 | 20 | 20 | 17 | 0.70 | 2.22 | 0 | 0 14.0 | 152 | P |
| X74801_at | 11 | 0 | 20 | 20 | 18 | 0.55 | 3.34 | 0 | 0 Inf | 152 | P |
| U70322_at | 13 | 1 | 20 | 20 | 18 | 0.65 | 2.19 | 0 | 0 13.0 | 151 | P |
| D86988_at | 7 | 0 | 20 | 20 | 18 | 0.35 | 1.09 | 0 | 0 Inf | 151 | P |
| V00563_at | 11 | 1 | 20 | 20 | 18 | 0.55 | 2.59 | 1 | 0 11.0 | 150 | P |
| X76029_at | 7 | 2 | 20 | 20 | 18 | 0.35 | 1.35 | 0 | 0 3.5 | 150 | P |
| U78798_at | 9 | 3 | 20 | 20 | 18 | 0.45 | 1.83 | 0 | 0 3.0 | 148 | P |
| X90872_at | 12 | 2 | 20 | 20 | 18 | 0.60 | 1.80 | 0 | 0 6.0 | 148 | P |
| U78524_at | 7 | 1 | 20 | 20 | 18 | 0.35 | 1.34 | 1 | 0 7.0 | 147 | P |
| X04500_at | 9 | 2 | 20 | 20 | 17 | 0.45 | 1.39 | 0 | 0 4.5 | 147 | P |
| X12791_at | 12 | 1 | 20 | 20 | 18 | 0.60 | 2.05 | 0 | 0 12.0 | 146 | P |
| X80199_at | 12 | 1 | 20 | 20 | 18 | 0.60 | 2.67 | 0 | 0 12.0 | 146 | P |
| X83425_at | 9 | 2 | 20 | 20 | 18 | 0.45 | 1.76 | 0 | 0 4.5 | 146 | P |
| X13967_at | 9 | 2 | 20 | 20 | 18 | 0.45 | 1.96 | 0 | 0 4.5 | 145 | P |
| X63422_at | 9 | 2 | 20 | 20 | 17 | 0.45 | 2.55 | 0 | 0 4.5 | 145 | P |
| X74008_at | 9 | 3 | 20 | 20 | 18 | 0.45 | 2.32 | 1 | 0 3.0 | 145 | P |
| X99920_at | 12 | 0 | 20 | 20 | 18 | 0.60 | 2.96 | 1 | 0 Inf | 145 | P |
| Z50022_at | 12 | 1 | 20 | 20 | 18 | 0.60 | 1.68 | 0 | 0 12.0 | 145 | P |
| X74795_at | 11 | 3 | 20 | 20 | 17 | 0.55 | 2.46 | 0 | 0 3.7 | 143 | P |
| X68733_ma1_at | 8 | 0 | 20 | 20 | 18 | 0.40 | 1.30 | 0 | 0 Inf | 142 | P |
| X76534_at | 15 | 0 | 20 | 20 | 17 | 0.75 | 4.66 | 1 | 0 Inf | 142 | P |
| X82456_at | 15 | 0 | 20 | 20 | 18 | 0.75 | 3.79 | 1 | 0 Inf | 142 | P |
| Z47727_at | 12 | 0 | 20 | 20 | 18 | 0.60 | 2.81 | 0 | 0 Inf | 142 | P |
| U82010_rna1_at | 12 | 0 | 20 | 20 | 18 | 0.60 | 2.54 | 1 | 0 Inf | 141 | P |
| U70451_at | 7 | 1 | 20 | 20 | 18 | 0.35 | 1.19 | 0 | 0 7.0 | 139 | P |
| X17620_at | 8 | 2 | 20 | 20 | 18 | 0.40 | 1.31 | 0 | 0 4.0 | 139 | P |
| X76770_at | 13 | 1 | 20 | 20 | 18 | 0.65 | 3.07 | 0 | 0 13.0 | 139 | P |
| AFFX-HUMRGE/M10098_5_at | 10 | 2 | 20 | 20 | 18 | 0.50 | 2.39 | 0 | 0 5.0 | 138 | P |
| U68063_at | 14 | 0 | 20 | 20 | 18 | 0.70 | 3.15 | 0 | 0 Inf | 137 | P |
| U77948_at | 14 | 0 | 20 | 20 | 18 | 0.70 | 3.86 | 0 | 0 Inf | 137 | P |
| D50405_at | 11 | 1 | 20 | 20 | 18 | 0.55 | 1.94 | 0 | 0 11.0 | 137 | P |
| HG651-HT4201_at | 7 | 0 | 20 | 20 | 18 | 0.35 | 1.44 | 0 | 0 Inf | 136 | P |
| U89336_cds3_at | 10 | 0 | 20 | 20 | 18 | 0.50 | 1.83 | 0 | 0 Inf | 134 | P |
| X76342_at | 13 | 2 | 20 | 20 | 18 | 0.65 | 2.84 | 0 | 0 6.5 | 132 | P |
| X54232_at | 10 | 1 | 20 | 20 | 17 | 0.50 | 1.70 | 0 | 0 10.0 | 131 | P |
| X70476_at | 12 | 0 | 20 | 20 | 17 | 0.60 | 2.84 | 1 | 0 Inf | 131 | P |
| U68488_at | 9 | 1 | 20 | 20 | 18 | 0.45 | 1.34 | 0 | 0 9.0 | 130 | P |
| X01060_at | 14 | 2 | 20 | 20 | 18 | 0.70 | 2.96 | 0 | 0 7.0 | 130 | P |
| X14675_at | 9 | 0 | 20 | 20 | 18 | 0.45 | 1.41 | 0 | 0 Inf | 130 | P |
| Y10032_at | 14 | 4 | 20 | 20 | 18 | 0.70 | 2.96 | 3 | 1 3.5 | 130 | P |
| 016105_at | 8 | 1 | 20 | 20 | 18 | 0.40 | 1.31 | 0 | 0 8.0 | 130 | P |
| U86070_at | 11 | 3 | 20 | 20 | 18 | 0.55 | 1.48 | 0 | 0 3.7 | 128 | P |
| Z24725_at | 15 | 0 | 20 | 20 | 18 | 0.75 | 4.60 | 2 | 0 Inf | 128 | P |
| X52882_at | 11 | 0 | 20 | 20 | 18 | 0.55 | 2.22 | 0 | 0 Inf | 127 | P |
| L00058_at | 10 | 0 | 20 | 20 | 18 | 0.50 | 2.95 | 1 | 0 Inf | 127 | P |
| U96915_at | 10 | 1 | 20 | 20 | 18 | 0.50 | 1.94 | 0 | 0 10.0 | 126 | P |
| X64364_at | 7 | 0 | 20 | 20 | 17 | 0.35 | 1.30 | 0 | 0 Inf | 126 | P |
| X86779_at | 7 | 0 | 20 | 20 | 17 | 0.35 | 1.19 | 0 | 0 Inf | 125 | P |
| Z84721_cds2_at | 12 | 4 | 20 | 20 | 18 | 0.60 | 1.56 | 0 | 0 3.0 | 125 | P |
| X03656_rna1_at | 10 | 2 | 20 | 20 | 17 | 0.50 | 1.82 | 1 | 0 5.0 | 124 | P |
| X82895_at | 9 | 1 | 20 | 20 | 18 | 0.45 | 1.91 | 0 | 0 9.0 | 124 | P |
| Y09616_at | 12 | 2 | 20 | 20 | 17 | 0.60 | 2.08 | 0 | 0 6.0 | 121 | P |
| U67784_at | 10 | 1 | 20 | 20 | 18 | 0.50 | 1.97 | 0 | 0 10.0 | 120 | P |
| U80040_at | 11 | 2 | 20 | 20 | 18 | 0.55 | 1.66 | 0 | 0 5.5 | 120 | P |
| X72755_at | 16 | 2 | 20 | 20 | 17 | 0.80 | 3.66 | 0 | 0 8.0 | 120 | P |
| X60592_at | 10 | 2 | 20 | 20 | 18 | 0.50 | 1.12 | 0 | 0 5.0 | 119 | P |
| AFFX-HUMISGF3A/M97935_3_at | 12 | 1 | 20 | 20 | 18 | 0.60 | 3.01 | 2 | 0 12.0 | 118 | P |
| U78793_at | 10 | 2 | 20 | 20 | 17 | 0.50 | 2.45 | 0 | 0 5.0 | 118 | P |
| X12451_at | 12 | 0 | 20 | 20 | 18 | 0.60 | 3.43 | 2 | 0 Inf | 118 | P |
| X75342_at | 11 | 2 | 20 | 20 | 17 | 0.55 | 1.51 | 0 | 0 5.5 | 117 | P |
| X01630_at | 10 | 1 | 20 | 20 | 18 | 0.50 | 2.24 | 1 | 0 10.0 | 114 | P |
| X82153_at | 13 | 0 | 20 | 20 | 18 | 0.65 | 2.42 | 0 | 0 Inf | 114 | P |
| L11066_at | 7 | 1 | 20 | 20 | 18 | 0.35 | 0.93 | 0 | 0 7.0 | 114 | P |
| U90426_at | 12 | 0 | 20 | 20 | 18 | 0.60 | 3.55 | 1 | 0 Inf | 113 | P |
| U91932_at | 11 | 1 | 20 | 20 | 17 | 0.55 | 2.45 | 0 | 0 11.0 | 113 | P |
| X92098_at | 10 | 0 | 20 | 20 | 18 | 0.50 | 2.12 | 0 | 0 Inf | 113 | P |
| Y08134_at | 8 | 1 | 20 | 20 | 18 | 0.40 | 1.74 | 0 | 0 8.0 | 113 | P |
| U79260_at | 7 | 0 | 20 | 20 | 18 | 0.35 | 1.62 | 0 | 0 Inf | 112 | P |
| U89336_cds1_at | 10 | 1 | 20 | 20 | 18 | 0.50 | 2.01 | 0 | 0 10.0 | 112 | P |
| X05409_at | 7 | 1 | 20 | 20 | 18 | 0.35 | 1.29 | 0 | 0 7.0 | 112 | P |
| X95735_at | 10 | 1 | 20 | 20 | 18 | 0.50 | 1.85 | 1 | 0 10.0 | 112 | P |
| Y11681_at | 8 | 1 | 20 | 20 | 18 | 0.40 | 1.40 | 0 | 0 8.0 | 112 | P |

-continued

Connective tissue C

| Gene Name | Posit | Negat | Pairs | Pairs | Pairs In | Pos Fracti | Log Avg | PM Ex MM Excess | Pos/Neg | Avg Diff | Abs Call |
|---|---|---|---|---|---|---|---|---|---|---|---|
| U97105_at | 12 | 0 | 20 | 20 | 18 | 0.60 | 2.99 | 0 | 0 Inf | 111 | P |
| X03934_at | 10 | 0 | 20 | 20 | 17 | 0.50 | 1.55 | 0 | 0 Inf | 111 | P |
| X61123_at | 14 | 0 | 20 | 20 | 17 | 0.70 | 4.15 | 2 | 0 Inf | 111 | P |
| X73113_at | 9 | 2 | 20 | 20 | 18 | 0.45 | 1.12 | 0 | 0 4.5 | 111 | P |
| X86163_at | 11 | 1 | 20 | 20 | 18 | 0.55 | 2.44 | 0 | 0 11.0 | 111 | P |
| U79267_at | 14 | 0 | 20 | 20 | 17 | 0.70 | 2.31 | 0 | 0 Inf | 110 | P |
| X15414_at | 10 | 0 | 20 | 20 | 17 | 0.50 | 1.76 | 0 | 0 Inf | 110 | P |
| U82671_cds2_at | 8 | 0 | 20 | 20 | 18 | 0.40 | 1.72 | 0 | 0 Inf | 109 | P |
| X99728_at | 9 | 2 | 20 | 20 | 18 | 0.45 | 1.44 | 0 | 0 4.5 | 109 | P |
| L10413_at | 12 | 1 | 20 | 20 | 18 | 0.60 | 1.98 | 0 | 0 12.0 | 109 | P |
| U79262_at | 10 | 3 | 20 | 20 | 18 | 0.50 | 1.67 | 0 | 0 3.3 | 106 | P |
| U78556_at | 11 | 1 | 20 | 20 | 18 | 0.55 | 2.08 | 0 | 0 11.0 | 104 | P |
| Z50194_at | 12 | 2 | 20 | 20 | 18 | 0.60 | 2.75 | 1 | 0 6.0 | 103 | P |
| X16416_at | 7 | 1 | 20 | 20 | 18 | 0.35 | 1.51 | 0 | 0 7.0 | 102 | P |
| X70340_at | 7 | 0 | 20 | 20 | 18 | 0.35 | 1.68 | 0 | 0 Inf | 101 | P |
| Y00815_at | 12 | 0 | 20 | 20 | 18 | 0.60 | 2.85 | 1 | 0 Inf | 101 | P |
| X62744_at | 7 | 2 | 20 | 20 | 18 | 0.35 | 1.34 | 0 | 0 3.5 | 100 | P |
| X65873_at | 12 | 3 | 20 | 20 | 18 | 0.60 | 2.43 | 1 | 0 4.0 | 100 | P |
| X02530_at | 9 | 1 | 20 | 20 | 18 | 0.45 | 2.34 | 0 | 0 9.0 | 99 | P |
| X71874_cds1_at | 8 | 1 | 20 | 20 | 18 | 0.40 | 1.24 | 0 | 0 8.0 | 99 | P |
| U90913_at | 9 | 0 | 20 | 20 | 18 | 0.45 | 1.97 | 0 | 0 Inf | 98 | P |
| Z35093_at | 9 | 1 | 20 | 20 | 18 | 0.45 | 1.74 | 0 | 0 9.0 | 98 | P |
| Z36531_at | 13 | 2 | 20 | 20 | 18 | 0.65 | 2.63 | 0 | 0 6.5 | 98 | P |
| Z148042_at | 10 | 1 | 20 | 20 | 18 | 0.50 | 1.45 | 0 | 0 10.0 | 98 | P |
| X82200_at | 10 | 2 | 20 | 20 | 18 | 0.50 | 2.28 | 0 | 0 5.0 | 97 | P |
| X06323_at | 16 | 0 | 20 | 20 | 18 | 0.80 | 3.63 | 0 | 0 Inf | 96 | P |
| X52151_at | 9 | 1 | 20 | 20 | 18 | 0.45 | 1.37 | 0 | 0 9.0 | 96 | P |
| U83463_at | 12 | 1 | 20 | 20 | 17 | 0.60 | 3.70 | 2 | 0 12.0 | 95 | P |
| X93499_at | 11 | 1 | 20 | 20 | 17 | 0.55 | 2.14 | 0 | 0 11.0 | 95 | P |
| HG2743-HT2845_at | 10 | 1 | 20 | 20 | 17 | 0.50 | 2.62 | 2 | 0 10.0 | 95 | P |
| X74295_at | 9 | 1 | 20 | 20 | 18 | 0.45 | 0.94 | 0 | 0 9.0 | 94 | P |
| X80695_at | 9 | 2 | 20 | 20 | 18 | 0.45 | 1.32 | 0 | 0 4.5 | 94 | P |
| X92744_at | 9 | 0 | 20 | 20 | 17 | 0.45 | 1.72 | 0 | 0 Inf | 94 | P |
| Z47087_at | 14 | 1 | 20 | 20 | 17 | 0.70 | 3.25 | 0 | 0 14.0 | 94 | P |
| U86782_at | 14 | 0 | 20 | 20 | 18 | 0.70 | 3.19 | 0 | 0 Inf | 93 | P |
| X77794_at | 14 | 1 | 20 | 20 | 17 | 0.70 | 3.63 | 1 | 0 14.0 | 93 | P |
| U89278_at | 8 | 2 | 20 | 20 | 18 | 0.40 | 0.95 | 0 | 0 4.0 | 91 | P |
| X76732_at | 13 | 0 | 20 | 20 | 18 | 0.65 | 3.90 | 0 | 0 Inf | 91 | P |
| X80910_at | 10 | 0 | 20 | 20 | 18 | 0.50 | 2.51 | 0 | 0 Inf | 91 | P |
| U81802_at | 7 | 1 | 20 | 20 | 18 | 0.35 | 1.52 | 0 | 0 7.0 | 90 | P |
| X66401_cds1_at | 12 | 1 | 20 | 20 | 18 | 0.60 | 2.65 | 0 | 0 12.0 | 90 | P |
| X97302_at | 8 | 0 | 20 | 20 | 17 | 0.40 | 1.60 | 0 | 0 Inf | 90 | P |
| X54942_at | 11 | 1 | 20 | 20 | 18 | 0.55 | 2.13 | 1 | 0 11.0 | 89 | P |
| X62466_at | 8 | 2 | 20 | 20 | 17 | 0.40 | 2.09 | 0 | 0 4.0 | 89 | P |
| X76104_at | 7 | 2 | 20 | 20 | 18 | 0.35 | 1.34 | 0 | 0 3.5 | 89 | P |
| X81003_at | 11 | 0 | 20 | 20 | 18 | 0.55 | 2.07 | 0 | 0 Inf | 89 | P |
| X98263_at | 13 | 0 | 20 | 20 | 17 | 0.65 | 2.37 | 0 | 0 Inf | 89 | P |
| U79287_at | 8 | 0 | 20 | 20 | 18 | 0.40 | 1.56 | 0 | 0 Inf | 88 | P |
| U86602_at | 8 | 1 | 20 | 20 | 18 | 0.40 | 1.57 | 0 | 0 8.0 | 88 | P |
| X57766_at | 9 | 2 | 20 | 20 | 18 | 0.45 | 1.69 | 1 | 0 4.5 | 88 | P |
| Y08999_at | 12 | 2 | 20 | 20 | 18 | 0.60 | 2.04 | 2 | 0 6.0 | 88 | P |
| U72209_at | 9 | 2 | 20 | 20 | 17 | 0.45 | 1.32 | 1 | 0 4.5 | 87 | P |
| X85372_at | 11 | 1 | 20 | 20 | 18 | 0.55 | 2.53 | 1 | 0 11.0 | 87 | P |
| Y08915_at | 9 | 0 | 20 | 20 | 18 | 0.45 | 1.86 | 0 | 0 Inf | 87 | P |
| U90919_at | 13 | 0 | 20 | 20 | 18 | 0.65 | 3.25 | 0 | 0 Inf | 86 | P |
| X64838_at | 11 | 1 | 20 | 20 | 18 | 0.55 | 1.77 | 0 | 0 11.0 | 84 | P |
| Z69720_at | 9 | 2 | 20 | 20 | 18 | 0.45 | 1.51 | 0 | 0 4.5 | 83 | P |
| U82130_at | 12 | 0 | 20 | 20 | 18 | 0.60 | 2.44 | 0 | 0 Inf | 82 | P |
| U90909_at | 12 | 0 | 20 | 20 | 18 | 0.60 | 3.01 | 0 | 0 Inf | 82 | P |
| X78925_at | 10 | 0 | 20 | 20 | 18 | 0.50 | 2.34 | 1 | 0 10.0 | 82 | P |
| U90716_at | 7 | 1 | 20 | 20 | 18 | 0.35 | 1.53 | 0 | 0 7.0 | 81 | P |
| X98261_at | 9 | 2 | 20 | 20 | 18 | 0.45 | 1.18 | 0 | 0 4.5 | 81 | P |
| AFFX-M27830_5_at | 7 | 0 | 20 | 20 | 18 | 0.35 | 1.44 | 0 | 0 Inf | 80 | P |
| U90547_at | 10 | 1 | 20 | 20 | 17 | 0.50 | 2.10 | 1 | 1 10.0 | 80 | P |
| X66364_at | 8 | 1 | 20 | 20 | 18 | 0.40 | 0.91 | 0 | 0 8.0 | 80 | P |
| Z22548_at | 8 | 1 | 20 | 20 | 17 | 0.40 | 1.97 | 0 | 0 8.0 | 80 | P |
| Z50853_at | 11 | 2 | 20 | 20 | 18 | 0.55 | 1.81 | 0 | 0 5.5 | 80 | P |
| X78520_at | 9 | 0 | 20 | 20 | 18 | 0.45 | 1.63 | 0 | 0 Inf | 79 | P |
| U96113_at | 11 | 1 | 20 | 20 | 18 | 0.55 | 3.13 | 1 | 0 11.0 | 78 | P |
| X68560_at | 10 | 0 | 20 | 20 | 18 | 0.50 | 2.62 | 0 | 0 Inf | 78 | P |
| Z37166_at | 10 | 0 | 20 | 20 | 17 | 0.50 | 1.47 | 0 | 0 Inf | 78 | P |
| U81006_at | 10 | 0 | 20 | 20 | 18 | 0.50 | 3.41 | 1 | 0 Inf | 76 | P |
| U81607_at | 9 | 1 | 20 | 20 | 18 | 0.45 | 2.66 | 2 | 0 9.0 | 76 | P |
| U90911_at | 10 | 0 | 20 | 20 | 18 | 0.50 | 3.00 | 0 | 0 Inf | 76 | P |

-continued

Connective tissue C

| Gene Name | Posit | Negat | Pairs | Pairs | Pairs In | Pos Fracti | Log Avg | PM Ex MM Excess | Pos/Neg | Avg Diff | Abs Call |
|---|---|---|---|---|---|---|---|---|---|---|---|
| X56807_at | 8 | 2 | 20 | 20 | 18 | 0.40 | 1.60 | 0 | 0 4.0 | 76 | P |
| X69141_at | 11 | 1 | 20 | 20 | 18 | 0.55 | 2.22 | 0 | 0 11.0 | 76 | P |
| X93921_at | 9 | 3 | 20 | 20 | 18 | 0.45 | 1.61 | 0 | 0 3.0 | 76 | P |
| X87176_at | 9 | 2 | 20 | 20 | 18 | 0.45 | 1.61 | 0 | 0 4.5 | 75 | P |
| Z23064_at | 10 | 2 | 20 | 20 | 18 | 0.50 | 2.21 | 0 | 0 5.0 | 75 | P |
| X61100_rna1_at | 11 | 2 | 20 | 20 | 18 | 0.55 | 2.99 | 1 | 1 5.5 | 74 | P |
| X63679_at | 13 | 1 | 20 | 20 | 18 | 0.65 | 3.39 | 2 | 0 13.0 | 74 | P |
| 2711_at | 12 | 1 | 20 | 20 | 18 | 0.60 | 2.00 | 2 | 1 12.0 | 73 | P |
| Z72499_at | 10 | 2 | 20 | 20 | 17 | 0.50 | 2.51 | 1 | 0 5.0 | 73 | P |
| X83973_at | 8 | 2 | 20 | 20 | 18 | 0.40 | 1.79 | 0 | 0 4.0 | 72 | P |
| X84373_at | 12 | 0 | 20 | 20 | 18 | 0.60 | 3.15 | 1 | 0 Int | 72 | P |
| Y08614_at | 7 | 2 | 20 | 20 | 18 | 0.35 | 1.33 | 0 | 0 3.5 | 72 | P |
| Z29064_at | 11 | 1 | 20 | 20 | 18 | 0.55 | 2.56 | 0 | 0 11.0 | 72 | P |
| U80017_rna3_at | 11 | 0 | 20 | 20 | 18 | 0.55 | 2.55 | 1 | 0 Inf | 71 | P |
| X72177_rna1 at | 11 | 3 | 20 | 20 | 18 | 0.55 | 1.45 | 0 | 0 3.7 | 71 | P |
| X80230_at | 10 | 1 | 20 | 20 | 18 | 0.50 | 2.04 | 1 | 0 10.0 | 71 | P |
| X63753_at | 10 | 1 | 20 | 20 | 18 | 0.50 | 2.63 | 1 | 0 10.0 | 70 | P |
| X64330_at | 9 | 2 | 20 | 20 | 18 | 0.45 | 1.59 | 0 | 0 4.5 | 70 | P |
| X81198_at | 7 | 1 | 20 | 20 | 18 | 0.35 | 2.33 | 1 | 0 7.0 | 70 | P |
| X83378_at | 10 | 2 | 20 | 20 | 17 | 0.50 | 1.68 | 0 | 0 5.0 | 70 | P |
| X98001_at | 8 | 1 | 20 | 20 | 18 | 0.40 | 1.30 | 0 | 0 8.0 | 70 | P |
| U65928_at | 13 | 1 | 20 | 20 | 18 | 0.65 | 1.82 | 0 | 0 13.0 | 69 | P |
| U70426_at | 8 | 2 | 20 | 20 | 18 | 0.40 | 1.24 | 0 | 0 4.0 | 69 | P |
| X79353_at | 7 | 1 | 20 | 20 | 18 | 0.35 | 1.61 | 1 | 0 7.0 | 69 | P |
| U76992_at | 9 | 2 | 20 | 20 | 18 | 0.45 | 1.85 | 1 | 0 4.5 | 68 | P |
| U87408_at | 7 | 1 | 20 | 20 | 18 | 0.35 | 1.05 | 0 | 0 7.0 | 68 | P |
| X07767_at | 7 | 2 | 20 | 20 | 17 | 0.35 | 1.41 | 0 | 0 3.5 | 68 | P |
| X63563_at | 7 | 1 | 20 | 20 | 18 | 0.35 | 2.04 | 1 | 0 7.0 | 68 | P |
| Y07867_at | 10 | 2 | 20 | 20 | 18 | 0.50 | 2.61 | 0 | 0 5.0 | 68 | P |
| X77548_at | 7 | 1 | 20 | 20 | 18 | 0.35 | 1.43 | 0 | 0 7.0 | 67 | P |
| Y11306_rna1_at | 8 | 2 | 20 | 20 | 18 | 0.40 | 1.81 | 1 | 1 4.0 | 67 | P |
| 222865_at | 8 | 2 | 20 | 20 | 18 | 0.40 | 1.48 | 0 | 0 4.0 | 67 | P |
| AFFX-BioB-3_at | 11 | 1 | 20 | 20 | 18 | 0.55 | 1.24 | 0 | 0 11.0 | 66 | P |
| X57522_at | 11 | 3 | 20 | 20 | 18 | 0.55 | 2.04 | 0 | 0 3.7 | 65 | P |
| X91788_at | 12 | 3 | 20 | 20 | 18 | 0.60 | 2.03 | 0 | 0 4.0 | 65 | P |
| U91327_at | 8 | 2 | 20 | 20 | 17 | 0.40 | 2.45 | 1 | 0 4.0 | 64 | P |
| U77665_at | 8 | 0 | 20 | 20 | 18 | 0.40 | 1.25 | 1 | 0 Inf | 63 | P |
| X03635_at | 11 | 2 | 20 | 20 | 18 | 0.55 | 1.87 | 0 | 0 5.5 | 63 | P |
| X59798_at | 7 | 2 | 20 | 20 | 18 | 0.35 | 1.34 | 0 | 0 3.5 | 63 | P |
| X72841_at | 13 | 1 | 20 | 20 | 18 | 0.65 | 3.41 | 1 | 0 13.0 | 63 | P |
| X99325_at | 8 | 1 | 20 | 20 | 18 | 0.40 | 1.08 | 0 | 0 8.0 | 63 | P |
| U76369_at | 8 | 1 | 20 | 20 | 18 | 0.40 | 1.26 | 1 | 0 8.0 | 62 | P |
| X66397_at | 11 | 0 | 20 | 20 | 17 | 0.55 | 2.33 | 0 | 0 Inf | 62 | P |
| X59405_at | 9 | 2 | 20 | 20 | 18 | 0.45 | 2.15 | 0 | 0 4.5 | 61 | P |
| Z68204_at | 7 | 0 | 20 | 20 | 18 | 0.35 | 1.69 | 0 | 0 Inf | 61 | P |
| U79297_at | 11 | 1 | 20 | 20 | 18 | 0.55 | 3.42 | 2 | 0 11.0 | 60 | P |
| X16354_at | 11 | 2 | 20 | 20 | 18 | 0.55 | 2.01 | 0 | 0 5.5 | 60 | P |
| X78627_at | 11 | 3 | 20 | 20 | 18 | 0.55 | 2.48 | 0 | 0 3.7 | 60 | P |
| X55544_at | 8 | 1 | 20 | 20 | 18 | 0.40 | 2.20 | 0 | 0 8.0 | 59 | P |
| Y09443_at | 7 | 0 | 20 | 20 | 18 | 0.35 | 1.56 | 0 | 0 Inf | 59 | P |
| U72508_at | 7 | 1 | 20 | 20 | 18 | 0.35 | 1.24 | 0 | 0 7.0 | 58 | P |
| U73682_at | 8 | 2 | 20 | 20 | 18 | 0.40 | 1.16 | 0 | 0 4.0 | 58 | P |
| U90549_at | 8 | 2 | 20 | 20 | 18 | 0.40 | 1.45 | 0 | 0 4.0 | 58 | P |
| X53586_rna1_at | 11 | 0 | 20 | 20 | 18 | 0.55 | 4.12 | 2 | 0 Inf | 57 | P |
| Z17227_at | 10 | 2 | 20 | 20 | 18 | 0.50 | 1.95 | 1 | 0 5.0 | 57 | P |
| X87212_at | 9 | 2 | 20 | 20 | 18 | 0.45 | 2.58 | 1 | 0 4.5 | 55 | P |
| X13482_at | 7 | 1 | 20 | 20 | 18 | 0.35 | 1.10 | 0 | 0 7.0 | 54 | P |
| X63469_at | 7 | 0 | 20 | 20 | 18 | 0.35 | 1.85 | 0 | 0 Inf | 54 | P |
| U69141_at | 7 | 1 | 20 | 20 | 18 | 0.35 | 1.20 | 0 | 0 7.0 | 53 | P |
| U71207_at | 9 | 3 | 20 | 20 | 18 | 0.45 | 1.54 | 0 | 0 3.0 | 53 | P |
| U85992_at | 9 | 2 | 20 | 20 | 18 | 0.45 | 1.82 | 0 | 0 4.5 | 52 | P |
| U79274_at | 8 | 1 | 20 | 20 | 18 | 0.40 | 1.17 | 0 | 0 8.0 | 51 | P |
| U79291_at | 13 | 0 | 20 | 20 | 17 | 0.65 | 4.11 | 3 | 0 Inf | 50 | P |
| X63337_at | 9 | 2 | 20 | 20 | 18 | 0.45 | 1.31 | 0 | 0 4.5 | 50 | P |
| X64229_at | 10 | 3 | 20 | 20 | 18 | 0.50 | 1.38 | 1 | 0 3.3 | 50 | P |
| X29331_at | 11 | 2 | 20 | 20 | 18 | 0.55 | 3.99 | 3 | 0 5.5 | 50 | P |
| 35491_at | 8 | 0 | 20 | 20 | 17 | 0.40 | 2.75 | 1 | 0 Inf | 50 | P |
| X16396_at | 9 | 0 | 20 | 20 | 18 | 0.45 | 2.61 | 1 | 0 Inf | 49 | P |
| X60673_rna1_at | 9 | 2 | 20 | 20 | 18 | 0.45 | 1.60 | 0 | 0 4.5 | 49 | P |
| U66669_at | 9 | 2 | 20 | 20 | 18 | 0.45 | 1.83 | 0 | 0 4.5 | 48 | P |
| U72342_at | 10 | 3 | 20 | 20 | 18 | 0.50 | 1.41 | 0 | 0 3.3 | 48 | P |
| U83908_at | 9 | 2 | 20 | 20 | 18 | 0.45 | 2.41 | 1 | 0 4.5 | 48 | P |
| X92396_at | 8 | 2 | 20 | 20 | 18 | 0.40 | 2.11 | 1 | 0 4.0 | 48 | P |
| D86550_at | 9 | 0 | 20 | 20 | 18 | 0.45 | 2.24 | 0 | 0 Inf | 48 | P |

-continued

Connective tissue C

| Gene Name | Posit | Negat | Pairs | Pairs | Pairs In | Pos Fracti | Log Avg | PM Ex MM Excess | Pos/Neg | Avg Diff | Abs Call |
|---|---|---|---|---|---|---|---|---|---|---|---|
| X76648_at | 9 | 1 | 20 | 20 | 18 | 0.45 | 2.11 | 0 | 0 9.0 | 47 | P |
| Z68129_cds1_at | 7 | 1 | 20 | 20 | 18 | 0.35 | 1.03 | 0 | 0 7.0 | 47 | P |
| D10040_at | 8 | 2 | 20 | 20 | 18 | 0.40 | 1.31 | 0 | 0 4.0 | 47 | P |
| U84573_at | 9 | 1 | 20 | 20 | 18 | 0.45 | 3.00 | 2 | 0 9.0 | 46 | P |
| X54941_at | 7 | 1 | 20 | 20 | 18 | 0.35 | 1.30 | 0 | 0 7.0 | 46 | P |
| X76057_at | 8 | 2 | 20 | 20 | 18 | 0.40 | 1.11 | 0 | 0 4.0 | 46 | P |
| X98248_rna1_at | 8 | 2 | 20 | 20 | 18 | 0.40 | 1.99 | 1 | 0 4.0 | 46 | P |
| Z24724_at | 10 | 0 | 20 | 20 | 18 | 0.50 | 2.59 | 1 | 0 Inf | 46 | P |
| U68111_at | 9 | 0 | 20 | 20 | 18 | 0.45 | 1.75 | 0 | 0 Inf | 45 | P |
| U94332_at | 7 | 1 | 20 | 20 | 18 | 0.35 | 1.71 | 1 | 0 7.0 | 45 | P |
| X98172_at | 9 | 0 | 20 | 20 | 18 | 0.45 | 1.23 | 0 | 0 Inf | 45 | P |
| X62048_at | 8 | 0 | 20 | 20 | 18 | 0.40 | 1.87 | 0 | 0 Inf | 44 | P |
| X87241_at | 10 | 2 | 20 | 20 | 18 | 0.50 | 2.53 | 0 | 0 5.0 | 44 | P |
| X94232_at | 8 | 0 | 20 | 20 | 17 | 0.40 | 1.63 | 0 | 0 Inf | 44 | P |
| Z95624_at | 7 | 0 | 20 | 20 | 18 | 0.35 | 1.20 | 0 | 0 Inf | 44 | P |
| X04011_at | 10 | 2 | 20 | 20 | 18 | 0.50 | 1.47 | 0 | 0 5.0 | 43 | P |
| X98260_at | 8 | 2 | 20 | 20 | 18 | 0.40 | 1.02 | 0 | 0 4.0 | 43 | P |
| X59841_at | 8 | 0 | 20 | 20 | 18 | 0.40 | 1.58 | 0 | 0 Inf | 42 | P |
| X65644_at | 7 | 1 | 20 | 20 | 17 | 0.35 | 0.97 | 0 | 0 7.0 | 42 | P |
| X74262_at | 9 | 2 | 20 | 20 | 18 | 0.45 | 2.21 | 0 | 0 4.5 | 42 | P |
| X96586_at | 8 | 1 | 20 | 20 | 18 | 0.40 | 1.20 | 0 | 0 8.0 | 42 | P |
| U67319_at | 7 | 1 | 20 | 20 | 18 | 0.35 | 0.93 | 1 | 0 7.0 | 41 | P |
| X07024_at | 8 | 1 | 20 | 20 | 18 | 0.40 | 1.31 | 0 | 0 8.0 | 41 | P |
| X52520_at | 9 | 1 | 20 | 20 | 18 | 0.45 | 2.59 | 0 | 0 9.0 | 41 | P |
| U90912_at | 8 | 1 | 20 | 20 | 18 | 0.40 | 1.12 | 0 | 0 8.0 | 40 | P |
| X06948_at | 8 | 2 | 20 | 20 | 18 | 0.40 | 1.65 | 1 | 0 4.0 | 40 | P |
| X61118_rna1_at | 10 | 0 | 20 | 20 | 18 | 0.50 | 2.33 | 0 | 0 Inf | 40 | P |
| X81788_at | 11 | 3 | 20 | 20 | 18 | 0.55 | 2.32 | 1 | 0 3.7 | 40 | P |
| X53793_at | 10 | 2 | 20 | 20 | 18 | 0.50 | 2.40 | 0 | 0 5.0 | 39 | P |
| X54326_at | 8 | 2 | 20 | 20 | 17 | 0.40 | 1.00 | 0 | 0 4.0 | 39 | P |
| U88666_at | 8 | 2 | 20 | 20 | 18 | 0.40 | 1.56 | 1 | 0 4.0 | 37 | P |
| X73608_at | 7 | 1 | 20 | 20 | 18 | 0.35 | 1.62 | 0 | 0 7.0 | 37 | P |
| X84002_at | 8 | 2 | 20 | 20 | 18 | 0.40 | 1.58 | 0 | 0 4.0 | 37 | P |
| U69127_at | 8 | 0 | 20 | 20 | 18 | 0.40 | 1.33 | 0 | 0 Inf | 35 | P |
| X17025_at | 8 | 2 | 20 | 20 | 17 | 0.40 | 1.78 | 1 | 0 4.0 | 35 | P |
| X57206_at | 8 | 2 | 20 | 20 | 17 | 0.40 | 1.15 | 0 | 0 4.0 | 35 | P |
| X76061_at | 8 | 2 | 20 | 20 | 18 | 0.40 | 2.02 | 1 | 0 4.0 | 35 | P |
| Z34897_at | 8 | 1 | 20 | 20 | 18 | 0.40 | 1.45 | 0 | 0 8.0 | 35 | P |
| Z37976_at | 8 | 0 | 20 | 20 | 17 | 0.40 | 0.95 | 0 | 0 Inf | 35 | P |
| X57303_at | 8 | 1 | 20 | 20 | 17 | 0.40 | 1.94 | 0 | 0 8.0 | 34 | P |
| X83368_at | 10 | 2 | 20 | 20 | 18 | 0.50 | 2.16 | 2 | 0 5.0 | 34 | P |
| Y10313_at | 8 | 2 | 20 | 20 | 18 | 0.40 | 1.25 | 0 | 0 4.0 | 34 | P |
| X63417_at | 7 | 1 | 20 | 20 | 18 | 0.35 | 1.43 | 0 | 0 7.0 | 33 | P |
| X94910_at | 8 | 1 | 20 | 20 | 18 | 0.40 | 1.26 | 0 | 0 8.0 | 32 | P |
| U77718_at | 9 | 2 | 20 | 20 | 18 | 0.45 | 1.27 | 0 | 0 4.5 | 31 | P |
| U90916_at | 10 | 2 | 20 | 20 | 18 | 0.50 | 3.47 | 3 | 0 5.0 | 31 | P |
| X06562_at | 9 | 2 | 20 | 20 | 18 | 0.45 | 2.44 | 1 | 0 4.5 | 31 | P |
| U73960_at | 9 | 2 | 20 | 20 | 17 | 0.45 | 1.15 | 0 | 0 4.5 | 30 | P |
| X07820_at | 8 | 1 | 20 | 20 | 17 | 0.40 | 1.86 | 1 | 0 8.0 | 30 | P |
| X57025_at | 7 | 0 | 20 | 20 | 17 | 0.35 | 1.51 | 0 | 0 Inf | 30 | P |
| D18481_at | 8 | 1 | 20 | 20 | 18 | 0.40 | 1.23 | 0 | 0 8.0 | 30 | P |
| U75679_at | 8 | 1 | 20 | 20 | 18 | 0.40 | 1.51 | 0 | 0 8.0 | 29 | P |
| X84195_at | 7 | 2 | 20 | 20 | 18 | 0.35 | 2.65 | 2 | 0 3.5 | 29 | P |
| Z46973_at | 8 | 2 | 20 | 20 | 18 | 0.40 | 1.73 | 1 | 0 4.0 | 28 | P |
| U79258_at | 8 | 1 | 20 | 20 | 18 | 0.40 | 2.27 | 0 | 0 8.0 | 27 | P |
| X58723_at | 9 | 2 | 20 | 20 | 18 | 0.45 | 2.60 | 1 | 0 4.5 | 27 | P |
| X92110_at | 8 | 2 | 20 | 20 | 18 | 0.40 | 2.38 | 2 | 0 4.0 | 27 | P |
| X99584_at | 7 | 1 | 20 | 20 | 18 | 0.35 | 1.22 | 0 | 0 7.0 | 27 | P |
| Z22535_at | 8 | 2 | 20 | 20 | 17 | 0.40 | 1.20 | 0 | 0 4.0 | 27 | P |
| U92015_at | 8 | 2 | 20 | 20 | 18 | 0.40 | 1.13 | 0 | 0 4.0 | 26 | P |
| X73882_at | 8 | 2 | 20 | 20 | 18 | 0.40 | 1.56 | 0 | 0 4.0 | 26 | P |
| U79245_at | 8 | 2 | 20 | 20 | 17 | 0.40 | 2.65 | 2 | 0 4.0 | 25 | P |
| X95592_at | 10 | 2 | 20 | 20 | 17 | 0.50 | 1.79 | 0 | 0 5.0 | 25 | P |
| U66561_at | 7 | 2 | 20 | 20 | 18 | 0.35 | 1.32 | 0 | 0 3.5 | 23 | P |
| U97018_at | 9 | 3 | 20 | 20 | 18 | 0.45 | 1.38 | 1 | 0 3.0 | 22 | P |

Connective tissue D

| Gene Name | Positiv | Nega | Pairs | Pairs | Pairs | Pos Fracti | Log Avg | PM Ex | MM Ex | Pos/Neg | Avg Diff | Abs Call |
|---|---|---|---|---|---|---|---|---|---|---|---|---|
| M26311_s_at | 17 | 0 | 19 | 19 | 17 | 0.89 | 5.63 | 2 | 0 | Inf | 15733 | P |
| X52426_at | 19 | 0 | 20 | 20 | 18 | 0.95 | 4.98 | 0 | 0 | Inf | 13355 | P |
| M86757_s_at | 20 | 0 | 20 | 20 | 18 | 1.00 | 6.88 | 2 | 0 | Inf | 10368 | P |
| L05187_at | 20 | 0 | 20 | 20 | 18 | 1.00 | 5.41 | 1 | 0 | Inf | 6544 | P |
| hum_alu_at | 62 | 0 | 69 | 69 | 66 | 0.90 | 4.64 | 2 | 0 | Inf | 5696 | P |
| L04483_s_at | 16 | 0 | 17 | 17 | 15 | 0.94 | 6.22 | 3 | 0 | Inf | 5632 | P |
| L42601J_f_at | 19 | 0 | 20 | 20 | 18 | 0.95 | 5.90 | 2 | 0 | Inf | 5155 | P |
| L42583_f_at | 20 | 0 | 20 | 20 | 18 | 1.00 | 6.01 | 3 | 0 | Inf | 4939 | P |
| J04617_s_at | 17 | 0 | 18 | 18 | 16 | 0.94 | 5.76 | 1 | 0 | Inf | 4935 | P |
| V01516_f_at | 19 | 0 | 20 | 20 | 18 | 0.95 | 6.01 | 2 | 0 | Inf | 4779 | P |
| M63438_s_at | 15 | 0 | 17 | 17 | 15 | 0.88 | 5.15 | 0 | 0 | Inf | 4579 | P |
| L05188_f_at | 19 | 0 | 20 | 20 | 18 | 0.95 | 6.42 | 2 | 0 | Inf | 4465 | P |
| M19888_at | 19 | 0 | 20 | 20 | 18 | 0.95 | 6.24 | 3 | 0 | Inf | 4441 | P |
| X53065_f_at | 20 | 0 | 20 | 20 | 18 | 1.00 | 5.72 | 1 | 0 | Inf | 4285 | P |
| AFFX-HSAC07/X00351_M_at | 20 | 0 | 20 | 20 | 18 | 1.00 | 5.33 | 0 | 0 | Inf | 4239 | P |
| X03689_s_at | 19 | 0 | 19 | 19 | 17 | 1.00 | 7.09 | 1 | 0 | Inf | 4233 | P |
| X00351_f_at | 19 | 0 | 20 | 20 | 18 | 0.95 | 7.19 | 2 | 0 | Inf | 4186 | P |
| AFFX-HUMGAPDH/M33197_3_at | 19 | 0 | 20 | 20 | 18 | 0.95 | 5.92 | 1 | 0 | Inf | 4106 | P |
| X98482_r_at | 2 | 0 | 3 | 3 | 3 | 0.67 | 2.08 | 0 | 0 | Inf | 3885 | P |
| M20030_f_at | 20 | 0 | 20 | 20 | 18 | 1.00 | 6.64 | 4 | 0 | Inf | 3809 | P |
| M10277_s_at | 19 | 0 | 20 | 20 | 18 | 0.95 | 5.59 | 3 | 0 | Inf | 3788 | P |
| J00105_s_at | 20 | 0 | 20 | 20 | 18 | 1.00 | 8.04 | 5 | 0 | Inf | 3664 | P |
| X76223_s_at | 18 | 1 | 20 | 20 | 18 | 0.90 | 4.92 | 1 | 1 | 18.0 | 3490 | P |
| M87789_s_at | 18 | 1 | 20 | 20 | 18 | 0.90 | 4.97 | 1 | 0 | 18.0 | 3447 | P |
| HG2815-HT4023_s_at | 19 | 0 | 20 | 20 | 18 | 0.95 | 5.41 | 1 | 0 | Inf | 3415 | P |
| X01677_f_at | 19 | 0 | 20 | 20 | 18 | 0.95 | 5.09 | 1 | 0 | Inf | 3234 | P |
| M14199_s_at | 20 | 0 | 20 | 20 | 18 | 1.00 | 6.09 | 1 | 0 | Inf | 3222 | P |
| AFFX-CreX-3_at | 19 | 0 | 20 | 20 | 18 | 0.95 | 6.81 | 2 | 0 | Inf | 3203 | P |
| X57348_s_at | 15 | 0 | 19 | 19 | 17 | 0.79 | 4.41 | 1 | 0 | Inf | 3031 | P |
| AFFX-HSAC07/X00351_3_at | 17 | 0 | 20 | 20 | 18 | 0.85 | 5.00 | 0 | 0 | Inf | 2862 | P |
| D49824_s_at | 7 | 0 | 7 | 7 | 7 | 1.00 | 5.51 | 0 | 0 | Inf | 2821 | P |
| LM3901_ma1_s_at | 18 | 0 | 20 | 20 | 18 | 0.90 | 5.08 | 0 | 0 | Inf | 2812 | P |
| V00594_s_at | 11 | 0 | 12 | 12 | 10 | 0.92 | 6.41 | 1 | 0 | Inf | 2805 | P |
| AFFX-HSAC07/X00351_5_at | 18 | 0 | 20 | 20 | 18 | 0.90 | 5.13 | 0 | 0 | Inf | 2776 | P |
| D13413_ma1_s_at | 17 | 0 | 18 | 18 | 16 | 0.94 | 5.38 | 0 | 0 | Inf | 2651 | P |
| U06155_s_at | 12 | 1 | 14 | 14 | 12 | 0.88 | 5.03 | 0 | 1 | 12.0 | 2575 | P |
| AFFX-CreX-5_at | 19 | 0 | 20 | 20 | 18 | 0.95 | 7.15 | 2 | 0 | Inf | 2535 | P |
| AFFX-HUMGAPDH/M33197_M_at | 16 | 1 | 20 | 20 | 18 | 0.80 | 4.41 | 0 | 0 | 16.0 | 2457 | P |
| S12297_at | 19 | 0 | 20 | 20 | 18 | 0.95 | 4.22 | 0 | 0 | Inf | 2360 | P |
| Z19148_s_at | 20 | 0 | 20 | 20 | 18 | 1.00 | 5.62 | 1 | 0 | Inf | 2303 | P |
| HG2815-HT2931_at | 5 | 0 | 6 | 6 | 6 | 0.83 | 4.17 | 0 | 0 | Inf | 2265 | P |
| M31520_rna1_s_at | 15 | 0 | 16 | 16 | 14 | 0.94 | 6.19 | 2 | 0 | Inf | 2242 | P |
| M34516_at | 5 | 0 | 5 | 5 | 5 | 1.00 | 4.11 | 0 | 0 | Inf | 2235 | P |
| M36072_at | 16 | 0 | 20 | 20 | 18 | 0.80 | 4.10 | 0 | 0 | Inf | 2150 | P |
| AFFX-HUMGAPDH/M33197_5_at | 18 | 0 | 20 | 20 | 18 | 0.90 | 5.78 | 3 | 0 | Inf | 2104 | P |
| M55409_s_at | 18 | 0 | 20 | 20 | 18 | 0.90 | 5.84 | 3 | 0 | Inf | 1992 | P |
| L42611_f_at | 14 | 0 | 20 | 20 | 18 | 0.70 | 3.86 | 0 | 0 | Inf | 1946 | P |
| X57351_s_at | 12 | 0 | 12 | 12 | 10 | 1.00 | 5.81 | 0 | 0 | Inf | 1945 | P |
| HG2815-HT2931_s_at | 13 | 0 | 14 | 14 | 12 | 0.93 | 6.37 | 0 | 0 | Inf | 1926 | P |
| X53296_s_at | 19 | 0 | 20 | 20 | 18 | 0.95 | 5.49 | 3 | 0 | Inf | 1652 | P |
| M55998_s_at | 18 | 0 | 20 | 20 | 18 | 0.90 | 6.05 | 2 | 0 | Inf | 1610 | P |
| X04470_s_at | 18 | 0 | 19 | 19 | 17 | 0.95 | 5.81 | 1 | 0 | Inf | 1525 | P |
| M24485_s_at | 17 | 0 | 20 | 20 | 18 | 0.85 | 3.86 | 0 | 0 | Inf | 1522 | P |
| S71043_rna1_s_at | 16 | 0 | 20 | 20 | 18 | 0.80 | 3.68 | 1 | 0 | Inf | 1473 | P |
| X51345_at | 16 | 1 | 20 | 20 | 18 | 0.80 | 5.18 | 3 | 0 | 16.0 | 1446 | P |
| HG4069-HT4339_s_at | 18 | 0 | 20 | 20 | 18 | 0.90 | 5.56 | 2 | 0 | Inf | 1416 | P |
| Y07909_at | 16 | 1 | 20 | 20 | 18 | 0.80 | 6.79 | 5 | 1 | 16.0 | 1399 | P |
| J04152_rna1_s_at | 18 | 0 | 20 | 20 | 18 | 0.90 | 5.26 | 1 | 0 | Inf | 1311 | P |
| Z48501_s_at | 16 | 1 | 19 | 19 | 17 | 0.84 | 5.15 | 0 | 0 | 16.0 | 1263 | P |
| S66896_at | 17 | 1 | 20 | 20 | 18 | 0.85 | 5.37 | 0 | 0 | 17.0 | 1239 | P |
| AFFX-BioDn-3_at | 14 | 2 | 20 | 20 | 18 | 0.70 | 3.13 | 0 | 0 | 7.0 | 1215 | P |
| X56681_s_at | 15 | 2 | 20 | 20 | 18 | 0.75 | 4.09 | 1 | 0 | 7.5 | 1204 | P |
| U19557_s_at | 20 | 0 | 20 | 20 | 18 | 1.00 | 5.25 | 0 | 0 | Inf | 1195 | P |
| Z19554_s_at | 16 | 1 | 18 | 18 | 16 | 0.89 | 5.89 | 1 | 1 | 16.0 | 1186 | P |
| S54005_s_at | 19 | 0 | 20 | 20 | 18 | 0.95 | 5.92 | 1 | 0 | Inf | 1175 | P |
| U68105_s_at | 15 | 0 | 20 | 20 | 18 | 0.75 | 6.45 | 6 | 0 | Inf | 1173 | P |
| HG417-HT417_s_at | 19 | 0 | 20 | 20 | 18 | 0.95 | 5.40 | 2 | 0 | Inf | 1172 | P |
| HG3431-HT3616_s_at | 18 | 0 | 20 | 20 | 18 | 0.90 | 5.80 | 1 | 0 | Inf | 1126 | P |
| M94880_f_at | 30 | 0 | 40 | 40 | 38 | 0.75 | 3.63 | 0 | 0 | Inf | 1095 | P |
| S72493_s_at | 17 | 1 | 20 | 20 | 18 | 0.85 | 2.94 | 0 | 0 | 17.0 | 1072 | P |
| U20734_s_at | 16 | 0 | 20 | 20 | 18 | 0.80 | 3.73 | 1 | 0 | Inf | 1069 | P |
| M34516_r_at | 11 | 0 | 11 | 11 | 9 | 1.00 | 5.23 | 1 | 0 | Inf | 1059 | P |
| X69654_at | 17 | 0 | 20 | 20 | 18 | 0.85 | 4.74 | 0 | 0 | Inf | 1050 | P |
| M92843_s_at | 19 | 0 | 20 | 20 | 18 | 0.95 | 5.73 | 0 | 0 | Inf | 1028 | P |

-continued

Connective tissue D

| Gene Name | Positiv | Nega | Pairs | Pairs | Pairs | Pos Fracti | Log Avg | PM Ex | MM Ex | Pos/Neg | Avg Diff | Abs Call |
|---|---|---|---|---|---|---|---|---|---|---|---|---|
| M13560_s_at | 15 | 0 | 20 | 20 | 18 | 0.75 | 3.95 | 1 | 0 | Inf | 952 | P |
| U57341_r_at | 1 | 0 | 2 | 2 | 2 | 0.50 | 2.92 | 0 | 0 | Inf | 941 | P |
| L33930_s_at | 15 | 1 | 20 | 20 | 18 | 0.75 | 4.28 | 0 | 0 | 15.0 | 917 | P |
| M26708_s_at | 19 | 0 | 20 | 20 | 18 | 0.95 | 5.11 | 3 | 0 | Inf | 917 | P |
| X04347_s_at | 18 | 0 | 20 | 20 | 18 | 0.90 | 4.90 | 1 | 0 | Inf | 911 | P |
| HG1980-HT2023_at | 12 | 0 | 20 | 20 | 18 | 0.60 | 2.78 | 0 | 0 | Inf | 903 | P |
| HG658-HT658_f_at | 30 | 0 | 40 | 40 | 38 | 0.75 | 3.12 | 0 | 0 | Inf | 869 | P |
| M11313_s_at | 17 | 1 | 20 | 20 | 18 | 0.85 | 5.16 | 2 | 0 | 17.0 | 842 | P |
| M83667_rna1_s_at | 17 | 0 | 20 | 20 | 18 | 0.85 | 3.60 | 0 | 0 | Inf | 838 | P |
| M19311_s_at | 12 | 1 | 16 | 16 | 14 | 0.75 | 5.56 | 0 | 0 | 12.0 | 822 | P |
| M14328_s_at | 14 | 1 | 20 | 20 | 18 | 0.70 | 3.92 | 0 | 0 | 14.0 | 819 | P |
| X57351_at | 5 | 0 | 8 | 8 | 8 | 0.63 | 2.90 | 0 | 0 | Inf | 816 | P |
| U06643_s_at | 13 | 0 | 19 | 19 | 17 | 0.68 | 2.94 | 0 | 0 | Inf | 802 | P |
| M21142_cds2_s_at | 13 | 2 | 20 | 20 | 18 | 0.65 | 3.48 | 0 | 0 | 6.5 | 782 | P |
| Z68228_s_at | 15 | 1 | 20 | 20 | 18 | 0.75 | 3.28 | 0 | 0 | 15.0 | 779 | P |
| HG2797-HT2906_s_at | 15 | 0 | 19 | 19 | 17 | 0.79 | 3.82 | 0 | 0 | Inf | 759 | P |
| D32129_f_at | 17 | 0 | 20 | 20 | 18 | 0.85 | 4.75 | 0 | 0 | Inf | 753 | P |
| X57809_s_at | 9 | 1 | 12 | 12 | 10 | 0.75 | 2.45 | 0 | 0 | 9.0 | 737 | P |
| V00594_at | 3 | 1 | 8 | 8 | 8 | 0.38 | 2.72 | 0 | 0 | 3.0 | 715 | P |
| HG1515-HT1515_f_at | 16 | 0 | 20 | 20 | 18 | 0.80 | 5.27 | 2 | 0 | Inf | 662 | P |
| HG3342-HT3519_s_at | 16 | 0 | 19 | 19 | 17 | 0.84 | 4.66 | 0 | 0 | Inf | 660 | P |
| S75256_s_at | 17 | 1 | 20 | 20 | 18 | 0.85 | 4.50 | 3 | 0 | 17.0 | 656 | P |
| M19045_f_at | 14 | 1 | 20 | 20 | 18 | 0.70 | 4.81 | 4 | 0 | 14.0 | 644 | P |
| M14483_rna1_s_at | 13 | 0 | 20 | 20 | 18 | 0.65 | 3.12 | 0 | 0 | Inf | 641 | P |
| Z30643_at | 10 | 3 | 20 | 20 | 17 | 0.50 | 2.07 | 0 | 0 | 3.3 | 640 | P |
| AFFX-HSAC07/X00351_3_st | 15 | 0 | 20 | 20 | 18 | 0.75 | 3.82 | 0 | 0 | Inf | 629 | P |
| X95240_s_at | 13 | 2 | 20 | 20 | 18 | 0.65 | 3.73 | 4 | 1 | 6.5 | 626 | P |
| M33600_f_at | 16 | 0 | 20 | 20 | 18 | 0.80 | 3.73 | 0 | 0 | Inf | 619 | P |
| X14008_rna1_f_at | 13 | 2 | 20 | 20 | 18 | 0.65 | 4.15 | 3 | 0 | 6.5 | 602 | P |
| M21302_at | 14 | 1 | 20 | 20 | 18 | 0.70 | 4.11 | 2 | 0 | 14.0 | 600 | P |
| X12671_rna1_at | 20 | 0 | 20 | 20 | 18 | 1.00 | 4.55 | 0 | 0 | Inf | 594 | P |
| L12711_s_at | 11 | 1 | 19 | 19 | 17 | 0.58 | 3.30 | 1 | 0 | 11.0 | 589 | P |
| M12125_at | 12 | 2 | 20 | 20 | 18 | 0.60 | 2.30 | 0 | 0 | 6.0 | 586 | P |
| M58026_at | 10 | 1 | 20 | 20 | 18 | 0.50 | 2.18 | 0 | 0 | 10.0 | 573 | P |
| J03801_f_at | 13 | 1 | 20 | 20 | 18 | 0.65 | 5.62 | 3 | 0 | 13.0 | 557 | P |
| D86974_at | 15 | 2 | 20 | 20 | 18 | 0.75 | 2.56 | 0 | 0 | 7.5 | 519 | P |
| J03077_s_at | 11 | 1 | 20 | 20 | 18 | 0.55 | 3.21 | 0 | 0 | 11.0 | 510 | P |
| M54915_s_at | 13 | 0 | 20 | 20 | 18 | 0.65 | 3.37 | 0 | 0 | Inf | 500 | P |
| HG3236-HT3413_f_at | 12 | 1 | 20 | 20 | 18 | 0.60 | 3.01 | 0 | 0 | 12.0 | 490 | P |
| D17408_s_at | 14 | 0 | 20 | 20 | 18 | 0.70 | 3.72 | 0 | 0 | Inf | 483 | P |
| M26730_s_at | 17 | 1 | 20 | 20 | 18 | 0.85 | 5.65 | 2 | 0 | 17.0 | 465 | P |
| X05130_s_at | 12 | 2 | 19 | 19 | 17 | 0.63 | 2.54 | 0 | 1 | 6.0 | 464 | P |
| U14394_at | 11 | 3 | 20 | 20 | 18 | 0.55 | 2.95 | 0 | 0 | 3.7 | 456 | P |
| X17093_at | 12 | 1 | 20 | 20 | 18 | 0.60 | 2.73 | 1 | 0 | 12.0 | 435 | P |
| L33075_at | 17 | 0 | 20 | 20 | 18 | 0.85 | 4.20 | 1 | 0 | Inf | 432 | P |
| HG3597-HT3800_f_at | 15 | 1 | 20 | 20 | 17 | 0.75 | 4.30 | 2 | 0 | 15.0 | 422 | P |
| U43916_s_at | 15 | 0 | 20 | 20 | 18 | 0.75 | 3.48 | 0 | 0 | Inf | 409 | P |
| L40397_at | 12 | 1 | 20 | 20 | 18 | 0.60 | 2.35 | 0 | 0 | 12.0 | 407 | P |
| HG1428-HT1428_s_at | 15 | 0 | 20 | 20 | 18 | 0.75 | 4.25 | 1 | 0 | Inf | 401 | P |
| X02761_s_at | 14 | 0 | 20 | 20 | 18 | 0.70 | 3.69 | 0 | 0 | Inf | 397 | P |
| X12876_s_at | 15 | 1 | 20 | 20 | 18 | 0.75 | 4.25 | 0 | 0 | 15.0 | 385 | P |
| X99133_at | 9 | 2 | 20 | 20 | 18 | 0.45 | 1.79 | 0 | 0 | 4.5 | 384 | P |
| L11672_at | 6 | 0 | 12 | 12 | 10 | 0.50 | 2.17 | 0 | 0 | Inf | 370 | P |
| HG2917-HT3061_f_at | 12 | 0 | 20 | 20 | 18 | 0.60 | 2.29 | 0 | 0 | Inf | 370 | P |
| HG3576-HT3779_f_at | 11 | 2 | 20 | 20 | 18 | 0.55 | 2.86 | 0 | 0 | 5.5 | 365 | P |
| U00947_s_at | 19 | 0 | 20 | 20 | 18 | 0.95 | 5.49 | 3 | 0 | Inf | 361 | P |
| HG2915-HT3059_f_at | 10 | 0 | 20 | 20 | 17 | 0.50 | 2.22 | 0 | 0 | Inf | 351 | P |
| Z49835_s_at | 14 | 3 | 20 | 20 | 18 | 0.70 | 3.25 | 1 | 1 | 4.7 | 349 | P |
| HG2994-HT4850_s_at | 8 | 2 | 20 | 20 | 18 | 0.40 | 1.29 | 0 | 0 | 4.0 | 346 | P |
| D43682_s_at | 9 | 3 | 20 | 20 | 18 | 0.45 | 2.40 | 0 | 0 | 3.0 | 345 | P |
| AFFX-BioDn-5_at | 14 | 2 | 20 | 20 | 18 | 0.70 | 2.39 | 0 | 0 | 7.0 | 344 | P |
| Z69043_s_at | 16 | 1 | 20 | 20 | 18 | 0.80 | 3.44 | 0 | 0 | 16.0 | 342 | P |
| X95325_s_at | 11 | 3 | 20 | 20 | 18 | 0.55 | 1.91 | 0 | 0 | 3.7 | 340 | P |
| HG1322-HT5143_s_at | 14 | 1 | 20 | 20 | 18 | 0.70 | 4.19 | 0 | 0 | 14.0 | 339 | P |
| AFFX-BioC-5_at | 16 | 1 | 20 | 20 | 18 | 0.80 | 3.17 | 0 | 0 | 16.0 | 337 | P |
| J02683_s_at | 11 | 0 | 20 | 20 | 18 | 0.55 | 2.60 | 0 | 0 | Inf | 337 | P |
| M62403_s_at | 11 | 0 | 20 | 20 | 18 | 0.55 | 2.19 | 0 | 0 | Inf | 337 | P |
| U48705_rna1_s_at | 12 | 1 | 20 | 20 | 18 | 0.60 | 3.02 | 1 | 0 | 12.0 | 327 | P |
| M33493_at | 12 | 1 | 20 | 20 | 18 | 0.60 | 3.10 | 1 | 0 | 12.0 | 313 | P |
| U92314_s_at | 14 | 4 | 20 | 20 | 18 | 0.70 | 2.77 | 0 | 0 | 3.5 | 311 | P |
| X15729_s_at | 16 | 2 | 20 | 20 | 18 | 0.80 | 4.10 | 1 | 0 | 8.0 | 305 | P |
| U05861_at | 14 | 0 | 20 | 20 | 18 | 0.70 | 3.11 | 0 | 0 | Inf | 297 | P |
| X13461_s_at | 9 | 2 | 20 | 20 | 18 | 0.45 | 1.33 | 0 | 0 | 4.5 | 296 | P |
| U70439_s_at | 12 | 1 | 20 | 20 | 18 | 0.60 | 2.88 | 0 | 0 | 12.0 | 288 | P |

-continued

Connective tissue D

| Gene Name | Positiv | Nega | Pairs | Pairs | Pairs | Pos Fracti | Log Avg | PM Ex | MM Ex | Pos/Neg | Avg Diff | Abs Call |
|---|---|---|---|---|---|---|---|---|---|---|---|---|
| M19267_s_at | 9 | 1 | 19 | 19 | 17 | 0.47 | 2.77 | 2 | 0 | 9.0 | 284 | P |
| L09209_s_at | 13 | 1 | 20 | 20 | 18 | 0.65 | 2.95 | 0 | 0 | 13.0 | 279 | P |
| V00599_s_at | 13 | 2 | 20 | 20 | 18 | 0.65 | 2.04 | 0 | 0 | 6.5 | 278 | P |
| M16750_s_at | 13 | 0 | 20 | 20 | 18 | 0.65 | 3.30 | 0 | 0 | Inf | 277 | P |
| M94046_at | 7 | 0 | 20 | 20 | 18 | 0.35 | 1.76 | 0 | 0 | Inf | 270 | P |
| M65292_s_at | 14 | 0 | 20 | 20 | 18 | 0.70 | 3.97 | 1 | 1 | 14.0 | 251 | P |
| M12963_s_at | 9 | 0 | 19 | 19 | 17 | 0.47 | 3.02 | 0 | 0 | Inf | 248 | P |
| M13690_s_at | 10 | 0 | 20 | 20 | 17 | 0.50 | 2.40 | 1 | 0 | Inf | 248 | P |
| U72649_at | 14 | 1 | 20 | 20 | 18 | 0.70 | 2.43 | 0 | 0 | 14.0 | 244 | P |
| M28213_s_at | 17 | 0 | 20 | 20 | 18 | 0.85 | 4.88 | 1 | 0 | Inf | 241 | P |
| HG3076-HT3238_s_at | 14 | 0 | 20 | 20 | 17 | 0.70 | 3.31 | 1 | 0 | Inf | 239 | P |
| M30448_s_at | 12 | 2 | 20 | 20 | 17 | 0.60 | 2.84 | 0 | 0 | 6.0 | 239 | P |
| M34996_s_at | 17 | 0 | 20 | 20 | 18 | 0.85 | 4.33 | 1 | 0 | Inf | 232 | P |
| D17793_at | 14 | 2 | 20 | 20 | 18 | 0.70 | 2.78 | 0 | 0 | 7.0 | 232 | P |
| X52022_at | 13 | 1 | 20 | 20 | 17 | 0.65 | 2.97 | 0 | 0 | 13.0 | 231 | P |
| X06700_s_at | 16 | 0 | 20 | 20 | 18 | 0.80 | 4.50 | 2 | 0 | Inf | 226 | P |
| Y00787_s_at | 12 | 0 | 20 | 20 | 18 | 0.60 | 2.65 | 0 | 0 | Inf | 224 | P |
| U16799_s_at | 14 | 2 | 20 | 20 | 18 | 0.70 | 3.85 | 2 | 0 | 7.0 | 223 | P |
| X57152_rna1_s_at | 14 | 2 | 20 | 20 | 18 | 0.70 | 2.80 | 0 | 0 | 7.0 | 223 | P |
| D87017_cds3_at | 8 | 0 | 20 | 20 | 18 | 0.40 | 1.43 | 0 | 0 | Inf | 222 | P |
| U05681_s_at | 12 | 2 | 20 | 20 | 18 | 0.60 | 1.94 | 0 | 0 | 6.0 | 221 | P |
| M31551_s_at | 13 | 1 | 20 | 20 | 18 | 0.65 | 3.30 | 1 | 1 | 13.0 | 219 | P |
| X01703_at | 14 | 2 | 20 | 20 | 18 | 0.70 | 2.83 | 1 | 0 | 7.0 | 218 | P |
| J02621_s_at | 11 | 0 | 20 | 20 | 18 | 0.55 | 2.51 | 1 | 0 | Inf | 217 | P |
| M21539_at | 13 | 0 | 20 | 20 | 18 | 0.65 | 2.60 | 1 | 0 | Inf | 215 | P |
| L13740_at | 7 | 0 | 20 | 20 | 18 | 0.35 | 1.21 | 0 | 0 | Inf | 212 | P |
| X52979_rna1_s_at | 14 | 1 | 20 | 20 | 18 | 0.70 | 2.51 | 0 | 0 | 14.0 | 209 | P |
| M27436_s_at | 13 | 0 | 20 | 20 | 18 | 0.65 | 3.39 | 0 | 0 | Inf | 206 | P |
| J03805_s_at | 16 | 0 | 18 | 18 | 16 | 0.89 | 5.53 | 3 | 0 | Inf | 206 | P |
| X17567_s_at | 10 | 2 | 20 | 20 | 17 | 0.50 | 2.32 | 0 | 0 | 5.0 | 206 | P |
| M32304_s_at | 9 | 2 | 20 | 20 | 18 | 0.45 | 1.56 | 0 | 0 | 4.5 | 202 | P |
| M16342_at | 13 | 1 | 20 | 20 | 17 | 0.65 | 2.88 | 0 | 0 | 13.0 | 201 | P |
| M16652_at | 3 | 0 | 4 | 4 | 4 | 0.75 | 2.05 | 0 | 0 | Inf | 201 | P |
| X03068_f_at | 18 | 3 | 40 | 40 | 38 | 0.45 | 1.61 | 0 | 0 | 6.0 | 194 | P |
| M23323_s_at | 11 | 2 | 20 | 20 | 18 | 0.55 | 1.80 | 0 | 0 | 5.5 | 192 | P |
| K02405_f_at | 10 | 2 | 20 | 20 | 18 | 0.50 | 1.27 | 0 | 0 | 5.0 | 192 | P |
| H04535-HT4940_s_at | 8 | 1 | 20 | 20 | 18 | 0.40 | 1.14 | 0 | 0 | 8.0 | 191 | P |
| M57466_s_at | 9 | 2 | 20 | 20 | 18 | 0.45 | 2.18 | 0 | 0 | 4.5 | 188 | P |
| M97935_s_at | 13 | 2 | 20 | 20 | 18 | 0.65 | 2.71 | 0 | 0 | 6.5 | 186 | P |
| X04526_at | 14 | 1 | 20 | 20 | 18 | 0.70 | 2.32 | 0 | 0 | 14.0 | 185 | P |
| M29874_s_at | 13 | 2 | 20 | 20 | 18 | 0.65 | 2.72 | 0 | 0 | 6.5 | 185 | P |
| U04636_rna1_at | 11 | 1 | 20 | 20 | 18 | 0.55 | 1.99 | 0 | 1 | 11.0 | 184 | P |
| Z15115_s_at | 14 | 2 | 20 | 20 | 18 | 0.70 | 2.33 | 0 | 0 | 7.0 | 184 | P |
| X72727_at | 15 | 1 | 20 | 20 | 18 | 0.75 | 3.16 | 0 | 0 | 15.0 | 183 | P |
| Y00264_at | 13 | 1 | 20 | 20 | 17 | 0.65 | 3.56 | 0 | 0 | 13.0 | 183 | P |
| AFFX-BioC-3_at | 11 | 0 | 20 | 20 | 18 | 0.55 | 1.90 | 0 | 0 | Inf | 175 | P |
| HG3044-HT3742_s_at | 11 | 0 | 20 | 20 | 18 | 0.55 | 2.78 | 0 | 0 | Inf | 175 | P |
| U61734_s_at | 10 | 1 | 19 | 19 | 17 | 0.53 | 2.84 | 1 | 0 | 10.0 | 175 | P |
| L49380_at | 8 | 2 | 20 | 20 | 18 | 0.40 | 1.18 | 0 | 0 | 4.0 | 171 | P |
| D10667_s_at | 14 | 1 | 17 | 17 | 15 | 0.82 | 3.23 | 0 | 0 | 14.0 | 171 | P |
| D78577_s_at | 11 | 1 | 20 | 20 | 18 | 0.55 | 2.47 | 2 | 0 | 11.0 | 170 | P |
| D83174_s_at | 9 | 0 | 20 | 20 | 17 | 0.45 | 1.86 | 0 | 0 | Inf | 169 | P |
| M37457_at | 3 | 0 | 4 | 4 | 4 | 0.75 | 2.10 | 0 | 0 | Inf | 168 | P |
| D78132_s_at | 14 | 0 | 20 | 20 | 18 | 0.70 | 5.12 | 2 | 0 | Inf | 167 | P |
| X71345_f_at | 9 | 2 | 20 | 20 | 18 | 0.45 | 1.93 | 1 | 0 | 4.5 | 166 | P |
| U08021_at | 10 | 0 | 20 | 20 | 17 | 0.50 | 2.15 | 0 | 0 | Inf | 165 | P |
| U01691_s_at | 9 | 0 | 20 | 20 | 18 | 0.45 | 3.00 | 3 | 0 | Inf | 164 | P |
| M83216_s_at | 15 | 1 | 20 | 20 | 18 | 0.75 | 3.89 | 0 | 0 | 15.0 | 163 | P |
| HG688-HT688_f_at | 10 | 1 | 20 | 20 | 18 | 0.50 | 1.61 | 0 | 0 | 10.0 | 163 | P |
| M30703_s_at | 10 | 1 | 20 | 20 | 18 | 0.50 | 2.67 | 1 | 1 | 10.0 | 160 | P |
| U79528_s_at | 7 | 0 | 20 | 20 | 18 | 0.35 | 1.46 | 0 | 0 | Inf | 160 | P |
| M93651_at | 10 | 0 | 20 | 20 | 18 | 0.50 | 2.68 | 1 | 0 | Inf | 159 | P |
| HG4541-HT4946_s_at | 10 | 0 | 18 | 18 | 16 | 0.56 | 2.35 | 0 | 0 | Inf | 159 | P |
| X73358_s_at | 9 | 1 | 19 | 19 | 17 | 0.47 | 1.75 | 1 | 0 | 9.0 | 159 | P |
| Z35402_rna1_s_at | 10 | 1 | 20 | 20 | 18 | 0.50 | 2.27 | 0 | 0 | 10.0 | 159 | P |
| U12767_at | 13 | 0 | 20 | 20 | 17 | 0.65 | 2.37 | 0 | 0 | Inf | 154 | P |
| X56841_at | 10 | 3 | 20 | 20 | 18 | 0.50 | 1.42 | 0 | 0 | 3.3 | 154 | P |
| Z74616_s_at | 7 | 0 | 20 | 20 | 18 | 0.35 | 1.67 | 0 | 0 | Inf | 153 | P |
| AFFX-HUMRGE/M10098_5_at | 12 | 2 | 20 | 20 | 18 | 0.60 | 2.04 | 0 | 0 | 6.0 | 152 | P |
| M69181_at | 8 | 1 | 20 | 20 | 18 | 0.40 | 1.76 | 0 | 0 | 8.0 | 151 | P |
| HG4312-HT4582_s_at | 13 | 1 | 20 | 20 | 18 | 0.65 | 3.18 | 2 | 0 | 13.0 | 149 | P |
| HG4264-HT4534_s_at | 8 | 1 | 18 | 18 | 16 | 0.44 | 2.33 | 0 | 0 | 8.0 | 149 | P |
| X85116_rna1_s_at | 12 | 2 | 20 | 20 | 17 | 0.60 | 1.88 | 0 | 0 | 6.0 | 149 | P |
| X05855_s_at | 14 | 0 | 15 | 15 | 12 | 0.93 | 5.08 | 1 | 0 | Inf | 148 | P |

-continued

Connective tissue D

| Gene Name | Positiv | Nega | Pairs | Pairs | Pairs | Pos Fracti | Log Avg | PM Ex | MM Ex | Pos/Neg | Avg Diff | Abs Call |
|---|---|---|---|---|---|---|---|---|---|---|---|---|
| M13452_s_at | 8 | 2 | 20 | 20 | 17 | 0.40 | 1.31 | 0 | 0 | 4.0 | 147 | P |
| J04029_s_at | 10 | 2 | 18 | 18 | 16 | 0.56 | 1.73 | 0 | 0 | 5.0 | 145 | P |
| U09587_at | 13 | 1 | 20 | 20 | 18 | 0.65 | 2.76 | 0 | 0 | 13.0 | 144 | P |
| U54644_s_at | 7 | 1 | 20 | 20 | 17 | 0.35 | 1.37 | 0 | 0 | 7.0 | 143 | P |
| X04602_s_at | 17 | 0 | 20 | 20 | 18 | 0.85 | 3.33 | 0 | 0 | Inf | 141 | P |
| U09510_s_at | 12 | 2 | 20 | 20 | 18 | 0.60 | 2.85 | 2 | 0 | 6.0 | 138 | P |
| X14684_s_at | 10 | 0 | 20 | 20 | 18 | 0.50 | 1.97 | 0 | 0 | Inf | 136 | P |
| S82447_s_at | 8 | 2 | 20 | 20 | 17 | 0.40 | 1.23 | 0 | 0 | 4.0 | 134 | P |
| Z84497_s_at | 11 | 1 | 20 | 20 | 18 | 0.55 | 1.92 | 1 | 0 | 11.0 | 131 | P |
| S40719_s_at | 9 | 3 | 20 | 20 | 18 | 0.45 | 1.49 | 0 | 0 | 3.0 | 130 | P |
| S69272_s_at | 9 | 2 | 20 | 20 | 18 | 0.45 | 1.94 | 0 | 0 | 4.5 | 129 | P |
| X83416_s_at | 9 | 1 | 20 | 20 | 18 | 0.45 | 2.63 | 1 | 0 | 9.0 | 128 | P |
| M96954_s_at | 8 | 1 | 19 | 19 | 17 | 0.42 | 2.02 | 0 | 0 | 8.0 | 127 | P |
| Z25521_s_at | 9 | 0 | 20 | 20 | 18 | 0.45 | 1.60 | 0 | 0 | Inf | 127 | P |
| K03431_cds1_at | 7 | 1 | 20 | 20 | 18 | 0.35 | 1.26 | 0 | 0 | 7.0 | 127 | P |
| M24069_at | 12 | 2 | 20 | 20 | 18 | 0.60 | 2.55 | 0 | 0 | 6.0 | 127 | P |
| L15189_s_at | 9 | 1 | 20 | 20 | 18 | 0.45 | 3.10 | 1 | 0 | 9.0 | 126 | P |
| M13929_s_at | 10 | 1 | 20 | 20 | 17 | 0.50 | 2.17 | 0 | 0 | 10.0 | 125 | P |
| Z47055_s_at | 13 | 1 | 20 | 20 | 17 | 0.65 | 2.45 | 0 | 0 | 13.0 | 124 | P |
| X80763_s_at | 8 | 0 | 20 | 20 | 18 | 0.40 | 1.74 | 0 | 0 | Inf | 124 | P |
| M36430_s_at | 9 | 1 | 20 | 20 | 17 | 0.45 | 1.82 | 0 | 0 | 9.0 | 118 | P |
| J03242_s_at | 9 | 1 | 20 | 20 | 18 | 0.45 | 1.42 | 0 | 0 | 9.0 | 117 | P |
| X14766_at | 11 | 2 | 20 | 20 | 18 | 0.55 | 1.49 | 0 | 0 | 5.5 | 115 | P |
| M18391_s_at | 11 | 0 | 20 | 20 | 18 | 0.55 | 2.29 | 0 | 0 | Inf | 114 | P |
| U26173_s_at | 13 | 0 | 20 | 20 | 18 | 0.65 | 2.98 | 2 | 0 | Inf | 114 | P |
| AC002045_xpt2_s_at | 12 | 2 | 20 | 20 | 17 | 0.60 | 1.73 | 0 | 0 | 6.0 | 113 | P |
| HG273-HT273_s_at | 6 | 2 | 15 | 15 | 13 | 0.40 | 1.42 | 0 | 0 | 3.0 | 113 | P |
| HG2743-HT2846_s_at | 10 | 1 | 20 | 20 | 18 | 0.50 | 1.52 | 0 | 0 | 10.0 | 113 | P |
| X03350_at | 14 | 1 | 20 | 20 | 18 | 0.70 | 3.75 | 2 | 0 | 14.0 | 112 | P |
| X65965_s_at | 12 | 1 | 18 | 18 | 16 | 0.67 | 2.86 | 0 | 0 | 12.0 | 112 | P |
| U27460_at | 10 | 2 | 20 | 20 | 18 | 0.50 | 1.91 | 0 | 0 | 5.0 | 111 | P |
| HG2639-HT2735_s_at | 10 | 1 | 20 | 20 | 18 | 0.50 | 2.56 | 1 | 0 | 10.0 | 110 | P |
| U32986_s_at | 10 | 0 | 20 | 20 | 18 | 0.50 | 1.68 | 0 | 0 | Inf | 110 | P |
| L06797_s_at | 8 | 2 | 20 | 20 | 17 | 0.40 | 2.24 | 0 | 0 | 4.0 | 109 | P |
| U41767_at | 8 | 2 | 20 | 20 | 17 | 0.40 | 1.12 | 0 | 0 | 4.0 | 108 | P |
| X12953_at | 9 | 1 | 20 | 20 | 18 | 0.45 | 1.30 | 0 | 0 | 9.0 | 108 | P |
| M97796_s_at | 7 | 2 | 19 | 19 | 16 | 0.37 | 1.59 | 0 | 0 | 3.5 | 107 | P |
| U50196_at | 12 | 3 | 20 | 20 | 18 | 0.60 | 1.98 | 0 | 0 | 4.0 | 106 | P |
| X05610_at | 8 | 2 | 20 | 20 | 17 | 0.40 | 1.75 | 0 | 0 | 4.0 | 104 | P |
| L24774_s_at | 10 | 2 | 20 | 20 | 18 | 0.50 | 1.83 | 0 | 0 | 5.0 | 102 | P |
| M13994_s_at | 7 | 2 | 20 | 20 | 18 | 0.35 | 1.52 | 1 | 0 | 3.5 | 102 | P |
| U41654_at | 12 | 2 | 20 | 20 | 18 | 0.60 | 2.21 | 0 | 0 | 6.0 | 101 | P |
| U46006_at | 13 | 0 | 20 | 20 | 18 | 0.65 | 3.02 | 0 | 0 | Inf | 101 | P |
| AFFX-HUMISGF3A/M97935_3_at | 13 | 2 | 20 | 20 | 18 | 0.65 | 2.69 | 1 | 0 | 6.5 | 99 | P |
| Y00081_s_at | 10 | 1 | 20 | 20 | 18 | 0.50 | 1.43 | 0 | 0 | 10.0 | 99 | P |
| X58528_s_at | 12 | 0 | 17 | 17 | 15 | 0.71 | 3.67 | 1 | 0 | Inf | 99 | P |
| U36341_rna1_at | 7 | 1 | 20 | 20 | 18 | 0.35 | 1.08 | 0 | 0 | 7.0 | 98 | P |
| U22431_at | 12 | 1 | 20 | 20 | 17 | 0.60 | 2.37 | 0 | 0 | 12.0 | 98 | P |
| M60974_s_at | 7 | 0 | 20 | 20 | 17 | 0.35 | 1.28 | 0 | 0 | Inf | 96 | P |
| AFFX-BioB-5_at | 8 | 2 | 20 | 20 | 18 | 0.40 | 1.15 | 0 | 0 | 4.0 | 95 | P |
| D42040_s_at | 8 | 2 | 20 | 20 | 18 | 0.40 | 1.51 | 0 | 0 | 4.0 | 94 | P |
| U67122_sat | 11 | 1 | 20 | 20 | 18 | 0.55 | 2.43 | 0 | 0 | 11.0 | 94 | P |
| U28014_at | 13 | 0 | 20 | 20 | 18 | 0.65 | 3.23 | 1 | 0 | Inf | 94 | P |
| D79206_s_at | 8 | 0 | 20 | 20 | 17 | 0.40 | 1.32 | 0 | 0 | Inf | 93 | P |
| S78771_s_at | 10 | 3 | 20 | 20 | 18 | 0.50 | 1.91 | 0 | 0 | 3.3 | 92 | P |
| M58525_s_at | 7 | 1 | 20 | 20 | 18 | 0.35 | 1.20 | 0 | 0 | 7.0 | 92 | P |
| M60483_rnal_s_at | 9 | 1 | 18 | 18 | 16 | 0.50 | 2.65 | 1 | 0 | 9.0 | 92 | P |
| HG2868-HT3012_s_at | 9 | 2 | 20 | 20 | 18 | 0.45 | 2.18 | 1 | 0 | 4.5 | 91 | P |
| U41518_at | 10 | 0 | 20 | 20 | 18 | 0.50 | 1.67 | 0 | 0 | Inf | 90 | P |
| Z74615_at | 8 | 1 | 20 | 20 | 17 | 0.40 | 1.78 | 1 | 0 | 8.0 | 90 | P |
| Z35085_s_at | 14 | 1 | 19 | 19 | 17 | 0.74 | 4.26 | 1 | 0 | 14.0 | 90 | P |
| L76517_at | 7 | 0 | 20 | 20 | 17 | 0.35 | 1.61 | 0 | 0 | Inf | 89 | P |
| M16276_at | 9 | 1 | 20 | 20 | 18 | 0.45 | 1.78 | 0 | 0 | 9.0 | 89 | P |
| D45917_s_at | 10 | 2 | 20 | 20 | 18 | 0.50 | 2.13 | 2 | 1 | 5.0 | 88 | P |
| U19495_s_at | 15 | 1 | 20 | 20 | 17 | 0.75 | 4.92 | 4 | 0 | 15.0 | 88 | P |
| X07438_s_at | 14 | 2 | 19 | 19 | 17 | 0.74 | 3.49 | 1 | 0 | 7.0 | 88 | P |
| U41740_at | 12 | 2 | 20 | 20 | 18 | 0.60 | 2.58 | 1 | 0 | 6.0 | 86 | P |
| X03363_s_at | 9 | 1 | 20 | 20 | 18 | 0.45 | 1.54 | 0 | 0 | 9.0 | 86 | P |
| M28882_s_at | 8 | 1 | 17 | 17 | 15 | 0.47 | 2.28 | 1 | 0 | 8.0 | 85 | P |
| HG4322-HT4592_at | 11 | 2 | 20 | 20 | 18 | 0.55 | 2.59 | 1 | 0 | 5.5 | 85 | P |
| L38490_s_at | 7 | 1 | 20 | 20 | 18 | 0.35 | 1.30 | 0 | 0 | 7.0 | 84 | P |
| X62083_s_at | 7 | 1 | 20 | 20 | 18 | 0.35 | 1.31 | 1 | 0 | 7.0 | 84 | P |
| U43944_at | 12 | 1 | 20 | 20 | 18 | 0.60 | 2.44 | 0 | 0 | 12.0 | 84 | P |
| HG3484-HT3678_s_at | 9 | 0 | 20 | 20 | 18 | 0.45 | 2.10 | 0 | 0 | Inf | 83 | P |

-continued

Connective tissue D

| Gene Name | Positiv | Nega | Pairs | Pairs | Pairs | Pos Fracti | Log Avg | PM Ex | MM Ex | Pos/Neg | Avg Diff | Abs Call |
|---|---|---|---|---|---|---|---|---|---|---|---|---|
| X62534_s_at | 10 | 0 | 20 | 20 | 18 | 0.50 | 2.63 | 0 | 0 | Inf | 83 | P |
| Y00097_s_at | 8 | 2 | 20 | 20 | 18 | 0.40 | 1.73 | 0 | 0 | 4.0 | 82 | P |
| S72024_s_at | 8 | 1 | 20 | 20 | 18 | 0.40 | 1.57 | 0 | 0 | 8.0 | 82 | P |
| U72509_s_at | 10 | 1 | 19 | 19 | 16 | 0.53 | 2.19 | 0 | 0 | 10.0 | 82 | P |
| X65488_at | 12 | 0 | 20 | 20 | 18 | 0.60 | 2.37 | 1 | 0 | Inf | 81 | P |
| L32831_s_at | 11 | 2 | 20 | 20 | 18 | 0.55 | 1.13 | 0 | 0 | 5.5 | 81 | P |
| U45448_s_at | 10 | 3 | 20 | 20 | 18 | 0.50 | 1.88 | 0 | 0 | 3.3 | 81 | P |
| M20867_s_at | 9 | 1 | 17 | 17 | 14 | 0.53 | 1.70 | 0 | 0 | 9.0 | 79 | P |
| U30827_s_at | 13 | 1 | 20 | 20 | 17 | 0.65 | 3.56 | 2 | 0 | 13.0 | 79 | P |
| M31932_at | 8 | 2 | 20 | 20 | 18 | 0.40 | 1.12 | 0 | 0 | 4.0 | 79 | P |
| Z69030_s_at | 6 | 1 | 18 | 18 | 16 | 0.33 | 1.85 | 1 | 0 | 6.0 | 78 | P |
| HG3638-HT3849_s_at | 9 | 1 | 20 | 20 | 18 | 0.45 | 1.88 | 1 | 0 | 9.0 | 77 | P |
| U35005_s_at | 10 | 2 | 20 | 20 | 18 | 0.50 | 2.08 | 0 | 0 | 5.0 | 76 | P |
| HG2981-HT3127_s_at | 11 | 1 | 19 | 19 | 17 | 0.58 | 1.75 | 0 | 0 | 11.0 | 75 | P |
| D14826_s_at | 7 | 1 | 20 | 20 | 18 | 0.35 | 1.19 | 0 | 0 | 7.0 | 74 | P |
| M63838_s_at | 9 | 0 | 20 | 20 | 18 | 0.45 | 2.69 | 1 | 0 | Inf | 73 | P |
| Y00451_s_at | 8 | 0 | 20 | 20 | 18 | 0.40 | 1.34 | 0 | 0 | Inf | 73 | P |
| U19247_rna1_s_at | 10 | 2 | 20 | 20 | 18 | 0.50 | 2.37 | 0 | 0 | 5.0 | 72 | P |
| J04093_s_at | 10 | 0 | 20 | 20 | 18 | 0.50 | 1.92 | 0 | 0 | Inf | 72 | P |
| X60003_s_at | 9 | 2 | 20 | 20 | 18 | 0.45 | 1.58 | 0 | 0 | 4.5 | 72 | P |
| M61832_s_at | 8 | 2 | 20 | 20 | 18 | 0.40 | 1.11 | 0 | 0 | 4.0 | 71 | P |
| U01337_at | 7 | 1 | 20 | 20 | 18 | 0.35 | 1.14 | 0 | 0 | 7.0 | 68 | P |
| Z26491_s_at | 10 | 0 | 20 | 20 | 18 | 0.50 | 2.52 | 1 | 0 | Inf | 66 | P |
| U33936_s_at | 12 | 2 | 20 | 20 | 18 | 0.60 | 1.80 | 0 | 0 | 6.0 | 66 | P |
| S68805_at | 10 | 0 | 20 | 20 | 18 | 0.50 | 2.36 | 0 | 0 | Inf | 65 | P |
| D83260_s_at | 8 | 1 | 19 | 19 | 16 | 0.42 | 1.83 | 0 | 0 | 8.0 | 65 | P |
| U20938_at | 11 | 0 | 20 | 20 | 18 | 0.55 | 1.93 | 0 | 0 | Inf | 64 | P |
| HG1400-HT1400_s_at | 11 | 2 | 20 | 20 | 18 | 0.55 | 2.42 | 0 | 0 | 5.5 | 63 | P |
| L14778_s_at | 12 | 0 | 19 | 19 | 17 | 0.63 | 4.34 | 4 | 0 | Inf | 61 | P |
| U96131_at | 8 | 1 | 20 | 20 | 18 | 0.40 | 1.46 | 1 | 0 | 8.0 | 60 | P |
| M17183_s_at | 8 | 1 | 20 | 20 | 18 | 0.40 | 1.95 | 1 | 0 | 8.0 | 60 | P |
| L00634_s_at | 10 | 1 | 19 | 19 | 17 | 0.53 | 3.14 | 2 | 0 | 10.0 | 60 | P |
| U58046_s_at | 12 | 1 | 20 | 20 | 18 | 0.60 | 3.04 | 1 | 0 | 12.0 | 59 | P |
| X53002_s_at | 8 | 2 | 20 | 20 | 18 | 0.40 | 1.14 | 0 | 0 | 4.0 | 59 | P |
| X69920_s_at | 8 | 1 | 20 | 20 | 18 | 0.40 | 2.17 | 0 | 0 | 8.0 | 59 | P |
| U33052_s_at | 8 | 0 | 20 | 20 | 17 | 0.40 | 3.36 | 1 | 0 | Inf | 59 | P |
| U44103_at | 10 | 2 | 20 | 20 | 17 | 0.50 | 2.57 | 0 | 0 | 5.0 | 59 | P |
| D28473_s_at | 10 | 2 | 20 | 20 | 18 | 0.50 | 2.16 | 0 | 0 | 5.0 | 58 | P |
| U60061_at | 9 | 2 | 20 | 20 | 18 | 0.45 | 2.22 | 2 | 0 | 4.5 | 57 | P |
| M21119_s_at | 7 | 1 | 20 | 20 | 18 | 0.35 | 0.94 | 0 | 0 | 7.0 | 57 | P |
| U33838_at | 2 | 0 | 4 | 4 | 4 | 0.50 | 2.70 | 0 | 0 | Inf | 57 | P |
| M24736_s_at | 7 | 1 | 20 | 20 | 18 | 0.35 | 1.12 | 0 | 0 | 7.0 | 57 | P |
| HG4518-HT4921_r_at | 1 | 0 | 2 | 2 | 2 | 0.50 | 1.26 | 0 | 0 | Inf | 56 | P |
| HG4557-HT4962_r_at | 3 | 0 | 5 | 5 | 5 | 0.60 | 1.98 | 0 | 0 | Inf | 56 | P |
| S77410_at | 7 | 1 | 20 | 20 | 18 | 0.35 | 1.04 | 0 | 0 | 7.0 | 55 | P |
| HG2090-HT2152_s_at | 7 | 2 | 19 | 19 | 17 | 0.37 | 1.63 | 1 | 1 | 3.5 | 55 | P |
| X81625_at | 9 | 1 | 20 | 20 | 18 | 0.45 | 2.01 | 1 | 0 | 9.0 | 54 | P |
| U41766_s_at | 8 | 2 | 20 | 20 | 18 | 0.40 | 1.27 | 1 | 0 | 4.0 | 53 | P |
| U61276_s_at | 9 | 2 | 20 | 20 | 18 | 0.45 | 2.01 | 0 | 0 | 4.5 | 53 | P |
| Y07566_at | 9 | 1 | 20 | 20 | 18 | 0.45 | 1.50 | 0 | 0 | 9.0 | 53 | P |
| U33632_at | 12 | 1 | 20 | 20 | 17 | 0.60 | 3.09 | 1 | 0 | 12.0 | 52 | P |
| M10321_at | 7 | 1 | 20 | 20 | 18 | 0.35 | 1.12 | 0 | 0 | 7.0 | 52 | P |
| J03934_s_at | 9 | 2 | 20 | 20 | 18 | 0.45 | 1.91 | 0 | 0 | 4.5 | 51 | P |
| X14253_s_at | 8 | 2 | 20 | 20 | 18 | 0.40 | 1.76 | 0 | 0 | 4.0 | 51 | P |
| L15326_s_at | 10 | 1 | 20 | 20 | 18 | 0.50 | 1.91 | 0 | 0 | 10.0 | 50 | P |
| M75715_s_at | 9 | 1 | 19 | 19 | 17 | 0.47 | 2.08 | 0 | 0 | 9.0 | 50 | P |
| L08010_at | 8 | 2 | 20 | 20 | 17 | 0.40 | 1.72 | 0 | 0 | 4.0 | 50 | P |
| M31516_s_at | 7 | 0 | 20 | 20 | 18 | 0.35 | 1.37 | 0 | 0 | Inf | 49 | P |
| M96843_at | 8 | 2 | 20 | 20 | 18 | 0.40 | 0.99 | 0 | 0 | 4.0 | 48 | P |
| X75918_at | 11 | 2 | 20 | 20 | 18 | 0.55 | 1.77 | 0 | 0 | 5.5 | 48 | P |
| D28235_s_at | 10 | 1 | 20 | 20 | 18 | 0.50 | 1.49 | 0 | 0 | 10.0 | 47 | P |
| M19508_xpt3_s_at | 8 | 1 | 20 | 20 | 18 | 0.40 | 0.95 | 0 | 0 | 8.0 | 47 | P |
| S79219_s_at | 9 | 3 | 20 | 20 | 18 | 0.45 | 1.79 | 0 | 0 | 3.0 | 46 | P |
| L35249_s_at | 7 | 1 | 18 | 18 | 16 | 0.39 | 1.78 | 0 | 0 | 7.0 | 45 | P |
| U84388_at | 10 | 0 | 20 | 20 | 18 | 0.50 | 3.54 | 1 | 0 | Inf | 45 | P |
| AFFX-HUMTFRR/M11507_5_at | 9 | 2 | 20 | 20 | 18 | 0.45 | 1.08 | 0 | 0 | 4.5 | 44 | P |
| HG2743-HT3926_s_at | 12 | 1 | 20 | 20 | 18 | 0.60 | 1.82 | 0 | 0 | 12.0 | 44 | P |
| HG945-HT945_s_at | 9 | 2 | 20 | 20 | 18 | 0.45 | 1.08 | 0 | 0 | 4.5 | 44 | P |
| U69140_s_at | 7 | 1 | 18 | 18 | 16 | 0.39 | 2.73 | 1 | 0 | 7.0 | 44 | P |
| AFFX-HUMRGE/M10098_M_at | 7 | 1 | 20 | 20 | 18 | 0.35 | 1.75 | 0 | 0 | 7.0 | 42 | P |
| U73936_at | 8 | 2 | 20 | 20 | 18 | 0.40 | 1.14 | 0 | 0 | 4.0 | 42 | P |
| AB000381_s_at | 9 | 2 | 20 | 20 | 18 | 0.45 | 2.66 | 2 | 0 | 4.5 | 42 | P |
| M29610_at | 9 | 2 | 14 | 14 | 12 | 0.64 | 4.77 | 4 | 0 | 4.5 | 42 | P |
| U04285_s_at | 9 | 3 | 20 | 20 | 17 | 0.45 | 1.90 | 1 | 0 | 3.0 | 42 | P |

-continued

Connective tissue D

| Gene Name | Positiv | Nega | Pairs | Pairs | Pairs | Pos Fracti | Log Avg | PM Ex | MM Ex | Pos/Neg | Avg Diff | Abs Call |
|---|---|---|---|---|---|---|---|---|---|---|---|---|
| HG3075-HT3236_s_at | 7 | 2 | 20 | 20 | 17 | 0.35 | 1.57 | 2 | 0 | 3.5 | 40 | P |
| X54993_s_at | 8 | 2 | 20 | 20 | 18 | 0.40 | 1.29 | 1 | 0 | 4.0 | 40 | P |
| U61397_s_at | 7 | 1 | 20 | 20 | 18 | 0.35 | 1.56 | 0 | 0 | 7.0 | 40 | P |
| X99886_s_at | 7 | 0 | 19 | 19 | 17 | 0.37 | 1.26 | 0 | 0 | Inf | 40 | P |
| S82597_rna1_s_at | 9 | 1 | 20 | 20 | 18 | 0.45 | 1.21 | 0 | 0 | 9.0 | 39 | P |
| X06182_s_at | 8 | 1 | 20 | 20 | 18 | 0.40 | 1.48 | 1 | 0 | 8.0 | 38 | P |
| X75091_s_at | 7 | 2 | 20 | 20 | 18 | 0.35 | 1.62 | 0 | 0 | 3.5 | 38 | P |
| X63741_s_at | 8 | 1 | 19 | 19 | 17 | 0.42 | 1.37 | 1 | 0 | 8.0 | 38 | P |
| D12775_s_at | 8 | 0 | 20 | 20 | 17 | 0.40 | 0.94 | 0 | 0 | Inf | 37 | P |
| D13720_s_at | 9 | 2 | 20 | 20 | 17 | 0.45 | 2.25 | 1 | 0 | 4.5 | 37 | P |
| D87716_s_at | 10 | 2 | 20 | 20 | 18 | 0.50 | 3.25 | 2 | 0 | 5.0 | 37 | P |
| D83017_s_at | 8 | 2 | 20 | 20 | 18 | 0.40 | 1.47 | 0 | 0 | 4.0 | 37 | P |
| M22348_s_at | 9 | 2 | 20 | 20 | 18 | 0.45 | 1.52 | 0 | 0 | 4.5 | 37 | P |
| X93511_s_at | 10 | 2 | 20 | 20 | 18 | 0.50 | 1.16 | 0 | 0 | 5.0 | 37 | P |
| L43575_s_at | 8 | 1 | 20 | 20 | 17 | 0.40 | 1.34 | 0 | 0 | 8.0 | 35 | P |
| M81182_s_at | 9 | 1 | 20 | 20 | 17 | 0.45 | 2.31 | 0 | 0 | 9.0 | 35 | P |
| L36870_at | 9 | 2 | 20 | 20 | 18 | 0.45 | 1.15 | 0 | 0 | 4.5 | 34 | P |
| U07969_s_at | 9 | 1 | 20 | 20 | 17 | 0.45 | 2.63 | 3 | 0 | 9.0 | 34 | P |
| HG2987-HT3136_s_at | 8 | 2 | 20 | 20 | 17 | 0.40 | 1.21 | 0 | 0 | 4.0 | 33 | P |
| X92493_s_at | 7 | 1 | 20 | 20 | 18 | 0.35 | 2.57 | 1 | 0 | 7.0 | 33 | P |
| X63468_at | 8 | 0 | 20 | 20 | 18 | 0.40 | 1.50 | 1 | 0 | Inf | 32 | P |
| D90070_s_at | 8 | 0 | 20 | 20 | 18 | 0.40 | 2.05 | 1 | 0 | Inf | 31 | P |
| X83490_s_at | 8 | 0 | 20 | 20 | 18 | 0.40 | 2.62 | 2 | 0 | Inf | 31 | P |
| M31169_s_at | 8 | 2 | 20 | 20 | 18 | 0.40 | 1.22 | 0 | 0 | 4.0 | 30 | P |
| X51435_s_at | 7 | 1 | 20 | 20 | 18 | 0.35 | 1.56 | 0 | 0 | 7.0 | 30 | P |
| X68505_s_at | 7 | 1 | 20 | 20 | 18 | 0.35 | 1.03 | 0 | 1 | 7.0 | 27 | P |
| S80267_s_at | 9 | 2 | 20 | 20 | 18 | 0.45 | 1.23 | 0 | 0 | 4.5 | 27 | P |
| HG855-HT855_s_at | 8 | 2 | 20 | 20 | 18 | 0.40 | 1.30 | 0 | 0 | 4.0 | 27 | P |
| Y00083_s_at | 7 | 2 | 20 | 20 | 17 | 0.35 | 1.31 | 1 | 0 | 3.5 | 27 | P |
| D10922_s_at | 9 | 0 | 20 | 20 | 18 | 0.45 | 3.22 | 1 | 0 | Inf | 26 | P |
| U08006_s_at | 8 | 2 | 20 | 20 | 17 | 0.40 | 0.91 | 0 | 0 | 4.0 | 25 | P |
| M57464_s_at | 7 | 0 | 20 | 20 | 17 | 0.35 | 1.21 | 0 | 0 | Inf | 23 | P |
| X12530_s_at | 9 | 2 | 19 | 19 | 17 | 0.47 | 2.24 | 1 | 0 | 4.5 | 23 | P |
| S79873_s_at | 8 | 1 | 20 | 20 | 17 | 0.40 | 0.94 | 0 | 0 | 8.0 | 22 | P |
| X65784_s_at | 7 | 1 | 18 | 18 | 16 | 0.39 | 0.98 | 0 | 0 | 7.0 | 21 | P |
| L14430_at | 7 | 1 | 20 | 20 | 18 | 0.35 | 0.98 | 0 | 0 | 7.0 | 21 | P |
| M24349_s_at | 7 | 2 | 20 | 20 | 17 | 0.35 | 1.71 | 1 | 1 | 3.5 | 20 | P |
| U20536_s_at | 8 | 0 | 20 | 20 | 18 | 0.40 | 1.18 | 1 | 0 | Inf | 20 | P |

TABLE 7

| Gene Name | Pos | Neg | Pairs | Pairs | Pair. Pos | Fr | Log Av | PM I | MM | Pos/N. | Avg Diff | Abs Call |
|---|---|---|---|---|---|---|---|---|---|---|---|---|
| hum_alu_·at | 69 | 0 | 69 | 69 | 671.00 | 7.38 | | 12 | 0 | Inf | 27021 | P |
| L06499_at | 20 | 0 | 20 | 20 | 181.00 | 7.57 | | 3 | 0 | Inf | 12530 | P |
| HG3214-HT3391_at | 19 | 0 | 20 | 20 | 180.95 | 7.36 | | 4 | 0 | Inf | 8561 | P |
| AFFX-CreX-3_at | 19 | 0 | 20 | 20 | 180.95 | 8.08 | | 2 | 0 | Inf | 5961 | P |
| HG3364-HT3541_at | 20 | 0 | 20 | 20 | 181.00 | 7.76 | | 7 | 0 | Inf | 5937 | P |
| M13934_cds2_at | 19 | 0 | 20 | 20 | 180.95 | 6.91 | | 1 | 0 | Inf | 5721 | P |
| HG1800-HT1823_at | 19 | 0 | 20 | 20 | 180.95 | 7.68 | | 4 | 0 | Inf | 5403 | P |
| M17886_at | 18 | 0 | 20 | 20 | 180.90 | 5.81 | | 1 | 0 | Inf | 5130 | P |
| M11147_at | 18 | 0 | 20 | 20 | 180.90 | 6.85 | | 3 | 0 | Inf | 4610 | P |
| 045370_at | 19 | 0 | 20 | 20 | 180.95 | 5.40 | | 2 | 0 | Inf | 4549 | P |
| HG2873-HT3017_at | 18 | 0 | 20 | 20 | 180.90 | 7.15 | | 3 | 0 | Inf | 4508 | P |
| AFFX-CreX-5_at | 20 | 0 | 20 | 20 | 181.00 | 7.29 | | 4 | 0 | Inf | 4443 | P |
| M18000_at | 20 | 0 | 20 | 20 | 181.00 | 8.01 | | 6 | 0 | Inf | 4368 | P |
| D23660_at | 19 | 0 | 20 | 20 | 180.95 | 7.99 | | 6 | 0 | Inf | 4257 | P |
| L06505_at | 17 | 0 | 20 | 20 | 180.85 | 5.35 | | 2 | 0 | Inf | 4194 | P |
| HG3549-HT3751_at | 19 | 0 | 20 | 20 | 180.95 | 6.73 | | 3 | 0 | Inf | 4127 | P |
| M17885_at | 19 | 1 | 20 | 20 | 180.95 | 6.97 | | 2 | 0 | 19.0 | 3866 | P |
| AFFX-HUMGAPDH/M331 | 19 | 0 | 20 | 20 | 180.95 | 5.62 | | 1 | 0 | Inf | 3862 | P |
| L38941_at | 20 | 0 | 20 | 20 | 181.00 | 8.01 | | 5 | 0 | Inf | 3734 | P |
| AFFX-BioDn-3_at | 17 | 0 | 20 | 20 | 180.85 | 4.18 | | 0 | 0 | Inf | 3458 | P |
| HG2788-HT2896_at | 18 | 0 | 20 | 20 | 180.90 | 6.08 | | 1 | 0 | Inf | 3126 | P |
| M17733_at | 18 | 0 | 20 | 20 | 180.90 | 6.92 | | 3 | 0 | Inf | 2982 | P |
| D79205_at | 20 | 0 | 20 | 20 | 181.00 | 8.85 | | 8 | 0 | Inf | 2864 | P |
| L19527_at | 18 | 0 | 20 | 20 | 180.90 | 5.82 | | 2 | 0 | Inf | 2522 | P |
| D78361_at | 18 | 0 | 20 | 20 | 180.90 | 5.73 | | 0 | 0 | Inf | 2513 | P |
| AFFX-HSAC07/X00351_3 | 18 | 0 | 20 | 20 | 180.90 | 5.45 | | 1 | 0 | Inf | 2382 | P |
| D14530_at | 20 | 0 | 20 | 20 | 181.00 | 7.43 | | 3 | 0 | Inf | 2301 | P |
| HG821-HT821_at | 18 | 0 | 20 | 20 | 180.90 | 5.85 | | 2 | 0 | Inf | 1918 | P |

TABLE 7-continued

| Gene Name | Pos | Neg | Pairs | Pairs | Pair. Pos | Fr Log Av | PM I MM | Pos/N. | Avg Diff Abs Call |
|---|---|---|---|---|---|---|---|---|---|
| HG613-HT613_at | 19 | 0 | 20 | 20 | 170.95 | 6.85 | 5 | 0 Inf | 1834 P |
| HG4319-HT4589_at | 19 | 0 | 20 | 20 | 180.95 | 6.05 | 1 | 0 Inf | 1746 P |
| HG384-HT384_at | 12 | 0 | 20 | 20 | 170.60 | 4.27 | 2 | 0 Inf | 1634 P |
| L20941_at | 15 | 0 | 20 | 20 | 170.75 | 3.62 | 1 | 0 Inf | 1530 P |
| HG4542-HT4947_at | 17 | 0 | 20 | 20 | 180.85 | 5.16 | 1 | 0 Inf | 1500 P |
| HG311-HT311_at | 18 | 1 | 20 | 20 | 170.90 | 6.14 | 3 | 0 18.0 | 1484 P |
| AC002115_cds1_at | 16 | 0 | 20 | 20 | 180.80 | 4.81 | 0 | 0 Inf | 1456 P |
| AC002115_cds4_at | 16 | 0 | 20 | 20 | 180.80 | 3.23 | 0 | 0 Inf | 1382 P |
| M11353_at | 18 | 1 | 20 | 20 | 170.80 | 6.14 | 3 | 0 16.0 | 1359 P |
| HG33-HT33_at | 18 | 0 | 20 | 20 | 170.90 | 5.44 | 1 | 0 Inf | 1327 P |
| D00017_at | 16 | 0 | 20 | 20 | 180.80 | 4.46 | 0 | 0 Inf | 1293 P |
| L11566_at | 14 | 0 | 20 | 20 | 180.70 | 3.86 | 0 | 0 Inf | 1195 P |
| D87735_at | 17 | 0 | 20 | 20 | 170.85 | 4.52 | 1 | 0 Inf | 1192 P |
| AFFX-HSAC07/X00351_at | 18 | 1 | 20 | 20 | 180.90 | 3.90 | 0 | 0 18.0 | 1181 P |
| J04164_at | 11 | 2 | 20 | 20 | 180.55 | 2.83 | 2 | 0 5.5 | 1166 P |
| J03592_at | 17 | 1 | 20 | 20 | 180.85 | 4.77 | 1 | 0 17.0 | 1140 P |
| HG662-HT662_at | 9 | 2 | 20 | 20 | 180.45 | 2.67 | 0 | 0 4.5 | 955 P |
| L19686_rna1_at | 14 | 2 | 20 | 20 | 180.70 | 3.02 | 0 | 0 7.0 | 919 P |
| L26247_at | 15 | 0 | 20 | 20 | 180.75 | 4.10 | 0 | 0 Inf | 886 P |
| HG2279-HT2375_at | 16 | 0 | 20 | 20 | 180.80 | 2.80 | 1 | 0 Inf | 872 P |
| D89667_at | 17 | 1 | 20 | 20 | 180.85 | 5.25 | 0 | 0 17.0 | 842 P |
| D38583_at | 18 | 1 | 20 | 20 | 180.90 | 4.55 | 1 | 0 18.0 | 841 P |
| AFFX-HSAC07/X00351_5 | 16 | 1 | 20 | 20 | 180.80 | 4.03 | 1 | 0 16.0 | 829 P |
| D00654_at | 15 | 0 | 20 | 20 | 180.75 | 3.92 | 1 | 0 Inf | 751 P |
| D30655_at | 14 | 0 | 20 | 20 | 180.70 | 4.02 | 1 | 0 Inf | 728 P |
| AFFX-HUMGAPDH/M331 | 14 | 2 | 20 | 20 | 180.70 | 2.59 | 0 | 0 7.0 | 725 P |
| M19283_at | 15 | 2 | 20 | 20 | 180.15 | 3.61 | 1 | 0 7.5 | 725 P |
| M19961_at | 14 | 3 | 20 | 20 | 180.70 | 2.67 | 2 | 0 4.7 | 705 P |
| J03827_at | 13 | 0 | 20 | 20 | 180.65 | 3.12 | 0 | 0 Inf | 694 P |
| AFFX-BioDn-5_at | 11 | 0 | 20 | 20 | 180.55 | 2.70 | 0 | 0 Inf | 692 P |
| D63874_at | 12 | 1 | 20 | 20 | 180.60 | 3.74 | 3 | 0 12.0 | 675 P |
| J03191_at | 17 | 0 | 20 | 20 | 180.85 | 4.97 | 0 | 0 Inf | 668 P |
| J04823_rna1_at | 15 | 1 | 20 | 20 | 180.75 | 3.33 | 0 | 0 15.0 | 638 P |
| K03460_at | 9 | 0 | 20 | 20 | 180.45 | 2.61 | 0 | 0 Inf | 632 P |
| D29012_at | 12 | 3 | 20 | 20 | 180.60 | 2.49 | 0 | 0 4.0 | 628 P |
| D14710_at | 15 | 0 | 20 | 20 | 180.75 | 3.42 | 2 | 0 Inf | 613 P |
| D45248_at | 14 | 1 | 20 | 20 | 180.70 | 3.48 | 0 | 0 14.0 | 603 P |
| M15661_at | 17 | 1 | 20 | 20 | 180.85 | 3.85 | 0 | 0 17.0 | 600 P |
| HG1153-HT1153_at | 13 | 1 | 20 | 20 | 180.65 | 3.12 | 0 | 0 13.0 | 583 P |
| 28124_at | 14 | 0 | 20 | 20 | 180.70 | 2.65 | 0 | 0 Inf | 580 P |
| 04988_at | 14 | 0 | 20 | 20 | 180.70 | 3.69 | 1 | 0 Inf | 578 P |
| AFFX-BioC-5_at | 15 | 1 | 20 | 20 | 180.75 | 2.69 | 0 | 0 15.0 | 557 P |
| K02765_at | 15 | 0 | 20 | 20 | 180.75 | 2.97 | 1 | 0 Inf | 540 P |
| J02854_at | 11 | 0 | 20 | 20 | 180.55 | 2.21 | 0 | 0 Inf | 522 P |
| D13118_at | 9 | 1 | 20 | 20 | 180.45 | 2.11 | 1 | 0 9.0 | 501 P |
| D23662_at | 14 | 1 | 20 | 20 | 180.70 | 2.87 | 0 | 0 14.0 | 496 P |
| D29963_at | 13 | 1 | 20 | 20 | 180.65 | 2.14 | 0 | 0 13.0 | 482 P |
| D00761_at | 15 | 0 | 20 | 20 | 180.75 | 2.92 | 0 | 0 Inf | 462 P |
| M12529_at | 9 | 1 | 20 | 20 | 180.45 | 2.16 | 0 | 0 9.0 | 448 P |
| L12168_at | 10 | 0 | 20 | 20 | 180.50 | 2.72 | 0 | 0 Inf | 445 P |
| M11119_at | 9 | 0 | 20 | 20 | 180.45 | 1.94 | 0 | 0 Inf | 437 P |
| D31883_at | 10 | 2 | 20 | 20 | 180.50 | 1.48 | 0 | 0 5.0 | 431 P |
| D31846_at | 10 | 0 | 20 | 20 | 180.50 | 1.89 | 0 | 0 Inf | 424 P |
| M20471_at | 15 | 0 | 20 | 20 | 180.75 | 2.97 | 0 | 0 Inf | 421 P |
| D38548_at | 9 | 1 | 20 | 20 | 180.45 | 2.00 | 0 | 0 9.0 | 417 P |
| J04456_at | 16 | 0 | 20 | 20 | 180.80 | 3.92 | 1 | 0 Inf | 413 P |
| AFFX-HUMGAPDH/M331 | 12 | 3 | 20 | 20 | 180.60 | 2.01 | 0 | 0 4.0 | 406 P |
| HG987-HT987_at | 15 | 3 | 20 | 20 | 180.75 | 3.80 | 2 | 0 5.0 | 404 P |
| D23673_at | 11 | 0 | 20 | 20 | 180.55 | 2.25 | 0 | 0 Inf | 401 P |
| AFFX-BioC-3_at | 13 | 0 | 20 | 20 | 180.65 | 2.46 | 0 | 0 Inf | 391 P |
| D14520_at | 10 | 1 | 20 | 20 | 180.50 | 2.04 | 0 | 0 10.0 | 387 P |
| D26598_at | 10 | 0 | 20 | 20 | 180.S0 | 2.32 | 0 | 0 Inf | 384 P |
| D16562_at | 15 | 1 | 20 | 20 | 170.75 | 4.14 | 1 | 1 15.0 | 364 P |
| L15702_at | 12 | 2 | 20 | 20 | 180.60 | 1.91 | 0 | 0 6.0 | 363 P |
| L33842_rna1_at | 14 | 1 | 20 | 20 | 180.70 | 3.38 | 0 | 0 14.0 | 358 P |
| L38486_at | 12 | 2 | 20 | 20 | 180.60 | 2.38 | 0 | 0 6.0 | 354 P |
| D13748_at | 12 | 1 | 20 | 20 | 180.60 | 2.07 | 0 | 0 12.0 | 353 P |
| HG2855-HT2995_at | 13 | 1 | 20 | 20 | 180.65 | 2.94 | 0 | 0 13.0 | 347 P |
| AFFX-HSAC07/X00351_3 | 12 | 0 | 20 | 20 | 170.60 | 3.21 | 0 | 0 Inf | 346 P |
| D85815_at | 11 | 3 | 20 | 20 | 180.55 | 1.88 | 0 | 0 3.7 | 344 P |
| D25274_at | 11 | 2 | 20 | 20 | 170.55 | 2.35 | 0 | 0 5.5 | 342 P |
| L21954_at | 13 | 4 | 20 | 20 | 180.65 | 2.18 | 0 | 0 3.3 | 341 P |
| D63475_at | 14 | 1 | 20 | 20 | 180.70 | 3.17 | 0 | 0 14.0 | 338 P |
| M19483_at | 13 | 1 | 20 | 20 | 180.65 | 2.28 | 0 | 0 13.0 | 338 P |
| D85429_at | 11 | 1 | 20 | 20 | 180.55 | 2.03 | 0 | 0 11.0 | 333 P |
| D63878_at | 12 | 3 | 20 | 20 | 180.60 | 1.71 | 0 | 0 4.0 | 331 P |
| D50310_at | 18 | 0 | 20 | 20 | 180.90 | 3.57 | 0 | 0 Inf | 325 P |

TABLE 7-continued

| Gene Name | Pos | Neg | Pairs | Pairs | Pair. Pos | Fr Log Av | PM I MM | Pos/N. | Avg Diff | Abs Call |
|---|---|---|---|---|---|---|---|---|---|---|
| D26068_at | 10 | 2 | 20 | 20 | 180.50 | 2.74 | 1 | 0 5.0 | 323 | P |
| D13640_at | 7 | 2 | 20 | 20 | 180.35 | 1.74 | 0 | 0 3.5 | 313 | P |
| M16279_at | 7 | 2 | 20 | 20 | 180.35 | 1.59 | 0 | 0 3.5 | 311 | P |
| D11428_at | 7 | 1 | 20 | 20 | 180.35 | 1.23 | 0 | 1 7.0 | 309 | P |
| HG2566-HT4867_at | 10 | 2 | 20 | 20 | 180.50 | 1.69 | 0 | 0 5.0 | 307 | P |
| AF015910_at | 8 | 0 | 20 | 20 | 180.40 | 1.59 | 0 | 0 Inf | 306 | P |
| L19605_at | 12 | 1 | 20 | 20 | 170.60 | 2.18 | 0 | 0 12.0 | 305 | P |
| D90209_at | 14 | 1 | 20 | 20 | 180.70 | 3.13 | 0 | 0 14.0 | 299 | P |
| D38047_at | 11 | 0 | 20 | 20 | 180.55 | 2.10 | 0 | 0 Inf | 298 | P |
| J04173_at | 9 | 2 | 20 | 20 | 180.45 | 2.20 | 0 | 0 4.5 | 297 | P |
| M13955_at | 11 | 3 | 20 | 20 | 180.55 | 1.67 | 0 | 0 3.7 | 295 | P |
| D49400_at | 9 | 1 | 20 | 20 | 180.45 | 1.94 | 0 | 0 9.0 | 293 | P |
| L09604_at | 10 | 2 | 20 | 20 | 180.50 | 2.00 | 0 | 0 5.0 | 292 | P |
| AB000584_at | 10 | 2 | 20 | 20 | 180.50 | 1.42 | 0 | 0 5.0 | 286 | P |
| L76200_at | 10 | 3 | 20 | 20 | 180.50 | 2.12 | 1 | 0 3.3 | 285 | P |
| J04611_at | 10 | 1 | 20 | 20 | 180.50 | 1.79 | 0 | 0 10.0 | 279 | P |
| M14200_rna1_at | 10 | 1 | 20 | 20 | 170.50 | 1.88 | 0 | 0 10.0 | 274 | P |
| HG1614-HT1614_at | 9 | 1 | 20 | 20 | 170.45 | 1.30 | 0 | 0 9.0 | 272 | P |
| J04794_at | 9 | 3 | 20 | 20 | 180.45 | 1.45 | 0 | 0 3.0 | 271 | P |
| AF00B084_at | 11 | 2 | 20 | 20 | 170.55 | 2.31 | 0 | 0 5.5 | 269 | P |
| D26599_at | 13 | 2 | 20 | 20 | 180.65 | 2.75 | 0 | 0 6.5 | 269 | P |
| DD26563_at | 13 | 2 | 20 | 20 | 180.65 | 2.43 | 0 | 1 6.5 | 269 | P |
| D16217_at | 11 | 0 | 20 | 20 | 170.55 | 2.34 | 0 | 0 Inf | 267 | P |
| J02874_at | 12 | 2 | 20 | 20 | 180.60 | 3.23 | 2 | 0 6.0 | 267 | P |
| D25216_at | 10 | 1 | 20 | 20 | 170.50 | 2.07 | 1 | 0 10.0 | 265 | P |
| D55696_at | 9 | 2 | 20 | 20 | 170.45 | 2.27 | 1 | 0 4.5 | 260 | P |
| D82348_at | 11 | 2 | 20 | 20 | 180.55 | 2.22 | 0 | 0 5.5 | 258 | P |
| D14694_at | 13 | 0 | 20 | 20 | 180.65 | 2.55 | 0 | 0 Inf | 255 | P |
| J03600_at | 11 | 2 | 20 | 20 | 180.55 | 2.56 | 0 | 0 5.5 | 255 | P |
| J03459_at | 10 | 1 | 20 | 20 | 180.50 | 1.97 | 1 | 0 10.0 | 254 | P |
| L25080_at | 10 | 2 | 20 | 20 | 180.50 | 2.35 | 1 | 0 5.0 | 250 | P |
| L07633_at | 12 | 0 | 20 | 20 | 180.60 | 3.26 | 0 | 0 Inf | 249 | P |
| D10522_at | 13 | 1 | 20 | 20 | 180.65 | 3.23 | 1 | 0 13.0 | 246 | P |
| L02426_at | 11 | 0 | 20 | 20 | 180.55 | 2.00 | 0 | 0 Inf | 242 | P |
| L10284_at | 13 | 1 | 20 | 20 | 180.65 | 2.61 | 0 | 0 13.0 | 239 | P |
| M14058_at | 11 | 0 | 20 | 20 | 180.55 | 2.20 | 0 | 0 Inf | 235 | P |
| L13977_at | 12 | 1 | 20 | 20 | 180.60 | 2.18 | 0 | 0 12.0 | 232 | P |
| J03069_rna1_at | 9 | 2 | 20 | 20 | 180.45 | 1.95 | 0 | 0 4.5 | 230 | P |
| M13755_at | 7 | 1 | 20 | 20 | 180.35 | 1.09 | 0 | 0 7.0 | 230 | P |
| HG1862-HT1897_at | 10 | 2 | 20 | 20 | 180.50 | 2.50 | 0 | 0 5.0 | 228 | P |
| L13852_at | 7 | 0 | 20 | 20 | 180.35 | 1.48 | 0 | 0 Inf | 225 | P |
| M12886_at | 11 | 2 | 20 | 20 | 170.55 | 1.57 | 0 | 0 5.5 | 222 | P |
| D88422_at | 11 | 2 | 20 | 20 | 180.55 | 2.38 | 0 | 0 5.5 | 221 | P |
| L25081_at | 7 | 0 | 20 | 20 | 180.35 | 1.12 | 0 | 0 Inf | 219 | P |
| D26600_at | 15 | 1 | 20 | 20 | 170.75 | 2.67 | 0 | 0 15.0 | 218 | P |
| L11285_at | 9 | 2 | 20 | 20 | 180.45 | 1.62 | 0 | 0 4.5 | 218 | P |
| L40904_at | 7 | 0 | 20 | 20 | 180.35 | 1.76 | 0 | 0 Inf | 218 | P |
| HG3494-HT3688_at | 8 | 1 | 20 | 20 | 170.40 | 1.31 | 0 | 0 8.0 | 217 | P |
| D21089_at | 10 | 1 | 20 | 20 | 170.50 | 2.25 | 1 | 0 10.0 | 215 | P |
| D86965_at | 8 | 1 | 20 | 20 | 180.40 | 1.45 | 0 | 0 8.0 | 215 | P |
| L24203_at | 11 | 0 | 20 | 20 | 180.55 | 1.98 | 0 | 0 Inf | 213 | P |
| M14676_at | 9 | 3 | 20 | 20 | 180.45 | 1.96 | 0 | 0 3.0 | 213 | P |
| K03430_at | 9 | 0 | 20 | 20 | 180.45 | 1.79 | 0 | 0 Inf | 212 | P |
| L40027_at | 10 | 2 | 20 | 20 | 180.50 | 1.97 | 1 | 0 5.0 | 212 | P |
| D00763_at | 11 | 1 | 20 | 20 | 180.55 | 1.92 | 0 | 0 11.0 | 211 | P |
| L19437_at | 10 | 0 | 20 | 20 | 180.50 | 2.35 | 1 | 0 Inf | 210 | P |
| HG1078-HT1078_at | 14 | 2 | 20 | 20 | 180.70 | 2.55 | 0 | 0 7.0 | 207 | P |
| L32977_at | 14 | 1 | 20 | 20 | 170.70 | 3.51 | 1 | 0 14.0 | 204 | P |
| D87953_at | 11 | 0 | 20 | 20 | 180.55 | 2.89 | 0 | 0 Inf | 203 | P |
| AB001325_at | 8 | 2 | 20 | 20 | 180.40 | 0.92 | 0 | 0 4.0 | 200 | P |
| D78134_at | 10 | 2 | 20 | 20 | 170.50 | 2.15 | 0 | 0 5.0 | 200 | P |
| D43642_at | 12 | 1 | 20 | 20 | 180.60 | 2.32 | 0 | 0 12.0 | 197 | P |
| D14662_at | 10 | 1 | 20 | 20 | 180.50 | 2.68 | 1 | 0 10.0 | 191 | p |
| D31884_at | 11 | 2 | 20 | 20 | 180.55 | 1.99 | 0 | 0 5.5 | 191 | P |
| D83542_at | 10 | 3 | 20 | 20 | 180.50 | 1.53 | 0 | 0 3.3 | 191 | P |
| HG3514-HT3708_at | 10 | 1 | 20 | 20 | 180.50 | 2.20 | 0 | 0 10.0 | 191 | P |
| D63486_at | 8 | 0 | 20 | 20 | 170.40 | 1.11 | 0 | 0 Inf | 190 | P |
| D31890_at | 13 | 1 | 20 | 20 | 170.65 | 3.06 | 1 | 0 13.0 | 186 | P |
| D49738_at | 11 | 3 | 20 | 20 | 180.55 | 1.83 | 0 | 0 3.7 | 186 | P |
| D50063_at | 9 | 2 | 20 | 20 | 180.45 | 1.60 | 1 | 1 4.5 | 183 | P |
| D63160_at | 7 | 0 | 20 | 20 | 180.35 | 1.23 | 0 | 0 Inf | 179 | P |
| D38305_at | 10 | 0 | 20 | 20 | 170.50 | 2.17 | 1 | 0 Inf | 176 | P |
| D38048_at | 11 | 1 | 20 | 20 | 180.55 | 2.31 | 0 | 0 11.0 | 173 | P |
| D49387_at | 9 | 1 | 20 | 20 | 180.45 | 2.24 | 1 | 0 9.0 | 173 | P |
| D31765_at | 8 | 1 | 20 | 20 | 180.40 | 1.61 | 0 | 0 8.0 | 172 | P |
| M15182_at | 8 | 2 | 20 | 20 | 180.40 | 1.10 | 0 | 0 4.0 | 171 | P |
| HG4297-HT4567_at | 14 | 2 | 20 | 20 | 180.70 | 2.88 | 1 | 0 7.0 | 170 | P |

TABLE 7-continued

| Gene Name | Pos | Neg | Pairs | Pairs | Pair. Pos | Fr Log Av | PM I MM | Pos/N. | Avg Diff | Abs Call |
|---|---|---|---|---|---|---|---|---|---|---|
| 12350_at | 11 | 0 | 20 | 20 | 180.55 | 2.36 | 0 | 0 Inf | 170 | P |
| 032050_at | 8 | 2 | 20 | 20 | 180.40 | 1.22 | 0 | 0 4.0 | 166 | P |
| L08246_at | 10 | 2 | 20 | 20 | 180.50 | 1.49 | 0 | 1 5.0 | 166 | P |
| L8010_at | 11 | 1 | 20 | 20 | 180.55 | 2.23 | 0 | 0 11.0 | 165 | P |
| M13450_at | 13 | 0 | 20 | 20 | 180.65 | 2.71 | 1 | 0 Inf | 165 | P |
| D85245_at | 10 | 2 | 20 | 20 | 180.50 | 2.05 | 1 | 0 5.0 | 160 | P |
| L11708_at | 9 | 3 | 20 | 20 | 180.45 | 1.60 | 0 | 0 3.0 | 159 | P |
| D79991_at | 7 | 1 | 20 | 20 | 180.35 | 1.81 | 0 | 0 7.0 | 158 | P |
| AJ001421_at | 10 | 0 | 20 | 20 | 180.50 | 1.17 | 0 | 0 Inf | 157 | P |
| D14043_at | 11 | 1 | 20 | 20 | 170.55 | 2.52 | 0 | 0 11.0 | 157 | P |
| D13370_at | 10 | 1 | 20 | 20 | 170.S0 | 1.50 | 0 | 0 10.0 | 153 | P |
| K03195_at | 10 | 2 | 20 | 20 | 180.S0 | 2.95 | 3 | 0 5.0 | 153 | P |
| L76465_at | 11 | 3 | 20 | 20 | 180.55 | 2.43 | 2 | 1 3.7 | 150 | P |
| O84239_at | 10 | 2 | 20 | 20 | 180.S0 | 1.69 | 0 | 0 5.0 | 149 | P |
| 089016_at | 8 | 1 | 20 | 20 | 170.40 | 1.63 | 0 | 0 8.0 | 149 | P |
| M11717_ma1_at | 12 | 3 | 20 | 20 | 180.60 | 2.87 | 3 | 1 4.0 | 146 | P |
| M11726_at | 8 | 1 | 20 | 20 | 180.40 | 1.57 | 0 | 0 8.0 | 145 | P |
| L13197_at | 7 | 0 | 20 | 20 | 180.35 | 1.59 | 0 | 0 Inf | 144 | P |
| L20773_at | 10 | 3 | 20 | 20 | 180.50 | 1.40 | 0 | 0 3.3 | 144 | P |
| HG2614-HT2710_at | 7 | 1 | 20 | 20 | 180.35 | 1.29 | 0 | 0 7.0 | 143 | P |
| L36531_at | 9 | 1 | 20 | 20 | 180.45 | 1.65 | 0 | 0 9.0 | 142 | P |
| D14686_at | 9 | 2 | 20 | 20 | 180.45 | 1.25 | 0 | 0 4.5 | 141 | P |
| D55654_at | 9 | 1 | 20 | 20 | 170.45 | 1.51 | 0 | 0 9.0 | 141 | P |
| HG1102-HT1102_at | 7 | 1 | 20 | 20 | 180.35 | 1.71 | 0 | 0 7.0 | 140 | P |
| L11669_at | 11 | 2 | 20 | 20 | 170.55 | 1.37 | 0 | 0 5.5 | 138 | P |
| L38696_at | 7 | 1 | 20 | 20 | 180.35 | 1.20 | 0 | 0 7.0 | 138 | P |
| L41559_at | 8 | 2 | 20 | 20 | 180.40 | 1.47 | 0 | 0 4.0 | 138 | P |
| D50911_at | 9 | 2 | 20 | 20 | 180.45 | 1.29 | 0 | 0 4.5 | 136 | P |
| D38076_at | 7 | 1 | 20 | 20 | 180.35 | 1.43 | 0 | 0 7.0 | 134 | P |
| D86978_at | 13 | 2 | 20 | 20 | 180.65 | 2.94 | 2 | 1 6.5 | 133 | P |
| L34587_at | 9 | 1 | 20 | 20 | 180.45 | 1.38 | 0 | 0 9.0 | 133 | P |
| AF006041_at | 11 | 3 | 20 | 20 | 180.55 | 1.49 | 0 | 0 3.7 | 132 | P |
| D90276_at | 8 | 1 | 20 | 20 | 180.40 | 1.48 | 0 | 0 8.0 | 132 | P |
| HG960-HT960_at | 10 | 1 | 20 | 20 | 180.50 | 1.36 | 0 | 0 10.0 | 132 | P |
| L39064_rna1_at | 9 | 2 | 20 | 20 | 180.45 | 1.38 | 0 | 0 4.5 | 132 | P |
| AC002045_xpt1_at | 8 | 0 | 20 | 20 | 180.40 | 1.50 | 0 | 0 Inf | 128 | P |
| D50912_at | 8 | 1 | 20 | 20 | 180.40 | 1.42 | 0 | 0 8.0 | 127 | P |
| D87438_at | 8 | 2 | 20 | 20 | 170.40 | 1.58 | 0 | 0 4.0 | 127 | P |
| D28915_at | 11 | 0 | 20 | 20 | 180.55 | 2.33 | 1 | 0 Inf | 125 | P |
| HG1602-HT1602_at | 7 | 1 | 20 | 20 | 180.35 | 0.98 | 0 | 0 7.0 | 124 | P |
| D21260_at | 8 | 0 | 20 | 20 | 170.40 | 1.58 | 0 | 0 Inf | 123 | P |
| D63478_at | 9 | 0 | 20 | 20 | 170.45 | 2.17 | 1 | 0 Inf | 123 | P |
| D80005_at | 8 | 2 | 20 | 20 | 180.40 | 1.84 | 0 | 0 4.0 | 123 | P |
| D84110_at | 14 | 1 | 20 | 20 | 170.70 | 2.96 | 2 | 0 14.0 | 123 | P |
| L06132_at | 9 | 3 | 20 | 20 | 180.45 | 2.09 | 2 | 0 3.0 | 122 | P |
| D87258_at | 9 | 2 | 20 | 20 | 180.45 | 1.61 | 0 | 0 4.5 | 121 | P |
| K01396_at | 12 | 2 | 20 | 20 | 180.60 | 1.50 | 0 | 0 6.0 | 121 | P |
| L07033_at | 10 | 2 | 20 | 20 | 180.50 | 1.90 | 0 | 0 5.0 | 121 | P |
| D29643_at | 10 | 3 | 20 | 20 | 180.50 | 1.96 | 1 | 0 3.3 | 120 | P |
| D50683_at | 13 | 1 | 20 | 20 | 180.65 | 2.42 | 0 | 0 13.0 | 120 | P |
| D85758_at | 9 | 3 | 20 | 20 | 170.45 | 1.94 | 2 | 0 3.0 | 119 | P |
| L19779_at | 7 | 1 | 20 | 20 | 180.35 | 1.34 | 0 | 0 7.0 | 119 | P |
| L27706_at | 12 | 2 | 20 | 20 | 180.60 | 3.22 | 1 | 0 6.0 | 118 | P |
| L40393_at | 9 | 1 | 20 | 20 | 180.45 | 2.17 | 2 | 0 9.0 | 118 | P |
| D83032_at | 7 | 2 | 20 | 20 | 180.35 | 1.81 | 3 | 1 3.5 | 117 | P |
| D30755_at | 7 | 2 | 20 | 20 | 180.35 | 1.53 | 0 | 0 3.5 | 116 | P |
| D49488_at | 14 | 2 | 20 | 20 | 180.70 | 3.79 | 3 | 0 7.0 | 116 | P |
| D83782_at | 7 | 2 | 20 | 20 | 180.35 | 1.58 | 1 | 0 3.5 | 116 | P |
| D56495_at | 8 | 0 | 20 | 20 | 180.40 | 1.57 | 0 | 0 Inf | 115 | P |
| M13207_at | 8 | 2 | 20 | 20 | 180.40 | 0.91 | 0 | 0 4.0 | 115 | P |
| D87673_at | 7 | 1 | 20 | 20 | 170.35 | 0.94 | 0 | 0 7.0 | 114 | P |
| M11437_cds2_at | 8 | 0 | 20 | 20 | 180.40 | 2.10 | 1 | 0 Inf | 114 | P |
| D21852_at | 12 | 2 | 20 | 20 | 180.60 | 2.95 | 2 | 0 6.0 | 113 | P |
| L19183_at | 8 | 2 | 20 | 20 | 180.40 | 1.49 | 0 | 0 4.0 | 113 | P |
| L77886_at | 12 | 4 | 20 | 20 | 180.60 | 2.61 | 1 | 0 3.0 | 113 | P |
| M18079_at | 10 | 2 | 20 | 20 | 180.50 | 1.91 | 1 | 0 5.0 | 113 | P |
| D43950_at | 7 | 1 | 20 | 20 | 180.35 | 1.79 | 0 | 0 7.0 | 111 | P |
| D14658_at | 8 | 1 | 20 | 20 | 180.40 | 1.69 | 0 | 0 8.0 | 110 | P |
| M18737_rna1_at | 8 | 2 | 20 | 20 | 180.40 | 1.29 | 1 | 0 4.0 | 110 | P |
| D78611_at | 10 | 1 | 20 | 20 | 180.50 | 1.91 | 1 | 0 10.0 | 109 | P |
| L49169_at | 10 | 0 | 20 | 20 | 170.50 | 1.50 | 0 | 0 Inf | 109 | P |
| D00760_at | 10 | 1 | 20 | 20 | 180.50 | 1.53 | 0 | 0 10.0 | 107 | P |
| L08666_at | 8 | 2 | 20 | 20 | 170.40 | 1.26 | 0 | 0 4.0 | 107 | P |
| AB000115_at | 7 | 1 | 20 | 20 | 180.35 | 0.97 | 0 | 0 7.0 | 106 | P |
| D79986_at | 9 | 1 | 20 | 20 | 180.45 | 1.89 | 1 | 0 9.0 | 106 | P |
| D86957_at | 12 | 2 | 20 | 20 | 170.60 | 2.67 | 1 | 1 6.0 | 106 | P |
| D14663_at | 9 | 0 | 20 | 20 | 180.45 | 2.11 | 0 | 0 Inf | 105 | P |

TABLE 7-continued

| Gene Name | Pos | Neg | Pairs | Pairs | Pair. Pos | Fr Log Av | PM I MM | Pos/N. | Avg Diff | Abs Call |
|---|---|---|---|---|---|---|---|---|---|---|
| D42043_at | 11 | 3 | 20 | 20 | 180.55 | 2.49 | 0 | 0 3.7 | 104 | P |
| M12759_at | 9 | 1 | 20 | 20 | 180.45 | 1.95 | 1 | 0 9.0 | 104 | P |
| HG3510-HT3704_at | 9 | 0 | 20 | 20 | 180.45 | 1.50 | 0 | 0 Inf | 103 | P |
| D90086_at | 10 | 1 | 20 | 20 | 180.50 | 2.04 | 1 | 0 10.0 | 102 | P |
| D79994_at | 8 | 1 | 20 | 20 | 180.40 | 1.46 | 0 | 0 8.0 | 101 | P |
| HG4058-HT4328_at | 10 | 3 | 20 | 20 | 180.50 | 1.62 | 1 | 0 3.3 | 100 | P |
| L21936_at | 8 | 0 | 20 | 20 | 180.40 | 2.02 | 1 | 0 Inf | 100 | P |
| M11718_at | 8 | 0 | 20 | 20 | 180.40 | 1.43 | 0 | 0 Inf | 100 | P |
| D84454_at | 7 | 1 | 20 | 20 | 180.35 | 1.27 | 0 | 0 7.0 | 99 | P |
| L04490_at | 9 | 2 | 20 | 20 | 180.45 | 1.69 | 1 | 0 4.5 | 99 | P |
| D21851_at | 8 | 1 | 20 | 20 | 170.40 | 1.34 | 0 | 0 8.0 | 98 | P |
| HG2274-HT2370_at | 7 | 1 | 20 | 20 | 180.35 | 1.22 | 0 | 0 7.0 | 98 | P |
| HGA073-HT4343_at | 11 | 2 | 20 | 20 | 180.55 | 1.92 | 1 | 0 5.5 | 97 | P |
| HG4243-HT4513_at | 9 | 1 | 20 | 20 | 180.45 | 2.06 | 0 | 0 9.0 | 97 | P |
| HG908-HT908_at | 8 | 1 | 20 | 20 | 180.40 | 1.04 | 0 | 0 8.0 | 97 | P |
| HG1879-HT1919_at | 9 | 0 | 20 | 20 | 180.45 | 2.15 | 1 | 0 Inf | 96 | P |
| L41668_rna1_at | 7 | 1 | 20 | 20 | 170.35 | 1.22 | 0 | 0 7.0 | 96 | P |
| D50640_at | 13 | 2 | 20 | 20 | 180.65 | 2.89 | 2 | 0 6.5 | 95 | P |
| HG1869-HT1904_at | 9 | 1 | 20 | 20 | 180.45 | 1.41 | 0 | 0 9.0 | 95 | P |
| HG2167-HT2237_at | 10 | 2 | 20 | 20 | 180.50 | 1.92 | 0 | 0 5.0 | 95 | P |
| L13391_at | 11 | 0 | 20 | 20 | 180.55 | 2.08 | 0 | 0 Inf | 95 | P |
| L16842_at | 8 | 1 | 20 | 20 | 180.40 | 0.91 | 0 | 0 8.0 | 95 | P |
| D44466_at | 10 | 1 | 20 | 20 | 180.50 | 1.47 | 0 | 0 10.0 | 94 | P |
| D49489_at | 11 | 3 | 20 | 20 | 180.55 | 2.45 | 1 | 0 3.7 | 92 | P |
| D85181_at | 11 | 3 | 20 | 20 | 180.55 | 2.17 | 1 | 0 3.7 | 92 | P |
| D14878_at | 10 | 2 | 20 | 20 | 180.50 | 1.95 | 0 | 0 5.0 | 91 | P |
| D86962_at | 12 | 4 | 20 | 20 | 180.60 | 1.83 | 0 | 1 3.0 | 91 | P |
| D21853_at | 7 | 1 | 20 | 20 | 180.35 | 1.41 | 1 | 0 7.0 | 90 | P |
| D38549_at | 10 | 3 | 20 | 20 | 170.50 | 2.39 | 2 | 0 3.3 | 89 | P |
| D84294_at | 10 | 2 | 20 | 20 | 180.50 | 2.10 | 2 | 1 5.0 | 89 | P |
| D87435_at | 8 | 2 | 20 | 20 | 180.40 | 1.46 | 0 | 0 4.0 | 89 | P |
| D25278_at | 11 | 2 | 20 | 20 | 170.55 | 2.02 | 1 | 0 5.5 | 88 | P |
| D79998_at | 10 | 3 | 20 | 20 | 180.50 | 1.52 | 1 | 0 3.3 | 88 | P |
| L12535_at | 9 | 1 | 20 | 20 | 180.45 | 3.21 | 3 | 0 9.0 | 88 | P |
| D63480_at | 8 | 1 | 20 | 20 | 180.40 | 1.90 | 0 | 0 8.0 | 87 | P |
| D79995_at | 7 | 0 | 20 | 20 | 180.35 | 1.31 | 0 | 0 Inf | 87 | P |
| L19314_at | 7 | 1 | 20 | 20 | 170.35 | 1.39 | 1 | 0 7.0 | 87 | P |
| L42379_at | 9 | 3 | 20 | 20 | 180.45 | 1.74 | 0 | 0 3.0 | 86 | P |
| D30756_at | 10 | 3 | 20 | 20 | 180.50 | 1.78 | 2 | 0 3.3 | 84 | P |
| D50857_at | 8 | 2 | 20 | 20 | 180.40 | 1.48 | 0 | 0 4.0 | 84 | P |
| HG1112-HT1112_at | 8 | 0 | 20 | 20 | 170.40 | 1.25 | 0 | 0 Inf | 82 | P |
| D83004_at | 8 | 2 | 20 | 20 | 180.40 | 0.98 | 0 | 0 4.0 | 80 | P |
| D87684_at | 10 | 2 | 20 | 20 | 180.50 | 2.64 | 3 | 0 5.0 | 80 | P |
| HG2059-HT2114_at | 8 | 1 | 20 | 20 | 180.40 | 1.45 | 0 | 0 8.0 | 78 | P |
| L29008_at | 9 | 3 | 20 | 20 | 180.45 | 1.64 | 1 | 0 3.0 | 78 | P |
| D29641_at | 9 | 1 | 20 | 20 | 180.45 | 2.71 | 3 | 0 9.0 | 77 | P |
| L18972_at | 7 | 1 | 20 | 20 | 180.35 | 1.12 | 0 | 0 7.0 | 77 | P |
| J04056_at | 10 | 3 | 20 | 20 | 170.50 | 1.73 | 0 | 0 3.3 | 76 | P |
| L40636_at | 7 | 2 | 20 | 20 | 180.35 | 1.43 | 0 | 0 13.5 | 76 | P |
| L24470_at | 7 | 1 | 20 | 20 | 180.35 | 0.96 | 0 | 0 7.0 | 75 | P |
| L40357_at | 9 | 2 | 20 | 20 | 180.45 | 1.40 | 0 | 1 4.5 | 75 | P |
| L27560_at | 9 | 2 | 20 | 20 | 180.45 | 1.59 | 1 | 0 4.5 | 74 | P |
| D13639_at | 9 | 2 | 20 | 20 | 180.45 | 1.59 | 0 | 0 4.5 | 70 | P |
| L43631_at | 8 | 2 | 20 | 20 | 180.40 | 1.65 | 1 | 0 4.0 | 70 | P |
| D28476_at | 8 | 1 | 20 | 20 | 180.40 | 1.63 | 0 | 0 8.0 | 69 | P |
| D42123_at | 7 | 1 | 20 | 20 | 180.35 | 1.11 | 0 | 0 7.0 | 69 | P |
| D88613_at | 9 | 2 | 20 | 20 | 170.45 | 1.38 | 2 | 0 4.5 | 68 | P |
| D17400_at | 9 | 1 | 20 | 20 | 180.45 | 1.53 | 0 | 0 9.0 | 67 | P |
| AF012270_at | 9 | 1 | 20 | 20 | 180.45 | 1.39 | 0 | 0 9.0 | 65 | P |
| D50927_at | 9 | 2 | 20 | 20 | 180.45 | 1.48 | 0 | 0 4.5 | 65 | P |
| D38521_at | 8 | 2 | 20 | 20 | 170.40 | 1.30 | 1 | 0 4.0 | 64 | P |
| D38553_at | 7 | 2 | 20 | 20 | 180.35 | 1.61 | 0 | 0 3.5 | 64 | P |
| D80006_at | 8 | 1 | 20 | 20 | 180.40 | 2.01 | 1 | 0 8.0 | 64 | P |
| L42542_at | 8 | 1 | 20 | 20 | 170.40 | 1.09 | 0 | 0 8.0 | 63 | P |
| D14695_at | 11 | 2 | 20 | 20 | 180.55 | 1.49 | 0 | 0 5.5 | 62 | P |
| L76703_at | 8 | 2 | 20 | 20 | 180.40 | 1.61 | 2 | 0 4.0 | 62 | P |
| HG433-HT4606_at | 9 | 2 | 20 | 20 | 180.45 | 1.91 | 0 | 0 4.5 | 61 | P |
| D50917_at | 11 | 3 | 20 | 20 | 180.55 | 2.24 | 2 | 1 3.7 | 58 | P |
| D86985_at | 12 | 3 | 20 | 20 | 180.60 | 1.04 | 0 | 1 4.0 | 58 | P |
| HG4390-HT4660_at | 8 | 1 | 20 | 20 | 180.40 | 1.15 | 0 | 0 8.0 | 58 | P |
| L33881_at | 12 | 4 | 20 | 20 | 180.60 | 1.80 | 1 | 0 3.0 | 58 | P |
| D80004_at | 7 | 1 | 20 | 20 | 170.35 | 1.02 | 0 | 0 7.0 | 57 | P |
| D43767_at | 8 | 2 | 20 | 20 | 170.40 | 0.90 | 0 | 0 4.0 | 55 | P |
| D50525_at | 9 | 2 | 20 | 20 | 170.45 | 2.21 | 3 | 0 4.5 | 55 | P |
| L76380_at | 11 | 3 | 20 | 20 | 180.55 | 1.90 | 0 | 0 3.7 | 55 | P |
| D42087_at | 9 | 3 | 20 | 20 | 180.45 | 2.32 | 2 | 1 3.0 | 54 | P |
| HG2460-HT2556_at | 9 | 3 | 20 | 20 | 180.45 | 1.85 | 2 | 0 3.0 | 50 | P |

TABLE 7-continued

| Gene Name | Pos | Neg | Pairs | Pairs | Pair. Pos | Fr Log Av | PM I MM | Pos/N. | Avg Diff | Abs Call |
|---|---|---|---|---|---|---|---|---|---|---|
| L07515_at | 8 | 2 | 20 | 20 | 180.40 | 1.10 | 0 | 0 4.0 | 50 | P |
| L20591_at | 8 | 2 | 20 | 20 | 180.40 | 1.30 | 0 | 2 4.0 | 50 | P |
| L77563_at | 7 | 2 | 20 | 20 | 180.35 | 1.69 | 2 | 0 3.5 | 50 | P |
| D63412_at | 8 | 1 | 20 | 20 | 180.40 | 1.08 | 0 | 0 8.0 | 48 | P |
| J04162_at | 7 | 2 | 20 | 20 | 180.35 | 1.57 | 0 | 0 3.5 | 48 | P |
| D15050_at | 8 | 1 | 20 | 20 | 170.40 | 0.97 | 0 | 0 8.0 | 46 | P |
| L10123_at | 10 | 2 | 20 | 20 | 180.50 | 2.00 | 2 | 0 5.0 | 45 | P |
| AFFX-HUMISGF3A/M979 | 9 | 3 | 20 | 20 | 180.45 | 1.96 | 0 | 0 3.0 | 44 | P |
| L32163_at | 8 | 2 | 20 | 20 | 180.40 | 1.79 | 1 | 0 4.0 | 42 | P |
| D14664_at | 9 | 3 | 20 | 20 | 180.45 | 1.51 | 1 | 1 3.0 | 41 | P |
| D86425_at | 9 | 3 | 20 | 20 | 180.45 | 2.58 | 2 | 0 3.0 | 37 | P |
| L11695_at | 9 | 2 | 20 | 20 | 180.45 | 1.08 | 0 | 0 4.5 | 34 | P |
| D63875_at | 9 | 2 | 20 | 20 | 180.45 | 1.25 | 0 | 0 4.5 | 29 | P |
| L40388_at | 9 | 1 | 20 | 20 | 180.45 | 1.79 | 0 | 0 9.0 | 23 | P |
| D87443_at | 7 | 2 | 20 | 20 | 180.35 | 1.71 | 1 | 0 3.5 | 22 | P |

| Gene Name | Positive | Negativ | Pairs | Pairs | Pairs In Pos | Fracti Log Avg | PM Ex MM | Ex Pos/Neg | Avg Diff | Abs Call |
|---|---|---|---|---|---|---|---|---|---|---|
| hum_alu_at | 69 | 0 | 69 | 69 | 671.00 | 7.56 | 14 | 0 Inf | 34065 | P |
| U14973_at | 18 | 0 | 20 | 20 | 180.90 | 5.89 | 1 | 0 Inf | 6948 | P |
| AFFX-CreX-3_at | 19 | 1 | 20 | 20 | 180.95 | 6.74 | 0 | 0 19.0 | 5673 | P |
| U14969_at | 20 | 0 | 20 | 20 | 181.00 | 6.25 | 1 | 0 Inf | 5259 | P |
| U14972_at | 19 | 0 | 20 | 20 | 180.95 | 5.76 | 0 | 0 Inf | 5247 | P |
| M24194_at | 19 | 0 | 20 | 20 | 180.95 | 5.19 | 0 | 0 Inf | 4955 | P |
| M81757_at | 18 | 0 | 20 | 20 | 180.90 | 6.35 | 1 | 0 Inf | 4759 | P |
| U14968_at | 16 | 0 | 20 | 20 | 180.80 | 6.52 | 2 | 0 Inf | 4706 | P |
| U12465_at | 20 | 0 | 20 | 20 | 181.00 | 5.57 | 0 | 0 Inf | 4503 | P |
| M31951_at | 15 | 3 | 20 | 20 | 180.75 | 5.49 | 7 | 0 5.0 | 4128 | P |
| AFFX-CreX-5_at | 20 | 0 | 20 | 20 | 181.00 | 5.75 | 1 | 0 Inf | 3983 | P |
| M60854_at | 18 | 0 | 20 | 20 | 180.90 | 6.80 | 4 | 0 Inf | 3548 | P |
| S79522_at | 17 | 0 | 20 | 20 | 180.85 | 4.80 | 2 | 0 Inf | 3543 | P |
| M84711_at | 17 | 0 | 20 | 20 | 180.85 | 6.85 | 0 | 0 Inf | 3365 | P |
| M84716_at | 14 | 3 | 20 | 20 | 180.70 | 3.58 | 1 | 0 4.1 | 3345 | P |
| AFFX-HUMGAPDH/M33197_3 | 19 | 0 | 20 | 20 | 170.95 | 4.60 | 1 | 0 Inf | 3257 | P |
| M77232_rna1_at | 16 | 1 | 20 | 20 | 180.80 | 6.0B | 1 | 0 16.0 | 3217 | P |
| AFFX-HSAC07/X00351_3_at | 16 | 0 | 20 | 20 | 180.80 | 4.43 | 1 | 0 Inf | 3110 | P |
| U49869_ma1_at | 19 | 0 | 20 | 20 | 170.95 | 6.26 | 2 | 0 Inf | 3081 | P |
| U58682_at | 17 | 1 | 20 | 20 | 180.85 | 5.01 | 2 | 0 17.0 | 3033 | P |
| U14971_at | 18 | 0 | 20 | 20 | 180.90 | 5.20 | 0 | 0 Inf | 2924 | P |
| U09953_at | 18 | 0 | 20 | 20 | 180.90 | 6.63 | 3 | 0 Inf | 2871 | P |
| U14970_at | 18 | 0 | 20 | 20 | 180.90 | 5.51 | 2 | 0 Inf | 2723 | P |
| U12404_at | 18 | 0 | 20 | 20 | 180.90 | 5.35 | 1 | 0 Inf | 2665 | P |
| M31520_at | 17 | 0 | 20 | 20 | 180.85 | 5.17 | 1 | 0 Inf | 2526 | P |
| M32405_at | 11 | 3 | 20 | 20 | 180.55 | 2.88 | 1 | 0 3.7 | 2461 | P |
| M33680_at | 17 | 0 | 20 | 20 | 180.85 | 4.24 | 2 | 0 Inf | 2367 | P |
| M84526_at | 13 | 0 | 20 | 20 | 180.65 | 3.35 | 0 | 0 Inf | 2281 | P |
| AFFX-BioDn-3_at | 15 | 2 | 20 | 20 | 170.75 | 3.46 | 0 | 0 7.5 | 2202 | P |
| U25789_at | 17 | 1 | 20 | 20 | 180.85 | 5.37 | 0 | 0 17.0 | 2092 | P |
| S73591_at | 15 | 0 | 20 | 20 | 180.75 | 4.61 | 1 | 0 Inf | 1714 | P |
| U15008_at | 13 | 2 | 20 | 20 | 180.65 | 3.24 | 0 | 0 6.5 | 1556 | P |
| M26880_at | 15 | 0 | 20 | 20 | 180.75 | 4.49 | 2 | 0 Inf | 1454 | P |
| U31875_at | 16 | 0 | 20 | 20 | 180.80 | 4.05 | 0 | 0 Inf | 1358 | P |
| AFFX-HSAC07/X00351_M_at | 15 | 1 | 20 | 20 | 180.75 | 3.17 | 0 | 0 15.0 | 1261 | P |
| M63138_at | 8 | 1 | 20 | 20 | 180.40 | 1.84 | 0 | 0 8.0 | 1215 | P |
| M63379_at | 15 | 0 | 20 | 20 | 180.75 | 3.69 | 1 | 0 Inf | 1169 | P |
| M57710_at | 17 | 0 | 20 | 20 | 170.85 | 4.16 | 0 | 0 Inf | 1035 | P |
| U50523_at | 13 | 3 | 20 | 20 | 180.65 | 3.04 | 1 | 1 4.3 | 946 | P |
| M95787_at | 12 | 0 | 20 | 20 | 180.60 | 2.32 | 0 | 0 Inf | 944 | P |
| AFFX-HSAC07/X00351_5_at | 13 | 1 | 20 | 20 | 180.65 | 2.89 | 0 | 0 13.0 | 943 | P |
| M27891_at | 11 | 2 | 20 | 20 | 180.55 | 1.99 | 0 | 0 5.5 | 943 | P |
| U21931_at | 14 | 0 | 20 | 20 | 170.70 | 4.30 | 3 | 0 Inf | 866 | P |
| U44839_at | 11 | 3 | 20 | 20 | 180.55 | 1.70 | 0 | 0 3.7 | 805 | P |
| M23613_at | 11 | 2 | 20 | 20 | 180.55 | 1.96 | 0 | 0 5.5 | 779 | P |
| M34182_at | 12 | 2 | 20 | 20 | 180.60. | 1.24 | 0 | 0 6.0 | 772 | P |
| U46692_rna1_at | 13 | 2 | 20 | 20 | 180.65 | 3.05 | 0 | 0 6.5 | 746 | P |
| U37690_at | 12 | 0 | 20 | 20 | 180.60 | 2.01 | 0 | 0 Inf | 688 | P |
| M80563_at | 11 | 0 | 20 | 20 | 180.55 | 2.34 | 0 | 0 Inf | 678 | P |
| U41635_at |  | 1 | 20 | 20 | 180.40 | 1.75 | 0 | 0 8.0 | 658 | P |
| U46751_at | 10 | 2 | 20 | 20 | 180.50 | 2.76 | 1 | 0 5.0 | 644 | P |
| U03057_at | 8 | 2 | 20 | 20 | 180.40 | 1.23 | 0 | 0 4.0 | 643 | P |

-continued

| Gene Name | Pos it ive | Neg at iv | Pairs | Pairs | Pairs In Pos | Fracti Log Avg | PM Ex MM | Ex Pos/Neg | Avg Diff | Abs Call |
|---|---|---|---|---|---|---|---|---|---|---|
| S65738_at | 14 | 1 | 20 | 20 | 180.70 | 3.33 | 0 | 0 14.0 | 621 | P |
| S77356_at | 13 | 3 | 20 | 20 | 180.65 | 2.78 | 0 | 0 4.3 | 615 | P |
| AFFX-HUMGAPDH/M33197_n | 12 | 3 | 20 | 20 | 170.60 | 2.00 | 0 | 0 4.0 | 614 | P |
| U62739_at | 10 | 2 | 20 | 20 | 180.S0 | 1.95 | 0 | 0 5.0 | 612 | P |
| S75463_at | 9 | 2 | 20 | 20 | 180.45 | 1.83 | 1 | 0 4.5 | 596 | P |
| U62962_at | 11 | 2 | 20 | 20 | 180.55 | 2.04 | 0 | 0 5.5 | 595 | P |
| M35878_at | 12 | 3 | 20 | 20 | 180.60 | 1.70 | 0 | 1 4.0 | 577 | P |
| U46570_at | 8 | 1 | 20 | 20 | 180.40 | 1.28 | 0 | 0 8.0 | 550 | P |
| AFFX-HUMGAPDH/M33197_5 | 12 | 0 | 20 | 20 | 180.60 | 2.95 | 0 | 0 Inf | 539 | P |
| U11861_at | 10 | 2 | 20 | 20 | 180.50 | 1.58 | 0 | 0 5.0 | 536 | P |
| M57567_at | 10 | 1 | 20 | 20 | 180.S0 | 1.70 | 0 | 0 10.0 | 525 | P |
| U01212_at | 10 | 2 | 20 | 20 | 180.50 | 1.25 | 0 | 0 5.0 | 517 | P |
| U03398_at | 10 | 3 | 20 | 20 | 180.50 | 2.46 | 2 | 0 3.3 | 500 | P |
| U45975_at | 7 | 2 | 20 | 20 | 180.35 | 1.31 | 0 | 0 3.5 | 485 | P |
| U46499_at | 10 | 3 | 20 | 20 | 170.50 | 1.65 | 0 | 0 3.3 | 484 | P |
| M76378_at | 8 | 2 | 20 | 20 | 180.40 | 1.16 | 0 | 0 4.0 | 476 | P |
| M55593_at | 10 | 1 | 20 | 20 | 180.50 | 2.09 | 1 | 0 10.0 | 471 | P |
| U09117_at | 7 | 2 | 20 | 20 | 180.35 | 1.38 | 0 | 0 3.5 | 464 | P |
| U46025_at | 11 | 2 | 20 | 20 | 180.55 | 1.76 | 1 | 0 5.5 | 463 | P |
| U51478_at | 13 | 1 | 20 | 20 | 180.65 | 3.39 | 0 | 0 13.0 | 459 | P |
| M29877_at | 10 | 0 | 20 | 20 | 180.50 | 1.79 | 1 | 0 Inf | 457 | P |
| M32053_at | 9 | 1 | 20 | 20 | 180.45 | 1.90 | 0 | 0 9.0 | 452 | P |
| AFFX-BioC-5_at | 8 | 1 | 20 | 20 | 180.40 | 1.19 | 0 | 0 8.0 | 434 | P |
| U09813_at | 12 | 1 | 20 | 20 | 180.60 | 2.90 | 0 | 0 12.0 | 434 | P |
| M97815_at | 9 | 2 | 20 | 20 | 180.45 | 1.38 | 0 | 0 4.5 | 431 | P |
| M88279_at | 11 | 0 | 20 | 20 | 180.55 | 2.28 | 0 | 0 Inf | 428 | P |
| S73149_at | 8 | 1 | 20 | 20 | 180.40 | 1.14 | 0 | 0 8.0 | 424 | P |
| M84349_at | 11 | 2 | 20 | 20 | 180.55 | 2.40 | 0 | 0 5.5 | 415 | P |
| U29656_at | 7 | 0 | 20 | 20 | 180.35 | 1.70 | 0 | 0 Inf | 412 | P |
| U37689_at | 10 | 0 | 20 | 20 | 180.50 | 1.42 | 0 | 0 Inf | 406 | P |
| M22382_at | 9 | 0 | 20 | 20 | 180.45 | 1.45 | 0 | 0 Inf | 396 | P |
| S68616_at | 8 | 2 | 20 | 20 | 180.40 | 1.37 | 0 | 0 4.0 | 391 | P |
| M86400_at | 11 | 1 | 20 | 20 | 180.55 | 2.44 | 1 | 0 11.0 | 387 | P |
| U57342_at | 9 | 1 | 20 | 20 | 180.45 | 1.93 | 0 | 0 9.0 | 387 | P |
| M60858_rna1_at | 10 | 2 | 20 | 20 | 180.50 | 2.42 | 0 | 0 5.0 | 376 | P |
| AFFX-BioDn-5_at | 9 | 0 | 20 | 20 | 180.45 | 1.37 | 0 | 0 Inf | 373 | P |
| M84332_at | 10 | 1 | 20 | 20 | 180.S0 | 1.49 | 0 | 0 10.0 | 370 | P |
| M38690_at | 10 | 0 | 20 | 20 | 180.50 | 2.51 | 1 | 0 Inf | 367 | P |
| M22538_at | 7 | 0 | 20 | 20 | 180.35 | 1.00 | 0 | 0 Inf | 365 | P |
| U57450_at | 10 | 0 | 20 | 20 | 180.S0 | 1.17 | 0 | 0 Inf | 365 | P |
| U30825_at | 11 | 3 | 20 | 20 | 180.55 | 1.59 | 0 | 0 3.7 | 355 | P |
| M75126_at | 9 | 1 | 20 | 20 | 180.45 | 1.67 | 0 | 0 9.0 | 347 | P |
| M95627_at | 7 | 0 | 20 | 20 | 180.35 | 1.S0 | 0 | 0 Inf | 344 | P |
| U50136_rna1_at | 8 | 2 | 203 | 20 | 180.40 | 1.16 | 0 | 0 4.0 | 338 | P |
| U14603_at | 12 | 0 | 20 | 20 | 180.60 | 2.56 | 0 | 0 Inf | 337 | P |
| M75099_at | 9 | 0 | 20 | 20 | 180.45 | 2.03 | 0 | 0 Inf | 336 | P |
| U33821_at | 10 | 1 | 20 | 20 | 180.50 | 1.67 | 0 | 0 10.0 | 336 | P |
| U21128_at | 12 | 3 | 20 | 20 | 180.60 | 2.20 | 1 | 1 4.0 | 327 | P |
| M28713_at | 7 | 1 | 20 | 20 | 180.35 | 1.35 | 0 | 0 7.0 | 324 | P |
| U37519_at | 7 | 2 | 20 | 20 | 180.35 | 1.68 | 0 | 0 3.5 | 321 | P |
| M73547_at | 12 | 4 | 20 | 20 | 180.60 | 2.03 | 1 | 0 3.0 | 318 | P |
| M96803_at | 12 | 2 | 20 | 20 | 180.60 | 1.31 | 0 | 1 6.0 | 310 | P |
| U41371_at | 12 | 1 | 20 | 20 | 180.60 | 2.45 | 0 | 0 12.0 | 310 | P |
| AFFX-HSAC07/X00351_3_st | 13 | 0 | 20 | 20 | 170.65 | 2.19 | 0 | 0 Inf | 303 | P |
| M94345_at | 10 | 2 | 20 | 20 | 180.50 | 1.48 | 0 | 0 5.0 | 302 | P |
| U02493_at | 8 | 0 | 20 | 20 | 180.40 | 1.74 | 0 | 0 Inf | 302 | P |
| M58285_at | 8 | 0 | 20 | 20 | 180.40 | 1.16 | 0 | 0 Inf | 293 | P |
| U02570_at | 7 | 1 | 20 | 20 | 180.35 | 1.53 | 0 | 0 7.0 | 293 | P |
| AFFX-BioC-3_at | 7 | 1 | 20 | 20 | 180.35 | 1.33 | 0 | 0 7.0 | 292 | P |
| M62831_at | 8 | 0 | 20 | 20 | 180.40 | 1.16 | 0 | 0 Inf | 291 | P |
| U32944_at | 13 | 1 | 20 | 20 | 180.65 | 3.00 | 2 | 0 13.0 | 290 | P |
| U52522_at | 7 | 2 | 20 | 20 | 180.35 | 1.74 | 0 | 0 3.5 | 288 | P |
| M88338_at | 7 | 1 | 20 | 20 | 180.35 | 0.97 | 0 | 0 7.0 | 283 | P |
| M77349_at | 14 | 0 | 20 | 20 | 180.10 | 2.49 | 0 | 0 Inf | 277 | P |
| U29607_at | 13 | 3 | 20 | 20 | 180.65 | 2.26 | 2 | 1 4.3 | 276 | P |
| M31303_rna1_at | 9 | 2 | 20 | 20. | 180.45 | 1.63 | 0 | 0 4.5 | 274 | P |
| M58459_at | 11 | 1 | 20 | 20 | 180.55 | 2.84 | 2 | 0 11.0 | 271 | P |
| M63959_at | 10 | 2 | 20 | 20 | 180.50 | 1.26 | 0 | 0 5.0 | 270 | P |
| M24899_at | 10 | 2 | 20 | 20 | 180.50 | 1.56 | 0 | 0 5.0 | 269 | P |
| U07857_at | 13 | 2 | 20 | 20 | 170.65 | 2.51 | 0 | 1 6.5 | 269 | P |
| U30888_at | 10 | 2 | 20 | 20 | 180.50 | 1.49 | 0 | 0 5.0 | 266 | P |
| M81780_cds5_at | 8 | 1 | 20 | 20 | 180.40 | 1.13 | 0 | 0 8.0 | 258 | P |
| M23254_at | 11 | 3 | 20 | 20 | 170.55 | 1.64 | 0 | 0 3.7 | 256 | P |
| U05659_at | 10 | 2 | 20 | 20 | 180.50 | 1.74 | 1 | 1 5.0 | 256 | P |
| U49785_at | 12 | 1 | 20 | 20 | 180.60 | 2.29 | 0 | 0 12.0 | 256 | P |

-continued

| Gene Name | Positive | Negativ | Pairs | Pairs | Pairs In Pos | Fracti Log Avg | PM Ex MM | Ex Pos/Neg | Avg Diff | Abs Call |
|---|---|---|---|---|---|---|---|---|---|---|
| U10323_at | 10 | 1 | 20 | 20 | 170.50 | 2.08 | 0 | 0 10.0 | 254 | P |
| M64347_at | 7 | 1 | 20 | 20 | 180.35 | 1.70 | 2 | 1 7.0 | 253 | P |
| U20285_at | 9 | 2 | 20 | 20 | 180.35 | 1.32 | 0 | 0 4.5 | 246 | P |
| U43286_at | 11 | 0 | 20 | 20 | 180.55 | 2.55 | 1 | 0 Inf | 246 | P |
| M82809_at | 13 | 1 | 20 | 20 | 180.65 | 2.26 | 0 | 0 13.0 | 243 | P |
| M96859_at | 10 | 3 | 20 | 20 | 180.50 | 2.22 | 1 | 0 3.3 | 243 | P |
| U56637_at | 7 | 2 | 20 | 20 | 170.35 | 1.37 | 0 | 1 3.5 | 240 | P |
| U40990_at | 7 | 0 | 20 | 20 | 180.35 | 1.09 | 0 | 0 Inf | 238 | P |
| U49082_at | 8 | 2 | 20 | 20 | 180.40 | 0.93 | 0 | 0 4.0 | 227 | P |
| M91029_cds2_at | 7 | 2 | 20 | 20 | 180.35 | 1.32 | 0 | 0 3.5 | 224 | P |
| U52100_at | 7 | 1 | 20 | 20 | 180.35 | 1.25 | 0 | 0 7.0 | 224 | P |
| U40998_at | 8 | 2 | 20 | 20 | 180.40 | 1.32 | 0 | 0 4.0 | 221 | P |
| M90299_at | 8 | 2 | 20 | 20 | 180.40 | 1.20 | 0 | 0 4.0 | 220 | P |
| S71824_at | 7 | 1 | 20 | 20 | 180.35 | 1.30 | 0 | 0 7.0 | 220 | p |
| M31627_at | 11 | 2 | 20 | 20 | 180.55 | 1.69 | 0 | 0 5.5 | 219 | P |
| M83751_at | 7 | 2 | 20 | 20 | 170.35 | 1.46 | 0 | 0 3.5 | 219 | P |
| U43077_at | 8 | 1 | 20 | 20 | 180.40 | 1.58 | 0 | 0 8.0 | 216 | P |
| M29960_at | 10 | 2 | 20 | 20 | 180.50 | 1.52 | 2 | 0 5.0 | 215 | P |
| M92449_at | 10 | 2 | 20 | 20 | 180.50 | 1.94 | 1 | 0 5.0 | 212 | P |
| M29536_at | 11 | 2 | 20 | 20 | 180.55 | 1.95 | 0 | 0 5.5 | 207 | P |
| S81083_cds1_at | 7 | 1 | 20 | 20 | 180.35 | 1.07 | 0 | 0 7.0 | 207 | P |
| M81601_at | 7 | 1 | 20 | 20 | 180.35 | 1.55 | 0 | 0 7.0 | 205 | P |
| U50535_at | 11 | 3 | 20 | 20 | 180.55 | 2.10 | 0 | 0 3.7 | 203 | P |
| M87284_at | 9 | 2 | 20 | 20 | 180.45 | 1.41 | 0 | 0 4.5 | 202 | P |
| U24152_at | 7 | 2 | 20 | 20 | 180.35 | 1.43 | 0 | 0 5.5 | 199 | P |
| U51678_at | 10 | 3 | 20 | 20 | 180.50 | 1.77 | 0 | 0 3.3 | 199 | P |
| M64571_at | 9 | 2 | 20 | 20 | 180.45 | 1.43 | 0 | 0 4.5 | 197 | P |
| S74017_at | 10 | 2 | 20 | 20 | 180.50 | 1.59 | 0 | 0 5.0 | 196 | P |
| U38846_at | 8 | 1 | 20 | 20 | 180.40 | 1.39 | 0 | 0 8.0 | 196 | P |
| M32313_at | 9 | 1 | 20 | 20 | 180.45 | 1.62 | 1 | 0 9.0 | 194 | P |
| U43148_at | 8 | 1 | 20 | 20 | 180.40 | 1.08 | 0 | 0 8.0 | 191 | P |
| M55543_at | 8 | 2 | 20 | 20 | 180.40 | 1.53 | 0 | 0 4.0 | 189 | P |
| U37122_at | 9 | 2 | 20 | 20 | 170.45 | 1.45 | 0 | 0 4.5 | 188 | P |
| M37245_at | 10 | 1 | 20 | 20 | 180.50 | 1.81 | 0 | 0 10.0 | 186 | P |
| U34962_at | 9 | 1 | 20 | 20 | 180.45 | 1.53 | 0 | 0 9.0 | 186 | P |
| M94556_at | 10 | 3 | 20 | 20 | 180.50 | 1.78 | 1 | 0 3.3 | 183 | P |
| M31013_at | 11 | 2 | 20 | 20 | 170.55 | 2.34 | 1 | 0 5.5 | 175 | P |
| U15174_at | 7 | 1 | 20 | 20 | 180.35 | 1.30 | 0 | 1 7.0 | 173 | P |
| M94856_at | 8 | 1 | 20 | 20 | 180.40 | 1.88 | 1 | 0 8.0 | 172 | P |
| U00952_at | 9 | 1 | 20 | 20 | 170.45 | 2.14 | 0 | 0 9.0 | 170 | P |
| U14193_at | 8 | 2 | 20 | 20 | 180.40 | 1.46 | 0 | 0 4.0 | 170 | P |
| U40343_at | 7 | 1 | 20 | 20 | 180.35 | 1.29 | 0 | 0 7.0 | 170 | P |
| U02020_at | 9 | 3 | 20 | 20 | 180.45 | 2.42 | 1 | 0 3.0 | 168 | P |
| U36784_at | 10 | 3 | 20 | 20 | 180.50 | 1.60 | 1 | 0 3.3 | 167 | P |
| M86867_at | 9 | 3 | 20 | 20 | 180.45 | 1.42 | 0 | 0 3.0 | 166 | P |
| S69115_at | 7 | 1 | 20 | 20 | 180.35 | 2.01 | 1 | 0 7.0 | 166 | P |
| M29971_at | 8 | 1 | 20 | 20 | 180.40 | 0.94 | 0 | 0 8.0 | 165 | P |
| U18937_at | 7 | 2 | 20 | 20 | 180.35 | 1.54 | 0 | 1 3.5 | 164 | P |
| U31384_at | 8 | 2 | 20 | 20 | 180.40 | 1.12 | 0 | 0 4.0 | 161 | P |
| S83364_at | 9 | 2 | 20 | 20 | 180.45 | 1.55 | 0 | 0 4.5 | 159 | P |
| U54778_at | 9 | 3 | 20 | 20 | 180.45 | 1.93 | 1 | 0 3.0 | 159 | P |
| U03486_at | 7 | 0 | 20 | 20 | 180.35 | 0.91 | 0 | 0 Inf | 158 | P |
| M74002_at | 7 | 1 | 20 | 20 | 180.35 | 1.06 | 0 | 0 7.0 | 157 | P |
| U20325_at | 7 | 2 | 20 | 20 | 180.35 | 1.74 | 1 | 0 3.5 | 157 | P |
| M80629_at | 11 | 1 | 20 | 20 | 180.55 | 1.58 | 0 | 0 11.0 | 156 | P |
| U20582_at | 7 | 1 | 20 | 20 | 180.35 | 1.01 | 0 | 0 7.0 | 154 | P |
| U27185_at | 9 | 2 | 20 | 20 | 180.45 | 1.57 | 0 | 0 4.5 | 152 | P |
| U57721_at | 10 | 1 | 20 | 20 | 180.50 | 2.47 | 1 | 0 10.0 | 150 | P |
| M34423_at | 8 | 1 | 20 | 20 | 180.40 | 1.03 | 0 | 0 8.0 | 149 | P |
| U47742_at | 8 | 1 | 20 | 20 | 170.40 | 1.12 | 0 | 0 8.0 | 149 | P |
| U34252_at | 10 | 3 | 20 | 20 | 180.50 | 2.26 | 2 | 0 3.3 | 148 | P |
| U30999_at | 9 | 3 | 20 | 20 | 170.45 | 1.48 | 0 | 0 3.0 | 146 | P |
| U53446_at | 9 | 2 | 20 | 20 | 180.45 | 1.43 | 0 | 0 4.5 | 145 | P |
| 681419_at | 7 | 2 | 20 | 20 | 180.35 | 1.38 | 0 | 0 3.5 | 143 | P |
| U31383_at | 9 | 3 | 20 | 20 | 180.45 | 1.62 | 1 | 0 3.0 | 142 | P |
| U29680_at | 8 | 2 | 20 | 20 | 180.40 | 1.47 | 0 | 0 4.0 | 139 | P |
| M58803_at | 8 | 2 | 20 | 20 | 180.40 | 1.01 | 0 | 0 4.0 | 138 | P |
| M93425_at | 9 | 1 | 20 | 20 | 180.45 | 1.39 | 0 | 0 9.0 | 137 | P |
| U21049_at | 9 | 1 | 20 | 20 | 180.45 | 1.31 | 0 | 0 9.0 | 130 | P |
| U59919_at | 9 | 2 | 20 | 20 | 180.45 | 1.33 | 0 | 0 4.5 | 128 | P |
| S76965_at | 8 | 1 | 20 | 20 | 180.40 | 2.11 | 0 | 0 8.0 | 123 | P |
| M28879_at | 9 | 2 | 20 | 20 | 180.45 | 1.50 | 2 | 0 4.5 | 122 | P |
| U15782_at | 7 | 2 | 20 | 20 | 180.35. | 1.53 | 1 | 0 3.5 | 122 | P |
| M85276_at | 8 | 2 | 20 | 20 | 180.40 | 0.90 | 0 | 0 4.0 | 120 | P |
| U03688_at | 8 | 1 | 20 | 20 | 180.40 | 1.65 | 0 | 0 8.0 | 116 | P |

-continued

| Gene Name | Positive | Negative | Pairs | Pairs | Pairs In Pos | Fracti Log Avg | PM Ex MM | Ex Pos/Neg | Avg Diff Abs Call |
|---|---|---|---|---|---|---|---|---|---|
| U28249_at | 7 | 1 | 20 | 20 | 180.35 | 1.69 | 1 | 0 7.0 | 115 P |
| U08316_at | 9 | 3 | 20 | 20 | 180.45 | 1.62 | 0 | 0 3.0 | 113 P |
| U07158_at | 8 | 2 | 20 | 20 | 180.40 | 1.19 | 1 | 1 4.0 | 111 P |
| U40369_rna1_at | 9 | 2 | 20 | 20 | 180.45 | 1.75 | 0 | 1 4.5 | 111 P |
| U49352_at | 12 | 3 | 20 | 20 | 180.60 | 2.61 | 2 | 0 4.0 | 111 P |
| U59423_at | 7 | 2 | 20 | 20 | 180.35 | 1.31 | 0 | 0 3.5 | 107 P |
| M65131_rna1_at | 7 | 1 | 20 | 20 | 180.35 | 1.23 | 0 | 0 7.0 | 102 P |
| U09412_at | 8 | 2 | 20 | 20 | 180.40 | 1.05 | 0 | 0 4.0 | 98 P |
| U50928_at | 11 | 1 | 20 | 20 | 180.55 | 1.92 | 1 | 1 11.0 | 98 P |
| U49114_at | 10 | 3 | 20 | 20 | 180.50 | 1.51 | 1 | 0 3.3 | 96 P |
| U02632_at | 9 | 2 | 20 | 20 | 180.45 | 1.22 | 0 | 0 4.5 | 90 P |
| U19345_at | 7 | 1 | 20 | 20 | 180.35 | 1.53 | 0 | 0 7.0 | 87 P |
| U53003_at | 9 | 3 | 20 | 20 | 180.45 | 1.78 | 1 | 0 3.0 | 82 P |
| U13616_at | 9 | 3 | 20 | 20 | 180.45 | 1.45 | 2 | 1 3.0 | 78 P |
| U47054_at | 7 | 2 | 20 | 20 | 180.35 | 1.58 | 2 | 0 3.5 | 78 P |
| M23161_at | 8 | 1 | 20 | 20 | 180.40 | 1.14 | 0 | 0 8.0 | 77 P |
| M90696_at | 9 | 1 | 20 | 20 | 180.45 | 1.46 | 2 | 0 9.0 | 76 P |
| U46752_at | 8 | 2 | 20 | 20 | 180.40 | 1.14 | 0 | 0 4.0 | 76 P |
| J03056_at | 7 | 2 | 20 | 20 | 180.35 | 1.44 | 2 | 0 3.5 | 70 P |
| 28386_at | 9 | 2 | 20 | 20 | 180.45 | 1.66 | 1 | 0 4.5 | 69 P |
| 55766_at | 7 | 1 | 20 | 20 | 180.35 | 0.96 | 0 | 1 7.0 | 69 P |
| 09367_at | 8 | 2 | 20 | 20 | 180.40 | 0.92 | 0 | 0 4.0 | 67 P |
| U31116_at | 7 | 2 | 20 | 20 | 180.35 | 1.42 | 1 | 0 3.5 | 67 P |
| U35735_at | 7 | 1 | 20 | 20 | 180.35 | 1.17 | 0 | 0 7.0 | 65 P |
| U05875_at | 7 | 2 | 20 | 20 | 180.35 | 1.52 | 0 | 0 3.5 | 37 P |

| Gene Name | Positive | Negative | Pairs | Pairs User Pairs | InAv Pos | Fracti Log Avg | PM Exces: MM | Exces Pos/Neg | Avg Diff Abs Call |
|---|---|---|---|---|---|---|---|---|---|
| hum_alu_at | 69 | 0 | 69 | 69 | 67 1.00 | 7.20 | 9 | 0 Inf | 22212 P |
| Z12962_at | 18 | 0 | 20 | 20 | 18 0.90 | 7.43 | 5 | 0 Inf | 11237 P |
| X56932_at | 20 | 0 | 20 | 20 | 18 1.00 | 8.65 | 9 | 0 Inf | 8427 P |
| Z70759_at | 20 | 0 | 20 | 20 | 18 1.00 | 8.49 | 8 | 0 Inf | 8169 P |
| X69150_at | 19 | 0 | 20 | 20 | 18 0.95 | 7.61 | 8 | 0 Inf | 6897 P |
| X15940_at | 19 | 0 | 20 | 20 | 18 0.95 | 7.00 | 4 | 0 Inf | 5994 P |
| X06617_at | 20 | 0 | 20 | 20 | 18 1.00 | 6.37 | 1 | 0 Inf | 5392 P |
| X03342_at | 20 | 0 | 20 | 20 | 18 1.00 | 7.66 | 5 | 0 Inf | 5147 P |
| AFFX-CreX-3_at | 19 | 0 | 20 | 20 | 18 0.95 | 8.47 | 6 | 0 Inf | 4809 P |
| X17206_at | 19 | 0 | 20 | 20 | 18 0.95 | 7.56 | 6 | 0 Inf | 4634 P |
| X64707_at | 15 | 0 | 20 | 20 | 18 0.75 | 6.10 | 3 | 0 Inf | 4230 P |
| Z23090_at | 17 | 0 | 20 | 20 | 18 0.85 | 5.02 | 0 | 0 Inf | 4116 P |
| X62691_at | 20 | 0 | 20 | 20 | 18 1.00 | 7.40 | 3 | 0 Inf | 4105 P |
| X65B14_at | 20 | 0 | 20 | 20 | 18 1.00 | 7.02 | 2 | 0 Inf | 4027 P |
| AB002533_at | 19 | 0 | 20 | 20 | 18 0.95 | 6.88 | 4 | 0 Inf | 4012 P |
| X16064_at | 17 | 0 | 20 | 20 | 18 0.85 | 7.60 | 4 | 0 Inf | 3795 P |
| X63527_at | 20 | 0 | 20 | 20 | 18 1.00 | 7.94 | 9 | 0 Inf | 3755 P |
| X55954_at | 20 | 0 | 20 | 20 | 18 1.00 | 7.24 | 4 | 0 Inf | 3744 P |
| AFFX-CreX-5_at | 20 | 0 | 20 | 20 | 18 1.00 | 8.02 | 5 | 0 Inf | 3538 P |
| X80822_at | 18 | 0 | 20 | 20 | 18 0.90 | 5.48 | 0 | 0 Inf | 3471 P |
| X67247_rna1_at | 20 | 0 | 20 | 20 | 17 1.00 | 8.00 | 6 | 0 Inf | 3402 P |
| 726876_at | 19 | 0 | 20 | 20 | 18 0.95 | 7.54 | 5 | 0 Inf | 3163 P |
| X73460_at | 19 | 0 | 20 | 20 | 18 0.95 | 6.44 | 4 | 0 Inf | 3009 P |
| X53777_at | 18 | 1 | 20 | 20 | 18 0.90 | 7.48 | 6 | 0 18.0 | 2851 P |
| _79234_at | 20 | 0 | 20 | 20 | 18 1.00 | 7.49 | 3 | 0 Inf | 2843 P |
| AFFX-HSAC07/X00351_3_at | 19 | 0 | 20 | 20 | 18 0.95 | 6.48 | 2 | 0 Inf | 2664 P |
| 39391_at | 20 | 0 | 20 | 20 | 18 1.00 | 6.86 | 4 | 0 Inf | 2656 P |
| FFX-BioDn-3_at | 18 | 0 | 20 | 20 | 18 0.90 | 5.07 | 0 | 0 Inf | 2613 P |
| 28407_at | 15 | 1 | 20 | 20 | 18 0.75 | 4.43 | 1 | 0 15.0 | 2557 P |
| AFFX-HUMGAPDH/M33197_3_a | 19 | 0 | 20 | 20 | 17 0.95 | 5.41 | 0 | 0 Inf | 2535 P |
| U78027_rna3_at | 18 | 2 | 20 | 20 | 18 0.90 | 7.15 | 4 | 0 9.0 | 2430 P |
| Z25749_rna1_at | 16 | 1 | 20 | 20 | 18 0.80 | 5.44 | 2 | 0 16.0 | 2348 P |
| X00274_at | 20 | 0 | 20 | 20 | 18 1.00 | 8.13 | 7 | 0 Inf | 2334 P |
| X56997_ma1_at | 19 | 0 | 20 | 20 | 18 0.95 | 5.12 | 2 | 0 Inf | 2279 P |
| Y00705_at | 18 | 0 | 20 | 20 | 18 0.90 | 7.34 | 5 | 0 Inf | 2124 P |
| X55715_at | 17 | 0 | 20 | 20 | 18 0.85 | 5.96 | 2 | 0 Inf | 1884 P |
| Y07755_at | 18 | 0 | 20 | 20 | 18 0.90 | 6.05 | 0 | 0 Inf | 1877 P |
| X52966_at | 15 | 2 | 20 | 20 | 17 0.75 | 5.36 | 2 | 0 7.5 | 1485 P |
| X52851_rna1_at | 20 | 0 | 20 | 20 | 18 1.00 | 6.46 | 1 | 0 Inf | 1384 P |
| X15183_at | 17 | 2 | 20 | 20 | 18 0.85 | 5.76 | 2 | 1 8.5 | 1273 P |
| X93036_at | 16 | 0 | 20 | 20 | 18 0.80 | 5.04 | 3 | 0 Inf | 1232 P |

-continued

| Gene Name | Positive | Negative | Pairs | Pairs User Pairs | InAv Pos | Fracti Log Avg | PM Exces: MM | Exces Pos/Neg | Avg Diff Abs Call |
|---|---|---|---|---|---|---|---|---|---|
| X95404_at | 14 | 0 | 20 | 20 | 18 0.70 | 4.70 | 2 | 0 Inf | 1170 P |
| X57959_at | 19 | 0 | 20 | 20 | 17 0.95 | 7.19 | 3 | 0 Inf | 1125 P |
| X15341_at | 19 | 0 | 20 | 20 | 18 0.95 | 6.40 | 0 | 0 Inf | 1071 P |
| AFFX-HSAC07/X00351_M_at | 16 | 1 | 20 | 20 | 18 0.80 | 4.07 | 0 | 0 16.0 | 1036 P |
| Y00433_at | 14 | 0 | 20 | 20 | 18 0.70 | 4.15 | 0 | 0 Inf | 1027 P |
| X60489_at | 17 | 0 | 20 | 20 | 18 0.85 | 5.73 | 2 | 0 Inf | 996 P |
| U90915_at | 17 | 0 | 20 | 20 | 18 0.85 | 5.47 | 2 | 0 Inf | 988 P |
| X16560_at | 18 | 1 | 20 | 20 | 18 0.90 | 6.30 | 4 | 0 18.0 | 983 P |
| X16832_at | 16 | 0 | 20 | 20 | 18 0.80 | 5.03 | 1 | 0 Inf | 971 P |
| X80909_at | 17 | 0 | 20 | 20 | 18 0.85 | 5.63 | 1 | 0 Inf | 939 P |
| X15822_at | 17 | 0 | 20 | 20 | 18 0.85 | 4.56 | 3 | 0 Inf | 830 P |
| AF001548_rna1_at | 13 | 1 | 20 | 20 | 18 0.65 | 3.77 | 0 | 0 13.0 | 826 P |
| U93205_at | 15 | 0 | 20 | 20 | 18 0.75 | 3.20 | 0 | 0 Inf | 818 P |
| X13839_at | 17 | 3 | 20 | 20 | 18 0.85 | 4.84 | 0 | 0 5.1 | 801 P |
| X12447_at | 12 | 1 | 20 | 20 | 18 0.60 | 2.54 | 1 | 0 12.0 | 797 P |
| Y00503_at | 18 | 0 | 20 | 20 | 18 0.90 | 4.80 | 1 | 0 Inf | 772 P |
| X51466_at | 16 | 0 | 20 | 20 | 18 0.80 | 3.85 | 0 | 0 Inf | 758 P |
| X68314_at | 16 | 0 | 20 | 20 | 17 0.80 | 3.82 | 0 | 0 Inf | 739 P |
| AFFX-HSAC07/X00351_5_at | 15 | 1 | 20 | 20 | 18 0.75 | 3.33 | 0 | 0 15.0 | 710 P |
| AFFX-HUMGAPDH/M33197_M_ϵ | 14 | 2 | 20 | 20 | 18 0.70 | 2.74 | 0 | 0 7.0 | 682 P |
| X01630_at | 13 | 1 | 20 | 20 | 18 0.65 | 3.61 | 0 | 0 13.0 | 645 P |
| X62654_rna 1_at | 16 | 1 | 20 | 20 | 17 0.80 | 4.22 | 0 | 0 16.0 | 637 P |
| X87951_at | 1 | 0 | 20 | 20 | 18 0.95 | 5.08 | 0 | 0 Inf | 608 P |
| Z84721_cds2_at | 13 | 3 | 20 | 20 | 18 0.65 | 3.07 | 0 | 0 4.3 | 604 P |
| U67171_at | 14 | 1 | 20 | 20 | 18 0.70 | 2.56 | 0 | 0 14.0 | 575 P |
| U94586_at | 18 | 0 | 20 | 20 | 17 0.90 | 6.10 | 2 | 0 Inf | 559 P |
| 120688_at | 14 | 0 | 20 | 20 | 17 0.70 | 3.12 | 0 | 0 Inf | 553 P |
| X56494_at | 12 | 2 | 20 | 20 | 18 0.60 | 2.68 | 1 | 0 6.0 | 527 P |
| AFFX-BioDn-5_at | 12 | 1 | 20 | 20 | 18 0.60 | 3.28 | 0 | 0 12.0 | 512 P |
| X13794_rna1_at | 18 | 1 | 20 | 20 | 18 0.90 | 5.60 | 2 | 0 18.0 | 508 P |
| X71973_at | 14 | 0 | 20 | 20 | 18 0.70 | 2.94 | 0 | 0 Inf | 499 P |
| X82693_at | 13 | 0 | 20 | 20 | 18 0.65 | 2.55 | 0 | 0 Inf | 492 P |
| X71874_cds1_at | 15 | 1 | 20 | 20 | 18 0.75 | 2.89 | 0 | 0 15.0 | 488 P |
| X55733_at | 12 | 0 | 20 | 20 | 18 0.60 | 2.95 | 1 | 0 Inf | 487 P |
| X51521_at | 16 | 1 | 20 | 20 | 18 0.80 | 4.65 | 1 | 0 16.0 | 485 P |
| X07979_at | 16 | 0 | 20 | 20 | 17 0.80 | 4.62 | 0 | 0 Inf | 484 P |
| AFFX-HSAC07_00351_3_st | 13 | 0 | 20 | 20 | 18 0.65 | 3.47 | 0 | 0 Inf | 449 P |
| V00572_at | 20 | 0 | 20 | 20 | 18 1.00 | 5.05 | 0 | 0 Inf | 447 P |
| Y00282_at | 18 | 0 | 20 | 20 | 18 0.90 | 4.22 | 1 | 0 Inf | 435 P |
| U78095_at | 13 | 0 | 20 | 20 | 18 0.65 | 2.64 | 0 | 0 Inf | 433 P |
| X02317_at | 18 | 0 | 20 | 20 | 18 0.90 | 5.43 | 1 | 0 Inf | 428 P |
| U79294_at | 10 | 2 | 20 | 20 | 18 0.50 | 1.45 | 0 | 0 5.0 | 417 P |
| U73843_at | 13 | 2 | 20 | 20 | 18 0.65 | 2.49 | 0 | 0 6.5 | 411 P |
| 0200_at | 14 | 1 | 20 | 20 | 17 0.70 | 3.92 | 1 | 0 14.0 | 409 P |
| AFFX-HUMGAPDH/M33197_5_a | 15 | 2 | 20 | 20 | 18 0.75 | 3.89 | 0 | 0 7.5 | 404 P |
| X3100_cds2_at | 11 | 2 | 20 | 20 | 18 0.55 | 2.55 | 0 | 0 5.5 | 403 P |
| X7584_at | 14 | 2 | 20 | 20 | 18 0.70 | 4.06 | 2 | 1 7.0 | 400 P |
| AFFX-BioC-5_at | 13 | 1 | 20 | 20 | 18 0.65 | 3.47 | 0 | 0 13.0 | 397 P |
| X81817_at | 16 | 2 | 20 | 20 | 18 0.80 | 3.53 | 1 | 0 8.0 | 395 P |
| Z21507_at | 14 | 2 | 20 | 20 | 18 0.70 | 3.46 | 1 | 0 7.0 | 395 P |
| V00563_at | 14 | 0 | 20 | 20 | 18 0.70 | 2.83 | 0 | 0 Inf | 393 P |
| U77604_at | 11 | 1 | 20 | 20 | 17 0.55 | 2.48 | 1 | 0 11.0 | 374 P |
| X02152_at | 12 | 3 | 20 | 20 | 18 0.60 | 2.55 | 1 | 0 4.0 | 374 P |
| X67698_at | 17 | 0 | 20 | 20 | 18 0.85 | 3.10 | 0 | 0 Inf | 372 P |
| J04182_at | 15 | 3 | 20 | 20 | 18 0.75 | 2.37 | 1 | 1 5.0 | 370 P |
| Z24727_at | 15 | 1 | 20 | 20 | 18 0.75 | 4.06 | 2 | 0 15.0 | 366 P |
| X69550_at | 11 | 2 | 20 | 20 | 18 0.55 | 1.96 | 0 | o 5.5 | 362 P |
| X75593_at | 10 | 1 | 20 | 20 | 18 0.50 | 2.70 | 3 | o 10.0 | 359 P |
| U72511_at | 13 | 0 | 20 | 20 | 18 0.65 | 2.89 | 0 | 0 Inf | 357 P |
| X99688_at | 11 | 1 | 20 | 20 | 18 0.55 | 2.18 | 0 | 0 11.0 | 355 P |
| J02783_at | 12 | 4 | 20 | 20 | 17 0.60 | 2.08 | 0 | 0 3.0 | 351 P |
| U85611_at | 12 | 1 | 20 | 20 | 18 0.60 | 3.33 | 1 | 0 12.0 | 342 P |
| X76013_at | 15 | 2 | 20 | 20 | 18 0.75 | 3.31 | 1 | 0 7.5 | 342 P |
| X13238_at | 15 | 1 | 20 | 20 | 18 0.75 | 4.48 | 0 | 0 15.0 | 339 P |
| X59892_at | 11 | 1 | 20 | 20 | 18 0.55 | 2.32 | 0 | 0 11.0 | 338 P |
| Y00764_at | 16 | 1 | 20 | 20 | 18 0.80 | 4.86 | 0 | 0 16.0 | 335 P |
| X59417_at | 13 | 0 | 20 | 20 | 18 0.65 | 3.47 | 1 | 0 Inf | 327 P |
| X16135_at | 11 | 3 | 20 | 20 | 18 0.55 | 2.42 | 0 | 0 3.7 | 326 P |
| Z48950_at | 16 | 1 | 20 | 20 | 18 0.80 | 3.45 | 0 | 0 16.0 | 308 P |
| X75252_at | 11 | 1 | 20 | 20 | 18 0.55 | 2.58 | 0 | 0 11.0 | 307 P |
| U90313_at | 13 | 0 | 20 | 20 | 18 0.65 | 3.28 | 1 | 0 Inf | 295 P |
| X86809_at | 9 | 1 | 20 | 20 | 18 0.45 | 1.66 | 0 | 0 9.0 | 295 P |
| U78521_at | 9 | 3 | 20 | 20 | 18 0.45 | 1.36 | 0 | 0 3.0 | 294 P |
| Z32765_at | 12 | 3 | 20 | 20 | 18 0.60 | 1.79 | 0 | 0 4.0 | 294 P |
| Z48199_at | 9 | 0 | 20 | 20 | 18 0.45 | 2.00 | 0 | 0 Inf | 294 P |

-continued

| Gene Name | Positive | Negative | Pairs | Pairs User Pairs | InAv Pos | Fracti Log Avg | PM Exces: MM | Exces Pos/Neg | Avg Diff Abs Call |
|---|---|---|---|---|---|---|---|---|---|
| X53331_at | 14 | 0 | 20 | 20 | 18 0.70 | 3.12 | 0 | 0 Inf | 293 P |
| X69908_rna1_at | 10 | 3 | 20 | 20 | 18 0.50 | 2.47 | 0 | 0 3.3 | 292 P |
| X75861_at | 12 | 0 | 20 | 20 | 18 0.60 | 3.38 | 0 | 0 Inf | 290 P |
| AFFX-BioC-3_at | 13 | 2 | 20 | 20 | 18 0.65 | 2.47 | 0 | 0 6.5 | 287 P |
| X69111_at | 13 | 3 | 20 | 20 | 18 0.65 | 2.18 | 0 | 0 4.3 | 284 P |
| X17042_at | 13 | 0 | 20 | 20 | 18 0.65 | 4.02 | 1 | 0 Inf | 280 P |
| X60221_at | 17 | 2 | 20 | 20 | 18 0.85 | 3.05 | 0 | 0 8.5 | 278 P |
| U84569_at | 10 | 2 | 20 | 20 | 17 0.50 | 1.74 | 0 | 0 5.0 | 270 P |
| U73824_at | 15 | 0 | 20 | 20 | 18 0.75 | 3.98 | 1 | 0 Inf | 268 P |
| X15880_at | 9 | 2 | 20 | 20 | 18 0.45 | 2.53 | 0 | 0 4.5 | 267 P |
| X91257_at | 11 | 0 | 20 | 20 | 18 0.55 | 2.57 | 0 | 0 Inf | 266 P |
| X56253_rna1_at | 10 | 2 | 20 | 20 | 18 0.50 | 1.39 | 0 | 1 5.0 | 263 P |
| U94855_at | 15 | 1 | 20 | 20 | 17 0.75 | 4.00 | 2 | 0 15.0 | 259 P |
| X91504_at | 10 | 1 | 20 | 20 | 17 0.50 | 1.34 | 0 | 0 10.0 | 256 P |
| X87838_at | 16 | 1 | 20 | 20 | 17 0.80 | 3.65 | 1 | 0 16.0 | 255 P |
| U86529_at | 9 | 0 | 20 | 20 | 18 0.45 | 1.84 | 0 | 0 Inf | 252 P |
| U72512_at | 7 | 0 | 20 | 20 | 17 0.35 | 1.27 | 0 | 0 Inf | 251 P |
| X74104_at | 14 | 1 | 20 | 20 | 18 0.70 | 3.37 | 1 | 0 14.0 | 249 P |
| U66879_at | 11 | 2 | 20 | 20 | 18 0.55 | 2.30 | 0 | 0 5.5 | 246 P |
| X04085_rna1_at | 11 | 2 | 20 | 20 | 18 0.55 | 2.04 | 0 | 0 5.5 | 246 P |
| X04412_at | 9 | 1 | 20 | 20 | 18 0.45 | 2.03 | 0 | 0 9.0 | 246 P |
| Y00281_at | 10 | 0 | 20 | 20 | 18 0.50 | 2.36 | 0 | 0 Inf | 244 P |
| 127113_at | 10 | 1 | 20 | 20 | 18 0.50 | 1.98 | 0 | 0 10.0 | 241 P |
| X78136_at | 12 | 2 | 20 | 20 | 18 0.60 | 3.45 | 1 | 0 6.0 | 240 P |
| X86779_at | 8 | 1 | 20 | 20 | 18 0.40 | 1.38 | 0 | 0 8.0 | 236 P |
| D13146_cds1_at | 10 | 1 | 20 | 20 | 18 0.50 | 1.62 | 0 | 0 10.0 | 235 P |
| X71428_at | 12 | 3 | 20 | 20 | 18 0.60 | 2.10 | 1 | 0 4.0 | 230 P |
| J70063_at | 11 | 1 | 20 | 20 | 18 0.55 | 2.39 | 0 | 0 11.0 | 229 P |
| 88964_at | 12 | 1 | 20 | 20 | 18 0.60 | 2.85 | 0 | 0 12.0 | 229 P |
| 63115_at | 12 | 3 | 20 | 20 | 18 0.60 | 1.65 | 0 | 1 4.0 | 228 P |
| 2466_at | 12 | 0 | 20 | 20 | 17 0.60 | 2.49 | 0 | 0 Inf | 224 P |
| X69699_at | 9 | 2 | 20 | 20 | 18 0.45 | 2.02 | 0 | 0 4.5 | 221 P |
| U90878_at | 13 | 2 | 20 | 20 | 18 0.65 | 2.60 | 0 | 0 6.5 | 220 P |
| X13546_rna1_at | 12 | 1 | 20 | 20 | 17 0.60 | 2.45 | 0 | 0 12.0 | 216 P |
| LJ77948_at | 11 | 1 | 20 | 20 | 18 0.55 | 2.66 | 1 | 0 11.0 | 215 P |
| X86693_at | 12 | 2 | 20 | 20 | 18 0.60 | 3.16 | 2 | 0 6.0 | 212 P |
| X74801_at | 10 | 1 | 20 | 20 | 18 0.50 | 2.36 | 0 | 0 10.0 | 211 P |
| X80199_at | 11 | 1 | 20 | 20 | 18 0.55 | 2.91 | 0 | 0 11.0 | 209 P |
| X59834_at | 13 | 3 | 20 | 20 | 18 0.65 | 3.06 | 1 | 0 4.3 | 208 P |
| X85785_rna1_at | 8 | 2 | 20 | 20 | 18 0.40 | 1.54 | 0 | 0 4.0 | 207 P |
| X89267_at | 7 | 0 | 20 | 20 | 18 0.35 | 1.18 | 0 | 0 Inf | 207 P |
| L10413_at | 10 | 0 | 20 | 20 | 18 0.50 | 2.06 | 0 | 0 Inf | 206 P |
| U68566_at | 9 | 2 | 20 | 20 | 18 0.45 | 1.55 | 0 | 0 4.5 | 203 P |
| U90716_at | 11 | 2 | 20 | 20 | 18 0.55 | 3.01 | 3 | 1 5.5 | 203 P |
| X83618_at | 12 | 1 | 20 | 20 | 18 0.60 | 1.90 | 0 | 0 12.0 | 202 P |
| X83425_at | 9 | 2 | 20 | 20 | 18 0.45 | 1.86 | 0 | 0 4.5 | 201 P |
| X12794_at | 9 | 1 | 20 | 20 | 18 0.45 | 1.47 | 0 | 0 7.0 | 197 P |
| X60036_at | 14 | 2 | 20 | 20 | 18 0.70 | 2.41 | 0 | 1 7.0 | 196 P |
| X67325_at | 10 | 2 | 20 | 20 | 18 0.50 | 2.46 | 0 | 0 5.0 | 194 P |
| U68142_at | 11 | 1 | 20 | 20 | 18 0.55 | 2.42 | 0 | 0 11.0 | 193 P |
| X52730_rna1_at | 8 | 1 | 20 | 20 | 18 0.40 | 1.28 | 0 | 0 8.0 | 192 P |
| X57346_at | 16 | 0 | 20 | 20 | 17 0.80 | 3.12 | 0 | 0 Inf | 191 P |
| X74795_at | 9 | 2 | 20 | 20 | 17 0.45 | 1.61 | 0 | 0 4.5 | 190 P |
| X82456_at | 13 | 2 | 20 | 20 | 18 0.65 | 3.07 | 0 | 0 6.5 | 190 P |
| X83218_at | 16 | 0 | 20 | 20 | 17 0.80 | 3.40 | 0 | 0 Inf | 190 P |
| U79254_at | 14 | 0 | 20 | 20 | 18 0.70 | 2.90 | 0 | 0 Inf | 188 P |
| X66401_cds1_at | 11 | 2 | 20 | 20 | 18 0.55 | 3.24 | 1 | 0 5.5 | 188 P |
| Z35093_at | 10 | 0 | 20 | 20 | 18 0.50 | 2.48 | 0 | 0 Inf | 188 P |
| X54304_at | 10 | 0 | 20 | 20 | 18 0.50 | 2.85 | 1 | 0 Inf | 187 P |
| X95586_at | 12 | 1 | 20 | 20 | 18 0.60 | 2.55 | 1 | 0 12.0 | 187 P |
| X70476_at | 13 | 2 | 20 | 20 | 18 0.65 | 3.26 | 1 | 0 6.5 | 186 P |
| X68733_rna1_at | 7 | 1 | 20 | 20 | 18 0.35 | 1.53 | 0 | 0 7.0 | 185 P |
| U73379_at | 11 | 2 | 20 | 20 | 17 0.55 | 1.92 | 0 | 0 5.5 | 181 P |
| U77396_at | 10 | 2 | 20 | 20 | 18 0.50 | 2.09 | 0 | 0 5.0 | 180 P |
| X17620_at | 7 | 1 | 20 | 20 | 18 0.35 | 1.16 | 0 | 0 7.0 | 178 P |
| X69910_at | 13 | 2 | 20 | 20 | 18 0.65 | 2.25 | 0 | 0 6.5 | 176 P |
| X99459_at | 8 | 1 | 20 | 20 | 18 0.40 | 1.40 | 0 | 0 8.0 | 176 P |
| X99920_at | 12 | 1 | 20 | 20 | 18 0.60 | 1.52 | 0 | 1 12.0 | 176 P |
| X15414_at | 12 | 0 | 20 | 20 | 17 0.60 | 2.21 | 0 | 0 Inf | 174 P |
| Z29505_at | 15 | 1 | 20 | 20 | 18 0.75 | 3.40 | 1 | 1 15.0 | 174 P |
| Z37986_at | 11 | 2 | 20 | 20 | 18 0.55 | 1.92 | 0 | 0 5.5 | 174 P |
| Z19574_rna1_at | 14 | 0 | 20 | 20 | 17 0.70 | 2.84 | 0 | 0 Inf | 173 P |
| U78525_at | 7 | 0 | 20 | 20 | 18 0.35 | 1.45 | 0 | 0 Inf | 172 P |
| X59434_at | 10 | 2 | 20 | 20 | 18 0.50 | 1.34 | 0 | 0 5.0 | 172 P |
| Y11681_at | 9 | 1 | 20 | 20 | 18 0.45 | 1.54 | 0 | 0 9.0 | 172 P |
| X99209_at | 9 | 2 | 20 | 20 | 18 0.45 | 1.65 | 0 | 0 4.5 | 170 P |
| U72515_at | 7 | 1 | 20 | 20 | 18 0.35 | 1.29 | 0 | 0 7.9 | 166 P |

-continued

| Gene Name | Positive | Negative | Pairs | Pairs User Pairs | InAv Pos | Fracti Log Avg | PM Exces: MM | Exces Pos/Neg | Avg Diff | Abs Call |
|---|---|---|---|---|---|---|---|---|---|---|
| U70660_at | 11 | 2 | 20 | 20 | 17 0.55 | 1.80 | 0 | 0 5.5 | 160 | P |
| X61970_at | 11 | 2 | 20 | 20 | 18 0.55 | 2.56 | 0 | 0 5.5 | 159 | P |
| U94592_at | 13 | 2 | 20 | 20 | 17 0.65 | 2.02 | 0 | 0 6.5 | 158 | P |
| X62078_at | 12 | 1 | 20 | 20 | 18 0.60 | 1.64 | 0 | 0 12.0 | 157 | P |
| U82010_rna1_at | 11 | 1 | 20 | 20 | 18 0.55 | 2.44 | 0 | 0 11.0 | 156 | P |
| X63422_at | 10 | 1 | 20 | 20 | 18 0.50 | 2.41 | 0 | 0 10.0 | 156 | P |
| X72964_at | 11 | 1 | 20 | 20 | 18 0.55 | 1.79 | 0 | 0 11.0 | 153 | P |
| X76228_at | 11 | 3 | 20 | 20 | 18 0.55 | 2.46 | 1 | 1 3.7 | 153 | P |
| U83246_at | 8 | 2 | 20 | 20 | 18 0.40 | 1.04 | 0 | 0 4.0 | 152 | P |
| U79266_at | 7 | 1 | 20 | 20 | 18 0.35 | 1.07 | 0 | 0 7.0 | 148 | P |
| 90547_at | 9 | 0 | 20 | 20 | 17 0.45 | 2.01 | 0 | 0 Inf | 148 | P |
| 97074_at | 8 | 0 | 20 | 20 | 18 0.40 | 1.27 | 0 | 0 Inf | 148 | P |
| 50405_at | 9 | 1 | 20 | 20 | 18 0.45 | 1.59 | 0 | 0 9.0 | 148 | P |
| U93237_rna2_at | 10 | 1 | 20 | 20 | 18 0.50 | 1.70 | 0 | 0 10.0 | 146 | P |
| X87237_at | 9 | 1 | 20 | 20 | 18 0.45 | 1.45 | 0 | 0 9.0 | 146 | P |
| Z14244_at | 13 | 2 | 20 | 20 | 18 0.65 | 2.65 | 1 | 0 6.5 | 146 | P |
| X74295_at | 10 | 1 | 20 | 20 | 18 0.50 | 1.75 | 0 | 0 10.0 | 145 | P |
| X89750_at | 14 | 0 | 20 | 20 | 18 0.70 | 3.67 | 1 | 0 Inf | 145 | P |
| U68233_at | 8 | 2 | 20 | 20 | 18 0.40 | 1.71 | 0 | 0 4.0 | 144 | P |
| U72517_at | 9 | 2 | 20 | 20 | 18 0.45 | 1.34 | 0 | 0 4.5 | 144 | P |
| X03934_at | 10 | 0 | 20 | 20 | 18 0.50 | 2.02 | 0 | 0 Inf | 144 | P |
| U70735_at | 12 | 0 | 20 | 20 | 18 0.60 | 1.96 | 0 | 0 Inf | 143 | P |
| U78524_at | 10 | 2 | 20 | 20 | 18 0.50 | 1.67 | 0 | 0 5.0 | 143 | P |
| X57398_at | 9 | 1 | 20 | 20 | 18 0.45 | 2.09 | 0 | 0 9.0 | 138 | P |
| U87459_at | 7 | 2 | 20 | 20 | 18 0.35 | 1.33 | 0 | 0 3.5 | 137 | P |
| X04366_at | 10 | 3 | 20 | 20 | 18 0.50 | 2.02 | 0 | 0 3.3 | 137 | P |
| Y00815_at | 10 | 1 | 20 | 20 | 18 0.50 | 2.29 | 0 | 0 10.0 | 137 | P |
| AFFX-HUMISGF3A/ M97935_3_a | 10 | 1 | 20 | 20 | 18 0.50 | 1.69 | 0 | 0 10.0 | 135 | P |
| U79287_at | 8 | 1 | 20 | 20 | 18 0.40 | 1.91 | 0 | 0 8.0 | 135 | P |
| X12451_at | 13 | 0 | 20 | 20 | 17 0.65 | 2.96 | 1 | 0 Inf | 135 | P |
| Z49099_at | 8 | 1 | 20 | 20 | 18 0.40 | 1.89 | 1 | 0 8.0 | 134 | P |
| X05409_at | 11 | 2 | 20 | 20 | 18 0.55 | 1.38 | 0 | 0 5.5 | 133 | P |
| X69433_at | 8 | 2 | 20 | 20 | 18 0.40 | 1.33 | 0 | 0 4.0 | 133 | P |
| U75968_at | 8 | 1 | 20 | 20 | 18 0.40 | 1.15 | 0 | 0 8.0 | 132 | P |
| L11066_at | 9 | 2 | 20 | 20 | 18 0.45 | 1.09 | 0 | 0 4.5 | 132 | P |
| X62744_at | 11 | 3 | 20 | 20 | 17 0.55 | 1.93 | 0 | 0 3.7 | 131 | P |
| U89336_cds1_at | 8 | 1 | 20 | 20 | 18 0.40 | 1.73 | 0 | 0 8.0 | 130 | P |
| U90907_at | 9 | 2 | 20 | 20 | 18 0.45 | 1.38 | 0 | 0 4.5 | 130 | P |
| X82434_at | 9 | 0 | 20 | 20 | 17 0.45 | 1.38 | 0 | 0 Inf | 130 | P |
| X822_0_at | 9 | 3 | 20 | 20 | 18 0.45 | 2.01 | 1 | 0 3.0 | 129 | P |
| X85373_at | 10 | 2 | 20 | 20 | 18 0.50 | 1.40 | 1 | 0 5.0 | 129 | P |
| Z47727_at | 9 | 0 | 20 | 20 | 18 0.45 | 1.96 | 0 | 0 Inf | 129 | P |
| X71129_at | 9 | 1 | 20 | 20 | 17 0.45 | 1.45 | 0 | 0 9.0 | 127 | P |
| U85193_at | 10 | 1 | 20 | 20 | 18 0.50 | 2.01 | 0 | 0 10.0 | 126 | P |
| X76534_at | 14 | 1 | 20 | 20 | 18 0.70 | 3.70 | 0 | 1 14.0 | 125 | P |
| Z71460_at | 8 | 2 | 20 | 20 | 18 0.40 | 1.42 | 0 | 0 4.0 | 125 | P |
| U81556_at | 8 | 1 | 20 | 20 | 17 0.40 | 1.50 | 0 | 0 8.0 | 124 | P |
| U68063_at | 10 | 1 | 20 | 20 | 18 0.50 | 3.10 | 2 | 0 10.0 | 123 | P |
| X82895_at | 7 | 0 | 20 | 20 | 18 0.35 | 1.31 | 0 | 0 Inf | 123 | P |
| X74262_at | 14 | 2 | 20 | 20 | 18 0.70 | 3.68 | 3 | 0 7.0 | 120 | P |
| Z56281_at | 7 | 1 | 20 | 20 | 18 0.35 | 1.17 | 0 | 0 7.0 | 120 | P |
| X77794_at | 16 | 2 | 20 | 20 | 17 0.80 | 3.79 | 1 | 0 8.0 | 119 | P |
| AFFX-BioB-3_at | 8 | 2 | 20 | 20 | 18 0.40 | 1.05 | 0 | 0 4.0 | 118 | P |
| X54232_at | 9 | 0 | 20 | 20 | 17 0.45 | 1.44 | 0 | 0 Inf | 118 | P |
| U78793_at | 8 | 2 | 20 | 20 | 18 0.40 | 1.81 | 0 | 0 4.0 | 115 | P |
| X80692_at | 10 | 1 | 20 | 20 | 18 0.50 | 2.36 | 1 | 0 10.0 | 115 | P |
| X98311_at | 9 | 1 | 20 | 20 | 18 0.45 | 1.43 | 0 | 0 9.0 | 113 | P |
| X16316_at | 8 | 2 | 20 | 20 | 18 0.40 | 0.98 | 0 | 04.0 | 111 | P |
| X94612_at | 10 | 3 | 20 | 20 | 18 0.50 | 1.80 | 0 | 0 3.3 | 111 | P |
| X99728_at | 11 | 2 | 20 | 20 | 18 0.55 | 1.92 | 0 | 0 5.5 | 110 | P |
| X59405_at | 12 | 1 | 20 | 20 | 18 0.60 | 2.86 | 0 | 0 12.0 | 109 | P |
| X92896_at | 9 | 3 | 20 | 20 | 17 0.45 | 1.52 | 0 | 0 3.0 | 108 | P |
| X76648_at | 13 | 1 | 20 | 20 | 18 0.65 | 4.02 | 1 | 0 13.0 | 107 | P |
| X15187_at | 9 | 2 | 20 | 20 | 17 0.45 | 2.15 | 0 | 0 4.5 | 106 | P |
| U89278_at | 8 | 2 | 20 | 20 | 17 0.40 | 0.91 | 0 | 0 4.0 | 105 | P |
| X62055_at | 9 | 1 | 20 | 20 | 17 0.45 | 1.53 | 0 | 0 9.0 | 105 | P |
| X68277_at | 11 | 2 | 20 | 20 | 18 0.55 | 1.64 | 0 | 0 5.5 | 105 | P |
| X74008_at | 11 | 1 | 20 | 20 | 17 0.55 | 2.21 | 0 | 0 11.0 | 105 | P |
| U78556_at | 9 | 1 | 20 | 20 | 18 0.45 | 1.41 | 0 | 0 9.0 | 104 | P |
| U89336_cds3_at | 9 | 0 | 20 | 20 | 17 0.45 | 1.26 | 0 | 0 Inf | 104 | P |
| X69141_at | 12 | 2 | 20 | 20 | 17 0.60 | 2.35 | 0 | 0 6.0 | 104 | P |
| X76180_at | 8 | 1 | 20 | 20 | 18 0.40 | 1.39 | 0 | 08.0 | 104 | P |
| U91932_at | 9 | 1 | 20 | 20 | 17 0.45 | 1.82 | 0 | 0 9.0 | 103 | P |
| Z69720_at | 9 | 2 | 20 | 20 | 17 0.45 | 1.15 | 0 | 0 4.5 | 101 | P |
| U91930_at | 11 | 1 | 20 | 20 | 18 0.55 | 2.15 | 0 | 0 11.0 | 100 | P |
| V01512_rna1_at | 10 | 1 | 20 | 20 | 18 0.50 | 1.73 | 0 | 0 10.0 | 100 | P |

-continued

| Gene Name | Positive | Negative | Pairs | Pairs User Pairs | InAv Pos | Fracti Log Avg | PM Exces: MM | Exces Pos/Neg | Avg Diff | Abs Call |
|---|---|---|---|---|---|---|---|---|---|---|
| Z48042_at | 10 | 2 | 20 | 20 | 18 0.50 | 1.74 | 0 | 0 | 5.0 | 99 P |
| X75962_at | 8 | 1 | 20 | 20 | 18 0.40 | 1.50 | 0 | 0 | 8.0 | 98 P |
| X84740_at | 7 | 2 | 20 | 20 | 18 0.35 | 1.33 | 0 | 0 | 3.5 | 98 P |
| U79241_at | 10 | 3 | 20 | 20 | 17 0.50 | 2.01 | 0 | 0 | 3.3 | 97 P |
| X98411_at | 8 | 1 | 20 | 20 | 18 0.40 | 1.35 | 0 | 0 | 8.0 | 97 P |
| X79781_at | 11 | 0 | 20 | 20 | 18 0.55 | 1.58 | 0 | 0 | Inf | 96 P |
| U65932_at | 7 | 0 | 20 | 20 | 17 0.35 | 1.22 | 0 | 0 | Inf | 95 P |
| X75304_at | 7 | 0 | 20 | 20 | 18 0.35 | 1.21 | 0 | 0 | Inf | 95 P |
| Z37166_at | 10 | 1 | 20 | 20 | 17 0.50 | 1.32 | 0 | 0 | 10.0 | 95 P |
| X61123_at | 12 | 1 | 20 | 20 | 17 0.60 | 2.74 | 1 | 0 | 12.0 | 94 P |
| U90426_at | 9 | 0 | 20 | 20 | 18 0.45 | 1.96 | 1 | 0 | Inf | 93 P |
| X94754_at | 9 | 0 | 20 | 20 | 18 0.45 | 1.46 | 0 | 0 | Inf | 93 P |
| X99585_at | 9 | 2 | 20 | 20 | 18 0.45 | 1.19 | 0 | 0 | 4.5 | 93 P |
| X12791_at | 9 | 3 | 20 | 20 | 18 0.45 | 1.69 | 1 | 0 | 3.0 | 92 P |
| U86602_at | 8 | 2 | 20 | 20 | 18 0.40 | 1.23 | 0 | 0 | 4.0 | 91 P |
| Z47087_at | 12 | 1 | 20 | 20 | 17 0.60 | 1.95 | 0 | 0 | 12.0 | 89 P |
| U67963_at | 7 | 2 | 20 | 20 | 18 0.35 | 1.81 | 0 | 0 | 3.5 | 87 P |
| Z15114_at | 10 | 2 | 20 | 20 | 18 0.50 | 1.12 | 0 | 0 | 5.0 | 87 P |
| AFFX-HUMRGE/M10098_5_at | 10 | 1 | 20 | 20 | 17 0.50 | 2.34 | 1 | 0 | 10.0 | 85 P |
| X57522_at | 8 | 2 | 20 | 20 | 18 0.40 | 1.13 | 1 | 0 | 4.0 | 85 P |
| Y08915_at | 9 | 2 | 20 | 20 | 18 0.45 | 0.93 | 0 | 1 | 4.5 | 85 P |
| U88629_at | 9 | 2 | 20 | 20 | 17 0.45 | 1.88 | 0 | 0 | 4.5 | 84 P |
| X61100_rna1_at | 10 | 0 | 20 | 20 | 18 0.50 | 2.11 | 0 | 0 | Inf | 84 P |
| X91247_at | 10 | 2 | 20 | 20 | 18 0.50 | 1.59 | 0 | 0 | 5.0 | 84 P |
| Y07867_at | 9 | 3 | 20 | 20 | 18 0.45 | 1.70 | 0 | 0 | 3.0 | 84 P |
| X76538_at | 7 | 2 | 20 | 20 | 18 0.35 | 1.88 | 0 | 0 | 3.5 | 82 P |
| X82103_at | 10 | 1 | 20 | 20 | 18 0.50 | 1.66 | 0 | 0 | 10.0 | 82 P |
| U72514_at | 8 | 2 | 20 | 20 | 18 0.40 | 1.89 | 0 | 0 | 4.0 | 81 P |
| X82153_at | 13 | 1 | 20 | 20 | 18 0.65 | 2.46 | 0 | 0 | 13.0 | 81 P |
| X06614_at | 8 | 2 | 20 | 20 | 18 0.40 | 1.41 | 1 | 0 | 4.0 | 80 P |
| Z68747_at | 7 | 2 | 20 | 20 | 18 0.35 | 1.32 | 0 | 0 | 3.5 | 80 P |
| U72508_at | 7 | 0 | 20 | 20 | 18 0.35 | 1.06 | 0 | 0 | Inf | 79 P |
| X07024_at | 9 | 2 | 20 | 20 | 18 0.45 | 2.76 | 2 | 0 | 4.5 | 78 P |
| Y13115_at | 9 | 2 | 20 | 20 | 18 0.45 | 1.27 | 0 | 0 | 4.5 | 78 P |
| U69645_at | 7 | 2 | 20 | 20 | 18 0.35 | 1.57 | 1 | 0 | 3.5 | 76 P |
| X63469_at | 11 | 3 | 20 | 20 | 18 0.55 | 1.93 | 0 | 0 | 3.7 | 75 P |
| X76057_at | 8 | 1 | 20 | 20 | 18 0.40 | 0.98 | 0 | 0 | 8.0 | 75 P |
| Z29083_at | 7 | 1 | 20 | 20 | 17 0.35 | 1.39 | 0 | 0 | 7.0 | 73 P |
| X80497_at | 8 | 2 | 20 | 20 | 18 0.40 | 1.82 | 1 | 0 | 4.0 | 72 P |
| 122551_at | 7 | 2 | 20 | 20 | 18 0.45 | 1.99 | 0 | 0 | 4.5 | 72 P |
| U77643_at | 8 | 2 | 20 | 20 | 18 0.40 | 0.96 | 0 | 0 | 4.0 | 71 P |
| U90919_at | 13 | 3 | 20 | 20 | 18 0.65 | 2.64 | 3 | 1 | 4.3 | 71 P |
| X02530_at | 7 | 1 | 20 | 20 | 18 0.35 | 1.63 | 0 | 0 | 7.0 | 71 P |
| X05276_at | 11 | 3 | 20 | 20 | 18 0.55 | 1.54 | 1 | 0 | 3.7 | 71 P |
| X67155_at | 10 | 3 | 20 | 20 | 18 0.50 | 1.51 | 1 | 0 | 3.3 | 71 P |
| U83463_at | 11 | 1 | 20 | 20 | 17 0.55 | 2.14 | 1 | 0 | 11.0 | 69 P |
| Z70219_at | 7 | 1 | 20 | 20 | 18 0.35 | 1.77 | 0 | 0 | 7.0 | 69 P |
| X73079_at | 8 | 2 | 20 | 20 | 17 0.40 | 1.14 | 0 | 0 | 4.0 | 68 P |
| Z24725_at | 8 | 1 | 20 | 20 | 18 0.40 | 1.83 | 1 | 0 | 8.0 | 68 P |
| Z36531_at | 9 | 3 | 20 | 20 | 18 0.45 | 1.96 | 0 | 1 | 3.0 | 68 P |
| X84709_at | 10 | 1 | 20 | 20 | 18 0.50 | 1.50 | 0 | 0 | 10.0 | 67 P |
| U95740_ma2_at | 8 | 2 | 20 | 20 | 18 0.40 | 1.27 | 0 | 0 | 4.0 | 66 P |
| X80910_at | 9 | 2 | 20 | 20 | 18 0.45 | 2.08 | 1 | 0 | 4.5 | 66 P |
| U83461_at | 8 | 1 | 20 | 20 | 18 0.40 | 1.88 | 1 | 0 | 8.0 | 65 P |
| Y10506_at | 9 | 0 | 20 | 20 | 17 0.45 | 2.85 | 1 | 0 | Inf | 65 P |
| Z35491_at | 8 | 2 | 20 | 20 | 17 0.40 | 1.14 | 0 | 0 | 4.0 | 65 P |
| X81003_at | 9 | 0 | 20 | 20 | 18 0.45 | 1.85 | 1 | 0 | Inf | 64 P |
| X04297_at | 10 | 2 | 20 | 20 | 17 0.50 | 1.80 | 1 | 0 | 5.0 | 63 P |
| X63753_at | 9 | 1 | 20 | 20 | 17 0.45 | 1.90 | 1 | 0 | 9.0 | 63 P |
| U79274_at | 11 | 2 | 20 | 20 | 18 0.55 | 2.73 | 2 | 0 | 5.5 | 62 P |
| U96629_rna2_at | 8 | 2 | 20 | 20 | 17 0.40 | 1.49 | 1 | 0 | 4.0 | 61 P |
| X83368_at | 11 | 3 | 20 | 20 | 18 0.55 | 2.01 | 2 | 0 | 3.7 | 60 P |
| Z50853_at | 7 | 0 | 20 | 20 | 18 0.35 | 0.92 | 0 | 0 | Inf | 59 P |
| AFFX-M27830_5_at | 8 | 2 | 20 | 20 | 18 0.40 | 1.43 | 0 | 0 | 4.0 | 58 P |
| X83378_at | 9 | 3 | 20 | 20 | 18 0.45 | 1.76 | 1 | 0 | 3.0 | 58 P |
| U79265_at | 8 | 2 | 20 | 20 | 18 0.40 | 0.98 | 0 | 0 | 4.0 | 57 P |
| X02612_at | 9 | 3 | 20 | 20 | 18 0.45 | 1.57 | 1 | 0 | 3.0 | 57 P |
| X96586_at | 11 | 3 | 20 | 20 | 18 0.55 | 2.67 | 2 | 0 | 3.7 | 56 P |
| X98263_at | 7 | 1 | 20 | 20 | 17 0.35 | 1.32 | 1 | 0 | 7.0 | 56 P |
| U66469_at | 7 | 1 | 20 | 20 | 18 0.35 | 0.92 | 0 | 0 | 7.0 | 55 P |
| X54941_at | 8 | 0 | 20 | 20 | 18 0.40 | 1.03 | 0 | 0 | Inf | 55 P |
| U78313_at | 9 | 1 | 20 | 20 | 17 0.45 | 1.42 | 0 | 0 | 9.0 | 54 P |
| U90651_at | 9 | 1 | 20 | 20 | 18 0.45 | 1.70 | 1 | 1 | 9.0 | 54 P |
| X65873_at | 10 | 3 | 20 | 20 | 17 0.50 | 1.71 | 0 | 0 | 3.3 | 52 P |
| 000860_at | 9 | 2 | 20 | 20 | 18 0.45 | 1.05 | 0 | 0 | 4.5 | 52 P |
| X92098_at | 8 | 1 | 20 | 20 | 18 0.40 | 1.56 | 0 | 0 | 8.0 | 51 P |

-continued

| Gene Name | Positive | Negative | Pairs | Pairs User Pairs | InAv Pos | Fracti Log Avg | PM Exces: MM | Exces Pos/Neg | Avg Diff | Abs Call |
|---|---|---|---|---|---|---|---|---|---|---|
| X68742_at | 7 | 1 | 20 | 20 | 18 0.35 | 1.11 | 0 | 1 7.0 | 49 | P |
| X92396_at | 10 | 1 | 20 | 20 | 18 0.50 | 2.18 | 3 | 0 10.0 | 49 | P |
| X59841_at | 8 | 2 | 20 | 20 | 18 0.40 | 1.44 | 0 | 0 4.0 | 48 | P |
| X61118_rna1_at | 11 | 0 | 20 | 20 | 18 0.55 | 2.36 | 2 | 0 Inf | 48 | P |
| Y12711_at | 9 | 2 | 20 | 20 | 18 0.45 | 1.00 | 1 | 1 4.5 | 48 | P |
| X63679_at | 9 | 3 | 20 | 20 | 18 0.45 | 1.37 | 0 | 0 3.0 | 47 | P |
| X85372_at | 8 | 2 | 20 | 20 | 18 0.40 | 1.84 | 0 | 0 4.0 | 47 | P |
| X87212_at | 8 | 2 | 20 | 20 | 18 0.40 | 1.73 | 0 | 0 4.0 | 47 | P |
| X76732_at | 8 | 2 | 20 | 20 | 18 0.40 | 1.22 | 1 | 0 4.0 | 46 | P |
| U79242_at | 9 | 1 | 20 | 20 | 18 0.45 | 2.45 | 2 | 0 9.0 | 45 | P |
| U79273_at | 8 | 2 | 20 | 20 | 17 0.40 | 1.90 | 0 | 0 4.0 | 45 | P |
| X02596_at | 8 | 2 | 20 | 20 | 18 0.40 | 1.59 | 1 | 0 4.0 | 43 | P |
| X53586_rna1_at | 8 | 1 | 20 | 20 | 18 0.40 | 1.38 | 0 | 1 8.0 | 43 | P |
| U66669_at | 9 | 2 | 20 | 20 | 18 0.45 | 1.19 | 0 | 0 4.5 | 40 | P |
| U77129_at | 10 | 2 | 20 | 20 | 18 0.50 | 1.39 | 0 | 0 5.0 | 40 | P |
| X84194_at | 9 | 1 | 20 | 20 | 18 0.45 | 2.24 | 2 | 0 9.0 | 39 | P |
| Z24724_at | 9 | 1 | 20 | 20 | 18 0.45 | 1.48 | 0 | 0 9.0 | 38 | P |
| U73191_at | 8 | 1 | 20 | 20 | 17 0.40 | 0.99 | 0 | 1 8.0 | 37 | P |
| U89336_cds6_at | 9 | 2 | 20 | 20 | 18 0.45 | 0.93 | 0 | 0 4.5 | 36 | P |
| X55544_at | 8 | 1 | 20 | 20 | 18 0.40 | 1.33 | 0 | 0 8.0 | 36 | P |
| X82207_at | 7 | 1 | 20 | 20 | 18 0.35 | 1.25 | 1 | 0 7.0 | 36 | P |
| X96752_at | 9 | 2 | 20 | 20 | 18 0.45 | 1.39 | 1 | 0 4.5 | 36 | P |
| X97544_at | 9 | 0 | 20 | 20 | 18 0.45 | 2.38 | 2 | 0 Inf | 36 | P |
| Y07701_at | 8 | 0 | 20 | 20 | 18 0.40 | 1.16 | 0 | 0 Inf | 36 | P |
| 179299_at | 11 | 3 | 20 | 20 | 17 0.55 | 1.62 | 0 | 0 3.7 | 35 | P |
| U91327_at | 10 | 3 | 20 | 20 | 18 0.50 | 1.46 | 0 | 0 3.3 | 34 | P |
| X06290_at | 7 | 1 | 20 | 20 | 17 0.35 | 1.24 | 0 | 0 7.0 | 34 | P |
| V00571_rna1_at | 12 | 4 | 20 | 20 | 18 0.60 | 1.83 | 1 | 0 3.0 | 33 | P |
| X15949_et | 9 | 1 | 20 | 20 | 18 0.45 | 1.90 | 0 | 0 9.0 | 33 | P |
| X54925_at | 9 | 1 | 20 | 20 | 18 0.45 | 2.36 | 1 | 0 9.0 | 33 | P |
| X64229_at | 9 | 3 | 20 | 20 | 18 0.45 | 2.19 | 1 | 0 3.0 | 33 | P |
| U89355_at | 7 | 1 | 20 | 20 | 18 0.35 | 1.a0 | 2 | 0 7.0 | 27 | P |
| X67337_at | 10 | 2 | 20 | 20 | 18 0.50 | 2.52 | 2 | 0 5.0 | 25 | P |
| Y09615_at | 9 | 3 | 20 | 20 | 18 0.45 | 1.54 | 0 | 0 3.0 | 25 | P |
| U75679_at | 8 | 2 | 20 | 20 | 18 0.40 | 2.29 | 2 | 1 4.0 | 24 | P |
| X52011_at | 7 | 1 | 20 | 20 | 18 0.35 | 1.01 | 0 | 0 7.0 | 23 | P |
| Y08991_at | 9 | 2 | 20 | 20 | 18 0.45 | 2.10 | 3 | 0 3.5 | 22 | P |
| Z48511_at | 7 | 2 | 20 | 20 | 18 0.35 | 1.36 | 2 | 0 3.5 | 22 | P |

| Gene name | Pos Fracti | Log Avg | Pos/Neg | Avg Diff | Abs Call |
|---|---|---|---|---|---|
| hum_alu_at | 0.93 | 4.78 | Undef | 19333 | P |
| L04483_s_at | 1.00 | 6.39 | Undef | 11710 | P |
| M63438_s_at | 0.94 | 5.38 | Undef | 8316 | P |
| AFFX-CreX-3_at | 1.00 | 7.08 | Undef | 7387 | P |
| M14199_s_at | 1.00 | 6.11 | Undef | 7240 | P |
| M31520_rna1_s_at | 1.00 | 7.41 | Undef | 7095 | P |
| D13413_rna1_s_at | 0.94 | 5.13 | Undef | 6543 | P |
| J04617_s_at | 0.94 | 6.13 | Undef | 6479 | P |
| J00105_s_at | 1.00 | 8.49 | Undef | 6165 | P |
| HG2815-HT4023_s_at | 0.95 | 5.52 | Undef | 6034 | P |
| AFFX-CreX-5_at | 1.00 | 7.24 | Undef | 5719 | P |
| U06155_s_at | 0.86 | 5.26 | Undef | 5581 | P |
| HG1428-HT1428_s_at | 0.90 | 6.57 | Undef | 5284 | P |
| M10277_s_at | 0.90 | 5.39 | Undef | 5189 | P |
| X52426_s_at | 0.95 | 4.65 | Undef | 5075 | P |
| M25079_s_at | 0.75 | 3.56 | Undef | 4613 | P |
| HG2815-HT2931_at | 1.00 | 4.67 | Undef | 4370 | P |
| X57351_s_at | 1.00 | 6.06 | Undef | 4215 | P |
| AFFX-HSAC07/X00351_3_at | 0.95 | 4.92 | Undef | 4111 | P |
| U43901_rna1_s_at | 0.90 | 4.89 | Undef | 4088 | P |
| M36072_at | 0.75 | 3.70 | 15.0 | 3875 | P |
| AFFX-HUMGAPDH/ M33197_3_a | 0.95 | 5.10 | Undef | 3815 | P |
| V00594_s_at | 1.00 | 6.24 | Undef | 3716 | P |
| X69654_at | 0.95 | 6.24 | Undef | 3615 | P |
| S70143_rna1_s_at | 0.80 | 3.63 | Undef | 3097 | P |
| D7491824_s_ | 1.00 | 5.66 | Undef | 3076 | P |
| Z49148_s_at | 1.00 | 5.41 | Undef | 2957 | P |
| X17093_at | 0.60 | 2.80 | 4.0 | 2844 | P |
| S82297_at | 0.95 | 4.02 | Undef | 2759 | P |
| AFFX-BioDn-3_at | 0.75 | 3.55 | 15.0 | 2730 | P |
| U68105_s_at | 0.95 | 7.09 | 19.0 | 2839 | P |
| M34516_at | 1.00 | 3.14 | Undef | 2613 | P |

-continued

| Gene name | Pos Fracti | Log Avg | Pos/Neg | Avg Diff Abs Call |
|---|---|---|---|---|
| M55409_s_at | 0.85 | 5.66 | Undef | 2532 P |
| X98482_r_at | 0.33 | 1.36 | Undef | 2448 P |
| X03689_s_at | 1.00 | 6.82 | Undef | 2419 P |
| HG658-HT658_f_at | 0.73 | 3.32 | Undef | 2332 P |
| X01677_t | 0.85 | 4.02 | Undef | 2281 P |
| M26708_s_at | 1.00 | 5.58 | Undef | 2172 P |
| D32129_f_at | 0.95 | 5.02 | Undef | 1884 P |
| M14483_rna1_s_at | 0.80 | 4.11 | Undef | 1837 P |
| X51345_at | 0.75 | 4.45 | Undef | 1817 P |
| HG3991-HT4261_r_at | 0.45 | 2.24 | Undef | 1796 P |
| M34516_r_at | 0.91 | 4.72 | Undef | 1747 P |
| X00351_f_at | 0.90 | 5.53 | Undef | 1737 P |
| D86974_at | 0.85 | 3.82 | Undef | 1677 P |
| AFFX-HSAC07/X00351_M_at | 0.75 | 3.80 | Undef | 1620 P |
| HG3342-HT3519_s_at | 0.89 | 5.01 | Undef | 1617 P |
| M55998_s_at | 0.65 | 5.62 | Undef | 1610 P |
| HG3431-HT3616_s_at | 0.85 | 6.16 | 17.0 | 1529 P |
| HG417-HT417_s_at | 0.90 | 5.16 | Undef | 1481 P |
| HG2147-HT2217_at | 0.83 | 1.76 | 5.0 | 1428 P |
| M33600_f_at | 0.80 | 3.73 | Undef | 1395 P |
| X99133_at | 0.60 | 2.86 | 12.0 | 1351 P |
| U57341_r_at | 1.00 | 4.39 | Undef | 1344 P |
| S54005_s_at | 0.80 | 4.83 | Undef | 1309 P |
| J04152_rna1_s_at | 0.90 | 5.26 | 18.0 | 1291 P |
| M13560_s_at | 0.80 | 4.20 | 16.0 | 1286 P |
| M24485_s_at | 0.65 | 3.17 | Undef | 1234 P |
| HG3597-HT3800_f_at | 0.80 | 4.54 | 16.0 | 1148 P |
| M12125_at | 0.65 | 3.02 | 13.0 | 1144 P |
| J03801_f_at | 0.90 | 5.19 | Undef | 1137 P |
| HG1980-HT2023_at | 0.45 | 2.42 | Undef | 1132 P |
| M87789_s_at | 0.75 | 2.57 | 15.0 | 1078 P |
| X04347_s_at | 0.90 | 5.03 | Undef | 1078 P |
| X14008_rna1_f_at | 0.75 | 4.95 | 15.0 | 1072 P |
| S75256_s_at | 0.80 | 3.92 | 16.0 | 1069 P |
| M94880_f_at | 0.50 | 2.24 | Undef | 1061 P |
| M19311_s_at | 0.81 | 5.08 | 13.0 | 1040 P |
| HG1S15-HT1515_f_at | 0.75 | 4.64 | 15.0 | 1005 P |
| AFFX-HSAC07_X00351_5_at | 0.80 | 3.09 | 16.0 | 958 P |
| J03077_s_at | 0.65 | 3.77 | 13.0 | 925 P |
| X12671_rna1_at | 0.90 | 4.19 | Undef | 917 P |
| M14328_s_at | 0.75 | 3.54 | 7.5 | 885 P |
| X74929_s_at | 0.65 | 2.81 | Undef | 869 P |
| L11672_at | 0.50 | 2.21 | Undef | 855 P |
| U05861_at | 0.70 | 3.82 | 14.0 | 850 P |
| 6730_s_at | 0.85 | 4.45 | 8.5 | 838 P |
| 2M29554_s_at | 0.78 | 4.15 | 14.0 | 827 P |
| AFFX-HUMGAPDH/ M33197_M_i | 0.60 | 2.75 | 6.0 | 802 P |
| M19045_f_at | 0.75 | 5.50 | 15.0 | 794 P |
| AFFX-HSAC07/X00351_3_st | 0.75 | 3.50 | Undef | 779 P |
| HG2815-HT2931_s_at | 0.93 | 4.96 | Undef | 767 P |
| U70439_s_at | 0.75 | 4.30 | Undef | 766 P |
| X56681_s_at | 0.65 | 2.68 | 6.5 | 766 P |
| Z48501_s_at | 0.74 | 3.63 | Undef | 748 P |
| X12876_s_at | 0.70 | 4.75 | 14.0 | 745 P |
| HG3576-HT3779_f_at | 0.65 | 2.88 | 6.5 | 734 P |
| Z69043_s_at | 0.70 | 3.45 | 7.0 | 722 P |
| HG2915-HT3059_f_at | 0.65 | 2.34 | Undef | 720 P |
| M11313_s_at | 0.65 | 3.19 | 13.0 | 717 P |
| M26311_s_at | 0.63 | 2.85 | 12.0 | 686 P |
| AFFX-BioDn-5_at | 0.80 | 3.30 | 16.0 | 653 P |
| HG2917-HT3061_f_at | 0.60 | 2.11 | Undef | 663 P |
| U04241_at | 0.45 | 2.22 | 9.0 | 659 P |
| D17793_at | 0.70 | 4.00 | 14.0 | 650 P |
| M62403_s_at | 0.65 | 2.40 | Undef | 648 P |
| HG3236-HT3413_f_at | 0.50 | 2.18 | 10.0 | 635 P |
| L33075_at | 0.55 | 2.57 | Undef | 634 P |
| X57809_s_at | 0.58 | 2.03 | Undef | 629 P |
| Z49107_s_at | 0.45 | 1.28 | 4.5 | 623 P |
| AFFX-HUMGAPDH/ M33197_5_a | 0.75 | 4.14 | 15.0 | 622 P |
| U48705_rna1_s_at | 0.55 | 2.63 | 3.7 | 610 P |
| X03068_f_at | 0.60 | 2.29 | 24.0 | 606 P |
| L02326_f_at | 0.55 | 2.32 | 3.7 | 566 P |
| AJ000099_s_at | 0.45 | 2.08 | 9.0 | 546 P |
| M21142_cds2_s_at | 0.65 | 2.18 | 3.3 | 546 P |
| Z15115_at | 0.80 | 3.51 | Undef | 543 P |
| X56841_at | 0.50 | 213 | 10.0 | 540 P |

-continued

| Gene name | Pos Fracti | Log Avg | Pos/Neg | Avg Diff Abs Call |
|---|---|---|---|---|
| AFFX-BioC-5_at | 0.65 | 2.87 | 6.5 | 537 P |
| L09209_s_at | 0.65 | 3.77 | Undef | 537 P |
| HG4264-HT4534_s_at | 0.78 | 4.39 | Undef | 530 P |
| V00599_s_at | 0.55 | 2.24 | 5.5 | 528 P |
| X04654_s_at | 0.60 | 2.30 | 4.0 | 488 P |
| L40397_at | 0.70 | 2.78 | 14.0 | 487 P |
| M96995_s_at | 0.40 | 1.58 | 4.0 | 470 P |
| AFFX-BioC-3_at | 0.60 | 2.22 | 6.0 | 459 P |
| M83667_rna1_s_at | 0.75 | 3.14 | 15.0 | 444 P |
| _00749_s_at | 0.47 | 1.30 | 4.5 | 438 P |
| U88898_r_at | 0.36 | 1.59 | Undef | 422 P |
| HG1322-HT5143_s_at | 0.70 | 3.87 | 14.0 | 415 P |
| U72649_at | 0.65 | 2.87 | 13.0 | 412 P |
| U00947_s_at | 0.85 | 4.51 | Undef | 403 P |
| M16336_s_at | 0.55 | 2.18 | 5.5 | 401 P |
| X_4470_s_at | 0.37 | 2.25 | Undef | 396 P |
| M65292_s_at | 0.65 | 2.96 | Undef | 394 P |
| HG688-HT688_f_at | 0.60 | 2.11 | 12.0 | 390 P |
| HG371-HT26388_s_at | 0.54 | 2.30 | 7.0 | 380 P |
| 6342_at | 0.55 | 2.08 | Undef | 374 P |
| M518072_at | 0.50 | 2.90 | Undef | 373 P |
| X57351_at | 0.50 | 2.13 | 4.0 | 369 P |
| M69013_at | 0.60 | 2.79 | 12.0 | 368 P |
| 226491_s_at | 0.75 | 3.48 | 7.5 | 361 P |
| M30448_s_at | 0.55 | 2.08 | 5.5 | 357 P |
| L49380_at | 0.45 | 1.37 | 4.5 | 354 P |
| U90552_s_at | 0.58 | 3.90 | Undef | 347 P |
| HG3076-HT3238_s_at | 0.60 | 2.99 | 12.0 | 346 P |
| X85116_rna1_s_at | 0.55 | 2.08 | 3.7 | 331 P |
| 017408_s_at | 0.50 | 2.31 | 10.0 | 325 P |
| J02871_s_at | 0.60 | 2.46 | 6.0 | 319 P |
| M57466_s_at | 0.50 | 2.81 | Undef | 312 P |
| K02405_f_at | 0.35 | 1.30 | 7.0 | 309 P |
| M23323_s_at | 0.55 | 1.87 | 11.0 | 309 P |
| L33930_s_at | 0.50 | 1.68 | Undef | 307 P |
| X04526_at | 0.55 | 2.22 | Undef | 305 P |
| Z35402_rna1_s_at | 0.70 | 3.12 | 14.0 | 305 P |
| Y00264_at | 0.65 | 3.15 | 13.0 | 302 P |
| L00389_f_at | 0.50 | 1.73 | Undef | 301 P |
| M12959_s_at | 0.35 | 2.34 | Undef | 295 P |
| X15729_s_at | 0.70 | 3.92 | 7.0 | 295 P |
| 078577_s_at | 0.60 | 2.40 | 4.0 | 291 P |
| M16276_at | 0.50 | 1.87 | Undef | 285 P |
| J05582_s_at | 0.50 | 1.55 | Undef | 283 P |
| U08021_at | 0.50 | 1.84 | 10.0 | 275 P |
| M97935_s_at | 0.60 | 2.49 | 4.0 | 273 P |
| 079206_s_at | 0.40 | 1.26 | Undef | 270 P |
| X01703_at | 0.65 | 2.91 | Undef | 267 P |
| J04093_s_at | 0.70 | 4.37 | Undef | 265 P |
| X17567_s_at | 0.45 | 1.85 | 3.0 | 261 P |
| HG4535-HT4940_s_at | 0.35 | 1.29 | 7.0 | 259 P |
| L24774_s_at | 0.45 | 1.63 | 4.5 | 259 P |
| M58525_s_at | 0.40 | 1.38 | 8.0 | 259 P |
| X14684_s_at | 0.50 | 1.79 | 5.0 | 258 P |
| M37457_at | 0.50 | 1.93 | Undef | 257 P |
| U49835_s_at | 0.60 | 2.17 | Undef | 257 P |
| X94563_xp2_r_at | 0.33 | 1.35 | Undef | 255 P |
| M13690_s_at | 0.50 | 2.07 | Undef | 252 P |
| S40719_s_at | 0.50 | 1.63 | 3.3 | 251 P |
| X05130_s_at | 0.58 | 1.95 | 11.0 | 247 P |
| U50079_s_at | 0.60 | 2.55 | 3.0 | 243 P |
| AC002045_xpt2_s_at | 0.55 | 2.10 | 11.0 | 231 P |
| M10942_at | 0.45 | 2.13 | 3.0 | 228 P |
| 042040_s_at | 0.40 | 1.08 | 4.0 | 224 P |
| L76517_at | 0.35 | 1.27 | 7.0 | 221 P |
| U32986_s_at | 0.40 | 1.48 | 8.0 | 218 P |
| X52979_rna1_s_at | 0.55 | 2.08 | 11.0 | 218 P |
| X53296_s_at | 0.55 | 2.54 | 5.5 | 217 P |
| X90846_at | 0.60 | 1.90 | Undef | 214 P |
| AFFX-HUMISGF3A/M97935_3_a | 0.65 | 3.14 | Undef | 209 P |
| L05187_at | 0.45 | 1.97 | 9.0 | 209 P |
| X65965_s_at | 0.67 | 2.90 | Undef | 209 P |
| S50017_s_at | 0.55 | 2.17 | 5.5 | 208 P |
| X72727_at | 0.55 | 1.95 | Undef | 204 P |
| X74874_rna1_s_at | 0.45 | 2.13 | 9.0 | 203 P |
| J03805_s_at | 0.50 | 3.17 | 9.0 | 202 P |
| X55037_s_at | 0.55 | 1.49 | 3.7 | 201 P |

-continued

| Gene name | Pos Fracti | Log Avg | Pos/Neg | Avg Diff Abs Call | |
|---|---|---|---|---|---|
| HG4541-HT4946_s_at | 0.61 | 1.85 | 3.7 | 197 | P |
| U79528_s_at | 0.50 | 1.17 | Undef | 195 | P |
| Z49835_s_at | 0.50 | 3.00 | 5.0 | 195 | P |
| U83598_at | 0.50 | 1.64 | Undef | 191 | P |
| L22524_s_at | 0.50 | 2.89 | 9.0 | 190 | P |
| M93651_at | 0.60 | 2.33 | Undef | 190 | P |
| U36341_rna1_at | 0.35 | 1.33 | 3.5 | 188 | P |
| M19267_s_at | 0.63 | 2.37 | 6.0 | 186 | P |
| U07806_s_at | 0.55 | 2.51 | 3.7 | 185 | P |
| M34996_s_at | 0.60 | 2.17 | 12.0 | 184 | P |
| X77588_s_at | 0.50 | 1.90 | 3.3 | 184 | P |
| L12711_s_at | 0.47 | 1.69 | 4.5 | 181 | P |
| S82447_s_at | 0.35 | 1.11 | 7.0 | 180 | P |
| U09587_at | 0.65 | 2.63 | 6.5 | 178 | P |
| S69272_s_at | 0.45 | 1.49 | 3.0 | 177 | p |
| X62083_s_at | 0.50 | 1.18 | 5.0 | 177 | P |
| J03242_s_at | 0.35 | 1.56 | 7.0 | 172 | P |
| AB006781_s_at | 0.35 | 1.23 | Undef | 171 | P |
| L42583_f_at | 0.50 | 1.38 | Undef | 169 | P |
| X98296_at | 0.35 | 0.96 | 7.0 | 169 | P |
| U28014_at | 0.60 | 3.02 | Undef | 168 | P |
| S80437_s_at | 0.45 | 1.55 | 9.0 | 166 | P |
| S82597_rna1_s_at | 0.50 | 1.67 | 10.0 | 166 | P |
| U16799_s_at | 0.60 | 2.36 | 4.0 | 163 | P |
| X57152_rna1_s_at | 0.45 | 1.57 | 4.5 | 160 | P |
| X07438_s_at | 0.63 | 3.50 | Undef | 159 | P |
| AFFX-HUMRGE/M10098_5_at | 0.55 | 2.14 | 5.5 | 158 | P |
| D00408_s_at | 0.45 | 1.41 | Undef | 156 | P |
| M28213_s_at | 0.65 | 1.93 | 6.5 | 156 | P |
| M92843_s_at | 0.45 | 1.62 | 9.0 | 154 | P |
| Z11899_s_at | 0.40 | 1.32 | 4.0 | 154 | P |
| X73358_s_at | 0.47 | 1.25 | 4.5 | 153 | P |
| U77846_rna1_s_at | 0.40 | 1.93 | 4.0 | 151 | P |
| X05855_s_at | 0.53 | 2.84 | 8.0 | 143 | P |
| M27394_s_at | 0.45 | 1.60 | 4.5 | 142 | P |
| U61734_s_at | 0.47 | 1.40 | 3.0 | 140 | P |
| Z25521_s_at | 0.40 | 1.23 | 4.0 | 140 | P |
| X83416_s_at | 0.55 | 2.60 | 5.5 | 139 | P |
| X52022_at | 0.45 | 2.00 | Undef | 138 | P |
| U22431_s_at | 0.50 | 2.19 | 5.0 | 135 | P |
| HG2090-HT2152_s_at | 0.42 | 1.54 | 8.0 | 132 | P |
| L14778_s_at | 0.58 | 2.72 | Undef | 132 | P |
| D83174_s_at | 0.40 | 1.41 | Undef | 131 | P |
| M13829_s_at | 0.45 | 1.75 | 3.0 | 131 | P |
| U41654_at | 0.60 | 1.95 | 12.0 | 129 | P |
| U61397_s_at | 0.45 | 1.61 | 9.0 | 129 | P |
| M20867_s_at | 0.53 | 2.56 | Undef | 127 | P |
| Y00787_s_at | 0.55 | 2.37 | 11.0 | 127 | P |
| Y00451_s_at | 0.45 | 1.77 | 4.5 | 125 | P |
| L15189_s_at | 0.50 | 2.51 | 5.0 | 124 | P |
| X06700_s_at | 0.50 | 1.59 | 3.3 | 124 | P |
| HG2743-HT2846_s_at | 0.40 | 0.91 | 8.0 | 123 | P |
| Y00097_s_at | 0.50 | 1.46 | 3.3 | 123 | P |
| D83260_s_at | 0.47 | 1.60 | 4.5 | 121 | P |
| HG4334-HT4604_s_at | 0.35 | 1.16 | 7.0 | 120 | P |
| Z47055_s_at | 0.35 | 1.65 | 3.5 | 120 | P |
| X02761_s_at | 0.55 | 1.65 | 5.5 | 119 | P |
| X89399_s_at | 0.45 | 0.97 | 4.5 | 118 | P |
| D78132_s_at | 0.60 | 1.92 | 3.0 | 117 | P |
| D28473_s_at | 0.70 | 2.95 | 7.0 | 115 | P |
| S57212_s_at | 0.40 | 1335 | 8.0 | 115 | P |
| HG4557-HT4962_r_at | 0.80 | 1.92 | Undef | 114 | P |
| U61276_s_at | 0.50 | 2.19 | 10.0 | 114 | P |
| U60061_at | 0.60 | 2.43 | 12.0 | 113 | P |
| J04130_s_at | 0.50 | 1.66 | 3.3 | 110 | p |
| M63838_s_at | 0.45 | 2.03 | 9.0 | 110 | P |
| S79219_s_at | 0.55 | 1.48 | 5.5 | 109 | P |
| U58046_s_at | 0.45 | 2.81 | 9.0 | 109 | P |
| X03363_s_at | 0.35 | 1.58 | 3.5 | 109 | P |
| X76942_s_at | 0.60 | 2.40 | 6.0 | 109 | P |
| HG3925-HT4195_at | 0.40 | 1.45 | Undef | 106 | P |
| M61832_s_at | 0.40 | 1.11 | 8.0 | 106 | P |
| U80226_s_at | 0.40 | 1.85 | 4.0 | 103 | P |
| X72889_at | 0.35 | 1.53 | Undef | 103 | P |
| HG3484-HT3678_s_at | 0.45 | 1.66 | Undef | 99 | P |
| D49372_s_at | 0.35 | 1.28 | 7.0 | 97 | P |
| AFFX-M27830_5_at | 0.40 | 1.18 | Undef | 95 | P |

-continued

| Gene name | Pos Fracti | Log Avg | Pos/Neg | Avg Diff Abs Call |
|---|---|---|---|---|
| S68805_at | 0.50 | 1.96 | Undef | 95 P |
| M14745_at | 0.50 | 1.09 | 10.0 | 94 P |
| U06155_at | 0.50 | 1.18 | Undef | 94 P |
| Z35085_s_at | 0.42 | 2.60 | 4.0 | 93 P |
| U44799_s_at | 0.40 | 1.60 | 4.0 | 92 P |
| X62534_s_at | 0.60 | 2.49 | 4.0 | 92 P |
| M33684_s_at | 0.35 | 1.42 | 3.5 | 91 P |
| U73936_at | 0.45 | 1.01 | Undef | 90 P |
| X85137_s_at | 0.40 | 1.80 | 8.0 | 90 P |
| HG1400-HT1400_s_at | 0.50 | 2.62 | 10.0 | 89 P |
| X90530_at | 0.55 | 2.41 | 3.7 | 88 P |
| X92368_at | 0.55 | 2.41 | 5.5 | 88 P |
| D26535_s_at | 0.45 | 1.84 | 4.5 | 87 P |
| HG4593-HT4998_at | 0.50 | 1.39 | 3.3 | 86 P |
| U41740_at | 0.45 | 2.35 | 9.0 | 86 P |
| X12530_s_at | 0.42 | 1.23 | Undef | 86 P |
| AFFX-HUMRGE/M10098_M_at | 0.45 | 1.35 | 4.5 | 85 P |
| 6424_at | 0.45 | 2.48 | Undef | 84 P |
| X527809_at | 0.50 | 1.27 | 4.0 | 84 P |
| HG210-H1210_s_at | 0.60 | 2.00 | 6.0 | 83 P |
| HG2981-HT3125_s_at | 0.50 | 1.51 | 5.0 | 82 P |
| U30827_s_at | 0.50 | 1.22 | 5.0 | 82 P |
| M34715_at | 0.45 | 1.39 | Undef | 80 P |
| 089377_s_at | 0.38 | 0.97 | Undef | 76 P |
| L12760_s_at | 0.42 | 1.78 | 8.0 | 75 P |
| M24069_at | 0.45 | 2.05 | 3.0 | 75 P |
| L43579_s_at | 0.40 | 1.48 | 3.0 | 74 P |
| U01691_s_at | 0.35 | 1.37 | Undef | 74 P |
| L00634_s_at | 0.53 | 2.30 | 3.3 | 71 P |
| U19495_s_at | 0.65 | 2.98 | 4.3 | 71 P |
| HG2148-HT2218_f_at | 0.35 | 1.33 | 3.5 | 70 P |
| L25931_s_at | 0.55 | 1.98 | 11.0 | 69 P |
| U20536_s_at | 0.45 | 1.79 | Undef | 69 P |
| U77846_rna1_at | 0.40 | 1.34 | Undef | 68 P |
| U19147_s_at | 0.55 | 3.75 | 11.0 | 66 P |
| L18877_f_at | 0.35 | 1.26 | Undef | 64 P |
| M90356_f_at | 0.40 | 0.92 | 4.0 | 63 P |
| D00003_s_at | 0.42 | 1.46 | Undef | 62 P |
| AF012024_s_at | 0.40 | 1.35 | 4.0 | 60 P |
| M16652_at | 0.50 | 1.24 | Undef | 58 P |
| U09279_at | 0.40 | 2.24 | 8.0 | 58 P |
| L78833_cds1_at | 0.40 | 1.22 | 8.0 | 57 P |
| M24736_s_at | 0.45 | 2.83 | Undef | 57 P |
| D63861_s_at | 0.65 | 3.10 | 4.3 | 56 P |
| U261 73_s_at | 0.40 | 0.93 | 4.0 | 55 p |
| U33632_at | 0.40 | 1.11 | 4.0 | 53 P |
| X70944_s_at | 0.40 | 1.97 | 4.0 | 53 P |
| X03350_at | 0.45 | 0.99 | 9.0 | 52 P |
| U20938_at | 0.45 | 1.36 | 3.0 | 50 P |
| X81625_at | 0.45 | 1.93 | 4.5 | 48 P |
| HG36-HT4101_s_at | 0.33 | 1.47 | 3.0 | 47 p |
| U47077_at | 0.40 | 1.22 | Undef | 47 P |
| X59244_f_at | 0.35 | 1.32 | 3.5 | 47 p |
| X92493_s_at | 0.45 | 2.05 | 3.0 | 47 P |
| U49020_cds2_s_at | 0.35 | 1.59 | 3.5 | 46 P |
| U72936_s_at | 0.35 | 1.32 | 7.0 | 45 P |
| M14758_at | 0.35 | 1.45 | 3.5 | 42 P |
| S76853_s_at | 0.45 | 1.56 | 4.5 | 42 P |
| M27093_s_at | 0.50 | 1.42 | Undef | 40 P |
| M64752_at | 0.45 | 1.07 | 4.5 | 38 P |
| X83490_s_at | 0.35 | 1.38 | 3.5 | 38 P |
| D28235_s_at | 0.40 | 1.37 | 8.0 | 37 P |
| X62429_s_at | 0.45 | 1.66 | 3.0 | 36 P |
| X67235_s_at | 0.44 | 1.44 | 4.0 | 35 P |
| X95632_s_at | 0.45 | 1.86 | 9.0 | 35 P |
| M27436_s_at | 0.45 | 1.65 | 4.5 | 32 P |
| J00219_s_at | 0.40 | 1.18 | 8.0 | 31 P |
| M26665_at | 0.50 | 1.48 | 3.0 | 27 P |
| U09716_s_at | 0.35 | 1.84 | 3.5 | 25 P |
| X91196_s_at | 0.35 | 0.95 | 7.0 | 22 P |

TABLE 8

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| A28102_at | Human GABAa receptor alpha-3 subunit. | 351 | 117 | 167 | 170 | 270 | 180 |
| AB000114_at | Human mRNA for "osteomodulin," complete cds | 184 | 62 | 81 | 37 | 42 | 51 |
| AB000115_at | Human "mRNA," complete cds | 183 | 106 | 44 | 20 | 75 | 92 |
| AB000220_at | Human mRNA for semaphorin "E," complete cds | 165 | 78 | 83 | 180 | 105 | 20 |
| AB000381_s_at | Human DNA for GPI-anchored motecule-like "protein," complete cds | 42 | 29 | 37 | 28 | 168 | 26 |
| AB000409_at | Human mRNA for "MNK1," complete cds | 37 | 70 | 20 | 97 | 235 | 58 |
| AB000410_s_at | Human hOGG1 "mRNA," complete cds | 20 | 20 | 20 | 20 | 20 | 20 |
| AB000449_at | Human mRNA for "VRK1," complete cds | 113 | 26 | 67 | 20 | 68 | 20 |
| AB000450_at | Human mRNA for "VRK2," complete cds | 95 | 65 | 53 | 97 | 20 | 82 |
| AB000460_at | Human "mRNA," done "RES4-22B," complete cds | 410 | 289 | 643 | 404 | 658 | 389 |
| AB000462_at | Human mRNA for SH3 binding "protein," clone "RES4-23A," complete cds | 88 | 106 | 20 | 79 | 213 | 24 |
| AB000464_at | Human "mRNA," done "RES4-24A," exon "1," "2," "3," 4 | 223 | 173 | 159 | 180 | 294 | 250 |
| AB000466_at | Human "mRNA," done "RES4-24C," exon "1," "2," 3 | 20 | 20 | 20 | 20 | 20 | 20 |
| AB000467_at | Human "mRNA," done "RES4-25," partial cds | 20 | 20 | 20 | 20 | 20 | 20 |
| AB000468_at | Human mRNA for zinc finger "protein," clone "RES4-26," complete cds | 134 | 99 | 164 | 138 | 266 | 43 |
| AB000584_at | Human mRNA for TGF-beta superfamily "protein," complete cds | 214 | 286 | 1029 | 838 | 448 | 249 |
| AB000816_at | Human "mRNA," done "BMAL1d," partial cds. /gb=AB000816 /ntype=RNA | 25 | 20 | 20 | 20 | 20 | 20 |
| AB000895_at | Homo sapiens mRNA for cadherin "FIB1," partial cds. /gb=AB000895 /ntype=RNA | 20 | 20 | 20 | 20 | 20 | 20 |
| AB000896_at | Homo sapiens mRNA for cadherin "FIB2," partial cds. /gb=AB000896 /ntype=RNA | 86 | 20 | 27 | 65 | 72 | 20 |
| AB000897_at | Homo sapiens mRNA for cadherin "FIB3," partial cds. /gb=AB000897 /ntype=RNA | 98 | 26 | 20 | 20 | 68 | 20 |
| AB000905_at | Human DNA for H4 "histone," complete cds | 55 | 24 | 20 | 20 | 20 | 59 |
| AB001106_at | Human mRNA for glia maturation "factor," complete cds | 20 | 66 | 62 | 20 | 20 | 103 |
| AB001325_at | Human AQP3 gene for aquaporine 3 (water "channel")," partail cds | 621 | 200 | 654 | 532 | 277 | 289 |
| AB902314_at | Human mRNA for KIAA0316 "gene," complete cds. /gb=AB002314 /ntype=RNA | 24 | 20 | 20 | 81 | 44 | 20 |
| AB902315_at | Human mRNA for KIAA0327 "gene," complete cds. /gb=AB002315 /intype=RNA | 259 | 131 | 241 | 57 | 133 | 112 |
| AB002318_at | Human mRNA for KIAA0320 "gene," partiat cds. /gb=AB002318 /ntype=RNA | 251 | 97 | 158 | 111 | 180 | 20 |
| AB002332_at | Human mRNA for KIAA0334 "gene," complet cds. /gb=AB002332 /ntype=RNA | 27 | 20 | 20 | 20 | 45 | 59 |
| AB002356_s_at | Human mRNA for KIAA0358 "gene," complet cds. /gb=AB002356 /ntype=RNA | 43 | 172 | 256 | 148 | 171 | 98 |
| AB002365_at | Human mRNA for KIAA0367 "gene," partial cds. /gb=AB002365 /ntype=RNA | 50 | 35 | 20 | 20 | 20 | 44 |
| AB002366_at | Human mRNA for KIAA0368 "gene," partial cds. /gb=AB002366 /ntype=RNA | 20 | 20 | 21 | 20 | 43 | 52 |
| AB002380_at | Human mRNA for KIAA0382 "gene," partial cds. /gb=AB002380 /ntype=RNA | 67 | 20 | 156 | 73 | 20 | 24 |
| AB002382_at | Human mRNA for KIAA0384 "gene," complete cds. /gb=AB002382 /ntype=RNA | 302 | 145 | 382 | 289 | 272 | 228 |
| AB002409_at | Homo sapiens mRNA for "SLC," complete cds. /gb=AB002409 /ntype=RNA | 37 | 58 | 20 | 20 | 39 | 69 |
| AB002533_at | Human mRNA for "Qip1," complete cds | 2063 | 4012 | 2243 | 2109 | 1832 | 2435 |
| AB002559_at | Human mRNA for "hunc18b2," complete cds | 360 | 209 | 249 | 433 | 592 | 582 |
| AB003102_at | Human mRNA for proteasome subunit "p44.5," complete cds | 114 | 87 | 121 | 141 | 357 | 264 |
| AB003103_at | Human mRNA for proteasome subunit "p55," complete cds | 43 | 20 | 48 | 20 | 20 | 20 |
| AB093177_at | Human mRNA for proteasome subunit "p27," complete cds | 109 | 67 | 89 | 95 | 149 | 127 |
| AB003698_at | Human mRNA for Cdc7-related "kinase," complete cds | 38 | 20 | 20 | 60 | 31 | 20 |
| AB004884_at | Human mRNA for "PKU-alpha," partial cds. /gb=AB004884 /ntype=RNA | 125 | 98 | 73 | 57 | 100 | 60 |
| AB005535_s_at | Homo sapiens mRNA for "Clock," partial cds. /gb=AB005535 /ntype=RNA | 20 | 20 | 20 | 20 | 20 | 20 |
| AB006190_at | Homo sapiens mRNA for aquaporin "6," complete cds. /gb=AB006190 /ntype=RNA | 222 | 138 | 240 | 209 | 489 | 341 |
| AB006781_s_at | Homo sapiena mRNA for galectin-4," complete cds. /gb=AB006781 /ntype=RNA | 20 | 171 | 317 | 121 | 820 | 160 |
| AB006782_at | Homo sapiens mRNA for galectin-9 "isoform," comptete cds. /gb=AB006782 /ntype=RNA | 137 | 307 | 280 | 158 | 497 | 589 |
| AC000061_cds2_at | Human BAC done 133K23 from 7q31.2, complete sequence. | 23 | 29 | 22 | 20 | 194 | 48 |
| AC000061_cds3_at | Human BAC done 133K23 from 7q31.2, complete sequence. | 23 | 20 | 20 | 20 | 20 | 20 |

TABLE 8-continued

Expressed RNA in Suburothelial connective tissue, Normal urothelium and Transitional cell carcinomas.

| Gene name | Description | Connect. Tiss. | Norm. uroth. | Ta GrI | TaGrII | T2GrIII | T2GrIV |
|---|---|---|---|---|---|---|---|
| AC000062_at | Human PAC clone 2G3A from 13q12–13q13 | 28 | 20 | 20 | 20 | 20 | 20 |
| AC000063_s_at | Human cosmid clone LUCA19 from 3p21.3 | 20 | 20 | 20 | 30 | 709 | 119 |
| AC000064_cds1_at | Human BAC clone RG083M05 from 7q21–7q22, complete sequence. | 73 | 51 | 176 | 92 | 49 | 114 |
| AC000964_cds2_at | Human BAC clone RG083M05 frcm 7q21–7q22, complete sequence. | 31 | 60 | 20 | 40 | 28 | 108 |
| AC000066_at | Human BAC clone RG293F11 from 7q21–7q22 | 40 | 34 | 20 | 20 | 20 | 62 |
| AC000099_at | Cosmid g0771a003 | 128 | 99 | 225 | 146 | 391 | 114 |
| AC000115_cds1_at | Human BAC clone GS188P18, complete sequence. | 20 | 20 | 227 | 41 | 125 | 20 |
| AC002045_xpt1_at | Homo sapiens Chromosome 16 BAC done CIT987-SKA-589H1 ~complete genomic sequence, complete sequence. | 69 | 128 | 137 | 46 | 251 | 71 |
| AC002045_xpt2_s_at | A-589H1.2 from Homo sapiens Chromosome 16 BAC clone CIT987-SKA-589H1 ~complete genomic "sequence," complete sequence. /g | 113 | 231 | 1092 | 469 | 1057 | 470 |
| AC002073_cds1_at | Human PAC done DJ515N1 from 22q11.2–q22, complete sequence. | 114 | 53 | 231 | 42 | 20 | 20 |
| AC002076_cds2_at | WUGSC:GS345D13.2 gene (G-protein gamma-1 subunit) extracted from Human BAC clone GS34SD13 from 7q31–q32 | 20 | 20 | 20 | 20 | 20 | 20 |
| AC002077_at | Human cosmid clone LUCA17 from 3p21.3 | 57 | 20 | 20 | 20 | 162 | 167 |
| AC002086_at | Human PAC clone DJ525N14 trorn Xq23 | 20 | 20 | 20 | 20 | 173 | 20 |
| AC002115_cds1_at | Human DNA from overlapping chromosome 19 cosmids R31396, F25451, and R31076 containing COX6B and UPKA, genomicsequence | 941 | 1456 | 953 | 790 | 1094 | 850 |
| AC002115_cds3_at | Human DNA from overlapping chromosome 19 cosmids R31396, F25451, and R31076 containing COX6B and UPKA, genomic sequence | 111 | 75 | 197 | 103 | 62 | 156 |
| AC002115_cds4_at | Human DNA from overlapping chromosome 19 cosmids R31396, F25451, and R31076 containing COX6B and UPKA, genomic sequence | 140 | 1382 | 453 | 1553 | 269 | 259 |
| AC002115_ms2_at | Human DNA from overlapping chromosome 19 cosmids R31396, F25451, and R31076 containing COX6B and UPKA, genomic sequence | 170 | 130 | 69 | 114 | 291 | 134 |
| AC002450_at | Human BAC clone GS244B22 from "7q21–q22," complete sequence. /gb=AC002450 /ntype=DNA /annot=CDS | 20 | 20 | 20 | 20 | 20 | 20 |
| AC002464_at | Human BAC clone "RG331P03," complete sequence. /gb=AC002464 /ntype=DNA /annot=CDS | 27 | 20 | 20 | 20 | 95 | 20 |
| AC002477_s_at | Human PAC clone DJ327A19 from "Xq25–q26," complete sequence. /gb=AC002477 /ntype=DNA /annot=CDS | 49 | 45 | 151 | 74 | 132 | 20 |
| AC002486_at | Human BAC done RG367O17 from "7p15–p21," complete sequence. /gb=AC002486 /ntype=DNA /annot=CDS | 101 | 22 | 20 | 36 | 102 | 26 |
| AD000092_cds1_at | Homo sapiens DNA from chromosome 19p13.2 cosmids R31240, R30272 and R28549 containing the EKLF, GCDH, CRTC, and RAD23/ | 375 | 138 | 139 | 207 | 864 | 485 |
| AD000092_cds2_at | Homo sapiens DNA from chromosome 19p13.2 cosmids R31240, R30272 and R28549 containing the EKLF, GCDH, CRTC, and RAD23/ | 20 | 20 | 20 | 20 | 20 | 20 |
| AD000092_cds7_s_at | RAD23A gene (human RAD23A homolog) extracted from Homo sapiens DNA from chromosome 19p13.2 cosmids "R31240," R30272 and | 41 | 20 | 20 | 20 | 20 | 29 |
| AF000545_at | Homo sapiens putative purtnergic receptor P2Y10 "gene," complete cds. /gb=AF000545 /ntype=DNA /annnt=CDS | 64 | 88 | 20 | 69 | 242 | 98 |
| AF000562_at | Homo sapiens TTF-I interacting peptide 20 "mRNA," partial cds | 20 | 20 | 43 | 24 | 20 | 20 |
| AF000684_cds1_at | Homo sapiens DNA from chromosome 19-cosmid R30879 containing USF2, genomic sequence. | 20 | 53 | 80 | 194 | 110 | 44 |
| AF001527_cds1_at | Homo sapiens DNA from chromosome 19-cosmid f24590 containing CAPNS and POLRI, genomic sequence. | 29 | 47 | 115 | 46 | 20 | 59 |
| AF000177_at | Homo sapiens Sm-like protein CaSm (CaSm) "mRNA," complete cds. /gb=AF000177 /ntype=RNA | 301 | 132 | 79 | 63 | 292 | 277 |
| AF000231_at | Homo sapiens rab1 1a GTPase "mRNA," complete cds. | 96 | 75 | 56 | 114 | 140 | 31 |
| AF000234_at | Homo sapiens P2x purinoceptor "mRNA," complete cds. | 20 | 20 | 20 | 20 | 20 | 20 |
| AF000424_s_at | Homo sapiens LST1 "mRNA," clST1/C splice "variant," complete cds. | 20 | 20 | 20 | 20 | 20 | 29 |
| AF000430_at | Homo sapiens dynamin-like protein "mRNA," complete cds. | 20 | 20 | 20 | 20 | 20 | 20 |
| AF000545_at | Homo sapiens putative purtnergic receptor P2Y10 "gene," complete cds. /gb=AF000545 /ntype=DNA /annnt=CDS | 64 | 88 | 20 | 69 | 242 | 98 |
| AF000562_at | Homo sapiens TTF-I interacting peptide 20 "mRNA," partial cds | 20 | 20 | 43 | 24 | 20 | 20 |
| AF000573_ma1_at | Homo sapiens uroplakin II "mRNA," partial cds | 99 | 285 | 157 | 780 | 1520 | 188 |
| AF000959_at | Homo sapiens homogentisate 1,2-dioxygenase gene, complete cds. | 20 | 20 | 20 | 20 | 20 | 20 |
| AF001294_at | Homo sapiens transmembrane protein "mRNA," complete cds. | 20 | 63 | 20 | 20 | 20 | 20 |
| AF001359_f_at | Homo sapiens IPL (IPL) "mRNA," complete cds. | 254 | 143 | 20 | 35 | 174 | 98 |
| AF001548_ma1_at | Homo sapiens DNA mismatch repair protein (hMLH1) "mRNA," alternatively "spliced," partial cds. /gb=AF001359 /ntype=RNA | 44 | 25 | 260 | 106 | 833 | 394 |
| AF001620_at | Homo sapiens chromosome 16 BAC done CIT987SK-815A9 complete sequence. | 950 | 826 | 26 | 25 | 136 | 20 |
| AF001787_s_at | Homo sapiens trabecular meshwork-induced glucocorticoid response protein (TIGR) "mRNA," complete cds. /gb=AF001787 /ntype=RNA | 55 | 20 | 67 | 20 | 76 | 20 |
| AF002020_at | Homo sapiens uncoupling protein 3 "mRNA," complete cds. /gb=AF002020 /ntype=RNA | 20 | 20 | 20 | 20 | 85 | 92 |
| AF002224_at | Homo sapiens Niemann-Pick C disease protein (NPC1) "mRNA," complete cds. /gb=AF002020 /ntype=RNA | 73 | 42 | 20 | 47 | 292 | 120 |
| AF002700_at | Homo sapiens Angelman Syndrome "Gene," E6-AP ubiquitin protein ligase 3A (UBE3A) mRNA from promoter "P1," 5'UTR. /gb=AF0022285 | 147 | 68 | 20 | 149 | 210 | 171 |
| AF003743_at | Homo sapiens TGf-beta related neurotrophic factor receptor 2 (TRNR2) "mRNA," 5'UTR and partial cds. /gb=AF003743 /ntype=RNA | 148 | 33 | 29 | 28 | 116 | 113 |
| AF005037_at | Homo sapiens delayed rectifier potassium channel (KVLQT-Iso5) "mRNA," complete cds. /gb=AF005037 /ntype=RNA | 43 | 99 | 20 | 20 | 20 | 26 |
| AF005043_at | Homo sapiens secretory carrier membrane protein (SCAMP1) "mRNA," complete cds. /gb=AF005043 /ntype=RNA | 70 | 32 | 20 | 20 | 20 | 20 |
| AF005043_at | Homo sapiens poly(ADP-ribose) glycohydrolase (hPARG) "mRNA," complete cds. | 25 | 20 | 20 | 235 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| AF005361_at | Homo sapiens importin alpha 6 "mRNA," complete cds. /gb=AF005361 /ntype=RNA | 39 | 20 | 20 | 20 | 20 | 20 |
| AF005775_at | Homo sapiens caspase-like apoptosis regulatory protein 2 (clarp) "mRNA," alternatively "spliced," complete cds. /gb=AF005775 /ntype=R | 253 | 192 | 237 | 165 | 94 | 199 |
| AF005887_at | Homo sapiens ATF family member ATF6 (ATF6) "mRNA," complete cds. /gb=AF005887 /ntype=RNA | 34 | 20 | 20 | 20 | 20 | 20 |
| AF006041_at | Homo sapiens Fas-binding protein (DAXX) "mRNA," partial cds. /gb=AF006041 /ntype=RNA | 84 | 132 | 20 | 57 | 81 | 48 |
| AF006084_at | Homo sapiens Arp2/3 protein complex subunit oti-Arc (ARC41) "mRNA," complete cds. /gb=AF006084 /ntype=RNA | 242 | 269 | 20 | 107 | 35 | 390 |
| AF006087_at | Homo sapiens Arp2/3 protein complex subunit p20-Arc (ARC20) "mRNA," complete cds. /gb=AF006087 /ntype=RNA | 24 | 30 | 52 | 27 | 20 | 29 |
| AF006609_at | Homo sapiens RGS3 "mRNA." 5'UTR. /gb=AF006609 /ntype=RNA | 31 | 233 | 20 | 20 | 20 | 20 |
| AF007111_at | Homo sapiens MDM2-like p53-binding protein (MDMX) "mRNA," complete cds. | 20 | 20 | 20 | 20 | 62 | 20 |
| AF007551_at | Homo sapiens Bet1p homolog (hbet1) "mRNA," complete cds. /gb=AF007551 /ntype=RNA | 89 | 20 | 20 | 59 | 196 | 20 |
| AF007875_at | Homo sapiens dolichol monophosphate mannose synthase (DPM1) "mRNA," partial cds. /gb=AF007875 /ntype=RNA | 123 | 44 | 20 | 23 | 136 | 32 |
| AF008445_at | Homo sapiens phospholipid scramblase "mRNA," complete cds. /gb=AF008445 /ntype=RNA | 65 | 20 | 101 | 35 | 105 | 68 |
| AF008937_at | Homo sapiens syntaxin-16C "mRNA," complete cds. /gb=AF008937 /ntype=RNA | 35 | 20 | 20 | 50 | 156 | 81 |
| AF009301_at | Homo sapiens TEB4 protein "mRNA," complete cds. /gb=AF009301 /ntype=RNA | 78 | 70 | 92 | 20 | 20 | 20 |
| AF009368_at | Homo sapiens Luman "mRNA," complete cds. /gb=AF009368 /ntype=RNA | 228 | 233 | 133 | 223 | 590 | 313 |
| AF009426_at | Homo sapiens clone 22 "mRNA," alternative splice variant "beta-1," complete cds. /gb=AF009426 /ntype=RNA | 20 20 | 20 | 20 | 20 | 20 | 20 |
| AF009674_at | Homo sapiens axin (AXIN) "mRNA," partial cds. | 148 | 110 | 33 | 114 | 20 | 52 |
| AF010193_at | Homo sapiens MAD-related gene SMAD7 (SMAD7) "mRNA," complete cds. | 91 | 29 | 80 | 54 | 20 | 25 |
| AF012024_s_at | Homo sapiens integrin cytoplasmic domain associated protein (Icap-1b) "mRNA," complete cds. /gb=AF012024 /ntype=RNA | 22 | 60 | 133 | 56 | 113 | 25 |
| AF012270_at | Homo sapiens peropsin (Rrh) "mRNA," complete cds. /gb=AF012270 /ntype=RNA | 32 | 65 | 20 | 29 | 20 | 33 |
| AF014958_at | Homo sapiens chemokine receptor X (CKRX) "mRNA," complete cds. /gb=AF014958 /ntype=RNA | 98 | 20 | 20 | 20 | 20 | 20 |
| AF015910_at | Homo sapiens unknown protein "mRNA," partial cds. /gb=AF015910 /ntype=RNA | 170 | 306 | 20 | 27 | 20 | 20 |
| AF015913_at | Homo sapiens SKB1Hs "mRNA," complete cds. /gb=AF015913 /ntype=RNA | 39 | 93 | 73 | 94 | 91 | 20 |
| AF015950_at | Homo sapiens telomerase reverse transcriptase (hTRT) "mRNA," complete cds. | 20 | 20 | 20 | 20 | 20 | 20 |
| AFFX-HUMGAPDH/ M33197_3_at | | 5588 | 3862 | 6792 | 5962 | 4642 | 4022 |
| AFFX-HUMGAPDH/M33197_5_at | | 1939 | 406 | 2788 | 2806 | 435 | 1381 |
| AFFX-HUMGAPDH/M33197_M_at | | 3413 | 725 | 4016 | 4668 | 833 | 2014 |
| AJ000099_at | Homo sapiens mRNA for hyaluronidase. /gb=AJ000099 /ntype=RNA | 325 | 546 | 1073 | 706 | 760 | 303 |
| AJ000480_at | Homo sapiens mRNA for C8FW pntosphoprotein. /gb=AJ000480 /ntype=RNA | 314 | 75 | 25 | 94 | 57 | 148 |
| AJ001047_at | Homo sapiens mRNA for matrilin-3. /gb=AJ001047 /ntype=RNA | 35 | 20 | 20 | 20 | 38 | 60 |
| AJ001421_at | Homo sapiens mRNA for Rer1 protein. /gb=AJ001421 /ntype=RNA | 276 | 157 | 272 | 221 | 152 | 227 |
| AJ001487_at | Homo sapiens mRNA for tansformation-sensitve "protein," 3'UTR. /gb=AJ001487 /ntype=RNA | 20 | 20 | 20 | 20 | 20 | 28 |
| D00003_at | Human liver cytochrome P-450 "mRNA," complete cds | 20 | 62 | 20 | 22 | 20 | 20 |
| D00017_at | Human lipocortin II mRNA | 2387 | 1293 | 1364 | 911 | 1022 | 1115 |
| D00097_at | Human serum amyloid P component (SAP) gene with upstream promoter | 20 | 20 | 20 | 20 | 160 | 20 |
| D00408_at | | 20 | 45 | 20 | 20 | 162 | 52 |
| D00408_s_at | | 41 | 156 | 198 | 251 | 20 | 34 |
| D00591_at | Human fetal liver cytochrome P-450 (P-450 "HFLa)," complete cds | 23 | 33 | 20 | 80 | 48 | 37 |
| D00596_at | Human RCC1 "gene," complete cds | 20 | 20 | 55 | 20 | 228 | 61 |
| D00632_at | Human thymidylate syntase (EC 2.1.1.45) "gene," complete cds | 484 | 90 | 20 | 34 | 902 | 101 |
| D00654_at | Human plasma (extracellular) mRNA for glutatnione "peroxidase," complete cds | 1245 | 751 | 20 | 23 | 251 | 100 |
| D00723_at | Human enteric smooth muscle gamma-actin "gene," 5'flank and | 20 | 20 | 20 | 27 | 20 | 20 |
| D00726_at | Human mRNA for hydrogen carrier "protein," a component of an enzyme "complex," glycine synthase (EC 4.99.1.1) | 123 | 20 | 84 | 35 | 20 | 103 |
| D00749_s_at | Human T cell surface antigen CD7 gene | 108 | 438 | 194 | 214 | 20 | 152 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| D00760_at | Human mRNA for proteasome subunit HC3 | 71 | 107 | 101 | 119 | 94 | 99 |
| D00761_at | Human mRNA for proteasome subunit HC5 | 310 | 462 | 251 | 308 | 132 | 192 |
| D00762_at | Human mRNA for proteasome subunit HC6 | 188 | 66 | 197 | 179 | 68 | 143 |
| D00763_at | Human mRNA for proteasome subunit HC9 | 166 | 211 | 237 | 152 | 234 | 182 |
| D00860_at | Human mRNA for phosphoibosyl pyrophosphate synthetase (EC 2.7.6.1) subunit I | 20 | 52 | 29 | 20 | 20 | 69 |
| D10040_at | Human mRNA for long-chain acyl-CoA synthetase | 47 | 24 | 32 | 41 | 20 | 26 |
| D10202_at | Human mRNA for platelet-activating factor "receptor," complete cds | 82 | 37 | 20 | 20 | 332 | 88 |
| D10326_s_at | Human mRNA for pyruvate kinase | 20 | 20 | 20 | 20 | 20 | 20 |
| D10495_at | Human mRNA for protein kinase C delta-type | 36 | 95 | 20 | 20 | 20 | 20 |
| D10511_at | Human gene for mitochondrial acetoacetyl-CoA thiolase | 66 | 20 | 20 | 38 | 20 | 20 |
| D10522_at | Human mRNA for 80K-L "protein," complete cds | 121 | 246 | 300 | 252 | 76 | 127 |
| D10523_at | Human mRNA for 2-oxoglutarate "dehydrogenase," complete cds | 126 | 55 | 20 | 53 | 170 | 126 |
| D10537_s_at | Human mRNA for major structural protein of "myelin," complete cds | 20 | 20 | 45 | 20 | 20 | 340 |
| D10856_at | Human mRNA for "CRK-II," complete cds | 20 | 20 | 25 | 20 | 70 | 20 |
| D10857_s_at | Human mRNA for smooth muscle myosin heavy chain | 171 | 40 | 20 | 20 | 20 | 20 |
| D1O704_at | Human mRNA for choline kinase | 110 | 47 | 20 | 60 | 202 | 63 |
| D10922_s_at | Human mRNA for FMLP-related receptor (HM63) | 26 | 20 | 57 | 20 | 495 | 40 |
| D10923_at | Human mRNA for HM74 | 132 | 20 | 259 | 33 | 123 | 47 |
| D10925_at | Human mRNA for HM145 | 20 | 20 | 20 | 20 | 20 | 20 |
| D10995_at | Human gene for serotonin 18 "receptor," complete cds | 133 | 56 | 27 | 105 | 51 | 156 |
| D11086_at | Human mRNA for interleukin 2 receptor gamma chain | 178 | 200 | 199 | 139 | 811 | 547 |
| D11094_at | Human mRNA for "MSS1," complete cds | 222 | 70 | 70 | 109 | 106 | 51 |
| D11139_at | Human gene for tissue inhibitor of "metalloproteinases," partial sequence | 52 | 27 | 20 | 20 | 20 | 20 |
| D11151_at | Human DNA for endothelin-A "receptor," 5'flanking region and | 26 | 20 | 20 | 20 | 20 | 21 |
| D11327_s_at | Human mRNA for protein-tyrosine "phosphatase," complete cds | 20 | 20 | 20 | 20 | 396 | 39 |
| D11428_at | Human mRNA for PMP-22(PAS-II/SR13/Gas-3) of peripheral "myelin," complete cds | 557 | 309 | 78 | 129 | 66 | 184 |
| D12485_at | Human mRNA for nucleotide "pyrophosphatase," complete cds | 95 | 39 | 20 | 31 | 193 | 101 |
| D12620_s_at | Human mRNA for cytochrome P450L TBV | 52 | 20 | 70 | 20 | 193 | 41 |
| D12625_at | Human mRNA for NF1 protein isoform (neurofibromin "Isoform)," complete cds | 86 | 20 | 20 | 20 | 20 | 40 |
| D12676_at | Human mRNA for lysosomal "sialoglycoprotein," complete cds | 20 | 49 | 20 | 20 | 20 | 20 |
| D12686_at | Human mRNA for eukaryotic initiation factor 4 gamma (eIF-4 gamma) | 20 | 20 | 20 | 301 | 244 | 263 |
| D12763_at | Homo sapiens mRNA for ST2 protein | 20 | 20 | 20 | 36 | 20 | 20 |
| D12775_s_at | Human mRNA for erythrocyte-specific AMP "deaminase," complete cds | 37 | 83 | 158 | 52 | 176 | 20 |
| D13118_at | Human mRNA for ATP synthase subunit c encoded by P1 gene | 611 | 501 | 575 | 432 | 1114 | 651 |
| D13146_cds1_at | Human 2',3'cyclic-nucleotide 3'-phosphodiesterase gene, exon 3. | 218 | 235 | 195 | 170 | 186 | 212 |
| D13168_at | Human gene for endothelin-B receptor (hET-BR) | 20 | 22 | 70 | 41 | 20 | 40 |
| D13264_at | Human mRNA for macrophage scavenger receptor type "I," 3'untranslated region | 20 | 21 | 20 | 42 | 45 | 46 |
| D13305_at | Human mRNA for brain cholecyatokinin receptor | 20 | 20 | 20 | 20 | 132 | 20 |
| D13315_at | Human mRNA for lactoyl glutathione lyase | 173 | 97 | 168 | 86 | 20 | 108 |
| D13370_at | Human APX gene encoding APEX "nuclease," complete cds | 185 | 153 | 259 | 249 | 179 | 322 |
| D13413_ms1_s_at | Human mRNA for tumor-associated 120 kDa nuclear protein "p120," partial cds(carboxyl terminus) | 2651 | 6543 | 5549 | 5695 | 2371 | 2727 |
| D13435_at | Human mRNA for PIG-F (phosphatidyl-inositol-glycan class "F)," complete cds | 20 | 20 | 32 | 46 | 20 | 81 |
| D13540_at | Human mRNA for protein-tyrosine phosphatase | 92 | 25 | 47 | 20 | 20 | 24 |
| D13626_at | Human mRNA for KIAA0001 "gene," complete cds | 42 | 20 | 81 | 49 | 70 | 86 |
| D13627_at | Human mRNA for KIAA0002 "gene," complate cds | 155 | 147 | 128 | 152 | 120 | 183 |
| D13628_at | Human mRNA for KIAA0003 "gene," complete cds | 20 | 20 | 62 | 20 | 20 | 41 |
| D13630_at | Human mRNA for KIAA0005 "gene," complete cds | 98 | 29 | 57 | 32 | 32 | 100 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| D13631_s_at | Human mRNA for KIAA0006 "gene," complete cds | 24 | 62 | 20 | 60 | 20 | 20 | 20 |
| D13633_at | Human mRNA for KIAA0008 "gene," complete cds | 20 | 24 | 64 | 54 | 20 | 71 | 30 |
| D13634_at | Human mRNA for KIAA0009 "gene," complete cds | 96 | 20 | 47 | 20 | 20 | 20 | 90 |
| D13635_at | Human mRNA for KIAA0010 "gene," complete cds | 24 | 20 | 33 | 20 | 20 | 20 | 20 |
| D13636_at | Human mRNA for KIAA0011 "gene," complete cds | 25 | 20 | 67 | 55 | 20 | 20 | 52 |
| D13637_at | Human mRNA for KIAA0012 "gene," complete cds | 40 | 20 | 20 | 20 | 20 | 20 | 108 |
| D13638_s_at | | 20 | 20 | 20 | 20 | 20 | 20 | 20 |
| D13639_at | Human mRNA for KIAK0002 "gene," complete cds | 100 | 70 | 78 | 36 | 20 | 32 | 143 |
| D13640_at | Human mRNA for KIAA0015 "gene," complete cds | 131 | 313 | 119 | 119 | 235 | 235 | 280 |
| D13641_at | Human mRNA for KIAA0016 "gene," complete cds | 104 | 123 | 300 | 178 | 20 | 99 | 56 |
| D13642_at | Human mRNA for KIAA0017 "gene," complete cds | 20 | 20 | 61 | 55 | 227 | 227 | 155 |
| D13643_at | Human mRNA for KIAA0018 "gene," complete cds | 110 | 20 | 20 | 20 | 194 | 194 | 20 |
| D13644_at | Human mRNA for KIAA0019 "gene," complete cds | 20 | 39 | 20 | 20 | 121 | 121 | 20 |
| D13645_at | Human mRNA for KIAA0020 "gene," complete cds | 115 | 29 | 20 | 50 | 62 | 62 | 128 |
| D13666_s_at | Homo sapiens mRNA for osteoblast specific factor 2 (OSF-2os) | 20 | 20 | 20 | 20 | 20 | 20 | 20 |
| D13705_s_at | Human mRNA for fatty acids omega-hydroxylase (cytochrome "P-450HKV)," complete cds | 106 | 171 | 321 | 182 | 703 | 703 | 218 |
| D13720_s_at | Human mRNA for "LYK," complete cds | 37 | 57 | 100 | 46 | 205 | 205 | 20 |
| D13748_at | Human mRNA for eukaryotic initiation factor 4AI | 744 | 353 | 717 | 816 | 573 | 573 | 630 |
| D13789_at | Human mRNA for N-acetylglucosaminyltransferase "III," complete cds | 20 | 20 | 20 | 20 | 153 | 153 | 28 |
| D13814_at | Human mRNA for angiotensin II type Ib "receptor," complete cds | 20 | 20 | 110 | 104 | 93 | 93 | 20 |
| D13897_m2_at | Human DNA for peptide YY, complete cds | 220 | 70 | 20 | 160 | 511 | 511 | 247 |
| D13900_at | Human mRNA for mitochondrial short-chain enoyl-CoA "hydralase," complete cds | 253 | 402 | 522 | 483 | 426 | 426 | 387 |
| D13969_at | Human mRNA for Mel-18 "protein," complete cds | 50 | 20 | 20 | 20 | 20 | 20 | 20 |
| D13988_at | Human rab GDI "mRNA," complete cds | 228 | 103 | 119 | 308 | 303 | 303 | 273 |
| D14043_at | Human mRNA for "MGC-24," complete cds | 159 | 157 | 328 | 299 | 20 | 20 | 39 |
| D14134_at | Human mRNA for "RAD51," complete cds | 20 | 24 | 20 | 20 | 50 | 50 | 20 |
| D14446_at | Human HFREP-1 mRNA for unknown "protein," complete cds | 20 | 20 | 20 | 20 | 20 | 20 | 20 |
| D14497_at | Human mRNA for proto-oncogene "protein," complete cds | 20 | 20 | 35 | 39 | 20 | 20 | 20 |
| D14520_at | Human mRNA for GC-Box binding protein "BTEB2," complete cds | 457 | 387 | 456 | 341 | 219 | 219 | 219 |
| D14530_at | Human homolog of yeast ribosomal protein "S28," complete cds | 2193 | 2301 | 2247 | 1956 | 777 | 777 | 1251 |
| D14533_at | Human mRNA for XPAC protein | 25 | 31 | 20 | 20 | 20 | 20 | 20 |
| D14657_at | Human mRNA for KIAA0101 "gene," complete cds | 52 | 20 | 53 | 39 | 20 | 20 | 104 |
| D14658_at | Human mRNA for KIAA0102 "gene," complete cds | 92 | 110 | 380 | 195 | 246 | 246 | 80 |
| D14659_at | Human mRNA for KIAA0103 "gene," complete cds | 54 | 20 | 20 | 71 | 20 | 20 | 24 |
| D14660_at | Human mRNA for KIAA0104 "gene," complete cds | 71 | 36 | 20 | 43 | 20 | 20 | 20 |
| D14661_at | Human mRNA for KIAA0105 "gene," complete cds | 27 | 20 | 89 | 67 | 20 | 20 | 57 |
| D14662_at | Human mRNA for KIAA0106 "gene," complete cds | 134 | 191 | 182 | 109 | 163 | 163 | 104 |
| D14663_at | Human mRNA for KIAA0107 "gene," complete cds | 123 | 105 | 147 | 129 | 20 | 20 | 116 |
| D14664_at | Human mRNA for KIAA0022 "gene," complete cds | 25 | 41 | 26 | 20 | 59 | 59 | 20 |
| D14678_at | Human mRNA for kinesin-related "protein," partial cds | 20 | 20 | 20 | 20 | 20 | 20 | 20 |
| D14686_at | Human gene for glycine cleavage system T-protein | 127 | 141 | 20 | 140 | 144 | 144 | 219 |
| D14689_at | Human mRNA for KIAA0023 "gene," complete cds | 242 | 105 | 62 | 134 | 298 | 298 | 151 |
| D14694_at | Human mRNA for KIAA0024 "gene," complete cds | 163 | 255 | 345 | 237 | 304 | 304 | 237 |
| D14695_at | Human mRNA for KIAA0025 "gene," complete cds | 20 | 62 | 86 | 48 | 20 | 20 | 105 |
| D14710_at | Human mRNA for ATP synthase alpha "subunit," complete cds | 980 | 613 | 1271 | 833 | 133 | 133 | 583 |
| D14811_at | Human mRNA for KIAA0110 "gene," complete cds | 49 | 20 | 20 | 27 | 20 | 20 | 68 |
| D14812_at | Human mRNA for KIAA0026 "gene," complete cds | 396 | 282 | 399 | 393 | 234 | 234 | 445 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| D14822_at | Human chimeric mRNA derived from AML1 gene and MTG8(ETO) gene, partial sequence. | 30 | 20 | 20 | 20 | 68 | 56 |
| D14823_at | Human chimeric mRNA derived from AML1 gene and MTG8(ETO) gene, partial sequence. | 20 | 20 | 20 | 20 | 20 | 20 |
| D14826_s_at | Human mRNA for hCREM (cyclic AMP-responsive element modulator) type 2 "protein," complete cds | 74 | 40 | 20 | 31 | 20 | 31 |
| D14827_at | Human mRNA for Tax helper protein "1," complete cds | 137 | 58 | 20 | 70 | 20 | 20 |
| D14838_at | Human mRNA for "FGF-9," complete cds | 20 | 21 | 20 | 20 | 20 | 20 |
| D14874_at | Human mRNA for "adrenomedullin," complete cds | 72 | 63 | 65 | 148 | 100 | 137 |
| D14878_at | Human mRNA for protein "D123," complete cds | 101 | 91 | 63 | 65 | 216 | 20 |
| D14889_at | Human mRNA for small GTP-binding "protein," "S10," complete cds | 37 | 78 | 52 | 65 | 178 | 128 |
| D15049_at | Human mRNA for protein tyrosine phosphatase | 101 | 79 | 30 | 107 | 258 | 126 |
| D15050_at | Human mRNA for transcription factor "AREB6," complete cds | 166 | 45 | 129 | 163 | 75 | 163 |
| D15057_at | Human mRNA for "DAD-1," complete cds | 171 | 111 | 130 | 145 | 64 | 134 |
| D16105_at | Human mRNA for leukocyte tyrosine "kinase," complete cds | 130 | 127 | 148 | 112 | 296 | 184 |
| D16154_at | Human gene for cytochrome "P-450c11," exon 3–9. /gb=D16154 /ntype=DNA/annot=exon | 20 | 20 | 20 | 20 | 48 | 20 |
| D16181_at | Human PMP2 gene for peripheral myelin protein 2 | 20 | 40 | 20 | 20 | 20 | 25 |
| D16217_at | Human mRNA for "calpastatin," complete cds | 23 | 20 | 20 | 20 | 20 | 20 |
| D16227_at | Human mRNA for BDP-1 protein (a member of the recoverin "family"), complete cds | 681 | 267 | 647 | 537 | 248 | 452 |
| D16294_at | Human mRNA for mitochondrial 3-oxoacyl-CoA "thiolase," complete cds | 83 | 20 | 20 | 56 | 20 | 134 |
| D16350_at | Human SA mRNA for SA gene "product," complete cds | 20 | 20 | 20 | 21 | 174 | 281 |
| D16469_at | Human mRNA for "ORF," Xq terminal portion | 20 | 40 | 20 | 27 | 100 | 20 |
| D16480_at | Human mRNA for mitochondrial enoyl-CoA hydratase/3-hydroxyacyl-CoA dehydrogenase alph-subunit of trifunctional "protein," complete | 20 | 91 | 357 | 339 | 221 | 73 |
| D16481_at | Human mRNA for mitochondrial 3-ketoacyl-CoA thiolase beta-subunit of trifunctional "protein," complete cds | 28 | 25 | 71 | 95 | 20 | 20 |
| D16532_at | Human gene for very low density lipoprotein "receptor," 5'flanking and | 30 | 66 | 78 | 101 | 20 | 84 |
| D16562_at | Human mRNA for ATP synthase gamma-subunit "(L-type)," complete cds | 41 | 20 | 20 | 20 | 20 | 20 |
| D16581_at | Human mRNA for "8-oxo-dGTPase," complete cds | 564 | 364 | 718 | 607 | 534 | 811 |
| D16583_at | Human gene for L-histidine "decarboxylase," complete cds | 135 | 100 | 118 | 125 | 370 | 179 |
| D16611_s_at | Human BDR-2 mRNA for "hippocalcin," complete cds | 20 | 20 | 20 | 20 | 20 | 20 |
| D16626_at | Human mRNA for coproporohyrinogen "oxidase," complete cds | 66 | 48 | 48 | 112 | 28 | 102 |
| D16688_at | Human mRNA for "histidase," complete cds | 24 | 20 | 49 | 20 | 20 | 20 |
| D16688_s_at | Human mRNA for "histidase," complete cds | 48 | 20 | 20 | 20 | 20 | 52 |
| D16815_at | Human mRNA for "EAR-1r," C-terminal | 20 | 66 | 20 | 20 | 20 | 20 |
| D16827_s_at | Human gene for fifth spomatostatin receptor subtype | 20 | 20 | 20 | 20 | 44 | 20 |
| D17357_at | Human activin beta-A "gene," regulatory sequence of 5'upstream region. /gb=D17357 /ntype=DNA /annot=exon | 20 | 20 | 24 | 28 | 20 | 20 |
| D17390_at | Human mRNA for MDC protein | 42 | 20 | 31 | 20 | 20 | 20 |
| D17391_at | Human mRNA for alpha 4(IV) "collagen," C-terminal | 187 | 67 | 20 | 23 | 211 | 51 |
| D17400_at | Human mRNA for 6-pyruvoyl-tetrahydropterin "synthase," complete cds | 483 | 325 | 20 | 20 | 101 | 20 |
| D17408_s_at | Human mRNA for "calponin," complete cds | 22 | 37 | 65 | 20 | 20 | 20 |
| D17427_at | Human mRNA for desmocollin type 4 | 109 | 23 | 20 | 25 | 51 | 56 |
| D17461_at | Human GULO gene for L-gulono-gamma-lactone "oxidase, exon "9,10" and 12 /gb=D17461 /ntype=DNA /annot=exon | 177 | 95 | 74 | 50 | 20 | 20 |
| D17516_at | Human mRNA for PACAP "receptor," complete cds | 211 | 62 | 81 | 43 | 429 | 226 |
| D17525_at | Human mRNA for precursor of P100 serine protease of Ra-reactive "factor," complete cds | 20 | 57 | 23 | 20 | 119 | 52 |
| D17532_at | Human mRNA for "RCK," complete cds | 20 | 20 | 20 | 20 | 112 | 41 |
| D17547_at | Human mRNA for DOPAchrome tautomerase (tyrosinase-related "protein-2)," complete cds | 20 | 20 | 20 | 20 | 61 | 20 |
| D17570_s_at | | 20 | 20 | 20 | 20 | 114 | 25 |
| D17716_at | Human mRNA for N-acetylglucosaminyltransferase "V," complete cds. /gb=D17716 /ntype=RNA | 56 | 20 | 49 | 24 | 105 | 50 |
| D17793_at | Human mRNA for KIAA0119 "gene," complete cds | 232 | 650 | 212 | 593 | 341 | 604 |
| D21063_at | Human mRNA for KIAA0030 "gene," partial cds | 20 | 20 | 20 | 25 | 90 | 34 |
| D21089_at | Human mRNA for XP-C repair complementing protein "(p125)," complete cds | 85 | 215 | 226 | 173 | 311 | 186 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| D21090_at | Human mRNA for XP-C repair complementing protein "(p58/HHR23B)," complete cds | 51 | 25 | 66 | 56 | 20 | 20 | 62 |
| D21163_at | Human mRNA for KIAA0031 "gene," complete cds | 28 | 26 | 20 | 20 | 20 | 20 | 20 |
| D21205_at | Human mRNA for estrogen responsive finger "protein," complete cds | 20 | 20 | 20 | 20 | 20 | 20 | 20 |
| D21235_at | Human mRNA for HHR23A "protein," complete cds | 21 | 43 | 56 | 101 | 53 | 20 | 83 |
| D21239_at | Human mRNA for C3G "protein," complete cds | 26 | 20 | 20 | 59 | 20 | 117 | 20 |
| D21241_xpt1_s_at | ovary- and prostate-specific exon 1 from Human cytochrome P-450 arometase "gene," multiple exons 1 and exon 2 /gb=D21241 /ntype=D | 20 | 20 | 20 | 20 | 20 | 383 | 41 |
| D21255_at | Human mRNA for "OB-cadherin-2," complete cds | 77 | 20 | 20 | 20 | 26 | 20 | 20 |
| D21260_at | Human mRNA for KIAA0034 "gene," complete cds | 211 | 123 | 661 | 304 | 370 | 20 | 334 |
| D21261_at | Human mRNA for KIAA0120 "gene," complete cds | 623 | 312 | 796 | 957 | 1250 | 20 | 1798 |
| D21262_at | Human mRNA for KIAA0035 "gene," partial cds | 47 | 20 | 23 | 62 | 91 | 20 | 151 |
| D21267_at | Human mRNA for highly expressed protein | 76 | 20 | 44 | 20 | 20 | 20 | 70 |
| D21337_at | Human mRNA for collagen | 20 | 56 | 40 | 20 | 20 | 20 | 20 |
| D21851_at | Human mRNA for KIAA0028 "gene," partial cds | 104 | 98 | 179 | 158 | 59 | 20 | 69 |
| D21852_at | Human mRNA for KIAA0029 "gene," partial cds | 20 | 113 | 72 | 68 | 20 | 20 | 77 |
| D21853_at | Human mRNA for KIAA0111 "gene," complete cds | 199 | 90 | 267 | 235 | 79 | 20 | 194 |
| D21878_at | Human mRNA for "BST-1," complete cds | 20 | 20 | 33 | 24 | 300 | 20 | 20 |
| D23660_at | Human mRNA for ribosomal "protein," complete cds | 5345 | 4257 | 5788 | 8243 | 1435 | 2421 |  |
| D23662_at | Human mRNA for ubiquitin-like "protein," complete cds | 417 | 496 | 567 | 435 | 247 | 400 |  |
| D23673_at | Human "mRNA," done HH109 (screened by the monoclonal antibody of insulin receptor substrate-1 (IRS-1)) | 312 | 401 | 620 | 315 | 564 | 448 |  |
| D25215_at | Human mRNA for KIAA0032 "gene," complete cds | 34 | 22 | 24 | 20 | 80 | 21 |  |
| D25216_at | Human mRNA for KIAA0014 "gene," partial cds | 127 | 265 | 561 | 474 | 572 | 532 |  |
| D25217_at | Human mRNA for KIAA0027 "gene," partial cds | 133 | 70 | 117 | 42 | 128 | 108 |  |
| D25218_at | Human mRNA for KIAA0112 "gene," partial cds | 300 | 43 | 192 | 51 | 718 | 20 | 20 |
| D25248_at | Human randomly sequenced mRNA | 124 | 57 | 95 | 20 | 508 | 20 | 20 |
| D25274_at | Human randomly sequenced mRNA | 378 | 342 | 585 | 330 | 309 | 294 |  |
| D25278_at | Human mRNA for KIAA0036 "gene," complete cds | 87 | 68 | 50 | 26 | 45 | 119 |  |
| D25303_at | Human mRNA for integrin alpha "subunit," complete cds | 69 | 52 | 20 | 20 | 20 | 167 |  |
| D25304_at | Human mRNA for KIAA0006 "gene," partial cds | 20 | 20 | 20 | 21 | 25 | 108 |  |
| D25328_at | Human mRNA for platelet-type "phosphofructokinase," complete cds | 27 | 20 | 52 | 37 | 20 | 20 |  |
| D25539_at | Human mRNA for KIAA0037 "gene," complete cds | 20 | 20 | 20 | 20 | 20 | 20 |  |
| D25538_at | Human mRNA for KIAA0040 "gene," complete cds | 96 | 50 | 87 | 36 | 20 | 20 |  |
| D25547_at | Human mRNA for PIMT isozyme "I," complete cds | 54 | 20 | 20 | 23 | 148 | 23 |  |
| D26018_at | Human mRNA for KIAA0039 "gene," partial cds | 43 | 20 | 91 | 28 | 98 | 20 |  |
| D26067_at | Human mRNA for KIAA0033 "gene," complete cds | 20 | 28 | 20 | 20 | 20 | 20 |  |
| D26068_at | Human mRNA for KIAA0038 "gene," partial cds | 821 | 323 | 554 | 438 | 29 | 408 |  |
| D26069_at | Human mRNA for KIAA0041 "gene," partial cds | 20 | 20 | 248 | 20 | 54 | 41 |  |
| D26070_at | Human mRNA for type 1 inositol "1,4,5-trisphosphate" "receptor," complete cds | 47 | 25 | 21 | 20 | 20 | 20 |  |
| D26129_at | Human mRNA for ribonuclease A (RNase "A)," complete cds | 237 | 129 | 20 | 57 | 140 | 1524 |  |
| D26135_at | Human mRNA for diacylglycerol kinase "gamma," complete cds | 20 | 20 | 20 | 20 | 20 | 20 |  |
| D26155_s_at | Human mRNA for transcriptional activator "hSNF2a," complete cds | 20 | 20 | 84 | 312 | 82 | 229 |  |
| D26156_s_at | Human mRNA for transcriptional activator "hSNF2b," complete cds | 86 | 36 | 288 | 168 | 116 | 255 |  |
| D26308_at | Human mRNA for NADPH-flavin "reductase," complete cds | 554 | 270 | 32 | 20 | 258 | 20 |  |
| D26350_at | Human mRNA for type 2 inositol "1,4,5-trisphosphate" "receptor," complete cds | 20 | 20 | 20 | 20 | 133 | 20 |  |
| D26361_at | Human mRNA for KIAA0042 "gene," complete cds | 20 | 29 | 91 | 20 | 20 | 71 |  |
| D26362_at | Human mRNA for KIAA0043 "gene," complete cds | 20 | 82 | 109 | 36 | 20 | 121 |  |
| D26443_at | Human mRNA for glutamate "transporter," complete cds | 20 | 20 | 63 | 20 | 20 | 36 |  |
| D26528_at | Human mRNA for RNA "helicase," complete cds | 108 | 20 | 20 | 41 | 20 | 43 |  |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| D26535_s_at | Human gene for dihydrolipoamide "succinyltranaferase," complete cds (exon 1-15) | 43 | 87 | 252 | 109 | 20 | 25 |
| D26561_cds1_at | Human papillomavirus 5b genome integrated into human carcinoma DNA. | 20 | 20 | 20 | 20 | 20 | 20 |
| D26561_cds2_at | Human papillomavirus 5b genome integrated into human carcinoma DNA. | 63 | 47 | 75 | 20 | 54 | 20 |
| D26561_cds3_at | Human papillomavirus 5b genome integrated into human carcinoma DNA. | 20 | 33 | 20 | 20 | 62 | 20 |
| D26579_at | Human mRNA for transmembrane "protein," complete cds | 68 | 99 | 20 | 141 | 116 | 209 |
| D26598_at | Human mRNA for proteasome subunit "HsC10-II," complete cds | 359 | 384 | 440 | 344 | 243 | 512 |
| D26599_at | Human mRNA for proteasome subunit "HsC7-I," complete cds | 387 | 269 | 352 | 358 | 375 | 557 |
| D26600_at | Human mRNA for proteasome subunit "HsN3," complete cds | 70 | 218 | 251 | 178 | 184 | 281 |
| D28114_at | Human mRNA for MOBP (myelin-associated oligodendrocytic basic "protein"), complete "cds," clone hOPRP2 | 58 | 65 | 136 | 46 | 135 | 181 |
| D28118_at | Human mRNA for "DB1," complete cds | 27 | 20 | 46 | 65 | 20 | 20 |
| D28124_at | Human mRNA for unknown "product," complete cds | 552 | 580 | 314 | 348 | 485 | 442 |
| D28137_at | Human mRNA for "BST-2," complete cds | 176 | 64 | 342 | 196 | 168 | 195 |
| D28235_s_at | Humsn PTGS2 gene for prostaglandin endoperoxide "synthase," complete cds | 47 | 37 | 41 | 55 | 20 | 33 |
| D28364_at | Human mRNA for annexin "II," 5'UTR (sequence from the 5'cap to the start codon). /gb=D28364 /ntype=RNA | 209 | 29 | 83 | 46 | 128 | 47 |
| D28383_at | Human mRNA for ATP synthase B "chain," 5'UTR (sequence from the 5'cap to the start codon). /gb=D28364 /ntype=RNA | 219 | 87 | 20 | 218 | 726 | 343 |
| D28416_at | Human mRNA for esterase "D," 5'UTR (sequence fom the 5'cap to the start codon). /gb=D28416 /ntype=RNA | 301 | 182 | 223 | 185 | 354 | 195 |
| D28423_at | Human mRNA for pre-MRNA splicing factor "SRp20," 5'UTR (sequence from the 5'cap to the start cadon). /gb=D28423 /intype=RNA | 241 | 91 | 260 | 259 | 55 | 312 |
| D28473_s_at | Human T-lymphocyte mRNA for isoleucyl-tRNA "synthetase," complete cds | 58 | 115 | 257 | 104 | 20 | 139 |
| D28476_at | Human mRNA for KIAA0045 "gene," complete cds | 76 | 69 | 204 | 45 | 58 | 20 |
| D28483_at | Human scr3 mRNA for RNA binding protein "SCR3," complete cds | 87 | 44 | 20 | 76 | 215 | 134 |
| D28532_at | Human mRNA for renal Na+-dependent phosphate "cotransporter," complete cds | 89 | 73 | 36 | 31 | 40 | 69 |
| D28539_s_at | Human mRNA for metabotropic glutamate receptor subtype "5b," complete cds | 20 | 20 | 20 | 20 | 20 | 20 |
| D28588_at | Human mRNA for KIAA0048 "gene," complete cds | 39 | 34 | 180 | 20 | 20 | 41 |
| D28589_at | Human mRNA "(KIAA00167)," partial sequence. /gb=D28589 /ntype=RNA | 20 | 20 | 20 | 104 | 20 | 38 |
| D28791_at | Human PIG-A "gene," 5'flanking region and | 24 | 20 | 29 | 26 | 41 | 20 |
| D28915_at | Human gene for hepatitis C-associated microtubular aggregate protein p44 | 65 | 125 | 50 | 28 | 66 | 154 |
| D29012_at | Human mRNA for proteasome subunit "y," complete cds | 600 | 628 | 441 | 463 | 895 | 854 |
| D29013_at | Human mRNA for DNA polymerase "beta," complete cds | 71 | 63 | 48 | 140 | 110 | 171 |
| D29640_s_at | Human mRNA for KIAA0051 "gene," complete cds | 45 | 32 | 227 | 202 | 137 | 41 |
| D29641_at | Human mRNA for KIAA0052 "gene," partial cds | 98 | 77 | 42 | 51 | 22 | 20 |
| D29642_at | Human mRNA for KIAA0053 "gene," complete cds | 78 | 36 | 20 | 30 | 46 | 79 |
| D29643_at | Human mRNA for KIAA0055 "gene," complete cds | 221 | 120 | 273 | 237 | 208 | 72 |
| D29875_at | Human mRNA for KIAA0116 "gene," partial cds | 20 | 20 | 20 | 20 | 243 | 51 |
| D29677_s_at | Human inducible nitric oxide synthase "gene," promoter and exon 1 /gb=D29675 /ntype=DNA /annot=exon | 65 | 93 | 75 | 121 | 705 | 111 |
| D29677_at | Human mRNA for KIAA0054 "gene," complete cds | 20 | 20 | 20 | 20 | 20 | 20 |
| D29805_at | Human mRNA for "beta-1,4-galactosyltransferase," complete cds | 291 | 77 | 171 | 116 | 96 | 82 |
| D29810_at | Human mRNA for unknown "product," partial cds | 29 | 20 | 20 | 20 | 20 | 53 |
| D29833_at | Human mRNA for salivary protein rich peptide "P-B," complete cds | 50 | 20 | 20 | 28 | 46 | 97 |
| D29954_at | Human mRNA for KIAA0056 "gene," partial cds | 159 | 120 | 203 | 146 | 449 | 397 |
| D29956_at | Human mRNA for KIAA0055 "gene," complete cds | 20 | 49 | 21 | 74 | 20 | 55 |
| D29958_at | Human mRNA for KIAA0116 "gene," partial cds | 63 | 39 | 20 | 88 | 33 | 45 |
| D29963_at | Human SFA-1 (a member of transmembrane 4 superfamily) "mRNA," complete cds | 277 | 482 | 415 | 445 | 475 | 331 |
| D29992_at | Human mRNA for placental protein 5 "(PP5)," complete cds | 20 | 20 | 20 | 20 | 35 | 20 |
| D30036_at | Human mRNA for phosphatidylinositol transfer protein "(PI-TPalpha)," complete cds | 20 | 33 | 20 | 20 | 20 | 82 |
| D30037_at | Human mRNA for phosphatidylinositol transfer protein "(PI-TPbeta)," complete cds | 85 | 41 | 49 | 44 | 105 | 45 |
| D30655_at | Human mRNA for eukaryotic initiation factor 4AII | 391 | 728 | 949 | 878 | 315 | 614 |
| D30715_xpt5_s_at | exon2s from Human PAP (pancreatitis-associated protein) "gene," 5'-flanking region. /gb=D30715 /ntype=DNA /annot=exon | 20 | 65 | 20 | 27 | 76 | 125 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| D30742_at | Human mRNA for calmodulin-dependent protein kinase "IV," complete cds | 20 | 20 | 20 | 20 | 20 | 20 |
| D30755_at | Human mRNA for KIAA0113 "gene," partial cds | 66 | 116 | 20 | 78 | 127 | 20 |
| D30756_at | Human mRNA for KIAA0049 "gene," complete cds | 106 | 84 | 109 | 103 | 195 | 107 |
| D30758_at | Human mRNA for KIAA0050 "gene," complete cds | 139 | 198 | 81 | 124 | 75 | 211 |
| D31628_s_at | Human gene for 4-hydroxyphenylpyruvic acid dioxygenase "(HPD)," complete cds | 25 | 20 | 72 | 21 | 115 | 140 |
| D31716_at | Human mRNA for GC box binding "protein," complete cds | 70 | 33 | 45 | 22 | 20 | 77 |
| D31762_at | Human mRNA for KIAA0057 "gene," complete cds | 20 | 20 | 20 | 20 | 20 | 20 |
| D31763_at | Human mRNA for KIAA0065 "gene," complete cds | 48 | 35 | 68 | 34 | 20 | 76 |
| D31784_at | Human mRNA for KIAA0064 "gene," complete cds | 117 | 57 | 20 | 20 | 20 | 80 |
| D31765_at | Human mRNA for KIAA0061 "gene," partial cds | 240 | 172 | 293 | 210 | 265 | 301 |
| D31766_at | Human mRNA for KIAA0060 "gene," complete cds | 138 | 85 | 162 | 157 | 397 | 20 |
| D31767_at | Human mRNA for KIAA0058 "gene," complete cds | 236 | 205 | 620 | 209 | 395 | 204 |
| D31784_at | Human mRNA for cadherin-6 | 44 | 20 | 20 | 20 | 20 | 20 |
| D31797_at | Human CD40 ligand (CD40L) "gene," 5'flanking region and | 20 | 46 | 35 | 20 | 20 | 46 |
| D31815_at | Human mRNA for SMP-30 (senescence marker "protein-30)," complete cds | 20 | 43 | 20 | 20 | 20 | 67 |
| D31833_s_at | Humsn mRNA for vasopressin V1b "receptor," complete cds | 20 | 20 | 20 | 20 | 20 | 20 |
| D31840_s_at | Human DRPLA mRNA for "ORF," complete cds | 20 | 20 | 54 | 71 | 20 | 20 |
| D31846_at | Human gene for aquaporin-2 water "channel," "exon1–4," complete cds | 402 | 424 | 353 | 370 | 870 | 594 |
| D31883_at | Human mRNA for KIAA0059 "gene," complete cds | 567 | 431 | 341 | 210 | 344 | 20 |
| D31884_at | Human mRNA for KIAA0063 "gene," complete cds | 209 | 191 | 143 | 182 | 342 | 257 |
| D31885_at | Human mRNA for KIAA0069 "gene," partial cds | 76 | 103 | 393 | 205 | 282 | 182 |
| D31886_at | Human mRNA for KIAA0066 "gene," partial cds | 20 | 20 | 20 | 20 | 20 | 20 |
| D31887_at | Human mRNA for KIAA0062 "gene," partial cds | 83 | 20 | 100 | 20 | 97 | 20 |
| D31888_at | Human mRNA for KIAA0071 "gene," partial cds | 56 | 28 | 62 | 20 | 199 | 50 |
| D31889_at | Human mRNA for KIAA0072 "gene," partial cds | 33 | 29 | 35 | 20 | 158 | 20 |
| D31890_at | Human mRNA for KIAA0070 "gene," partial cds | 135 | 186 | 267 | 218 | 55 | 188 |
| D31891_at | Human mRNA for KIAA0067 "gene," complete cds | 99 | 64 | 79 | 145 | 328 | 309 |
| D31897_at | Human mRNA for Doc2 (Double "C2)," complete cds | 141 | 25 | 27 | 125 | 188 | 66 |
| D32001_at | Human HuSAA1g gene for serum amyloid A1 "gamma," exon 3 and intron 3 | 86 | 37 | 95 | 41 | 165 | 153 |
| D32002_s_at | Human mRNA for nuclear cap binding "protein," complete cds | 20 | 20 | 20 | 20 | 20 | 20 |
| D32050_at | Human mRNA for alanyl-tRNA "synthetase," complete cds | 41 | 166 | 268 | 111 | 154 | 122 |
| D32129_f_at | Human mRNA for HLA class-1 (HLAA-A26) heavy "chain," complete cds (clone cMY-1) | 753 | 1884 | 1462 | 1368 | 405 | 1528 |
| D32202_at | Human mRNA for alpha 1C adrenergic receptor isoform "2," complete cds | 44 | 20 | 20 | 20 | 84 | 82 |
| D37781_s_at | Human mRNA for protein-tyrosine phosphatase "HPTPeta," complete cds | 20 | 20 | 20 | 20 | 20 | 20 |
| D37931_at | Human mRNA for RNase "4," complete cds | 41 | 70 | 68 | 107 | 161 | 101 |
| D37965_at | Human mRNA for PDGF receptor beta-like tumor suppressor "(PRLTS)," complete cds | 20 | 20 | 20 | 20 | 20 | 33 |
| D37984_s_at | Human mRNA for DNA helicase "Q1," partial cds | 20 | 20 | 29 | 20 | 39 | 20 |
| D38024_at | Human facioscapulohumeral muscular dystriphy (FSHD) gene "region," D4Z4 tandem repeat unit | 20 | 20 | 20 | 20 | 328 | 80 |
| D38037_at | Human mRNA for FK506-binding protein 12kDa (hFKBP-12) "homologue," complete cds | 20 | 20 | 20 | 20 | 52 | 24 |
| D38047_at | Human mRNA for 26S proteasome subunit "p31," complete cds | 481 | 298 | 527 | 541 | 347 | 700 |
| D38048_at | Human mRNA for proteasome subunit "z," complete cds | 264 | 173 | 196 | 131 | 20 | 138 |
| D38073_at | Human mRNA for hRlf beta subunit (p102 "protein)," complete cds | 44 | 84 | 95 | 97 | 31 | 116 |
| D38076_at | Human mRNA for RanBP1 (Ran-binding protein "1)," cpmplete cds | 106 | 134 | 46 | 215 | 65 | 472 |
| D38081_at | Human mRNA for thromboxane A2 "receptor," complete cds | 20 | 20 | 20 | 20 | 45 | 20 |
| D38122_at | Human mRNA for Fas "ligand," complete cds | 20 | 20 | 20 | 20 | 28 | 20 |
| D38128_at | Human IP gene for prostacyclin receptor | 20 | 20 | 20 | 20 | 20 | 20 |
| D38145_at | Human mRNA for prostacyclin "synthase," complete cds | 40 | 48 | 29 | 26 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| D38163_s_at | Human mRNA for a1(XIX) collagen "chain," complete cds | 20 | 40 | 20 | 20 | 20 | 81 |
| D38251_s_at | Human mRNA for RPB5 "(XAP4)," complete cds | 20 | 20 | 20 | 20 | 20 | 99 |
| D38293_at | Human mRNA for clathrin-like "protein," complete cds | 35 | 83 | 61 | 42 | 20 | 35 |
| D38305_at | Human mRNA for "Tob," complete cds | 143 | 176 | 255 | 77 | 174 | 83 |
| D38437_f_at | Human DNA mismatch repair mRNA | 20 | 20 | 20 | 20 | 20 | 25 |
| D38449_at | Human mRNA for G protein-coupled "receptor," complete cds | 22 | 20 | 20 | 20 | 289 | 20 |
| D38462_at | Human gene for a1 chain of type XIX "collagen," exon +3'/gb=D38462 /ntype=DNA /annot=exon | 20 | 20 | 20 | 20 | 20 | 20 |
| D38491_at | Human mRNA for KIAA0117 "gene," partial cds | 20 | 20 | 20 | 20 | 20 | 20 |
| D38496_s_at | Human mRNA for "LZTR-1," complete cds | 39 | 20 | 20 | 20 | 73 | 20 |
| D38498_f_at | Human PMS5 mRNA (yeast mismatch repair gene PMS1 "homologue)," partial cds (C-terminal region) | 20 | 20 | 27 | 20 | 37 | 20 |
| D38500_at | Human PMS6 mRNA (yeast mismatch repair gene PMS1 "homologue)," partial cds (C-terminal region) | 20 | 20 | 20 | 20 | 34 | 20 |
| D38502_at | Human PMS4 mRNA (yeast mismatch repair gene PMS1 "homologue)," partial cds (C-terminal region) | 20 | 20 | 20 | 20 | 20 | 20 |
| D38503_at | Human PMS8 mRNA (yeast mismatch repair gene PMS1 "homologue)," partial cds (C-terminal retion) | 20 | 20 | 20 | 20 | 20 | 20 |
| D38521_at | Human mRNA for KIAA0077 "gene," partial cds | 58 | 64 | 109 | 77 | 170 | 33 |
| D38522_at | Human mRNA for KIAA0080 "gene," partial cds | 20 | 31 | 41 | 20 | 20 | 53 |
| D38524_at | Human mRNA for 5'-nucleotidase | 37 | 20 | 90 | 56 | 54 | 86 |
| D38535_at | Human mRNA for PK-120 | 162 | 31 | 144 | 220 | 406 | 176 |
| D38537_s_at | | 20 | 20 | 20 | 20 | 20 | 33 |
| D38548_at | Human mRNA for KIAA0076 "gene," complete cds | 404 | 417 | 447 | 445 | 1301 | 668 |
| D38549_at | Human mRNA for KIAA0068 "gene," partial cds | 201 | 89 | 185 | 107 | 46 | 104 |
| D38550_at | Human mRNA for KIAA0075 "gene," partial cds | 20 | 45 | 101 | 34 | 20 | 105 |
| D38551_at | Human mRNA for KIAA0078 "gene," complete cds | 64 | 44 | 95 | 68 | 69 | 34 |
| D38522_at | Human mRNA for KIAA0073 "gene," partial cds | 54 | 53 | 55 | 73 | 20 | 157 |
| D38553_at | Human mRNA for KIAA0074 "gene," partial cds | 116 | 64 | 97 | 25 | 188 | 36 |
| D38555_at | Human mRNA for KIAA0079 "gene," complete cds | 33 | 22 | 20 | 77 | 20 | 23 |
| D38583_at | Human mRNA for "calgizzarin," complete cds | 2101 | 841 | 1920 | 1456 | 1023 | 1657 |
| D38751_at | Human mRNA for Kid (kinesin-like DNA binding "protein)," complete cds | 20 | 70 | 20 | 20 | 110 | 243 |
| D42038_at | Human mRNA for KIAA0087 "gene," complete cds | 20 | 20 | 20 | 20 | 20 | 20 |
| D42039_at | Human mRNA for KIAA0081 "gene," partial cds | 27 | 20 | 20 | 20 | 20 | 20 |
| D42040_s_at | Human mRNA for KIAA9001 "gene," complete cds | 94 | 224 | 418 | 232 | 320 | 225 |
| D42041_at | Human mRNA for KIAA0088 "gene," partial cds | 83 | 73 | 68 | 88 | 283 | 60 |
| D42032_at | Human mRNA for KIAA0084 "gene," partial cds | 155 | 104 | 168 | 67 | 206 | 166 |
| D42044_at | Human mRNA for KIAA0090 "gene," partial cds | 73 | 53 | 36 | 42 | 99 | 76 |
| D42045_at | Human mRNA for KIAA0086 "gene," complete cds | 20 | 20 | 23 | 31 | 20 | 20 |
| D42046_at | Human mRNA for KIAA0083 "gene," partial cds | 94 | 168 | 20 | 20 | 572 | 415 |
| D42047_at | Human mRNA for KIAA0089 "gene," partial cds | 54 | 70 | 53 | 137 | 144 | 81 |
| D42053_at | Human mRNA for KIAA0091 "gene," complete cds | 94 | 153 | 130 | 54 | 420 | 238 |
| D42054_at | Human mRNA for KIAA0092 "gene," partial cds | 35 | 65 | 132 | 200 | 138 | 45 |
| D42055_at | Human mRNA for KIAA0094 "gene," partial cds | 20 | 20 | 48 | 66 | 74 | 20 |
| D42063_at | Human mRNA for KIAA0095 "gene," complete cds | 20 | 44 | 40 | 40 | 125 | 20 |
| D42072_at | Human mRNA for RanBP2 (Ran-binding protein "2)," complete cds | 20 | 20 | 20 | 20 | 20 | 20 |
| D42073_at | Human mRNA for NF1 "N-isoform-exon11," complete cds | 36 | 20 | 20 | 20 | 20 | 20 |
| D42084_at | Human mRNA for "reticulocalbin," complete cds | 135 | 418 | 195 | 192 | 179 | 114 |
| D42085_at | Human mRNA for KIAA0094 "gene," partial cds | 106 | 81 | 174 | 112 | 20 | 52 |
| D42087_at | Human mRNA for KIAA0118 "gene," partial cds | 110 | 20 | 20 | 20 | 420 | 20 |
| D42108_at | Human mRNA for phospholipase "C," complete cds | 75 | 54 | 50 | 64 | 20 | 41 |
| D42123_at | Human mRNA for "ESP1/CRP2," complete cds | 223 | 69 | 179 | 156 | 172 | 246 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| D42138_at | Human mRNA for "PIG-B," complete cds | 52 | 70 | 20 | 47 | 20 | 81 |
| D43636_at | Human mRNA for KIAA0096 "gene," partial cds | 20 | 20 | 20 | 20 | 20 | 20 |
| D43638_at | Human mRNA for MTG8a "protein," complete cds | 20 | 20 | 50 | 44 | 55 | 20 |
| D43642_at | Human YL-1 mRNA for YL-1 protein (nuclear protein with DNA-binding "ability") complete cds | 164 | 197 | 402 | 239 | 101 | 262 |
| D43682_s_at | Human mRNA for very-long-chain acyl-CoA dehydrogenase "(VLCAD)," complete cds | 345 | 557 | 1205 | 1127 | 981 | 448 |
| D43767_at | Human mRNA for "chemokine," complete cds | 67 | 55 | 94 | 97 | 20 | 45 |
| D43768_at | Human mRNA for SCM-1 (single cysteine "motif-1)," complete cds | 20 | 20 | 20 | 20 | 20 | 20 |
| D43772_at | Human squamous cell carcinoma of esophagus mRNA for GRB-7 SH2 domain "protein," complete cds | 45 | 90 | 20 | 62 | 20 | 20 |
| D43947_at | Human mRNA for KIAA0100 "gene," complete cds | 20 | 52 | 20 | 128 | 26 | 47 |
| D43948_at | Human mRNA for KIAA0097 "gene," complete cds | 86 | 158 | 129 | 52 | 55 | 51 |
| D43949_at | Human mRNA for KIAA0082 "gene," partial cds | 145 | 111 | 34 | 92 | 388 | 283 |
| D43950_at | Human mRNA for KIAA0098 "gene," partial cds | 27 | 21 | 62 | 151 | 152 | 213 |
| D43951_at | Human mRNA for KIAA0099 "gene," complete cds | 53 | 76 | 86 | 20 | 20 | 20 |
| D43968_at | Human AML1 mRNA for AML1b protein (alternatively spliced "product)," complete cds | 173 | 94 | 162 | 36 | 87 | 92 |
| D44466_at | Human mRNA for proteasome subunit "p112," complete cds | 44 | 20 | 60 | 17 | 286 | 48 |
| D45132_at | Human kidney mRNA for zinc-finger DNA-binding "protein," complete cds | 300 | 603 | 292 | 34 | 81 | 90 |
| D45248_at | Human mRNA for proteasome activator hPA28 subunit "beta," complete cds | 1127 | 4549 | 9294 | 269 | 60 | 416 |
| D45370_at | Human apM2 mRNA for GS2374 (unknown product specific to adipose "tissue)," complete cds | 178 | 194 | 268 | 9828 | 9991 | 4564 |
| D45371_at | Human apM1 mRNA for GS3109 (novel adipose specific collagen-like "factor)," complete cds | 104 | 20 | 20 | 151 | 860 | 392 |
| D45399_at | Human adult neural retina mRNA for human cone cGMP phosphodiesterase gamma "subunit," complete cds | 84 | 45 | 132 | 20 | 20 | 20 |
| D45906_at | Human mRNA for "LIMK-2," complete cds | 88 | 27 | 134 | 80 | 20 | 67 |
| D45917_s_at | Human mRNA for "TIMP-3," partial cds (C-terminus region) | 20 | 20 | 36 | 100 | 312 | 27 |
| D49354_s_at | Human mRNA for enhancer protein in hsp70 "gene," partial cds | 49 | 20 | 37 | 52 | 269 | 26 |
| D49357_at | Human mRNA for S-adenosylmethionine "synthetase," complete cds | 77 | 97 | 38 | 20 | 20 | 26 |
| D49372_s_at | Human mRNA for "eotaxin," complete cds | 226 | 173 | 199 | 42 | 98 | 65 |
| D49387_at | Human mRNA for NADP dependent leukotriene b4 "12-hydroxydehydrogenase," partial cds /gb=D49387 /ntype=RNA | 20 | 20 | 20 | 189 | 238 | 225 |
| D49394_at | Human mRNA for serotonin 5-HT3 "receptor," complete cds | 104 | 22 | 116 | 20 | 154 | 20 |
| D49396_at | Human mRNA for Apo1_Human (MERS(Aop1-Mouse)-like "protein)," complete cds | 239 | 293 | 359 | 58 | 129 | 81 |
| D49400_at | Human fetus brain mRNA for vacuolar "ATPase," complete cds | 132 | 132 | 217 | 375 | 619 | 629 |
| D49410_at | Human gene for interleukin 3 receptor alpha subunit | 71 | 85 | 136 | 142 | 253 | 183 |
| D49487_s_at | Human mRNA for obese "gene," complete cds | 20 | 116 | 39 | 93 | 551 | 81 |
| D49488_at | Human mRNA for alpha-tocopherol transfer "protein," complete cds | 83 | 92 | 219 | 20 | 142 | 36 |
| D49489_at | Human mRNA for protein disulfide isomerase-related protein "P5," complete cds | 148 | 73 | 20 | 109 | 20 | 80 |
| D49490_at | Human mRNA for protein disulfide isomerase-related protein "(PDIR)," complete cds | 20 | 20 | | 20 | 143 | 20 |
| D49493_at | Human gene for human bone morphogenetic protein-3b | 20 59 20 20 | | | | | |
| | | 20 125 | | | | | |
| D49677_at | Human U2AF1-RS2 "mRNA," complete cds | 20 | 20 | 20 | 20 | 20 | 20 |
| D49728_at | Human NAK1 mRNA for DNA binding "protein," complete cds | 37 | 112 | 367 | 118 | 793 | 407 |
| D49738_at | Human cytoskeleton associated protein (CG22) "mRNA," complete cds | 114 | 186 | 322 | 113 | 160 | 242 |
| D49742_at | Human mRNA for HGF activator like "protein," complete cds | 20 | 20 | 20 | 20 | 20 | 20 |
| D49817_at | Human mRNA for fructose "6-phosphate,2-kinase/fructose" "2,6-bisphosphatase," complete cds | 20 | 59 | 20 | 20 | 22 | 55 |
| D49818_at | Human mRNA for fructose "6-phosphste,2-kinase/fructose" "2,6-bisphosphatase," partial cds | 170 | 46 | 181 | 123 | 211 | 20 |
| D49824_s_at | Human HLA-B null allele mRNA | 20 | 20 | 20 | 20 | 20 | 20 |
| D49824_at | Human Liver mRNA for interferon-gamma inducing "factor(IGIF)," complete cds | 2821 | 3076 | 5271 | 4505 | 776 | 3898 |
| D49950_at | Human fetus brain mRNA for membrane glycoprotein "M6," complete cds | 126 | 25 | 20 | 20 | 20 | 20 |
| D49958_at | | 55 | 20 | 20 | 20 | 105 | 24 |
| D50063_at | Human mRNA for proteasome subunit p40_/ Mov34 "protein," complete cds | 108 | 183 | 198 | 190 | 400 | 261 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| D50310_at | Human mRNA for cyclin "I," complete cds | 247 | 325 | 237 | 161 | 143 | 221 |
| D50312_at | Human mRNA for "uKATP-1," complete cds | 20 | 20 | 20 | 20 | 20 | 20 |
| D50370_at | Human mRNA for nucleosome assembly "protein," complete cds | 20 | 37 | 20 | 20 | 20 | 41 |
| D50402_at | Human mRNA for "NRAMP1," complete cds | 20 | 20 | 20 | 20 | 189 | 20 |
| D50405_at | Human mRNA for RPD3 "protein," complete cds | 137 | 148 | 158 | 135 | 20 | 67 |
| D50477_s_at | Human mRNA for mambrane-type matrix metalioproteinase "3," complete cds | 32 | 20 | 105 | 20 | 356 | 21 |
| D50487_at | Human mRNA for RNA helicase "(HRH1)," complete cds | 20 | 20 | 20 | 38 | 30 | 20 |
| D50495_at | Human mRNA for transcription elongation factor "S-II," "hS-II-T1," complete cds | 35 | 55 | 233 | 20 | 20 | 20 |
| D50525_at | Human mRNA for Tf-227H /gb=D50525 /ntype=RNA | 20 | 20 | 20 | 83 | 26 | 109 |
| D50532_at | Human mRNA for macophage lectin "2," complete cds | 20 | 20 | 20 | 20 | 20 | 20 |
| D50550_at | Human LLGL "mRNA," complete cds | 37 | 20 | 20 | 20 | 20 | 20 |
| D50582_at | Human gene for inward rectifier K "channel," complete cds | 73 | 48 | 27 | 48 | 151 | 178 |
| D50640_at | Human DNA for phosphodiearease 3B | 20 | 95 | 32 | 20 | 29 | 29 |
| D50645_at | Human mRNA for "SDF2," complete cds | 20 | 44 | 89 | 72 | 44 | 36 |
| D50663_at | Human mRNA for TCTEL1 "gene," complete cds | 199 | 269 | 210 | 211 | 102 | 350 |
| D50678_at | Human mRNA for apolipoprotein E receptor "2," complete cds | 25 | 20 | 20 | 20 | 20 | 20 |
| D50683_at | Human mRNA for TGF-betaIIR "alpha," complete cds | 100 | 120 | 20 | 95 | 74 | 42 |
| D50692_at | Human mRNA for c-myc binding "protein," complete cds | 136 | 31 | 87 | 111 | 292 | 190 |
| D50810_at | Human mRNA for placental leucine "aminopeptidase," complete cds | 68 | 20 | 115 | 30 | 273 | 20 |
| D50840_at | Human mRNA for ceramide "glucosyltransferase," complete cds | 851 | 209 | 462 | 180 | 54 | 177 |
| D50855_s_at | Human mRNA for Ca-sensing "receptor," complete cds | 39 | 88 | 64 | 20 | 170 | 114 |
| D50857_at | Human DOCK180 protein "mRNA," complete cds | 47 | 84 | 166 | 96 | 226 | 121 |
| HG1877-HT1917_s_at | Myelin Basic "Protein," Alt. Splice Form 4 | 20 | 20 | 48 | 20 | 20 | 20 |
| HG1879-HT1919_at | Ras-Like Protein Tc10 | 28 | 96 | 69 | 20 | 20 | 108 |
| HG1980-HT2023_at | "Tubulin," Beta 2 | 903 | 1132 | 2507 | 1529 | 844 | 1006 |
| HG1996-HT2044_at | Guanine Nucleotide-Binding Protein "Rap2," Ras-Oncogene Related | 20 | 20 | 20 | 20 | 20 | 20 |
| HG20O7-HT2056_s_at | Proto-Oncogene "Sno," Alt. Splice N | 20 | 20 | 27 | 26 | 20 | 20 |
| HG2028-HT2082_at | Laminin, A Polypeptide | 85 | 33 | 35 | 49 | 73 | 146 |
| HG2036-HT2090_at | Stimulatory Gdp/Gtp Exchange Protein For C-Ki-Ras P21 And Smg P21 | 100 | 20 | 20 | 20 | 334 | 25 |
| HG2059-HT2114_at | Arrestin, Beta 2 | 38 | 78 | 25 | 21 | 20 | 50 |
| HG2075-HT2137_s_at | Camp-Responsive Element "Modulator," Alt. Splice 1 | 20 | 20 | 20 | 20 | 37 | 20 |
| HG2090-HT2152_s_at | External Membrane "Protein," 130 Kda (Gb:Z22971) | 55 | 132 | 109 | 31 | 20 | 134 |
| HG210-HT210_s_at | Galactokinase 2 | 33 | 83 | 83 | 72 | 170 | 99 |
| HG213-HT2208_f_at | Beta-1-Glycoprotein "1," Pregnancy-Specific (Gb:M25384) | 20 | 20 | 20 | 20 | 20 | 20 |
| HG2147-HT2217_at | Mucin "3," Intestinal (Gb:M55405) | 724 | 1428 | 1745 | 1308 | 1593 | 684 |
| HG2147-HT2217_r_at | Mucin "3," Intestinal (Gb:M55405) | 20 | 20 | 50 | 20 | 1614 | 541 |
| HG2148-HT2218_f_at | Mucin "3," Intestinal (Gb:M55406) | 36 | 70 | 133 | 51 | 184 | 84 |
| HG2149-HT2219_at | Mucin (Gb:M57417) | 22 | 42 | 256 | 20 | 479 | 186 |
| HG2152-HT2222_at | Zinc Finger Protein 92 | 20 | 20 | 20 | 21 | 20 | 25 |
| HG2157-HT2227_at | Mucin "4," Tracheobronchial | 55 | 20 | 20 | 20 | 20 | 20 |
| HG2160-HT2230_at | Translocation-Associated Notch (Drosophila) Homolog 1 | 20 | 132 | 109 | 31 | 258 | 61 |
| HG2161-HT2231_at | Protein Kinase "Ht31," Camp-Dependent | 20 | 83 | 83 | 20 | 20 | 20 |
| HG2167-HT2237_at | 12-Lipoxygenase | 99 | 95 | 64 | 143 | 20 | 76 |
| HG2171-HT2241_at | 12-Lipoxygenase | 20 | 20 | 20 | 20 | 20 | 20 |
| HG2171-HT2241_r_at | "Myosin," Heavy Polypeptide "10," Non-Muscle | 26 | 20 | 78 | 20 | 20 | 186 |
| HG2175-HT2245_s_at | Paired Box Hup1 (Gb:X15042) | 20 | 20 | 20 | 20 | 20 | 20 |
| HG2188-HT2258_at | | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| HG2190-HT2260_at | Crystallin, Beta B3 (Gb:X15144) | 20 | 20 | 20 | 20 | 49 | 20 |
| HG2191-HT2261_at | Crystallin, Beta B3 (Gb:X15145) | 20 | 24 | 20 | 20 | 20 | 20 |
| HG2197-HT2267_s_at | "Cottage," Type "VII," Alpha 1 | 20 | 99 | 155 | 111 | 696 | 224 |
| HG2228-HT2305_at | Crystallin, Beta B | 20 | 20 | 20 | 20 | 20 | 20 |
| HG2229-HT2308_at | Paired Box Hup1 (Gb:X15250) | 20 | 20 | 20 | 20 | 20 | 20 |
| HG2238-HT2321_s_at | Nuclear Mitotic Apparatus Protein "1," Alt. Splice Form 2 | 40 | 31 | 296 | 436 | 786 | 256 |
| HG2239-HT2324_at | Potassium Channel Protein (Gb:Zl1585) | 20 | 20 | 20 | 20 | 20 | 84 |
| HG2239-HT2324_r_at | Potassium Channel Protein (Gb:Zl1585) | 41 | 20 | 138 | 93 | 1169 | 375 |
| HG2247-HT2332_at | Major Intrinsic Protein | 20 | 20 | 20 | 20 | 20 | 20 |
| HG2255-HT2344_f_at | Phosphoribosyl Pyrophosphate "Synthetase," Subunit Iii | 20 | 20 | 20 | 20 | 20 | 44 |
| HG2259-HT2348_s_at | "Tubulin," Alpha "1," isoform 44 | 20 | 20 | 20 | 20 | 20 | 20 |
| HG2260-HT2349_s_at | Duchenne Muscular Dystrophy Protein (Dmd) | 20 | 20 | 20 | 20 | 81 | 20 |
| HG2261-HT2351_s_at | "Antigen," Prostate "Specific," Alt. Splice Form 2 | 20 | 20 | 20 | 20 | 55 | 27 |
| HG2261-HT2352_at | Antigen, Prostate "Specific," Alt. Splice Form 3 | 20 | 20 | 20 | 20 | 30 | 20 |
| HG2264-HT2360_at | Alpase, Ca2+ "Transporting," Plasma Membrane "1," Alt. Splice 6 | 180 | 26 | 20 | 103 | 400 | 326 |
| HG2271-HT2367_at |  | 20 | 20 | 20 | 20 | 20 | 21 |
| HG2271-HT2367_s_at | Profilaggrin | 20 | 20 | 20 | 20 | 20 | 20 |
| HG2274-HT2370_at | Rna Polymerase "II," 14.5 Kda Subunit | 86 | 98 | 20 | 51 | 20 | 90 |
| HG2279-HT2375_at | Triosephosphate isomerase | 1112 | 872 | 1858 | 1837 | 788 | 910 |
| HG2280-HT2376_at | D-Amino-Acid Oxidase | 176 | 102 | 232 | 121 | 201 | 153 |
| HG2290-HT2386_at | Calcitonin | 71 | 20 | 20 | 20 | 25 | 20 |
| HG2309-HT2405_at | Insulin-Like Growth Factor Ib | 20 | 20 | 20 | 20 | 20 | 57 |
| HG2314-HT2410_at | 4-Beta-Galactosyltransferase | 20 | 20 | 20 | 59 | 20 | 34 |
| HG2320-HT2416_at | Integrin, Beta 3 Subunit | 127 | 100 | 20 | 20 | 20 | 20 |
| HG2325-HT2421_at | Retinoic Acid "Receptor," Gamma 2 | 22 | 23 | 20 | 21 | 20 | 20 |
| HG2339-HT2435_at | Nuclear Factor "1," Variant Hepatic | 20 | 22 | 20 | 28 | 20 | 20 |
| HG2348-HT2444_s_at | Peptide Yy | 20 | 20 | 137 | 20 | 20 | 92 |
| HG2358-HT4858_s_at | Proto-Oncogene "Ets-1," Alt. Splice 2 | 20 | 20 | 20 | 20 | 20 | 20 |
| HG2365-HT2461_at | Glyceraldehyde-3-Phosphate Dehydrogenase (Gb:K03121) | 20 | 20 | 20 | 20 | 31 | 20 |
| HG2367-HT2463_at | Trithorax Homolog Hrx | 20 | 20 | 20 | 20 | 95 | 50 |
| HG2379-HT3996_s_at | Serine "Hydroxymethyltransferase," "Cytosolic," Alt. Splice 2 | 20 | 20 | 20 | 20 | 20 | 20 |
| HG23790-HT3997_s_at | Serine "Hydroxymethyltransferase," "Cytosolic," Alt. Splice 3 | 20 | 20 | 20 | 20 | 20 | 20 |
| HG2380-HT2476_s_at | Adp-Ribosylarginine Hydrolase | 20 | 20 | 20 | 20 | 89 | 96 |
| HG2414-HT2510_s_at | Cystathionine Beta "Synthase," Alt. Splice 3 | 20 | 20 | 132 | 72 | 186 | 53 |
| HG2415-HT2511_at | Prostaglandin Receptor Ep1 Subtype | 20 | 20 | 20 | 20 | 20 | 57 |
| HG2416-HT2512_at | Transcription Factor E2f-2 | 135 | 95 | 195 | 113 | 515 | 301 |
| HG2417-HT2513_at | Gal Beta "1,3(4)Glcnac" "Alpha2,3-Sialyltransferase" | 22 | 20 | 29 | 35 | 75 | 20 |
| HG243-HT243_s_at | Dynein, Heavy "Chain," Cytoplasmic | 20 | 30 | 20 | 20 | 20 | 20 |
| HG2441-HT2537_s_at | Lowe Oculocerebrenal Syndrome Protein | 34 | 28 | 97 | 20 | 189 | 96 |
| HG2442-HT2538_at | Retinoblastoma "Protein," Mutated | 32 | 39 | 179 | 59 | 31 | 53 |
| HG2460-HT2556_at | Tropomyosin, "Alpha," "Muade," Alt. Splice "2," Skeletal Muscle (Fibroblast) | 88 | 31 | 65 | 22 | 20 | 20 |
| HG2463-HT2559_at | Integrin Beta 1 (Gb:M34189) | 20 | 50 | 20 | 31 | 119 | 54 |
| HG2465-HT4871_at | Guanine Nucleotide-Binding Protein G25k | 194 | 63 | 144 | 125 | 243 | 192 |
| HG2479-HT2575_at | Dna-Binding Protein "Ap-2," Alt. Splice 3 | 45 | 37 | 27 | 20 | 20 | 59 |
| HG2479-HT2575_s_at | Helix-Loop-Helix Protein Sef2-1d | 20 | 20 | 20 | 20 | 20 | 20 |
| HG2480-HT2576_at | Fmlp-Related Receptor I | 47 | 33 | 82 | 43 | 20 | 31 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| HG2492-HT2588_at | Glutamate Receptor Subunit | 20 | 20 | 20 | 20 | 20 | 20 |
| HG2507-HT2603_at | Potassium "Channel," Voltage-Gated Kcnc1 | 54 | 20 | 20 | 25 | 20 | 86 |
| HG2510-HT2606_at | Ras-Specific Guanine Nucleotide-Releasing Factor | 20 | 20 | 20 | 20 | 20 | 20 |
| HG2525-HT2621_at | Helix-Loop-Helix Protein Delta "Max," Alt. Splice 1 | 83 | 55 | 20 | 48 | 345 | 250 |
| HG2530-HT2626_at | Adenylyl Cyclase-Associated Protein 2 | 20 | 20 | 20 | 20 | 105 | 20 |
| HG2535-HT2634_at | Heterogeneous Nuclear Ribonucleoprotein C | 20 | 20 | 20 | 20 | 20 | 20 |
| HG2562-HT2658_s_at | A-Myb (Gb:X13294) | 20 | 20 | 20 | 83 | 20 | 20 |
| HG2564-HT2660_s_at | Gamma-Aminobutyric Acid (Gaba) A "Receptor," Alpha Subunit | 20 | 20 | 21 | 22 | 20 | 20 |
| HG2566-HT4792_r_at | Microtubule-Associated Protein "Tau," Alt. Splice "3," Exon 8 | 20 | 20 | 20 | 20 | 20 | 20 |
| HG2566-HT4867_at | Microtubule-Associated Protein "Tau," Alt. Splice "5," Exon 4a | 286 | 307 | 355 | 174 | 409 | 491 |
| HG2573-HT2669_at | Zinc Finger Protein Kup (Gb:X16576) | 20 | 20 | 20 | 20 | 67 | 20 |
| HG2591-HT2687_s_at | Transcription Factor Itf-1 | 20 | 20 | 20 | 20 | 20 | 20 |
| HG25930-HT26386_at |  | 20 | 20 | 20 | 20 | 127 | 26 |
| HG2600-HT2696_at | Guanine Nucleotide-Binding Protein "Rap2b," Ras-Oncogene Related | 20 | 20 | 20 | 20 | 20 | 20 |
| HG2602-HT2698_at | Succinate "Dehydrogenase," Flavoprotein Subunit | 20 | 20 | 48 | 20 | 163 | 20 |
| HG2604-HT2700_at | Pan-2 | 20 | 20 | 20 | 20 | 20 | 20 |
| HG2614-HT2710_at | Collagen, Type "Viii," Alpha 1 | 138 | 143 | 68 | 95 | 118 | 36 |
| HG2639-HT2735_s_at | Single-Stranded Dna-Binding Protein Mssp-1 | 110 | 67 | 219 | 183 | 226 | 158 |
| HG2649-HT2745_s_at | Serine/Threonine Protein Kinase Cdk3 | 20 | 20 | 20 | 20 | 20 | 33 |
| HG2662-HT2758_at | Homeotic Protein Emx1 | 20 | 20 | 20 | 20 | 20 | 20 |
| HG2663-HT2759_at | Homeotic Protein Emx2 | 20 | 20 | 20 | 20 | 20 | 20 |
| HG2668-HT2764_at | Bradykinin Receptor | 97 | 46 | 28 | 25 | 34 | 209 |
| HG2686-HT2782_at | Ryanodine Receptor 3 | 20 | 20 | 20 | 20 | 20 | 20 |
| HG2689-HT2785_at | Mucin "5b," Tracheobronchial (Gb:X74955) | 67 | 113 | 26 | 63 | 176 | 117 |
| HG270-HT270_at | Lymphocyte Chemoattractant Factor | 20 | 20 | 20 | 20 | 20 | 20 |
| HG2702-HT2798_r_at | Serine/Threonine Kinase (Gb:225424) | 20 | 20 | 20 | 20 | 20 | 250 |
| HG2705-HT2801_s_at | Serine/Threonine Kinase (Gb:225427) | 90 | 360 | 467 | 231 | 186 | 35 |
| HG2706-HT2802_at | Serine/Threonine Kinase (Gb:225428) | 20 | 20 | 20 | 20 | 151 | 20 |
| HG2707-HT2803_at | Serine/Threonine Kinase (Gb:225429) | 20 | 20 | 20 | 20 | 20 | 20 |
| HG2709-HT2805_at | Serine/Threonine Kinase (Gb:225431) | 20 | 29 | 20 | 21 | 70 | 20 |
| HG2714-HT2810_at | Tyrosine Kinase (Gb:225436) | 20 | 20 | 20 | 20 | 20 | 20 |
| HG2715-HT2811_at | Tyrosine Kinase (Gb:225437) | 24 | 20 | 30 | 23 | 20 | 117 |
| HG2723-HT2819_at | Proto-Oncogene N-Cym | 20 | 20 | 20 | 20 | 20 | 20 |
| HG2724-HT2820_at | Oncogene "Tls/Chop," Fusion Activated | 20 | 20 | 20 | 20 | 20 | 20 |
| HG273-HT273_at |  | 20 | 20 | 20 | 20 | 91 | 20 |
| HG273-HT273_s_at | Lymphocyte Antigen Hla-G3 | 113 | 115 | 470 | 329 | 154 | 71 |
| HG273-HT2827_s_at | "Fibrinogen," A Alpha "Polypeptide," Alt. Splice "2," E | 27 | 76 | 21 | 42 | 452 | 43 |
| HG273-HT2828_s_at | "Fibrinogen," A Alpha "Polypeptide," Alt. Splice "3," E | 20 | 20 | 20 | 20 | 20 | 25 |
| HG2730-HT274_s_at | Gamma-Glutamyltransferase 1 (Gb:J04131) | 20 | 92 | 65 | 99 | 268 | 189 |
| HG2743-HT2845_at | Caldesmon "1," Alt. Splice "3," Non-Muscle | 95 | 20 | 20 | 20 | 20 | 24 |
| HG2743-HT2846_s_at | Caldesmon "1," Alt. Splice "4," Non-Muscle | 113 | 123 | 20 | 20 | 20 | 51 |
| HG2743-HT3926_at | Caldesmon "1," Alt. Splice "6," Non-Muscle | 44 | 37 | 20 | 21 | 31 | 20 |
| HG2755-HT2862_at | T-Plastin | 90 | 27 | 50 | 80 | 55 | 83 |
| HG2788-HT2896_at | Calcyclin | 973 | 3126 | 4602 | 3790 | 3984 | 1515 |
| HG2795-HT2904_at | Neural Cell Adhesion Molecule | 51 | 20 | 38 | 53 | 101 | 20 |
| HG2797-HT2005_at |  | 20 | 20 | 20 | 20 | 20 | 20 |
| HG2797-HT2905_s_at | "Clathrin," Light Polypeptide "B," Alt. Splice 1 | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| HG2797-HT2906_s_at | "Clathrin," Light Polypeptide "B," Alt. Splice 2 | 759 | 20 | 20 | 113 | 20 | 20 |
| HG2809-HT2920_s_at | Lung Surfactant Protein D | 124 | 158 | 362 | 227 | 438 | 114 |
| HG2810-HT2921_at | Homeotic Protein Pl2 | 20 | 20 | 98 | 52 | 60 | 20 |
| HG2815-HT2931_at |  | 2265 | 4370 | 1774 | 1339 | 972 | 1035 |
| HG2815-HT2931_at | "Myosin," Light "Chain," "Alkali;" Smooth Muscle "(Gb:U02629)," "Non-Muscle," Alt. Splice 2 | 1926 | 767 | 1730 | 1500 | 199 | 652 |
| HG2825-HT4023_s_at | "Myosin," Light "Chain," "Alkali;" Smooth Muscle "(Gb:U02629);" Smooth "Muscle," Alt. Splice 4 | 3415 | 6034 | 3570 | 3313 | 3344 | 2134 |
| HG2825-HT2949_at | Ret Transforming Gene | 84 | 63 | 20 | 120 | 232 | 142 |
| HG2841-HT2968_s_at | "Albumin," Alt. Splice 1 | 27 | 20 | 35 | 30 | 20 | 20 |
| HG2841-HT2969_s_at | "Albumin," Alt. Splice "3;" Missplicing In Alloalbumin Venezia | 20 | 20 | 20 | 20 | 20 | 38 |
| HG2841-HT2970_at | Albumin, Alt. Splice 5 | 20 | 28 | 20 | 20 | 20 | 20 |
| HG2846-HT2983_at | Dihydrofolate "Reductase," Alt. Splice 6 | 24 | 20 | 23 | 20 | 97 | 84 |
| HG2850-HT4814_s_at | Biliary "Glycoprotein," Alt. Splice "5," A | 34 | 32 | 44 | 20 | 417 | 60 |
| HG2855-HT2995_at | Heat Shock "Protein," "70 Kda (Gb:Y00371) | 240 | 347 | 487 | 539 | 178 | 379 |
| HG2868-HT3012_s_at | "Xe7," pseudoautosomal "Gene," Alt. Splice 2 | 91 | 107 | 241 | 136 | 371 | 176 |
| HG2873-HT3017_at | Ribosomal Protein L30 Homolog | 4372 | 4508 | 5593 | 5315 | 3389 | 4981 |
| HG2874-HT3018_at | Ribosomal Protein L39 Homolog | 20 | 22 | 20 | 20 | 20 | 20 |
| HG2887-HT3031_r_at | Sry-Related Hmg-Box 12 Protein (Gb:X73039) | 20 | 20 | 20 | 20 | 20 | 20 |
| HG2915-HT3059_f_at | Major Histocompatibility "Complex," Class "I," E (Gb:M20022) | 351 | 720 | 594 | 736 | 345 | 550 |
| HG2917-HT3061_f_at | Major Histocompatibility "Complex," Class "I," E (Gb:M21533) | 370 | 663 | 554 | 642 | 20 | 380 |
| HG2936-HT3080_at | Immunoglobulin Heavy "Chain," Enhancer Element | 58 | 31 | 51 | 117 | 257 | 157 |
| HG2981-HT3125_s_at | "Epican," Alt. Splice 1 | 26 | 82 | 39 | 20 | 20 | 20 |
| HG2981-HT3127_s_at | "Epican," Alt. Splice 11 | 75 | 46 | 59 | 99 | 20 | 20 |
| HG2981-HT3138_s_at | "Epican," Alt. Splice 12 | 20 | 20 | 20 | 20 | 20 | 20 |
| HG2987-HT3136_s_at | Vasoactive Intestinal Peptide | 33 | 26 | 51 | 61 | 29 | 123 |
| HG2992-HT5186_at | Beta-Hexosaminidase, Alpha "Polypeptide," Abnormal Splice Mutation | 20 | 20 | 20 | 73 | 20 | 20 |
| HG2994-HT4850_s_at | "Elastin," Alt. Splice 2 | 346 | 365 | 615 | 341 | 218 | 123 |
| HG2999-HT4756_s_at | Thyroid "Peroxidase," Alt. Splice 2 | 20 | 20 | 20 | 20 | 20 | 27 |
| HG3033-HT3194_at | Spliceosomal Protein Sap 62 | 20 | 20 | 20 | 20 | 125 | 20 |
| HG3033-HT3194_r_at | Spliceosomal Protein Sap 62 | 20 | 20 | 20 | 20 | 412 | 387 |
| HG3039-HT3200_at | Adp-Ribosylation-Like Factor | 76 | 23 | 20 | 52 | 20 | 20 |
| HG3044-HT3742_s_at | "Fibronectin," Alt. Splice 1 | 175 | 20 | 20 | 20 | 68 | 38 |
| HG3063-HT3224_at | Major Histocompatibility "Complex," Class (Gb:L19693) | 20 | 20 | 20 | 20 | 20 | 20 |
| HG3075-HT3236_s_at | Focal Adhesion Kinase | 40 | 44 | 135 | 138 | 20 | 77 |
| HG3076-HT3238_s_at | Heterogeneous Nuclear Ribonucleoprotein "K," Alt. Splice 1 | 239 | 346 | 621 | 546 | 36 | 247 |
| HG3085-HT3254_at | Phosphodiesterase | 25 | 20 | 28 | 20 | 20 | 20 |
| HG3068-HT3263_at | Splicing Factor "Sc35," Alt Splice Form 3 | 20 | 20 | 20 | 61 | 20 | 62 |
| HG3104-HT3280_at | Serine Protease Met1 | 20 | 20 | 20 | 20 | 20 | 20 |
| HG3105-HT3281_s_at | "Atpase," Cu2+ Transporting | 20 | 20 | 20 | 20 | 170 | 70 |
| HG3107-HT3283_s_at | Plasma Membrane Calcium Pump Hpmca2a | 47 | 23 | 50 | 20 | 112 | 150 |
| HG3111-HT311_at | Ribosomal Protein L30 | 1067 | 1484 | 1984 | 1421 | 542 | 749 |
| HG3111-HT3287_at | Autoantigen (Gb:567069) | 20 | 20 | 20 | 56 | 20 | 20 |
| HG311-HT3236_s_at | Golli-Mbp (Gb:L18862) | 20 | 20 | 20 | 20 | 20 | 77 |
| HG3117-HT3291_at | Mps1 (Gb:L20314) | 20 | 20 | 20 | 20 | 20 | 20 |
| HG3123-HT3299_at | Homeotic Protein Gbx2 | 20 | 48 | 55 | 61 | 20 | 62 |
| HG3125-HT3301_s_at | Estrogen Receptor (Gb:S67777) | 20 | 48 | 55 | 58 | 203 | 55 |
| HG3132-HT3308_s_at | Cea "Family," Bi-Like Domain | 41 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| HG3137-HT3313_at | Zinc Finger Protein Znf81 (Gb:X0729) | 84 | 38 | 20 | 41 | 20 | 20 |
| HG3141-HT3317_f_at | Nadh-Ubiquinone "Oxidoreductase," 39 Kda Subunit | 20 | 20 | 20 | 20 | 136 | 54 |
| HG3148-HT3324_s_at | Major Histocompatibility "Complex," Class "Iii," "Rp1," Alt. Splice 1 | 30 | 56 | 45 | 20 | 20 | 123 |
| HG315-HT3315_at | Beta-1-Glycoprotein "11," Pregnancy-Specific | 159 | 20 | 20 | 82 | 181 | 179 |
| HG3162-HT3339_at | Transcription Factor Iia | 241 | 212 | 58 | 205 | 420 | 380 |
| HG3175-HT3352_at | Carcinoembryonic Antigen | 86 | 91 | 122 | 80 | 120 | 49 |
| HG3187-HT3366_s_at | Tyrosine Phosphatase "1," Non-Receptor," Alt. Splice 3 | 20 | 90 | 197 | 123 | 309 | 73 |
| HG3214-HT3391_at | Metallopanstimulin 1 | 4966 | 8561 | 5804 | 4889 | 3342 | 3701 |
| HG3227-HT3404_at | Guanine Nucleotide-Binding Protein Hsr1 | 148 | 20 | 20 | 26 | 277 | 67 |
| HG3231-HT3408_at | Protease "Receptor-1," Effector Cell | 20 | 20 | 20 | 28 | 56 | 67 |
| HG3236-HT3413_f_at | Neurofibromatosis 2 Tumor Suppressor (Gb:L27065) | 490 | 635 | 399 | 807 | 1803 | 657 |
| HG3238-HT4861_s_at | Prostaglandin Ep3 "Receptor," Alt. Splice 8 | 20 | 20 | 20 | 20 | 20 | 20 |
| HG3242-HT3419_s_at | Calcium "Channel," Voltage-Gated," Alpha 1e "Subunit," Alt. Splice 2 | 20 | 20 | 20 | 20 | 233 | 72 |
| HG3242-HT42231_s_at | Calcium "Channel," Voltage-Gated," Alpha 1e "Subunit," Alt. Splice 3 | 20 | 20 | 20 | 20 | 20 | 20 |
| HG3248-HT3425_at | Fibroblast Growth "Factor," Antisense Mrna | 48 | 20 | 20 | 49 | 20 | 795 |
| HG3254-HT3431_at | Phosphatidylinositol 3-Kinase "P110," Beta Isoform | 75 | 30 | 20 | 20 | 20 | 20 |
| HG3255-HT3432_at | Gamma-Aminobutyric Acid (Gaba) A Receptor Beta 2 Subunit | 103 | 67 | 68 | 69 | 142 | 104 |
| HG3264-HT3441_at | Af-6 (Gb:U02478) | 20 | 20 | 20 | 20 | 20 | 213 |
| HG3286-HT3463_at | Crystallin, Alpha A | 135 | 31 | 33 | 35 | 531 | 20 |
| HG3288-HT3465_at | Xanthine Dehydrogenase (Gb:U06117) | 20 | 20 | 106 | 29 | 20 | 147 |
| HG3299-HT3476_at | Acetyl-Coenzyme A Carboxylase | 20 | 20 | 20 | 20 | 20 | 55 |
| HG33-HT33_at | Tenascin | 2077 | 1327 | 2566 | 2515 | 413 | 951 |
| HG3331-HT331_at | Thyroid Hormone "Receptor," Beta-2 | 20 | 20 | 20 | 20 | 20 | 20 |
| HG3313-HT3490_at | Split Gene 1 "Enhancer," Tup1-Like | 49 | 91 | 169 | 128 | 475 | 72 |
| HG3319-HT3496_s_at | Dna-Binding Protein Hrfx2 | 20 | 20 | 20 | 20 | 20 | 20 |
| HG3327-HT3504_s_at | Id1 | 660 | 1617 | 3768 | 3301 | 965 | 795 |
| HG3342-HT3519_s_at | Ubiquitin-Conjugating Enzyme Ubch5 | 20 | 21 | 102 | 27 | 20 | 20 |
| HG3344-HT3521_at | Pou Domain-Containing Protein (Gb:Z21065) | 20 | 20 | 20 | 20 | 20 | 20 |
| HG3345-HT3522_at | Peroxisome Proliferator Activated Receptor (Gb:Z30972) | 131 | 123 | 213 | 154 | 214 | 228 |
| HG3355-HT3532_at | Chromosomal-Translocation Associated Gene Ltg19/Enl | 20 | 20 | 20 | 20 | 20 | 62 |
| HG3362-HT3539_s_at | Ribosomal Protein L37 | 4242 | 5937 | 6423 | 5602 | 3876 | 3233 |
| HG3364-HT3541_at | Potassium "Channel," Voltage-Gated," Isk-Related "Family," Member 1 | 20 | 20 | 20 | 20 | 51 | 45 |
| HG3369-HT3546_at | Dnaj Homolog "(Gb:X63368)," Alt. Splice Form 2 | 20 | 73 | 35 | 20 | 105 | 68 |
| HG3395-HT3573_a_at | Nestin | 20 | 20 | 20 | 20 | 20 | 20 |
| HG3400-HT3579_at | Zinc Finger Protein HzF3 (Gb:X60153) | 72 | 20 | 20 | 20 | 28 | 20 |
| HG3405-HT3586_at | Blue Cone Photoreceptor Pigment | 20 | 20 | 149 | 127 | 174 | 164 |
| HG3412-HT3593_s_at | Poliovirus Receptor | 120 | 38 | 63 | 52 | 20 | 74 |
| HG3415-HT3598_at | Gtp Cyclohydrolase "I," Alt. Splice 1 | 43 | 67 | 37 | 40 | 20 | 21 |
| HG3417-HT3600_s_at | Zinc Finger Protein "Hzf-16," "Kruppel-Like," Alt. Splice 1 | 20 | 67 | 20 | 20 | 20 | 20 |
| HG3426-HT3610_s_at | "Decorin," Alt. Splice 1 | 1126 | 1529 | 76 | 127 | 42 | 97 |
| HG3431-HT3616_s_at | Fibroblast Growth Factor Receptor "K-Sam," Alt. Splice 1 | 35 | 29 | 76 | 20 | 20 | 64 |
| HG3432-HT3618_at | Fibroblast Growth Factor Receptor "K-Sam," Alt. Splice "3," K-Sam Iii | 20 | 20 | 20 | 20 | 20 | 47 |
| HG3432-HT3620_s_at | Fibroblast Gnowth Factor Receptor "K-Sam," Alt. Splice "4," K-Sam Iv | 20 | 20 | 20 | 20 | 86 | 20 |
| HG3437-HT3621_at | Myelin Proteolipid "Protein," Alt. Splice 2 | 20 | 80 | 175 | 50 | 20 | 20 |
| HG3454-HT3647_at | Zinc Finger Protein 20 | 54 | 47 | 49 | 23 | 20 | 20 |
| HG3477-HT3670_at | Cd4 Antigen | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| HG3484-HT3678_s_at | Protein Kinase (Gb:M59287) | 83 | 99 | 278 | 187 | 158 | 158 | 38 |
| HG3491-HT3685_at | Zinc Finger Protein Zfp-36 | 20 | 20 | 20 | 20 | 20 | 20 | 20 |
| HG3492-HT3686_at | Uncoupling Protein Ucp | 49 | 125 | 20 | 43 | 249 | 249 | 85 |
| HG3494-HT1688_at | Nuclear Factor Nf-Il6 | 410 | 217 | 89 | 136 | 136 | 136 | 158 |
| HG3495-HT1689_at | Collagen, Type "Ix," Alpha 1 | 22 | 20 | 20 | 20 | 47 | 47 | 22 |
| HG3502-HT3696_at | Homeotic Protein Hox5.4 | 54 | 20 | 20 | 78 | 54 | 54 | 20 |
| HG3510-HT3704_at | V-Erba Related Ear-3 Protein | 48 | 103 | 20 | 20 | 20 | 20 | 20 |
| HG3513-HT3707_at | "Myosin," Heavy "Polypeptide," Light Meromyosin | 20 | 20 | 20 | 20 | 20 | 20 | 20 |
| HG3514-HT3708_at | Tropomyosin "Tm30nm," Cytoskeletal | 190 | 191 | 408 | 213 | 240 | 240 | 398 |
| HG3517-HT3711_at | Alpha-1-Antitrypsin, 5' End | 164 | 59 | 72 | 191 | 121 | 121 | 200 |
| HG3521-HT3715_at | Ras-Related Protein Rap1b | 26 | 20 | 57 | 55 | 20 | 20 | 51 |
| HG3523-HT4899_s_at | Proto-Oncogene "C-Myc," Alt. Splice "3," Orf 114 | 122 | 20 | 49 | 76 | 287 | 287 | 77 |
| HG3527-HT3721_f_at | Luteinizing "Hormone," Beta Subunit | 51 | 93 | 164 | 140 | 20 | 20 | 166 |
| HG3543-HT3739_at | Insulin-Like Growth Factor 2 | 150 | 143 | 2089 | 2041 | 371 | 371 | 632 |
| HG3546-HT3744_s_at | Pre-Mrna Splicing Factor "Sf2p33," Alt. Splice Form 1 | 20 | 20 | 43 | 53 | 233 | 233 | 28 |
| HG3546-HT3749_at | Ccaat Displacement "Protein," Cut "Homolog," Alt. Splice 1 | 39 | 50 | 20 | 20 | 20 | 20 | 20 |
| HG3549-HT3751_at | Wilm'S Tumor-Related Protein | 3843 | 4127 | 5744 | 4506 | 1741 | 1741 | 3321 |
| HG3565-HT3768_at | Zinc Finger Protein (Gb:M88357) | 20 | 20 | 20 | 20 | 20 | 20 | 20 |
| HG3565-HT3768_at | Zinc Finger Protein (Gb:M88357) | 488 | 39 | 20 | 45 | 86 | 86 | 115 |
| HG3566-HT3769_at | Zinc Finger Protein (Gb:M88359) | 74 | 110 | 153 | 41 | 134 | 134 | 89 |
| HG3570-HT3773_at | Protein Phosphatase inhibitor Homolog | 144 | 26 | 163 | 20 | 20 | 20 | 88 |
| HG3576-HT3779_f_at | Major Histocompatibility "Complex," Class II Beta W52 | 365 | 734 | 20 | 94 | 20 | 20 | 1039 |
| HG3578-HT3761_at | Autoimmune "Antigen," Thyroid Disease-Related Antigen | 54 | 77 | 54 | 94 | 294 | 294 | 105 |
| HG358-HT358_at | Homeotic Protein "7," Notch Group | 153 | 178 | 277 | 260 | 489 | 489 | 396 |
| HG3597-HT3800_f_at | Major Hiatocompatibility "Complex," Class I (Gb:X12432) | 422 | 1148 | 803 | 1024 | 71 | 71 | 995 |
| HG36-HT4101_s_at |  | 24 | 47 | 20 | 27 | 94 | 94 | 20 |
| HG3627-HT3836_at | Calcium "Channel," "Voltage-Gated," Beta 1 "Subunit," L "Type," Alt. Splice "2," Skeletal Muscle isoform | 93 | 74 | 80 | 127 | 233 | 699 | 322 |
| HG363-HT363_at | Epidermal Growth Factor Receptor-Related Protein | 20 | 97 | 20 | 130 | 20 | 20 | 135 |
| HG3835-HT3845_f_at | Zinc Finger "Protein," Kruppel-Like | 20 | 23 | 55 | 27 | 20 | 20 | 20 |
| HG3636-HT3846_at | "Myosin," Heavy Polypeptide "9," Non-Muscle | 80 | 72 | 171 | 49 | 194 | 194 | 88 |
| HG3638-HT3849_s_at | Amyloid Beta (A4) Precursor "Protein," Alt. Splice "2," A4(751) | 77 | 97 | 371 | 207 | 20 | 20 | 125 |
| HG3638-HT3993_s_at | Amyloid Beta (A4) Precursor "Protein," Alt. Splice 4 | 20 | 20 | 20 | 20 | 20 | 20 | 20 |
| HG37-HT37_at | Epiligrin, Alpha 3 | 20 | 20 | 44 | 46 | 58 | 58 | 20 |
| HG3703-HT3915_s_at | Udp-Glucuronosyltransferase 1 "Family," Polypeptide "1," Alt. Splice 1 | 93 | 74 | 80 | 127 | 233 | 233 | 39 |
| HG3707-HT3922_f_at | Guanine Nucleotide-Binding "Protein," Alpha inhibiting Activity Polypeptide 2 | 20 | 97 | 20 | 130 | 20 | 20 | 20 |
| HG371-HT1063_s_at | Mucin "1," "Epithelial," Alt. Splice 6 | 20 | 23 | 55 | 27 | 154 | 154 | 20 |
| HG371-HT26388_at |  | 20 | 20 | 20 | 20 | 20 | 20 | 20 |
| HG3371-HT26388_s_at | Mucin "1," "Epithelial," Alt. Splice 9 | 70 | 380 | 262 | 84 | 302 | 302 | 298 |
| HG3725-HT3981_s_at | Insulin-Like Leydig Hormone | 20 | 20 | 23 | 20 | 460 | 460 | 129 |
| HG3729-HT3999_f_at | Homeotic Protein Hpx-5 | 20 | 28 | 37 | 34 | 74 | 74 | 60 |
| HG3730-HT4000_s_at | Tyrosine Kinase Syk | 20 | 20 | 20 | 20 | 20 | 20 | 20 |
| HG3731-HT4001_s_at | Immunoglobulin Heavy "Chain," Vdjrc Regions (Gb:L23566) | 32 | 20 | 20 | 29 | 39 | 39 | 27 |
| HG3731-HT4001_r_at | Immunoglobulin Heavy "Chain," Vdjrc Regions (Gb:L23566) | 20 | 20 | 20 | 20 | 20 | 20 | 20 |
| HG3733-HT4003_at | Epiligrin, Alpha 3 | 20 | 48 | 20 | 20 | 151 | 151 | 20 |
| HG3749-HT4010_at | Basic Transcription Factor "2," 34 Kda Subunit | 20 | 25 | 20 | 20 | 20 | 20 | 20 |
| HG3748-HT4018_at | Basic Transcription "Factor," 44 Kda Subunit | 20 | 20 | 20 | 20 | 20 | 20 | 20 |
| HG3799-HT4060_at | Immunoglobulin Heavy "Chain," Fd Fragment | 20 | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| HG384-HT384_at | Ribosomal Protein L26 | 1409 | 1634 | 1982 | 1871 | | 388 | 683 |
| HG3859-HT4129_at | Mage-4a Antigen | 20 | 20 | 20 | 20 | | 20 | 20 |
| HG3672-HT4142_at | Immunoglobulin Gamma Heavy "Chain," V(6)Djc Regions (Gb:U13200) | 20 | 26 | 20 | 28 | | 97 | 20 |
| HG3884-HT4154_at | Homeotic Protein Hpx-42 | 227 | 20 | 20 | 20 | | 20 | 20 |
| HG3893-HT4163_at | Phosphoglucomutase "1," Alt. Splice | 20 | 20 | 42 | 20 | | 27 | 20 |
| HG3897-HT4167_at | Sodium "Channel," Type "Iii," "Alpha" "Subunit," Brain | 20 | 20 | 20 | 20 | | 20 | 20 |
| HG3914-HT4184_s_at | Cell Division Cycle Protein 2-Related Protein Kinase (Pissire) | 20 | 20 | 20 | 20 | | 20 | 20 |
| HG3920-HT4521_s_at | Homeotic Protein "A1," Class "I," Alt. Splice 1 | 56 | 27 | 124 | 82 | | 282 | 56 |
| HG3921-HT4191_f_at | Homeotic Protein "C6," Class I | 20 | 20 | 20 | 20 | | 51 | 47 |
| HG3925-HT4195_at | | 23 | 106 | 106 | 20 | | 171 | 87 |
| HG3928-HT4195_s_at | Surfacant Protein Sp-A2 Delta | 30 | 20 | 73 | 47 | | 48 | 75 |
| HG3928-HT4198_at | | 131 | 42 | 20 | 20 | | 887 | 214 |
| HG3928-HT4198_s_at | Surfacent Protein Sp-A1 Delta | 20 | 20 | 20 | 20 | | 20 | 20 |
| HG3930-HT4200_at | Stearoyl-Coenzymea Desaturase | 56 | 20 | 55 | 47 | | 20 | 20 |
| HG3934-HT4204_at | G1 Phas-Specific Gene | 78 | 20 | 20 | 20 | | 20 | 26 |
| HG3938-HT4206_at | Interleukin 9 Receptor (Gb:S71404) | 55 | 20 | 31 | 20 | | 98 | 69 |
| HG3942-HT4212_at | Interferon | 20 | 36 | 20 | 33 | | 25 | 20 |
| HG3945-HT4215_at | Phospholipid Transfer Protein | 72 | 20 | 20 | 47 | | 20 | 133 |
| HG3954-HT4224_s_at | Landsteiner-Wiener Blood Group Glycoprotein (Lw) (Gb:L7671) | 20 | 20 | 20 | 20 | | 89 | 66 |
| HG3962-HT4232_at | Sialyltransferase, Stx | 20 | 20 | 20 | 20 | | 20 | 20 |
| HG3971-HT4241_at | Transcription Factor (Gb:L32162) | 79 | 36 | 80 | 78 | | 114 | 20 |
| HG3976-HT4246_at | Pou-Domain Dna Binding Factor "Pit1," Pituitary-Specific | 20 | 20 | 20 | 20 | | 26 | 26 |
| HG3985-HT4255_at | Cpg-Enriched "Dna," Clone E04 | 62 | 42 | 53 | 57 | | 98 | 233 |
| HG3987-HT4257_at | Cpg-Enriched "Dna," Clone E06 | 185 | 20 | 20 | 22 | | 20 | 45 |
| HG3989-HT4259_at | Cpg-Enriched "Dna," Clone E14 | 119 | 56 | 20 | 43 | | 39 | 20 |
| HG3991-HT4261_at | Cpg-Enriched "Dna," Clone E18 | 20 | 20 | 20 | 20 | | 555 | 188 |
| HG3991-HT4261_r_at | Cpg-Enriched "Dna," Clone E18 | 1109 | 1796 | 3269 | 1884 | | 5165 | 1732 |
| HG3992-HT4262_at | Cpg-Enriched "Dna," Clone E35 | 20 | 20 | 20 | 20 | | 20 | 20 |
| HG3993-HT4263_at | Cpg-Enriched "Dna," Clone S12 | 20 | 20 | 20 | 20 | | 20 | 20 |
| HG3994-HT4264_at | Cpg-Enriched "Dna," Clone S16 | 47 | 114 | 251 | 73 | | 244 | 91 |
| HG3995-HT4265_at | Cpg-Enriched "Dna," Clone S19 | 186 | 223 | 251 | 81 | | 98 | 93 |
| HG3998-HT4266_at | Cpg-Enriched "Dna," Clone S21 | 20 | 20 | 20 | 20 | | 20 | 20 |
| HG3999-HT4269_at | L-Glycerol-3-Phosphate:Nad+ Oxidoreductase | 20 | 20 | 20 | 20 | | 20 | 36 |
| HG4011-HT4804_s_at | Retinoic Acid "Receptor," "Beta," Isoform 1 | 56 | 55 | 265 | 131 | | 799 | 48 |
| HG4018-HT4288_at | Dystrophin-Associated "Glycoprotein," 50 "Kda," Alt. Splice 2 | 20 | 38 | 63 | 80 | | 25 | 182 |
| HG4029-HT4290_s_at | Opioid-Binding Cell Adhesion Molecule | 280 | 320 | 604 | 334 | | 1114 | 87 |
| HG4027-HT4297_f_at | Transglutaminase | 20 | 20 | 20 | 20 | | 20 | 373 |
| HG4036-HT4306_at | "Beta-1-Glycoprotein," Domains N And "Iia," Pregnancy-Specific | 20 | 181 | 83 | 63 | | 117 | 20 |
| HG4051-HT4321_at | Retinoblastoma 1 | 20 | 20 | 20 | 20 | | 20 | 101 |
| HG4052-HT4322_at | Choline Acetyltransferase | 20 | 20 | 20 | 20 | | 60 | 20 |
| HG4068-HT4328_at | Glutamate Ionotropic Receptor 1 | 38 | 100 | 172 | 58 | | 20 | 48 |
| HG4069-HT4406_at | Oncogene "Aml1-Evi-1," Fusion Activated | 20 | 20 | 20 | 33 | | 228 | 120 |
| HG4063-HT4333_s_at | P97 "Antigen," Melanoma-Specific | 90 | 31 | 20 | 20 | | 20 | 20 |
| HG4068-HT4338_at | Transcription Factor Hbf-2 | 20 | 20 | 20 | 20 | | 20 | 68 |
| HG4069-HT4339_s_at | Phosphoprotein Tal2 | 1416 | 166 | 204 | 110 | | 410 | 104 |
| HG4073-HT4343_at | Monocyte Chemotactic Protein 1 | 96 | 97 | 62 | 143 | | 284 | 149 |
| | Cytosolic Acetoacetyl-Coenzyme A Thiolase | | | | | | | |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| HG4074-HT4344_at | Rad2 | 100 | 26 | 20 | 20 | 333 | 85 |
| HG4094-HT4364_s_at | Transcription Factor Lsf1d | 20 | 20 | 22 | 24 | 237 | 75 |
| HG4099-HT4369_s_at | Adrenergic "Receptor," Alpha 1b | 20 | 20 | 20 | 20 | 20 | 20 |
| HG4102-HT4372_at | N-Ethylmaleimide-Sensitive Factor | 109 | 40 | 167 | 58 | 43 | 72 |
| HG4108-HT4378_at | Olfactory Receptor Or17–24 | 20 | 56 | 80 | 20 | 90 | 49 |
| HG4109-HT4379_at | Olfactory Receptor Or17–30 | 20 | 60 | 20 | 34 | 103 | 20 |
| HG4113-HT4383_s_at | Olfactory Receptor Or17–201 | 40 | 35 | 27 | 20 | 196 | 109 |
| HG4114-HT4364_at | Olfactory Receptor Or17–209 | 183 | 97 | 228 | 123 | 255 | 137 |
| HG4115-HT4385_at | Olfactory Receptor Or17–210 | 62 | 136 | 134 | 70 | 329 | 149 |
| HG4116-HT4386_s_at | Olfactory Receptor Or17–219 | 20 | 20 | 20 | 20 | 99 | 20 |
| HG4120-HT4392_s_at | Protein Kinase "Pitslre," "Alpha," Alt. Splice 1-Feb | 20 | 20 | 20 | 20 | 79 | 20 |
| HG4126-HT4396_at | Zinc Finger Protein Hzf4 | 20 | 26 | 20 | 26 | 34 | 20 |
| HG4128-HT4398_at | Anion Exchanger "3," Cardiac Isoform | 44 | 20 | 20 | 20 | 20 | 20 |
| HG4144-HT4414_at | Zinc Finger Protein Hzf6 | 20 | 20 | 20 | 20 | 20 | 20 |
| HG4415-HT4415_at | Lectin, "Galactoside-Binding," "Soluble," 2 | 20 | 20 | 20 | 20 | 145 | 20 |
| HG4415-HT4425_s_at | Zinc Finger Protein Hzf8 | 20 | 20 | 20 | 20 | 20 | 20 |
| HG4157-HT4427_at | Glycinamide Ribonucleotide Synthetase | 20 | 20 | 20 | 20 | 277 | 20 |
| HG4165-HT4435_at | Hpc-1 | 43 | 20 | 53 | 20 | 20 | 20 |
| HG4167-HT4437_at | Nuclear Factor "1," A Type | 20 | 46 | 20 | 61 | 20 | 101 |
| HG4169-HT4439_s_at | Syntaxin 1b | 20 | 20 | 20 | 20 | 20 | 20 |
| HG4178-HT4448_at | Cathepsin B | 1172 | 1481 | 1031 | 977 | 463 | 1783 |
| HG4178-HT4417_s_at | Af-17 | 106 | 50 | 135 | 86 | 235 | 211 |
| HG4185-HT4455_at | Estrogen "Sulfotransferase," Ste | 20 | 20 | 20 | 37 | 126 | 52 |
| HG4188-HT4458_at | N-Methyl-D-Aspartate Receptor "Subunit," Splice Variant Hnr1n | 20 | 20 | 20 | 20 | 20 | 20 |
| HG4194-HT4464_at | Sodium/Hydrogen Exchanger 5 | 87 | 20 | 20 | 74 | 52 | 83 |
| HG4234-HT4504_at | Methylenetetrahydrofolate Reductase | 20 | 20 | 20 | 20 | 20 | 20 |
| HG4236-HT4506_f_at | Zinc Finger Protein Znf138 | 20 | 20 | 50 | 20 | 20 | 20 |
| HG4243-HT4513_at | Zinc Finger Protein Znf155 | 58 | 97 | 87 | 57 | 219 | 87 |
| HG4245-HT4515_at | Forkhead Family Ax1 | 20 | 20 | 20 | 23 | 20 | 20 |
| HG4258-HT4528_at | Kinase Inhibitor "P27kip1," Cyclin-Dependent | 20 | 20 | 20 | 20 | 28 | 56 |
| HG4263-HT4533_at | Nkr-P1a Protein | 20 | 20 | 20 | 20 | 20 | 20 |
| HG4264-HT4534_s_at | Guanine Nucleotide-Binding Protein Rab5c-Like Protein | 149 | 530 | 660 | 411 | 522 | 349 |
| HG4272-HT4542_at | Hepatocyte Growth Factor Receptor | 177 | 49 | 104 | 56 | 315 | 127 |
| HG4429-HT4429_at | Cell Growth Factor 1 | 20 | 20 | 20 | 20 | 107 | 31 |
| HG4297-HT4567_at | Transcriptional Coactivator Pc4 | 147 | 170 | 134 | 121 | 95 | 117 |
| HG4310-HT4580_at | Cellular Retinol Binding Protein II | 20 | 20 | 20 | 20 | 20 | 20 |
| HG4312-HT4582_s_at | Transcription Factor Iiia | 149 | 220 | 290 | 227 | 179 | 216 |
| HG4316-HT4586_at | Transketolase-Like Protein | 29 | 20 | 20 | 20 | 20 | 20 |
| HG4318-HT4588_s_at | Lim-Domain Transcription Factor Lim-1 | 100 | 148 | 127 | 125 | 530 | 101 |
| HG4319-HT4589_at | Ribosomal Protein L5 | 1950 | 1746 | 2300 | 2102 | 712 | 1043 |
| HG4321-HT4591_at | Ahnak-Related Sequence | 49 | 20 | 20 | 48 | 20 | 24 |
| HG4322-HT4592_at | "Tubulin," Beta | 85 | 61 | 20 | 20 | 20 | 20 |
| HG4332-HT4602_at | Zinc Finger Protein Znfpt1 | 96 | 129 | 181 | 115 | 278 | 275 |
| HG4333-HT4603_at | Zinc Finger Protein Znfpt7 | 20 | 41 | 97 | 42 | 94 | 26 |
| HG4334-HT4604_s_at | Glycogenin | 45 | 120 | 78 | 104 | 20 | 89 |
| HG4336-HT4606_at | Bactericidal Bpi'Gene | 20 | 61 | 84 | 20 | 69 | 107 |
| HG4340-HT4610_at | Soxa | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| HG4390-HT4660_at | Ribosomal Protein L18a Homolog | 20 | 58 | 20 | 23 | 20 | 24 |
| HG4411-HT4681_at | Mucin, Gastric | 49 | 20 | 20 | 26 | 95 | 20 |
| HG4417-HT4687_f_at | Homeotic Protein Hpx-2 | 20 | 20 | 20 | 20 | 20 | 50 |
| HG4433-HT4703_at | Cyclin D1 Promoter | 20 | 20 | 20 | 20 | 20 | 20 |
| HG4458-HT4727_at | Immunoglobulin Heavy "Chain," Vdjc Regions (Gb:L23563) | 93 | 20 | 20 | 53 | 233 | 65 |
| HG4460-HT4729_at | Immunoglobulin Heavy "Chain," Vdjc Regions (Gb:L23564) | 20 | 24 | 20 | 20 | 165 | 81 |
| HG4462-HT4731_at | Immunoglobulin Heavy "Chain," Vdjc Regions (Gb:L23565) | 20 | 20 | 20 | 20 | 106 | 20 |
| HG4480-HT4833_at | Collagen, Type "Vf," Alpha "2," N-Terminal Domain | 20 | 20 | 20 | 20 | 20 | 43 |
| HG4490-HT4876_f_at | Proline-Rich Protein "Prb4," Allele | 20 | 20 | 20 | 20 | 20 | 45 |
| HG4517-HT4920_s_at | Immunoglobulin Recombination Signal Sequence Binding "Protein," Alt. Splice 3 | 20 | 65 | 98 | 20 | 100 | 20 |
| HG4518-HT4921_at | Transcription Factor Btf3 Homolog (Gb:M90355) | 20 | 20 | 20 | 20 | 20 | 20 |
| HG4518-HT4921_at | Transcription Factor Btf3 Homolog (Gb:M90355) | 56 | 45 | 20 | 49 | 20 | 20 |
| HG4533-HT4938_at | Kallistatin, Protease Inhibitor 4 | 87 | 75 | 73 | 99 | 87 | 87 |
| HG4535-HT4940_s_at | Dematin | 191 | 259 | 364 | 221 | 609 | 140 |
| HG4541-HT4946_s_at | Transformation-Related Protein | 159 | 197 | 479 | 391 | 250 | 252 |
| HG4542-HT4947_at | Ribosomal Protein L10 | 1378 | 1500 | 2381 | 2133 | 549 | 1098 |
| HG4557-HT4962_at | Small Nuclear Ribonucleoprotein "U1," 1snrp | 28 | 112 | 55 | 65 | 20 | 100 |
| HG4557-HT4962_r_at | Small Nuclear Ribonucleoprotein "U1," 1snrp | o 56 | 114 | 156 | 94 | 20 | 20 |
| HG4558-HT458_f_at | Beta-1-Glycoprotein "1," Pregnancy-Specific (Gb:M20882) | 20 | 20 | 20 | 20 | 20 | 20 |
| HG4582-HT4987_at | Glucocorticoid "Receptor," Beta | 20 | 28 | 40 | 20 | 20 | 20 |
| HG4593-HT4998_at | Sodium Channel 1 | 56 | 86 | 188 | 110 | 417 | 266 |
| HG4606-HT5011_at | Centractin, Alpha | 20 | 55 | 40 | 105 | 64 | 107 |
| HG4638-HT5050_at | - Spliceosomal Protein Sap 49 | 78 | 20 | 20 | 198 | 54 | 232 |
| HG4660-HT5073_at | Microtubule-Associated Protein 1b | 182 | 104 | 59 | 110 | 258 | 223 |
| HG4662-HT5075_at | Omega Light "Chain," Immunoglobulin Lambda Light Chain Related | 20 | 20 | 20 | 63 | 349 | 356 |
| HG4668-HT5083_s_at | Transcription Factor "Mef2," Alt. Splice 2 | 44 | 38 | 20 | 51 | 442 | 189 |
| HG4677-HT5102_s_at | Oncogene "Ret/Ptc2," Fusion Activated | 20 | 35 | 96 | 34 | 160 | 69 |
| HG4679-HT5104_at | Oncogene "Ret/Ptc," Fusion Activated | 20 | 20 | 20 | 20 | 20 | 20 |
| HG4683-HT5108_s_at | Tumor Necrosis Factor Receptor 2 Associated Protein Trap3 | 20 | 30 | 100 | 27 | 25 | 39 |
| HG491-HT491_at | Glial Growth Factor 2 | 31 | 85 | 20 | 20 | 502 | 33 |
| HG4704-HT5146_at | Guanosine 5'-Monophosphate Synthase | 58 | 36 | 20 | 20 | 70 | 51 |
| HG4716-HT5158_at | Atp-Binding Cassette Protein | 36 | 20 | 49 | 79 | 20 | 74 |
| HG4724-HT5166_at | Transcription Factor Eb | 20 | 20 | 20 | 31 | 167 | 51 |
| HG4740-HT5187_at | Nadh-Ubiquinone "Oxidoreductase," 51 Kda Subunit | 20 | 20 | 20 | 50 | 108 | 20 |
| HG4747-HT5195_at | Calmitine Calcium-Binding "Protein," Mitochondrial | 20 | 20 | 20 | 24 | 20 | 20 |
| HG4749-HT5197_at | Spinal Muscular Atrophy 4 | 20 | 38 | 98 | 33 | 20 | 27 |
| HG4755-HT5203_s_at | Oncogene "Mll-Af4," Fusion Activated | 20 | 20 | 20 | 20 | 20 | 51 |
| HG4757-HT5207_s_at | Fc Receptor Iib3 For "Igg," Low Affinity | 20 | 30 | 100 | 27 | 502 | 33 |
| HG511-HT491_at | Ras Inhibitor Inf | 20 | 20 | 20 | 20 | 20 | 20 |
| HG511-HT511_at | Collagen, Type "Viii," Alpha 2 | 39 | 20 | 26 | 20 | 103 | 21 |
| HG537-HT537_at | Endothelial Cell Growth Factor 1 | 20 | 20 | 20 | 20 | 20 | 20 |
| HG544-HT544_at | Ribosomal Protein S12 | 20 | 20 | 20 | 20 | 167 | 20 |
| HG613-HT613_at | Tyrosine "Phosphatase," Epsilon | 1873 | 1834 | 2423 | 2166 | 89 | 809 |
| HG620-HT620_at | Rhesus (Rh) Blood Group System "Ce-Antigen," Alt. Splice "2," Rhvi | 26 | 20 | 95 | 20 | 115 | 93 |
| HG627-HT5097_s_at | Rhesus (Rh) Blood Group System "Ce-Antigen," Alt. Splice "3," Rhvii | 20 | 20 | 20 | 20 | 225 | 108 |
| HG627-HT5098_s_at | | 72 | 20 | 55 | 104 | 140 | 112 |
| HG64-HT64_at | Histone H1.1 | 20 | 20 | 20 | 20 | 53 | 20 |
| HG644-HT644_at | | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| HG651-HT4201_at | Adducin, Alpha "Subunit," Alt. Splice 2 | 136 | 69 | 121 | 158 | 151 | 135 |
| HG541-HT5209_s_at | "Adducin," Alpha "Subunit," Alt. Splice 3 | 20 | 20 | 20 | 20 | 20 | 20 |
| HG858-HT658_f_at | Major Histocompatibility, "Complex," Class "I," C (Gb-X58536) | 869 | 2332 | 1526 | 1686 | 1161 | 2354 |
| HG662-HT662_at | Epstein-Barr Virus Small Rna-Associated Protein | 475 | 955 | 655 | 528 | 308 | 245 |
| HG668-HT4793_at | T-Cell Factor "1," "A/B/C," Alt. Splice "1," A | 23 | 20 | 20 | 20 | 20 | 89 |
| HG67-HT67_f_at |  | 20 | 20 | 20 | 20 | 20 | 20 |
| HG688-HT688_f_at | Major Histompatibility "Complex," Class "Ii," Dr Beta 2 (Gb-X65561) | 163 | 390 | 266 | 170 | 245 | 472 |
| HG721-HT4827_s_at | Placental Protein "14," Endometrial Alpha 2 "Globulin," Alt. Splice 2 | 20 | 20 | 20 | 20 | 20 | 20 |
| HG721-HT4828_s_at | Placental Protein "14," Endometrial Alpha 2 "Globulin," Alt. Splice 3 | 36 | 72 | 103 | 21 | 176 | 20 |
| HG732-HT732_at | Serum Amyloid A1 | 170 | 20 | 20 | 20 | 93 | 47 |
| HG742-HT742_at | Latent Membrane Protein Lmp1 | 21 | 20 | 20 | 20 | 164 | 20 |
| HG759-HT759_s_at | Adrenergic "Receptor," Beta 1 | 20 | 20 | 20 | 20 | 20 | 28 |
| HG821-HT821_at | Ribosomal Protein S13 | 2159 | 1918 | 2482 | 1978 | 796 | 1030 |
| HG825-HT825_at | Guanine Nucleotide-Binding "Protein," Alpha 12 | 20 | 20 | 20 | 20 | 20 | 20 |
| HG830-HT830_at | Potassium Channel (Gb:L02750) | 20 | 22 | 81 | 36 | 70 | 57 |
| HG831-HT831_at | Potassium Channel (Gb:L02752) | 78 | 31 | 33 | 27 | 78 | 30 |
| HG846-HT846_at | Cyclophilin-Related Protein | 65 | 62 | 193 | 76 | 301 | 155 |
| HG855-HT855_s_at | Dna Excision Repair Protein Ercc6 | 27 | 33 | 41 | 20 | 20 | 20 |
| HG862-HT862_s_at | Transition Protein 2 | 20 | 20 | 20 | 20 | 20 | 20 |
| HG870-HT870_at | Golgin, 165 Kda Polypeptide | 74 | 46 | 59 | 118 | 1793 | 116 |
| HG880-HT880_s_at | Mucin "6," Gastric (G:L07517) | 20 | 20 | 20 | 20 | 20 | 493 |
| HG881-HT881_at | Mucin "6," Gastric (Gb:L07518) | 20 | 51 | 20 | 64 | 145 | 20 |
| HG884-HT884_s_at | Oncogene "E6-Ap," Papillomavirus | 20 | 20 | 29 | 20 | 330 | 87 |
| HG896-HT896_at | Thrombospondin 2 (Gb:L07803) | 38 | 61 | 80 | 106 | 40 | 68 |
| HG907-HT907_at | Mg44 | 20 | 20 | 20 | 20 | 77 | 93 |
| HG908-HT908_at | MG61 Protein (Gb:L08239) | 20 | 20 | 20 | 20 | 20 | 20 |
| HG909-HT909_at | Mg81 | 56 | 97 | 67 | 41 | 72 | 110 |
| HG919-HT919_at | Dna "Polymerase," "Epsilon," Catalytic Subunit | 20 | 20 | 20 | 32 | 20 | 20 |
| HG921-HT3995_at | Serine/Threonine "Kinase," Receptor "202," Alt. Splice 3 | 21 | 51 | 20 | 64 | 145 | 32 |
| HG944-HT3995_s_at | Dopamine Receptor D4 | 20 | 20 | 29 | 20 | 136 | 23 |
| HG945-HT945_s_at | Nucleic Acid-Binding Protein (Gb:L12693) | 20 | 20 | 20 | 20 | 20 | 20 |
| HG960-HT960_at | Guanine Nucleotide Exchange Factor 1 | 44 | 59 | 67 | 80 | 146 | 20 |
| HG961-HT961_at | Guanine Nucleotide Exchange Factor 2 | 175 | 132 | 139 | 183 | 282 | 217 |
| HG982-HT982_s_at | Pre-T/Nk-Cell-Associated Protein 1f6 | 59 | 36 | 20 | 61 | 209 | 31 |
| HG987-HT987_at | Mac25 | 26 | 51 | 91 | 38 | 20 | 59 |
| HG998-HT998_s_at | "Sulfotransferase," Phenol-Preferring | 640 | 404 | 110 | 114 | 20 | 40 |
| hum_alu_at |  | 21 | 76 | 151 | 114 | 20 | 40 |
| J00073_at | human alpha-cardiac actin "gene," 5' flank and | 200 | 125 | 178 | 140 | 86 | 144 |
| J00105_s_at | Human beta-2 microglobulin gene "mRNA," 3' end | 3664 | 6165 | 5659 | 5767 | 1137 | 4892 |
| J00116_s_at | Human alpha-1(II) collagen gene "COL2A1," partial cds | 20 | 20 | 20 | 20 | 20 | 20 |
| J0017_f_at | Human chorionic gonadotropin (hcg) beta susunit "mRNA," complete cds | 20 | 20 | 20 | 20 | 57 | 20 |
| J00123_at | Human enkephalin gene | 44 | 20 | 20 | 20 | 40 | 32 |
| J00124_at | Homo sapiens 50 kDa type I epidermal keratin "gene," complete cds | 1210 | 20 | 20 | 56 | 244 | 230 |
| J00129_at | Human fibrinogen beta-chain "mRNA," partial cds | 20 | 20 | 20 | 20 | 23 | 21 |
| J00139_s_at | Human dihydrofolate reductase gene | 20 | 25 | 35 | 20 | 222 | 55 |
| J00146_at | 20 | 20 | 20 | 33 | 20 | 38 |  |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| J00148_cds2_f_at | Human growth hormone "(somatotropin," GH1) "gene," complete cds | 20 | 20 | 20 | 20 | 20 | 20 |
| J00207_ma2_at | IFNA gene (interferon alpha-a) extracted from Human leukocyte interferon (leif) alpha-a gene | 20 | 20 | 20 | 21 | 30 | 20 |
| J00209_f_at | Human leukocyte interferon (ifn-alpha) alpha-c "mRNA, complete" cds | 28 | 20 | 40 | 20 | 20 | 20 |
| J00210_maf_at | IFNA gene (interferon alpha-d) extracted from Human leukocyte interferon (IFN-alpha) alpha-d "gene," complete cds | 20 | 20 | 25 | 20 | 20 | 20 |
| J00212_f_at | Human leukocyte interferon (ifn-alpha) alpha-f "mRNA," complete cds | 42 | 31 | 87 | 38 | 274 | 103 |
| J00219_s_at | Human immune interferon (IFN-gamma) "gene," complete cds | 20 | 31 | 20 | 20 | 20 | 37 |
| J00220_cds4_at | Human ig germline G-E-A region A: alphaO1 constant region | 69 | 20 | 20 | 47 | 149 | 20 |
| J00220_cds5_at | IGHA1 gene extracted from Human Ig germline H-chain G-E-A region A: gamma-3,5' glank | 20 | 25 | 20 | 20 | 206 | 20 |
| J00268_s_at | Human insulin gene | 20 | 20 | 20 | 20 | 20 | 20 |
| J00277_at | Human (genomic clones "lambda-[SK2-T2;" HS578T]; cDNA clones "RS-[3,4;" g]) c-Ha-ras1 "proto-oncogene," complete coding sequence | 20 | 116 | 87 | 141 | 122 | 103 |
| J00287_at | Human pepsinogen gene | 20 | 20 | 20 | 20 | 20 | 20 |
| J00301_at | Human parathyroid (pth) "gene," 3' nd | 20 | 20 | 20 | 20 | 115 | 20 |
| J00306_at | Human somatostatin I gene and flanks | 54 | 30 | 85 | 71 | 104 | 20 |
| J00314_at | Human beta-tubulin "gene," clone m40 | 20 | 44 | 34 | 95 | 31 | 68 |
| J02611_at | Human apolipoprotein D "mRNA," complete cds | 226 | 104 | 217 | 85 | 1942 | 179 |
| J02621_s_at | Human non-histone chromosomal protein HMG-14 "mRNA," complete cds | 217 | 282 | 659 | 509 | 217 | 307 |
| J02645_s_at | Human translational initiation factor "(eIF02)," alpha subunit "mRNA," complete cds | 56 | 107 | 25 | 150 | 176 | 191 |
| J02683_s_at | Human ADP/ATP carrier protein "mRNA," complete cds | 337 | 168 | 614 | 740 | 20 | 408 |
| J02758_s_at | Human apolipoprotein A-IV "gene," complete cds | 20 | 20 | 20 | 20 | 36 | 21 |
| J02783_at | Human thyroid hormone binding protein (p55) "mRNA," complete cds | 495 | 351 | 710 | 705 | 331 | 343 |
| J02843_at | Human cytochrome P450IIe1 (ethanol-inducible) "gene," complete cds | 20 | 20 | 20 | 20 | 20 | 20 |
| J02854_at | Human 20-kDa myosin light chain (MLC-2) "mRNA," complete cds | 412 | 522 | 20 | 30 | 141 | 170 |
| J02871_s_at | Human lung cytochrome P450 (IV subfamily) BI "protein," complete cds | 20 | 319 | 410 | 687 | 445 | 420 |
| J02874_at | Human adipocyte lipid-binding "protein," complete cds | 499 | 267 | 425 | 558 | 207 | 420 |
| J02876.at | Human placental folate binding protein, "mRNA," complete cds | 20 | 33 | 20 | 20 | 20 | 110 |
| J02883_at | Human colipase "mRNA," complete cds | 20 | 20 | 20 | 20 | 173 | 20 |
| J02888_at | Human quinone oxidoreductase (NQO2) "mRNA," complete cds | 69 | 131 | 127 | 69 | 154 | 173 |
| J02902_at | Human protein phosphatase 2A regulatory subunit alpha-isotype (alpha-PR65) "mRNA," complete cds | 391 | 155 | 202 | 379 | 451 | 426 |
| J02906_at | Human cytochrome PA450IIF1 protein (CYP2F) "mRNA," complete cds | 109 | 20 | 32 | 20 | 86 | 94 |
| J02923_at | Human 65-kilodalton phosphoprotein (p65) "mRNA," complete cds | 20 | 66 | 20 | 20 | 45 | 239 |
| J02943_at | Human corticosteroid binding globulin "mRNA," complete cds | 20 | 36 | 20 | 31 | 282 | 48 |
| J02947_at | Human extracellular-superoxide dismutase (SOD3) "mRNA," complete cds | 117 | 52 | 24 | 20 | 541 | 87 |
| J02960_cds1_s_at | unknown protein gene extracted from Human beta-2-adrenergic receptor "gene," complete cds | 45 | 20 | 20 | 20 | 232 | 20 |
| J02963_at | Human platelet glycoprotein IIb "mRNA," 3' end | 20 | 20 | 20 | 20 | 84 | 53 |
| J02973_ma1_at | Human thrombomodulin gene, complete cds. | 24 | 20 | 20 | 34 | 61 | 20 |
| J02982_f_at | Human glycophorin B "mRNA," complete cds | 20 | 20 | 31 | 30 | 47 | 27 |
| J02986_cds1_at | Human transforming protein (hsf) gene, complete cds. | 30 | 20 | 42 | 138 | 27 | 45 |
| J03027_at | Human NHC class I HLA-6.09 "gene," complete cds | 31 | 20 | 20 | 20 | 20 | 20 |
| J03040_at | Human SPARC/osteonectin "mRNA," complete cds | 383 | 64 | 20 | 20 | 20 | 20 |
| J03060_at | Human glucocerbrosidase (GCB) gene | 20 | 20 | 20 | 20 | 20 | 20 |
| J03068_at | Human DNF1552 (lung) "mRNA," complete cds | 57 | 20 | 20 | 33 | 20 | 20 |
| J03069_ma1_at | Human MYCL2 gene, complete cds. | 204 | 230 | 297 | 272 | 470 | 356 |
| J03071_cds3_f_at | chorionic somatomammotropin CS-1 gene extracted from Human growth hormone (GH-1 and GH-2) and chorionic somatomammotropin | 20 | 39 | 42 | 25 | 136 | 21 |
| J03077_s_at | Human co-beta glucosidase (proactivator) "mRNA," complete cds | 510 | 925 | 1569 | 1457 | 1188 | 1251 |
| J03133_at | Human transcription factor SP1 "mRNA," 3' end | 20 | 22 | 20 | 44 | 138 | 24 |
| J03161_at | Human serum response factor (SRF) "mRNA," complete cds | 96 | 53 | 29 | 84 | 184 | 130 |
| J03171_at | Human interferon-alpha receptor (HuIFN-alpha-Rec) "mRNA," complete cds | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| J03191_at | Human profilin "mRNA," complete cds | 799 | 668 | 760 | 976 | 597 | 1090 |
| J03241_s_at | Human transforming growth factor-beta 3 (TGF-beta3) "mRNA," complete cds | 60 | 51 | 42 | 38 | 172 | 20 |
| J03242_s_at | Human insulin-like growth factor II "mRNA," complete cds | 117 | 172 | 4115 | 2568 | 542 | 390 |
| J03258_at | Human vitamin D receptor "mRNA," complete cds | 20 | 20 | 20 | 20 | 20 | 20 |
| J03260_s_at | Human transducin alpha-subunit (GNAZ) "mRNA," complete cds | 20 | 20 | 20 | 20 | 20 | 64 |
| J03263_s_at | Human lysosome-associated membrane glycoprotein (lamp A) "mRNA," complete cds | 22 | 20 | 20 | 20 | 20 | 20 |
| J03278_at | Human platelet-derived growth factor (PDGF) receptor "mRNA," complete cds | 81 | 93 | 91 | 20 | 20 | 20 |
| J03459_s_at | Human leukotriene A-4 hydrolase "mRNA," complete cds | 381 | 254 | 287 | 289 | 327 | 329 |
| J03473_at | Human poly(ADP-ribose) synthetase "mRNA," complete cds | 78 | 42 | 82 | 43 | 71 | 87 |
| J03474_at | Human serum amyloid A "gene," complete cds | 20 | 20 | 20 | 20 | 20 | 20 |
| J03507_at | Human complement protein comonent C7 "mRNA," complete cds | 70 | 36 | 20 | 20 | 20 | 20 |
| J03589_at | Human ubiquitin-like protein (GdX) "gene," complete cds | 28 | 20 | 66 | 26 | 20 | 85 |
| J03592_at | Human ADP/ATP transiocase "mRNA," 3' end," clone pHAT8 | 905 | 1140 | 1599 | 2042 | 807 | 683 |
| J03600_at | Human lipoxygenase "mRNA," complete cds | 20 | 255 | 233 | 263 | 220 | 82 |
| J03626_ma1_s_at | UMPS gene extracted from Human UMP synthase "mRNA," complete cds | 24 | 20 | 20 | 52 | 155 | 42 |
| J03634_at | Human erythroid differentiation protein mRNA "(EDF)," complete cds | 20 | 20 | 20 | 20 | 20 | 67 |
| J03756_at | Human growth hormone-variant (GH1) and growth hormone-variant-2 (GH2) "mRNA," complete cds | 96 | 131 | 20 | 146 | 145 | 218 |
| J03764_at | Human plasminogen activator inhibitor-1 "gene," exons 2 to 9 | 165 | 49 | 39 | 120 | 135 | 83 |
| J03778_s_at | Human microtubule-associated protein tau "mRNA," complete cds | 20 | 20 | 20 | 20 | 20 | 20 |
| J03779_at | Human common acute lymphoblastic leukemia antigen (CALLA) "mRNA," complete cds | 110 | 185 | 164 | 139 | 177 | 208 |
| J03798_at | Human autoantigen small nuclear ribonucleoprotein Sm-D "mRNA," complete cds | 32 | 35 | 33 | 20 | 60 | 20 |
| J03801_f_at | Human lysozyme "mRNA," complete cds with an Alu repeat in the 3' flank | 557 | 1137 | 321 | 434 | 623 | 1036 |
| J03805_s_at | Human phosphatase 2A "mRNA," partial cds | 206 | 202 | 245 | 174 | 37 | 74 |
| J03810_at | Human liver glucose transporter-like protein "(GLUT2)," complete cds | 20 | 20 | 20 | 32 | 20 | 20 |
| J03824_at | Human uroporphyrinogen III synthase "mRNA," complete cds | 20 | 20 | 20 | 20 | 20 | 20 |
| J03827_at | Y box binding protein-1 (YB-1) mRNA | 1439 | 694 | 1147 | 1294 | 342 | 1262 |
| J03890_ma1_at | Human pulmonary surfactant protein C (SP-c) and pulmonary surfactant protein C1 (SP-C1) genes, complete cds. | 20 | 38 | 20 | 20 | 20 | 80 |
| J03909_at | Human gamma-interferon-inducible protein (IP-30) "mRNA," complete cds | 248 | 214 | 20 | 69 | 125 | 756 |
| J03910_ma1_at | Human (clone 14VS) metallothionein-IG (MT1G) "gene," complete cds | 20 | 20 | 20 | 20 | 20 | 20 |
| J03915_s_at | Human chromogranin A "mRNA," complete cds | 20 | 20 | 20 | 20 | 200 | 67 |
| J03925_at | Human Mac-1 gene encoding complement receptor type "3; "CD11b," complete cds | 45 | 20 | 20 | 28 | 52 | 80 |
| J03930_at | Human intestinal alkaline phosphatase (ALPI) "gene," complete cds | 111 | 20 | 85 | 72 | 154 | 20 |
| J03934_s_at | "Human," NAD(P)H:menadione oxidoreductase "mRNA," complete cds | 51 | 21 | 121 | 153 | 20 | 89 |
| J04027_at | Human plasma membrane Ca2+ pumping ATPase "mRNA," complete cds | 20 | 45 | 20 | 20 | 168 | 20 |
| J04029_s_at | Homo sapiens keratin 10 type I intermediate filament (KRT10) "mRNA," complete cds | 145 | 103 | 146 | 134 | 20 | 109 |
| J04031_at | Human methylenetetrahydrofolate dehydrogenase- methenyltetrahydrofolate cyclohydrolase-formyltetrahydrofolate synthetase "mRNA," | 20 | 20 | 48 | 20 | 52 | 37 |
| J04040_at | Human glucagon "mRNA," complete cds | 39 | 24 | 85 | 39 | 20 | 53 |
| J04046_s_at | Human calmodulin "mRNA," complete cds | 162 | 220 | 292 | 365 | 159 | 348 |
| J04056_at | Human carbonyl reductase "mRNA," complete cds | 89 | 76 | 43 | 20 | 20 | 20 |
| J04058_at | Human electron transfer flavoprotein alpha-subunit "mRNA," complete cds | 22 | 53 | 20 | 33 | 20 | 20 |
| J04076_at | Human early growth response 2 protein (EGR2) "mRNA," complete cds | 20 | 20 | 25 | 22 | 20 | 43 |
| J04080_at | Human complement component C1r "mRNA," complete cds | 497 | 225 | 20 | 20 | 20 | 143 |
| J04088_at | Human DNA topoisomerase 11 (top2) "mRNA," complete cds | 50 | 33 | 30 | 63 | 48 | 20 |
| J04093_s_at | Homo sapiens phenol UDP-glucuronosyltransferase (UDPGT) "mRNA," complete cds | 72 | 265 | 498 | 801 | 137 | 348 |
| J04101_at | Human erythroblastosis virus oncogene homolog 1 (ets-1) "mRNA," complete cds. | 20 | 20 | 20 | 20 | 20 | 91 |
| J04102_at | Human erythroblastosis virus oncogene homolog 2 (ets-2) "mRNA," complete cds | 24 | 20 | 20 | 20 | 43 | 77 |
| J04111_at | Human C-jun proto oncogene "(JUN)," complete "cds," done hCJ-1 | 44 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| J04130_s_at | Human activation (Act-2) "mRNA," complete cds | 51 | 110 | 51 | 20 | 20 | 195 |
| J04132_at | Human T cell receptor zeta-chain "mRNA," complete cds | 20 | 47 | 20 | 33 | 20 | 89 |
| J04152_ma1_s_at | M1S1 gene extracted from Human gastrointestinal tumor-associated antigen GA733-1 protein "gene," complete "cds," clone 5516 | 1311 | 1291 | 2743 | 2561 | 835 | 758 |
| J04156_at | Human interleukin 7 (IL-7) "mRNA," complete cds | 54 | 20 | 89 | 20 | 86 | 20 |
| J04162_at | Human leukocyte IgG receptor (Fc-gamma-R) "mRNA," complete cds | 37 | 48 | 90 | 45 | 128 | 111 |
| J04164_at | Human interferon-inducible protein 27-Sep "mRNA," complete cds | 580 | 1166 | 30 | 94 | 902 | 825 |
| J04168_at | Human leukostatin "mRNA," Complete cds | 20 | 20 | 31 | 27 | 42 | 20 |
| J04173_at | Homo sapiens phosphoglycerate mutase (PGAM-B) "mRNA," complete cds | 546 | 297 | 307 | 512 | 279 | 207 |
| J04177_at | Human alpha-1 type XI collagen (COL11A1) "mRNA," complete cds | 20 | 20 | 23 | 20 | 94 | 59 |
| J04182_at | Homo sapiens lysosomal membrane glycoprotein-1 (LAMP1) "mRNA," complete cds | 157 | 370 | 418 | 257 | 145 | 271 |
| J04430_s_at | Human tartrate-resistant acid phosphatase type 5 "mRNA," complete cds | 20 | 20 | 20 | 22 | 221 | 108 |
| J04444_at | Human cytochrome c-1 "gene," complete cds | 20 | 20 | 20 | 119 | 20 | 20 |
| J04449_at | Homo sapiens (clone NF 10) cytochrome P-450 nifedipine oxidase "mRNA," complete cds | 20 | 20 | 20 | 20 | 20 | 20 |
| J04456_at | Human 14 kd lectin "mRNA," complete cds | 549 | 413 | 20 | 144 | 20 | 488 |
| J04469_at | Human mitochondrial creatine kinase (CKMT) "gene," complete cds | 82 | 61 | 95 | 78 | 299 | 92 |
| J04501_at | Human muscle glycogen synthase "mRNA," complete cds | 73 | 70 | 20 | 68 | 20 | 30 |
| J04513_at | Human basic fibroblast growth factor (bFGF) 22.5 "kd," 21 kd and 18 kd protein "mRNA," complete cds | 20 | 20 | 20 | 20 | 20 | 20 |
| J04543_at | Human synexin "mRNA," complete cds | 96 | 44 | 55 | 65 | 20 | 65 |
| J04599_s_at | Human hPGI mRNA encoding bone small proteoglycan I "(biglycan)," complete cds | 67 | 171 | 58 | 238 | 436 | 519 |
| J04605_at | Human prolidase (imidodipeptidase) "mRNA," complete cds | 117 | 24 | 85 | 188 | 189 | 239 |
| J04611_at | Human lupus p70 (KU) autoantigen protein "mRNA," complete cds | 205 | 279 | 238 | 375 | 20 | 193 |
| J04615_at | Human lupus autoantigen (small nuclear "ribonucleoprotein," "snRNP," SM-D) "mRNA," complete cds | 106 | 121 | 237 | 142 | 20 | 129 |
| J04617_s_at | Human elongation factor EF-1-alpha "gene," complete cds | 4935 | 6479 | 8978 | 8095 | 1707 | 3336 |
| J04821_at | Human heparan sulfate proteoglycan (HSPG) core "protein," 3' end | 20 | 20 | 20 | 20 | 20 | 20 |
| J04739_at | Human bactericidal permeability increasing protein (BPI) "mRNA," complete cds | 20 | 20 | 20 | 20 | 20 | 20 |
| J04742_at | Human autonomous replicating sequence H1 (ARSH1) | 20 | 20 | 34 | 20 | 20 | 20 |
| J04760_at | Human slow-twitch skeletal troponin I (TNNI) "mRNA," complete cds | 20 | 20 | 20 | 20 | 20 | 36 |
| J04794_at | Human aldehyde reductase "mRNA," complete cds | 228 | 271 | 167 | 259 | 240 | 466 |
| J04809_ma1_at | Human cytosolic adenylate kinase (AK1) gene, complete cds. | 154 | 70 | 20 | 143 | 271 | 208 |
| J04810_s_at | Human MSH3 "gene," complete cds | 20 | 52 | 68 | 53 | 20 | 20 |
| J04823_ma1_at | Human cytochrome c oxidase subunit VIII (COX8) mRNA, complete cds. | 559 | 838 | 399 | 615 | 849 | 464 |
| J04948_at | Human alkaline phosphatase (ALP-1) "mRNA," complete cds | 57 | 20 | 20 | 20 | 20 | 20 |
| J04970_at | Human carboxypeptidase "M," 3' end | 20 | 20 | 20 | 29 | 20 | 24 |
| J04973_at | Human cytochrome bc-1 complex core protein II "mRNA," complete cds | 154 | 67 | 128 | 131 | 20 | 34 |
| J04982_at | Human heart/skeletal muscle ATP/ADP translocator (ANT1) "gene," complete cds | 20 | 20 | 20 | 20 | 20 | 20 |
| J04988_at | Human 90 kD heat shock protein "gene," complete cds | 527 | 578 | 1441 | 1103 | 431 | 819 |
| J04990_at | Human cathepsin G "gene," complete cds | 112 | 66 | 54 | 86 | 76 | 147 |
| J05008_at | Homo sapiens endothelin-1 (EDN1) "gene," complete cds | 20 | 38 | 20 | 20 | 20 | 31 |
| J05016_ma1_at | Human (clone pA3) protein disulfide isomerase related protein (ERp72) "mRNA," complete cds | 20 | 20 | 20 | 20 | 20 | 20 |
| J05032_at | Human aspartyl-tRNA synthetase alph-2 subunit "mRNA," complete cds | 64 | 44 | 59 | 100 | 111 | 40 |
| J05036_s_at | Human cathepsin E "mRNA," complete cds | 20 | 24 | 689 | 1145 | 85 | 24 |
| J05037_at | Human serine dehydratase "mRNA," complete cds | 20 | 20 | 20 | 20 | 98 | 20 |
| J05068_at | human transcobalamin I "mRNA," complete cds | 20 | 84 | 20 | 129 | 20 | 34 |
| J05070_at | Human type IV collagenase "mRNA," complete cds | 20 | 61 | 1441 | 48 | 20 | 20 |
| J05073_at | Human phosphoglycerate mutase (PGAM-M) "gene," complete cds | 527 | 20 | 54 | 20 | 165 | 819 |
| J05096_ma1_at | Human Na,K-ATPase subunit alpha 2 (ATP1A2) gene, complete cds. | 27 | 32 | 20 | 20 | 62 | 147 |
| J05125_at | Human triglyceride lipase "mRNA," complete cds | 20 | 20 | 20 | 20 | 20 | 29 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| J05158_at | Human carboxypeptidase N "mRNA," 3' end | 20 | 20 | 20 | 20 | 20 | 20 | 20 |
| J05200_ma1_s_at | Human ryanodine receptor "mRNA," complete cds | 20 | 20 | 20 | 20 | 20 | 20 | 20 |
| J05213_at | Human sialoprotein "mRNA," complete cds | 26 | 20 | 20 | 20 | 20 | 20 | 20 |
| J05243_at | Human nonerythroid alph-spectrin (SPTAN1) "mRNA," complete cds | 122 | 55 | 93 | 110 | 20 | 20 | 91 |
| J05249_at | Human replication protein A 32-kDa subunit "mRNA," complete cds | 128 | 83 | 133 | 66 | 159 | 20 | 220 |
| J05252_s_at | | 20 | 20 | 20 | 20 | 31 | 20 | 20 |
| J05253_s_at | Human intestinal retinol-binding protein (IRBP) "gene," complete cds | 20 | 20 | 20 | 20 | 84 | 20 | 67 |
| J05257_at | Homo sapiens (clones "MDP4," MDP7) microsomal dipeptidase (MDP) "mRNA," complete cds | 20 | 20 | 20 | 42 | 91 | 20 | 110 |
| J05272_at | Human IMP dehydrogenase type 1 mRNA complete cds | 154 | 108 | 162 | 124 | 344 | 20 | 244 |
| J05401_at | Human sarcomeric mitochondrial creatine kinase (MtCK) "gene," complete cds | 20 | 20 | 20 | 20 | 20 | 20 | 20 |
| J05412_at | Human regenerating protein (reg) "gene," complete cds | 57 | 50 | 95 | 51 | 238 | 20 | 40 |
| J05426_at | Human "3,4-catechol" estrogen UDP-glucuronosyltransferase "mRNA," complete cds | 20 | 20 | 26 | 20 | 20 | 20 | 20 |
| J05448_at | Human RNA polymerase subunit hRPB "33," mRNA | 20 | 20 | 20 | 20 | 20 | 20 | 20 |
| J05459_at | Human glutathione transferase M3 (GSTM3) "mRNA," complete cds | 20 | 20 | 20 | 20 | 100 | 20 | 20 |
| J05500_at | Human beta-spectrin (SPTB) "mRNA," complete cds | 104 | 110 | 93 | 88 | 116 | 20 | 135 |
| J05556_at | Homo sapiens collagenase "mRNA," complete cds | 20 | 20 | 20 | 20 | 20 | 20 | 20 |
| J05582_at | Human pancreatic mucin "mRNA," complete cds | 20 | 283 | 68 | 20 | 170 | 20 | 66 |
| J05614_at | Human proliferating cell nuclear antigen (PCNA) "gene," promoter region. /gb=J05614 /ntype=DNA /annot=mRNA | 20 | 32 | 23 | 20 | 20 | 20 | 20 |
| J05633_at | Human integrin beta-5 subunit "mRNA," complete cds | 25 | 22 | 41 | 32 | 40 | 20 | 22 |
| J05682_at | Human subunit C of V-ATPase (vat C) "mRNA," 3' end | 23 | 37 | 44 | 36 | 197 | 20 | 23 |
| K01160_s_at | Human class II histocompatibility antigen Dc-alpha chain mRNA | 20 | 20 | 56 | 45 | 222 | 20 | 167 |
| K01383_at | Human matallothionein-1-A "gene," complete coding sequence | 32 | 20 | 57 | 103 | 123 | 20 | 23 |
| K01396_at | Human alpha-1-antitrypsin "mRNA," complete cds | 96 | 121 | 20 | 20 | 130 | 20 | 47 |
| K01884_at | Human Blym-1 transforming "gene," complete coding region | 20 | 20 | 20 | 22 | 20 | 20 | 30 |
| K01900_at | Human lymphocyte interferon alpha type 201 "mRNA," complete cds | 24 | 75 | 20 | 20 | 20 | 20 | 44 |
| K01911_at | Human neuropeptide Y (NPY) "mRNA," complete cds | 22 | 20 | 20 | 30 | 36 | 20 | 20 |
| K02054_at | Human gastrin-releasing peptide "mRNA," complete cds | 78 | 20 | 28 | 20 | 20 | 20 | 20 |
| K02100_at | Human ornithine transcarbamylase (OTC) "mRNA," complete coding sequence | 20 | 20 | 20 | 20 | 20 | 20 | 25 |
| K02215_at | Human angiotensinogen "mRNA," complete CDS | 20 | 20 | 20 | 20 | 104 | 20 | 20 |
| K02268_at | Human enkephalin B (enkB) "gene," 5' flank and | 143 | 20 | 20 | 20 | 188 | 20 | 20 |
| K02402_at | Human coagulation factor IX "gene," complete cds | 20 | 20 | 20 | 20 | 29 | 20 | 20 |
| K02405_f_at | Human MHC class II HLA-DC-3-beta gene "(DR3,3)" | 192 | 309 | 275 | 196 | 812 | 20 | 669 |
| K02545_cds2_at | Human T-cell receptor germline beta-chain J-beta-1 gene cluster: J-beta-1-1 and J-beta-1-2 genes; and D-beta-1-1 gene. | 20 | 20 | 20 | 33 | 39 | 20 | 20 |
| K02574_at | Human purine nucleoside phosphorylase (PNP) "mRNA," complete cds | 138 | 20 | 140 | 134 | 191 | 20 | 105 |
| K02765_at | Human complement component C3 "mRNA," alpha and beta "subunits," complete cds | 455 | 540 | 20 | 20 | 155 | 20 | 103 |
| K02766_at | Human complement component C9 "mRNA," complete cds | 20 | 37 | 20 | 20 | 20 | 20 | 33 |
| K02777_s_at | Human T-cell receptor active alpha-chain mRNA from Jurkat cell line | 20 | 20 | 20 | 20 | 20 | 20 | 20 |
| K02862_cds1_s_at | IGHD gene (immunoglobulin delta-chain) extracted from Human germline IgD chain "gene," "C-region," C-delta-1 domain | 20 | 20 | 59 | 20 | 46 | 20 | 20 |
| K03008_cds1_at | Human gamma-E-crystallin pseudogene (gamma-G2-psi), exon 3. | 26 | 20 | 20 | 20 | 62 | 20 | 20 |
| K03008_cds2_at | Human gamma-E-crystallin pseudogene (gamma-G2-psi), exon 3. | 25 | 20 | 20 | 32 | 20 | 20 | 20 |
| K03021_at | Human tissue plasminogen activator (PLAT) "gene," complete cds | 99 | 143 | 50 | 25 | 35 | 20 | 47 |
| K03183_f_at | Human chorionic gonadotropin beta subunit gene | 20 | 20 | 20 | 20 | 20 | 20 | 20 |
| K03189_f_at | Human chorionic gonadotropin beta subunit gene | 20 | 182 | 201 | 169 | 20 | 20 | 20 |
| K03192_f_at | | 20 | 20 | 20 | 20 | 114 | 20 | 20 |
| K03195_at | Human (HepG2) glucose transporter gene "mRNA," complete cds | 274 | 153 | 520 | 451 | 160 | 20 | 190 |
| K03204_f_at | Human PRB1 locus salivary protine-rich protein "mRNA," clone "cP3," complete cds | 20 | 20 | 20 | 20 | 20 | 20 | 20 |
| K03207_f_at | Human PR84 locus salivary protine-rich protein "mRNA," complete cds | 20 | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| K03218_at | Human c-src-1 proto-oncogene | 20 | 20 | 20 | 96 | 166 | 35 |
| K03430_at | Human complement C1q B-chain gene | 61 | 212 | 20 | 47 | 212 | 630 |
| K03431_cds1_at | HPR gene (haptoglobin-related protein) extracted from Human haptoglobin gene (alpha-2 allele) | 127 | 163 | 319 | 186 | 382 | 203 |
| K03460_at | Human alpha-tubulin isotype H2-alpha "gene," last exon | 215 | 632 | 659 | 359 | 192 | 232 |
| K03474_at | Human Mullerian inhibiting substance "gene," complete cds | 20 | 20 | 20 | 20 | 20 | 20 |
| K03494_s_at | Human green cone photoreceptor pigment gene 1 | 20 | 20 | 20 | 20 | 20 | 20 |
| K03498_xpt1_s_at | pot protein from Human endogenous retrovirus HERV-K22 pot and envelope ORF region. /gb=K03498 /ntype=DNA /annot=CDS | 97 | 124 | 266 | 148 | 514 | 172 |
| K03515_at | Human neuroleukin "mRNA," complete cds | 183 | 88 | 311 | 338 | 150 | 20 |
| L00022_s_at | Human Ig active epsilon1 5' "UT," V-D-J region subgroup "VH-I," gene | 20 | 20 | 20 | 20 | 20 | 107 |
| L00058_at | Human (GH) germline c-myc "protooncogene," 5' flank | 127 | 21 | 24 | 36 | 399 | 32 |
| L00137_cds1_at | Human growth hormone-releasing factor (GRF) gene, exon 5. | 59 | 20 | 20 | 65 | 20 | 52 |
| L00190_s_at | | 20 | 20 | 20 | 20 | 131 | 20 |
| L00205_at | Human K6b (epidermal "keratin," type II) gene | 154 | 20 | 20 | 20 | 20 | 20 |
| L00352_at | Human low density lipoprotein receptor gene | 169 | 51 | 20 | 38 | 80 | 20 |
| L00354_at | Human cholecystokinin (CCK) gene | 20 | 20 | 20 | 20 | 224 | 20 |
| L00389_f_at | Human cytochrome P-450 4 gene | 78 | 301 | 157 | 167 | 20 | 222 |
| L00634_s_at | Human farnesyl-protein transferase alpha-subunit "mRNA," complete cds | 60 | 71 | 134 | 197 | 524 | 35 |
| L00635_at | Human farnesyl-protein transferase beta-subunit "mRNA," complete cds | 31 | 20 | 95 | 82 | 34 | 38 |
| L00972_at | Human cystathionine-beta-synthase (CBS) mRNA | 55 | 66 | 93 | 66 | 20 | 69 |
| L01042_at | Human HIV1 tata element modulatory factor mRNA sequence from chromosome 3 | 20 | 27 | 20 | 20 | 25 | 20 |
| L01087_at | Human protein kinase C-theta (PRKCT) "mRNA," complete cds | 20 | 20 | 20 | 20 | 89 | 77 |
| L01406_at | Human growth hormone-releasing hormone receptor "mRNA," complete cds | 20 | 20 | 20 | 20 | 20 | 20 |
| L01664_at | Human eosinophil Charcot-Leyden crystal (CLC) protein (tysophospholipase) "mRNA," complete cds | 20 | 20 | 31 | 20 | 20 | 30 |
| L02320_at | Human radixin "mRNA," complete cds | 20 | 37 | 20 | 59 | 20 | 59 |
| L02321_at | Human glutathione S-transferase (GSTM5) "mRNA," complete cds | 168 | 61 | 110 | 56 | 30 | 111 |
| L02326_f_at | Homo sapiens (clone Hu lambda-17) lambda-like "gene," complete cds | 409 | 566 | 61 | 81 | 20 | 734 |
| L02426_at | Human 26S protease (64) regulatory subunit "mRNA," complete cds | 191 | 242 | 248 | 191 | 170 | 178 |
| L02547_at | Homo sapiens (clone p250-19) cleavage stimulation factor 50kDa "subunit," complete cds | 20 | 20 | 20 | 20 | 20 | 20 |
| L02648_at | Homo sapiens (clone V6) transcobalamin II TCN2) "mRNA," complete cds | 20 | 20 | 20 | 20 | 52 | 30 |
| L02785_at | Homo sapiens colon mucosa-associated (DRA) "mRNA," complete cds | 20 | 20 | 20 | 20 | 20 | 38 |
| L02840_at | Homo sapiens potassium channel Kv2.1 "mRNA," complete cds | 30 | 20 | 42 | 71 | 142 | 20 |
| L02867_at | Homo sapiens 62 kDa paraneoplastic antigen "mRNA," 3' end | 30 | 20 | 20 | 126 | 149 | 70 |
| L02932_at | Human peroxisome proliferator activated receptor "mRNA," complete cds | 20 | 20 | 20 | 39 | 101 | 20 |
| L02950_at | Human mu-crystallin "mRNA," complete cds | 63 | 20 | 20 | 20 | 20 | 42 |
| L03411s_at | Human RD protein (RD) "mRNA," complete cds | 55 | 118 | 100 | 110 | 20 | 155 |
| L03427_at | Human zinc finger protein basonuclin "mRNA," complete cds | 38 | 20 | 23 | 20 | 20 | 21 |
| L03532_at | Human M4 protein "mRNA," complete cds | 187 | 112 | 159 | 204 | 45 | 152 |
| L03785_at | Human regulatory myosin tight chain (MYLS) "mRNA," complete cds | 139 | 140 | 53 | 144 | 198 | 194 |
| L03640_s_at | Human fibroblast growth factor receptor 4 (FGFR4) "mRNA," complete cds | 20 | 72 | 20 | 20 | 136 | 20 |
| L04270_at | Homo sapiens (xlone CD18) tumor necrosis factor receptor 2 related protein "mRNA," complete cds | 143 | 20 | 20 | 303 | 20 | 20 |
| L04282_at | Human CACCC bos-binding protein "mRNA," complete cds | 20 | 31 | 20 | 39 | 128 | 20 |
| L04483_s_at | Human ribosomal protein S21 (RPS21) "mRNA," complete cds | 5632 | 11710 | 13374 | 9903 | 4063 | 3700 |
| L04490_at | Homo sapiens (clone CC6) NADH-ubiquinone oxidoreductase subunit "mRNA," 3' end cds | 85 | 99 | 152 | 61 | 20 | 20 |
| L04510_at | Human nucleotide binding protein "mRNA," complete cds | 20 | 20 | 20 | 20 | 20 | 23 |
| L04569_at | Homo sapiens (clone hHT-1) L-type voltage-dependent calcium channel a1 subunit (hHT) "mRNA," complete cds | 20 | 20 | 23 | 20 | 30 | 155 |
| L04656_at | Homo sapiens carbonic anhydrase related protein (CARP) "mRNA," complete cds | 20 | 20 | 33 | 20 | 20 | 20 |
| L04731_at | Homo sapiens translocation T(4;11) of ALL-1 gene to chromosome 4 | 20 | 110 | 49 | 22 | 21 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| L04733_at | Homo sapiens kinesin light chain "mRNA," complete cds | 20 | 63 | 20 | 25 | 20 | 20 |
| L04751_at | Human cytochrome p-450 4A (CYP4A) "mRNA," complete cds | 20 | 20 | 20 | 20 | 44 | 20 |
| L04947_at | Homo sapiens (clones "B73.081.8," BT3.129,5 and BT4.169) receptor tyrosine kinase (KDR) "mRNA," 3' end cds | 20 | 20 | 20 | 20 | 20 | 20 |
| L04953_at | Human x11 protein (x11) "mRNA," 3' end | 20 | 20 | 29 | 20 | 42 | 140 |
| L05072_s_at | Homo sapiens interferon regulatory factor 1 "gene," complete cds | 20 | 36 | 20 | 20 | 108 | 69 |
| L05144_at | Homo sapiens (clone lamda-hPEC-3) phosphoenolpyruvate carboxykinase (PCK1) "mRNA," complete cds | 20 | 20 | 20 | 26 | 164 | 91 |
| L05147_at | Human dual specificity phosphatase tyrosine/serine "mRNA," complete cds | 20 | 37 | 20 | 36 | 20 | 49 |
| L06148_at | Human protein tyrosine kinase related mRNA sequence | 63 | 20 | 20 | 20 | 20 | 96 |
| L05187_at | Homo sapiens small proline-rich protein 1 (SPRR1A) "gene," complete cds | 6544 | 209 | 170 | 173 | 956 | 362 |
| L05188_f_at | Homo sapiens small proline-rich protein 2 (SPRR28) "gene," complete cds | 4465 | 72 | 100 | 80 | 20 | 20 |
| L05424_cds2_at | Human cell surface glycoprotein CD44 (CD44) "gene," 3' end of long tailed isoform. | 20 | 25 | 20 | 20 | 20 | 20 |
| L05425_at | Homo sapiens autoantigen "mRNA," complete cds | 20 | 23 | 59 | 27 | 20 | 70 |
| L05500_at | Human fetal brain adenylyl cyclase "mRNA," 3' end | 20 | 20 | 20 | 20 | 20 | 20 |
| L05512_at | Human histatin 1 (HIS1) gene | 115 | 93 | 20 | 104 | 479 | 480 |
| L05514_f_at | Human histatin 3 (HIS2) gene | 20 | 20 | 20 | 20 | 35 | 20 |
| L05515_at | Homo sapiens CAMP response element-binding protein (CRE-BP1) "mRNA," complete cds | 20 | 20 | 20 | 20 | 20 | 20 |
| L05568_at | Homo sapiens Na+/Cl- dependent serotonin transporter "mRNA," complete cds | 20 | 20 | 58 | 20 | 20 | 29 |
| L05597_at | Human serotonin receptor "gene," complete cds | 20 | 20 | 20 | 20 | 20 | 20 |
| L05606_at | Human myosin binding protein H "mRNA," complete cds | 20 | 20 | 20 | 20 | 20 | 70 |
| L05624_s_at | Homo sapiens MAP kinase kinase "mRNA," complete cds | 20 | 20 | 20 | 20 | 20 | 20 |
| L05628_s_at | Homo sapiens cytosolic epoxide hydrolase "mRNA," complete cds | 20 | 36 | 98 | 126 | 74 | 20 |
| L05779_at | Human multidrug resistance-associated protein (MRP) "mRNA," complete cds | 109 | 122 | 316 | 320 | 28 | 163 |
| L06132_at | Human voltage-dependent anion channel isoform 1 (VDAC) "mRNA," complete cds | 159 | 20 | 20 | 20 | 20 | 20 |
| L06133_at | Human putative Cu++-transporting P-type ATPase "mRNA," complete cds | 20 | 20 | 20 | 52 | 20 | 20 |
| L06139_at | Homo sapiens receptor protein-tyrosine kinase (TEK) "mRNA," complete cds | 20 | 20 | 20 | 20 | 20 | 20 |
| L06147_at | Human (clone SY11) golgin-95 "mRNA," complete cds | 31 | 20 | 20 | 20 | 20 | 20 |
| L06175_at | Homo Sapiens P5-1 "mRNA," complete cds | 21 | 20 | 20 | 20 | 20 | 20 |
| L06419_at | Homo sapiens tysyl hydroxylase (PLOD) "mRNA," complete cds | 89 | 20 | 20 | 20 | 20 | 20 |
| L06499_at | Homo sapiens ribosomal protein L37a (RPL37A) "mRNA," complete cds | 6064 | 12530 | 9976 | 6472 | 5173 | 4453 |
| L06505_at | Human ribosomal protein L12 "mRNA," complete cds | 3024 | 4194 | 3548 | 3986 | 1317 | 2187 |
| L06633_at | Human transcription factor "mRNA," complete cds | 25 | 20 | 20 | 49 | 183 | 38 |
| L06797_s_at | Human (clone L5) orphan G protein-coupled receptor "mRNA," complete cds | 109 | 89 | 89 | 20 | 589 | 150 |
| L06845_at | Human cysteinyl-tRNA synthetase "mRNA," partial cds | 20 | 20 | 20 | 20 | 92 | 20 |
| L06895_at | Homo sapiens antagonizer of myc transcriptional activity (Mad) "mRNA," complete cds | 20 | 20 | 20 | 20 | 20 | 20 |
| L07033_at | Human hydroxymethylglutaryl-COA lyase "mRNA," complete cds | 20 | 121 | 105 | 158 | 207 | 222 |
| L07044_at | Homo sapiens calcium/calmodulin-dependent protein kinase (CAMK) isoform B mRNA sequence | 20 | 20 | 74 | 100 | 169 | 158 |
| L07077_at | Human enyol-COA: hydratase 3-hydroxyacyl-CoA dehydrogenase (EHHADH) "mRNA," complete cds with repeats | 20 | 20 | 23 | 20 | 20 | 20 |
| L07261_s_at | Human alpha adducin "mRNA," partial cds including alternate exons A and B (trimmed to 889 nts - region of identity with D44632) | 20 | 20 | 20 | 20 | 20 | 40 |
| L07493_s_at | Homo sapiens replication protein A 14kDa subunit (RPA) "mRNA," complete cds | 20 | 25 | 30 | 48 | 20 | 20 |
| L07515_at | Human heterochromatin protein homologue (HP1) "mRNA," complete cds | 20 | 50 | 20 | 20 | 29 | 20 |
| L07540_at | Human replication factor "C," 36-kDa subunit "mRNA," complete cds | 20 | 20 | 20 | 20 | 20 | 20 |
| L07541_at | Human replication factor "C," 38-kDa subunit "mRNA," complete cds | 20 | 20 | 20 | 20 | 20 | 255 |
| L07548_at | Human aminoacylase-1 (ACY1) "mRNA," complete cds | 71 | 91 | 130 | 275 | 176 | 93 |
| L07590_at | Human protein phosphatase 2A 130 kDa regulatory subunit "mRNA," complete cds | 39 | 20 | 27 | 20 | 20 | 37 |
| L07592_at | Human peroxisome proliferator activated receptor "mRNA," complete cds | 20 | 20 | 20 | 20 | 20 | 56 |
| L07594_at | Human transforming growth factor-beta type III receptor (TGF-beta) "mRNA," complete cds | 20 | 37 | 74 | 47 | 144 | 20 |
| L07597_at | Homo sapiens ribosomal protein S6 kinase 2 (RPS6KA2) "mRNA," complete cds | 20 | 58 | 20 | 28 | 182 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| L07615_at | Human neuropeptide Y receptor Y1 (NPYY1) "mRNA," exon 3-Feb and complete cds. /gb=L07615/ntype=RNA | 20 | 20 | 20 | 20 | 20 | 20 |
| L07633_at | Homo sapiens (done 1950.2) interferon-gamma IEF SSP 5111 "mRNA," complete cds | 270 | 249 | 382 | 357 | 28 | 346 |
| L07648_at | Human MXII "mRNA," complete cds | 102 | 42 | 69 | 32 | 20 | 20 |
| L07738_at | Homo sapiens DHP-sensitive calcium channel gamma subunit (CACNLG) "mRNA," complete cds | 93 | 20 | 20 | 75 | 100 | 94 |
| L07758_at | Human IEF SSP 9502 "mRNA," complete cds | 21 | 24 | 69 | 36 | 20 | 47 |
| L07765_at | Human carboxylesterase "mRNA," complete cds | 171 | 78 | 181 | 75 | 45 | 211 |
| L07807_s_at | Human dynamin "mRNA," alternative exons and complete cds | 52 | 35 | 75 | 20 | 354 | 61 |
| L07868_at | Homo sapiens receptor tyrosine kinase (ERBB4) "gene," complete cds | 20 | 20 | 20 | 29 | 110 | 20 |
| L07919_at | Human homeodomain protein DLX-2 "mRNA," 3' end | 20 | 20 | 20 | 20 | 20 | 20 |
| L07949_at | Homo sapiens GnRH receptor "mRNA," complete cds | 28 | 20 | 20 | 20 | 20 | 20 |
| L07956_at | Human "1,4-alph-glucan" branching enzyme (HGBE) "mRNA," complete cds | 50 | 29 | 79 | 20 | 20 | 20 |
| L08010_at | Human intestinal trefoil factor "mRNA," complete cds | 20 | 33 | 132 | 20 | 196 | 20 |
| L08044_s_at | Human reg gene "homologue," complete cds | 118 | 90 | 177 | 121 | 27 | 186 |
| L08089_at | Human heat shock "protein," E. coli DnaJ homologue "mRNA," complete cds | 20 | 82 | 51 | 85 | 144 | 85 |
| L08096_s_at | Human EBV induced G-protein coupled receptor (EBI2) "mRNA," complete cds | 20 | 20 | 20 | 20 | 20 | 20 |
| L08177_at | Human cytokine receptor (EBI3) "mRNA," complete cds | 101 | 114 | 136 | 44 | 173 | 186 |
| L08187_at | Homo sapiens myeloid cell differentiation protein (MCL1) mRNA | 260 | 186 | 49 | 92 | 101 | 146 |
| L08246_at | Homo sapiens achaete scute homologous protein (ASH1) "mRNA," complete cds | 43 | 20 | 20 | 22 | 23 | 42 |
| L08424_at | Human GABA-benzodiazepine receptor alpha-5-subunit (GABRA5) "mRNA," complete cds | 20 | 20 | 60 | 26 | 20 | 20 |
| L08485_at | Human inositol polyphosphate 1-phosphatase "mRNA," complete cds | 187 | 20 | 20 | 20 | 20 | 20 |
| L08488_at | Homo sapiens porin (por) "mRNA," complete cds and truncated cds | 581 | 107 | 240 | 398 | 20 | 134 |
| L08666_at | DM kinase gene (myotonic dystrophy kinase) extracted from Human myotonic dystrophy kinase (DM kinase) "gene," complete cds | 133 | 251 | 484 | 342 | 506 | 366 |
| L08835_ma2_a_at | Homo sapiens MADS/MEF2-family transcription factor (MEF2C) "mRNA," complete cds | 20 | 22 | 20 | 20 | 20 | 20 |
| L08895_at | Homo sapiens H2K binding factor 2 (KBF2) "mRNA," complete cds | 20 | 139 | 20 | 20 | 20 | 20 |
| L08904_at | Human trichohyalin (TRHY) gene, complete cds. | 20 | 71 | 58 | 45 | 75 | 54 |
| L09190_ma1_at | Homo sapiens amyloid protein homologue "mRNA," complete cds | 279 | 537 | 1082 | 924 | 585 | 202 |
| L09209_s_at | Human long-chain acyl-coenzyme A synthetase (FACL1) "mRNA," complete cds | 51 | 120 | 175 | 197 | 84 | 305 |
| L09229_at | Human C-C chemokine receptor type 1 (C-C CKR-1) "mRNA," complete cds | 20 | 20 | 20 | 20 | 318 | 20 |
| L09230_s_at | Human vacuolar ATPase (isoform H068) "mRNA," complete cds | 20 | 20 | 20 | 20 | 84 | 20 |
| L09234_at | Human vacuolar ATPase (isoform VA68) "mRNA," complete cds | 20 | 20 | 55 | 20 | 57 | 20 |
| L09235_at | Human (chromosome 3p25) membrane protein mRNA | 69 | 24 | 145 | 112 | 104 | 162 |
| L09260_at | Homo sapiens differentiation-dependent A4 protein "mRNA," complete cds | 588 | 292 | 471 | 609 | 331 | 299 |
| L09604_at | Human complement component 2 (C2) gene allele b | 75 | 62 | 75 | 111 | 151 | 80 |
| L09708_at | Homo sapiens lysosomal membrane glycoprotein-2 (LAMP2) "gene," 5' end and flanking region | 20 | 20 | 20 | 20 | 20 | 20 |
| L09717_at | Homo sapiens (clone F4) transmembrane protein mRNA sequence | 20 | 41 | 20 | 32 | 20 | 20 |
| L09749_at | Homo sapiens CD30 ligand "mRNA," complete cds | 20 | 20 | 20 | 20 | 20 | 20 |
| L09753_at | Human crystallin beta-B2 "mRNA," complete cds | 20 | 20 | 20 | 20 | 20 | 20 |
| L10102_ma1_at | Homo sapiens sex-determining region Y (SRY) gene, complete cds | 20 | 45 | 20 | 20 | 30 | 21 |
| L10123_at | Homo sapiens surfactant protein A "mRNA," complete cds | 20 | 20 | 20 | 20 | 20 | 20 |
| L10284_at | Homo sapiens integral membrane "protein," "calnexin," (IP90) "mRNA," complete cds | 388 | 239 | 577 | 399 | 154 | 269 |
| L10333_s_at | Homo sapiens neuroendocrine-specific protein A (NSP) "mRNA," complete cds | 20 | 40 | 24 | 25 | 20 | 28 |
| L10338_s_at | Human sodium channel beta-1 subunit (SCN1B) "mRNA," complete cds | 32 | 84 | 101 | 76 | 414 | 162 |
| L10343_at | Human elafin "gene," complete cds | 5388 | 101 | 20 | 33 | 20 | 188 |
| L10373_at | Human (clone CCG-B7) mRNA sequence | 42 | 20 | 20 | 20 | 20 | 20 |
| L10374_at | Human (clone CTG-A4) mRNA sequence | 20 | 22 | 20 | 20 | 38 | 20 |
| L10377_s_at | Human (clone CTGB37) mRNA sequence | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| L10378_at | Human (clone CTG-B43a) mRNA sequence | 70 | 65 | 150 | 108 | 253 | 154 |
| L10381_at | Human 2-5A-dependent RNase "gene," complete cds | 20 | 20 | 32 | 20 | 20 | 21 |
| L10386_at | Homo sapiens transglutaminase E3 (TGASE3) "mRNA," complete cds | 102 | 20 | 58 | 58 | 20 | 39 |
| L10403_at | Homo sapiens DNA binding protein for surfactant protein B "mRNA," complete cds | 20 | 20 | 20 | 20 | 20 | 20 |
| L10405_at | Homo sapiens DNA binding protein for surfactant protein B "mRNA," complete cds. /gb=L10405 /ntype=RNA | 50 | 49 | 20 | 44 | 20 | 185 |
| L10413_at | Human farnesyltransferase alpha-subunit "mRNA," complete cds | 109 | 206 | 169 | 243 | 20 | 236 |
| L10615_s_at | Homo Sapiens beta casein (CSN2) "gene," complete cds | 120 | 60 | 233 | 24 | 735 | 62 |
| L10665_at | Homo sapiens GTP-binding protein "superfamily," G protein alpha-olf subunit (olfactory) "mRNA," complete cds | 20 | 35 | 20 | 21 | 122 | 62 |
| L10878_at | Human profilin II "mRNA," complete cds | 32 | 20 | 91 | 139 | 89 | 20 |
| L10717_at | Homo sapiens T cell-specific tyrosine kinase "mRNA," complete cds | 20 | 20 | 74 | 20 | 20 | 315 |
| L10838_at | Homo sapiens SR protein "family," pre-mRNA splicing factor (SRp20) "mRNA," complete cds | 166 | 106 | 278 | 173 | 148 | 131 |
| L10844_at | Human cellular growth-regulating protein "mRNA," complete cds | 97 | 20 | 20 | 20 | 20 | 42 |
| L10910_at | Homo sapiens splicing factor (CC1.3) "mRNA," complete cds | 20 | 32 | 136 | 20 | 20 | 20 |
| L10955_cds1_s_at | carbonic anhydrase IV gene extracted from Human carbonic anhydrase IV "gene," promoter region and | 20 | 20 | 20 | 20 | 153 | 20 |
| L11005_at | Human mRNA sequence | 20 | 20 | 57 | 20 | 20 | 20 |
| L11086_at | Homo sapiens platelet membrane glycoprotein V "mRNA," complete cds | 114 | 132 | 142 | 141 | 20 | 183 |
| L11238_s_at | Homo sapiens homeobox protein (HOX) "gene," 3' end | 20 | 20 | 20 | 20 | 20 | 20 |
| L11239_at | | 20 | 20 | 37 | 20 | 91 | 20 |
| L11244_s_at | | 20 | 20 | 20 | 20 | 20 | 40 |
| L11284_at | Homosapiens ERK activator kinase (MEK1) mRNA | 81 | 218 | 285 | 49 | 20 | 410 |
| L11285_at | Homosapiens ERK activator kinase (MEK2) mRNA | 244 | 62 | 20 | 309 | 309 | 20 |
| L11329_at | Homo sapiens protein tyrosine phosphatase (PAC-1) "mRNA," complete cds | 20 | 20 | 20 | 90 | 20 | 20 |
| L11353_at | Human moesin-ezrin-radixin-like protein "mRNA," complete cds | 20 | 31 | 49 | 20 | 20 | 20 |
| L11369_at | Human protocadherin 42 "mRNA," 3' end of cds for alternative splicing PC42-8 | 50 | 82 | 361 | 53 | 113 | 86 |
| L11370_at | Human protocadherin 42 "mRNA," complete cds for abbreviated PC42 | 311 | 48 | 20 | 170 | 310 | 248 |
| L11372_at | Human protocadherin 43 "mRNA," 3' end of cds for alternative splicing PC43-12 | 34 | 20 | 20 | 31 | 20 | 20 |
| L11373_at | Human protocadherin 43 "mRNA," complete cds for abbreviated PC43 | 214 | 106 | 284 | 184 | 47 | 206 |
| L11568_at | Homo sapiens ribosomal protein L18 (RPL18) "mRNA," complete cds | 1399 | 1195 | 2489 | 2170 | 522 | 1172 |
| L11573_at | Human surfactant protein B "mRNA," complete cds. /gb=L11573 /ntype=RNA | 20 | 20 | 20 | 20 | 20 | 20 |
| L11669_at | Human tetracycline transporter-like protein "mRNA," complete cds | 20 | 138 | 308 | 212 | 28 | 186 |
| L11672_at | Human Kruppel related zinc finger protein (HTF10) "mRNA," complete cds | 370 | 855 | 1513 | 1144 | 3690 | 1219 |
| L11672_r_at | Human Kruppel related zinc finger protein (HTF10) "mRNA," complete cds | 20 | 67 | 202 | 168 | 125 | 198 |
| L11695_at | Human activin receptor-like kinase (ALK-5) "mRNA," complete cds | 22 | 35 | 20 | 20 | 20 | 94 |
| L11701_at | Human phospholipase D "mRNA," complete cds | 20 | 20 | 53 | 20 | 187 | 20 |
| L11702_at | Human phospholipase D "mRNA," complete cds | 20 | 20 | 20 | 20 | 20 | 20 |
| L11708_at | Human 17 beta hydroxysteroid dehydrogenase type 2 "mRNA," complete cds | 61 | 159 | 661 | 365 | 143 | 26 |
| L11931_at | Human cytosolic serine hydroxymethyltransferase (SHMT) "mRNA," complete cds | 20 | 20 | 20 | 20 | 20 | 20 |
| L12052_at | Human cAMP phosphodiesterase "mRNA," 3' end | 20 | 20 | 20 | 20 | 20 | 20 |
| L12060_s_at | Homo sapiens retinoic acid receptor (gamma-7) mRNA | 20 | 20 | 20 | 20 | 20 | 20 |
| L12168_at | Homo sapiens adenylyl cyclase-associated protein (CAP) "mRNA," complete cds | 390 | 445 | 323 | 273 | 276 | 431 |
| L12350_at | Human thrombospondin 2 (THBS2) "mRNA," complete cds | 32 | 170 | 99 | 23 | 20 | 122 |
| L12392_at | Homo sapiens Huntington's Disease (HD) "mRNA," complete cds | 148 | 148 | 188 | 162 | 187 | 153 |
| L12468_at | Homo sapiens aminopeptidase A "mRNA," complete cds | 50 | 20 | 21 | 20 | 20 | 20 |
| L12535_at | Human RSU-1/RSP-1 "mRNA," complete cds | 69 | 88 | 117 | 63 | 165 | 23 |
| L12701_cds2_at | Human engrailed protein (EN2) gene, 3' end. | 71 | 20 | 20 | 33 | 11 | 27 |
| L12711_s_at | Hoo sapiens transketolase (tk) "mRNA," complete cds | 589 | 181 | 534 | 1219 | 216 | 206 |
| L12723_at | Human heat shock protein 70 (hsp70) "mRNA," complete cds | 101 | 74 | 142 | 130 | 20 | 152 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| L12760_s_at | Human phosphoenolpyruvate carboxykinase (PCK1) "gene," complete cds with repeats | 21 | 75 | 43 | 21 | 20 | 42 |
| L13042_at | Homo sapiens calbindin D-9k "gene," 5' end cds | 20 | 20 | 74 | 37 | 172 | 76 |
| L13197_at | Human (clone D21S418E) pregnancy-associated plasma protein A (PAPP-A) "gene," 5' UTR | 76 | 144 | 104 | 107 | 239 | 189 |
| L13203_at | Human HNF-3/fork-head homolog-3 HFH-3' "mRNA," complete cds | 145 | 97 | 181 | 20 | 146 | 136 |
| L13210_at | Human Mac-2 binding protein "mRNA," complete cds | 133 | 181 | 660 | 708 | 89 | 479 |
| L13258_at | Homo sapiens renal Na/Pi-cotransporter "mRNA," complete cds | 20 | 46 | 20 | 20 | 20 | 20 |
| L13266_s_at | Homo sapiens N-methyl-d-aspartate receptor (NR1-1) "mRNA," complete cds | 20 | 58 | 20 | 37 | 381 | 74 |
| L13278_at | Homo sapiens zeta-crystallin/quinone reductase "mRNA," complete cds | 20 | 20 | 20 | 57 | 20 | 20 |
| L13286_at | Human mitochondrial "1,25-dihydroxyvitamin" D3 24-hydroxylase "mRNA," complete cds | 20 | 20 | 20 | 20 | 91 | 20 |
| L13329_at | Homo sapiens iduronate-2-sulfatase (IDS) gene | 20 | 40 | 20 | 20 | 20 | 20 |
| L13391_at | Human helix-loop-helix basic phosphoprotein (G0S8) "gene," complete cds | 288 | 95 | 48 | 20 | 20 | 59 |
| L13434_at | Human chromosome 3p21.1 gene "sequence," complete cds | 81 | 41 | 122 | 89 | 20 | 86 |
| L13436_at | Homo sapiens guanylate cyclase "mRNA," complete mature peptide | 20 | 20 | 20 | 20 | 20 | 144 |
| L13689_at | Human prot-oncogene (BMI-1) "mRNA," complete cds | 20 | 57 | 77 | 55 | 25 | 59 |
| L13698_at | Human gas1 "gene," complete cds | 60 | 20 | 31 | 20 | 20 | 54 |
| L13720_at | Homo sapiens growth-arrest-specific protein (gas) "mRNA," complete cds | 62 | 20 | 20 | 20 | 20 | 20 |
| L13738_at | Human activated p21cdc42Hs kinase (ack) "mRNA," complete cds | 20 | 77 | 45 | 122 | 132 | 103 |
| L13740_at | Homo sapiens TR3 orphan receptor "mRNA," complete cds | 212 | 258 | 466 | 373 | 782 | 329 |
| L13744_at | Human AF-4 "mRNA," complete cds | 20 | 20 | 20 | 20 | 20 | 20 |
| L13761_ma1_at | Human dihydrolipoamide dehydrogenase gene, exon 14. | 119 | 22 | 115 | 30 | 64 | 99 |
| L13773_at | Human AF-4 "mRNA," complete cds | 24 | 20 | 75 | 56 | 20 | 71 |
| L13800_at | Homo sapiens liver expressed protein "gene," 3' end. /gb=L13800 /ntype=RNA | 32 | 20 | 56 | 51 | 49 | 44 |
| L13848_at | Human RNA helicase A "mRNA," complete cds | 51 | 29 | 20 | 37 | 20 | 99 |
| L13852_at | Homo sapiens ubiquitin-activating enzyme E1 related protein "mRNA," complete cds | 86 | 225 | 281 | 216 | 222 | 363 |
| L13923_at | Homo sapiens fibrillin "mRNA," complete cds | 75 | 83 | 146 | 39 | 48 | 73 |
| L13939_s_at | Human beta adaptin protein "mRNA," complete cds | 209 | 275 | 419 | 405 | 897 | 311 |
| L13943_at | Human glycerol kinase (GK) mRNA exons "1–4," complete cds | 20 | 38 | 20 | 20 | 20 | 20 |
| L13972_at | Homo sapiens beta-galactoside "alph-2,3-sialyltransferase" (SIAT4A) "mRNA," complete cds | 20 | 20 | 20 | 56 | 20 | 20 |
| L13977_at | Human prolylcarboxypeptidase "mRNA," complete cds | 97 | 232 | 85 | 95 | 137 | 66 |
| L13994_at | Homo sapiens preC "gene," complete cds; ORF "X," complete cds | 20 | 20 | 20 | 20 | 20 | 62 |
| L14076_at | Homo sapiens pre-mRNA splicing factor SRp75 "mRNA," complete cds | 60 | 54 | 211 | 112 | 204 | 44 |
| L14269_at | Homo sapiens synaptic vesicle amine transporter (SVAT) "mRNA," complete cds | 20 | 20 | 20 | 26 | 20 | 27 |
| L14430_at | Human UDP-glucose pyrophosphorylase "mRNA," complete cds and flanking regions | 21 | 20 | 285 | 414 | 58 | 290 |
| L14542_at | Human lectin-like type II integral membrane protein (NKG2-E) "mRNA," complete cds | 20 | 20 | 54 | 38 | 20 | 20 |
| L14565_at | Human peripherin (PRPH) gene exons "1–9," complete cds | 20 | 20 | 20 | 20 | 20 | 20 |
| L14595_at | Human alanine/serine/cysteine/threonine transporter (ASCT1) "mRNA," complete cds | 20 | 77 | 120 | 207 | 81 | 97 |
| L14754_at | Human calmodul-dependent protein phosphatase catalytic subunit (PPP3CA) "mRNA," complete cds | 26 | 20 | 20 | 59 | 271 | 202 |
| L14778_s_at | Homo sapiens DNA-binding protein (SMBP2) "mRNA," complete cds | 61 | 132 | 115 | 136 | 255 | 24 |
| L14787_at | Human DNA-binding protein "mRNA," 3'end | 20 | 20 | 20 | 20 | 20 | 20 |
| L14812_at | Human retinoblastoma related protein (p107) "mRNA," complete cds | 20 | 20 | 23 | 20 | 20 | 20 |
| L14813_at | Human carboxyl ester lipase like protein (CELL) "mRNA," complete cds | 631 | 360 | 285 | 414 | 136 | 290 |
| L14837_at | Human tight junction (zonula occludens) protein ZO-1 "mRNA," complete cds | 113 | 35 | 82 | 38 | 92 | 20 |
| L14848_s_at | Human MHC class I-related protein "mRNA," complete cds | 20 | 20 | 20 | 20 | 20 | 20 |
| L14856_at | Human somatostatin receptor "gene," complete cds | 262 | 97 | 120 | 207 | 354 | 199 |
| L14922_at | Homo sapiens DNA-binding protein (PO-GA) "mRNA," complete cds | 20 | 20 | 20 | 59 | 20 | 85 |
| L14927_at | Human tear prealbumin (TP) "gene," complete cds and promoter region | 20 | 20 | 20 | 20 | 20 | 20 |
| L15189_s_at | MITOCHONDRIAL STRESS-70 PROTEIN PRECURSOR | 126 | 124 | 310 | 295 | 232 | 180 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| L15296_s_at | Homo sapiens clone hRCNC2b retinal rod cyclic nucleotide-gated cation channel "gene," complete cds | 71 | 20 | 20 | 20 | 69 | 20 |
| L15309_at | Human zinc finger protein (ZNF141) "mRNA," complete cds | 20 | 29 | 82 | 31 | 39 | 20 |
| L15326_s_at | Human endoperoxide synthase type II "mRNA," complete cds | 50 | 20 | 20 | 20 | 20 | 42 |
| L15344_at | Human high molecular weight B cell growth factor mRNA sequence | 20 | 20 | 20 | 78 | 20 | 20 |
| L15388_at | Human G protein-coupled receptor kinase (GRK5) "mRNA," complete cds | 20 | 20 | 20 | 20 | 20 | 55 |
| L15409_at | Homo sapiens (done g7) von Hippel-Lindau disease tumor suppressor mRNA sequence | 124 | 20 | 81 | 79 | 215 | 20 |
| L15440_at | Homo sapiens tyrosine hydroxylase (Th) "gene," 3' end; insulin (INS) "gene," complete cds; insulin-like growth factor 2 (IGF2) "gene," 5' e | 20 | 20 | 20 | 20 | 20 | 20 |
| L15533_ma1_at | Homo sapiens pancreatitis-associated protein (PAP) gene, complete cds. | 20 | 61 | 20 | 34 | 26 | 55 |
| L15702_at | Human complement factor B "mRNA," complete cds | 158 | 363 | 374 | 178 | 495 | 389 |
| L16464_at | Human ETS oncogene (PEP1) "mRNA," complete cds | 20 | 20 | 30 | 54 | 36 | 97 |
| L16782_at | Human putative M pbsse phosphoprotein 1 (MPP1) "mRNA," partial cds | 23 | 25 | 20 | 20 | 20 | 55 |
| L16842_at | Human ubiquinol cytochrome-reductase core I protein "mRNA," complete cds | 66 | 95 | 147 | 176 | 40 | 149 |
| L16862_at | Homo sapiens G protein-coupled receptor kinase (GRK6) "mRNA," complete cds | 190 | 115 | 337 | 217 | 538 | 356 |
| L16895_at | Human lysyl oxidase (LOX) "gene," exon 7 | 68 | 20 | 20 | 39 | 20 | 59 |
| L16896_at | Human zinc finger protein "mRNA," complete cds | 20 | 20 | 20 | 20 | 20 | 20 |
| L16991_at | Homo sapiens pancreatitis-associated protein (PAP) gene, complete cds | 51 | 20 | 20 | 30 | 20 | 20 |
| L17075_s_at | Human thymidylate kinase (CDC8) "mRNA," complete cds | 20 | 20 | 20 | 28 | 20 | 20 |
| L17128_at | Homo sapiens (clone H4/H16) gamma-glutamic carboxylase "mRNA," complete cds | 32 | 36 | 20 | 83 | 49 | 133 |
| L17131_ma1_at | Human high mobility group protein (HMG-I(Y)) gene exons 1-B, complete cds. | 160 | 100 | 20 | 167 | 20 | 160 |
| L17325_at | Human preT/NK cell associated protein (1D12A2) "mRNA," complete cds | 20 | 20 | 20 | 20 | 20 | 20 |
| L17327_at | Human preT/NK cell associated protein (3B3) "mRNA," 3' end | 88 | 63 | 54 | 115 | 210 | 88 |
| L17326_at | Human preT/NK cell associated protein (3C1) "mRNA," complete cds | 46 | 20 | 20 | 20 | 20 | 58 |
| L17330_at | Human preT/NK cell associated protein (6H9A) "mRNA," complete cds | 20 | 20 | 20 | 20 | 20 | 20 |
| L17418_cds2_s_at | complement receptor 1 gene extracted from Human complement receptor type 1 (alleles S and F) "gene," enhancer and | 20 | 84 | 78 | 84 | 20 | 20 |
| L18877_f_at | Human MAGE-12 protein "gene," complete cds | 25 | 20 | 23 | 20 | 20 | 20 |
| L18920_f_at | Human MAGE-2 gene exons "1-4," complete cds | 20 | 20 | 73 | 37 | 20 | 20 |
| L18960_at | Human protein synthesis factor (eIF-4C) "mRNA," complete cds | 37 | 75 | 93 | 78 | 66 | 76 |
| L18972_at | Human anonymous "gene," complete cds | 38 | 77 | 476 | 218 | 602 | 55 |
| L18983_at | Human tyrosine phosphatase (IA-2/PTP) "mRNA," complete cds | 220 | 151 | 20 | 20 | 20 | 440 |
| L19058_at | Human glutamate receptor (GLUR5) "mRNA," 3' end of cds | 89 | 87 | 20 | 20 | 20 | 113 |
| L19063_at | Human glial-derived neurotrophic factor "gene," complete cds. /gb=L19063 /ntype=DNA /annot=exon | 20 | 20 | 69 | 20 | 20 | 20 |
| L19067_at | Human NF-kappa-B transcription factor p65 subunit "mRNA," complete cds | 20 | 24 | 20 | 22 | 20 | 20 |
| L19161_at | Human translation initiation factor eIF-2 gamma subunit "mRNA," complete cds | 20 | 34 | 20 | 20 | 20 | 20 |
| L19183_at | Humsn MAC30 "mRNA," 3' end | 20 | 113 | 156 | 147 | 328 | 84 |
| L19267_at | Homo sapiens 59 protein "mRNA," 3' end | 139 | 239 | 304 | 200 | 452 | 357 |
| L19297_at | Human nuclear-encoded mitochondrial carbonic anhydrase (CA5) "mRNA," complete cds | 20 | 20 | 20 | 20 | 25 | 20 |
| L19314_at | Human HRY "gene," complete cds | 143 | 87 | 285 | 135 | 141 | 105 |
| L19401_at | Human myosin I homologue (MYH12) "mRNA," 3' end of cds | 20 | 20 | 20 | 42 | 38 | 20 |
| L19437_at | Human transaldolase mRNA containing transposable "element," complete cds | 532 | 210 | 157 | 177 | 52 | 277 |
| L19493_s_at | Human FMR1 "gene," 3' end | 20 | 69 | 144 | 86 | 20 | 61 |
| L19527_at | Homo sapiens ribosomal protein L27 (RPL27) "mRNA," complete cds | 1991 | 2522 | 2225 | 2459 | 1621 | 1206 |
| L19593_at | Homo sapiens interleukin 8 receptor beta (IL8RB) "mRNA," complete cds | 20 | 20 | 54 | 20 | 39 | 55 |
| L19605_at | Homo sapiens 56K autoantigen annexin XI gene "mRNA," complete cds | 336 | 305 | 598 | 346 | 292 | 275 |
| L19686_ma1_at | Homo sapiens macrophage migration inhibitory factor (MIF) gene, complete cds. | 612 | 919 | 1439 | 2210 | 97 | 425 |
| L19711_at | Human dystroglycan (DAG1) "mRNA," complete cds | 84 | 40 | 104 | 20 | 225 | 79 |
| L19778_at | Homo sapiens histone (H2A.1b) "mRNA," complete cds | 20 | 20 | 20 | 20 | 31 | 20 |
| L19779_at | Homo sapiens histone H2A.2 "mRNA," complete cds | 99 | 119 | 170 | 175 | 176 | 548 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| L19783_at | Human GPI-H "mRNA," complete cds | 20 | 20 | 73 | 37 | 20 | 20 |
| L19871_at | Human activating transcription factor 3 (AITF3) "mRNA," complete cds | 145 | 20 | 32 | 20 | 73 | 74 |
| L19872_at | Human AH-receptor "mRNA," complete cds | 43 | 20 | 131 | 55 | 20 | 21 |
| L20010_at | Human HCF1 gene related mRNA sequence | 20 | 20 | 20 | 20 | 20 | 55 |
| L20298_at | Homo sapiens transcription factor (CBFB) "mRNA," 3′ end | 20 | 32 | 40 | 20 | 22 | 52 |
| L20316_at | Human glucagon receptor "mRNA," complete cds | 150 | 151 | 157 | 62 | 304 | 291 |
| L20320_at | Human protein serine/threonine kinase stk1 "mRNA," complete cds | 100 | 20 | 23 | 48 | 20 | 23 |
| L20321_at | Human protein serine/threonine kinase stk2 "mRNA," complete cds | 32 | 20 | 20 | 20 | 20 | 20 |
| L20348_at | Homo sapiens oncomodulin gene | 20 | 20 | 20 | 20 | 20 | 20 |
| L20433_at | Human octamer binding transcription factor 1 (OTF1) "mRNA," complete cds | 20 | 28 | 144 | 31 | 204 | 30 |
| L20469_s_at | Human annexin III (ANX3) "gene," alternative | 122 | 50 | 46 | 20 | 40 | 70 |
| L20591_at | Human GDP-dissociation inhibitor protein (Ly-GDI) "mRNA," complete cds | 356 | 553 | 472 | 444 | 379 | 1078 |
| L20688_at | Homo sapiens mRNA in the region near the btk gene involved in a-gamma-globulinemia | 134 | 144 | 276 | 145 | 268 | 298 |
| L20773_at | Human glutamate receptor 2 (HBGR2) "mRNA," complete cds | 28 | 22 | 20 | 20 | 72 | 54 |
| L20814_at | Human S protein "mRNA," complete cds | 32 | 20 | 101 | 39 | 20 | 93 |
| L20815_at | Human I-plastin "mRNA," complete cds | 20 | 20 | 101 | 22 | 99 | 20 |
| L20826_at | Human leukemia virus receptor 2 (GlVR2) "mRNA," complete cds | 20 | 20 | 20 | 20 | 20 | 20 |
| L20852_at | Human leukemia virus receptor 1 (GlVR1) "mRNA," completet cds | 27 | 40 | 91 | 249 | 61 | 27 |
| L20859_at | Human glycoprotein Ib beta "mRNA," complete cds | 20 | 20 | 20 | 20 | 20 | 20 |
| L20860_at | Homo sapiens proto-oncogene (Wnt-5a) "mRNA," complete cds | 73 | 61 | 30 | 49 | 20 | 229 |
| L20861_at | Human ferritin heavy chain "mRNA," complete cds | 1771 | 1530 | 1325 | 1326 | 2713 | 1698 |
| L20941_at | Human phosphodiesterase "mRNA," complete cds | 59 | 134 | 254 | 121 | 245 | 157 |
| L20965_at | Human phosphodiesterase "mRNA," complete cds | 20 | 20 | 20 | 44 | 20 | 44 |
| L20971_at | Homo sapiens troponin I fast-twitch isoform "mRNA," complete cds | 20 | 52 | 60 | 357 | 72 | 77 |
| L21715_at | Human Na/taurocholate cotransporting polypeptide "mRNA," complete cds | 49 | 63 | 69 | 80 | 300 | 103 |
| L21893_at | Human acyl coenzyme A:cholesterol acyltransferase "mRNA," complete cds | 21 | 20 | 20 | 20 | 20 | 20 |
| L21934_at | Human succinate dehydrogenase flavoprotein subunit (SDH) "mRNA," complete cds | 106 | 100 | 123 | 130 | 168 | 124 |
| L21936_at | Human peripheral benzodiazepine receptor gene | 337 | 341 | 406 | 485 | 20 | 87 |
| L21954_at | Human adenylyl cyclase "mRNA," 3′ end of cds | 20 | 20 | 20 | 20 | 20 | 20 |
| L21993_at | Human intestinal mucin (MUC2) "mRNA," complete cds | 65 | 139 | 180 | 153 | 20 | 20 |
| L21998_at | Human ubiquitin conjugating enzyme "mRNA," partial cds | 20 | 36 | 20 | 63 | 32 | 74 |
| L22005_at | Human hnRNP H "mRNA," complete cds | 175 | 187 | 654 | 268 | 20 | 173 |
| L22009_at | Human guanine nucleotide regulatory protein (G13) "mRNA," complete cds | 24 | 33 | 20 | 20 | 20 | 77 |
| L22075_at | Human vasopressin receptor V2 "gene," complete cds | 20 | 20 | 20 | 20 | 20 | 65 |
| L22206_at | Human adenosine A1 receptor (ADORA1) mRNA exons "1-6," complete cds | 110 | 98 | 153 | 153 | 270 | 301 |
| L22214_at | Human nuclear phosphoprotein "mRNA," complete cds | 46 | 39 | 20 | 51 | 169 | 30 |
| L22342_at | Human nuclear phosphoprotein "mRNA," complete cds | 20 | 20 | 97 | 20 | 20 | 20 |
| L22343_at | Homo sapiens nuclear respiratory factor-1 (NRF-1) "mRNA," complete cds | 20 | 20 | 20 | 20 | 177 | 20 |
| L22454_at | Human matrilysin gene | 20 | 190 | 90 | 55 | 188 | 63 |
| L22524_s_at | Human collagen type XVIII alpha 1 (COL18A1) "mRNA," partial cds | 27 | 77 | 20 | 20 | 90 | 71 |
| L22548_at | Homo sapiens cathepsin B "mRNA," 3′ UTR with a stem-loop structure providing mRNA stability | 20 | 20 | 20 | 20 | 109 | 20 |
| L22650_at | Human early lymphoid activation protein (EPAG) mRNA sequence | 20 | 20 | 50 | 84 | 102 | 20 |
| L23116_at | Homo sapiens galactocerebrosidase (GALS) "mRNA," complete cds | 20 | 36 | 20 | 20 | 54 | 23 |
| L23333_s_at | Human corticotropin releasing factor receptor "mRNA," complete cds | 128 | 293 | 385 | 299 | 343 | 146 |
| L23808_at | Human metalloproteinase (HME) "mRNA," complete cds | 44 | 22 | 267 | 180 | 130 | 20 |
| L23852_at | Homo sapiens (clone Zl46) retinal "mRNA," 3′ end and repeat region | 22 | 30 | 122 | 52 | 20 | 114 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| L23959_at | Homo sapiens E2F-related transcription factor (DP-1) "mRNA," complete cds | 20 | 20 | 20 | 20 | 20 | 20 |
| L24203_at | Homo sapiens ataxia-telangiectasia group D-associated protein "mRNA," complete cds | 762 | 213 | 485 | 426 | 150 | 239 |
| L24470_at | Homo sapiens prostanoid FP receptor "mRNA," complete cds | 77 | 75 | 20 | 20 | 20 | 36 |
| L24559_at | Homo sapiens DNA polymerase alpha "mRNA," complete cds | 20 | 20 | 20 | 20 | 20 | 48 |
| L24564_at | Human Rad "mRNA," complete cds | 20 | 20 | 20 | 20 | 20 | 20 |
| L24774_s_at | Homo sapiens "delta3," delta2-CoA-isomerase "mRNA," 3' end | 102 | 259 | 176 | 250 | 338 | 79 |
| L24783_at | Homo sapiens mRNA fragment /gb=L24783 /ntype=RNA | 42 | 104 | 168 | 111 | 178 | 185 |
| L24804_at | Human (p23) "mRNA," complete cds | 133 | 48 | 39 | 36 | 20 | 20 |
| L24893_s_at | Human myelin protein zero (PO) gene | 20 | 20 | 20 | 20 | 20 | 85 |
| L25080_at | Human GTP-binding protein (rhoA) "mRNA," complete cds | 284 | 250 | 524 | 308 | 246 | 309 |
| L25081_at | Human GTPase (rhoC) "mRNA," complete cds | 185 | 219 | 49 | 111 | 169 | 187 |
| L25085_at | Human Sec61-complex beta-subunit "mRNA," complete cds | 222 | 103 | 20 | 62 | 290 | 185 |
| L25119_at | Human Mu opiate receptor (MOR1) "mRNA," complete cds | 24 | 20 | 20 | 23 | 20 | 96 |
| L25270_at | Human X#169 "mRNA," complete cds | 20 | 78 | 20 | 99 | 158 | 89 |
| L25286_s_at | Homo sapiens alpha-1 type XV collagen "mRNA," complete cds | 20 | 20 | 21 | 23 | 95 | 20 |
| L25441_at | Human geranylgeranyltransferase type I beta-subunit "mRNA," complete cds | 100 | 37 | 20 | 20 | 20 | 20 |
| L25444_at | Homo sapiens (TAFII70-alpha) "mRNA," complete cds | 101 | 20 | 20 | 118 | 341 | 77 |
| L25798_at | Homo sapiens 3-hydroxy-3-methylglutaryl coenzyme A synthase "mRNA," complete cds | 20 | 20 | 39 | 28 | 20 | 96 |
| L25851_at | Homo sapiens integrin alpha E "mRNA," complete cds | 20 | 55 | 51 | 20 | 20 | 20 |
| L25876_at | Homo sapiens protein tyrosine phosphatase "(CIP2)mRNA," complete cds | 36 | 20 | 67 | 20 | 20 | 126 |
| L25878_s_at | Homo sapiens p33/HEH epoxide hydrolase (EPHX) "mRNA," complete cds | 20 | 20 | 20 | 20 | 20 | 61 |
| L25931_s_at | Human lamin B receptor (LBR) "mRNA," complete cds | 43 | 59 | 81 | 46 | 216 | 20 |
| L26081_at | Homo sapiens semaphorin-III (Hsema-I) "mRNA," complete cds | 20 | 20 | 20 | 20 | 34 | 37 |
| L26234_at | Homo sapiens apolipoprotein B mRNA editing "enzyme," catalytic polypeptide 1 (APOBEC1) "mRNA," complete cds | 1375 | 886 | 1440 | 1336 | 565 | 898 |
| L26247_at | Homo sapiens sullisol "mRNA," complete cds | 20 | 20 | 20 | 20 | 20 | 20 |
| L26336_at | Human heat shock protein HSPA2 "gene," complete cds | 108 | 78 | 20 | 68 | 67 | 44 |
| L26339_at | Human autoantigen "mRNA," complete cds | 20 | 43 | 39 | 30 | 20 | 20 |
| L26494_at | Homo sapiens (oct-6) "mRNA," complete cds | 47 | 20 | 28 | 20 | 20 | 20 |
| L26584_at | Human (CDC25) "mRNA," complete cds | 20 | 32 | 20 | 20 | 20 | 92 |
| L26953_at | Homo sapiens chromosomal protein "mRNA," complete cds | 20 | 20 | 20 | 20 | 81 | 20 |
| L27050_at | Human apolipoprotein F (APOF) "mRNA," complete cds | 20 | 20 | 20 | 20 | 20 | 20 |
| L27071_at | Human tyrosine kinase (TXX) "mRNA," complete cds | 41 | 38 | 111 | 103 | 20 | 154 |
| L27080_at | Human melanocortin 5 receptor (MC5R) "gene," complete cds | 20 | 118 | 24 | 20 | 95 | 42 |
| L27213_s_at | Homo sapiens anion exchange protein "mRNA," complete cds | 104 | 22 | 80 | 40 | 20 | 48 |
| L27476_at | Human X104 "mRNA," complete cds | 92 | 74 | 73 | 30 | 20 | 36 |
| L27479_at | Human X123 "mRNA," 3' end | 392 | 277 | 222 | 180 | 21 | 93 |
| L27559_s_at | Human insulin-like growth factor binding protein 5 (IGFBP5) gene | 26 | 35 | 65 | 22 | 20 | 397 |
| L27560_at | Human insulin-like growth factor binding protein 5 (IGFBP5) mRNA | 20 | 20 | 20 | 20 | 20 | 20 |
| L27584_s_at | Homo sapiens Ca channel B3 subunit (CAL Bet 3) "mRNA," complete cds | 20 | 20 | 225 | 65 | 81 | 92 |
| L27586_at | Human TR4 orphan receptor "mRNA," complete cds | 20 | 185 | 225 | 208 | 102 | 181 |
| L27624_s_at | Homo sapiens tissue factor pathway inhibitor-2 "mRNA," complete cds | 55 | 20 | 20 | 20 | 20 | 20 |
| L27706_at | Human chaperonin protein (Tcp20) gene complete cds | 20 | 30 | 20 | 21 | 20 | 20 |
| L27841_at | Human autoantigen pericentriol material 1 (PCM-1) "mRNA," complete cds | 37 | 20 | 20 | 20 | 134 | 87 |
| L27943_s_at | Homo sapiens cytidine deaminase (CDA) "mRNA," complete cds | | | | | | |
| L28010_at | Homo sapiens HnRNP F protein "mRNA," complete cds | | | | | | |
| L28175_at | Homo sapiens prostaglandin E2 receptor EP2 subtype "mRNA," complete cds | | | | | | |
| L28821_at | Homo sapiens alpha mannosidase II isozyme "mRNA," complete cds | | | | | | |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| L28957_at | Homo sapiens CTP:phosphocholine cytidyltransferase "mRNA," complete cds | 20 | 57 | 20 | 86 | 20 | 20 | 37 |
| L28997_at | Homo sapiens ARL1 "mRNA," complete cds | 46 | 20 | 33 | 119 | 20 | 20 | 23 |
| L29008_at | Human L-iditol-2 dehydrogenase "mRNA," complete cds | 118 | 78 | 198 | 210 | 266 | 131 | 131 |
| L29217_at | Homo sapiens clk3 "mRNA," complete cds | 20 | 20 | 20 | 20 | 20 | 20 | 20 |
| L29218_at | Homo sapiens clk2 "mRNA," complete cds | 20 | 35 | 63 | 101 | 114 | 170 | 170 |
| L29277_at | Homo sapiens DNA-binding protein (APRF) "mRNA," complete cds | 173 | 98 | 182 | 167 | 439 | 200 | 200 |
| L29306_s_at | Homo sapiens tryptophan hydroxylase (Tph) "mRNA," complete cds. /gb=L29306 /ntype=RNA | 20 | 20 | 23 | 20 | 145 | 20 | 20 |
| L29339_at | Homo sapiens Na+/glucose co-transporter (SGlT1) gene | 78 | 20 | 20 | 20 | 20 | 20 | 20 |
| L29376_at | Homo sapiens (clone 3.8-1) MHC class I mRNA fragment | 20 | 50 | 20 | 20 | 20 | 20 | 20 |
| L29433_at | Human factor X (blood coagulation factor) gene | 100 | 20 | 20 | 20 | 20 | 20 | 101 |
| L31529_at | Human beta1-syntrophin (SNT B1) "gene," complete cds | 20 | 20 | 20 | 67 | 20 | 20 | 20 |
| L31573_at | Human sulfite oxidase "mRNA," complete cds | 20 | 51 | 211 | 71 | 20 | 20 | 33 |
| L31584_at | Human G protein-coupled receptor (EBI 1) gene | 79 | 36 | 20 | 65 | 275 | 76 | 76 |
| L31801_at | Human sapiens monocarboxylate transporter 1 (SLC16A1) "mRNA," complete cds | 82 | 20 | 20 | 20 | 20 | 25 | 25 |
| L31860_at | Human glycophorin "A," MN-types (GYPA) "mRNA," complete cds | 82 | 34 | 20 | 131 | 86 | 32 | 32 |
| L31881_at | Human nuclear factor I-X "mRNA," complete cds | 20 | 20 | 20 | 20 | 20 | 20 | 20 |
| L32137_at | Human germline oligomeric matrix protein (COMP) "mRNA," complete cds | 20 | 20 | 20 | 20 | 20 | 20 | 20 |
| L32140_at | Human afamin "mRNA," complete cds | 20 | 20 | 20 | 20 | 20 | 20 | 20 |
| L32163_at | Homo sapiens zinc finger protein "mRNA," 3' end | 26 | 42 | 56 | 28 | 20 | 26 | 26 |
| L32164_at | Homo sapiens zinc finger protein "mRNA," 3' end | 32 | 20 | 28 | 28 | 68 | 26 | 26 |
| L32179_at | Human arylacetamide deacetylase "mRNA," complete cds | 70 | 20 | 20 | 20 | 284 | 22 | 22 |
| L32606_at | Human homeobox-like mRNA | 20 | 20 | 20 | 20 | 20 | 20 | 20 |
| L32831_s_at | Human G protein-coupled receptor (GPR3) "gene," complete cds | 81 | 57 | 106 | 25 | 288 | 178 | 178 |
| L32832_s_at | | 36 | 118 | 247 | 187 | 20 | 36 | 36 |
| L32866_at | Human effector cell protease receptor-1 (EPR-1) "gene," partial cds | 20 | 36 | 20 | 20 | 20 | 99 | 99 |
| L32961_at | Human 4-aminobutyrate aminotransferase (GABAT) "mRNA," complete cds | 36 | 20 | 20 | 20 | 20 | 20 | 20 |
| L32976_at | Human protein kinase (MLK-3) "mRNA," complete cds | 45 | 77 | 20 | 44 | 231 | 78 | 78 |
| L32977_at | Homo sapiens (clone f17252) ubiquinol cytochrome c reductase Rieske iron-sulphur protein (UQCRFS1) gene | 237 | 204 | 234 | 180 | 116 | 175 | 175 |
| L33075_at | Homo sapiens ras GTPase-activating-like protein (IQGAP1) "mRNA," complete cds | 432 | 634 | 1082 | 903 | 190 | 215 | 215 |
| L33243_at | Homo sapiens polycystic kidney disease 1 protein (PKD1 "mRNA," complete cds | 115 | 45 | 42 | 81 | 20 | 20 | 20 |
| L33262_s_at | Homo sapiens DNA repair and recombination homologue (RAD52) "gene," complete cds | 20 | 31 | 20 | 20 | 20 | 54 | 54 |
| L33404_at | Human stratum corneum chymotryptic enzyme "mRNA," complete cds | 20 | 20 | 20 | 20 | 181 | 20 | 20 |
| L33477_at | Human (clone 8B1) Br-cadherin "mRNA," complete cds | 20 | 28 | 20 | 20 | 46 | 57 | 57 |
| L33798_at | Human dihydropyridine-sensitive L-type calcium channel alpha-1 subunit (CACNL1A3) "mRNA," complete cds | 20 | 20 | 20 | 20 | 20 | 20 | 20 |
| L33799_at | Human procollagen C-proteinase enhancer protein (PCOLCE) "mRNA," complete cds | 108 | 90 | 37 | 86 | 212 | 45 | 45 |
| L33801_at | Human protein kinase "mRNA," complete cds | 115 | 42 | 85 | 49 | 139 | 20 | 20 |
| L33842_ma1_at | Homo sapiens (clone FFE-7) type II inosine monophosphate dehydrogenase (IMPDH2) gene, exons 1-13, complete cds. | 126 | 358 | 678 | 635 | 92 | 170 | 170 |
| L33881_at | Human protein kinase C-iota "isoform," complete cds | 22 | 58 | 63 | 40 | 124 | 52 | 52 |
| L33930_s_at | Homo sapiens CD24 signal transducer "mRNA," complete cds and 3' region | 917 | 307 | 1127 | 1264 | 338 | 394 | 394 |
| L34035_at | Homo sapiens NADP-dependent malic enzyme "mRNA," complete cds. /gb=L34035 /ntype=RNA | 20 | 20 | 20 | 20 | 20 | 20 | 20 |
| L34059_at | Homo sapiens cadherin-4 "mRNA," complete cds | 39 | 24 | 20 | 69 | 20 | 41 | 41 |
| L34075_at | Homo sapiens cadherin-8 "mRNA," complete cds | 52 | 40 | 155 | 20 | 109 | 108 | 108 |
| L34081_at | Human FKBP-rapamycin associated protein (FRAP) "mRNA," complete cds | 20 | 20 | 20 | 20 | 20 | 20 | 20 |
| L34155_at | Human bile acid CoA: Amino acid N-acyltransferase "mRNA," complete cds | 93 | 20 | 67 | 56 | 20 | 46 | 46 |
| L34219_at | Homo sapiens laminin-related protein (LamA3) 'mRNA,' complete cds | 20 | 74 | 81 | 89 | 20 | 20 | 20 |
| L34355_at | Homo sapiens retinaldehyde-binding protein (CRALBP) "gene," complete cds | 81 | 20 | 20 | 20 | 20 | 59 | 59 |
| | Homo sapiens (clone p4) 50 kD dystrophin-associated glycoprotein "mRNA," complete cds | 20 | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| L34357_at | Homo sapiens GATA-4 "mRNA," complete cds | 81 | 74 | 81 | 89 | 20 | 59 |
| L34363_s_at | Human X-linked nuclear protein (XNP) "gene," complete cds | 20 | 20 | 20 | 20 | 20 | 20 |
| L34409_at | Homo Sapiens (clone B3B3E13) chromosome 4p16.3 DNA fragment | 20 | 20 | 20 | 25 | 20 | 20 |
| L34587_at | Homo sapiens RNA polymerase II elongation factor "SIII," p15 subunit "mRNA," complete cds | 1659 | 133 | 189 | 234 | 221 | 77 |
| L34600_at | Human nuclear-encoded mitochondrial initiation factor 2 "mRNA," complete cds | 95 | 20 | 94 | 20 | 20 | 43 |
| L34657_at | Homo sapiens platelet/endothelial cell adhesion molecule-1 (PECAM-1) gene | 20 | 65 | 20 | 20 | 66 | 56 |
| L34673_at | Human "ATPase," DNA-binding protein (HIP116) "mRNA," 3' end | 20 | 20 | 20 | 39 | 20 | 20 |
| L34820_at | Human NAD+-dependent succinate-semialdehyde dehydrogenase (SSADH) "mRNA," 3' end | 50 | 51 | 51 | 102 | 116 | 54 |
| L34838_at | Homo sapiens early placenta insulin-like peptide EPIL (INSL4) "mRNA," complete cds | 20 | 20 | 20 | 20 | 20 | 20 |
| L35035_at | Homo sapiens ribose 5-phosphate isomerase (RPI) mRNA | 20 | 20 | 51 | 20 | 20 | 20 |
| L35240_at | Human enigma "gene," complete cds | 67 | 30 | 53 | 37 | 147 | 69 |
| L35249_s_at | Homo sapiens vacuolar H+-ATPase Mr "56,000" subunit (HO57) "mRNA," complete cds | 45 | 31 | 40 | 23 | 20 | 20 |
| L35251_ma1_at | Homo sapiens extracellular matrix matrix protein (MEAP3) gene, complete cds. | 81 | 51 | 52 | 42 | 172 | 68 |
| L35253_s_at | Homo sapiens p38 mitogen activated protein (MAP) kinase "mRNA," complete cds | 20 | 20 | 20 | 20 | 252 | 96 |
| L35263_at | Human CSaids binding protein (CSBP1) "mRNA," cmplete cds | 29 | 64 | 132 | 162 | 68 | 37 |
| L35269_at | Homo sapiens zinc finger protein 35 (ZNF35) gene | 58 | 28 | 49 | 52 | 146 | 20 |
| L35475_at | Homo sapiens olfactory receptor-like "gene," complete cds | 126 | 54 | 204 | 99 | 250 | 91 |
| L35545_at | Homo sapiens endothelial cell protein C/APC receptor (EPCR) "mRNA," complete cds | 20 | 27 | 20 | 20 | 36 | 30 |
| L35546_at | Homo sapiens gamma-glutamylcysteine synthetase light subunit "mRNA," complete cds | 20 | 28 | 20 | 20 | 20 | 20 |
| L35592_at | Homo sapiens germline mRNA sequence | 20 | 36 | 20 | 20 | 20 | 30 |
| L35594_at | Human autotaxin "mRNA," complete cds | 43 | 20 | 20 | 20 | 27 | 33 |
| L35854_at | Human dystrophin (dp140) "mRNA," 5' end. /gb=L35854 /ntype=RNA | 20 | 20 | 20 | 20 | 30 | 37 |
| L36033_at | Human pre-B cell stimulating factor homologue (SDF1b) "mRNA," complete cds | 25 | 20 | 20 | 20 | 20 | 20 |
| L36051_at | Human thrombopoietin "gene," complete cds | 20 | 20 | 20 | 20 | 45 | 23 |
| L36069_at | Homo sapiens high conductance inward rectifier potassium channel alpha subunit "mRNA," complete cds | 20 | 20 | 20 | 20 | 20 | 20 |
| L36151_at | Homo sapiens phosphatidylinositol 4-kinase "mRNA," complete cds | 40 | 112 | 277 | 242 | 302 | 209 |
| L36463_at | Homo sapiens ras inhibitor (Rin1) "mRNA," complete cds | 20 | 20 | 59 | 32 | 20 | 20 |
| L36529_at | Human (clone N5-4) protein p84 "mRNA," complete cds | 44 | 36 | 74 | 20 | 28 | 34 |
| L36531_at | Homo sapiens integrin alpha 8 subunit "mRNA," 3' end | 116 | 142 | 129 | 41 | 94 | 111 |
| L36642_at | Human (clone 51C-3) 51C protein "mRNA," complete cds | 20 | 20 | 20 | 20 | 20 | 33 |
| L36644_at | Homo sapiens (clone p15INK48/HA5) CDK inhibitory protein "mRNA," complete cds | 141 | 156 | 150 | 160 | 226 | 250 |
| L36645_at | Human (clone p17/90) rearranged iduronate-2-sulphatase homologue gene. /gb=L36847 /ntype=DNA /annot=CDS | 20 | 20 | 20 | 20 | 168 | 20 |
| L36720_at | Homo sapiens guanylate cyclase activating protein (GCAP) gene exons "1–4," complete cds | 20 | 96 | 37 | 77 | 56 | 77 |
| L36818_at | Homo sapiens MAP kinase kinase 4 (MKK4) "mRNA," complete cds | 34 | 32 | 20 | 24 | 36 | 20 |
| L36844_at | Homo sapeins casein Kinase I epsilon "mRNA," complete cds | 38 | 38 | 80 | 75 | 82 | 21 |
| L36847_at | Homo sapiens Met-ase "gene," exon 1 | 168 | 132 | 86 | 140 | 278 | 173 |
| L36861_at | Homo sapiens bystin "mRNA," complete cds | 27 | 20 | 20 | 86 | 20 | 20 |
| L36922_at | Homo sapiens dynamin (DNM) "mRNA," complete cds | 265 | 151 | 185 | 333 | 326 | 335 |
| L36983_at | Human FK-506 binding protein homologue (FKBP38) "mRNA," complete cds | 42 | 20 | 59 | 20 | 20 | 26 |
| L37033_at | Homo sapiens (clone p17/90) rearranged neutrophil-activating peptide 78 (ENA-78) "gene," complete cds | 169 | 20 | 20 | 20 | 168 | 80 |
| L37036_s_at | Homo sapiens casein kinase I alpha isoform (CSNK1A1) "mRNA," complete cds | 38 | 20 | 80 | 24 | 128 | 80 |
| L37042_at | Homo sapeins casein Kinase I epsilon "mRNA," complete cds | 54 | 112 | 211 | 50 | 82 | 21 |
| L37043_at | Homo sapiens vasopressin V3 receptor "mRNA," complete cds | 168 | 20 | 86 | 163 | 278 | 173 |
| L37112_at | Homo sapiens (clone mf.18) RNA polymerase II "mRNA," complete cds | 20 | 20 | 20 | 68 | 404 | 221 |
| L37127_at | Homo sapiens (clone cD24-1) Huntington's disease candidate region mRNA fragment | 53 | 20 | 20 | 20 | 48 | 36 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| L37347_at | Human integral membrane protein (Nramp2) "mRNA," partial | 30 | 31 | 20 | 31 | 20 | 20 |
| L37360_s_at | Homo sapiens (clone hEHK10L) EHK1 receptor tyrosine kinase ligand (EFL-2) "mRNA," complete cds | 20 | 20 | 78 | 46 | 20 | 20 |
| L37362_at | Homo sapiens (clone d2-115) kappa opioid receptor (OPRK1) "mRNA," complete cds | 20 | 20 | 27 | 20 | 20 | 20 |
| L37368_at | Human (clone E5.1) RNA-binding protein "mRNA," complete cds | 64 | 84 | 116 | 114 | 140 | 154 |
| L37378_at | Homo sapiens guanylyl cyclase (RetGC-2_ mRNA, "complete cds. | 20 | 20 | 20 | 20 | 20 | 20 |
| L37792_at | Human syntaxin 1A "mRNA," complet cds | 129 | 129 | 148 | 97 | 93 | 189 |
| L37868_s_at | Homo sapiens POU-domain transcription factor "(N-Oct-3)," complete cds | 20 | 20 | 20 | 20 | 134 | 20 |
| L37882_at | Human frizzled gene product "mRNA," complete cds | 20 | 20 | 20 | 20 | 203 | 87 |
| L37936_at | Human nuclear-encoded mitochondrial elongation factor Ts (EF-Ts) "mRNA," 3' end of cds | 74 | 50 | 86 | 103 | 25 | 131 |
| L38025_at | Homo sapiens ciliary neurotrophic factor alpha receptor gene | 20 | 89 | 20 | 131 | 321 | 68 |
| L38486_at | Human microfibril-associated glycoprotein 4 (MFAP4) "mRNA," 3' end of cds | 505 | 354 | 254 | 237 | 332 | 394 |
| L38487_at | Human estrogne receptor-related protein (hERRa1) "mRNA," 3+ end," partial cds | 20 | 20 | 20 | 20 | 20 | 20 |
| L38490_s_at | Homo sapiens ADP-ribosylation factor "mRNA," complete cds | 84 | 85 | 127 | 74 | 653 | 145 |
| L38500_at | Homo sapiens Na+/myo-inositol cotransporter (SLC5A3) "gene," complete cds. /gb=L38500 /ntype=DNA /annot=CDS | 20 | 20 | 20 | 20 | 20 | 20 |
| L38503_at | Homo sapiens glutathione S-transferase theta 2 (GSTT2) "mRNA," complete cds | 32 | 20 | 67 | 107 | 124 | 20 |
| L38517_at | Homo sapiens protein tyrosine phosphatase delta "mRNA," 5' end | 20 | 42 | 20 | 20 | 20 | 20 |
| L38593_s_at | Homo sapiens indian hedgehog protein (IHH) "mRNA," 5' end | 20 | 20 | 20 | 20 | 22 | 42 |
| L38608_at | Homo sapiens CD6 ligand (ALCAM) "mRNA," complete cds | 22 | 20 | 20 | 67 | 20 | 50 |
| L38616_at | Homo sapiens brain and reproductive organ-expressed protein (BRE) "gene," complete cds | 87 | 35 | 20 | 132 | 188 | 219 |
| L38696_at | Homo sapiens autoantigen p542 "mRNA," 3' end of cds | 107 | 138 | 130 | 247 | 118 | 215 |
| L38707_at | Human diaclyglycerol kinase (DAGK) mRNA, complete cds. | 20 | 43 | 20 | 66 | 20 | 84 |
| L38810_at | Homo sapiens thyroid receptor interactor (TRIP1) "mRNA," complete cds | 240 | 142 | 121 | 191 | 20 | 216 |
| L38820_at | Homo sapiens HMC class I antigen-like glycoprotein (CD1D) gene | 20 | 24 | 20 | 39 | 20 | 20 |
| L38928_at | Homo sapiens "5,10-methenyltetrahydrofolate" synthetase "mRNA," complete cds | 33 | 20 | 64 | 20 | 20 | 41 |
| L38929_at | Homo sapiens protein tyrosine phosphatase delta "mRNA," complete cds | 20 | 20 | 20 | 20 | 127 | 25 |
| L38932_at | Homo sapiens GT197 partial ORF "mRNA," 3' end of cds | 152 | 71 | 188 | 134 | 303 | 149 |
| L38933_ma1_at | Homo sapiens GT198 mRNA, complete ORF. | 20 | 20 | 20 | 20 | 20 | 20 |
| L38935_at | Homo sapiens GT212 mRNA | 75 | 66 | 20 | 84 | 20 | 127 |
| L38941_at | Homo sapiens ribosomal protein L34 (RPL34) "mRNA," complete cds | 2460 | 3734 | 3807 | 2670 | 880 | 1472 |
| L38951_at | Homo sapiens importin beta subunit "mRNA," complete cds | 119 | 49 | 63 | 65 | 77 | 88 |
| L38961_at | Homo sapiens (clone hKvBeta.3) K+ channel beta subunit "mRNA," complete cds | 20 | 20 | 37 | 22 | 36 | 30 |
| L38969_at | Human putative transmembrane protein precursor (B5) "mRNA," complete cds | 20 | 37 | 34 | 34 | 22 | 20 |
| L39009_at | Homo sapiens thrombospondin 3 (THBS3) "gene," complete cds | 20 | 20 | 20 | 20 | 229 | 185 |
| L39009_ma1_at | Homo sapiens class IV alcohol dehydrogenase 7 (ADH7) "gene," 5' flanking region. /gb=L39009 /ntype=DNA /annot=mRNA | 20 | 20 | 20 | 30 | 20 | 28 |
| L39059_at | Human endosome-associated protein (EEA1) "mRNA," complete cds | 20 | 51 | 102 | 26 | 104 | 113 |
| L39060_at | Homo sapiens transcription factor SL1 "mRNA," complete cds | 20 | 20 | 20 | 20 | 20 | 20 |
| L39061_at | Homo sapiens transcription factor SL1 "mRNA," partial cds | 20 | 57 | 20 | 20 | 20 | 20 |
| L39064_ma1_at | Homo sapiens interleukin 9 receptor (IL9R) gene, complete cds. | 36 | 132 | 88 | 20 | 22 | 23 |
| L39211_at | Homo sapiens mitochondrial carnitine palmitoyltransferase I "mRNA," complete cds | 20 | 20 | 71 | 20 | 20 | 20 |
| L39833_at | Homo sapiens (clone hKvBeta.3) K+ channel beta subunit "mRNA," complete cds | 46 | 20 | 37 | 22 | 36 | 30 |
| L39874_at | Homo sapiens deoxycylidylate deaminase "gene," complete cds | 74 | 52 | 184 | 100 | 20 | 160 |
| L40027_at | Homo sapiens glycogen synthase kinase 3 "mRNA," complete cds | 193 | 212 | 150 | 185 | 293 | 283 |
| L40157_at | Human endosome-associated protein (EEA1) "mRNA," complete cds | 45 | 39 | 20 | 22 | 20 | 35 |
| L40366_at | Homo sapiens thyroid receptor interactor (TRIP7) "mRNA," 3' end of cds | 56 | 75 | 71 | 74 | 20 | 20 |
| L40357_at | Homo sapiens thyroid receptor interactor (TRIP2) "mRNA," partial cds. /gb=L40366 /ntype=RNA | 53 | 20 | 20 | 20 | 20 | 20 |
| L40371_at | Homo sapiens thyroid receptor interactor (TRIP4) "mRNA," 3' end of cds | 48 | 64 | 20 | 98 | 107 | 20 |
| L40377_at | Homo sapiens cytoplasmic antiproteinase 2 (CAP2) "mRNA," complete cds | 91 | 20 | 35 | 20 | 20 | 20 |
| L40379_at | Homo sapiens thyroid receptor interactor (TRIP10) "mRNA," 3' end of cds | 224 | 63 | 184 | 123 | 107 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| L40380_at | Homo sapiens thyroid receptor interactor (TRIP11) "mRNA," 3' end of cds | 20 | 38 | 48 | 24 | 27 | 67 |
| L40384_s_at | Homo sapiens thyroid receptor interactor (TRIP13) "mRNA," partial cds. /gb=L40384 /ntype=RNA | 20 | 20 | 20 | 20 | 20 | 20 |
| L40386_s_at | Homo DP-2 "mRNA," complete cds | 49 | 72 | 80 | 20 | 158 | 20 |
| L40387_at | Homo sapiens thyroid receptor interactor (TRIP14) "gene," 3' end of cds. /gb=L40387 /ntype=DNA /annot=CDS | 196 | 165 | 107 | 135 | 527 | 473 |
| L40388_at | Homo sapiens thyroid receptor interactor (TRIP15) "mRNA," 5' end of cds. /gb=L40388 /ntype=RNA | 29 | 23 | 20 | 20 | 20 | 20 |
| L40391_at | Homo sapiens (clone s153) mRNA fragment | 20 | 49 | 84 | 49 | 20 | 61 |
| L40392_at | Homo sapiens (clone s164) "mRNA," 3' end of cds | 98 | 111 | 109 | 52 | 20 | 27 |
| L40393_at | Homo sapiens (clone S171) "mRNA," complete cds | 89 | 118 | 35 | 42 | 82 | 59 |
| L40394_at | Homo sapiens (clone S194) "mRNA," 3' end of cds | 28 | 20 | 61 | 45 | 20 | 64 |
| L40395_at | Homo sapiens (clone S20ii115) "mRNA," 3' end of cds | 107 | 45 | 20 | 79 | 41 | 50 |
| L40396_at | Homo sapiens (clone s22171) mRNA fragment | 20 | 20 | 22 | 20 | 57 | 20 |
| L40397_at | Homo sapiens (clone S31i125) "mRNA," 3' end of cds | 407 | 487 | 587 | 954 | 194 | 246 |
| L40399_at | Homo sapiens (clone S240i117/zap112) "mRNA," complete cds | 20 | 20 | 20 | 20 | 20 | 20 |
| L40400_at | Homo sapiens (clone zap113) "mRNA," 3' end of cds | 20 | 20 | 20 | 33 | 20 | 20 |
| L40401_at | Homo sapiens (clone zap128) "mRNA," 3' end of cds | 197 | 101 | 95 | 72 | 42 | 69 |
| L40402_at | Homo sapiens (clone Zap2) mRNA fragment | 20 | 20 | 39 | 31 | 55 | 20 |
| L40403_at | Homo sapiens (clone zap3) "mRNA," 3' end of cds | 20 | 20 | 20 | 20 | 20 | 93 |
| L40407_at | Homo sapiens thyroid receptor interactor (TRIP9) "gene," complete cds | 20 | 111 | 20 | 73 | 20 | 103 |
| L40410_at | Homo sapiens thyroid receptor interactor (TRIP3) "mRNA," 3' end of cds | 112 | 70 | 112 | 77 | 71 | 32 |
| L40411_at | Homo sapiens thyroid receptor interactor (TRIP8) "mRNA," 3' end of cds | 20 | 20 | 23 | 20 | 20 | 20 |
| L40586_at | Homo sapiens iduronate-2-sulphatase (IDS) "mRNA," complete cds | 20 | 20 | 20 | 20 | 100 | 20 |
| L40636_at | Homo sapiens (clone FBK III 16) protein tyrosine kinase (NET PTK) "mRNA," complete cds | 112 | 76 | 32 | 55 | 62 | 64 |
| L40904_at | H. sapiens peroxisome proliferator activated receptor "gamma," complete cds | 145 | 218 | 425 | 342 | 653 | 344 |
| L40933_at | Homo sapiens phosphoglucomutase-related protein (PGMRP) "gene," complete cds | 20 | 20 | 20 | 20 | 20 | 29 |
| L40992_at | Homo sapiens (clone PEBP2aA1) core-binding factor, runt domain, alpha subunit 1 (CBFA1) mRNA, 3' end of cds. | 142 | 58 | 73 | 123 | 520 | 142 |
| L41066_at | Homo sapiens NF-at3 "mRNA," complete cds | 20 | 20 | 20 | 20 | 20 | 36 |
| L41067_at | Homo sapiens NF-AT4c "mRNA," complete cds | 20 | 65 | 20 | 23 | 20 | 127 |
| L41143_at | Homo sapiens expressed pseudo TCTA mRNA at 1(1:3) translocation site, complete cds. | 125 | 25 | 20 | 20 | 117 | 303 |
| L41147_at | Homo sapiens 5-HT6 serotonin receptor "mRNA," complete cds | 20 | 36 | 20 | 55 | 20 | 23 |
| L41162_at | Homo sapiens collagen alpha 3 type IX (COL9A3) "mRNA," complete cds. | 20 | 20 | 20 | 20 | 20 | 20 |
| L41268_f_at | Homo sapiens natural killer-associated transcript 2 (NKAT2) "mRNA," complete cds | 20 | 37 | 20 | 46 | 20 | 78 |
| L41349_at | Homo sapiens phospholipase C beta 4 (PLCB4) "mRNA," complete cds | 20 | 20 | 31 | 20 | 27 | 20 |
| L41351_at | Homo sapiens prostasin "mRNA," complete cds | 39 | 28 | 55 | 91 | 40 | 90 |
| L41559_at | Homo sapiens core 2 "beta-1,6-N-acetylglucosaminyltransferase" (core 2 GnT) "gene," exon 1 /gb=L41390 /ntype=DNA /annot=exon | 26 | 20 | 50 | 20 | 98 | 21 |
| L41559_at | Homo sapiens pterin-4a-carbinolamine dehydratase (PCBD) "mRNA," complete cds. | 37 | 138 | 85 | 222 | 122 | 140 |
| L41607_at | Human "beta-1,6-N-acetylglucosaminyltransferase" (IGnT) gene | 34 | 20 | 47 | 20 | 70 | 39 |
| L41668_ma1_at | Homo sapiens UDP-galactose-4-epimerase (GALE) mRNA, complete cds. | 142 | 99 | 60 | 79 | 180 | 74 |
| L41680_at | Homo sapiens "alpha-2,8-polysialyltransferase" (PST) "gene," complete cds. | 20 | 20 | 20 | 20 | 20 | 20 |
| L41690_at | Homo sapiens TNF receptor-1 associated protein (TRADD) "mRNA," 3' end of cds | 146 | 99 | 60 | 79 | 180 | 74 |
| L41816_at | Homo sapiens cam kinase I "mRNA," complete cds | 20 | 20 | 31 | 20 | 69 | 20 |
| L41870_at | Homo sapiens retinoblastoma susceptibility protein (RB1) mRNA and mutations | 20 | 28 | 55 | 91 | 40 | 90 |
| L41857_ma1_at | Homo sapiens splicing factor, arginine/serine-rich 7 (SFRS7) gene, complete cds. | 25 | 32 | 26 | 25 | 205 | 65 |
| L41913_at | Homo sapiens retinoblastoma susceptibility protein (RB1) "gene," exon "26," bases 174145-174668 in L11910 | 20 | 20 | 20 | 20 | 20 | 20 |
| L41919_ma1_at | Homo sapiens HIC-1 gene fragment. | 20 | 20 | 20 | 20 | 20 | 20 |
| L41939_at | Homo sapiens (clone FBK III 11c) protein-tyrosine kinase (DRT) "mRNA," complete cds | 20 | 86 | 126 | 30 | 307 | 115 |
| L42025_ma1_at | Homo sapiens cellular co-factor (RAB) gene, complete cds. | 23 | 20 | 52 | 20 | 25 | 20 |
| L42176_at | Homo sapiens (clone 35.3) DRAL "mRNA," complete cds | 20 | 20 | 20 | 20 | 24 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| L42243_cds1_at | Homo sapiens (clone 51H8) alternatively spliced interferon receptor (IFNAR2) gene, exon 9 and complete cds's. | 37 | 35 | 20 | 77 | 20 | 45 |
| L42324_at | Homo sapiens (clone GPCR W) G protein-linked receptor gene (GPCR) "gene," 5' end of cds. /gb=L42324 /ntype=DNA /annot=CDS | 20 | 43 | 20 | 20 | 20 | 20 |
| L42354_at | Homo sapiens (clone 46ES4) mRNA fragment. /gb=L42354 /ntype=RNA | 20 | 39 | 20 | 20 | 20 | 20 |
| L42373_at | Homo sapiens protein phosphatase 2A B56-alpha "mRNA," complete cds | 36 | 76 | 86 | 42 | 29 | 36 |
| L42374_s_at | Homo sapiens PP$_2$A B56-beta "mRNA," complete cds | 20 | 20 | 106 | 70 | 149 | 108 |
| L42379_at | Homo sapiens bone-derived growth factor (BPGF-1) "mRNA," complete cds | 87 | 86 | 124 | 26 | 123 | 36 |
| L42450_at | Homo sapiens pyruvate dehydrogenase kinase isoenzyme 1 (PDK1) "mRNA," complete cds | 20 | 20 | 20 | 107 | 238 | 215 |
| L42451_at | Homo sapiens pyruvate dehydrogenase kinase isoenzyme 2 (PDK2) "mRNA," complete cds | 136 | 103 | 164 | 20 | 152 | 35 |
| L42452_at | Homo sapiens pyruvate dehydrogenase kinase isoenzyme 3 (PDK3) "mRNA," complete cds | 23 | 20 | 20 | 205 | 20 | 211 |
| L42563_at | Human RLIP76 protein "mRNA," complete cds | 77 | 63 | 129 | 28 | 166 | 85 |
| L42572_at | Homo sapiens (clone ISW34) non-gastric "H,K-ATPase" (ATP1AL1) gene | 66 | 20 | 20 | 71 | 131 | 100 |
| L42583_f_at | Homo sapiens p87/89 "gene," complete cds | 91 | 33 | 65 | 190 | 77 | 289 |
| L42601_f_at | Homo sapiens keratin 6 isoform K6a (KRT6A) gene | 4939 | 169 | 333 | 214 | 472 | 267 |
| L42611_f_at | Homo sapiens keratin 6 isoform K6c (KRT6C) gene | 5155 | 170 | 436 | 208 | 330 | 236 |
| L42621_at | Homo sapiens keratin 6 isoform K6e (KRT6E) "mRNA," complete cds | 1946 | 234 | 271 | 22 | 256 | 50 |
| L43338_at | Homo sapiens Ly-9 "mRNA," complete cds | 84 | 49 | 117 | 20 | 23 | 122 |
| L43366_at | Homo sapiens (clone JJ1a) cadherin mRNA fragment. /gb=L43338 /ntype=RNA | 27 | 52 | 20 | 64 | 129 | 186 |
| L43575_s_at | Homo sapiens (clone jj1b) cadherin mRNA fragment. /gb=L43366 /ntype=RNA | 23 | 20 | 20 | 20 | 20 | 75 |
| L43576_at | Homo sapiens (clone 48A8) mRNA | 35 | 35 | 168 | 191 | 115 | 128 |
| L43579_at | Homo sapiens (clone ESTO2946) mRNA | 40 | 136 | 274 | 126 | 743 | 20 |
| L43579_s_at | Homo sapiens (clone 110298) mRNA. /gb=L43579 /ntype=RNA | 23 | 41 | 121 | 35 | 20 | 169 |
| L43631_at | Homo sapiens scaffold attachment factor (SAF-B) "gene," partial cds | 43 | 74 | 118 | 135 | 344 | 20 |
| L43821_at | Homo sapiens enhancer of filamentation (HEF1) "mRNA," complete cds | 66 | 70 | 91 | 36 | 117 | 20 |
| L43964_at | Homo sapiens (clone F-T03796) STM-2 "mRNA," complete cds | 31 | 43 | 20 | 20 | 20 | 20 |
| L44140_cds4_s_at | DNL1L gene extracted from Homo sapiens chromosome X region from filamin (FLN) gene to glucose-6-phosphate dehydrogenase (G6PC) | 20 | 20 | 20 | 20 | 490 | 75 |
| L46353_at | Homo sapiens high-mobility group phosphoprotein (HMGI-C) "gene," exons 3-Jan | 20 | 21 | 115 | 63 | 538 | 170 |
| L46720_s_at | Human autotaxin-t (atx-t) "mRNA," complete cds | 33 | 50 | 20 | 20 | 20 | 31 |
| L47125_s_at | Homo sapiens (chromosome X) glypican (GPC3) "mRNA," complete cds | 20 | 20 | 20 | 20 | 20 | 20 |
| L47276_at | Homo sapiens (cell line HL-60) alpha topoisomerase truncated-form "mRNA," 3'UTR. /gb=L47276 /ntype=RNA | 20 | 21 | 72 | 68 | 78 | 128 |
| L47345_at | Homo sapiens elongin A "mRNA," complete cds | 20 | 20 | 20 | 20 | 20 | 55 |
| L47726_at | Homo sapiens inducible protein "mRNA," complete cds | 20 | 38 | 20 | 45 | 20 | 20 |
| L47738_at | Homo Sapiens angiotensin II receptor "gene," complete cds | 105 | 66 | 38 | 20 | 20 | 81 |
| L48211_at | Homo sapiens paraoxonase 2 (PON2) "mRNA," complete cds | 20 | 20 | 39 | 20 | 20 | 20 |
| L48513_at | Homo sapiens paraoxonase 3 (PON3) "mRNA," 3' end of cds | 77 | 55 | 164 | 32 | 67 | 46 |
| L48516_at | Homo sapiens tuberin (TSC2) gene | 60 | 20 | 20 | 20 | 20 | 20 |
| L48546_at | Human GOS3 "mRNA," complete cds | 286 | 139 | 167 | 217 | 363 | 376 |
| L48692_at | Human OCP2 "gene," partial cds. /gb=L49173 /ntype=DNA /annot=CDS | 20 | 36 | 20 | 20 | 20 | 20 |
| L48728_cds1_at | Homo sapiens T cell receptor beta (TCRBV10S1) gene, complete cds. | 48 | 30 | 76 | 29 | 144 | 132 |
| L49054_at | Homo sapiens t(3;5)(q25.1;p34) fusion gene NPM-MLF1 mRNA, complete cds. | 20 | 20 | 32 | 20 | 20 | 98 |
| L49169_at | Homo sapiens retinoblastoma susceptibility protein (RB1) L486W 4 bp deletion mutant (reulting in premature stop at amino acid 490 "g | 306 | 109 | 164 | 137 | 249 | 373 |
| L49173_f_at | Homo sapiens retinoblastoma susceptibility protein (RB1) "gene," with a 3 bp deletion in exon 22 (L11910 bases 161855-162161). /gb=L4 | 20 | 20 | 26 | 46 | 20 | 20 |
| L49209_s_at | Human OCP2 "gene," partial cds. /gb=L49173 /ntype=DNA /annot=CDS | 20 | 20 | 20 | 20 | 189 | 20 |
| L49218_f_at | | 20 | 20 | 20 | 20 | 20 | 20 |
| L49219_f_at | | 20 | 20 | 20 | 20 | 20 | 20 |
| L49229_f_at | | 20 | 354 | 687 | 412 | 1002 | 369 |
| L49380_at | Homo sapiens clone B4 transcription factor ZFM1 "mRNA," complete cds | 171 | | | | | |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| L75847_at | Human zinc finger protein 45 (ZNF34) "mRNA," complete cds | 20 | 20 | 20 | 20 | 20 | 20 |
| L76159_at | Homo sapiens FRG1 "mRNA," complete cds | 55 | 75 | 59 | 31 | 20 | 20 |
| L76191_at | Homo sapiens interleukin-1 receptor-associated kinase (IRAK) "mRNA," complete cds | 225 | 78 | 333 | 169 | 200 | 190 |
| L76200_at | Human guanylate kinase (GUK1) "mRNA," complete cds | 384 | 285 | 87 | 40 | 20 | 20 |
| L76224_at | Homo sapiens NMDA receptor "mRNA," complete cds | 38 | 20 | 37 | 51 | 51 | 38 |
| L76380_at | Homo sapiens (clone HSNME29( CGRP type1 receptor "mRNA," complete cds | 20 | 55 | 20 | 38 | 20 | 42 |
| L76465_at | Homo sapiens NAD+-dependent 15 hydroxyprostaglandin dehydrogenase (PGDH) "mRNA," complete cds | 47 | 150 | 172 | 155 | 20 | 34 |
| L76517_at | Homo sapiens (clone cc44) senilin 1 (PS1; S182) "mRNA," complete cds | 89 | 221 | 563 | 342 | 289 | 170 |
| L76528_s_at | Homo sapiens presenilin 1 (PS1; S182) gene | 20 | 20 | 20 | 20 | 20 | 20 |
| L76568_xpt3_f_at | S26 from Homo sapiens excision and cross link repair ptorein (ERCC4) "gene," complete genomic sequence. /gb=L76568 /ntype=DNA /a | 125 | 327 | 78 | 279 | 157 | 20 |
| L76569_at | Homo sapiens (clone "cYG3;" B5P6C4) fragile X E mental retardation syndrome protein (FMR2) "mRNA," complete cds | 20 | 20 | 20 | 20 | 20 | 20 |
| L76571_at | Homo sapiens nuclear hormone receptor (shp) "gene," 3' end of cds | 20 | 45 | 76 | 24 | 139 | 55 |
| L76627_at | Homo sapiens metabotropic glutamate receptor 1 alpha (mGluR1alpha) "mRNA," complete cds | 20 | 20 | 20 | 20 | 20 | 20 |
| L76670_f_at | Homo sapiens nkat7 "mRNA," complete cds | 20 | 26 | 20 | 20 | 20 | 20 |
| L76687_at | Homo sapiens Grb14 "mRNA," complete cds | 20 | 20 | 20 | 58 | 20 | 20 |
| L76702_at | Homo sapiens B56-delta "mRNA," complete cds | 83 | 62 | 20 | 46 | 20 | 20 |
| L76703_at | Homo sapiens B56epsilon "mRNA," complete cds | 84 | 20 | 20 | 20 | 20 | 20 |
| L76927_ma1_at | Human galactokinase (GALK1) gene, complete cds. | 20 | 20 | 20 | 20 | 20 | 20 |
| L76937_ma1_at | Homo sapiens Werner syndrom gene, complete cds. | 24 | 20 | 20 | 42 | 20 | 20 |
| L77213_at | Homo sapiens phosphomevalonate kinase "mRNA," complete cds | 136 | 51 | 20 | 42 | 251 | 200 |
| L77559_at | Homo sapiens DGS-B partial mRNA. /gb=L77559 /ntype=RNA | 20 | 20 | 20 | 20 | 20 | 107 |
| L77561_at | Homo sapiens DGS-D "mRNA," 3' end | 73 | 97 | 82 | 119 | 180 | 163 |
| L77563_at | Homo sapiens DGS-F partial mRNA. /gb=L77563 /ntype=RNA | 20 | 50 | 20 | 20 | 98 | 20 |
| L77566_at | Homo sapiens DGS-I "mRNA," 3' end | 20 | 20 | 54 | 20 | 20 | 36 |
| L77567_s13_at | Homo sapiens mitochondrial citrate transport protein (CTP) "mRNA," 3' end | 20 | 20 | 20 | 20 | 20 | 20 |
| L77571_at | Homo sapiens DGS-A "mRNA," 3' end | 20 | 79 | 20 | 20 | 20 | 45 |
| L77701_at | Homo sapiens COX17 "mRNA," complete cds | 62 | 20 | 20 | 20 | 20 | 20 |
| L77730_at | Homo sapiens A3 adenosine receptor (ADORA3) gene | 20 | 20 | 20 | 68 | 20 | 45 |
| L77864_at | Human stat-like protein (Fe65) "mRNA," complete cds | 59 | 113 | 228 | 51 | 85 | 20 |
| L77886_at | Human protein tyrosine phosphatase "mRNA," complete cds | 20 | 20 | 30 | 20 | 20 | 20 |
| L78132_at | Human prostate carcinoma tumor antigen (pcta-1) "mRNA," complete cds | 20 | 20 | 20 | 46 | 175 | 128 |
| L78267_at | Homo sapiens PAR-5 "mRNA," probable 5' end | 20 | 28 | 146 | 20 | 254 | 121 |
| L78440_at | Homo sapiens STAT4 "mRNA," complete cds | 71 | 21 | 91 | 84 | 216 | 20 |
| L78833_cds1_at | ifp35 gene extracted from Human "BRCA1," Rho7 and vat1 "genes," complete "cds," and ipf35 "gene," partial cds | 26 | 57 | 64 | 21 | 20 | 20 |
| L78833_cds2_at | Human BRCA1, Rho7 and vat1 genes, complete cds, and ipf35 gene, partial cds | 20 | 20 | 20 | 20 | 20 | 20 |
| L78833_cds4_at | ifp35 gene extracted from Human "BRCA1," Rho7 and vat1 "genes," complete "cds," and ipf35 "gene," partial cds | 20 | 20 | 98 | 34 | 20 | 20 |
| M10014_cds1_at | Human firbinogen gamma chain and gamma0prime chain genes. | 39 | 20 | 20 | 46 | 20 | 45 |
| M10050_at | Human liver fatty acid binding protein (FABP) "mRNA," complete cds | 20 | 20 | 20 | 51 | 20 | 20 |
| M10051_s_at | Human insulin receptor "mRNA," complete cds | 20 | 20 | 20 | 20 | 20 | 78 |
| M10058_at | Human asialoglycoprotein receptor H1 "mRNA," complete cds | 20 | 21 | 20 | 84 | 254 | 20 |
| M10277_s_at | Human cytoplasmic beta-actin "gene," complete cds | 3788 | 5189 | 3616 | 3081 | 2991 | 3405 |
| M10321_s_at | Human von Willebrand factor "mRNA," 3' end | 52 | 20 | 20 | 20 | 20 | 20 |
| M10612_at | Human apolipoprotein C-II "gene," complete cds | 20 | 20 | 20 | 43 | 167 | 111 |
| M10901_at | Human glucocorticoid receptor alpha "mRNA," complete cds | 38 | 20 | 33 | 38 | 164 | 79 |
| M10942_at | Human metallothionein-Ie gen (hMT-Ie) | 147 | 228 | 172 | 82 | 615 | 327 |
| M10943_at | Human metallothionein-If gene (hMT-If) | 20 | 20 | 20 | 20 | 20 | 20 |
| M10950_cds2_at | Human alph-fetoprotein (AFP) gene, exons 14 and 15. | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M11025_s_at | Human asialoglycoprotein receptor H2 "mRNA," complete cds | 20 | 20 | 20 | 20 | 97 | 20 |
| M11058_at | Human 3-hydroxy-3-methylglutaryl coenzyme A reductase "mRNA," complete cds | 45 | 20 | 72 | 41 | 20 | 20 |
| M11119_at | Human endogenous retrovirus envelope region mRNA (PL1) | 308 | 437 | 20 | 250 | 588 | 666 |
| M11147_at | Human ferritin L chain "mRNA," complete cds | 3172 | 4610 | 2401 | 1838 | 2696 | 8178 |
| M11186_at | Human prepro-oxytocin-neurophysin I (OXT) "gene," complete cds | 92 | 43 | 42 | 36 | 134 | 88 |
| M11313_s_at | Human alpha-2-macroglobulin "mRNA," complete cds | 842 | 717 | 20 | 20 | 20 | 139 |
| M11321_at | Human group-specific component vitamin D-binding protein "mRNA," complete cds | 90 | 20 | 23 | 20 | 154 | 20 |
| M11353_at | Human H3.3 histone class C "mRNA," complete cds | 1697 | 1359 | 3018 | 1843 | 1061 | 1462 |
| M11433_at | Human cellular retinol-binding protein "mRNA," complete cds | 20 | 20 | 20 | 20 | 20 | 20 |
| M11437_cds1_at | Human kininogen gene, exon 10, encoding bradykinin and exon 11. | 36 | 114 | 20 | 36 | 20 | 146 |
| M11437_cds2_at | Human kininogen gene, exon 10, encoding bradykinin and exon 11. | 20 | 20 | 20 | 20 | 20 | 20 |
| M11567_ma1_at | Human anglogenin gene, complete cds, and three Alu repetitive sequences. | 20 | 145 | 51 | 82 | 120 | 150 |
| M11591_at | Human MHC class II HLA-SX-alpha gene | 45 | 20 | 20 | 34 | 59 | 24 |
| M11717_ma1_at | Human heat shock protein (hsp 70) gene, complete cds. | 186 | 146 | 116 | 194 | 20 | 110 |
| M11718_at | Human alpha-2 type V collagen "gene," 3′ end | 123 | 100 | 20 | 20 | 60 | 34 |
| M11722_at | Human terminal transferase "mRNA," complete cds | 20 | 20 | 20 | 20 | 237 | 23 |
| M11726_at | Human pancreatic polypeptide "gene," complete cds | 147 | 145 | 51 | 82 | 120 | 150 |
| M11749_at | Human Thy-1 glycoprotein "gene," complete cds | 71 | 20 | 20 | 34 | 59 | 24 |
| M11973_cds1_at | Human gamma-C-crystallin gene (gamma 201), exon 3. | 20 | 20 | 20 | 20 | 20 | 20 |
| M12036_at | Human tyrosine kinase-type receptor (HER2) "gene," partial cds | 586 | 1144 | 99 | 37 | 20 | 69 |
| M12125_at | Human fibroblast muscle-type tropomyosin "mRNA," complete cds | 58 | 44 | 20 | 20 | 20 | 98 |
| M12174_at | Human ras-related rho mRNA (clone "6)," partial cds | 153 | 448 | 20 | 20 | 113 | 2928 |
| M12529_at | Human apolipoprotein E "mRNA," complete cds | 52 | 20 | 20 | 31 | 49 | 20 |
| M12625_at | Human lecithin-cholesterol acyltranferase "mRNA," complete "cds," with 5′ and 3′ flanking DNA sequences | 131 | 104 | 20 | 20 | 50 | 158 |
| M12759_at | Human Ig J chain gene | 20 | 20 | 52 | 20 | 33 | 20 |
| M12783_at | Human c-sis/platelet-derived growth factor 2 (SIS/PDGF2) "mRNA," complete cds | 71 | 222 | 36 | 40 | 176 | 614 |
| M12886_at | Human T-cell receptor active beta-chain "mRNA," complete cds | 104 | 295 | 159 | 80 | 313 | 181 |
| M12959_s_at | Human T-cell receptor active alpha-chain mRNA from JM cell "line," complete cds | 248 | 20 | 20 | 20 | 20 | 131 |
| M12963_s_at | Human class I alcohol dehydrogenase (ADH1) alpha subunit "mRNA," complete cds | 20 | 20 | 20 | 20 | 210 | 38 |
| M13058_s_at | Human acidic proline-rich protein (PRH2) "gene," complete cds | 48 | 32 | 20 | 34 | 36 | 51 |
| M13143_at | Nucleotide sequence of the cDNA insert of lambda PK129 coding for human plasma prekallikrein | 71 | 20 | 20 | 20 | 20 | 20 |
| M13149_at | Human histidine-rich glycoprotein "mRNA," complete cds | 24 | 35 | 52 | 69 | 496 | 20 |
| M13150_s_at | Human excision repair protein (ERCC1) "mRNA," complete "cds," clone pcDE | 127 | 108 | 54 | 28 | 21 | 60 |
| M13194_at | Human granulocyte-macrophage colony-stimulating factor (CSF1) "gene," complete cds | 99 | 115 | 138 | 86 | 63 | 159 |
| M13207_at | Human factor VII serine protease precursor "mRNA," complete "cds," clone lambda-HVII2463 | 20 | 112 | 315 | 61 | 62 | 87 |
| M13232_s_at | Human N-myc "gene," exons 2 and 3 | 20 | 20 | 20 | 46 | 120 | 67 |
| M13241_at | Human esterase D "mRNA," 3+end | 148 | 165 | 202 | 50 | 132 | 160 |
| M13450_at | Human lamin A "mRNA," 3′end | 147 | 108 | 379 | 350 | 501 | 300 |
| M13452_s_at | Human metallothionein I-B gene | 42 | 20 | 72 | 44 | 20 | 52 |
| M13485_at | Human Ia-associated invariant gamma-chain gene | 952 | 1286 | 292 | 233 | 206 | 2632 |
| M13560_s_at | Human myelin basic protein (MBP) "mRNA," complete cds | 20 | 20 | 20 | 20 | 75 | 20 |
| M13577_at | Human c-myb mRNA, 3′ end | 20 | 20 | 20 | 20 | 203 | 54 |
| M13666_s_at | Human pulmonary surfactant-associated protein "mRNA," comlete "cds," clone MPSAP-6A | 29 | 27 | 82 | 62 | 331 | 30 |
| M13686_s_at | Human plasma protease (C1) inhibitor "mRNA," complete cds | 248 | 252 | 151 | 110 | 280 | 179 |
| M13690_s_at | Human ceruloplasmin (ferroxidase) "mRNA," complete cds | 85 | 80 | 20 | 20 | 40 | 136 |
| M13699_at | Human interferon-induced 17-kDa/15-kDa protein "mRNA," complete cds | 200 | 230 | 109 | 181 | 93 | 921 |
| M13755_at |  |  |  |  |  |  |  |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M13792_at | Human adenosine deaminase (ADA) "gene," complete cds | 138 | 96 | 216 | 85 | 77 | 150 |
| M13829_s_at | Human putative raf related protein (pks/a-raf) "mRNA," partial cds | 81 | 131 | 186 | 147 | 589 | 284 |
| M13903_at | Human involuorin mRNA | 1000 | 20 | 366 | 360 | 20 | 78 |
| M13928_s_at |  | 20 | 20 | 20 | 20 | 66 | 20 |
| M13929_s_at |  | 125 | 82 | 93 | 39 | 529 | 208 |
| M13934_cds1_at | Human c-myc-P64 "mRNA," initiating from promoter "P0," (HLmyc2.5) partial cds | 20 | 20 | 20 | 20 | 20 | 20 |
| M13934_cds2_at | Human ribosomal protein S14 gene, complete cds. | 3281 | 5721 | 6183 | 3882 | 1080 | 2000 |
| M13955_at | Human ribosomal protein S14 gene, complete cds | 117 | 295 | 3435 | 4022 | 2461 | 1332 |
| M13981_at | Human mesothelial keratin K7 (type II) "mRNA," 3' end | 37 | 20 | 224 | 65 | 20 | 74 |
| M13982_at | Human inhibin A-subunit "mRNA," complete cds | 20 | 20 | 20 | 20 | 20 | 20 |
| M13994_s_at | Human interleukin 4 (IL-4) "mRNA," complete cds | 102 | 119 | 195 | 133 | 169 | 20 |
| M14016_at | Human B-cell leukemia/lymphoma 2 (bcl-2 proto-oncogene mRNA encoding bcl-2-alpha "protein," complete cds | 201 | 121 | 155 | 148 | 28 | 20 |
| M14058_at | Human uroporphyrinogen decarboxylase "mRNA," complete cds | 240 | 235 | 73 | 50 | 32 | 257 |
| M14091_at | Human complement C1r "mRNA," complete cds | 24 | 20 | 20 | 39 | 265 | 94 |
| M14113_at | Human throxine-binding blobulin "mRNA," complete cds | 40 | 20 | 20 | 30 | 20 | 20 |
| M14123_xpt1_at | Human coagulation factor VIII:C "mRNA," complete cds | 20 | 20 | 20 | 20 | 20 | 214 |
| M14123_xpt2_at | neutral protease large subunit from Human endogenous retrovirus HERV-K10. /gb=M14123 /ntype=DNA /annot=CDS | 93 | 54 | 36 | 20 | 20 | 20 |
| M14123_xpt3_at | Human endogenous retrovirus HERV-K10. | 20 | 24 | 20 | 20 | 54 | 199 |
| M14123_xpt4_at | Human endogenous retrovirus HERV-K10. | 3222 | 7240 | 6332 | 6160 | 1568 | 2332 |
| M14158_cds4_at | Human T-cell receptor germline beta-chain D1.1 and J1.1 to J1.6 genes. | 584 | 274 | 199 | 239 | 367 | 453 |
| M14159_cds2_at | Human T-cell receptor germline beta-chain D2.1 and J2.1 to J2.7 genes. | 113 | 49 | 20 | 22 | 20 | 20 |
| M14199_at | Human laminin receptor (2H4 epitope) "mRNA," 5' end | 86 | 20 | 25 | 20 | 47 | 75 |
| M14200_ma1_at | Human diazepam binding inhibitor (DBI) mRNA, complete cds. | 20 | 20 | 20 | 20 | 20 | 20 |
| M14218_at | Human argininosuccinate lyase "mRNA," complete cds | 819 | 885 | 1518 | 2137 | 354 | 751 |
| M14219_at | Human chondroitin/dermatan sulfate proteoglycan (PG40) core protein "mRNA," complete cds | 20 | 20 | 20 | 20 | 20 | 20 |
| M14306_at | Human beta-A3/A1-crystallin gene (Hu-beta-A3/A1) | 641 | 1837 | 1401 | 886 | 307 | 948 |
| M14328_s_at | Human alpha enolase "mRNA," complete cds | 86 | 25 | 20 | 20 | 20 | 48 |
| M14338_at | Human mRNA for protein S and intron | 20 | 35 | 20 | 20 | 83 | 20 |
| M14483_ma1_s_at | PTMA gene extracted from Human prothymosin alpha "mRNA," complete cds | 73 | 47 | 69 | 57 | 20 | 77 |
| M14539_at | Human factor XIII subunit a "mRNA," 3' end | 20 | 20 | 20 | 20 | 50 | 20 |
| M14565_at | Human cholesterol side-chain cleavage enzyme P450scc "mRNA," complete cds | 20 | 20 | 20 | 20 | 20 | 20 |
| M14636_at | Human liver glycogen phosphorylase "mRNA," complete cds | 20 | 59 | 20 | 32 | 50 | 285 |
| M14648_at | Human cell adhesion protein (vitronectin) receptor alpha subunit "mRNA," complete cds | 66 | 213 | 165 | 128 | 375 | 95 |
| M14660_at | KHuman ISG-54K gene (interferon stimulated gene) encoding a 54 kDa protein | 26 | 94 | 260 | 98 | 255 | 28 |
| M14676_at | Human src-like kinase (slk) "mRNA," complete cds | 20 | 42 | 20 | 20 | 20 | 169 |
| M14745_at | Human bcl-2 mRNA | 20 | 20 | 20 | 20 | 225 | 20 |
| M14758_at | Human P-glycoprotein (MDR1) "mRNA," complete cds | 20 | 23 | 20 | 20 | 135 | 20 |
| M14764_at | Human nerve growth factor receptor "mRNA," complete cds | 160 | 208 | 107 | 137 | 383 | 295 |
| M14949_at | Human R-ras gene | 20 | 20 | 20 | 20 | 20 | 41 |
| M15059_at | Human Fc-epsilon receptor (IgE receptor) "mRNA," complete cds (H107 epitope) | 196 | 171 | 322 | 191 | 482 | 209 |
| M15169_at | Human beta-2-adrenergic receptor "mRNA," complete cds | 86 | 23 | 23 | 45 | 249 | 174 |
| M15205_at | KHuman beta-glucoronidase "mRNA," complete cds | 20 | 20 | 20 | 20 | 20 | 20 |
| M15353_at | Human thymidine kinase "gene," complete "cds," with clustered Alu repeats in the introns | 20 | 20 | 20 | 20 | 123 | 110 |
| M15395_at | Homo sapiens cap-binding protein "mRNA," complete cds | 20 | 26 | 20 | 20 | 20 | 20 |
| M15465_s_at | Human leukocyte adhesion protein "(LFA-1/Mac-1/p150,95" family) beta subunit mRNA | 20 | 20 | 20 | 20 | 20 | 20 |
| M15517_cds3_s_at | TTR gene (prealbumin) extracted from Human mutant prealbumin gene directly linked to familial amyloidotic polyneuropathy (FAP) | 20 | 61 | 80 | 38 | 271 | 51 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M15517_cds5_at | Human mutant prealbumin gene directly linked to familial amyloidotic polyneuropathy (FAP), exon 4. | 20 | 20 | 20 | 20 | 265 | 20 |
| M15656_at | Human aldolase B (ALDOB) gene | 20 | 20 | 20 | 20 | 20 | 20 |
| M15661_at | Human ribosomal protein "mRNA," complete cds | 653 | 600 | 540 | 599 | 20 | 339 |
| M15780_at | Human DNA/endogenous human papillomavirus type 16 (HPV) "DNA," right flank and viral host junction. /gb=M15780 /ntype=DNA /annot | 20 | 20 | 20 | 20 | 73 | 20 |
| M15796_at | Human cyclin protein "gene," complete cds | 73 | 31 | 20 | 20 | 20 | 81 |
| M15841_at | Human U2 small nuclear RNA-associated B" antigen "mRNA," complete cds | 70 | 33 | 20 | 25 | 20 | 20 |
| M15856_at | Human lipoprotein lipase "mRNA," complete cds | 20 | 20 | 49 | 20 | 20 | 20 |
| M15881_at | Human uromodulin (Tamm-Horsfall glycoprotein) "mRNA," complete cds | 20 | 40 | 20 | 55 | 104 | 26 |
| M15958_at | Human gastrin "gene," complete cds | 20 | 20 | 20 | 20 | 20 | 20 |
| M15990_at | Human c-yes-1 mRNA | 41 | 37 | 69 | 27 | 20 | 42 |
| M16038_at | Human lyn mRNA encoding a tyrosine kinase | 131 | 96 | 20 | 81 | 111 | 180 |
| M16276_at | Human MHC class II HLA-DR2-Dw12 mRNA "DQw1-beta," complete cds | 89 | 285 | 20 | 20 | 20 | 20 |
| M16279_at | Human MIC2 "mRNA," complete cds | 418 | 311 | 50 | 57 | 20 | 208 |
| M16282_at | Human fragile X locus M2C containing an unidentified open reading "frame," 3' end | 72 | 54 | 20 | 20 | 122 | 28 |
| M16336_s_at | Human T-cell surface antigen CD2 (T11) "mRNA," complete "cds," clone PB1 | 20 | 401 | 20 | 20 | 20 | 142 |
| M16342_at | Human nuclear ribonucleoprotein particle (hnRNP) C protein "mRNA," complete cds | 201 | 374 | 769 | 608 | 387 | 393 |
| M16364_at | Human creatine kinase-B "mRNA," complete cds | 20 | 20 | 20 | 20 | 33 | 20 |
| M16404_at | Human m2 muscarinic acetylcholine receptor gene | 20 | 33 | 20 | 20 | 20 | 25 |
| M16405_at | Human m4 muscarinic acetylcholine receptor gene | 38 | 20 | 143 | 20 | 20 | 20 |
| M16424_at | Human beta-hexosaminidase alpha chain (HEXA) gene | 79 | 43 | 47 | 20 | 115 | 20 |
| M16441_s_at | Human tumor necrosis factor and lymphotoxin genes, complete cds. | 20 | 20 | 31 | 20 | 20 | 20 |
| M16447_at | Human dihydropteridine reductase (hDHPR) "mRNA," complete cds | 20 | 27 | 23 | 25 | 29 | 44 |
| M16474_s_at | Human fetal butyrylcholinesterase "mRNA," complete cds | 20 | 20 | 20 | 20 | 20 | 20 |
| M16505_at | Human steroid sulfatase (STS) "mRNA," complete cds | 20 | 20 | 20 | 20 | 20 | 70 |
| M16591_s_at | Human hemopoietic cell protein-tyrosine kinase (HCK) "gene," complete "cds," clone lambda-a2/1a | 20 | 20 | 20 | 20 | 20 | 20 |
| M16594_at | Human glutathione S-transferase Ha subunit 2 (GST) "mRNA," complete cds | 20 | 20 | 20 | 20 | 20 | 20 |
| M16652_at | | 201 | 58 | 305 | 235 | 20 | 222 |
| M16652_s_at | Human pancreatic alastase IIA "mRNA," complete cds | 20 | 58 | 20 | 20 | 20 | 25 |
| M16653_at | | 20 | 20 | 20 | 20 | 20 | 20 |
| M16707_ma1_at | | 20 | 20 | 20 | 20 | 20 | 108 |
| M16707_ma1_s_at | Human histone H4 "gene," complete "cds," clone FO108 | 20 | 23 | 20 | 20 | 20 | 77 |
| M16714_at | Human MHC class I divergent lymphocyte antigen "gene," complete "cds," clone RS5 | 277 | 48 | 107 | 209 | 44 | 20 |
| M16750_s13_at | Human pim-1 oncogene "mRNA," complete cds | 20 | 20 | 26 | 20 | 20 | 90 |
| M16801_at | Human mineralocorticoid receptor mRNA "(hMR)," complete cds | 33 | 34 | 112 | 63 | 23 | 20 |
| M16937_at | Human homeo box c1 "protein," "mRNA," complete cds | 26 | 20 | 93 | 20 | 66 | 53 |
| M16938_s_at | Human homeo box c8 "protein," "mRNA," complete cds | 35 | 20 | 20 | 20 | 20 | 20 |
| M16961_at | Human alpha-2-HS-glycoprotein alpha and beta chain "mRNA," complete cds | 28 | 20 | 20 | 28 | 20 | 20 |
| M16967_at | Human coagulation factor V "mRNA," complete cds | 20 | 20 | 20 | 20 | 132 | 20 |
| M16973_at | Human complement protein C8 beta subunit "mRNA," complete cds | 60 | 20 | 57 | 48 | 40 | 20 |
| M17183_s_at | Human parathyroid hormone-related protein "mRNA," complete cds | 61 | 20 | 97 | 20 | 20 | 20 |
| M17219_at | Human brain guanine nucleotide-binding protein alpha-i subunit "mRNA," 5' end | 20 | 20 | 20 | 20 | 20 | 20 |
| M17236_at | | 20 | 34 | 20 | 20 | 20 | 20 |
| M17236_s_at | Human MHC class II HLA-DQ-alpha gene "(DR4,w6)" | 20 | 20 | 20 | 20 | 20 | 20 |
| M17252_at | | 20 | 20 | 20 | 20 | 20 | 20 |
| M17254_s_at | Human erg2 gene encoding erg2 "protein," complete cds | 20 | 20 | 20 | 20 | 20 | 20 |
| M17262_at | Human prohrombin (F2) "gene," complete "cds," and Alu and Kpni repeats | 83 | 46 | 20 | 20 | 20 | 75 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M17316_at | Human gamma-A-crystallin gene (gamma-G5) | 20 | 20 | 20 | 20 | 20 | 37 |
| M17446_s_at | Human Kaposi's sarcoma oncogene fibroblast growth factor "mRNA," complete cds | 20 | 20 | 20 | 20 | 119 | 34 |
| M17466_at | Human blood coagulation factor XII (F12) gene | 20 | 20 | 20 | 20 | 20 | 24 |
| M17733_at | Human thymosin beta-4 "mRNA," complete cds | 2774 | 2982 | 4457 | 2457 | 1107 | 5326 |
| M17754_at | Human BN51 "mRNA," complete cds | 20 | 54 | 20 | 20 | 203 | 80 |
| M17863_s_at | Human prepoinsulin-like growth factor II (IGF-II) variant "mRNA," complete cds | 73 | 161 | 1288 | 1663 | 473 | 105 |
| M17885_at | Human acidic ribosomal phosphoprotein P0 "mRNA," complete cds | 3690 | 3866 | 6294 | 6346 | 3139 | 2716 |
| M17886_at | Human acidic ribosomal phosphoprotein P1 "mRNA," complete cds | 3488 | 5130 | 6144 | 4145 | 1684 | 1992 |
| M18000_at | Human ribosomal protein S17 "gene," complete cds | 3315 | 4368 | 4750 | 3985 | 1502 | 1784 |
| M18079_at | Human, intestinal fatty acid binding protein "gene," complete "cds," and an Alu repetitive element | 20 | 113 | 20 | 41 | 20 | 99 |
| M18185_at | Human gastric inhibitory polypeptide (GIP) "mRNA," complete cds | 59 | 46 | 20 | 20 | 20 | 20 |
| M18255_cds2_s_at | PRKACB gene (protein kinase C-beta-2) extracted from Human protein kinase C beta 1 and 2 "genes," next to last | 20 | 32 | 34 | 47 | 20 | 41 |
| M18391_s_at | Human tyrosine kinase receptor (eph) "mRNA," complete cds | 114 | 43 | 109 | 106 | 150 | 140 |
| M18533_at | Homo sapiens dystrophin (DMD) "mRNA," complete cds | 119 | 45 | 20 | 33 | 20 | 34 |
| M18700_s_at |  | 20 | 24 | 74 | 38 | 250 | 67 |
| M18728_at | Human nonspecific crossreacting antigen "mRNA," complete cds | 412 | 35 | 65 | 92 | 20 | 20 |
| M18731_at | Human galactose-1-phosphate uridyltransferase (GALT) "mRNA," complete cds | 20 | 20 | 20 | 20 | 20 | 20 |
| M18737_ma1_at | Human Hanakah factor serine protease (HuHF) mRNA, complete cds. | 104 | 110 | 20 | 86 | 134 | 117 |
| M19045_f_at | Human lysozyme "mRNA," complete cds | 644 | 794 | 208 | 318 | 374 | 948 |
| M19154_at | Human transforming growth factor-beta-2 "mRNA," complete cds | 20 | 20 | 20 | 20 | 26 | 20 |
| M19159_at | Human placental heat-stable alkaline phosphatase (PLAP-1) "gene," complete cds | 20 | 57 | 20 | 20 | 286 | 116 |
| M19267_s_at | Human tropomyosin "mRNA," complete cds | 64 | 188 | 70 | 67 | 25 | 24 |
| M19283_at | Human cytoskeletal gamma-actin "gene," complete cds | 284 | 725 | 1463 | 597 | 259 | 875 |
| M19301_at | Human branched-chain alpha-keto acid dehydrogenase (E2) "mRNA," complete cds | 1086 | 20 | 20 | 20 | 51 | 137 |
| M19309_s_at | Human slow skeletal muscle troponin T "mRNA," clone H22h | 20 | 20 | 20 | 20 | 20 | 20 |
| M19311_s_at |  | 20 | 20 | 20 | 20 | 20 | 20 |
| M19481_at | Human calmodulin "mRNA," complete cds | 822 | 1040 | 1010 | 1113 | 302 | 625 |
| M19483_at | Human follistatin gene | 20 | 20 | 20 | 20 | 20 | 20 |
| M19507_at | Human ATP synthase beta subunit gene | 683 | 338 | 1159 | 522 | 123 | 343 |
| M19508_xpt3_s_at | Human myeloperoxidase "mRNA," complete cds | 20 | 20 | 20 | 20 | 125 | 20 |
| M19645_at | MPO from Human myeloperoxidase "gene," exons 1–4. /gb=M19508 /ntype=DNA /annot=exon | 47 | 69 | 86 | 63 | 159 | 116 |
| M19650_s_at | Human 78 kdalton glucose-regulated fprotein (GrP78) "gene," complete cds | 137 | 74 | 180 | 27 | 94 | 150 |
| M19684_at | Human "2',3'-cyclic" nucleotide 3'-phosphodiesterase "mRNA," complete cds | 32 | 39 | 74 | 39 | 20 | 20 |
| M19720_ma1_at | Human alpha-1-antitrypsin-related protein gene | 20 | 20 | 20 | 20 | 20 | 20 |
| M19720_ma2_at | Human L-myc protein gene, complete cds. | 32 | 48 | 20 | 20 | 170 | 143 |
| M19722_at | Human L-myc protein gene, complete cds | 40 | 20 | 70 | 20 | 20 | 60 |
| M19828_s_at | Human fgr proto-oncogene encoded p55-c-fgr "protein," complete cds | 20 | 20 | 20 | 20 | 41 | 20 |
| M19878_at | Human apolipoprotein B-100 (apoB) gene | 20 | 20 | 20 | 20 | 20 | 20 |
| M19878_s_at | Homo sapiens calbindin 27 "gene," exons 1 and "2," and Alu repeat. /gb=M19878 /ntype=DNA /annot=exon | 20 | 20 | 20 | 20 | 365 | 625 |
| M19888_at | Human small proline rich protein (sprt) "mRNA," clone 128 | 4441 | 20 | 20 | 20 | 360 | 70 |
| M19961_at | Human cytochrome c oxidase subunit Vb (coxVb) "mRNA," complete cds | 485 | 705 | 569 | 392 | 570 | 385 |
| M19989_cds1_at | Human platelet-derived growth factor (PDGFA) A chain gene, exon 7. | 20 | 20 | 33 | 37 | 20 | 59 |
| M19989_cds2_at | Human platelet-derived growth factor (PDGFA) A chain gene, exon 7. | 20 | 20 | 284 | 45 | 20 | 20 |
| M20030_f_at | Human small proline rich protein (sprtII) "mRNA," clone 930 | 3809 | 20 | 20 | 20 | 20 | 20 |
| M20137_at | Human interleukin 3 (IL-3_ "mRNA," comlete "cds," clone pcD-SR-alpha | 20 | 20 | 20 | 20 | 50 | 20 |
| M20203_s_at | Human neutrophil elastase gene | 20 | 20 | 20 | 20 | 26 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M20218_at | Human coagulation factor XI gene | 20 | 20 | 20 | 20 | 20 | 20 |
| M20471_at | Human brain-type clathrin light-chain a "mRNA," complete cds | 114 | 421 | 416 | 238 | 57 | 404 |
| M20530_at | Human pancreatic secretory trypsin inhibitor (PSTI) gene | 20 | 46 | 223 | 21 | 20 | 20 |
| M20543_at | Human skeletal alpha-actin "gene," complete cds | 20 | 20 | 20 | 20 | 20 | 20 |
| M20566_at | Human interleukin 6 receptor "mRNA," complete cds | 20 | 20 | 20 | 20 | 20 | 20 |
| M20642_s_at | Human alkali myosin light chain 1 "mRNA," complete cds | 20 | 20 | 20 | 20 | 20 | 20 |
| M20681_at | Human glucose transporter-like protein-III "(GLUT3)," complete cds | 70 | 20 | 20 | 50 | 51 | 59 |
| M20747_s_at | Human insulin-responsive glucose transporter (GLUT4) "mRNA," complete cds | 20 | 20 | 142 | 20 | 167 | 59 |
| M20777_s_at | Homo "sapiens," alpha-2 (VI) collagen | 124 | 20 | 20 | 21 | 138 | 62 |
| M20778_s_at | Homo "sapien," alpha-3 (VI) collagen | 20 | 20 | 20 | 20 | 225 | 62 |
| M20786_at | Human alpha-2-plasmin inhibitor gene | 96 | 20 | 20 | 20 | 253 | 20 |
| M20867_s_at | Human glutamate dehydrogenase (GDH) "mRNA," complete cds | 79 | 127 | 181 | 114 | 227 | 110 |
| M20902_at | Human apolipoprotein C-I (VLDL) "gene," complete cds | 132 | 112 | 82 | 59 | 382 | 654 |
| M20919_at | Human DNA with a hepatitis B virus surface antigen (HBsAg) gene (complete cds) insertion | 20 | 20 | 20 | 20 | 20 | 20 |
| M21005_at | KHuman migration inhibitory factor-related protein 8 (MRP8) "gene," complete cds | 4930 | 48 | 20 | 20 | 20 | 20 |
| M21056_at | Human pancreatic phospholipase A-2 (PLA-2_ gene | 20 | 20 | 20 | 20 | 20 | 20 |
| M21064_at | Human migration inhibitory factor-related protein 14 (MRP14) "gene," complete cds | 20 | 20 | 21 | 20 | 20 | 20 |
| M21119_s_at | Human lysozyme "mRNA," complete cds | 57 | 44 | 29 | 20 | 125 | 211 |
| M21121_at | Human T cell-specific protein (RANTES) "mRNA," complete cds | 20 | 20 | 20 | 20 | 20 | 20 |
| M21142_cds2_s_at | guanine nucleotide-binding protein G-s-alpha-3 gene extracted from Human guanine nucleotide-binding protein alpha-subunit gene (G-s-a | 782 | 546 | 1777 | 1509 | 20 | 839 |
| M21154_at | Human S-adenosylmethionine decarboxylase "mRNA," complete cds | 20 | 20 | 107 | 39 | 20 | 24 |
| M21186_at | Human neutrophil cytochrome b light chain p22 phagocyte b-cytochrome "mRNA," complete cds | 20 | 65 | 319 | 386 | 20 | 20 |
| M21188_at | Human insulin-degrading enzyme (IDE) "mRNA," complete cds | 20 | 20 | 20 | 37 | 20 | 20 |
| M21259_at | Human Alu repeats in the region 5′ to the small nuclear ribonucleoprotein E gene | 20 | 103 | 103 | 124 | 117 | 20 |
| M21302_at | Human small proline rich protein (sprII) "mRNA," clone 174N | 20 | 20 | 165 | 20 | 112 | 20 |
| M21305_at | Human T-cell receptor delta chain mRNA "(VJC-region)," complete cds | 600 | 20 | 20 | 20 | 20 | 20 |
| M21388_at | Human alpha satellite and satellite 3 junction DNA sequence /gb=M21305 /ntype=DNA /annot=CDS | 20 | 20 | 30 | 20 | 20 | 20 |
| M21388_r_at |  | 20 | 20 | 20 | 20 | 20 | 215 |
| M21389_at | Human keratin type II (58 kD) "mRNA," complete cds | 1572 | 52 | 20 | 47 | 20 | 20 |
| M21494_at | Human muscle creatine kinase gene "(CKMM)," 5′ flank | 20 | 20 | 20 | 20 | 20 | 33 |
| M21535_at | M17390 Human erg protein (ets-related gene) "mRNA," complete cds. | 35 | 299 | 566 | 296 | 166 | 499 |
| M21539_at | Human small proline rich protein (sprII) "mRNA," clone 1292 | 215 | 20 | 416 | 20 | 710 | 96 |
| M21551_ma1_at | Human neuromedin B mRNA, complete cds. | 92 | 85 | 77 | 20 | 20 | 191 |
| M21574_at | Human pletelet-derived growth factor receptor alpha (PDGFRA) "mRNA," complete cds | 20 | 32 | 68 | 142 | 193 | 307 |
| M21624_at | Human T-cell receptor TR2 "mRNA," complete cds | 256 | 48 | 1490 | 699 | 237 | 177 |
| M21642_at |  | 20 | 20 | 20 | 28 | 20 | 20 |
| M21642_s_at | Human (dysfunctional) antithrombin III (ATIII) Utah gene | 20 | 20 | 36 | 26 | 294 | 20 |
| M21665_s_at | Human beta-myosin heavy chain "mRNA," 3′ end | 56 | 225 | 148 | 104 | 20 | 62 |
| M21812_at | Human (clone PWH1.C2024) myosin light chain 2 "mRNA," complete cds | 20 | 20 | 22 | 21 | 20 | 33 |
| M21904_at | Human 4F2 glycosylated heavy chain (4F2HC) antigen gene | 20 | 52 | 20 | 52 | 20 | 20 |
| M21934_at | Human rearranged and truncated 1g gamma heavy chain disease (RIV) protein gene V-J6 region | 175 | 20 | 20 | 20 | 20 | 20 |
| M21985_at | Human (clone PWH1nT16) skeletal muscle Troponin T "mRNA," complete cds | 20 | 305 | 20 | 20 | 20 | 20 |
| M22005_at | Human steroid receptor TR2 "mRNA," complete cds | 20 | 20 | 20 | 36 | 325 | 68 |
| M22092_at | Human interleukin 2 "gene," clone "pAT taciL-2C/2TT;"]complete "cds," clone pAT taciL-2C/2TT. /gb=M22005 /ntype=DNA /annot=CDS | 20 | 198 | 213 | 20 | 20 | 20 |
| M22324_at | Human neural cell adhesion molecule (N-CA) "gene," exon SEC and partial cds. /gb=M22092 /ntype=DNA /annot=exon | 20 | 20 | 20 | 20 | 20 | 20 |
| M22348_s_at | Human aminopeptidase N/CD13 mRNA encoding aminopeptidase "N," complete cds | 37 | 36 | 85 | 106 | 78 | 51 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M22382_at | Human mitochondrial matrix protein P1 (nuclear encoded) "mRNA," complete cds | 382 | 396 | 1610 | 688 | 306 | 660 |
| M22403_s_at | Human blood platelet membrane glycoprotein IIb-alpha (GPIB) "gene," complete "cds," clone N10 | 20 | 52 | 48 | 20 | 655 | 26 |
| M22430_at | Human RASF-A PLA2 "mRNA," complete cds | 75 | 61 | 361 | 1347 | 176 | 149 |
| M22489_at | Human bone morphogenetic protein 2A (BMP-2A) mRNA | 20 | 88 | 25 | 20 | 110 | 20 |
| M22490_at | Human bone morphogenetic protein-2B (BMP-2B) mRNA | 377 | 419 | 464 | 491 | 760 | 707 |
| M22538_at | Human nuclear-encoded mitochondrial NADH-ubiquinone reductase 24Kd subunit "mRNA," complete cds | 468 | 365 | 683 | 515 | 206 | 360 |
| M22612_f_at | Human pancreatic trypsin 1 (TRY1) "mRNA," complete cds | 20 | 20 | 20 | 20 | 20 | 20 |
| M22643_at | Human mitochondrial aspartate aminotransferase "mRNA," complete cds | 199 | 148 | 465 | 305 | 286 | 169 |
| M22638_at | Human LYL-1 protein "gene," complete cds | 85 | 20 | 20 | 64 | 135 | 142 |
| M22760_at | Homo sapiens nuclear-encoded mitochondrial cytochrome c oxidase Va subunit "mRNA," complete cds | 426 | 208 | 602 | 532 | 87 | 286 |
| M22877_at | Human somatic cytochrome c (HCS) "gene," complete cds | 129 | 57 | 203 | 156 | 39 | 52 |
| M22898_at | Human phosphoprotein p53 gene | 20 | 132 | 91 | 77 | 20 | 20 |
| M22919_ma2_at | Human nonmuscle/smooth muscle alkali myosin light chain gene, complete cds. | 146 | 137 | 20 | 259 | 326 | 487 |
| M22960_at | Human protective protein "mRNA," complete cds | 285 | 149 | 220 | 281 | 173 | 181 |
| M22976_at | Human cytochrome b5 "mRNA," 3' end | 69 | 195 | 829 | 757 | 478 | 244 |
| M22995_at | Human ras-related protein (Krev-1) "mRNA," complete cds | 76 | 114 | 282 | 76 | 166 | 112 |
| M23114_at | Homo sapiens calcium-ATPase (HK1) "mRNA," complete cds | 167 | 118 | 227 | 101 | 93 | 20 |
| M23161_at | human transposon-like element mRNA | 78 | 77 | 23 | 20 | 68 | 70 |
| M23178_s_at | Human homologue-1 of gene encoding alpha subunit of murine cytokine "(MIP 1/SCI)," complete cds | 23 | 50 | 38 | 20 | 275 | 72 |
| M23197_at | Human differentiation antigen (CD33) "mRNA," complete cds | 111 | 20 | 121 | 26 | 240 | 20 |
| M23234_at | Human membrane glycoprotein P (mdr3) "mRNA," complete cds | 20 | 20 | 96 | 20 | 91 | 23 |
| M23254_at | Human Ca2-activated neutral protease large subunit (CANP) "mRNA," complete cds | 574 | 256 | 515 | 98 | 174 | 321 |
| M23263_at | Human androgen receptor "mRNA," complete cds | 23 | 21 | 43 | 28 | 20 | 86 |
| M23294_at | Human beta-hexaosaminidase beta-subunit (HEXB) gene | 66 | 118 | 260 | 131 | 20 | 20 |
| M23323_s_at | Human membrane protein (CD3-epsilon) gene | 192 | 309 | 544 | 302 | 453 | 302 |
| M23379_at | Human GTPase-activating protein ras p21 (RASA) "mRNA," complete cds | 20 | 76 | 102 | 43 | 260 | 88 |
| M23533_at | Human alpha 2 adrenergic receptor "gene," complete cds | 20 | 20 | 20 | 20 | 20 | 20 |
| M23575_f_at | Human pregnancy-specific beta-1 glycoprotein "mRNA," complete cds | 20 | 20 | 20 | 20 | 20 | 20 |
| M23613_at | Human nucleophosmin "mRNA," complete cds | 1448 | 779 | 2015 | 1421 | 281 | 492 |
| M23688_at | Homo sapiens adrenodoxin gene | 20 | 20 | 20 | 20 | 20 | 20 |
| M23892_s_at | Human 15-lipoxygenase "mRNA," complete cds | 32 | 20 | 60 | 33 | 20 | 49 |
| M24069_at | Human DNA-binding protein A (dbpA) "gene," 3' end | 127 | 75 | 122 | 76 | 131 | 101 |
| M24122_s_at | Human myosin alkali light chain (ventricular) "mRNA," complete cds | 22 | 20 | 20 | 20 | 201 | 20 |
| M24194_at | Human MHC protein homologous to chicken B complex protein "mRNA," complete cds | 3378 | 4955 | 7071 | 4673 | 843 | 1330 |
| M24248_at | Homo sapiens MLC-1V/Sb isoform gene | 64 | 236 | 20 | 155 | 81 | 20 |
| M24283_at | Human major group rhinovirus receptor (HRV) "mRNA," complete cds | 61 | 20 | 29 | 20 | 57 | 20 |
| M24349_s_at | Human parathyroid hormone-like protein (PLP) "gene," exon "t," clones "lambda-PLPg(1,3,7-2)," /gb=M24349 /ntype=DNA /annot=exon | 20 | 20 | 20 | 20 | 104 | 25 |
| M24351_cds2_at | Human parathyroid hormone-like protein (PLP) gene, exon 6, clones lambda-PLPg(1,3,7-2). | 51 | 35 | 36 | 32 | 20 | 20 |
| M24351_cds3_s_at | PTHLH gene (parathyroid hormone-like protein A) extracted from Human parathyroid hormone-like protein (PLP) gene | 21 | 20 | 20 | 20 | 61 | 20 |
| M24364_at | Human MHC class II lymphocyte antigen DQB "mRNA," complete "cds," haplotype "DR7," DQw9 | 20 | 45 | 20 | 36 | 20 | 32 |
| M24398_at | Human parathymosin "mRNA," complete cds | 212 | 196 | 20 | 123 | 20 | 20 |
| M24400_at | Human chymotrypsinogen "mRNA," complete cds | 20 | 20 | 20 | 20 | 20 | 20 |
| M24439_at | Human liver/bone/kidney-type alkaline phosphatase (ALPL) gene | 310 | 435 | 287 | 409 | 574 | 414 |
| M24461_at | Human pulmonary surfactant-associated protein SP-B (SFTP3) "mRNA," complete cds | 43 | 132 | 44 | 52 | 53 | 20 |
| M24470_at | Human glucose-6-phosphate "dehydrogenase," complete cds | 148 | 172 | 81 | 192 | 310 | 29 |
| M24485_s_at | Homo sapiens (clone pHGST-pi) glutathione S-transferase pi (GSTP1) "gene," complete cds | 1522 | 1234 | 2641 | 2009 | 1163 | 863 |
| M24486_s_at | Human prolyl 4-hydroxylase alpha subunit "mRNA," complete "cds," clone PA-11 | 20 | 20 | 195 | 252 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M24594_at | Human interferon-inducible 56 Kd protein "mRNA," complete cds | 20 | 83 | 83 | 67 | 92 | 111 |
| M24736_s_at | Human endothelial leukocyte adhesion molecule 1 (ELAM-1) "mRNA," complete cds | 57 | 57 | 20 | 32 | 20 | 20 |
| M24748_cds2_s_at | THRA1 gene (thyroid receptor alpha-1) extracted from Human thyroid hormone receptor alpha 1 (TR-alpha-1) "gene," complete cds | 20 | 20 | 20 | 20 | 142 | 20 |
| M24766_s_at | Human (clone pHAIV2-12) alpha-2 collagen type IV (COL4A2) "mRNA," 3′ end | 20 | 269 | 20 | 20 | 20 | 20 |
| M24899_at | Human triiodothyronine (ear7) "mRNA," complete cds | 74 | 23 | 20 | 20 | 37 | 20 |
| M24900_at | Human triiodothyronine receptor "(THRA1," "ear1)," and ear2 "genes," last 2 exons each | 42 | 51 | 46 | 20 | 20 | 40 |
| M24902_at | Human prostatic acid phosphatase "mRNA," complete cds | 193 | 95 | 115 | 59 | 232 | 99 |
| M25077_at | Human SS-A/Ro ribonucleoprotein autoantigen 60 kd subunit "mRNA," complete cds | 20 | 4613 | 75 | 54 | 20 | 77 |
| M25079_s_at | Human sickle cell beta-globin "mRNA," complete cds | 32 | 87 | 1019 | 20 | 7667 | 14514 |
| M25164_at | Human thyrotropin beta subunit gene | 77 | 20 | 144 | 69 | 48 | 65 |
| M25269_at | Homo sapiens tyrosine kinase (ELK1) oncogene "mRNA," complete cds | 20 | 20 | 41 | 59 | 113 | 94 |
| M25280_s_at | Human lymph node homing receptor "mRNA," complete cds | 20 | 20 | 20 | 20 | 20 | 161 |
| M25296_at | Human natriuretic peptide precursor "mRNA," complete cds | 20 | 53 | 20 | 20 | 201 | 85 |
| M25322_at | Human granule membrane protein-140 "mRNA," complete cds | 66 | 20 | 74 | 40 | 20 | 48 |
| M25393_at | Human protein tyrosine phosphatase (PTPase) "mRNA," complete cds | 62 | 20 | 20 | 89 | 48 | 20 |
| M25629_at | Human kallikrein "mRNA," complete "cds," clone clone phKK25 | 24 | 115 | 49 | 85 | 20 | 20 |
| M25667_at | Human neuronal growth protein 43 (GAP-43) "mRNA," complete cds | 20 | 20 | 20 | 40 | 20 | 20 |
| M25753_at | Human cyclin B "mRNA," 3′ end | 45 | 20 | 35 | 68 | 20 | 20 |
| M25756_at | Human secretogranin II "gene," complete cds | 20 | 39 | 40 | 20 | 24 | 37 |
| M25809_at | Human endomembrane proton pump subunit "mRNA," complete cds | 20 | 159 | 138 | 20 | 20 | 57 |
| M25897_at | Human platelet factor 4 (PF4) "mRNA," complete cds | 20 | 20 | 20 | 20 | 114 | 20 |
| M26004_s_at | Human CR2/CD21/C3d/Epstein-Barr virus receptor "mRNA," complete cds | 20 | 22 | 52 | 33 | 20 | 35 |
| M26041_s_at | Human MHC class II DQ alpha "mRNA," complete cds | 81 | 158 | 150 | 66 | 228 | 20 |
| M26061_at | Human cGMP phosphodiesterase alpha subunit (CGPR-A) "mRNA," complete cds | 47 | 84 | 20 | 89 | 20 | 151 |
| M26062_at | Human interleukin 2 receptor beta chain (p70–75) "mRNA," complete cds | 20 | 20 | 20 | 40 | 102 | 20 |
| M26167_ma1_at | Human platelet factor 4 variation 1 (PF4var1) gene, complete cds. | 20 | 20 | 20 | 20 | 20 | 20 |
| M26311_s_at | | 15733 | 686 | 203 | 484 | 471 | 1403 |
| M26576_cds2_at | Human alpha-1 collagen type IV gene, exon 52. | 207 | 136 | 201 | 123 | 233 | 137 |
| M26602_at | Human defensin 1 protein "mRNA," complete cds | 20 | 20 | 20 | 20 | 20 | 20 |
| M26665_at | Human testicular angiotensin converting enzyme "mRNA," complete cds | 20 | 20 | 20 | 20 | 182 | 20 |
| M26665_s_at | | 20 | 27 | 20 | 20 | 210 | 41 |
| M26679_at | Human histatin 2 (HIS2) "mRNA," complete cds | 41 | 20 | 153 | 20 | 20 | 20 |
| M26683_at | Homo sapiens homeobox protein (HOX-1.3) "gene," complete cds | 20 | 20 | 20 | 20 | 20 | 20 |
| M26692_s_at | Human T-cell translocation gene 1 (Ttg-1) "mRNA," complete cds | 20 | 81 | 20 | 20 | 20 | 20 |
| M26683_at | Human interferon gamma treatment inducible mRNA | 51 | 20 | 168 | 107 | 20 | 20 |
| M26692_s_at | Homo sapiens lymphocyte-specific protein tyrosine kinase (LCK) "gene," exon "1," and downstream promoter region. /gb=M26692 /ntype= | 20 | 20 | 20 | 20 | 20 | 20 |
| M26708_at | Human prothymosin alpha mRNA "(ProT-alpha)," complete cds | 917 | 2172 | 2018 | 1675 | 753 | 1142 |
| M26730_s_at | Human mitochondrial ubiquinon-binding protein "gene," 5′ flank with an LTR-like sequence | 465 | 838 | 698 | 893 | 311 | 220 |
| M26856_s_at | Human 21-hydroxylase B "gene," complete cds | 20 | 20 | 20 | 20 | 20 | 20 |
| M26880_at | Human ubiquitin "mRNA," complete cds | 1506 | 1454 | 1342 | 698 | 800 | 557 |
| M26901_at | Human renin gene | 20 | 25 | 20 | 20 | 20 | 20 |
| M26958_s_at | Human parathyroid hormone-related protein (PTHrP) "mRNA," 5′ "flank," clone pBRF52. /gb=M26958 /ntype=RNA | 21 | 51 | 20 | 20 | 291 | 20 |
| M27093_s_at | Homo sapiens nuclear-encoded mitochondrial branched chain alpha-keto acid dehydrogenase transacylase subunit (E2b) "mRNA," comp | 20 | 40 | 54 | 26 | 20 | 61 |
| M27160_at | Human tyrosinase (TYR) "mRNA," complete cds | 20 | 20 | 20 | 20 | 93 | 20 |
| M27161_at | Human MHC class I CD8 alpha-chain (Leu-2/T8) "gene," complete cds | 68 | 20 | 22 | 153 | 140 | 82 |
| M27281_at | Human vascular permeability factor "mRNA," complete cds | 53 | 20 | 153 | 108 | 20 | 20 |
| M27288_at | Human oncostatin M gene | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M27318_f_at | Human interferon (IFN-alpha-M1) "mRNA," complete cds | 44 | 20 | 29 | 20 | 79 | 28 |
| M27394_s_at | Human B-lymphocyte cell-surface antigen B1 (CD20) | 20 | 142 | 20 | 20 | 20 | 20 |
| M27396_s_at | Human asparagine synthetase "mRNA," complete cds | 20 | 25 | 68 | 39 | 20 | 21 |
| M27436_at | Human tissue factor "gene," complete "cds," with a Alu repetitive sequence in the 3' untranslated region | 206 | 32 | 20 | 24 | 20 | 20 |
| M27492_at | Human interleukin 1 receptor "mRNA," complete cds | 121 | 98 | 110 | 74 | 56 | 66 |
| M27504_s_at | Homo sapiens topoisomerase type II (Topo II) "mRNA," partial cds. /gb=M27504 /ntype=RNA | 20 | 20 | 20 | 30 | 20 | 25 |
| M27533_s_at |  | 20 | 20 | 20 | 20 | 126 | 88 |
| M27543_at | Human guanine nucleotide-binding protein (Gi) alpha subunit "mRNA," complete cds | 28 | 20 | 38 | 20 | 20 | 20 |
| M27691_at | Human transactivator protein (CREB) "mRNA," complete cds | 20 | 20 | 20 | 20 | 20 | 20 |
| M27749_at | Human immunoglobulin-related 14.1 protein "mRNA," complete cds | 20 | 152 | 20 | 20 | 256 | 132 |
| M27749_r_at | Human immunoglobulin-related 14.1 protein "mRNA," complete cds | 20 | 20 | 20 | 20 | 1119 | 173 |
| M27783_s_at |  | 20 | 24 | 20 | 21 | 132 | 156 |
| M27819_at | Human anion exchange protein 1 "(AE1," band 3) "mRNA," complete cds | 20 | 21 | 52 | 20 | 236 | 20 |
| M27826_at | Human endogenous retroviral protease "mRNA," complete cds | 210 | 49 | 20 | 20 | 345 | 372 |
| M27878_at | Human DNA binding protein (HPF2) "mRNA," complete cds | 20 | 59 | 20 | 20 | 20 | 20 |
| M27891_at | Human cystatin C (CST3) gene | 1363 | 943 | 1769 | 1850 | 835 | 827 |
| M27968_s_at | Human basic fibroblast growth factor (FGF) "mRNA," complete cds | 20 | 20 | 20 | 24 | 20 | 34 |
| M28130_ma1_s_at | Human interleukin 8 (IL8) "gene," complete cds | 54 | 20 | 20 | 20 | 20 | 104 |
| M28170_at | Human Human cell surface protein CD19 (CD19) "gene," complete cds | 20 | 20 | 20 | 20 | 20 | 20 |
| M28209_at | Homo sapiens GTP-binding protein RAB1 "mRNA," complete cds | 321 | 175 | 347 | 175 | 58 | 328 |
| M28210_at | Homo sapiens GTP-binding protein (RAB3A) "mRNA," complete cds | 20 | 20 | 20 | 20 | 20 | 20 |
| M28211_at | Homo sapiens GTP-binding protein (RAB4) "mRNA," complete cds | 85 | 20 | 20 | 125 | 56 | 149 |
| M28212_at | Homo sapiens GTP-binding protein (RAB6) "mRNA," complete cds | 48 | 20 | 56 | 84 | 258 | 112 |
| M28213_s_at | Homo sapiens GTP-binding protein (RAB2) "mRNA," complete cds | 241 | 156 | 252 | 269 | 118 | 112 |
| M28214_at | Homo sapiens GTP-binding protein (RAB3B) "mRNA," complete cds | 20 | 20 | 20 | 20 | 20 | 20 |
| M28215_at | Homo sapiens GTP-binding protein (RAB5) "mRNA," complete cds | 68 | 20 | 46 | 125 | 66 | 41 |
| M28219_at | Homo sapiens low density lipoprotein receptor (FH 10 mutant causing familial hypercholesterolemia) mRNA, 3' end | 55 | 98 | 20 | 125 | 66 | 41 |
| M28249_at | Human very late antigen-2 (VLA-2)/collagen receptor alpha-2 subunit "mRNA," complete cds | 20 | 37 | 32 | 78 | 53 | 20 |
| M28439_at | Human keratin type 16 gene | 20 | 20 | 20 | 23 | 20 | 26 |
| M28585_f_at | Human leukocyte interferon-alpha "mRNA," complete "cds," clone pIFN105 | 20 | 20 | 28 | 20 | 21 | 152 |
| M28713_at | Homo sapiens NADH-cytochrome b5 reductase (b5R) gene | 241 | 324 | 96 | 204 | 435 | 152 |
| M28825_at | Homo sapiens thymocyte antigen CD1a "mRNA," complete cds | 20 | 20 | 20 | 53 | 82 | 20 |
| M28826_at | Homo sapiens thymocyte antigen CD1b "mRNA," complete cds | 20 | 20 | 23 | 35 | 20 | 40 |
| M28827_at | Homo sapiens thymocyte antigen CD1c "mRNA," complete cds | 50 | 20 | 20 | 20 | 39 | 20 |
| M28879_at | Human granzyme B (CTLA-1) "gene," complete cds | 25 | 122 | 136 | 89 | 171 | 77 |
| M28882_s_at | Human MUC18 glycoprotein "mRNA," complete cds | 85 | 95 | 33 | 20 | 446 | 150 |
| M28983_at | Homo sapiens interleukin 1 alpha (IL 1) "mRNA," complete cds | 74 | 44 | 57 | 50 | 140 | 51 |
| M29037_s_at | Human 17 beta-hydroxysteroid dehydrogenase (17BHSDI) "gene," exons "1–5," complete cds | 26 | 20 | 20 | 20 | 485 | 77 |
| M29064_at | Human hnRNP B1 protein mRNA | 353 | 270 | 694 | 323 | 132 | 252 |
| M29194_at | Human triglyceride lipase gene | 20 | 41 | 20 | 20 | 148 | 109 |
| M29204_at | Human DNA-binding factor "mRNA," complete cds | 55 | 20 | 123 | 32 | 85 | 99 |
| M29273_at | Human myelin-associated glycoprotein (MAG) "mRNA," complete cds | 128 | 36 | 20 | 242 | 386 | 550 |
| M29277_at | Human isolate JuSo MUC18 glycoprotein mRNA (3' "variant)," complete cds | 208 | 89 | 403 | 198 | 520 | 287 |
| M29335_at | Human NHC class II DO-alpha "mRNA," partial cds | 20 | 20 | 20 | 20 | 20 | 217 |
| M29335_s_at |  | 20 | 20 | 20 | 20 | 1043 | 217 |
| M29386_s_at | Human prolactin "mRNA," 3' end | 21 | 28 | 98 | 61 | 259 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M29458_at | Human carbonic anhydrase III gene | 20 | 20 | 20 | 38 | 20 | 20 |
| M29474_at | Human recombination activating protein (RAG-1) "gene," complete cds | 20 | 23 | 20 | 20 | 20 | 20 |
| M29536_at | Human translational initiation factor 2 beta subunit (eIF-2-beta) "mRNA," complete cds | 238 | 207 | 312 | 213 | 140 | 78 |
| M29540_at | Human carcinoembryonic antigen mRNA "(CEA)," complete cds | 483 | 20 | 116 | 20 | 108 | 20 |
| M29550_at | Human calcineurin A1 "mRNA," complete cds | 21 | 80 | 134 | 51 | 49 | 20 |
| M29551_at | Human calcineurin A2 "mRNA," complete cds | 21 | 31 | 20 | 27 | 20 | 20 |
| M29580_at | Human zinc-finger protein 7 (ZFP7) "mRNA," complete cds | 20 | 20 | 20 | 23 | 20 | 20 |
| M29581_at | Human zinc-finger protein 8 (ZFP8) "mRNA," 3' end | 98 | 65 | 161 | 112 | 124 | 111 |
| M29610_at | | 42 | 22 | 31 | 20 | 20 | 20 |
| M29610_s_at | Human glycophorin E "mRNA," complete cds | 20 | 27 | 20 | 31 | 126 | 41 |
| M29696_at | Human interleukin-7 receptor (IL-7) "mRNA," complete cds | 246 | 251 | 192 | 178 | 387 | 457 |
| M29874_s_at | Human cytochrome P450-IIB (hIIB1) "mRNA," complete cds | 185 | 20 | 20 | 20 | 20 | 20 |
| M29877_at | Human "alpha-L-fucosidase," complete cds | 181 | 457 | 1112 | 462 | 416 | 275 |
| M29927_at | Human ornithine aminodtransferase gene | 147 | 49 | 20 | 20 | 20 | 20 |
| M29932_s_at | Huma nbeta030adrenergic receptor gene | 89 | 137 | 328 | 136 | 190 | 86 |
| M29960_at | Human steroid receptor (TR2011) "mRNA," complete cds | 68 | 215 | 173 | 146 | 142 | 130 |
| M29971_at | Human 6-O-methylguanine-DNA methyltransferase (MGMT) "mRNA," complete cds | 51 | 165 | 20 | 136 | 89 | 232 |
| M29994_s_at | Human alpha-I spectrin "gene," exon 12 /gb=M29994 /ntype=DNA /annot=exon | 20 | 56 | 62 | 32 | 20 | 37 |
| M30135_at | Human P40 T-cell and mast cell growth factor (hP40) "gene," complete cds | 20 | 20 | 20 | 20 | 20 | 20 |
| M30185_at | Human cholesteryl ester transfer protein "mRNA,"|complete cds | 59 | 85 | 59 | 45 | 39 | 29 |
| M30257_s_at | Human vascular cell adhesion molecule 1 "mRNA," complete cds | 82 | 20 | 28 | 29 | 20 | 90 |
| M30269_at | Human ridogen "mRNA," complete cds | 239 | 357 | 738 | 687 | 536 | 273 |
| M30448_s_at | Human ubiquitin carboxyl-terminal hydrolase (PGP "9.5," UCH-L3) isozyme L3 "mRNA," complete cds | 33 | 44 | 57 | 44 | 26 | 20 |
| M30496_at | Human zinc finger protein Y-linked (ZFY) "mRNA," complete cds | 30 | 21 | 127 | 70 | 113 | 25 |
| M30607_s_at | Human dopamine D2 "receptor," "mRNA," complete cds | 20 | 20 | 20 | 20 | 70 | 20 |
| M30625_s_at | Human amphiregulin (AR) gene | 160 | 20 | 20 | 20 | 49 | 20 |
| M30703_at | Human calcineurin B "mRNA," complete cds | 20 | 20 | 20 | 20 | 20 | 20 |
| M30773_at | Human interferon-induced cellular resistance mediator protein (MxB) "mRNA," complete cds | 63 | 98 | 52 | 40 | 333 | 204 |
| M30818_at | Human pulmonary surfactant apoprotein (PSAP) "gene," complete cds | 50 | 56 | 28 | 32 | 97 | 40 |
| M30838_at | human T-cell receptor Ti rearranged gamma-chain mRNA V-J-C "region," complete cds | 95 | 75 | 171 | 117 | 149 | 59 |
| M30984_at | Human Ku (p70/p80) subunit "mRNA," complete cds | 121 | 93 | 507 | 196 | 45 | 35 |
| M30938_at | Human nonmuscle myosin heavy chain (NMHC) "mRNA," 3' end | 274 | 175 | 792 | 266 | 232 | 258 |
| M31013_at | Human steroid 17-alpha-hydroxylase gene | 20 | 20 | 20 | 20 | 20 | 20 |
| M31153_at | Human cAMP-dependent protein kinase subunit RIII-beta "mRNA," complete cds | 51 | 20 | 35 | 28 | 20 | 20 |
| M31158_at | Human tumor necrosis factor-inducible (TSG-6) mRNA "fragment," adhesion receptor CD44 putative CDS | 20 | 20 | 20 | 20 | 60 | 20 |
| M31165_at | Human tumor necrosis factor-inducible (TSG-14) "mRNA," complete cds | 20 | 20 | 20 | 20 | 20 | 20 |
| M31166_at | Human propionyl-CoA carboxylase beta-subunit (beta-PCC) "gene," partial cds (mutant delta-ATC). /gb=M31169 /ntype=DNA /annot=CD | 36 | 29 | 20 | 20 | 20 | 66 |
| M31169_s_at | Human endothelial differentiation protein (edg-1) gene "mRNA," complete cds | 30 | 49 | 33 | 67 | 20 | 20 |
| M31210_at | Human myosin light chain 1 show a (MLC1sa) "mRNA," complete cds | 35 | 20 | 20 | 20 | 20 | 20 |
| M31211_s_at | Human complement receptor 1 (CR1) gene | 25 | 40 | 20 | 26 | 26 | 71 |
| M31241_s_at | Human oncoprotein 18 (Op18) gene, complete cds. | 271 | 274 | 373 | 245 | 752 | 751 |
| M31303_ma1_at | Human guanine nucleotide-binding protein beta-3 subunit "mRNA," complete cds | 182 | 112 | 211 | 140 | 182 | 255 |
| M31328_at | Human cerebellar-degeneration-related antigen (CDR34) "gene," complete cds | 20 | 20 | 20 | 27 | 92 | 20 |
| M31423_s_at | Human decay-accelerating factor "mRNA," complete cds | 49 | 20 | 45 | 62 | 20 | 66 |
| M31516_at | Human ribosomal protein S24 mRNA | 1876 | 2526 | 3539 | 2479 | 885 | 1027 |
| M31520_at | | 20 | 20 | 36 | 55 | 20 | 20 |
| M31520_ma1_at | | | | | | | |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M31520_ma1_s_at | Human ribosomal protein S24 mRNA | 2242 | 7095 | 5080 | 4489 | 1497 | 1572 |
| M31523_at | Human transcription factor (E2A) "mRNA," complete cds | 20 | 39 | 40 | 106 | 205 | 120 |
| M31525_at | Human NHC class II lymphocyte antigen (HLA-DNA) "gene," complete cds | 314 | 176 | 281 | 263 | 580 | 522 |
| M31551_s_at | Human urokinase inhibitor (PAI-2) gene | 219 | 20 | 20 | 41 | 59 | 20 |
| M31606_at | Human phosphorylase kinase (PSK-C3) "mRNA," complete cds | 20 | 20 | 20 | 20 | 93 | 20 |
| M31627_at | Human X box binding protein-1 (XBP-1) "mRNA," complete cds | 177 | 219 | 464 | 246 | 44 | 44 |
| M31642_at | Human hypoxanthine phosphoribosyltransferase (HPRT) "mRNA," complete cds | 51 | 55 | 145 | 121 | 44 | 39 |
| M31651_at | Human human sex hormon-binding globulin (SHBG) "gene," complete cds | 20 | 20 | 20 | 20 | 20 | 20 |
| M31659_at | Human GT mitochondrial solute carrier protein homologue "mRNA," complete cds | 20 | 79 | 55 | 65 | 20 | 20 |
| M31661_at | Human prolactin (PRL) receptor "mRNA," complete cds | 20 | 20 | 20 | 20 | 22 | 83 |
| M31667_f_at | Human cytochrome P450 (CYP1A2) gene | 156 | 337 | 102 | 233 | 20 | 189 |
| M31682_at | Human testicular inhibin beta-B-subunit "mRNA," 3' end | 20 | 20 | 20 | 20 | 20 | 20 |
| M31724_at | Humanphosphotyrosyl-protein phosphatase (PTP-1B) "mRNA," complete cds | 20 | 50 | 44 | 35 | 20 | 25 |
| M31774_s_at | Human thyrotropin receptor (TSH) "mRNA," complete cds | 20 | 20 | 20 | 20 | 253 | 20 |
| M31776_s_at | | 20 | 20 | 20 | 20 | 20 | 20 |
| M31899_at | Human DNA repair helicase (ERCC3) "mRNA," complete cds | 38 | 1397 | 20 | 75 | 20 | 20 |
| M31932_at | Human IgG low affinity Fc fragment receptor (FcRIIa) "mRNA," complete cds | 79 | 151 | 252 | 122 | 303 | 122 |
| M31951_at | Human perforin (PRF1) "gene," complete cds | 20 | 4128 | 20 | 20 | 20 | 20 |
| M31994_at | Human cytosolic aldehyde dehydrogenase (ALDH1) gene | 257 | 123 | 20 | 20 | 276 | 226 |
| M32011_at | Human neutrophil oxidase factor (p67-phox) "mRNA," complete cds | 20 | 20 | 79 | 101 | 20 | 116 |
| M32304_at | Human H19 RNA "gene," complete cds (spliced in silicon) | 2486 | 452 | 10414 | 1556 | 1259 | 341 |
| M32313_at | Human metalloproteinase inhibitor "mRNA," complete cds | 202 | 46 | 249 | 122 | 707 | 221 |
| M32315_at | Human steroid 5-alpha-reductase "mRNA," complete cds | 113 | 194 | 164 | 160 | 373 | 235 |
| M32334_at | Human tumor necrosis factor receptor "mRNA," complete cds | 69 | 125 | 72 | 100 | 112 | 204 |
| M32373_at | Human intercellular adhesion molecule 2 (ICAM-2) gene | 20 | 131 | 72 | 60 | 20 | 70 |
| M32402_at | Human arylsulfatase B (ASB) "mRNA," complete cds | 23 | 20 | 20 | 20 | 231 | 20 |
| M32405_at | Human placental protein (PP11) "mRNA," complete cds | 87 | 20 | 20 | 20 | 20 | 20 |
| M32578_at | Human homologue of rat insulinoma gene "(trig)," exons 4-Jan | 2005 | 2461 | 4500 | 3488 | 1906 | 1616 |
| M32598_at | Human NHC class II HLA-DR beta-1 mRNA "(DR2.3)," 5'end | 32 | 111 | 20 | 20 | 105 | 77 |
| M32639_at | Human muscle glycogen phosphorylase (PYGM) gene | 20 | 20 | 20 | 20 | 82 | 68 |
| M32879_at | Human salivary statherin "gene," 5' flank | 20 | 20 | 20 | 20 | 20 | 20 |
| M32879_s_at | Human steroid 11-beta-hydroxylase (CYP11B1) gene | 20 | 20 | 20 | 20 | 20 | 20 |
| M32886_at | Human sorcin CP-22 "mRNA," complete cds | 66 | 46 | 353 | 219 | 20 | 44 |
| M33195_at | Human Fc-epsilon-receptor gamma-chain "mRNA," complete cds | 133 | 20 | 20 | 21 | 119 | 154 |
| M33308_at | Human vinculin "mRNA," complete cds | 231 | 120 | 224 | 140 | 28 | 148 |
| M33317_f_at | Human cytochrome P450IIA4 (CYP2A4) "mRNA," complete cds | 20 | 60 | 87 | 20 | 39 | 20 |
| M33336_r_at | Human cytochrome P450IIA3 (CYP2A3) "mRNA," complete cds | 20 | 20 | 20 | 20 | 517 | 184 |
| M33374_at | Human cAMP-dependent protein kinase type I-alpha subunit (PRKAR1A) "mRNA," complete cds | 217 | 136 | 365 | 232 | 117 | 48 |
| M33478_at | Human cell adhesion protein (SQM1) "mRNA," complete cds | 40 | 20 | 20 | 94 | 20 | 20 |
| M33493_s_at | Human 33-kDa phototransducing protein "mRNA," complete cds | 77 | 24 | 20 | 20 | 71 | 20 |
| M33518_at | Human tryptase-III "mRNA," 3' end | 313 | 40 | 75 | 20 | 213 | 88 |
| M33521_at | Human HLA-B-associated transcript 2 (BAT2) "gene," 5' flank | 20 | 20 | 20 | 93 | 20 | 67 |
| M33552_at | Human HLA-B-associated transcript 3 (BAT3) "gene," 5' end | 142 | 189 | 207 | 294 | 258 | 466 |
| M33600_f_at | Human lymphocyte-specific protein 1 (LSP1) "mRNA," complete cds | 205 | 31 | 251 | 191 | 234 | 295 |
| M33653_f_at | Human MHC class II HLA-DR-beta-1 (HLA-DRB1) "mRNA," complete cds | 619 | 1395 | 203 | 147 | 20 | 1381 |
| | Human (clones "HT-[125,133])" alpha-2 type IV collagen (COL4A2) "mRNa," complete cds | 20 | 20 | 20 | 20 | 317 | 65 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| M33680_at | Human 26-kDa cell surface protein TAPA-1 "mRNA," complete cds | 1423 | 2367 | 2541 | 1805 | 831 | 1133 |
| M33684_s_at | Human (clone lambda-10-2) non-receptor tyrosine phosphatase 1 (PTPN1) gene | 66 | 91 | 146 | 82 | 20 | 110 |
| M33764_at | Human ornithine decarboxylase "gene," complete cds | 399 | 306 | 566 | 313 | 243 | 271 |
| M33772_s_at | Human fast skeletal muscle tropoin C gene | 44 | 33 | 20 | 20 | 20 | 20 |
| M33882_at | Human p78 protein "mRNA," complete cds | 20 | 20 | 75 | 20 | 20 | 65 |
| M33987_at | Human carbonic anhydrase I (CAI) "mRNA," complete cds | 31 | 34 | 35 | 20 | 20 | 131 |
| M34041_at | Human alpha-2-adrenergic receptor (alpha-2 c2) "gene," complete cds | 517 | 287 | 300 | 519 | 1390 | 1256 |
| M34057_at | Human transforming growth factor-beta 1 binding protein "mRNA," complete cds | 145 | 123 | 194 | 141 | 20 | 85 |
| M34065_at | Human cdc25Hs "mRNA," complete cds | 47 | 20 | 20 | 84 | 52 | 28 |
| M34079_at | Human immunodeficiency virus tat transactivator binding protein-1 (tbp-1) "mRNA," complete cds | 280 | 227 | 251 | 308 | 236 | 354 |
| M34175_at | Human beta adaptin "mRNA," complete cds | 144 | 110 | 253 | 143 | 145 | 164 |
| M34181_at | Human testis-specific protein kinase gamma-subunit "mRNA," complete cds | 20 | 20 | 43 | 22 | 20 | 20 |
| M34182_s_at | Human testis-specific protein kinase gamma-subunit "mRNA," complete cds | 924 | 772 | 1027 | 722 | 1221 | 1193 |
| M34192_at | Human isovaleryl-coA dehydrogenase (IVD) "mRNA," complete cds | 30 | 158 | 104 | 98 | 303 | 275 |
| M34276_at | Human plasminogen gene | 37 | 64 | 100 | 110 | 177 | 104 |
| M23309_at | Human epidermal growth factor receptor (HER3) "mRNA," complete cds | 82 | 20 | 243 | 179 | 51 | 20 |
| M34338_s_at | Human spermidine synthase "mRNA," complete cds | 42 | 33 | 63 | 78 | 20 | 84 |
| M34344_at | Human platelet glycoprotein IIb (GPIIb) gene | 91 | 129 | 20 | 58 | 107 | 94 |
| M34353_s_at | Human transmembrane tyrosine-specific protein kinase (ROS1) "mRNA," complete cds | 57 | 85 | 107 | 56 | 283 | 46 |
| M34376_s_at | Homo sapiens (clone lambda MSP131) beta-microseminoprotein (MSP) gene | 20 | 26 | 37 | 280 | 20 | 29 |
| M34423_at | Human beta-galactosidase (GLB1) "mRNA," complete cds | 54 | 149 | 308 | 247 | 94 | 20 |
| M34455_at | Human interferon-gamma-inducible indoleamine "2,3-dioxygenase" (IDO) "mRNA," complete cds | 134 | 142 | 217 | 164 | 108 | 115 |
| M34458_ma1_s_at | Human lamin B "mRNA," complete cds | 20 | 52 | 55 | 37 | 98 | 42 |
| M34516_at | Human omega light chain protein 14.1 (Ig lambda chain related) gene | 2235 | 2613 | 731 | 419 | 20 | 6258 |
| M34516_r_at | Human omega light chain protein 14.1 (Ig lambda chain related) gene | 1059 | 1747 | 485 | 299 | 778 | 3381 |
| M34539_at | Human FK506-binding protein (FKBP) "mRNA," complete cds | 152 | 48 | 141 | 284 | 20 | 392 |
| M34667_at | Human phospholipase C-gamma "mRNA," complete cds | 20 | 73 | 56 | 97 | 108 | 85 |
| M34668_at | Human protein tyrosine phosphatase (PTPase-alpha) mRNA | 77 | 20 | 124 | 89 | 20 | 44 |
| M34677_at | Human nested gene protein "gene," complete cds | 20 | 20 | 20 | 20 | 20 | 20 |
| M34715_at | Human pregnancy-specific beta-1-glycoprotein mRNA "PSG95," complete cds | 20 | 80 | 64 | 39 | 99 | 32 |
| M34996_s_at | Human NHC cell surface glycoprotein (HLA-DQA) "mRNA," 3'end | 232 | 184 | 75 | 57 | 110 | 430 |
| M35093_s_at | Human secreted epithelial tumor mucin antigen (MUC1) "gene," complete cds | 20 | 20 | 20 | 20 | 20 | 20 |
| M35128_at | Human muscarinic acetylcholine receptor "gene," complete cds | 42 | 203 | 43 | 255 | 324 | 234 |
| M35198_at | Human integrin B-6 "mRNA," complete cds | 36 | 20 | 20 | 118 | 20 | 20 |
| M35252_at | Human CO-029 | 20 | 20 | 74 | 198 | 20 | 46 |
| M35296_at | Human tyrosine kinase arg gene mRNA | 105 | 88 | 135 | 149 | 381 | 223 |
| M35416_at | Human GTP-binding protein (RALB) "mRNA," complete cds | 122 | 23 | 58 | 20 | 72 | 126 |
| M35531_s_at | Human GDP-L-fucose:beta-D-galactoside 2-alpha-I-fucosyltransferase "mRNA," complete cds | 20 | 20 | 81 | 117 | 166 | 80 |
| M35851_s_at | Human androgen receptor gene | 20 | 20 | 20 | 20 | 20 | 20 |
| M35878_at | Human insulin-like growth factor-binding protein-3 "gene," complete "cds," clone HL1006d | 255 | 577 | 3521 | 1809 | 2510 | 1317 |
| M35999_at | Human platelet glycoprotein IIIa (GPIIIa) "mRNA," complete cds | 20 | 20 | 20 | 20 | 20 | 20 |
| M36067_at | Human DNA ligase I "mRNA," complete cds | 20 | 20 | 20 | 20 | 104 | 20 |
| M36072_at | Human ribosomal protein L7a (surf 3) large subunit "mRNA," complete cds | 2150 | 3875 | 4953 | 4145 | 1479 | 1748 |
| M36089_at | Human DNA-repair protein (XRCC1) "mRNA," complete cds | 99 | 161 | 232 | 107 | 350 | 293 |
| M36118_s_at | Human cytotoxin serine protease-C "mRNA," complete cds | 20 | 20 | 31 | 20 | 20 | 93 |
| M36200_at | Human synaptobrevin 1 (SYB1) gene | 53 | 166 | 100 | 43 | 56 | 142 |
| M36205_at | Human synaptobrevin 2 (SYB2) gene | 22 | 20 | 20 | 36 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M36284_s_at | Human glycophorin C "mRNA," complete cds | 59 | 104 | 20 | 20 | 20 | 20 |
| M36341_at | Human ADP-ribosylation factor 4 (ARF4) "mRNA," complete cds | 225 | 225 | 402 | 212 | 198 | 98 |
| M36429_s_at | Human transducin beta-2 subunit "mRNA," complete cds | 91 | 20 | 193 | 180 | 107 | 59 |
| M36430_s_at | human transducin beta-1 subunit "mRNA," 3' end | 118 | 118 | 269 | 335 | 45 | 265 |
| M36542_s_at | Human lymphoid-specific transcription factor "mRNA," complete cds | 63 | 20 | 263 | 208 | 20 | 20 |
| M36634_at | Human vasoactive intestinal peptide (VIP) "mRNA," complete cds | 20 | 38 | 20 | 29 | 20 | 20 |
| M36653_s_at | Human 2-Oct factor "mRNA," complete cds | 20 | 20 | 20 | 20 | 20 | 20 |
| M36803_at | Human hemopexin gene | 229 | 393 | 461 | 275 | 265 | 581 |
| M37033_at | Human CD53 glycoprotein "mRNA," complete cds | 20 | 20 | 20 | 20 | 20 | 20 |
| M37075_at | Human embryonic/atrial myosin light chain (MLC-1-emb/A isoform) gene | 338 | 111 | 241 | 175 | 188 | 144 |
| M37104_at | Human mitochondrial ATPase couling factor 6 subunit (ATP5A) "mRNA," complete cds | 50 | 120 | 20 | 20 | 70 | 81 |
| M37190_at | Human ras inhibitor "mRNA," 3' end | 82 | 66 | 115 | 83 | 20 | 67 |
| M37197_at | Human CCAAT-box-binding factor (CBF) "mRNA," complete cds | 33 | 57 | 281 | 144 | 20 | 43 |
| M37238_s_at | Human phospholipase C "mRNA," complete cds | 46 | 186 | 91 | 41 | 305 | 316 |
| M37245_at | Human Ig superfamily cytotoxic T-lymphocyte-associated protein (CTLA-4) gene | 20 | 20 | 20 | 20 | 20 | 20 |
| M37271_s_at | Human CD7 antigen "gene," exons 4-Jan | 35 | 20 | 20 | 20 | 20 | 20 |
| M37400_at | Human cytosolic aspartate aminotransferase "mRNA," complete cds | 197 | 181 | 163 | 152 | 605 | 420 |
| M37435_at | Human macrophage-specific colony-stimulating factor (CSF-1) "mRNA," complete cds | 168 | 257 | 323 | 190 | 361 | 134 |
| M37457_at | Human "Na+,K+" #NAME? catalytic subunit alpha-III isoform gene | 20 | 20 | 20 | 20 | 20 | 20 |
| M37485_cds1_at | IGH@ gene (Ig Dxp heavy-chain gene) extracted from Human Ig germline H-chain D-reflon Dxp 1 and Dxp'1 "genes," 3' end | 20 | 20 | 20 | 20 | 38 | 29 |
| M37583_at | Human histone (H2AZ) "mRNA," complete cds | 288 | 108 | 359 | 240 | 41 | 349 |
| M37712_at | Human p58/GTA (galactosyltransferase associated protein kinase) "mRNA," complete cds | 20 | 20 | 29 | 25 | 20 | 20 |
| M37721_at | Human peptidylglycine alpha-amidating monooxygenase "mRNA," complete cds | 122 | 88 | 96 | 44 | 20 | 98 |
| M37755_f_at | Human pregnancy-specific beta 1-glycoprotein gene PSGGA | 34 | 84 | 162 | 81 | 265 | 24 |
| M37763_at | Human neurotrophin-3 (INT-3) "gene," complete cds | 31 | 20 | 36 | 45 | 20 | 142 |
| M37766_at | Human MEM-102 glycoprotein "mRNA," complete cds | 69 | 302 | 48 | 49 | 78 | 229 |
| M37815_cds1_at | Human T-cell membrane glycoprotein CD28 mRNA, exon 4 | 20 | 54 | 20 | 48 | 212 | 172 |
| M37825_at | Human fibroblast growth factor05 (FGF-5) "mRNA," complete cds | 70 | 99 | 36 | 67 | 24 | 120 |
| M37981_at | Human alpha-3 neuronal nicotinic acetylcholine receptor subunit "mRNA," complete cds | 20 | 31 | 20 | 20 | 20 | 20 |
| M37984_ma1_at | Human slow witch skeletal muscle/cardiac muscle troponin C gene, complete cds | 267 | 225 | 406 | 237 | 207 | 370 |
| M38180_ma1_at | Human 3-beta-hydroxysteroid dehydrogenase/delta-5-delta-4-isomerase (3-beta-HSD) "gene," complete cds | 20 | 20 | 22 | 20 | 20 | 20 |
| M38258_at | Human retinoic acid receptor gamma 1 "mRNA," complete cds | 53 | 20 | 20 | 69 | 179 | 68 |
| M38449_s_at | Human transforming growth factor-beta "mRNA," complete "cds," clone pTGF-beta-trp114 | 101 | 33 | 108 | 24 | 159 | 191 |
| M38591_at | Homo sapiens cellular ligand of annexin II (p11) "mRNA," complete cds | 1891 | 75 | 90 | 228 | 20 | 230 |
| M38690_at | Human CD9 antigen "mRNA," complete cds | 1172 | 367 | 1654 | 1216 | 189 | 264 |
| M54914_s_at | Human follicle-stimulating hormone beta-subunit gene | 20 | 24 | 20 | 20 | 20 | 20 |
| M54915_s_at | Human h-pim-1 protein (h-pim-1) "mRNA," complete cds | 500 | 154 | 436 | 506 | 184 | 169 |
| M54927_at | Human connective tissue activation peptide III "mRNA," complete cds | 33 | 48 | 20 | 20 | 20 | 186 |
| M54951_at | Human atrial natriuretic factor gene | 62 | 20 | 20 | 20 | 20 | 60 |
| M54968_at | Human K-ras oncogene protein "mRNA," complete cds | 20 | 35 | 28 | 20 | 41 | 20 |
| M54992_at | Human B-cell differentiation antigen "mRNA," complete cds | 70 | 20 | 22 | 20 | 20 | 20 |
| M54995_at | Human cell surface glycoprotein P3.58 "mRNA," partial cds. /gb=M55024 /ntype=RNA | 20 | 99 | 58 | 31 | 72 | 93 |
| M55024_s_at | Human acetylcholinesterase (ACHE) "mRNA," complete cds | 20 | 20 | 20 | 20 | 20 | 21 |
| M55040_at | Human synaptotagmin "mRNA," complete cds | 225 | 208 | 115 | 280 | 286 | 656 |
| M55047_at | Human 47-kD autosomal chronic granulomatous disease protein "mRNA," complete cds | 35 | 60 | 56 | 77 | 55 | 128 |
| M55067_at | | 174 | 137 | 91 | 137 | 157 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M55131_at | Human cystic fibrosis transmembrane conductance regulator (CFTR) gene | 39 | 40 | 207 | 20 | 20 | 25 |
| M55150_at | Human fumarylacetoacetate hydrolase "mRNA," complete cds | 166 | 371 | 435 | 309 | 518 | 467 |
| M55153_at | Human transglutaminase (TGase) "mRNA," complete cds | 20 | 28 | 20 | 78 | 169 | 238 |
| M55172_at | Human large aggregating cartilage proteoglycan core protein "mRNA," complete cds | 20 | 46 | 20 | 20 | 180 | 77 |
| M55210_at | Human laminin B2 chain (LAMB2) gene | 20 | 50 | 132 | 124 | 319 | 20 |
| M55265_at | Human casein kinase II alpha subunit "mRNA," complete cds | 108 | 116 | 193 | 112 | 330 | 88 |
| M55267_at | Human EV12 protein gene | 20 | 95 | 35 | 20 | 205 | 20 |
| M55268_at | Human casein kinas II alpha subunit "mRNA," complete cds | 57 | 114 | 254 | 254 | 200 | 20 |
| M55284_at | Human protein kinase C-L (PRKCL) "mRNA," complete cds | 20 | 20 | 20 | 20 | 20 | 20 |
| M55409_s_at | Human pancreatic tumor-related protein "mRNA," 3' end | 1992 | 2532 | 4850 | 4627 | 719 | 906 |
| M55418_at | Human amelogenin (AMELX) "gene," 3' end of cds | 20 | 34 | 20 | 20 | 238 | 20 |
| M55419_at | Human amelogenin (AMELY) "gene," 3' end of cds | 20 | 20 | 20 | 20 | 20 | 20 |
| M55420_at | Human IgE "chain," last 2 exons | 105 | 43 | 64 | 168 | 20 | 121 |
| M55422_at | Human Kneuppel-related zinc finger protein (H-plk) "mRNA," complete cds | 20 | 78 | 178 | 96 | 37 | 90 |
| M55513_s_at | Human potassium channel (HPCN1) "mRNA," complete cds | 52 | 20 | 120 | 57 | 260 | 93 |
| M55531_at | Human glucose transport-like 5 (GLUT5) "mRNA," complete cds | 82 | 121 | 208 | 141 | 90 | 96 |
| M55542_at | Human guanylate binding protein isoform I (GBP-2) "mRNA," complete cds | 117 | 20 | 58 | 26 | 20 | 96 |
| M55543_at | Human guanylate binding protein isoform II (GBP-2) "mRNA," complete cds | 77 | 189 | 292 | 251 | 33 | 129 |
| M55593_at | Human collagenase type IV (CLG4) gene | 739 | 471 | 351 | 274 | 271 | 384 |
| M55621_at | Human N-acetylglucosaminyltransferase 1 (GlcNac-TI) "mRNA," complete cds | 304 | 20 | 215 | 600 | 397 | 80 |
| M55671_at | Human protein Z (plus 55 bp insertion) "mRNA," complete cds | 122 | 162 | 20 | 100 | 268 | 105 |
| M55682_s_at | Human carglage matrix protein (CMP) gene | 20 | 20 | 20 | 20 | 20 | 20 |
| M55683_at | Human cartilage matrix protein (CMP) "mRNA," exon 8-Mar | 20 | 20 | 20 | 20 | 20 | 20 |
| M55905_at | Human mitochondrial NAD(P)+ dependent malic enzyme "mRNA," complete cds | 20 | 76 | 20 | 58 | 20 | 20 |
| M55998_s_at | Human alpha-1 collagen type I "gene," 3' end | 1610 | 1610 | 360 | 46 | 221 | 326 |
| M57230_at | Human membrane glycoprotein gp130 "mRNA," complete cds | 20 | 20 | 20 | 20 | 27 | 33 |
| M57293_at | Human parathyroid hormone-related peptide (PTHRP) "gene," exons "1A," "1B," "1C," and 2 /gb=M57293 /ntype=DNA /annot=mRNA | 20 | 20 | 20 | 20 | 202 | 210 |
| M57399_at | Human nerve growth factor (HBNF-1) "mRNA," complete cds | 150 | 128 | 45 | 135 | 299 | 481 |
| M57423_f_at |  | 20 | 20 | 20 | 20 | 103 | 20 |
| M57464_s_at | Human ret proto-oncogene "mRNA," complete cds | 23 | 20 | 41 | 20 | 20 | 49 |
| M57466_s_at | Human NHC class II HLA-DP light chain "mRNA," complete cds | 188 | 312 | 20 | 20 | 20 | 880 |
| M57471_at | Homo sapiens urate oxidase (UOX) "gene," exon 5 /gb=M57471 /ntype=DNA /annot=exon | 29 | 20 | 20 | 20 | 20 | 92 |
| M57506_mal_at | Human secreted protein (I-309) gene, complete cds. | 20 | 20 | 20 | 42 | 20 | 20 |
| M57567_at | Human ADP-ribosylation factor (hARF4) "mRNA," complete cds | 377 | 525 | 138 | 339 | 484 | 399 |
| M57609_at | Human DNA-binding protein (GLI3) "mRNA," complete cds | 20 | 49 | 20 | 20 | 539 | 397 |
| M57703_s_at | Human melanin concentrating hormone (MCH) "mRNA," complete cds | 20 | 20 | 71 | 55 | 93 | 48 |
| M57710_at | Human IgE-binding protein (epsilon-BP) "mRNA," complete cds | 1449 | 1035 | 1888 | 1046 | 363 | 852 |
| M57731_s_at | Human B61 "mRNA," complete cds | 20 | 154 | 20 | 163 | 578 | 193 |
| M57732_at | Human gro-beta "mRNA," complete cds | 42 | 45 | 20 | 26 | 20 | 20 |
| M57763_at | Human hepatic nuclear factor 1 (TCF1) "mRNA," complete "cds," clones "HCL10," "HCL12," "HCL17," and HCL20 | 20 | 118 | 20 | 112 | 38 | 261 |
| M57892_at | Human ADP-ribosylation factor (hARF6) "mRNA," complete cds | 222 | 50 | 120 | 101 | 20 | 20 |
| M58026_at | Human carbonic anhydrase isozyme VI (CA6) "mRNA," complete cds | 20 | 20 | 20 | 20 | 20 | 52 |
| M58028_at | Human NB-1 "mRNA," complete cds | 573 | 122 | 241 | 214 | 467 | 172 |
| M58285_at | Human ubiquitin-activating enzyme E1 (UBE1) "mRNA," complete cds | 213 | 360 | 216 | 497 | 385 | 434 |
| M58286_s_at | Human membrane-associated protein (HEM01) "mRNA," complete cds | 62 | 293 | 105 | 302 | 491 | 211 |
| M48297_at | Homo sapiens tumor necrosis factor receptor "mRNA," complete cds | 113 | 107 | 32 | 137 | 83 | 20 |
| | Human zinc finger protein 42 (MZF-1) "mRNA," complete cds | 20 | 20 | 20 | 20 | 353 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M58378_cds1_at | Human synapsin I (SYN1) gene, exon 13. | 49 | 208 | 20 | 284 | 1185 | 322 |
| M58459_at | Human ribosomal protein (RPS4Y) isoform "mRNA," complete cds | 22 | 271 | 411 | 271 | 673 | 124 |
| M58460_at | Human 75-kD autoantigen (PM-Sc1) "mRNA," complete cds | 20 | 20 | 20 | 20 | 20 | 20 |
| M58509_cds1_at | FDXR gene (adrenodoxin reductase) extracted from Human adrenodoxin reductase gene | 20 | 20 | 20 | 20 | 20 | 20 |
| M58525_s_at | Homo sapiens catechol-O-methyltransferase (COMT) "mRNA," complete cds | 92 | 259 | 1065 | 1134 | 444 | 328 |
| M58569_s_at | Human fibrinogen alpha-subunit bipartite "transcript," complete cds of extended (alpha-E) variant | 41 | 65 | 57 | 20 | 77 | 20 |
| M58583_at | Human precerebellin and cerebellin "mRNA," complete cds | 20 | 25 | 25 | 56 | 604 | 20 |
| M58597_at | Human ELAM-1 ligand fucosyltransferase (ELFT) "mRNA," complete cds | 20 | 20 | 20 | 75 | 76 | 20 |
| M58600_ma1_at | Human heparin cofactor II (HCF2) gene, exons 1 through 5. | 43 | 20 | 20 | 55 | 382 | 20 |
| M58603_at | Human nuclear factor kappa-B DNA binding subunit (NF-kappa-B) "mRNA," complete cds | 202 | 138 | 37 | 110 | 27 | 20 |
| M59216_s_at | Human gamma-aminobutyric acid-A (GABA-A) receptor beta-1 subunit | 56 | 62 | 43 | 30 | 348 | 128 |
| M59371_at | Human protein tyrosine kinase "mRNA," complete cds | 170 | 60 | 20 | 171 | 537 | 188 |
| M59465_at | Human tumor necrosis factor alpha inducible protein A20 "mRNA," complete cds | 289 | 165 | 109 | 83 | 207 | 242 |
| M59488_at | Human S100 protein beta-subunit gene | 20 | 168 | 20 | 85 | 20 | 126 |
| M59499_at | Human lipoprotein-associated coagulation inhibitor (LACI) gene | 56 | 20 | 22 | 25 | 123 | 20 |
| M59807_at | Human NK4 "mRNA," complete cds | 597 | 546 | 682 | 442 | 1219 | 1118 |
| M59815_at | Human complement component C4A gene | 337 | 250 | 20 | 209 | 20 | 407 |
| M59820_at | Human granulocyte colony-stimulating factor receptor (CSF3R) "mRNA," complete cds | 20 | 20 | 20 | 20 | 20 | 26 |
| M59829_at | Human MHC class III HSP70-HOM gene "(HLA)," complete cds | 46 | 20 | 73 | 154 | 189 | 29 |
| M59830_at | Human MHC class III HSP70-2 gene "(HLA)," complete cds | 133 | 88 | 325 | 176 | 28 | 120 |
| M59911_at | Human integrin alpha-3 chain "mRNA," complete cds | 36 | 20 | 172 | 150 | 20 | 20 |
| M59916_at | Human acid sphingomyelinase (ASM) "mRNA," complete cds | 115 | 20 | 20 | 136 | 20 | 185 |
| M59941_at | Human GM-CSF receptor beta chain "mRNA," complete cds | 28 | 20 | 20 | 20 | 20 | 25 |
| M59964_at | Human stem cell factor "mRNA," complete cds. | 20 | 20 | 20 | 20 | 72 | 31 |
| M59979_at | Human prostaglandin endoperoxide synthase "mRNA," complete cds | 20 | 20 | 20 | 20 | 20 | 20 |
| M60047_at | Human heparin binding protein (HBp17) "mRNA," complete cds | 847 | 20 | 20 | 28 | 20 | 20 |
| M60052_at | Human histidine-rich calcium binding protein (HRC) "mRNA," complete cds | 20 | 20 | 20 | 20 | 20 | 20 |
| M60091_at | Human galactose-1-phosphate uridyl transferase "mRNA," complete cds | 197 | 339 | 188 | 275 | 649 | 620 |
| M60092_at | Human myoadenylate deaminase (AMPD1) "mRNA," complete cds | 28 | 20 | 20 | 20 | 20 | 20 |
| M60094_ma1_at | Human testicular H1 histone (H1) gene, complete cds. | 66 | 39 | 82 | 64 | 20 | 37 |
| M60165_cds1_at | Human guanine nucleotide-binding regulatory protein (Go-alpha) gene, exon 9. | 53 | 115 | 217 | 112 | 234 | 268 |
| M60278_at | Human heparin-binding EGF-like growth factor "mRNA," complete cds | 308 | 38 | 20 | 89 | 99 | 278 |
| M60284_at | Human neurokinin A receptor (NK-2R) gene | 25 | 59 | 106 | 74 | 185 | 45 |
| M60298_at | Human erythrocyte membrane protein band 4.2 (EPB42) "mRNA," complete cds | 27 | 41 | 20 | 20 | 158 | 68 |
| M60299_at | Human alpha-1 collagen type II "gene," exons "1," 2 and 3 /gb=M60299 /ntype=DNA /annot=exon | 29 | 20 | 20 | 304 | 20 | 20 |
| M60314_at | Human transforming growth factor-beta (tgf-beta) "mRNA," complete cds | 24 | 36 | 20 | 20 | 20 | 20 |
| M60315_at | Human transforming growth factor-beta (tgf-beta) "mRNA," complete cds | 20 | 20 | 20 | 20 | 20 | 20 |
| M60331_at | Human protamine 1 "gene," complete cds | 75 | 44 | 20 | 108 | 308 | 242 |
| M60450_s_at | Human voltage-gated potassium channel (KH1) "mRNa," complete cds | 20 | 20 | 20 | 20 | 70 | 20 |
| M60459_at | Human erythropoietin receptor "mRNA," complete cds | 60 | 60 | 20 | 81 | 121 | 125 |
| M60483_ma1_s_at | Human protein phosphatase-2A catalytic subunit-alpha gene extracted from Human protein phosphatase 2A catalytic subunit-alpha "gene," comp | 92 | 48 | 122 | 61 | 20 | 26 |
| M60503_at | Human profilaggrin "gene," partial cds | 20 | 20 | 20 | 34 | 20 | 20 |
| M60527_at | Human deoxycylidine kinase "mRNA," complete cds | 50 | 22 | 37 | 20 | 20 | 20 |
| M60556_ma2_at | Human transforming growth factor beta-3 gene, 5' end | 20 | 20 | 20 | 20 | 20 | 20 |
| M60614_at | Human Wilms' tumor (WT-1) associated protein "mRNA," complete cds | 20 | 44 | 20 | 108 | 363 | 20 |
| M60626_at | Human N-formylpeptide receptor (fMLP-R98) "mRNA," complete cds | 20 | 20 | 20 | 83 | 20 | 20 |
| M60721_at | Human homeobox "gene," complete cds | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M60724_at | Human p70 ribosomal S6 kinase alpha-I "mRNA," complete cds | 20 | 105 | 20 | 25 | 99 | 28 |
| M60746_at | Human histone H3.1 (H1F3) "gene," complete cds | 20 | 20 | 26 | 20 | 20 | 33 |
| M60748_at | Human histone H1 (H1F4) "gene," complete cds | 20 | 20 | 20 | 21 | 20 | 20 |
| M60749_at | Human histone H4 (H4) "gene," complete cds | 20 | 20 | 20 | 28 | 20 | 20 |
| M60750_f_at | Human histone H2B.1 (H2B) "gene," complete cds. /gb=M60750 /ntype=DNA /annot=CDS | 50 | 53 | 47 | 58 | 83 | 211 |
| M60751_at | Human histone H2B.1 (H2B) "gene," complete cds | 20 | 20 | 20 | 20 | 20 | 20 |
| M60752_at | Human histone H2A.1 (H2A) "gene," complete cds | 45 | 20 | 20 | 20 | 45 | 154 |
| M60784_s_at | Human U1 snRNP-specific protein A gene | 20 | 20 | 20 | 20 | 20 | 20 |
| M60828_at | Human keratinocyte growth factor "mRNA," complete cds | 20 | 20 | 20 | 20 | 87 | 20 |
| M60830_at | Human EVI2B3P "gene," exon and complete cds | 20 | 20 | 29 | 20 | 77 | 20 |
| M60854_at | Human ribosomal protein S16 "mRNA," complete cds | 4473 | 3548 | 9124 | 5176 | 1828 | 3833 |
| M60858_ma1_at | Human nucleolin gene, complete cds | 501 | 376 | 728 | 431 | 257 | 309 |
| M60891_s_at | Human uroporphyrinogen decarboxylase (URO-D) "gene," partial cds. /gb=M60891 /ntype=DNA /annot=mRNA | 20 | 20 | 20 | 20 | 20 | 20 |
| M60922_at | Human surface antigen "mRNA," complete cds | 88 | 535 | 398 | 519 | 585 | 341 |
| M60974_s_at | Human growth arrest and DNA-damage-inducible protein (gadd45) "mRNA," complete cds | 96 | 62 | 230 | 162 | 253 | 113 |
| M61156_at | Human activator protein 2B (AP-2B) "mRNA," complete cds | 20 | 20 | 20 | 20 | 20 | 20 |
| M61176_at | Human brain-derived neurotrophic factor (BDNF) "mRNA," complete cds | 55 | 20 | 20 | 20 | 40 | 61 |
| M61199_at | Human cleavage signal 1 protein "mRNA," complete cds | 59 | 58 | 20 | 30 | 20 | 51 |
| M61733_at | Homo sapiens erythroid membrane protein 4.1 "mRNA," complete cds | 28 | 112 | 20 | 90 | 20 | 48 |
| M61764_at | Human gamma-tubulin "mRNA," complete cds | 20 | 93 | 20 | 61 | 20 | 250 |
| M61826_s_at | Human alpha-spectrin gene | 20 | 20 | 85 | 20 | 41 | 40 |
| M61827_ma1_s_at | Human leukosialin (CD43) "gene," complete cds | 20 | 147 | 196 | 124 | 279 | 207 |
| M61832_s_at | Human S-adenosylhomocysteine hydrolase (AHCY) "mRNA," complete cds | 71 | 106 | 227 | 256 | 20 | 129 |
| M61853_at | Human cytochrome P4502C18 (CYP2C18) "mRNA," clone 6b | 77 | 21 | 24 | 55 | 230 | 57 |
| M61855_at | Human cytochrome P4502C9 (CYP2C9) "mRNA," clone 20 | 20 | 20 | 20 | 37 | 77 | 40 |
| M61906_at | Human P13-kinase associated p85 mRNA sequence | 20 | 40 | 21 | 40 | 77 | 20 |
| M61916_at | Human laminin B2 chain "mRNA," complete cds | 89 | 87 | 166 | 149 | 49 | 20 |
| M62302_at | Human growth/differentiation factor 1 (GDF-1) "mRNA," complete cds | 105 | 20 | 20 | 36 | 20 | 81 |
| M62303_at | Human retinoic acid receptor-beta associated open reading "frame," complete sequence | 20 | 20 | 27 | 20 | 20 | 20 |
| M62324_at | Human modulator recognition factor I (MRF-1) "mRNA," 3' end | 84 | 107 | 23 | 154 | 57 | 213 |
| M62397_at | Human colorectal mutant cancer protein "mRNA," complete cds | 60 | 70 | 43 | 20 | 41 | 65 |
| M62400_at | Human gamma-aminobutyric acid receptor type A rho-1 subunit (GAVA-A rho-1) "mRNA," complete cds | 20 | 20 | 20 | 20 | 34 | 20 |
| M62402_at | Homo sapiens insulin-like growth factor binding protein 5 (IGFBP-5) "mRNA," complete cds | 350 | 110 | 100 | 77 | 20 | 20 |
| M62403_s_at | Human insulin-like growth factor binding protein 6 (IGFBP6) "mRNA," complete cds | 337 | 648 | 942 | 968 | 133 | 79 |
| M62424_at | Human insulin-like growth factor binding protein 4 (IGFBP4) "mRNA," complete cds | 20 | 20 | 39 | 20 | 20 | 20 |
| M62486_at | Human thrombin receptor "mRNA," complete cds | 60 | 20 | 99 | 112 | 36 | 61 |
| M62505_at | Human C4b-binding protein gene | 20 | 20 | 20 | 20 | 20 | 53 |
| M62628_s_at | Human C5a anaphylatoxin receptor "mRNA," complete cds | 20 | 20 | 100 | 20 | 20 | 48 |
| M62762_at | Human alpha-1 Ig germline C-region membrane-coding "region," 3' end | 283 | 200 | 315 | 269 | 104 | 82 |
| M62782_s_at | Human vacuolar H+ ATPase proton channel subunit "mRNA," complete cds | 20 | 20 | 20 | 20 | 469 | 56 |
| M62783_at | Human alpha-N-acetylgalactosaminidase "mRNA," complete cds | 103 | 67 | 123 | 106 | 32 | 222 |
| M62800_s_at | Human 52-kD SS-A/Ro autoantigen "mRNA," complete cds | 20 | 20 | 20 | 20 | 20 | 20 |
| M62810_at | Human mitochondrial transcription factor 1 "mRNA," complete cds | 20 | 20 | 69 | 80 | 35 | 58 |
| M62831_at | Human transcription factor ETR101 "mRNA," complete cds | 180 | 291 | 214 | 156 | 244 | 65 |
| M62840_at | Human acyloxyacyl hydrolase "mRNA," complete cds | 20 | 20 | 20 | 20 | 20 | 124 |
| M62843_at | Human brain protein recognized by the sera of patients with paraneoplastic sensory neuronopathy "mRNA," complete cds | 20 | 20 | 20 | 20 | 20 | 20 |
| M62958_at | Human retinal degradation slow (RDS) mRNA | 127 | 125 | 20 | 260 | 260 | 78 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M62982_at | Human arachidonata 12-lipoxygenase "mRNA," complete cds | 561 | 20 | 20 | 20 | 20 | 20 |
| M62994_at | Homo sapiens thyroid autoantigen (truncated actin-binding protein) "mRNA," complete cds | 135 | 96 | 334 | 318 | 269 | 246 |
| M63138_at | Human cathepsin D (catD) gene | 1489 | 1215 | 1536 | 1857 | 2340 | 2366 |
| M63154_at | Human intrinsic factor "mRNA," complete cds | 20 | 20 | 20 | 20 | 20 | 20 |
| M63167_at | Human rac protein kinase alpha "mRNA," complete cds | 306 | 204 | 230 | 358 | 147 | 433 |
| M63175_at | Human autocrine motility factor receptor mRNA | 138 | 20 | 173 | 168 | 326 | 127 |
| M63180_at | Human threonyl-tRNA synthetase "mRNA," complete cds | 64 | 53 | 89 | 42 | 25 | 23 |
| M63256_at | Human major Yo paraneoplastic antigen (CDR2) "mRNA," 3' end | 20 | 48 | 71 | 24 | 61 | 253 |
| M63262_at | Human 5-lipoxygenase activating protein (FLAP) gene | 102 | 101 | 130 | 106 | 49 | 225 |
| M63379_at | Human TRPM-2 protein gene | 891 | 1169 | 4213 | 1552 | 1063 | 620 |
| M63391_ma1_at | Human desmin gene, complete cds. | 392 | 142 | 20 | 100 | 235 | 100 |
| M63438_s_at | Human Ig rearranged gamma chain "mRNA," V-J-C region and complete cds | 4579 | 8316 | 139 | 95 | 20 | 7075 |
| M63483_at | Human major nuclear matrix protein mRNA | 238 | 219 | 302 | 251 | 20 | 225 |
| M63488_at | Human replication protein A 70kDa subunit mRNA complete cds | 20 | 20 | 20 | 20 | 20 | 20 |
| M63573_at | Human secreted cyclophilin0like protein (SCYLP) "mRNA," complete cds | 213 | 20 | 242 | 515 | 20 | 20 |
| M63582_at | Human preprothyrotropin-releasing hormone gene | 74 | 105 | 20 | 147 | 163 | 63 |
| M63589_at | Human stem cell leukemia gene product | 20 | 32 | 20 | 53 | 300 | 158 |
| M63603_at | Human phospholamban "mRNA," complete cds | 103 | 67 | 73 | 22 | 25 | 79 |
| M63623_at | Human oligodendrocyte-myelin glycoprotein (OMgP) "mRNA," complete cds | 57 | 20 | 20 | 23 | 20 | 20 |
| M63835_at | Human IgGFc receptor I gene | 20 | 20 | 20 | 20 | 20 | 41 |
| M63838_s_at | Human interferon-gamma induced protein (IFI 18) "gene," complete cds | 73 | 110 | 152 | 50 | 20 | 88 |
| M63896_at | Homo sapiens transcriptional enhancer factor (TEF1) "DNA," complete cds | 97 | 20 | 20 | 20 | 176 | 70 |
| M63904_at | Human G-alpha 16 protein "mRNA," complete cds | 120 | 20 | 20 | 71 | 61 | 20 |
| M63928_at | Homo sapiens T cell activation antigen (CD27) "mRNa," complete cds | 20 | 20 | 20 | 20 | 20 | 20 |
| M63959_at | Human alpha-2-macroglobulin receptor-associated protein "mRNA," complete cds | 188 | 270 | 294 | 457 | 286 | 184 |
| M63962_ma1_at | Human gastric H,K-ATPase catalytic subunit gene, complete cds. | 20 | 20 | 20 | 20 | 20 | 20 |
| M63967_at | Human mitochondrial aldehyde dehydrogenase x "gene," complete cds | 21 | 20 | 20 | 73 | 20 | 178 |
| M64082_at | Human flavin-containing monooxygenase (FMO1) "mRNA," complete cds | 22 | 93 | 20 | 22 | 140 | 20 |
| M64098_at | Human high density lipoprotein binding protein (HBP) "mRNA," complete cds | 197 | 256 | 180 | 205 | 101 | 95 |
| M64099_at | Human gamma-glutamyl transpeptidase-related protein (GGT-Rel) "mRNA," complete cds | 23 | 20 | 20 | 20 | 20 | 20 |
| M64108_at | Human udulin 1 "mRNA," 3' end | 134 | 97 | 133 | 111 | 228 | 123 |
| M64174_at | Human protein-tyrosine kinase (JAK1) "mRNA," complete cds | 20 | 31 | 104 | 58 | 100 | 80 |
| M64231_ma1_at | Human spermidine synthase "gene," complete cds | 20 | 20 | 20 | 20 | 349 | 134 |
| M64269_s_at | Human mast cell chymase "gene," complete cds | 20 | 20 | 45 | 28 | 133 | 20 |
| M64347_at | Human novel growth factor receptor "mRNA," 3' cds | 186 | 253 | 1679 | 1128 | 20 | 153 |
| M64358_at | Human rhom-3 "gene," exon. /gb=M64358 /ntype=DNA /annot=exon | 20 | 20 | 20 | 20 | 20 | 20 |
| M64497_at | Human apolipoprotein AI regulatory protein (ARP-1) "mRNA," complete cds | 29 | 127 | 135 | 128 | 20 | 126 |
| M64554_ma1_at | Human factor XIII b subunit gene, complete cds. | 20 | 63 | 33 | 22 | 20 | 20 |
| M64571_at | Human microtubule-associated protein 4 "mRNA," complete cds | 20 | 197 | 208 | 176 | 47 | 98 |
| M64572_at | Human protein tyrosine phosphatase "mRNA," complete cds | 20 | 88 | 126 | 120 | 21 | 226 |
| M64590_at | Human glycine decarboxylase "mRNA," complete cds | 44 | 52 | 55 | 37 | 89 | 39 |
| M64595_at | Human small G protein (Gx) "mRNA," 3' end | 20 | 20 | 20 | 20 | 74 | 278 |
| M64673_at | Human heat shock factor 1 (TCF5) "mRNA," complete cds | 126 | 157 | 20 | 286 | 505 | 352 |
| M64676_at | Human K+ channel subunit "gene," complete cds | 42 | 20 | 20 | 20 | 159 | 101 |
| M64710_s_at | Human C-type natriuretic peptide "gene," complete cds | 20 | 20 | 20 | 20 | 20 | 20 |
| M64716_at | Human ribosomal protein S25 "mRNA," complete cds | 3228 | 3345 | 5463 | 2397 | 1282 | 1554 |
| M64752_at | Human glutamate receptor subunit (GluH1) "mRNA," complete cds | 20 | 38 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M64788_at | Human GTPase activating protein (rap1GAP) "mRNA," complete cds | 20 | 20 | 20 | 20 | 20 | 20 |
| M64925_at | Human palmitoylated erythrocyte membrane protein (MPP1) "mRNA," complete cds | 106 | 64 | 20 | 29 | 20 | 36 |
| M64929_at | Human protein phosphatase 2A alpha subunit "mRNA," complete cds | 124 | 20 | 106 | 68 | 20 | 51 |
| M64930_at | Human protein phosphatase 2A beta subunit "mRNA,"]complete cds | 20 | 55 | 20 | 20 | 33 | 20 |
| M64934_at | Human kell blood group protein mRNA | 74 | 57 | 56 | 143 | 410 | 370 |
| M64936_at | Homo sapiens retinoic acid-inducible endogenous retroviral DNA | 20 | 20 | 20 | 34 | 113 | 20 |
| M64992_at | Human prosomal protein P30-33K (pros-30) "mRNA," complete cds | 210 | 90 | 238 | 174 | 20 | 20 |
| M65062_at | Human insulin-like growth factor binding protein 5 (IGFBP-5) "mRNA," complete cds | 20 | 20 | 20 | 20 | 20 | 20 |
| M65066_at | Human cAMP-dependent protein kinase regulatory subunit RI-beta "mRNA," 3' end | 98 | 75 | 20 | 231 | 311 | 469 |
| M65085_at | Human follicle stimulating hormone receptor "mRNA," complete cds. | 73 | 20 | 138 | 105 | 237 | 141 |
| M65131_ma1_at | Human methylmalonyl-CoA mutase (MCM) mRNA, complete cds. | 60 | 102 | 76 | 55 | 35 | 156 |
| M65134_s_at | Human complement component C5 "mRNA," 3'end | 40 | 26 | 74 | 30 | 100 | 39 |
| M65199_at | Human endothelin 2 (ET2) "mRNA," complete cds | 20 | 20 | 20 | 20 | 20 | 20 |
| M65214_at | Human (HeLa) hexli-loop-helix protein HE47 (E2A) "mRNA," 3' end | 20 | 20 | 20 | 20 | 20 | 49 |
| M65217_at | Human heat shock factor 2 (HSF2) "mRNA," complete cds | 72 | 20 | 65 | 64 | 20 | 33 |
| M65254_at | Protein phosphatase 2A 65 kDa regulatory subunit-beta "mRNA," complete cds., clone p40 | 89 | 145 | 200 | 158 | 346 | 240 |
| M65290_at | Human natural killer cell stimulatory factor (NKSF) "mRNA," complete "cds," clone p40 | 20 | 20 | 20 | 20 | 20 | 20 |
| M65291_at | Human naturla killer cell stimulatory factor (NKSF) "mRNA," complete "cds," clone p35 | 43 | 86 | 20 | 59 | 88 | 173 |
| M65292_s_at | Human factor H homologue "mRNA," complete cds | 251 | 394 | 389 | 327 | 20 | 35 |
| M67439_at | Human D5 dopamine receptor (DRD5) gene, complete cds. | 20 | 20 | 20 | 20 | 20 | 158 |
| M67468_s_at | Human Fragile X mental retardation 1 FMR-1 "gene," 3' "end," clones BC72 and BC22 | 20 | 20 | 47 | 55 | 20 | 36 |
| M68516_ma1_at | Human protein C inhibitor gene, complete cds. | 20 | 20 | 20 | 20 | 20 | 20 |
| M68519_ma1_at | Human pulmonary surfactant-associated protein SP-A (SFTP1) "gene," complete cds. | 20 | 20 | 20 | 20 | 109 | 198 |
| M68520_at | Human cdc2-related protein kinase "mRNA," complete cds | 90 | 169 | 20 | 166 | 281 | 163 |
| M68840_at | Human monoamine oxidase A (MAOA) "mRNA," complete cds | 129 | 138 | 217 | 189 | 20 | 128 |
| M68874_at | Human ORF "mRNA," complete cds | 260 | 255 | 235 | 269 | 391 | 128 |
| M68891_at | Human phosphatidylcholine 2-acylhydrolase (cPLA2) "mRNA," complete cds | 20 | 20 | 66 | 30 | 61 | 20 |
| M68895_ma1_at | Human GATA-binding protein (GATA2) "mRNA," complete cds | 142 | 291 | 320 | 327 | 102 | 464 |
| M68907_s_at | Homo sapiens MAD-3 mRNA encoding IkB-like "activity," complete cds | 748 | 489 | 498 | 274 | 608 | 478 |
| M69013_at | Human tachykinin-A (gamma-PPT-A) "gene," partial cds. /gb=M68907 /ntype=RNA | 278 | 110 | 20 | 71 | 83 | 124 |
| M69023_at | Human protein-tyrosine phosphatase "mRNA," complete cds | 20 | 20 | 20 | 20 | 42 | 20 |
| M69039_at | Human guanine nucleotide-binding regulatory protein (G-γ-alpha) "mRNA," complete cds | 43 | 44 | 66 | 53 | 115 | 144 |
| M69043_at | Human globin gene | 103 | 368 | 366 | 216 | 761 | 202 |
| M69066_at | Human pre-mRNA splicing factor "SF2p32," complete sequence | 35 | 20 | 320 | 128 | 20 | 20 |
| M69177_at | Human moesin "mRNA," complete cds | 194 | 150 | 432 | 303 | 28 | 399 |
| M69181_at | Human monoamine oxidase B (MAOB) "mRNA," complete cds | 60 | 93 | 20 | 74 | 52 | 20 |
| M69197_xpl2_s_at | HPR from Human haptoglobin and haptoglobin-related protein (HP and HPR) "genes," complete cds. /gb=M69197 /ntype=DNA /annot=m | 151 | 192 | 508 | 261 | 349 | 117 |
| M69203_s_at | Human cytokine (SCYA2) gene | 20 | 30 | 20 | 20 | 124 | 47 |
| M69225_at | Human bullous pamphigoid antigen (BPAG1) "mRNA," complete cds | 25 | 20 | 92 | 20 | 48 | 53 |
| M69238_at | Human aryl hydrocarbon receptor nuclear translocator (ARNT) "mRNA," complete cds | 88 | 41 | 20 | 67 | 20 | 20 |
| M71243_f_at | Human glycophorin Sta (type A) exons 3 and "4," partial. /gb=M71243 /ntype=DNA /annot=exon | 20 | 67 | 20 | 20 | 226 | 207 |
| M72885_ma1_s_at | G0S2 gene extracted from Human G0S2 "gene," 5' flank and cds | 20 | 20 | 20 | 20 | 20 | 20 |
| M73047_at | Homo sapiens tripeptidyl peptidase II "mRNA," complete cds | 28 | 20 | 66 | 22 | 372 | 20 |
| M73077_at | Human glucocorticoid receptor repression factor 1 (GRF-1) "mRNA," complete cds | 20 | 20 | 20 | 20 | 277 | 166 |
| M73239_s_at | Human (clone SF1) hepatocyte growth factor (HGF) "mRNA," complete cds | 20 | 20 | 20 | 20 | 205 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M73481_at | Human gastrin releasing peptide receptor (GRPR) "mRNA," complete cds | 20 | 20 | 20 | 42 | 20 | 107 |
| M73482_at | Human neuromedin B receptor (NMB-R) "mRNA," complete cds | 20 | 20 | 20 | 20 | 20 | 20 |
| M73489_at | Human heat-stable enterotoxin receptor "mRNA," complete cds | 30 | 47 | 127 | 34 | 174 | 144 |
| M73547_at | Human polyposis locus (DP1 gene) "mRNA," complete cds | 165 | 318 | 527 | 208 | 69 | 142 |
| M73548_s_at | Human polyposis locus (DP2.5 gene) "mRNA," complete cds | 25 | 20 | 29 | 32 | 20 | 21 |
| M72720_at | Human mast cell carboxypeptidase A (MC-CPA) gene | 246 | 66 | 83 | 40 | 20 | 185 |
| M73746_s_at | Homo sapiens lutropin/choriogonadotropin receptor (LHCGR) "mRNA," complete cds | 20 | 20 | 20 | 20 | 20 | 20 |
| M73780_at | Human integrin beta-8 subunit "mRNA," complete cds | 46 | 137 | 66 | 74 | 20 | 20 |
| M74002_at | Human arginine-rich nuclear protein "mRNA," complete cds | 107 | 157 | 352 | 160 | 130 | 156 |
| M74047_at | Human steroid 5-alpha-reductase 2 (SRD5A2) "mRNA," complete cds | 20 | 20 | 20 | 20 | 20 | 29 |
| M74088_s_at | Human APC gene "mRNA," complete cds | 20 | 20 | 20 | 20 | 20 | 20 |
| M74089_at | Human TB1 gene "mRNA," 3' end | 23 | 20 | 49 | 48 | 20 | 20 |
| M74091_at | Human cyclin mRNA | 48 | 20 | 25 | 20 | 20 | 20 |
| M74093_at | Human cyclin mRNA | 20 | 20 | 20 | 20 | 20 | 20 |
| M74096_at | Human long chain acyl-CoA dehydrogenase (ACADL) "mRNA," complete cds | 20 | 43 | 54 | 51 | 202 | 76 |
| M74099_at | Human displacement protein (CCAAT) mRNA | 22 | 45 | 39 | 20 | 64 | 63 |
| M74161_at | Human inositol polyphosphate 5-phosphatase (5ptase) "mRNA," 3' end | 20 | 73 | 20 | 49 | 20 | 20 |
| M74290_at | Human substance P receptor protein mRNA | 20 | 20 | 20 | 20 | 20 | 20 |
| M74297_at | Human homeobox 1.4 protein "mRNA," complete cds | 20 | 20 | 20 | 26 | 143 | 149 |
| M74447_at | Human PSF-2 "mRNA," complete cds | 20 | 20 | 20 | 47 | 20 | 20 |
| M74491_at | Human ADP-ribosylation factor 3 "mRNA," complete cds | 363 | 337 | 666 | 402 | 797 | 410 |
| M74509_s_at | | 63 | 207 | 235 | 172 | 20 | 234 |
| M74524_at | Human HHR6A (yeast RAD 6 homologue) "mRNA," complete cds | 114 | 95 | 161 | 37 | 57 | 158 |
| M74525_at | Human HHR6B (yeast RAD 6 homologue) "mRNA," complete cds | 20 | 20 | 20 | 20 | 89 | 119 |
| M74542_at | Human aldehyde dehydrogenase type III (ALDHIII) "mRNA," complete cds | 1233 | 20 | 20 | 26 | 20 | 24 |
| M74558_at | Human SIL "mRNA," complete cds | 34 | 150 | 90 | 43 | 20 | 93 |
| M74587_ma1_s_at | Human insulin-like growth factor binding protein (hIGFBP1) "gene," complete cds | 22 | 20 | 88 | 22 | 78 | 34 |
| M74715_s_at | Human alpha-L-iduronidase (IDUA) "mRNA," complete cds | 20 | 91 | 274 | 144 | 27 | 93 |
| M74719_at | Human SEF2-1B protein (SEF2-1B) "mRNA," complete cds | 31 | 20 | 20 | 20 | 20 | 49 |
| M74826_at | Human glutamate decarboxylase (GAD-2) "mRNA," complete cds | 62 | 64 | 72 | 52 | 173 | 29 |
| M75099_at | Human rapamycin- and FK506-binding "protein," complete cds | 331 | 336 | 596 | 509 | 379 | 234 |
| M75106_at | Human prepro-plasma carboxypeptidase B "mRNA," complete cds | 49 | 20 | 20 | 44 | 108 | 20 |
| M75110_at | Human "H,K-ATPase" beta subunit "mRNA," complete cds | 20 | 20 | 20 | 20 | 20 | 20 |
| M75126_at | Human hexokinase 1 (HK1) "mRNA," complete cds | 444 | 347 | 602 | 454 | 366 | 124 |
| M75715_s_at | Human TB3-1 "mRNA," complete cds | 50 | 21 | 20 | 57 | 20 | 20 |
| M76125_s_at | Human tyrosine kinase receptor (axl) "mRNA," complete cds | 20 | 20 | 20 | 20 | 20 | 20 |
| M76180_at | Human aromatic amino acid decarboxylase (ddc) "mRNA," complete cds | 26 | 20 | 20 | 20 | 233 | 33 |
| M76231_at | Human sepiapterin reductase "mRNA," complete cds | 20 | 64 | 20 | 45 | 97 | 150 |
| M76378_at | Human cysteine-rich protein (CRP) gene | 839 | 476 | 258 | 301 | 378 | 419 |
| M76424_at | H. sapiens carbonic anhydrase VII (CA VII) gene | 137 | 289 | 51 | 317 | 311 | 145 |
| M76446_at | Human alpha-A1-adrenergic receptor "mRNA," complete cds | 20 | 20 | 20 | 20 | 20 | 20 |
| M76482_at | Human 130-kD pemphigus vulgaris antigen "mRNA," complete cds | 389 | 20 | 20 | 74 | 89 | 129 |
| M76558_at | Human neuronal "DHP-sensitive," "voltage-dependent," calcium channel alpha-1D subunit "mRNA," complete cds | 20 | 109 | 20 | 20 | 20 | 134 |
| M76559_at | Human neuronal "DHP-sensitive," "voltage-dependent," calcium channel alpha-2b subunit "mRNA," complete cds | 27 | 20 | 42 | 46 | 20 | 59 |
| M76665_at | Human 11-beta-hydroxysteroid dehydrogenase (HSD11) gene | 48 | 20 | 76 | 62 | 57 | 20 |
| M76729_at | Human pro-alpha-1 (V) collagen "mRNA," complete cds | 20 | 20 | 20 | 48 | 117 | 20 |
| M76732_s_at | Human HOX7 gene | 20 | 20 | 20 | 20 | 20 | 35 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M76766_at | Human transcription factor (TFIIB) "mRNA," complete cds | 62 | 52 | 144 | 77 | 92 | 40 |
| M77016_at | Human tropomodulin "mRNA," complete cds | 20 | 20 | 20 | 20 | 76 | 20 |
| M77140_at | H. sapiens pro-galanin "mRNA," 3' end | 20 | 20 | 20 | 20 | 20 | 96 |
| M77142_at | Human polyadenylate binding protein (TIA-1) "mRNA," complete cds | 20 | 20 | 78 | 48 | 20 | 20 |
| M77144_ma1_at | 3-beta-hydroxysteroid dehydrogenase gene extracted from Human type II 3-beta hydroxysteroid dehydrogenase/ 5-delta-4-delta isomera | 20 | 20 | 104 | 20 | 142 | 38 |
| M77232_ma1_at | Human ribosomal protein S6 gene, complete cds and flanking regions. | 2616 | 3217 | 5323 | 4003 | 538 | 1703 |
| M77235_at | Human cardiac tetrodotoxin-insensitive voltage-dependent sodium channel alpha subunit (HH1) "mRNA," complete cds | 52 | 20 | 53 | 20 | 20 | 20 |
| M77348_ma1_s_at | Human pmel 17 "mRNA," complete cds | 20 | 20 | 20 | 20 | 20 | 22 |
| M77349_at | Human transforming growth factor-beta induced gene product (BIGH3) "mRNA," complete cds | 333 | 277 | 121 | 71 | 162 | 357 |
| M77481_ma1_f_at | Human antigen (MAGE-1) "gene," complete cds | 20 | 20 | 20 | 20 | 20 | 20 |
| M77698_at | Homo sapiens GLI-Krupple related protein (YY1) "mRNA," complete cds | 94 | 20 | 213 | 171 | 20 | 44 |
| M77810_at | Human transcription factor GATA-2 (GATA-3) "mRNA," complete cds | 20 | 20 | 20 | 88 | 149 | 20 |
| M77829_s_at | Human channel-like integral membrane protein (CHIP28) "mRNA," complete cds | 20 | 20 | 20 | 20 | 20 | 20 |
| M77836_at | Human pyrroline 5-carboxylate reductase "mRNA," complete cds | 167 | 120 | 47 | 244 | 687 | 535 |
| M79462_at | Human PML-1 "mRNA," complete CDS | 78 | 76 | 54 | 96 | 127 | 20 |
| M79463_s_at | Human PML-2 "mRNA," complete CDS | 23 | 116 | 78 | 119 | 240 | 357 |
| M80244_at | Human E16 "mRNA," complete cds | 249 | 74 | 58 | 168 | 121 | 87 |
| M80254_at | H. sapiens cyclophilin isoform (hCyP3) "mRNA," complete cds | 223 | 110 | 248 | 187 | 20 | 86 |
| M80333_at | Human m5 nuscarinic acetylcholine receptor "gene," complete cds | 85 | 117 | 134 | 95 | 209 | 121 |
| M80335_at | Homo sapiens protein kinase A catalytic subunit "mRNA," 3' end | 194 | 217 | 96 | 147 | 232 | 247 |
| M80359_at | Human protein p78 "mRNA," complete cds | 20 | 45 | 195 | 159 | 415 | 321 |
| M80397_s_at | Human DNA polymerase delta catalytic subunit "mRNA," complete cds | 20 | 20 | 20 | 56 | 20 | 135 |
| M80478_at | Human platelet glycoprotein IX precursor (gpIX) "gene," complete cds | 20 | 20 | 20 | 20 | 20 | 20 |
| M80482_at | Human subtilisin-like protein (PACE4) "mRNA," complete cds | 100 | 20 | 95 | 77 | 66 | 20 |
| M80563_at | Human CAPL protein "mRNA," complete cds | 482 | 678 | 2212 | 2605 | 1278 | 435 |
| M80629_at | Human cdc2-related protein kinase (CHED) "mRNA," complete cds | 96 | 156 | 162 | 130 | 186 | 323 |
| M80647_at | Homo sapiens thromboxane synthase "mRNA," complete cds | 20 | 20 | 20 | 20 | 20 | 20 |
| M80783_at | Human B12 protein "mRNA," complete cds | 108 | 51 | 149 | 60 | 116 | 62 |
| M80899_at | Human novel protein AHNAK "mRNA," partial sequence | 157 | 183 | 440 | 187 | 529 | 439 |
| M81057_at | Human procarboxypeptidase B "mRNA," complete cds | 43 | 89 | 143 | 75 | 205 | 170 |
| M81118_at | H. sapiens alcohol dehydrogenase chi polypeptide (ADH5) gene | 75 | 68 | 96 | 110 | 20 | 20 |
| M81181_s_at | Human sodium/potassium ATPase beta-2 subunit (atpb2) "mRNA," complete cds | 20 | 20 | 58 | 20 | 164 | 48 |
| M81182_s_at | Human sodium/potassium ATPase peroxisomal 70 kD membrane protein "mRNA," complete cds | 35 | 45 | 28 | 63 | 20 | 20 |
| M81379_at | H. sapiens alpha-3 type IV collagen (COL4A3) "mRNA," 3' end | 63 | 45 | 28 | 20 | 20 | 48 |
| M81601_at | Human transcription elongatin factor (SII) "mRNA," complete cds | 199 | 205 | 422 | 338 | 216 | 273 |
| M81637_at | Human grancalcin "mRNA," complete cds | 30 | 28 | 35 | 20 | 20 | 43 |
| M81650_ma1_at | Human semenogelin I (SEMGI) "gene," complete cds | 20 | 20 | 20 | 20 | 20 | 20 |
| M81695_s_at | H. sapiens leukocyte adhesion glycoprotein "p150.95" mRNA," complete cds | 20 | 55 | 188 | 91 | 445 | 144 |
| M81750_at | H. sapiens myeloid cell nuclear differentiation antigen "mRNA," complete cds | 20 | 20 | 20 | 20 | 76 | 118 |
| M81757_at | H. sapiens S19 ribosomal protein "mRNA," complete cds | 4369 | 4759 | 5558 | 4830 | 2048 | 3678 |
| M81758_at | Homo sapiens skeletal muscle voltage-dependent sodium channel alpha subunit (SkMI) "mRNA," complete cds | 36 | 105 | 53 | 42 | 216 | 308 |
| M81778_s_at | Human serotonin 5-HT1C receptor "mRNA," complete cds | 20 | 20 | 20 | 20 | 20 | 20 |
| M81780_cds3_at | Homo sapiens acid sphingomyelinase (SMPD1) gene, complete cds, ORF's 1-3, complete ccds's. | 125 | 40 | 20 | 127 | 397 | 284 |
| M81780_cds4_at | Homo sapiens acid sphingomyelinase (SMPD1) gene, complete cds, ORF's 1-3, complete cds's. | 20 | 44 | 20 | 20 | 20 | 48 |
| M81780_cds5_at | Homo sapiens acid sphingomyelinase (SMPD1) gene, complete cds, ORF's 1-3, complete cds's. | 186 | 258 | 147 | 224 | 332 | 342 |
| M81829_at | Human somatostain receptor isoform 1 "gene," complete cds | 114 | 110 | 75 | 87 | 92 | 72 |
| M81830_at | Human somatostatin receptor isoform 2 (SSTR2) "gene," complete cds | 97 | 62 | 24 | 48 | 72 | 155 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M81882_at | Human glutamate decarboxylase (GAD65) "mRNA," complete cds | 31 | 20 | 20 | 47 | 20 | 84 |
| M81883_at | Human glutamate decarboxylase (GAD67) "mRNA," complete cds | 20 | 20 | 20 | 20 | 20 | 20 |
| M81886_s_at | Human glutamate receptor type 1 (HBGR1) "mRNA," complete cds | 20 | 20 | 20 | 20 | 20 | 20 |
| M81933_at | Human cdc25A "mRNA," complete cds | 183 | 274 | 227 | 186 | 167 | 352 |
| M82809_at | Human annexin IV (ANX4) "mRNA," complete cds | 116 | 243 | 446 | 108 | 167 | 97 |
| M82827_s_at | Human cis-acting sequence | 20 | 20 | 20 | 20 | 20 | 20 |
| M82882_at | Human gamma amino butyric acid (GABAA) receptor beta-3 subunit "mRNA," complete cds | 20 | 20 | 228 | 70 | 20 | 46 |
| M82919_at | Human N-benzoyl-L-tyrosyl-p-amino-benzoic acid hydrolase alpha subunit (PPH alpha) "mRNA," complete cds | 72 | 24 | 30 | 51 | 98 | 20 |
| M82962_at | Human phosphoglucomutase 1 (PGM1) "mRNA," complete cds | 25 | 20 | 20 | 20 | 20 | 55 |
| M83088_at | Human serotonin receptor "gene," complete cds | 221 | 195 | 311 | 189 | 227 | 274 |
| M83181_at | Human cytochrome c oxidase subunit VIIa (COX7A) muscle isoform "mRNA," complete cds | 71 | 168 | 217 | 121 | 54 | 20 |
| M83186_at | Human aorta caldesmon "mRNA," complete cds | 238 | 204 | 20 | 20 | 62 | 20 |
| M83216_s_at | Homo sapiens I-Rel "mRNA," complete cds | 163 | 41 | 24 | 20 | 20 | 20 |
| M83221_at | Homo sapiens transcription factor (HTF4A) "mRNA," complet cds | 307 | 282 | 20 | 277 | 498 | 442 |
| M83233_at | Human mitochondrial cytochrom-c oxidase subunit VIa (COX6A) "mRNA," complete cds | 20 | 20 | 20 | 48 | 20 | 56 |
| M83308_at | Human plasma membrane calcium-pumping ATPase (PMCA4) "mRNA," complete cds | 20 | 20 | 66 | 20 | 20 | 20 |
| M83363_at | H. sapiens lymphocyte activation antigen CD30 "mRNA," complete cds | 20 | 20 | 20 | 20 | 20 | 20 |
| M83554_at | Human "beta-1,4" N-acetylgalactomsaminyltransferase "mRNA," complete cds | 20 | 20 | 52 | 20 | 20 | 20 |
| M83651_at | Homo sapiens complement component properdin "mRNA," complete cds | 20 | 20 | 20 | 20 | 20 | 286 |
| M83652_s_at | Human MHC class II lymphocyte antigen (HLA-DP) beta chain "mRNA," complete cds | 58 | 154 | 168 | 161 | 610 | 286 |
| M83664_s_at | Human NF-IL6-beta protein "mRNA," complete cds | 838 | 444 | 479 | 257 | 99 | 485 |
| M83712_ma1_s_at | | 20 | 29 | 20 | 20 | 20 | 25 |
| M83738_at | Human protein-tyrosine phosphatase (PTPase MEG2) "mRNA," complete cds | 114 | 84 | 20 | 40 | 20 | 78 |
| M83751_at | Human arginine-rich protein (ARP) "gene," complete cds | 307 | 219 | 221 | 280 | 44 | 227 |
| M83822_at | Human flavin-containing monooxygenase form II (FMO2) "mRNA," complete cds | 20 | 20 | 20 | 20 | 20 | 20 |
| M83941_at | Human beige-like protein (BGL) "mRNA," partial cds | 20 | 20 | 20 | 20 | 20 | 20 |
| M84332_at | Human receptor tyrosine kinase (HEK) "mRNA," complete cds | 20 | 20 | 20 | 20 | 20 | 20 |
| M84349_at | Human ADP-ribosylation factor 1 gene | 767 | 370 | 1019 | 590 | 490 | 731 |
| M84371_ma1_s_at | Human transmembrane protein (CD59) gene | 286 | 415 | 287 | 169 | 428 | 20 |
| M84424_at | Human CD19 "gene," complete cds | 20 | 85 | 20 | 20 | 20 | 20 |
| M84526_at | Human cathepsin E (CTSE) gene | 1875 | 29 | 300 | 413 | 136 | 30 |
| M84711_at | Human adipsil/complement factor D "mRNA," complete cds | 50 | 2281 | 20 | 31 | 20 | 93 |
| M84711_at | Human putative opioid receptor "mRNA," complete cds | 20 | 20 | 20 | 20 | 65 | 93 |
| M84711_at | H. sapiens v-fos transformation effector protein "(Fte-1)," mRNA complete cds | 3651 | 3365 | 5586 | 3824 | 595 | 2287 |
| M84739_at | Human autoantigen calreticulin "mRNA," complete cds | 238 | 108 | 20 | 218 | 460 | 196 |
| M84820_s_at | Human retinoid X receptor beta (RXR-beta) "mRNA," complete cds | 45 | 20 | 22 | 20 | 29 | 122 |
| M85085_at | Human cleavage stimulation "factor," complete cds | 97 | 74 | 20 | 23 | 66 | 164 |
| M85164_at | Homo sapiens SRF accessory protein 1B (SAP-1) "mRNA," complete cds | 44 | 27 | 60 | 43 | 20 | 71 |
| M85165_at | Homo sapiens SRF accessory protein 1A (SAP-1) "mRNA," complete cds | 36 | 20 | 55 | 20 | 33 | 63 |
| M85169_at | Human homologue of yeast sec7 "mRNA," complete cds | 80 | 20 | 20 | 20 | 33 | 20 |
| M85217_at | H. sapiens K+ channel protein (HLK3) "mRNA," complete cds | 20 | 48 | 20 | 20 | 20 | 20 |
| M85220_at | Human heavy chain disease IgA chain "gene," CH3 region with a 369 bp "deletion," 3′ end | 22 | 496 | 20 | 74 | 20 | 265 |
| M85247_at | H. sapiens dopamine D1A receptor "gene," complete exon "1," and exon "2," 5′ end. /gb=M85247 /ntype=DNA /annot=mRNA | 93 | 141 | 20 | 111 | 175 | 31 |
| M85276_at | Homo sapiens NKG5 "gene," complete cds | 50 | 120 | 20 | 71 | 100 | 144 |
| M85289_at | Human heparan sulfate proteoglycan (HSPG2) "mRNA," complete cds | 33 | 171 | 20 | 57 | 265 | 70 |
| M86383_s_at | H. sapiens nicotinic acetylcholine receptor alpha 3 subunit "mRNA," complete cds | 28 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M86400_at | Human phospholipase A2 "mRNA," complete cds | 1653 | 387 | 1250 | 1056 | 399 | 1550 |
| M86406_at | Homo sapiens skeletal muscle alpha 2 actinin (ACTN20 "mRNA," complete cds | 20 | 20 | 20 | 20 | 20 | 20 |
| M86407_at | Homo sapiens alpha actinin 3 (ACTN3) "mRNA," complete cds | 20 | 36 | 20 | 20 | 199 | 109 |
| M86528_at | Human neurotrophin-4 (NT-4) "gene," complete cds | 200 | 150 | 192 | 120 | 319 | 268 |
| M86546_at | H. sapiens PBX1a and PBX1b "mRNA," complete cds | 140 | 189 | 194 | 156 | 315 | 243 |
| M86667_at | H. sapiens NAP (nucleosome assembly protein) "mRNA," complete cds | 233 | 166 | 342 | 252 | 184 | 242 |
| M86699_at | Human kinase (TTK) "mRNA," complete cds | 20 | 32 | 20 | 20 | 256 | 148 |
| M86707_at | Homo sapiens myristoyl CoA:protein N-myristoyltransferase mRNA | 20 | 56 | 104 | 90 | 23 | 128 |
| M86737_at | Human high mobility group box (SSRP1) "mRNA," complete cds | 32 | 20 | 147 | 141 | 254 | 234 |
| M86752_at | Human transformation-sensitive protein (IEF SSP 3521) "mRNA," complete cds | 106 | 20 | 20 | 92 | 85 | 20 |
| M86757_s_at | | 10368 | 20 | 20 | 20 | 20 | 20 |
| M86808_at | Human pyruvate dehydrogenase complex (PDHA2) "gene," complete cds | 28 | 20 | 20 | 21 | 128 | 82 |
| M86826_at | Human IGF binding protein complex acid-labile subunit a "mRNA," complete cds | 75 | 20 | 188 | 206 | 334 | 47 |
| M86849_at | Human connexin 26 (GJB2) mRNA | 675 | 202 | 212 | 83 | 161 | 148 |
| M86852_at | H. sapiens peroxisome assembly factor-1 "mRNA," complete cds | 43 | 20 | 20 | 20 | 20 | 20 |
| M86868_at | Human gamma amino butyric acid (GABA rho2) gene "mRNA," complete cds. | 30 | 69 | 39 | 84 | 75 | 378 |
| M86873_s_at | H. sapiens type A plasminogen related gene | 20 | 20 | 20 | 20 | 20 | 20 |
| M86917_at | Human oxysterol-binding protein (OSBP) "mRNA," complete cds | 22 | 33 | 214 | 69 | 37 | 155 |
| M86933_at | | 24 | 20 | 20 | 20 | 20 | 26 |
| M86933_s_at | Human amelogenin (AMELY) "mRNA," complete cds | 20 | 20 | 108 | 67 | 20 | 82 |
| M86934_at | Human GS1 (protein of unknown function) "mRNA," complete cds | 56 | 20 | 188 | 130 | 156 | 47 |
| M87313_s_at | Human 69 kDa 2'5' oligoadenylate synthetase (P69 2-5A synthetase) "mRNA," complete cds | 113 | 202 | 212 | 83 | 161 | 148 |
| M87284_at | Homo sapiens myotonin protein kinase (DM) mRNA | 20 | 20 | 20 | 20 | 20 | 20 |
| M87338_at | Human replication factor "C," 40-kDa subunit (A1) "mRNA," complete cds | 20 | 69 | 20 | 58 | 154 | 78 |
| M87339_at | Human replication factor "C," 37-kDa subunit "mRNA," complete cds | 21 | 20 | 39 | 20 | 26 | 35 |
| M87434_at | Human 71 kDa 2'5' oligoadenylate synthetase (p69 2-5A synthetase) "mRNA," complete cds | 85 | 20 | 214 | 33 | 20 | 152 |
| M87499_at | Human uracil-DNA glycosylase (UNG) "gene," complete cds | 20 | 20 | 20 | 24 | 20 | 267 |
| M87503_at | Human IFN-responsive transcription factor subunit "mRNA," complete cds | 111 | 140 | 244 | 131 | 191 | 267 |
| M87507_s_at | Homo sapien interleukin-1 beta convertase (IL1BCE) "mRNA," complete cds | 20 | 26 | 20 | 20 | 20 | 20 |
| M87770_at | Human fibroblast growth factor receptor (K-sam) "mRNA," complete cds | 54 | 63 | 147 | 109 | 20 | 115 |
| M87889_s_at | Human (hybridoma H210) anti-hepatitis A IgG variable "region," constant "region," complementarity-determining regions "mRNA," comple | 3447 | 1078 | 20 | 20 | 303 | 4769 |
| M87860_at | Human S-lac lectin L-14-II (LGALS2) gene | 91 | 53 | 20 | 110 | 62 | 177 |
| M88108_at | Human p62 "mRNA," complete cds | 112 | 88 | 297 | 266 | 76 | 160 |
| M88163_at | Human global transcription activator homologous sequence "mRNA," complete cds | 34 | 74 | 130 | 23 | 67 | 25 |
| M88279_at | Human immunophilin (FKBP52) "mRNA," complete cds | 276 | 428 | 373 | 352 | 450 | 350 |
| M88282_at | Human tactile protein "mRNA," complete cds | 24 | 122 | 20 | 75 | 104 | 27 |
| M88338_at | Human serum constituent protein (MSE55) "mRNA," complete cds | 391 | 283 | 93 | 354 | 480 | 510 |
| M88458_at | Human ELP-1 mRNA sequence | 265 | 133 | 317 | 227 | 352 | 251 |
| M88461_s_at | Human neuropeptide Y peptide YY receptor "mRNA," complete cds | 20 | 20 | 20 | 20 | 20 | 20 |
| M88468_at | Homo sapiens mevalonate kinase "mRNA," complete cds | 538 | 317 | 229 | 523 | 697 | 511 |
| M88579_at | Human zinc finger protein (SRE-ZBP) "mRNA," 3' end | 62 | 89 | 66 | 20 | 20 | 20 |
| M89470_at | Human paired-box protein (PAX2) "mRNA," complete cds | 20 | 20 | 20 | 20 | 20 | 20 |
| M89473_at | Huma neurokin 3 receptor (NK3R) "mRNA," complete cds | 174 | 133 | 305 | 131 | 156 | 260 |
| M89796_ma1_at | Human high affinity IgE receptor beta chain gene, complete cds. | 20 | 55 | 37 | 20 | 30 | 28 |
| M89914_s_at | Human neurofibromin (NF1) "gene," complete cds | 20 | 20 | 20 | 20 | 40 | 20 |
| M89955_at | Human 5-HT 1D-type serotonin receptor "gene," complete cds | 20 | 20 | 20 | 20 | 20 | 20 |
| M89957_at | Human immunoglobulin superfamily member B cell receptor complex cell surface glycoprotein (IGB) "mRNA," complete cds | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M90299_at | Human glucokinase (GCK) "mRNA," complete cds | 174 | 220 | 162 | 234 | 492 | 245 |
| M90354_at | Human BTF3 protein homologue "gene," complete cds | 20 | 20 | 20 | 20 | 20 | 20 |
| M90356_f_at | Human BTF3 protein homologue "gene," complete cds | 44 | 63 | 114 | 165 | 48 | 41 |
| M90359_at | Human cAMP-dpendent protein kinase (AKAP 79) "mRNA," complete cds | 20 | 20 | 20 | 20 | 20 | 20 |
| M90366_at | Human zone pellucida glycoprotein 2 (ZP2) "mRNA," complete cds | 57 | 52 | 110 | 84 | 148 | 20 |
| M90391_s_at | Human putative IL-16 protein "precursor," "mRNA," complete cds | 55 | 61 | 106 | 32 | 33 | 71 |
| M90516_at | Human glutamine fructose-6-phosphate amidotransferase (GFAT) "mRNA," complete cds | 20 | 20 | 60 | 20 | 20 | 20 |
| M90656_at | Human gamma-glutamylcysteine synthetase (GCS) "mRNA," complete cds | 139 | 32 | 298 | 248 | 259 | 175 |
| M90657_at | Human tumor antigen (L5) "mRNA," complete cds | 609 | 20 | 20 | 20 | 20 | 20 |
| M90696_at | Human cathepsin S (CTSS) "mRNA," complete cds | 91 | 75 | 68 | 20 | 20 | 33 |
| M90820_at | Human rapamycin-binding protein (FKBP25) "mRNA," complete cds | 92 | 28 | 20 | 24 | 327 | 54 |
| M91029_cds2_at | Human AMP deaminase (AMPD2) mRNA. | 86 | 224 | 119 | 157 | 60 | 174 |
| M91036_ma1_at | H. sapiens G-gamma globin and A-gamma globin genes, complete cds's. | 128 | 87 | 36 | 89 | 248 | 310 |
| M91083_at | Human DNA-binding protein (HRC1) "mRNA," complete cds | 214 | 329 | 136 | 336 | 503 | 316 |
| M91196_at | Human DNA-binding protein "mRNA," complete cds | 20 | 20 | 20 | 20 | 20 | 20 |
| M91368_s_at | Human Na+/Ca+ exchanger(CNC) "mRNA," complete cds | 20 | 20 | 20 | 20 | 20 | 42 |
| M91432_at | Human medium-chain acyl-CoA dehydrogenase (MCAD) gene | 49 | 20 | 42 | 34 | 55 | 52 |
| M91438_at | Human kazal-type serine proteinase (HUSI-II) "gene," complete cds | 85 | 84 | 20 | 38 | 152 | 136 |
| M91463_ma1_at | Human glucose transporter (GLUT4) "gene," complete cds | 143 | 132 | 227 | 128 | 308 | 146 |
| M91467_at | Human serotonin receptor (5HT1E) "mRNA," complete cds | 95 | 71 | 39 | 53 | 289 | 177 |
| M91556_s_at | | 20 | 20 | 20 | 20 | 20 | 20 |
| M91592_at | Human Br140 "mRNA," complete cds | 24 | 51 | 20 | 134 | 321 | 125 |
| M91669_s_at | Human zinc-finger protein (ZNF76) "gene," partial cds | 191 | 200 | 116 | 228 | 344 | 355 |
| M91670_at | Human Bullous pemphigoid autoantigen BP180 "gene," 3' end | 20 | 20 | 20 | 55 | 20 | 20 |
| M92269_f_at | Human ubiquitin carrier protein (E2-EPF) "mRNA," complete cds | 156 | 45 | 36 | 244 | 346 | 405 |
| M92287_at | Human L-type calcium channel HFCC "mRNA," complete cds | 20 | 20 | 20 | 20 | 88 | 70 |
| M92303_at | Homo sapiens cyclin D3 (CCND3) "mRNA," complete cds | 82 | 186 | 214 | 121 | 79 | 22 |
| M92357_at | Human voltage-dependent calcium channel beta-1 subunit "mRNA," complete cds | 240 | 293 | 87 | 188 | 119 | 221 |
| M92424_at | Human p53-associated "mRNA," complete cds | 80 | 120 | 620 | 435 | 505 | 278 |
| M92432_at | Human B94 protein "mRNA," complete cds | 24 | 145 | 55 | 34 | 58 | 29 |
| M92439_at | Homo sapiens retinal guanylyl cyclase (retGC) "mRNA," complete cds | 58 | 24 | 20 | 71 | 20 | 20 |
| M92449_at | Human leucine-rich protein "mRNA," complete cds | 71 | 20 | 88 | 69 | 20 | 55 |
| M92642_at | Human LTR "mRNA," 3' end of coding region and 3' flank | 129 | 212 | 84 | 87 | 70 | 50 |
| M92843_s_at | Homo sapiens alpha-1 type XVI collagen (COL16A1) "mRNA," complete cds | 25 | 180 | 179 | 83 | 95 | 44 |
| M92934_at | H. sapiens zinc finger transcriptional regulator "mRNA," complete cds | 1028 | 154 | 248 | 216 | 108 | 237 |
| M93036_s_at | Human connective tissue growth "factor," complete cds | 898 | 108 | 35 | 58 | 138 | 160 |
| M93056_at | Human (clone 21726) carcinoma-associated antigen GA733-2 (GA733-2) mRNA | 31 | 86 | 173 | 149 | 149 | 176 |
| M93107_at | Human mononcyte/neutrophil elastase inhibitor mRNA sequence | 834 | 20 | 20 | 29 | 149 | 61 |
| M93119_at | Homo sapiens heart (R)-3-hydroxybutyrate dehydrogenase "mRNA," 3' end | 54 | 20 | 146 | 126 | 304 | 231 |
| M93143_at | Human zinc-finger DNA-binding motifs (IA-1) "mRNA," complete cds | 20 | 77 | 21 | 20 | 20 | 20 |
| M93221_at | Human plasminogen-like protein (PLGL) "mRNA," complete cds. | 20 | 20 | 71 | 20 | 20 | 47 |
| M93283_at | Human macrophage mannose receptor (MRC1) gene | 45 | 148 | 64 | 69 | 120 | 39 |
| M93284_at | Human pancreatic lipase related protein 1 (PLRP1) "mRNA," complete cds | 138 | 231 | 163 | 219 | 285 | 243 |
| M93311_at | Human pancreatic lipase related protein 2 (PLRP2) "mRNA," complete cds | 103 | 77 | 39 | 201 | 362 | 153 |
| M93405_at | Human metallothionein-III "gene," complete cds | 20 | 24 | 20 | 20 | 78 | 60 |
| M93415_at | Human methylmalonate semialdehyde dehydrogenase "gene," complete cds | 229 | 94 | 121 | 217 | 425 | 274 |
| | Human activin type II receptor "mRNA," complete cds | 21 | 20 | 51 | 43 | 51 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| M93425_at | Human protein tyrosine phosphatase (PTP-PEST) "mRNA," complete cds | 68 | 137 | 98 | 85 | 20 | 20 | 20 |
| M93426_at | Human protein tyrosine phosphatase zeta-polypeptide (PTPRZ) "mRNA," complete cds | 35 | 20 | 40 | 20 | 20 | 20 | 20 |
| M93650_at | Human paired box gene (PAX6) "homologue," complete cds | 95 | 136 | 191 | 130 | 215 | 20 | 377 |
| M93651_at | Human set "gene," complete cds | 159 | 190 | 449 | 288 | 20 | 20 | 213 |
| M93718_at | Human nitric oxide synthase "mRNA," complete cds | 157 | 200 | 249 | 151 | 264 | 20 | 298 |
| M94046_at | Human zinc finger protein (MAZ) mRNA | 270 | 501 | 742 | 667 | 844 | 20 | 431 |
| M94055_at | Human voltage-gated sodium channel "mRNA," complete cds | 20 | 20 | 20 | 20 | 20 | 20 | 20 |
| M94065_at | Human dihydroorotate dehydrogenase "mRNA," 3′ end | 48 | 50 | 40 | 58 | 38 | 20 | 107 |
| M94077_at | Human loricrin gene exons 1 and "2," complete cds | 20 | 20 | 20 | 20 | 20 | 20 | 20 |
| M94151_at | human cadherin-associated protein-related (cap-r) "mRNA," complete cds | 20 | 20 | 20 | 20 | 20 | 20 | 69 |
| M94167_at | Human heregulin-geta2 "gene," complete cds | 93 | 20 | 20 | 200 | 49 | 20 | 20 |
| M94172_s_at | Human N-type calcium channel alpha-1 subunit "mRNA," complete cds | 20 | 20 | 20 | 95 | 20 | 20 | 1527 |
| M94250_at | Human retinoic acid inducible factor (MK) gene exons "1–5," complete cds | 74 | 81 | 992 | 724 | 198 | 20 | 500 |
| M94345_at | Homo sapiens macrophage capping protein "mRNA," complete cds | 274 | 302 | 371 | 491 | 415 | 215 | 365 |
| M94362_at | Human lamin B2 (LAMB2) "mRNA," partial cds | 176 | 132 | 210 | 196 | 305 | 20 | 20 |
| M94547_at | HUMMLC2A1; Homo sapiens;; 593 base-pairs | 20 | 24 | 20 | 20 | 69 | 20 | 151 |
| M94556_at | Human mitochondrial specific single stranded DNA binding protein "mRNA," complete cds | 199 | 183 | 269 | 198 | 104 | 20 | 269 |
| M94630_at | Homo sapiens hnRNP-C like protein "mRNA," complete cds | 290 | 225 | 550 | 291 | 214 | 20 | 79 |
| M94633_at | Human recombination activating protein (RAG2) "gene," last exon. /gb=M94633 /ntype=DNA /annot=exon | 20 | 23 | 20 | 50 | 107 | 20 | 223 |
| M94856_at | Human fatty acid binding protein homologue (PA-FABP) "mRNA," complete cds | 2525 | 172 | 1517 | 1051 | 288 | 408 | 1612 |
| M94880_f3_at | Human MHC class I (HLA-A *8001) mRNA | 1095 | 1061 | 1748 | 1540 | 20 | 209 | 194 |
| M94893_at | Homo sapiens dopamine transporter (SLC8A3) "mRNA," complete cds | 50 | 20 | 20 | 20 | 20 | 66 | 20 |
| M95167_at | Homo sapiens non-muscle alpha-actinin "mRNA," complete cds | 20 | 22 | 20 | 52 | 20 | 59 | 68 |
| M95178_3at | Homo sapiens tesis-specific protein (TSPY) "mRNA," 3' "end," clone pJA923 | 36 | 162 | 38 | 149 | 20 | 122 | 290 |
| M95549_at | Homo sapiens sodium/glucose cotransporter-like protein "mRNA," complete cds | 150 | 20 | 20 | 20 | 20 | 20 | 20 |
| M95585_s_at | H. sapiens centromere autoantigen C (CENPC) "mRNA," complete cds | 20 | 166 | 55 | 196 | 277 | 324 | 20 |
| M95610_at | Human alpha 2 type IX collagen (COL9A2) "mRNA," partial cds | 143 | 230 | 44 | 134 | 111 | 406 | 47 |
| M95623_cds1_at | Homo sapiens hydroxymethylbilane synthase "gene," complete cds | 89 | 344 | 63 | 42 | 482 | 495 | 20 |
| M95827_at | Homo sapiens 22kDa smooth muscle protein (SM22) "mRNA," complete cds | 251 | 517 | 206 | 393 | 307 | 732 | 206 |
| M95678_at | Homo sapiens anglo-associated migratory cell protein (AAMP) "mRNA," complete cds | 318 | 88 | 519 | 415 | 108 | 225 | 134 |
| M95925_at | Homo sapiens phospholipase C-beta-2 "mRNA," complete cds | 45 | 20 | 541 | 20 | 704 | 20 | 123 |
| M95712_at | Human leucine zipper on the D14S46E locus "mRNA," complete cds | 20 | 20 | 193 | 20 | 20 | 182 | 47 |
| M95929_at | Human homeobox protein (PHOX1) "mRNA," 3′ end | 74 | 20 | 44 | 59 | 20 | 20 | 20 |
| M95936_s_at | H. sapiens B-raf "mRNA," complete cds | 20 | 20 | 20 | 24 | 20 | 20 | 20 |
| M95724_at | Human alpha-L-iduronidase gene | 20 | 36 | 63 | 20 | 39 | 86 | 20 |
| M95767_at | Homo sapiens di-N-acetylchitoblase "mRNA," complete cds | 20 | 944 | 20 | 901 | 12518 | 268 | 20 |
| M95787_at | Human glutathione transferase class mu number 4 (GSTM4) "gene," complete cds | 1735 | 86 | 20 | 246 | 20 | 640 | 206 |
| M95809_at | Human azurocidin gene, complete cds | 20 | 20 | 44 | 42 | 52 | 20 | 20 |
| M95925_at | Human basic transcription factor 62kD subunit "(BTF2)," complete cds | 256 | 20 | 20 | 52 | 307 | 20 | 471 |
| M95712_at | Human somatostatin receptor subtype 3 (SSTR3) "gene," complete cds | 20 | 20 | 20 | 20 | 108 | 20 | 39 |
| M96132_s_at | Human MHC class II HLA-DR-beta-1*09012 (HLA-DRB1*09012) "gene," 3′end cds | 45 | 20 | 20 | 65 | 225 | 20 | 495 |
| M96233_s_at | Human NSCL-1 mRNA sequence | 20 | 20 | 20 | 20 | 20 | 20 | 732 |
| M96326_ma1_at | Human NSCL-2 gene sequence | 25 | 20 | 193 | 59 | 20 | 20 | 123 |
| M96684_at | H. sapiens Pur (pur-alpha) "mRNA," complete cds | 429 | 359 | 483 | 375 | 421 | 243 | 268 |
| M96738_s_at | Human somatostatin receptor subtype 3 (SSTR3) "gene," complete cds | 32 | 66 | 54 | 20 | 20 | 29 | 20 |
| M96739_at | Human NSCL-1 mRNA sequence | 87 | 34 | 95 | 118 | 102 | 268 | 268 |
| M96740_at | Human NSCL-2 gene sequence | | | | | | | |
| M96759_ma1_at | Human rod outer segment membrane protein 1 (ROM1) gene exons 1–3, complete cds. | | | | | | | |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| M96789_at | Homo sapiens connexin 37 (GJA4) "mRNA," complete cds | 20 | 20 | 20 | 20 | 68 | 20 |
| M96803_at | Human general beta-spectrin (SPTBN1) "mRNA," complete cds | 99 | 310 | 345 | 183 | 61 | 140 |
| M96843_at | Human striated muscle contraction regulatory protein (Id2B) "mRNA," complete cds | 48 | 66 | 285 | 254 | 230 | 150 |
| M96859_at | Human dipeptidyl aminopeptidase like protein "mRNA," complete cds | 91 | 243 | 60 | 74 | 124 | 165 |
| M96944_at | Human B-cell specific transcription factor (BSAP) "mRNA," complete cds | 20 | 20 | 20 | 20 | 20 | 140 |
| M96954_s_at | Homo sapiens nucleolysin TIAR "mRNA," complete cds | 127 | 89 | 314 | 241 | 487 | 20 |
| M96956_at | Human (clone CR-3) teratocarcinoma-derived growth factor 3 (TDGF3) "mRNA," complete cds | 20 | 20 | 38 | 20 | 231 | 402 |
| M96980_at | Homo sapiens myelin transcription factor 1 (MTF1) "mRNA," 3' end | 94 | 52 | 20 | 73 | 235 | 53 |
| M96982_at | Homo sapiens U2 snRNP auxiliary factor small "subunit," complete cds | 99 | 70 | 133 | 125 | 50 | 221 |
| M96995_s_at | Homo sapiens epidermal growth factor receptor-binding protein GRB (EGFRBP-GRB2) mRNA sequence | 137 | 470 | 299 | 205 | 357 | 20 |
| M97016_s_at | | 20 | 20 | 20 | 20 | 87 | 51 |
| M97252_at | Homo sapiens Kallmann syndrome (KAL) "mRNA," complete cds | 20 | 56 | 41 | 20 | 100 | 447 |
| M97287_s_at | Human MAR/SAR DNA binding protein (SATB1) "mRNA," complete cds | 137 | 52 | 337 | 96 | 171 | 20 |
| M97347_s_at | Human "beta-1,6-N-acetylglucosaminyltransferase" "mRNA," complete cds | 20 | 20 | 22 | 20 | 20 | 39 |
| M97388_at | Human TAIA binding protein-associated phosphoprotein (DR1) "mRNA," complete cds | 27 | 20 | 78 | 46 | 67 | 20 |
| M97496_at | Homo sapiens guanylin "mRNA," complete cds | 143 | 185 | 20 | 149 | 371 | 392 |
| M97639_at | Human transmembrane receptor (ror2) "mRNA," complete cds | 106 | 61 | 20 | 57 | 172 | 170 |
| M97675_at | Human transmembrane receptor (ror2) "mRNA," complete cds | 21 | 122 | 69 | 53 | 77 | 221 |
| M97676_at | Homo sapiens (region 7) homeobox protein (HOX7) "mRNA," complete cds | 72 | 51 | 106 | 79 | 257 | 144 |
| M97796_s_at | Human helix-loop-helix protein (Id-2) "mRNA," complete cds | 107 | 142 | 212 | 130 | 20 | 131 |
| M97815_at | Human retinoic acid-binding protein II (CRABP-II) gene | 1655 | 431 | 62 | 313 | 1180 | 1020 |
| M97856_at | Homo sapiens histone-binding protein "mRNA," complete cds | 49 | 20 | 20 | 20 | 20 | 20 |
| M97925_ma1_at | H. sapiens defensin 5 gene, complete cds | 84 | 74 | 67 | 137 | 25 | 180 |
| M97935_s_at | Human transcription factor ISGF-3 mRNA sequence | 186 | 273 | 285 | 272 | 166 | 325 |
| M97936_at | Human transcription factor ISGF-3 mRNA sequence | 37 | 20 | 20 | 20 | 20 | 227 |
| M98045_at | Homo sapiens folylpolyglutamate synthetase "mRNA," complete cds | 134 | 40 | 20 | 147 | 20 | 101 |
| M98343_at | Homo sapiens amplaxin (EMS1) (clone 21) "mRNA," complete cds | 20 | 60 | 143 | 127 | 20 | 20 |
| M98399_s_at | Human antigen CD36 "mRNA," complete cds | 20 | 50 | 85 | 33 | 155 | 20 |
| M98447_ma1_at | H. sapiens keratinocyte transglutaminase gene, complet cds. | 705 | 91 | 20 | 20 | 70 | 320 |
| M98528_at | Homo sapiens neuron-specific protein "gene," last "exon," clone D4S234 | 67 | 74 | 20 | 138 | 181 | 164 |
| M98539_at | Human prostaglandin D2 synthase gene | 489 | 262 | 20 | 37 | 181 | 109 |
| M98776_ma1_at | Human keratin 1 gene, complete cds. | 130 | 113 | 84 | 143 | 64 | 127 |
| M98833_at | Human ERGB transcription factor (FLI-1 homolog) "mRNA," complete cds | 20 | 20 | 20 | 83 | 20 | 20 |
| M99063_at | Homo sapiens cytokeratin 2 "mRNA," complete cds | 20 | 20 | 21 | 20 | 20 | 39 |
| M99435_at | Human transducin-like enhancer protein (TLE1) "mRNA," complete cds | 20 | 27 | 20 | 20 | 20 | 20 |
| M99436_at | Human transducin-like enhancer protein (TLE2) "mRNA," complete cds | 20 | 20 | 20 | 20 | 20 | 20 |
| M99438_at | Human transducin-like enhancer protein (TLE3) "mRNA," complete cds | 20 | 34 | 29 | 20 | 20 | 77 |
| M99439_at | Human transducin-like enhancer protein (TLE4) "mRNA," 3' end | 22 | 20 | 20 | 20 | 20 | 20 |
| M99487_at | Human prostate-specific membrane antigen (PSM) "mRNA," complete cds | 20 | 20 | 20 | 20 | 107 | 320 |
| M99584_at | Homo sapiens (clone DN10mel) P protein "mRNA," complete cds | 20 | 74 | 20 | 20 | 20 | 20 |
| M99701_at | Homo sapiens (pp21) "mRNA," complete cds | 282 | 262 | 280 | 196 | 181 | 256 |
| S34389_at | heme oxygenase-2 "[human," "kidney," "mRNA," 1627 nt] | 43 | 25 | 20 | 20 | 282 | 37 |
| S37730_s_at | insulin-like growth factor binding protein-2 "[human," "mRNA," 1988 nt] | 20 | 285 | 144 | 104 | 20 | 20 |
| S38742_s_at | NOX11=HOX11 homeodomain [homeodomain] "[human," "mRNA," 1988 nt] XA "[human," "Genomic," 6873 nt] | 20 | 46 | 97 | 20 | 161 | 20 |
| S38953_s_at | glandular kallikrein-1 [alternatively spliced] "[human," "prostate," "mRNA," 1541 nt] | 57 | 53 | 127 | 77 | 436 | 74 |
| S39329_s_at | | 20 | 59 | 20 | 43 | 46 | 20 |
| S40719_s_at | glial fibrillary acidic protein "[human," glioma cell line U-251 "MG," "mRNA," 3033 nt] | 130 | 251 | 460 | 217 | 583 | 268 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| S41458_at | rod cGMP phosphodiesterase beta-subunit "[human," "mRNA," 3231 nt] | 37 | 44 | 83 | 61 | 204 | 29 |
| S42303_at | N-cadherin "[human," umbilical vein endothelial "cells," "mRNA," 4132 nt] | 21 | 20 | 20 | 20 | 20 | 20 |
| S42457_at | CNCG=rod photoreceptor cGMP-gated channel "∂human," "retina," "mRNA," 2857 nt] | 28 | 111 | 81 | 33 | 109 | 109 |
| S43646_at | cytokeratin 2 "[human," "epidermia," "mRNA," 2427 nt] | 114 | 246 | 138 | 64 | 237 | 93 |
| S45630_at | alpha B-crystallin=Rosenthal fiber comonent "[human," glioma cell "line," "mRNA," 691 nt] | 495 | 246 | 99 | 153 | 564 | 369 |
| S46622_at | calcineurin A catalytic subunit "[human," "testis," "mRNA," 2134 nt] | 50 | 28 | 20 | 20 | 20 | 70 |
| S48983_at | SAA4=serum amyloid A "[human," "Genomic," 858 nt 4 segments] | 20 | 63 | 20 | 23 | 20 | 20 |
| S49592_s_at | transcription factor E2F like protein "[human," "mRNA," 2492 nt] | 22 | 60 | 92 | 49 | 20 | 55 |
| S50017_at | "2',3'-cyclic" nucleotide 3'-phosphodiesterase "[human," "Genomic," 2029 nt 4 segments] | 65 | 208 | 155 | 117 | 340 | 206 |
| S50223_at | HKR-T1=Kruppel-like zinc finger protein "[human," MOLT 4 "T-cells," "mRNA," 798 nt] | 20 | 20 | 20 | 20 | 117 | 20 |
| S52028_s_at | cystathionine gamma-lyase (clone HCL-1) "[human," "liver," "mRNA," 1194 nt] | 20 | 20 | 20 | 20 | 20 | 20 |
| S52969_cds1_s_at | Description: "alpha-1,3" fucosyltransferase gene extracted from "alpha-(1.3/1.4)" fucosyltransferase/FucT-III," "alpha-1,3" fucosyltransfera | 60 | 20 | 38 | 20 | 20 | 20 |
| S53911_at | CD34=glycoprotein expressed in lymphochematopoietic progenitor cells [alternatively "apliced," truncated form] "(human," "UT7," "mRNA," | 233 | 189 | 117 | 103 | 216 | 241 |
| S54005_s_at | thymosin beta-10 "[human," metastatic melanoma cell "line," "mRNA," 453 nt] | 1175 | 1309 | 1833 | 1533 | 781 | 1961 |
| S55606_at | betacellulin "[human," "mRNA," 1271 nt] | 25 | 20 | 53 | 34 | 175 | 20 |
| S58151_s_at | HMFG=milk fat globule protein "[human," "mRNA "Partial," 1270 nt] | 34 | 60 | 117 | 20 | 512 | 25 |
| S57132_s_at | COL 16A1=type XVI collagen alpha 1 chain "[human," "placenta," mRNA "Partial," 3720 nt] | 24 | 72 | 90 | 20 | 301 | 133 |
| S57153_s_at | RBP1=retinoblastoma binding protein 1 isoform I [alternatively spliced] "[human," "mRNA "Partial," 3000 nt] | 20 | 20 | 20 | 20 | 20 | 20 |
| S57212_s_at | hMEF2C=myocyte enhancer-binding factor 2 "[human," skeletal "muscles," mRNA," 2161 nt] | 54 | 115 | 139 | 84 | 136 | 90 |
| S57235_at | CD68=110kda transmembrane glycoprotein "[human," promonocyte cell line "U937," "mRNA," 1722 nt] | 20 | 20 | 20 | 20 | 20 | 20 |
| S57887_at | (T1)=elastin translocation allele {exon "28," translocation} "[human," "Genomic "Mutant," 1300 nt] | 35 | 20 | 20 | 20 | 20 | 20 |
| S58544_at | 75 kda infertility-related sperm protein "[human," "testis," mRNA "Partial," 2427 nt] | 43 | 20 | 20 | 20 | 155 | 73 |
| S58733_at | pp52=B lymphocyte signal transduction gene {group "3," inverted repeat} "[human," tumor cell line "TC-32," Genomic "Mutant," 356 nt] | 43 | 21 | 30 | 35 | 30 | 162 |
| S59049_at | BL34=B cell activation gene "[human," "mRNA," 1398 nt] | 67 | 24 | 20 | 20 | 25 | 118 |
| S59184_at | RYK=related to receptor tyrosine kinase "[human," fetal "brain," "mRNA," 3068 nt] | 20 | 36 | 20 | 60 | 20 | 20 |
| S60415_at | myasthenic syndrome antigen B "[human," fetal "brain," "mRNA," 3477 nt] | 20 | 20 | 20 | 20 | 20 | 20 |
| S61953_at | c-erbB3=receptor tyrosine kinase [alternatively spliced] "[human," gastric cancer cell line "MNK45," "mRNA," 1042 nt] | 50 | 66 | 20 | 75 | 28 | 90 |
| S62027_s_at | transducin gamma subunit "[human," "mRNA," 408 nt] | 20 | 20 | 20 | 20 | 20 | 20 |
| S62028_s_at | recoverin "[human," "retine," "mRNA," 1108 nt] | 20 | 20 | 20 | 20 | 20 | 52 |
| S62539_at | insulin receptor substrate-1 "[human," skeletal "muscle," "mRNA," 5828 nt] | 41 | 20 | 193 | 42 | 45 | 252 |
| S62696_s_at | EBV/C3d receptor [alternatively "spliced," exons "8a,9,10]" "[human," Jurkat T "cells," mRNA "Partial," 151 nt] | 20 | 168 | 242 | 164 | 288 | 20 |
| S62904_s_at | thiopurine methyltransferase "[human," T84 colon carcinoma "cell," "mRNA," 2742 nt] | 1151 | 621 | 727 | 626 | 482 | 361 |
| S62907_s_at | gamma-aminobutyric acidA receptor alpha 2 subunit "[human," fetal "brain," "mRNA," 2189 nt] | 28 | 75 | 60 | 68 | 20 | 34 |
| S63912_at | D10S102=FBRNP "[human," fetal "brain," "mRNA," 3043 nt] | 20 | 99 | 25 | 20 | 25 | 37 |
| S65583_ma1_at | SP-10=intra-acrosomal protein [alternatively spliced] [human, liver, Genomic, 714 nt, segment 4 of 4] | 23 | 20 | 20 | 20 | 20 | 86 |
| S65738_at | actin depolymerizing factor "[human," fetal "brain," "mRNA," 1452 nt] | 57 | 90 | 116 | 82 | 92 | 20 |
| S66427_at | RBP1=retinoblastoma binding protein 1 "[human," Nalm-6 pre-B cell "leukemia," "mRNA," 4834 nt] | 141 | 20 | 20 | 20 | 20 | 39 |
| S66431_s_at | RBP2=retinoblastoma binding protein 2 "[human," Nalm-6 pre-B cell "leukemia," "mRNA," 6455 nt] | 20 | 20 | 20 | 51 | 69 | 20 |
| S66541_s_at | B-50=neural phosphoprotein "[human," "Genomic," 1845 nt 3 segments] | 70 | 46 | 20 | 20 | 95 | 20 |
| S66793_at | X-arrestin=S-antigen homolog "[human," "retina," "mRNA," 1314 nt] | 1239 | 46 | 20 | 20 | 95 | 20 |
| S66896_at | squamous cell carcinoma antigen=serine protease inhibitor "[human," "mRNA," 1711 nt] | 220 | 79 | 20 | 161 | 236 | 187 |
| S67070_at | heat shock protein HSP72 homolog "[human," thyroid associated ophthalmopathy "patient," mRNA "Partial," 450 nt] | 86 | 99 | 20 | 49 | 161 | 52 |
| S67156_at | ASP=aspartoacylase "[human," "kidney," "mRNA," 1435 nt] | 25 | 20 | 68 | 30 | 209 | 22 |
| S67247_s_at | smooth muscle myosin heavy chain isoform SMemb "[human," umbilical "cord," fetal "aorta," mRNA "Partial," 971 nt] | 163 | 132 | 20 | 112 | 128 | 159 |
| S67325_at | propionyl CoA carboxylase beta subunit "[human," "liver," "placenta," "HL1008," "mRNA," 1791 nt] | 49 | 24 | 46 | 62 | 170 | 20 |
| S67798_at | PH-20 "[human," "testis," "mRNA," 1973 nt] | 49 | 24 | 46 | 62 | 170 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| S67970_at | ZNF75=KRAB zinc finger "human," lung "fibroblast," "mRNA," 1563 nt] | 20 | 20 | 20 | 21 | 100 | 38 |
| S68134_s_at | CREM=cyclic AMP-responsive element modulator beta isoform "human,", "mRNA," 1030 nt] | 20 | 20 | 20 | 20 | 20 | 20 |
| S68271_s_at | CREM=cyclic AMP-responsive element modulator "human,", "mRNA," 1431 nt] | 33 | 20 | 20 | 20 | 20 | 20 |
| S68287_at | chlordecone reductase {lone HAKRa} "human," "liver," "mRNA," 1167 nt] | 20 | 20 | 20 | 20 | 20 | 20 |
| S68616_at | Na+/H+ exchanger NHE-1 isoform "human," "heart," "mRNA," 4516 nt] | 279 | 391 | 188 | 429 | 402 | 206 |
| S68805_at | L-arginine:glycine amidinotransferase "human," kidney carcinoma "cells," "mRNA," 2330 nt] | 65 | 95 | 74 | 71 | 221 | 142 |
| S68874_s_at | EP3 prostanoid receptor EP3-I {3' "region," alternatively spliced} "human," "mRNA" "Partial," 598 nt] | 54 | 95 | 125 | 73 | 20 | 85 |
| S69115_at | granulocyte colony-stimulating factor induced gene "human," CML "patient," bone marrow mononuclear "cells," "mRNA," 833 nt] | 20 | 166 | 20 | 52 | 248 | 557 |
| S69189_at | peroxisomal acyl-coenzyme A oxidase "human," "liver," "mRNA," 3086 nt] | 20 | 84 | 140 | 88 | 123 | 20 |
| S69231_s_at | TYRP2=tyrosinase-related-protein-2 "human," melanocytic cell line "SK-MEL-19," "mRNA," 2056 nt] | 38 | 20 | 20 | 20 | 20 | 20 |
| S69232_at | electron transfer flavoprotein-ubiquinone oxidoreductase "human," fetal "liver," "mRNA," 2124 nt] | 20 | 58 | 108 | 32 | 20 | 20 |
| S69265_s_at | neuron-specific RNA recognition motifs (RRMs)-containing protein "human," "hippocampus," "mRNA," 1992 nt] | 20 | 177 | 178 | 27 | 806 | 133 |
| S66272_s_at | cytoplasmic antiproteinase=38 kda intracellular serine proteinase inhibitor "human," "placenta," "mRNA," 1485 nt] | 129 | 20 | 20 | 176 | 98 | 185 |
| S69369_at | PAX3A=transcription factor "human," adult "cerebellum," "mRNA," 1248 nt] | 25 | 98 | 49 | 20 | 166 | 20 |
| S69370_s_at | PAX3B=transcription factor {alternatively spliced} "human," adult "cerebellum," "mRNA," 841 nt] | 20 | 20 | 20 | 20 | 20 | 20 |
| S69790_at | Brush-1=tumor suppressor {3' region} "human," breast "epithelium," mRNA "Partial," 1485 nt] | 20 | 59 | 20 | 20 | 49 | 20 |
| S69965_at | beta-synuclein "human," "brain," "mRNA," 730 nt] | 33 | 20 | 20 | 20 | 25 | 20 |
| S70004_at | glycogen synthase "human," "brain," "mRNA," 730 nt] | 45 | 45 | 67 | 79 | 20 | 167 |
| S70348_at | integrin beta 3 {alternatively "spliced," clone beta 3C} "human," "tumor cell "lines," "Genomic," 847 nt] | 51 | 45 | 64 | 34 | 52 | 20 |
| S70585_ma1_at | thyroid-stimulating hormone alpha subunit [human, Genomic, 397 nt, segment 4 of 4]. | 20 | 20 | 20 | 20 | 20 | 20 |
| S70609_at | glycine transporter type 1b "human," substantia "nigra," "mRNA," 2364 nt] | 31 | 41 | 20 | 20 | 20 | 20 |
| S71018_at | cyclophilin C "human," "kidney," "mRNA," 883 nt] | 95 | 77 | 44 | 44 | 254 | 20 |
| S71043_ma1_s_at | Ig alpha 2=immunoglobulin A heavy chain allotype 2 {constant "region," germ line} "human," peripheral blood "neutrophils," "Genomic," 1 | 1473 | 3097 | 912 | 560 | 207 | 2609 |
| S71129_at | acetylcholinesterase {14-E5 domain} "human," "tumor cell "lines," "Genomic," 847 nt] | 20 | 37 | 20 | 79 | 346 | 314 |
| S71824_at | N-CAM=145 kda neural cell adhesion molecule "human," small cell lung cancer cell line "OS2-R," "mRNA," 2960 nt] | 107 | 220 | 69 | 106 | 211 | 254 |
| S72008_at | hCFC10=CDC10 homolog "human," fetal "lung," "mRNA," 2314 nt] | 124 | 23 | 198 | 104 | 20 | 127 |
| S72024_s_st | elf-5A=eukaryotic initiation factor 5A {clone cos 9,1} "human," "placenta," "Genomic," 558 nt] | 82 | 20 | 175 | 129 | 93 | 26 |
| S72043_ma1_at | GIF=growth inhibitory factor "human," "brain," "Genomic," 2015 nt] | 20 | 35 | 20 | 20 | 20 | 84 |
| S72370_at | pyruvate carboxylase "human," "kidney," "mRNA," 4017 nt] | 20 | 20 | 20 | 20 | 20 | 20 |
| S72487_at | orf1 5'lo PD-ECGF/TP . . . orf2 5' to PD-ECGF/TP "human," epidermoid carcinoma cell line "A431," "mRNA," 3 "genes," 1718 nt] | 301 | 136 | 20 | 268 | 417 | 646 |
| S72493_s_at | keratin-keratin 16 homolog "human," tracheobronchial epithelial "cells," mRNA "Partial," 976 nt] | 1072 | 58 | 25 | 52 | 20 | 20 |
| S72503_s_at | HRK1=inward rectifier potassium channel "human," "thyroid," "mRNA," 3011 nt] | 20 | 50 | 172 | 20 | 62 | 20 |
| S72669_at | H4(D10S170)=putative cytoskeletal proten "human," "thyroid," "mRNA," 3011 nt] | 21 | 20 | 59 | 20 | 20 | 138 |
| S72904_at | APK1 antigen=MAb K1 recognized "human," ovarian carcinoma cell line "OVCAR-3," "mRNA," 2444 nt] | 20 | 24 | 60 | 64 | 56 | 20 |
| S73149_at | insulin-like growth factor II {intron 7} "human," "Genomic," 1702 nt] /gb=S73149 /ntype=DNA /annot=mRNA | 346 | 424 | 245 | 448 | 119 | 418 |
| S73205_at | insulin activator factor "human," pancreatic "insulinoma," mRNA "Partial," 2622 nt] /gb=S73205 /ntype=RNA | 30 | 20 | 20 | 20 | 20 | 20 |
| S73591_at | brain-expressed HHCPA78 homolog "human," HL-60 acute promyelocytic leukemia "cells," mRNA," 2704 nt] | 400 | 1714 | 4488 | 2012 | 248 | 844 |
| S73813_at | CD39=lymphoid cell activation antigen "human," B lymphoblastoid cell "line," "MP-1," "mRNA," 1818 nt] | 67 | 41 | 20 | 20 | 85 | 68 |
| S73840_at | type Iix myosin heavy chain {3' region} "human," "skeletal "muscle," mRNA "Partial," 827 nt] | 21 | 20 | 20 | 20 | 116 | 31 |
| S73885_s_at | AP-4=basic helix-loop-helix DNA-binding protein "human," cervical "carcinoma," HeLa "cells," "mRNA," 2149 nt] | 49 | 85 | 236 | 99 | 20 | 37 |
| S74017_at | Nrf2=NF-E2-like basic leucine zipper transcriptional activator "human," hemin-induced K562 "cells," "mRNA," 2304 nt] | 372 | 196 | 289 | 160 | 197 | 87 |
| S74221_at | IK=IK factor "human," leukemic cells "K562," chronic myeloid leukemia "paiine," "mRNA," 756 nt] | 42 | 20 | 46 | 25 | 20 | 20 |
| S74445_at | cellular retinoic acid-binding protein "human," "skin," "mRNA," 735 nt] | 84 | 96 | 20 | 33 | 78 | 20 |
| S74683_at | ADP-ribosyltransferase "human," skeletal "muscle," "mRNA," 1334 nt] | 93 | 20 | 60 | 69 | 135 | 20 |
| S74720_at | DAX-1=DSS-AHC critical region on X "chromosome," gene 1 "human," adrenal hypoplasia "congenita," "testis," fetal adrenal "gland," mR | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| S74728_at | antiquitin=26g turgor protein homolog "[human," "kidney," mRNA," 1809 nt] | 54 | 89 | 42 | 49 | 35 | 113 |
| S75168_ma1_at | Matk=metakaryocyte-associated tyrosine kinase [human, Genomic 233 nt, segment 13 of 13]. | 165 | 231 | 20 | 78 | 250 | 20 |
| S75174_at | E2F-4=transcription factor "[human," Malm6 and HeLa "cells," "mRNA," 1539 nt] | 20 | 20 | 20 | 20 | 74 | 85 |
| S75213_s_at | type-IVA cyclic AMP specific phosphodiesterase HPDE4A "[human," "T-cells," mRNA "Partial," 2319 nt] | 143 | 222 | 332 | 218 | 558 | 195 |
| S75256_s_at | HNL=neutrophil lipocalin "[human," ovarian cancer cell line "OC6," mRNA "Partial," 534 nt]. /gb=S75256 /ntype=RNA | 656 | 1069 | 219 | 20 | 20 | 23 |
| S75295_at | nucleoprotein interactor 1=SRP1 homolog "[human," cervical carcinoma HeLa "cells," "mRNA," 2940 nt] | 36 | 34 | 20 | 91 | 20 | 101 |
| S75313_at | MJD1=MJD1 protein ::CAG repeats}]=[human," "brain," "mRNA," 1776 nt] | 20 | 81 | 35 | 20 | 20 | 143 |
| S75463_at | P43=mitochondrial elongation factor homolog "[human," "liver," mRNA," 1644 nt] | 484 | 596 | 967 | 735 | 70 | 287 |
| S75578_at | 4-aminobutyrate aminotransferase "[human," neuroblastoma BE "cells," mRNA "Partial," 1352 nt]. /gb=S75578 /ntype=RNA | 20 | 20 | 20 | 20 | 36 | 47 |
| S75881_s_at | A-myb=DNA-binding transactivator {3' region} "[human," fetal "brain," "mRNA," 1991 nt] | 20 | 20 | 20 | 20 | 20 | 20 |
| S75989_at | gamma-aminobutyric acid transporter type 3 "[human," fetal "brain," "mRNA," 1991 nt] | 20 | 20 | 20 | 20 | 20 | 20 |
| S76067_at | CNG2=cyclic nucleotide-gated cation channel "[human," peripheral "leucocytes," "Genomic," "784 nt]. /gb=S76067 /ntype=DNA /annot=CD | 20 | 52 | 20 | 20 | 20 | 20 |
| S76473_at | trkB "[human," "brain," "mRNA," 3194 nt] | 20 | 20 | 20 | 69 | 120 | 26 |
| S76475_at | trkC "[human," "brain," "mRNA," 2715 nt] | 20 | 92 | 20 | 20 | 20 | 59 |
| S76617_at | glk=protein tyrosine kinase "[human," B "lymphocytes," "mRNA," 2608 nt] | 33 | 20 | 20 | 50 | 20 | 104 |
| S76638_at | p50=NF-kappa B homolog "[human," peripheral blood T "cells," "mRNA," 3113 nt] | 20 | 20 | 20 | 20 | 20 | 117 |
| S76756_s_at | 4R-MAP2=microtubule-associated protein 2 r% isoform "[human," mRNA "Partial," 1012 nt]. /gb=S76756 /ntype =RNA | 42 | 20 | 100 | 73 | 221 | 74 |
| S76853_at | cerebrin-50=cerebrospinal fluid protein "[human," cerebral "brain," "mRNA," 2295 nt] | 20 | 42 | 20 | 20 | 20 | 20 |
| S76942_s_at | dopamine D4 receptor {exon 1} "[human," brain tumor "tissue," mRNA Partial "Mutant," 386 nt]. | 20 | 20 | 20 | 20 | 20 | 176 |
| S76965_at | protein kinase inhibitor "[human," neuroblastoma cell line "SH-SY-5Y," "mRNA," 2147 nt] | 65 | 123 | 21 | 105 | 113 | 52 |
| S76978_s_at | prostate-specific membrane antigen {alternatively spliced} "[human," primary prostatic "tissues," mRNA "Partial," 251 nt]. /gb=S76978 /nty | 20 | 20 | 20 | 20 | 20 | 234 |
| S76992_at | VAV2=VAV oncogen homolog "[human," fetal "brain," mRNA "Partial," 2753 nt] | 155 | 193 | 20 | 71 | 315 | 70 |
| S77094_at | nicotinic acetylcholine receptor alpha subunit|AChR alpha subunit "[human," thymic "carcinoma," myasthenia gravis-associated thymoma | 20 | 20 | 20 | 20 | 65 | 40 |
| S77154_s_at | TINUR=]NGFI-B/nur77 beta-type transcription factor homolog "[human," thymic "carcinoma," myasthenia gravis-associated thymoma | 20 | 20 | 20 | 20 | 215 | 1696 |
| S77356_at | transcript ch21=oligomycin sensitivity conferral protein oscp homolog "[human," "T lymphoid cell "line," "PEER," "mRNA," 2469 nt] | 579 | 615 | 732 | 974 | 2331 | 20 |
| S77361_at | transcript ch132 "[human," RF1,RF48" stomach cancer cell "lines," "mRNA," 216 nt]. /gb=S77361 /ntype=RNA | 29 | 86 | 20 | 44 | 20 | 109 |
| S77393_at | transcript ch138 "[human," RF1,RF48" stomach cancer cell "lines," "mRNA," 235 nt]. /gb=S77393 /ntype=RNA | 61 | 68 | 138 | 47 | 138 | 20 |
| S77410_at | type 1 angiotensin II receptor "[human," "Genomic," 1671 nt] | 55 | 36 | 105 | 88 | 93 | 20 |
| S77415_at | melanocortin-4 receptor "[human," "Genomic," 1671 nt] | 96 | 97 | 111 | 47 | 44 | 196 |
| S77575_at | ERV9 reverse transcriptase homolog ({clone RT11} "[human," fetal "brain," mRNA "Partial," 84 nt]. /gb=S77575 /nt | 20 | 20 | 20 | 20 | 20 | 20 |
| S77576_at | ERV9 reverse transcriptase homolog {clone RT18} "[human," multiple "sclerosis," brain "plaques," mRNA "Partial," 84 nt]. /gb=S77576 /nt | 61 | 96 | 90 | 38 | 225 | 178 |
| S77582_at | HERVK10/HUMMTV reverse transcriptase homolog {clone RT240} "[human," multiple "sclerosis," brain "plaques," mRNA "Partial," 89 nt | 20 | 20 | 27 | 20 | 256 | 85 |
| S77583_at | HERVK10/HUMMTV reverse transcriptase homolog {clone RT244} "[human," multiple "sclerosis," brain "plaques," mRNA "Partial," 90 nt] | 52 | 20 | 20 | 20 | 20 | 118 |
| S77763_at | nuclear factor erythroid 2 isoform f=basic leucine zipper protein {alternatively "apliced," exon 1f} "[human," fetal "liver," mRNA," 1678 nt] | 126 | 106 | 20 | 81 | 94 | 20 |
| S77812_at | flt=vascular endothelial growth factor receptor/VEGF receptor/cell surface tyrosine kinase {clone FLIT14} "[human," ovarian carcinoma asc | 206 | 170 | 157 | 136 | 194 | 159 |
| S77835_s_at | IL-1=interleukin-2 "[human," "brain," "mRNA," 418 nt]. /gb=S77835 /ntype=RNA | 20 | 20 | 20 | 20 | 20 | 20 |
| S77893_s_at | GPSAT=glycophorin SAT "[human," peripheral "bloods," mRNA "Partial," 407 nt] | 20 | 20 | 20 | 20 | 20 | 20 |
| S78085_at | PDCD2=programmed cell death-2/Rp8 homolog "[human," fetal "lung," "mRNA," 1282 nt] | 31 | 20 | 20 | 92 | 20 | 98 |
| S78187_at | CDC25Hu2=cdc25+ homolog "[human," "kidney," "mRNA," 3118 nt] | 44 | 120 | 20 | 65 | 20 | 107 |
| S78203_at | PEPT2=H+/peptide cotransporter "[human," "kidney," mRNA "Partial," 2685 nt] | 20 | 20 | 48 | 114 | 84 | 186 |
| S78234_at | nuc2 homolog "[human," "fibroblasts," "mRNA," 3320 nt] | 20 | 20 | 111 | 23 | 153 | 45 |
| S78271_s_at | SB1.8/DXS423E=mitosis-specific chromosome segregation protein SMC1 homolog "[human," HT1080 and M426 fibroblast cell "lines," "n | 20 | 56 | 111 | 59 | 304 | 123 |
| S78296_at | neurofilament-66 "[human," fetal "grain," mRNA," 3197 nt] | 57 | 156 | 217 | 215 | 485 | 122 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| S78432_xpt1_at | SAS=transmembrane 4 protein {5' region} [human, sarcomas, Genomic, 390 nt] | 20 | 20 | 20 | 20 | 20 | 20 |
| S78467_s_at | PIG-A-II=glycinositol phospholipid anchor synthetic element "[human," paroxysmal nocturnal hemoglobinuria "patient," B "lymphocytes," | 20 | 20 | 20 | 20 | 20 | 20 |
| S78569_at | laminin alpha 4 chain "[human," fetal "lung," "mRNA," 6204 nt] | 35 | 20 | 31 | 20 | 151 | 20 |
| S78653_at | mrg=mas-related "[human," Genomic, 2416 nt] | 20 | 28 | 20 | 20 | 85 | 20 |
| S78693_f_at | alpha CREB-1=cyclic AMP esponse element-binding protein-1 alpha isoform ∴alternatively "spliced," internal fragment}]"[human," "placenta | 20 | 35 | 20 | 20 | 20 | 20 |
| S78723_ma2_at | 5-HT2AR=serotonin 5-HT2A receptor ∴ promoter} [human, Genomic, 1678 nt]. | 20 | 78 | 20 | 46 | 20 | 76 |
| S78771_s_at | NAT=CpG island-associated gene "[human," "mRNA," 1741 nt] | 92 | 207 | 354 | 260 | 20 | 76 |
| S78774_at | Na+/Ca2+ exchanger "[human," neuroblastoma x glioma hybrid NG108-15 "cells," mRNA 'Partial," 760 nt]./gb=S78774 /ntype=RNA | 20 | 20 | 20 | 20 | 20 | 20 |
| S78798_s_at | 1-phosphatidylinositol-4-phosphate 5-kinase isoform C "[human," peripheral blood "leukocytes," "mRNA," 1835 nt] | 24 | 24 | 53 | 20 | 103 | 51 |
| S78825_at | Id1 (Id1-b)=transcription regulator helix-loop-helix protein ∴alternatively spliced} "[human," globlastoma cell line "U251," "mRNA," 1146 nt | 20 | 20 | 83 | 89 | 20 | 22 |
| S78873_s_at | mss4=Zn2+ binding protein/guanine nucleotide exchange factor "[human," "brain," mRNA 'Partial," 922 nt] | 20 | 20 | 20 | 32 | 20 | 37 |
| S79048_at | LPRP=pHL EIF1 "[human," "lacrimal "gland," mRNA "Partial," 507 nt] | 76 | 20 | 20 | 88 | 154 | 209 |
| S79219_s_at | metastasis-associated gene "[human," highly metastatic lung cell subline "Anip[937]," mRNA "Partial," 978 nt] | 46 | 109 | 184 | 85 | 20 | 77 |
| S79267_at | CD4 receptor {exons 1 and 2} "[human," "T-lymphocyte," "mRNA," 3429 nt] | 54 | 29 | 20 | 47 | 94 | 20 |
| S79281_at | pancreatic ribonuclease "[human," mRNA Recombinant "Partial," 491 nt]./gb=S79281 /ntype=RNA | 20 | 20 | 20 | 20 | 20 | 20 |
| S79522_at | ubiquitin carboxyl extension protein "[human," "mRNA," 540 nt] | 3161 | 3543 | 4889 | 2565 | 1337 | 1870 |
| S79639_at | EXT1=putative tumour suppressor/heredity multiple exostoses candidate gene "[human," "placenta," "mRNA," 3183 nt]./gb=S79639 /nt | 116 | 250 | 87 | 94 | 20 | 134 |
| S79781_at | WT1 {antisense "promoter," intron 1} "[human," "kidney," "Genomic," 780 nt]./gb=S79781 /ntype=DNA /annot=mRNA | 20 | 27 | 20 | 43 | 172 | 20 |
| S79854_at | type 3 iodothyronine deiodinase=selencenzyme "[human," "placenta," "mRNA," 2066 nt] | 20 | 20 | 20 | 20 | 20 | 20 |
| S79862_s_at | 26 S protease subunit 5b=50 kda subunit "[human," HeLa "cells," mRNA "Partial," 2253 nt] | 76 | 20 | 34 | 20 | 20 | 24 |
| S79873_s_at | h-lamp-2=lysosome-associated membrane protein-2 {alternatively spliced} "[human," "liver," "mRNA," 4006 nt] | 22 | 38 | 24 | 52 | 92 | 20 |
| S80050_at | UDP-N-acetylglucosamine: alpha-6-D-mannoside "beta-1,6-N-acetylglucosaminyltransferase "V}GlcNAc transferase V {5' region} "[human, | 20 | 43 | 66 | 20 | 20 | 20 |
| S80267_s_at | p72syk {G insertion nucleotide 92} "[human," ataxia-telangiectasia "patients," EBV-lymphoblastoid "cells," "mRNA," 2120 nt] | 20 | 20 | 20 | 40 | 208 | 145 |
| S80335_at | integrin beta 7 subunit "[human," "mRNA," 2798 nt] | 27 | 20 | 20 | 20 | 20 | 20 |
| S80343_at | ArgRS=arginyl-tRNA synthetase "[human," breast and HepG2 "cells," mRNA "Partial," 2237 nt] | 72 | 85 | 20 | 72 | 20 | 73 |
| S80437_s_at | fatty acid synths ∴3' region} "[human," breast and HepG2 "cells," mRNA "Partial," 2237 nt] | 79 | 166 | 314 | 375 | 183 | 165 |
| S80562_at | acidic calponin "[human," "kidney," "mRNA," 1607 nt] | 77 | 20 | 31 | 20 | 176 | 94 |
| S80905_f_at | PRB2 {PRB2L CON1+ =Con1 {exon 3} "[human," peripheral blood "leukocytes," "subject "R.S.," [Genomic "Mutant," 1179 nt] | 20 | 20 | 27 | 20 | 237 | 114 |
| S81003_at | L-UBC=ubuquitin conjugating enzyme "[human," odontogenic "keratocysts," mRNA "Partial," 683 nt] | 103 | 128 | 20 | 188 | 51 | 228 |
| S81083_cds1_at | beta -ADD=adducin beta subunit 63 kda isoform/membrane skeleton protein, beta -ADD=adducin beta subunit 63 kda isoform/membrane | 73 | 207 | 33 | 163 | 79 | 145 |
| S81221_at | lanosterol synthase "[human," fetal "liver," mRNA "Partial," 2637 nt] | 20 | 20 | 20 | 35 | 20 | 20 |
| S81243_s_at | CHN=steroid/thyroid orphan receptor homolog gene "[human," fetal "brain," mRNA "Partial," 2714 nt] | 20 | 20 | 20 | 21 | 287 | 20 |
| S81264_s_at | Hs-TBX2=T-box gene ∴ T-box region} "[human," fetal "kidney," mRNA "Partial," 382 nt]./gb=S81264 /ntype=RNA | 20 | 42 | 48 | 67 | 122 | 118 |
| S81294_at | DCC=deleted in colorectal cancer ∴alternatively "spliced," exon 1A}0 "[human," brain "tumor," tumor no. "245," mRNA "Partial," 216 nt]./gb | 26 | 20 | 20 | 20 | 20 | 20 |
| S81419_at | dystrophin, dystrophin ∴ Purkinje "promoter," alternatively spliced} "[human," cortical brain and adult "heart," mRNA "Partial," 377 nt]./gb=S | 117 | 143 | 82 | 79 | 244 | 207 |
| S81439_at | EGR alpha=early growth response gene alpha "[human," "prostate," "mRNA," 3228 nt] | 51 | 23 | 37 | 20 | 20 | 20 |
| S81578_at /gb=S81578 A | dioxin-responsive gene ∴putative polyadenylation signal region} "[human," hepatoma G2 cell "line," mRNA "Partial," 302 nt]. | 20 | 56 | 20 | 43 | 156 | 20 |
| S81661_s_at | Keratinocyte growth factor "[human," "mRNA," 1200 nt] | 39 | 20 | 20 | 20 | 20 | 20 |
| S81737_s_at | alpha 1 syntrophin "[human," mRNA "Partial," 1771 nt] | 20 | 20 | 20 | 20 | 20 | 20 |
| S81893_at | MESI3/15=extracellular matrix induced gene "[human," endometrial adenocarcinoma cells "HEC1B(L)," mRNA "Partial," 453 nt]./gb=S81 | 20 | 116 | 101 | 29 | 20 | 108 |
| S81914_at | IEX-1=radiation-inducible immediate-early gene "[human," "placenta," mRNA "Partial," 1223 nt] | 1310 | 86 | 20 | 67 | 109 | 20 |
| S81916_at | phosphoglycerate kinase {alternatively spliced} "[human," phosphoglycerate kinase deficient patient with episodes of "muscl"," mRNA Part | 20 | 21 | 40 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| S81944_at | gamma-aminobutyric acid type A receptor alpha 5 subunit "[human," "cerebellum," mRNA "Partial," 1732 nt] | 20 | 20 | 20 | 20 | 20 | 20 |
| S81957_at | BMP-5=bone morphogenic protein-5 {promoter} "[human," "Genomic," 1116 nt]. /gb=S81957 /ntype=DNA /annot=mRNA | 20 | 83 | 20 | 41 | 20 | 84 |
| S82024_at | SCG10=neuron-specific growth-associated protein/stathmin homolog "[human," "embryo," "mRNA," 696 nt]. (trimmed to 621 nts) | 54 | 20 | 20 | 20 | 20 | 87 |
| S82075_at | PA4=candidate oncogene {3' region} "[human," "HEN-16," HEN-16T transformed endocervical cell "lines," mRN "Partial," 315 nt]. /gb=S | 20 | 69 | 20 | 20 | 20 | 20 |
| S82185_at | BRAG-1=brain-related apoptosis gene/Bcl-2 homolog "[human," MG-107 "glioma," mRNA "Partial," 960 nt]. /gb=S82185/ntype=RNA | 20 | 20 | 20 | 20 | 45 | 527 |
| S82198_at | caldecrin=serum calcium-dereasing factor "[human," "pancreas," mRNA "Partial," 894 nt] | 338 | 382 | 401 | 449 | 475 | 75 |
| S82240_at | RhoE=26 kda GTPase homolog "[human," HeLa cell "line," "mRNA," 833 nt] | 201 | 20 | 20 | 20 | 133 | 3909 |
| S82297_at | beta 2-microglobulin {11 bp deleted between nucleotides 98–99} "[human," colon cancer cell line "HCT," mRNA "Mutant," 416 nt] | 2360 | 2759 | 3365 | 2886 | 618 | 20 |
| S82362_s_at | hRAR-beta 2=retinoic-acid-receptor beta/suspected tumor suppressor {5' region, "transcription control region} "[human," mRNA "Partial, | 20 | 20 | 20 | 20 | 20 | 116 |
| S82447_s_at | GCN5-like 1=BCN5 homolog/putative regulator of transcriptional activation {clone GCN5L1} "[human," "mRNA," 545 nt] | 134 | 180 | 118 | 183 | 144 | 191 |
| S82470_at | BB1=malignant cell expression-enhanced gene/tumor progression-enhanced gene "[human," UM-UC-9 bladder carcinoma cell "line," "mR | 65 | 184 | 647 | 225 | 20 | 21 |
| S82471_s_at | SSX3=Kruppel-associated box containing SSX gene "[human," "testis," mRNA "Partial," 675 nt]. /gb=S82471 /ntype=RNA | 24 | 20 | 20 | 22 | 20 | 21 |
| S82472_at | beta #NAME? polymerase beta {exon alpha to exon VII region} "[human," "Genomic," 124 "nt," segment 1 of 2]. /gb=S82472 /ntype=DNA | 20 | 20 | 20 | 20 | 20 | 20 |
| S82592_at | Evi-1=Evi-1 protein {3' "region," "deletion region} "[human," megakaryoblastoid cell line "MOLM-1," chronic myelocytic leukemia "patien," | 20 | 82 | 27 | 20 | 20 | 20 |
| S82597_ma1_s_at | Description: UDP-GalNAc:polypeptide N-acetylgalactosaminyltransferase gene extracted from UDP-GalNAc:polypeptide N-acetylgalacto | 39 | 166 | 237 | 192 | 20 | 92 |
| S83198_at | BPLP=basic proline-rich protein "[human," "lacrimal "gland," "mRNA," 947 nt] | 20 | 20 | 20 | 20 | 20 | 20 |
| S83249_at | NG-TRA=transporter protein/putative hormone extrusion pump "[human," "liver and various other "tissues," mRNA "Partial," 377 nt]. /gb=S | 20 | 20 | 20 | 20 | 67 | 20 |
| S83308_at | SOX5-SRY-related HMG box gene {alternatively spliced} "[human," "testis," "mRNA," 1473 nt] | 39 | 46 | 20 | 20 | 75 | 100 |
| S83309_s_at | germ cell nuclear factor "[human," embryonal carcinoma "NT2/D1," mRNA "Partial," 1916 nt] | 36 | 44 | 77 | 35 | 171 | 90 |
| S83325_s_at | aspartyl(asparaginyl)beta-hydroxylase "[human," hepatoblastoma cell line "HepG2," mRNA "Partial," 2234 nt] | 20 | 20 | 24 | 20 | 20 | 20 |
| S83362_s_at | differentiation-stimulating factor/leukemia inhibitory factor receptor .:5' "region," exon 1} "[human," "placenta," "Genomic," 1350 nt]. /gb=S8 | 20 | 20 | 36 | 20 | 20 | 100 |
| S83364_at | putative Rab5-interacting protein {clone L1–57} "[human," HeLa "cells," mRNA "Partial," 366 nt]. /gb=S83364 /ntype=RNA | 231 | 159 | 127 | 90 | 109 | 108 |
| S83365_at | putative Rab5-interacting protein {clone L1–94} "[human," HeLa "cells," mRNA "Partial," 369 nt]. /gb=S83365 /ntype=RNA | 20 | 20 | 20 | 20 | 20 | 20 |
| S83366_cds1_at | retion centromeric to t(12:17) brakepoint: orfl/unknown 43 amino acid transcript . . . orf3/unknown 50 amino acid transcript [human, testis, a | 101 | 81 | 66 | 75 | 191 | 45 |
| S83366_cds3_at | region centromeric to t(12:17) brakepoint: orfl/unknown 43 amino acid transcript . . . orf3/unknown 50 amino acid transcript [human, testis, a | 53 | 37 | 20 | 20 | 40 | 20 |
| S83390_s_at | T3 receptor-associating cofactor-1 "[human," fetal "liver," "mRNA," 2930 nt] | 20 | 20 | 20 | 20 | 20 | 20 |
| S83513_s_at | pituitary adenylate cyclase activating polypeptide "[human," "mRNA," 1940 nt] | 20 | 20 | 82 | 45 | 20 | 60 |
| S83549_at | Na+/H+ exchanger isoform NHE-2 "[human," "various "tissues," mRNA "Partial," 595 nt]. /gb=S83549 /ntype=RNA | 20 | 20 | 20 | 20 | 67 | 20 |
| S85655_at | prohibitin "[human," "mRNA," 1043 nt] | 67 | 60 | 56 | 143 | 20 | 54 |
| S85963_at | hIRS-1=rat insulin receptor substrate-1 homolog "[human," "teratocarcinoma," "cell line "FOCUS," "Genomic," 6152 nt] | 20 | 20 | 20 | 20 | 20 | 20 |
| S87759_at | protein phosphatase 2C alpha "[human," "teratocarcinoma," "mRNA," 2346 nt] | 44 | 20 | 114 | 108 | 77 | 126 |
| S90469_at | cytochrome P450 reductase "[human," "placenta," mRNA "Partial," 2403 nt] | 190 | 87 | 20 | 127 | 20 | 20 |
| S94421_at | TCR eta #NAME? cell receptor eta-exon "[human," "Genomic," 806 nt] | 20 | 20 | 20 | 20 | 20 | 37 |
| S95936_at | transferrin "[human," "liver," "mRNA," 2347 nt] | 55 | 33 | 20 | 21 | 20 | 100 |
| U00001_s_at | Human homologue of S. pombe nuc2+ and A. ridulans bimA | 20 | 20 | 20 | 20 | 20 | 20 |
| U00115_at | Human zinc-finger protein (bcl-6) "mRNA," complete cds | 30 | 95 | 139 | 64 | 144 | 131 |
| U00238_ma1_at | Homo sapiens glutamine PRPP amidotransferase (GPAT) mRNA complete cds. | 40 | 20 | 51 | 20 | 20 | 20 |
| U00672_at | Human interleukin-1- receptor "mRNA," complete cds | 27 | 20 | 20 | 41 | 48 | 20 |
| U00802_s_at | Human drebrin E2 mRNA "(DBN1)," complete cds | 20 | 20 | 20 | 20 | 20 | 20 |
| U00921_at | Homo sapiens Lst-1 "gene," complete cds | 20 | 20 | 20 | 35 | 20 | 59 |
| U00928_at | Human clone CE29 4.1 (CAC)n/(GTG) repeat-containing mRNA | 20 | 20 | 20 | 20 | 20 | 20 |
| U00930_at | Human clone C4E 1.63 (CAC)n/(GTG)n repeat-containing mRNA | 70 | 139 | 174 | 79 | 352 | 135 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U00943_at | Human clone A9A2BRB2 (CAC)n/(GTG)n repeat-containing mRNA | 35 | 46 | 112 | 68 | 87 | 20 |
| U00944_at | Human clone A9A2BRB6 (CAC)n/(GTG)n repeat-containing mRNA | 34 | 20 | 20 | 20 | 20 | 20 |
| U00946_at | Human clone A9A2BRB5 (CAC)n/(GTG)n repeat-containing mRNA | 20 | 46 | 20 | 51 | 20 | 20 |
| U00947_s_at | Human clone C4E 3.2 (CAC)n/(GTG)n repeat-containing mRNA | 361 | 403 | 1056 | 730 | 254 | 385 |
| U00951_at | Human clone A9A2BR11 (CAC)n/(GTG)n repeat-containing mRNA | 47 | 20 | 20 | 20 | 71 | 20 |
| U00952_at | Human clone A9A2BR17 (CAC)n/(GTG)n repeat-containing mRNA | 114 | 170 | 139 | 116 | 181 | 236 |
| U00954_at | Human clone CE29 7.2 (CAC)n/(GTG)n repeat-containing mRNA | 20 | 20 | 20 | 20 | 20 | 20 |
| U00957_at | Human clone KD81.2 (CAC)n/(GTG)n repeat-containing mRNA | 20 | 20 | 20 | 20 | 20 | 69 |
| U00968_at | Human SREBP-1 "mRNA," complete cds | 301 | 337 | 405 | 483 | 279 | 177 |
| U01038_at | Human pLK "mRNA," complete cds | 172 | 240 | 259 | 222 | 207 | 341 |
| U01062_at | Human type 3 inositol "1,4,5-trisphosphate" receptor (ITPR3) "mRNA," complete cds | 23 | 20 | 71 | 32 | 20 | 20 |
| U01102_at | Human lung clara cells 10 kDa secretory protein (CC10) "gene," satellite and Alu repeat "sequences," complete cds | 20 | 20 | 20 | 20 | 20 | 20 |
| U01120_at | Human glucose-6-phosphatase "mRNA," complete cds | 115 | 31 | 102 | 82 | 181 | 100 |
| U01147_at | human guanine nucleotide regulatory protein (ABR) "mRNA," complete cds | 116 | 95 | 137 | 57 | 192 | 184 |
| U01157_at | Human glucagon-like peptide-1 receptor mRNA with CA dinucleotide "repeat," complete cds | 37 | 86 | 67 | 60 | 20 | 20 |
| U01160_at | Human transmembrane 4 superfamily protein (SAS) "mRNA," complete cds | 109 | 61 | 65 | 67 | 34 | 149 |
| U01212_at | Human olfactory marker protein (OMP) "gene," complete cds | 184 | 517 | 537 | 428 | 292 | 414 |
| U01317_cds1_at | Human beta globin region on chromosome 11. | 20 | 20 | 20 | 20 | 20 | 116 |
| U01317_cds4_at | beta-globin thalassemia gene extracted from Human beta globin region on chromosome 11 | 20 | 20 | 23 | 20 | 20 | 27 |
| U01317_cds6_at | Human beta globin region on chromosome 11. | 68 | 141 | 281 | 200 | 348 | 217 |
| U01337_at | Human Ser/Thr protein kinase (A-RAF-1) "gene," complete cds | 164 | 74 | 122 | 90 | 120 | 265 |
| U01691_s_at | Human annexin V (ANX5) "gene," 5'-untranslated region | 124 | 216 | 147 | 206 | 468 | 110 |
| U01824_at | Human glutamate/aspartate transporter II "mRNA," complete cds | 20 | 20 | 50 | 35 | 20 | 20 |
| U01828_at | Human microtubule-associated protein 2 (MAP2) "mRNA," complete cds | 20 | 20 | 50 | 35 | 20 | 20 |
| U01833_at | Human nucleotide-binding protein "mRNA," complete cds | 20 | 20 | 20 | 20 | 20 | 20 |
| U01877_at | Human p300 protein "mRNA," complete cds | 57 | 55 | 20 | 34 | 20 | 20 |
| U01922_at | Human BTK region clone fci-12 mRNA | 48 | 20 | 20 | 20 | 30 | 20 |
| U01923_at | Human BTK region clone fjtp-3 mRNA | 41 | 117 | 95 | 44 | 20 | 178 |
| U02019_at | Human AU-rich element RNA-binding protein AUF1 "mRNA," complete cds | 41 | 110 | 48 | 26 | 274 | 20 |
| U02020_at | Human pe-B cell enhancing factor (PBEF) "mRNA," complete cds | 315 | 168 | 135 | 80 | 20 | 63 |
| U02031_at | Human sterol regulatory element binding protein-2 "mRNA," complete cds | 20 | 20 | 20 | 36 | 20 | 20 |
| U02081_at | Human guanine nucleotide regulatory protein (NET1) "mRNA," complete cds | 41 | 34 | 134 | 48 | 20 | 78 |
| U02082_at | Human microtubule-associated regulatory protein (tim1) "mRNA," complete cds | 108 | 96 | 54 | 27 | 192 | 24 |
| U02310_at | Human fork head domain protein (FKHR) "mRNA," complete cds | 35 | 20 | 40 | 20 | 41 | 20 |
| U02388_at | Human cytochrome P450 4F2 (CYP4F2) "mRNA," complete cds | 20 | 20 | 20 | 20 | 224 | 42 |
| U02493_at | Human 54 kDa protein "mRNA," complete cds | 247 | 302 | 730 | 518 | 546 | 596 |
| U02556_at | Human RP3 "mRNA," complete cds | 170 | 85 | 198 | 139 | 137 | 192 |
| U02566_s_at | Human receptor tyrosine kinase tif "mRNA," partial cds | 20 | 20 | 20 | 20 | 20 | 20 |
| U02570_at | Human CDC42 TTPase-activating protein "mRNA," partial cds | 263 | 293 | 86 | 230 | 356 | 226 |
| U02609_at | Human transducin-like protein "mRNA," complete cds | 20 | 20 | 20 | 20 | 27 | 20 |
| U02619_at | Human TFIIIC box B-binding subunit "mRNA,38 complete cds | 190 | 195 | 20 | 229 | 224 | 317 |
| U02632_at | Human calcium-activated potassium channel "mRNA," partial cds | 43 | 90 | 71 | 90 | 41 | 95 |
| U02680_at | Human protein tyrosine kinase "mRNA," complete cds | 116 | 72 | 208 | 69 | 224 | 42 |
| U02683_s_at | Human alpha palindromic binding protein "mRNA," complete cds | 20 | 20 | 20 | 20 | 20 | 20 |
| U02687_at | Human growth factor receptor tyrosine kinase (STK-1) "mRNA," complete cds | 20 | 20 | 20 | 20 | 20 | 20 |
| U03056_at | Human tumor suppressor (LUCA01) "mRNA," complete cds | 20 | 70 | 20 | 54 | 20 | 51 |
| U03057_at | Human actin bundling protein (HSN) "mRNA," complete cds | 430 | 643 | 957 | 527 | 412 | 890 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U03090_at | Human Ca2+-dependent phospholipase A2 "mRNA," complete cds | 37 | 62 | 20 | 20 | 20 | 20 |
| U03100_at | Human alpha2(E)-catenin "mRNA," complete cds | 189 | 105 | 274 | 190 | 24 | 119 |
| U03105_at | Human B4-2 protein "mRNA," complete cds | 101 | 52 | 20 | 94 | 29 | 38 |
| U03187_at | Human IL12 receptor component "mRNA," complete cds | 20 | 20 | 20 | 56 | 20 | 20 |
| U03270_at | Human centrin "mRNA," complete cds | 133 | 200 | 173 | 197 | 432 | 379 |
| U03272_at | Human fibrillin-2 "mRNA," complete cds | 83 | 56 | 99 | 39 | 46 | 210 |
| U03274_at | human biotinidase "mRNA," complete cds | 20 | 20 | 20 | 20 | 20 | 20 |
| U03397_s_at | Human receptor protein 4-1BB "mRNA," complete cds | 33 | 80 | 126 | 46 | 20 | 136 |
| U03398_at | Human receptor 4-1BB ligand "mRNA," complete cds | 377 | 500 | 357 | 375 | 1924 | 1433 |
| U03399_at | Human T-complex protein 10A (TCP10A) "mRNA," complete cds | 312 | 507 | 505 | 488 | 248 | 500 |
| U03486_at | Human connexin40 "gene," complete cds | 122 | 158 | 202 | 105 | 220 | 311 |
| U03494_at | Human transcription factor LSF "mRNA," complete cds | 20 | 73 | 20 | 20 | 20 | 20 |
| U03634_at | Human P47 LBC oncogene "mRNA," complete cds | 72 | 45 | 20 | 37 | 74 | 107 |
| U03642_at | Human flt3 ligand "mRNA," complete cds | 20 | 157 | 62 | 46 | 20 | 220 |
| U03644_at | Human G protein-coupled receptor APJ "gene," complete cds | 61 | 102 | 43 | 71 | 234 | 112 |
| U03688_at | Human recepin "mRNA," complete cds | 172 | 116 | 26 | 20 | 193 | 91 |
| U03735_f_at | human dioxin-inducible cytochrome P450 (CYP1B1) "mRNA," complete cds | 20 | 20 | 59 | 20 | 450 | 20 |
| U03851_at | Human MAGE-3 antigen (MAGE-3) "gene," complete cds | 91 | 32 | 29 | 39 | 20 | 20 |
| U03858_at | Human capping protein alpha "mRNA," partial cds | 20 | 22 | 20 | 20 | 223 | 25 |
| U03877_at | Human extracellular protein (S1-50 "mRNA," complete cds | 20 | 59 | 20 | 20 | 31 | 28 |
| U03886_at | Human GS2 "mRNA," complete cds | 27 | 35 | 34 | 20 | 94 | 64 |
| U03891_at | Human phorbolin I "mRNA," partial cds | 182 | 130 | 134 | 183 | 293 | 401 |
| U03905_at | Human monocyte chemoattractant protein 1 receptor (MCP-1RB) alternatively spliced "mRNA," complete cds | 20 | 20 | 20 | 20 | 20 | 20 |
| U03911_at | Human mutator gene (hMSH2) "mRNA," complete cds | 20 | 20 | 20 | 20 | 20 | 20 |
| U04209_at | Human associated microfibrillar protein "mRNA," complete cds | 40 | 20 | 25 | 66 | 329 | 38 |
| U04241_at | human homolog of Drosophila enhancer of split m9/m10 "mRNA," complete cds | 343 | 659 | 729 | 919 | 681 | 653 |
| U04270_at | Human putative potassium channel subunit (h-erg) "mRNA," complete cds | 20 | 20 | 20 | 20 | 20 | 20 |
| U04285_s_at | Human lysosomal acid "lipase," cholesteryl ester hydrolase (LIPA) gene | 42 | 20 | 20 | 20 | 20 | 94 |
| U04313_at | Human maspin "mRNA," complete cds | 667 | 119 | 611 | 254 | 139 | 46 |
| U04325_cds3_at | Human pregnancy-specific beta-1-glycoprotein alternatively spliced C-R, C-S, C-B, and C-A domains (PSG11) gene, partial cds. | 20 | 20 | 71 | 20 | 20 | 20 |
| U04343_at | Human CD86 antigen "mRNA," complete cds | 67 | 57 | 161 | 57 | 20 | 61 |
| U04520_at | Human type IV collagen a5 chain (COL4A5) gene | 46 | 20 | 82 | 20 | 20 | 20 |
| U04636_ma1_at | Human cyclooxygenase-2 (hCox-2) "gene," complete cds | 184 | 25 | 79 | 100 | 47 | 27 |
| U04735_at | Human Ini1 "mRNA," complete cds | 27 | 46 | 20 | 20 | 20 | 20 |
| U04806_s_at | Human microsomal stress 70 protein ATPase core (stch) "mRNA," complete cds | 20 | 30 | 28 | 50 | 257 | 31 |
| U04810_at | Human tastin "mRNA," complete cds | 51 | 35 | 20 | 51 | 98 | 35 |
| U04811_at | Human trophinin "mRNA," complete cds | 37 | 75 | 27 | 28 | 20 | 20 |
| U04840_at | Human onconeural ventral antigen-1 (Nova-1) "mRNA," complete cds | 21 | 48 | 70 | 20 | 20 | 82 |
| U04847_at | Human Ini1 "mRNA," complete cds | 84 | 20 | 20 | 20 | 20 | 85 |
| U04898_at | human orphan hormone nuclear receptor RORalpha2 "mRNA," complete cds | 20 | 46 | 20 | 37 | 42 | 110 |
| U05012_s_at | Human receptor tyrosine kinase TrkC (NTRK3) "mRNA," complete cds | 69 | 99 | 84 | 20 | 20 | 20 |
| U05227_at | Human FUSE binding protein "mRNA," complete cds | 20 | 20 | 20 | 20 | 41 | 20 |
| U05237_at | Human Rar protein "mRNA," complete cds | 33 | 43 | 146 | 133 | 91 | 153 |
| U05255_s_at | Human fetal Alz-50-reactive clone 1 (FAC1) "mRNA," complete cds | 20 | 20 | 20 | 20 | 20 | 39 |
| U05255_at | Human glycophorin HeP2 "mRNA," partial cds | 20 | 20 | 20 | 20 | 20 | 20 |
| U05259_ma1_at | Human MB-1 gene, complete cds. | 34 | 82 | 20 | 108 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U05291_at | Human fibromodulin "mRNA," partial cds | 123 | 118 | 175 | 86 | 199 | 55 |
| U05321_at | Human X-linked PEST-containing transporter (XPCT) "gene," promoter and | 20 | 20 | 20 | 20 | 20 | 20 |
| U05340_at | Human p55CDC "mRNA," complete cds | 161 | 206 | 38 | 151 | 130 | 328 |
| U05572_s_at | Human lysosomal alpha-mannosidase (MANB) "mRNA," complete cds | 20 | 20 | 20 | 20 | 20 | 20 |
| U05589_at | Human ribosomal protein S1 homolog "mRNA," partial cds | 20 | 20 | 20 | 20 | 100 | 428 |
| U05659_at | Human 17beta-hydroxysteroid dehydrogenase type 3 "mRNA," complete cds | 133 | 256 | 234 | 225 | 547 | 428 |
| U05681_s_at | Human proto-oncogene BCL3 gene | 221 | 209 | 343 | 223 | 362 | 172 |
| U05861_s_at | Human hepatic dihydrodiol dehydrogenase gene | 297 | 850 | 619 | 710 | 445 | 638 |
| U05875_at | Human clone pSK1 interferon gamma receptor accessory factor-1 (AF-1) "mRNA," complete cds | 62 | 37 | 20 | 34 | 101 | 20 |
| U06088_at | Human N-acetylgalactosamine 6-sulphatase (GALNS) gene | 117 | 95 | 20 | 24 | 171 | 278 |
| U06155_at | | 20 | 94 | 20 | 20 | 20 | 20 |
| U06155_s_at | Human chromosome 1q subtelomeric sequence D1S553. /gb=U06155 /ntype=DNA /annot=CDS | 2575 | 5581 | 7302 | 6354 | 6999 | 4281 |
| U06233_at | Human POU domain protein (Brn-3b) "mRNA," complete cds | 20 | 20 | 20 | 20 | 20 | 20 |
| U06452_at | Human melanoma antigen recognized by T-cells (MART-1) mRNA | 230 | 87 | 20 | 20 | 61 | 77 |
| U06454_at | Human AMP-activated protein kinase (hAMPK) "mRNA," complete cds | 20 | 20 | 97 | 20 | 20 | 65 |
| U06631_at | Human (H326) "mRNA," complete cds | 20 | 20 | 20 | 60 | 20 | 60 |
| U06632_at | Human p80-coilin "mRNA," complete cds | 35 | 56 | 120 | 60 | 20 | 20 |
| U06643_s_at | | 802 | 20 | 20 | 62 | 64 | 20 |
| U06681_at | Human clone CCA12 mRNA contaning CCA trinucleotide repeat | 20 | 20 | 20 | 20 | 20 | 20 |
| U06698_at | Human neuronal kinesin heavy chain "mRNA," complete cds | 22 | 41 | 53 | 20 | 20 | 150 |
| U06863_at | Human follistatin-related protein precursor "mRNA," complete cds | 230 | 87 | 110 | 31 | 61 | 77 |
| U07000_cds4_at | Human breakpoint cluster region (BCR) gene, complete cds | 51 | 165 | 80 | 86 | 736 | 452 |
| U07132_at | Human steroid hormone receptor Ner-1 "mRNA," complete cds | 148 | 204 | 20 | 116 | 140 | 118 |
| U07139_at | Human voltage-gated calcium channel beta subunit "mRNA," complete cds | 25 | 79 | 171 | 166 | 496 | 297 |
| U07151_at | Human GTP binding protein (ARL3) "mRNA," complete cds | 40 | 20 | 20 | 115 | 189 | 102 |
| U07158_at | Human syntaxin "mRNA," complete cds | 56 | 111 | 66 | 20 | 20 | 59 |
| U07223_at | Human beta2-chimaerin "mRNA," complete cds | 41 | 84 | 22 | 62 | 20 | 20 |
| U07225_at | Human P2U nucleotide receptor "mRNA," complete cds | 20 | 31 | 20 | 22 | 137 | 115 |
| U07231_at | Human G-rich sequence factor-1 (GRSF-1) "mRNA," complete cds | 20 | 23 | 68 | 68 | 184 | 47 |
| U07349_at | Human B lymphocyte serine/threonine protein kinase "mRNA," complete cds | 20 | 20 | 20 | 20 | 71 | 452 |
| U07358_at | Human protein kinase (zpk) "mRNA," complete cds | 103 | 20 | 20 | 129 | 320 | 242 |
| U07418_at | Human DNA mismatch repair (hmlh1) "mRNA," complete cds | 43 | 67 | 125 | 143 | 262 | 191 |
| U07424_at | Human putative tRNA synthetase-like protein "mRNA," complete cds | 177 | 140 | 147 | 215 | 293 | 462 |
| U07550_at | Human chaperonin 10 "mRNA," complete cds | 59 | 20 | 186 | 88 | 80 | 196 |
| U07559_at | Human ISL-1 (islet-1) "mRNA," complete cds | 76 | 112 | 68 | 62 | 179 | 96 |
| U07583_cds1_at | Human proto-oncogenic tyrosine-protein kinase (ABL) gene, exon 1s and exons 2–10, complete cds. | 76 | 20 | 20 | 47 | 20 | 100 |
| U07620_at | Human MAP kinase "mRNA," complete cds | 81 | 20 | 20 | 20 | 20 | 51 |
| U07664_at | Human HB9 homeobox gene | 43 | 295 | 20 | 152 | 144 | 342 |
| U07681_at | Human NAD(H)-specific isocitrate dehydrogenase alpha subunit precursor "mRNA," complete cds | 33 | 26 | 20 | 30 | 76 | 67 |
| U07695_at | Human tyrosine kinase (HTK) "mRNA," complete cds | 220 | 214 | 236 | 194 | 412 | 438 |
| U07794_cds2_at | Human tyrosine kinase (TXK) gene, exon 12 and 13, partial cds. | 20 | 36 | 63 | 20 | 20 | 20 |
| U07802_at | human Tis11d "gene," complete cds | 133 | 99 | 160 | 21 | 71 | 61 |
| U07804_s_at | Human DNA topoisomerase I "mRNA," partial cds | 20 | 20 | 20 | 20 | 46 | 23 |
| U07806_s_at | Human camptothecin resistant clone CEM/C2 DNA topoisomerase I "mRNA," complete cds | 76 | 185 | 105 | 163 | 20 | 70 |
| U07807_at | Human metallothionein IV (MITV) "gene," complete cds | 41 | 25 | 20 | 21 | 129 | 124 |
| U07856_s_at | Human endogenous retrovirus in complement C4A "gene," A3 "allele," HERV-K(C4) "(gag)," "(pol)," reverse "transcriptase," integrase and | 20 | 20 | 20 | 20 | 153 | 20 |
| U07857_at | Human 18 kDa Alu RNA binding protein "mRNA," complete cds | 330 | 269 | 483 | 328 | 20 | 219 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| U07882_at | Human delta opioid receptor "mRNA," complete cds | 20 | 20 | 20 | 44 | 61 | 138 |
| U07919_at | Human aldehyde dehydrogenase 6 "mRNA," complete cds | 200 | 205 | 64 | 75 | 20 | 20 |
| U07969_s_at | Human intestinal peptide-associated transporter HPT-1 "mRNA," complete cds | 34 | 39 | 20 | 39 | 122 | 20 |
| U08006_s_at | Human complement 8 alpha subunit (C8A) gene | 25 | 20 | 48 | 58 | 28 | 55 |
| U08015_at | Human NF-ATc "mRNA," complete cds | 20 | 65 | 20 | 20 | 150 | 62 |
| U08021_at | Human nicotinamide N-methyltransferase (NNMT) "mRNA," complete cds | 165 | 275 | 20 | 20 | 20 | 20 |
| U08023_at | Human cellular proto-oncogene (c-mer) "mRNA," complete cds | 20 | 41 | 66 | 118 | 319 | 155 |
| U08049_at | Human peripheral myelin protein-22 (PMP22) "gene," non-coding exon 1A. /gb=U08049 /ntype=DNA /annot=exon | 20 | 67 | 20 | 20 | 189 | 21 |
| U08096_at | Human peripheral myelin protein-22 (PMP22) "gene," non-coding exon 1B. /gb=U08096 /ntype=DNA /annot=exon | 20 | 20 | 20 | 20 | 20 | 133 |
| U08191_s_at | Human R kappa B "mRNA," complete cds | 20 | 20 | 27 | 20 | 215 | 20 |
| U08198_ma1_at | Human complement C8 gamma subunit precursor (C8G) gene, complete cds. | 20 | 93 | 20 | 20 | 179 | 20 |
| U08316_at | Human insulin-stimulated protein kinase 1 (ISPK-1) "mRNA," complete cds | 22 | 113 | 25 | 72 | 70 | 84 |
| U08336_at | Human basic helix-loop-helix transcription factor "mRNA," complete cds | 127 | 169 | 30 | 161 | 48 | 154 |
| U08377_at | Human homolog of Drosophila splicing regulator suppressor-of-white-apricot "mRNA," complete cds | 20 | 93 | 20 | 47 | 20 | 20 |
| U08438_at | Human beta-adrenergic receptor kinase (ADRBK1) gene | 20 | 41 | 20 | 20 | 20 | 20 |
| U08471_at | Human folate receptor 3 "mRNA," complete cds | 20 | 20 | 20 | 20 | 137 | 112 |
| U08815_at | Human spliceosomal protein (SAP 61) "mRNA," complete cds | 47 | 20 | 20 | 43 | 133 | 72 |
| U80054_s_at | Human UDP glucuronosyltransferase precursor (UGT2B15) "mRNA," complete cds | 20 | 42 | 35 | 20 | 148 | 43 |
| U08989_at | Human glutamate transporter "mRNA," complete cds | 88 | 20 | 20 | 100 | 159 | 20 |
| U08998_at | Human TAR RNA binding protein 2 (TRBP2) "mRNA," complete cds | 20 | 20 | 20 | 20 | 20 | 20 |
| U09002_at | Human N-methyl-D-aspartate receptor modulatory subunit 2A (nNR2A) "mRNA," complete cds | 20 | 41 | 20 | 48 | 60 | 22 |
| U09087_s_at | Human thymopoietin beta "mRNA," complete cds | 20 | 45 | 20 | 20 | 20 | 1198 |
| U09117_at | Human phospholipase c delta 1 "mRNA," complete cds | 344 | 464 | 206 | 612 | 638 | 20 |
| U09178_s_at | Human dihydropyrimidine dehydrogenase "mRNA," complete cds | 20 | 44 | 56 | 27 | 57 | 314 |
| U09196_at | Human 1.1 kb mRNA upregulated in retinoic acid treated HL-60 neutrophilic cells | 95 | 213 | 339 | 197 | 408 | 20 |
| U09210_at | Human vesicular acetylcholine transporter "mRNA," complete cds | 20 | 131 | 20 | 20 | 23 | 20 |
| U09278_at | Human fibroblast activation protein "mRNA," complete cds | 47 | 98 | 69 | 87 | 78 | 109 |
| U09279_at | Human type XIX collagen (COL19A1) "mRNA," partial cds | 20 | 72 | 20 | 20 | 118 | 25 |
| U09284_at | Human PINCH protein "mRNA," complete cds | 20 | 74 | 102 | 96 | 24 | 91 |
| U09303_at | Human T cell leukemia LERK-2 (EPLG2) "mRNA," complete cds | 89 | 99 | 127 | 99 | 129 | 192 |
| U09366_at | Human clone 53BP1 p53-binding protein "mRNA," partial cds | 138 | 121 | 197 | 141 | 210 | 111 |
| U09367_at | Human zinc finger protein ZNF133 | 20 | 20 | 20 | 29 | 38 | 20 |
| U09368_at | Human zinc finger protein ZNF136 | 76 | 109 | 98 | 156 | 283 | 308 |
| U09410_at | Human zinc finger protein ZNF140 | 20 | 67 | 20 | 20 | 20 | 210 |
| U09411_at | Human zinc finger protein ZNF131 "mRNA," partial cds | 20 | 25 | 41 | 20 | 47 | 50 |
| U09412_at | Human zinc finger protein ZNF132 "mRNA," complete cds | 20 | 42 | 36 | 61 | 82 | 212 |
| U09413_at | Human zinc finger protein ZNF134 "mRNA," complete cds | 20 | 104 | 55 | 21 | 186 | 234 |
| U09414_at | Human zinc finger protein ZNF135 "mRNA," complete cds | 47 | 98 | 69 | 87 | 78 | 109 |
| U09477_at | Human zinc finger protein ZNF137 "mRNA," complete cds | 20 | 72 | 20 | 20 | 118 | 25 |
| U09510_s_at | Human glycyl-tRNA synthetase "mRNA," complete cds | 20 | 74 | 102 | 96 | 24 | 91 |
| U09550_at | Human oviductal glycoprotein "mRNA," complete cds | 89 | 99 | 127 | 99 | 129 | 192 |
| U09564_at | Human serine kinase "mRNA," complete cds | 117 | 79 | 247 | 104 | 132 | 43 |
| U09578_at | Human MAPKAP kinase (3pK) "mRNA," complete cds | 20 | 20 | 20 | 68 | 20 | 25 |
| U09579_at | Human melanoma differentiation associated (mda-6) "mRNA," complete cds | 242 | 61 | 20 | 203 | 315 | 131 |
| U09584_at | Human PL6 protein (PL6) "mRNA," complete cds | 136 | 130 | 83 | 104 | 40 | 20 |
| U09587_at | Human clone 53BP1 p53-binding protein "mRNA," partial cds | 144 | 178 | 135 | 163 | 50 | 210 |
| U09607_at | Human JAK family protein tyrosine kinase (JAK3) "mRNA," complete cds | 68 | 85 | 20 | 86 | 320 | 321 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| U09609_at | Human p80HT (p80HT/NKFB-2) "mRNA," complete cds | 20 | 42 | 88 | 20 | 20 | 20 | 71 |
| U09648_at | Human carnitine palmitoyltransferase II precursor (CPT1) gene | 20 | 20 | 20 | 20 | 29 | 20 | 20 |
| U09716_s_at | Human mannose-specific lectin (MR60) "mRNA," complete cds | 20 | 25 | 154 | 62 | 115 | 89 | 89 |
| U09759_at | Human protein kinase (JNK2) "mRNA," complete cds | 23 | 20 | 44 | 20 | 227 | 255 | 20 |
| U09777_at | Human cysteine-rich heart protein (hCRHP) "mRNA," complete cds | 114 | 150 | 64 | 173 | 62 | 255 | 255 |
| U09813_at | Human mitochondrial ATP synthase subunit "9," P3 gene "copy," "mRNA," nuclear gene encoding mitochondrial "protein," complete cds | 715 | 434 | 1114 | 771 | 138 | 403 | 403 |
| U09820_s_at | | 25 | 36 | 111 | 51 | 224 | 82 | 82 |
| U09825_at | Human acid finger protein "mRNA," complete cds | 85 | 52 | 204 | 164 | 20 | 197 | 197 |
| U09848_at | Human zinc finger protein (ZNF139) "mRNA," partial cds | 39 | 147 | 169 | 35 | 160 | 26 | 26 |
| U09850_at | Human zinc finger protein (ZNF143) "mRNA," complete cds | 20 | 44 | 20 | 20 | 114 | 170 | 170 |
| U09851_s_at | Human zinc finger protein (ZNF148) "mRNA," partial cds | 20 | 23 | 67 | 45 | 20 | 20 | 20 |
| U09860_at | Human enterokinase "mRNA," complete cds | 20 | 20 | 40 | 42 | 36 | 94 | 94 |
| U09877_at | Human helicase-like protein (HLP) "mRNA," complete cds | 20 | 20 | 20 | 20 | 20 | 20 | 20 |
| U09937_ma1_s_at | urokinase-type plasminogen activator gene extracted from Human urokinase-type plasminogen receptor | 20 | 40 | 82 | 124 | 33 | 136 | 136 |
| U09953_at | Human ribosomal protein L9 "mRNA," complete cds | 2506 | 2871 | 3863 | 2285 | 930 | 959 | 959 |
| U10099_s_at | Human POM-ZP3 "mRNA," complete cds | 20 | 20 | 20 | 39 | 20 | 20 | 20 |
| U10117_at | Human endothelial-monocyte activating polypeptide II "mRNA," complete cds | 70 | 20 | 116 | 20 | 20 | 20 | 20 |
| U10323_at | Human nuclear factor NF45 "mRNA," complete cds | 172 | 254 | 655 | 456 | 263 | 685 | 685 |
| U10324_at | Human nuclear factor NF90 "mRNA," complete cds | 20 | 20 | 20 | 20 | 20 | 42 | 42 |
| U10362_at | Human GP36b glycoprotein "mRNA," complete cds | 65 | 20 | 20 | 35 | 20 | 20 | 20 |
| U10439_at | Human double-stranded RNA adenosin deaminase "mRNA," complete cds | 116 | 154 | 163 | 234 | 221 | 251 | 251 |
| U10473_s_at | Human clone p4betaGT/3 "beta-1,4-galactosyltransferase" "mRNA," partial cds. /gb=U10473 /ntype=RNA | 42 | 35 | 20 | 38 | 20 | 31 | 31 |
| U10485_at | Human lymphoid-restricted membrane protein (Jaw1) "mRNA," complete cds | 47 | 20 | 75 | 116 | 20 | 229 | 229 |
| U10492_at | Human Mox1 protein (MOX1) "mRNA," complete cds | 156 | 153 | 74 | 79 | 20 | 125 | 125 |
| U10550_at | Human Gem GTPase (gem) "mRNA," complete cds | 129 | 24 | 87 | 20 | 116 | 24 | 24 |
| U10685_at | Human MAGE-10 antigen (MAGE10) "gene," complete cds | 89 | 25 | 99 | 63 | 178 | 93 | 93 |
| U10686_at | Human MAGE-11 antigen (MAGE11) "gene," complete cds | 132 | 125 | 277 | 102 | 231 | 231 | 231 |
| U10687_s_at | Human MAGE-4a antigen (MAGE4a) "gene," complete cds | 20 | 20 | 20 | 20 | 20 | 71 | 71 |
| U10689_f_at | Human MAGE-5a antigen (MAGE5a) "gene," complete cds | 20 | 20 | 58 | 20 | 412 | 29 | 29 |
| U10690_f_at | Human MAGE-5b antigen (MAGE5b) "gene," complete cds | 137 | 127 | 259 | 201 | 215 | 407 | 407 |
| U10693_at | Human MAGe-8 antigen (MAGE8) "gene," complete cds | 20 | 20 | 64 | 49 | 20 | 83 | 83 |
| U10868_at | Human aldehyde dehydrogenase ALDH7 "mRNA," complete cds | 35 | 68 | 20 | 20 | 104 | 70 | 70 |
| U10886_at | Human density enhanced phosphatase-1 "mRNA,38 complete cds | 77 | 144 | 122 | 105 | 65 | 61 | 61 |
| U10991_at | Human G2 protein "mRNA," partial cds | 20 | 20 | 37 | 20 | 20 | 20 | 20 |
| U11036_at | Human lbd1 "mRNA," partial cds. /gb=U11036 /ntype=RNA | 30 | 59 | 57 | 38 | 236 | 81 | 81 |
| U11037_at | Human Sel-1 like "mRNA," complete cds | 20 | 24 | 20 | 20 | 20 | 20 | 20 |
| U11090_at | Human hydroxyindole-O-methyltransferase promoter A-derived (HIOMT) "mRNA," complete cds | 26 | 25 | 20 | 45 | 266 | 266 | 266 |
| U11287_at | Human N-methyl-D-aspartate receptor subunit NR3 (hNR3) "mRNA," complete cds | 63 | 32 | 107 | 38 | 52 | 20 | 20 |
| U11292_at | Human Ki nuclear autoantigen "mRNA," complet ecds | 20 | 20 | 20 | 20 | 20 | 20 | 20 |
| U11313_at | Human sterol carrier protein-X/sterol carrier protein-2 (SCP-X/SCP-2) "gene," promoter and | 137 | 127 | 259 | 201 | 366 | 407 | 407 |
| U11690_at | Human faciogenital dysplasia (FGD1) "mRNA," complete cds | 20 | 20 | 64 | 49 | 20 | 83 | 83 |
| U11701_at | Human LIM-homeobox domain protein (hLH-2) "mRNA," complete cds | 74 | 68 | 20 | 20 | 215 | 85 | 85 |
| U11717_s_at | Human calcium activated potassium channel (hslo) "mRNA," complete cds | 20 | 20 | 20 | 20 | 20 | 20 | 20 |
| U11732_at | Human ets-like gene (tel) "mRNA," complete cds | 66 | 59 | 57 | 75 | 236 | 81 | 81 |
| U11791_at | Human cyclin H "mRNA," complete cds | 85 | 20 | 20 | 81 | 66 | 24 | 24 |
| U11821_s_at | Human Fas ligand (FasL) "mRNA," complete cds | 20 | 20 | 20 | 20 | 70 | 193 | 193 |
| U11861_at | Human G10 homolog (edg-2) "mRNA," complete cds | 432 | 536 | 525 | 431 | 585 | 462 | 462 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U11862_s_at | Human clone HP-DAO1 diamine "oxidase," copper/topa quinone-containing "mRNA," complete cds | 20 | 20 | 20 | 20 | 250 | 20 |
| U11863_at | Human clone HP-DAO2 diamine "oxidase," copper/topa quinone containing "mRNA," complete cds | 20 | 20 | 20 | 20 | 20 | 20 |
| U11870_ma1_at | Human interleukin-8 receptor type A (IL8RBA) gene, promoter and complete cds. | 20 | 22 | 20 | 48 | 20 | 67 |
| U11872_at | Human interleukin-9 receptor type B (IL8RB) "mRNA," splice variant "IL8RB1," partial cds. /gb=U11872 /ntype=RNA | 20 | 71 | 53 | 49 | 135 | 105 |
| U11875_s_at | Human interleukin-8 receptor type B (IL8RB) "mRNA," splice variant "IL8RB4," partial cds. /gb=U11875 /ntype=RN | 56 | 39 | 136 | 29 | 275 | 140 |
| U11877_at | Human interleukin-8 receptor type B (IL8RB) "mRNA," splice variant "IL8RB9," partial cds. /gb=U11877 /ntype=RNA | 51 | 60 | 20 | 20 | 177 | 20 |
| U11878_at | Human interleukin-8 receptor type B (IL8RB) "mRNA," splice variant "IL8RB10," partial cds. /gb=U11878 /ntype=RNA | 20 | 20 | 20 | 20 | 20 | 86 |
| U12139_at | Human alpha(XI) collagen (COL11A1) gene, 5' region and exon 1 /gb=U12139 /ntype=DNA /annot=exon | 261 | 243 | 20 | 169 | 548 | 20 |
| U12140_at | Human tyrosine kinase receptor p145TRK-B (TRK-B) "mRNA," complete cds | 27 | 20 | 84 | 52 | 106 | 66 |
| U12255_at | Human IgG Fc receptor hFcRn "mRNA," complete cds | 195 | 195 | 332 | 133 | 321 | 261 |
| U12259_cds2_s_at | Human paired box homeotic protein (PAX3) gene | 20 | 20 | 20 | 20 | 283 | 24 |
| U12387_s_at | Human thiopurine methyltransferase (TPMT) "mRNA," complete cds | 25 | 22 | 70 | 27 | 20 | 129 |
| U12404_s_at | Human Csa-19 "mRNA," complete cds | 2522 | 2665 | 5158 | 3551 | 551 | 932 |
| U12424_s.at | Human mitochondrial glycerol-3-phosphate dehydrogenase "mRNA," complete cds | 20 | 23 | 20 | 20 | 20 | 20 |
| U12465_at | Human ribosomal protein L35 "mRNA," complete cds | 3327 | 4503 | 3996 | 2911 | 1024 | 2021 |
| U12471_cds1_at | Human thrombospondin-1 gene, partial cds. | 70 | 75 | 20 | 61 | 156 | 135 |
| U12535_at | Human epidermal growth factor receptor kinase substrate (Eps8) "mRNA,"]complete cds | 20 | 50 | 62 | 65 | 89 | 84 |
| U12595_at | Human tumor necrosis factor type 1 receptor associated protein (TRAP1) "mRNA," partial cds | 41 | 20 | 47 | 23 | 20 | 20 |
| U12622_at | Human beaded intermediate filament protein CP115 "mRNA," partial cds. /gb=U12622 /ntype=RNA | 71 | 107 | 107 | 117 | 242 | 148 |
| U12707_s_at | Human Wiskott-Aldrich syndrome protein (WASP) "mRNA," complete cds | 20 | 20 | 20 | 20 | 20 | 20 |
| U12767_at | Human mitogen induced nuclear orphan receptor (MINOR) "mNRA," complete cds | 154 | 20 | 20 | 20 | 20 | 20 |
| U12775_at | Human agouti gene | 35 | 20 | 20 | 20 | 20 | 20 |
| U12778_at | Human acyl-CoA dehydrogenase "mRNA," complete cds | 20 | 20 | 20 | 20 | 20 | 45 |
| U12779_at | Human MAP kinase activated protein kinase 2 "mRNA," complete cds | 434 | 367 | 50 | 345 | 962 | 756 |
| U12897_at | Human non-translated mRNA sequence | 20 | 20 | 20 | 20 | 185 | 20 |
| U12978_at | Human sperm membrane protein BS-84 (HSD-1) "mRNA," complete cds | 20 | 127 | 20 | 20 | 89 | 64 |
| U13021_s_at | Human positive regulator of programmed cell death ICH-1L (Ich-1) "mRNA," complete cds | 20 | 20 | 20 | 20 | 20 | 20 |
| U13022_at | Human negative regulator of programmed cell death ICH-1S (Ich-1) "mRNA," complete cds | 26 | 84 | 75 | 112 | 109 | 33 |
| U13044_at | Human nuclear respiratory factor-2 subunit alpha "mRNA," complete cds | 20 | 22 | 26 | 29 | 171 | 161 |
| U13045_at | Human nuclear respiratory factor-2 subunit beta 1 "mRNA," complete cds | 20 | 87 | 74 | 20 | 205 | 187 |
| U13061_ma1_at | Human dehydroepiandrosterone sulfotransferase (STD) gene, exon 6 and complete cds. | 20 | 107 | 20 | 20 | 20 | 20 |
| U13219_at | Human forkhead protein FREAC-1 "mRNA," complete cds | 111 | 160 | 72 | 20 | 36 | 135 |
| U13220_at | Human forkhead protein FREAC-2 "mRNA," partial cds | 20 | 20 | 69 | 20 | 67 | 20 |
| U13369_at | Human ribosomal DNA complete repeating unit. /gb=U13369 /ntype=DNA /annot=CDS | 20 | 20 | 20 | 20 | 38 | 20 |
| U13395_at | Human oxidoreductase (HHCMA56) "mRNA," complete cds | 96 | 128 | 113 | 124 | 250 | 137 |
| U13616_at | Human ankyrin G (ANK-3) "mRNA," complete cds | 20 | 78 | 81 | 61 | 91 | 59 |
| U13666_at | Human G protein-coupled receptor (GPR1) "gene," complete cds | 85 | 29 | 125 | 87 | 168 | 163 |
| U13680_at | Human lactate dehydrogenase0C (LDH-C) "mRNA," complete cds | 20 | 20 | 20 | 20 | 20 | 20 |
| U13695_at | Human homolog of yeast mutL (hPMS1) "gene," complete cds | 95 | 126 | 156 | 31 | 147 | 20 |
| U13696_s_at | Human homolog of yeast mutL (hPMS2) "gene," complete cds | 20 | 20 | 20 | 20 | 20 | 20 |
| U13706_at | Human ELAV-like neuronal protein 1 isoform Hel-N2 (Hel-N1) "mRNA," partial cds. /gb=U13706 /ntype=RNA | 84 | 73 | 20 | 20 | 20 | 20 |
| U13737_at | Human cysteine protease CPP32 isoform alpha "mRNA," complete cds | 20 | 20 | 49 | 27 | 20 | 43 |
| U13896_at | Human homolog of Drosophila discs large "protein," isoform 2 (hdlg-2) "mRNA," complete cds | 20 | 20 | 20 | 20 | 20 | 20 |
| U13913_s_at | Human large-conductance calcium-activated potassium channel (hSlo) "mRNA," complete cds | 20 | 128 | 113 | 20 | 20 | 20 |
| U13948_at | Human zinc finger/leucine zipper protein (AF10) "mRNA," complete cds | 37 | 78 | 81 | 35 | 20 | 27 |
| U13991_at | Human TATA-binding protein associated factor 30 kDa subunit (tafII30) "mRNA," complete cds | 67 | 22 | 76 | 32 | 20 | 20 |
| U14187_at |  | 77 | 113 | 127 | 106 | 396 | 203 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U14193_at | Human TFIIA gamma subunit "mRNA," complete cds | 109 | 170 | 150 | 128 | 162 | 45 |
| U14383_at | Human mucin (MUC8) "mRNA," partial cds | 20 | 20 | 20 | 24 | 161 | 76 |
| U14391_at | Human myosin-IC "mRNA," complete cds | 129 | 33 | 180 | 116 | 20 | 20 |
| U14394_at | Human tissue inhibitor of metalloproteinases-3 "mRNA," complete cds | 456 | 273 | 527 | 397 | 666 | 191 |
| U14407_at | Human interleukin 15 (IL15) "mRNA," complete cds | 20 | 20 | 20 | 20 | 20 | 20 |
| U14417_at | Human Ral guanine nucleotide dissociation stimulator "mRNA," partial cds | 108 | 80 | 129 | 80 | 62 | 147 |
| U14518_at | Human centromere protein-A (CENP-A) "mRNA," complete cds | 20 | 98 | 20 | 47 | 66 | 20 |
| U14528_at | Human sulfate transporter (DTD) "mRNA," complete cds | 20 | 20 | 38 | 41 | 20 | 20 |
| U14550_at | Human sialyltransferase SThM (sthm) "mRNA," complete cds | 31 | 95 | 126 | 30 | 106 | 20 |
| U14575_at | Human (ard-1) "mRNA," complete cds | 20 | 20 | 20 | 22 | 99 | 20 |
| U14577_s_at | Human microtubule-associated protein 1A (MAP1A) "mRNA," complete cds | 20 | 20 | 20 | 20 | 20 | 20 |
| U14588_at | Human paxillin "mRNA," complete cds | 111 | 104 | 227 | 90 | 23 | 1967 |
| U14603_at | Human protein-tyrosine phosphatase (HU-PP-1) "mRNA," partial sequence | 78 | 337 | 250 | 111 | 20 | 75 |
| U14747_at | Human visinin-like peptide 1 homolog "mRNA," complete cds | 76 | 36 | 20 | 43 | 20 | 20 |
| U14910_at | Human RPE-retinal G protein-coupled receptor (rgr) "mRNA," complete cds | 20 | 20 | 20 | 20 | 182 | 20 |
| U14968_at | Human ribosomal protein L27a "mRNA," complete cds | 3885 | 4706 | 5688 | 3843 | 1324 | 1967 |
| U14969_at | Human ribosomal protein L28 "mRNA," complete cds | 4539 | 5259 | 8309 | 7017 | 2386 | 5283 |
| U14970_at | Human ribosomal protein S5 "mRNA," complete cds | 3928 | 2723 | 7035 | 5089 | 858 | 2541 |
| U14971_at | Human ribosomal protein S9 "mRNA," complete cds | 2645 | 2924 | 4114 | 2854 | 412 | 1012 |
| U14972_at | Human ribosomal protein S10 "mRNA," complete cds | 3695 | 5247 | 4461 | 4046 | 594 | 1689 |
| U14973_at | Human ribosomal protein S29 "mRNA," complete cds | 4281 | 6948 | 8336 | 3884 | 2327 | 3059 |
| U15008_at | Human SnRNP core protein Sm D2 "mRNA," complete cds | 816 | 1556 | 1853 | 1076 | 974 | 1223 |
| U15009_at | Human SnRNP core protein SM D3 "mRNA," complete cds | 113 | 91 | 155 | 82 | 20 | 130 |
| U15085_at | Human HLA-DMB "mRNA," complete cds | 306 | 275 | 146 | 175 | 438 | 524 |
| U15128_at | Human "beta-1,2-N-acetylglucosaminyltransferase" II (MGAT2) "gene," complete cds | 20 | 20 | 60 | 25 | 20 | 55 |
| U15131_at | Human p126 (ST5) "mRNA," complete cds | 20 | 49 | 20 | 20 | 20 | 57 |
| U15172_at | Human Nip1 (NIP1) "mRNA," complete cds | 136 | 203 | 220 | 38 | 205 | 125 |
| U15173_at | Human Nip2 (NIP2) "mRNA," complete cds | 20 | 20 | 55 | 22 | 20 | 41 |
| U15174_at | Human Nip3 (NIP3) "mRNA," complete cds | 83 | 20 | 121 | 69 | 20 | 20 |
| U15177_at | Human cosmid CFJ-JC2015 at D10S289 in 10sp13 | 99 | 173 | 88 | 102 | 189 | 137 |
| U15197_at | Human histo-blood group ABO protein "mRNA," partial 3' UTR sequence | 199 | 286 | 201 | 205 | 570 | 390 |
| U15306_at | Human cysteine-rich sequence-specific DNA-binding protein NFX1 "mRNA," complete cds | 20 | 20 | 20 | 20 | 20 | 20 |
| U15422_cds2_at | Human protamine 1 (PRM1), protamine 2 (PRM2) and transition protein 2 (TNP2) genes, complete cds. | 20 | 20 | 20 | 20 | 20 | 20 |
| U15460_at | Human bZip protein B-ATF "mRNA," complete cds | 20 | 20 | 20 | 20 | 20 | 20 |
| U15552_at | Human acidic 82 kDaprotein "mRNA," complete cds | 31 | 75 | 109 | 66 | 544 | 114 |
| U15555_at | Human serine palmitoyltransferase (LCB2) "mRNA," partial cds | 20 | 20 | 20 | 20 | 20 | 20 |
| U15590_at | Human heat shock protein 27 (HSP27) "mRNA," complete cds | 20 | 73 | 86 | 56 | 32 | 44 |
| U15637_s_at | Human CD40 (binding protein (CD40bp) "mRNA," complete cds | 70 | 20 | 20 | 20 | 20 | 20 |
| U15641_s_at | Human transcription factor E2F-4 "mRNA," complete cds | 114 | 122 | 208 | 105 | 20 | 180 |
| U15642_s_at | Human transcription factor E2F-5 "mRNA," complete cds | 375 | 67 | 90 | 49 | 70 | 20 |
| U15655_at | Human ets domain protein ERF "mRNA," complete cds | 103 | 37 | 20 | 20 | 168 | 81 |
| U15782_at | Human cleavage stimulation factor 77kDa subunit "mRNA," complete cds | 20 | 20 | 20 | 20 | 246 | 93 |
| U15932_at | Human dual-specificity protein phosphatase IL-4 Stat "mRNA," complete cds | 20 | 20 | 20 | 20 | 52 | 20 |
| U16031_at | Human placental taurine transporter "mRNA," complete cds | 20 | 20 | 20 | 56 | 20 | 20 |
| U16120_s_at | Human glutamate/kainate receptor subunit (EAA4) "mRNA," complete cds | 20 | 20 | 20 | 118 | 20 | 20 |
| U16126_at | Human glutamate/kainate receptor subunit (EAA5) "mRNA," complete cds | 173 | 196 | 53 | 247 | 107 | 107 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U16129_at | Human glutamate receptor (GluR4) "mRNA," complete cds. | 55 | 20 | 20 | 20 | 84 | 20 |
| U16258_at | Human I kappa BR "mRNA," complete cds | 58 | 20 | 20 | 20 | 20 | 20 |
| U16261_at | Human MDA-7 (mda-7) "mRNA," complete cds | 20 | 20 | 20 | 20 | 192 | 39 |
| U16282_at | Human ELL "mRNA," complete cds | 97 | 115 | 20 | 66 | 192 | 20 |
| U16296_at | Human T-lymphoma invasion and metastasis inducing TIAM1 protein (TIAM1) "mRNA," complete cds | 65 | 44 | 71 | 51 | 98 | 53 |
| U16306_at | Human chondroitin sulfate proteoglycan versican VD splice-variant precursor peptide "mRNA," complete cds | 20 | 42 | 20 | 20 | 98 | 48 |
| U16307_at | Human glioma pathogenesis-related protein (GliPR) "mRNA," complete cds | 20 | 33 | 60 | 29 | 107 | 20 |
| U16660_at | Human peroxisomal enoyl-CoA hydratase-like protein (HPXEL) "mRNA," complete cds | 39 | 74 | 20 | 43 | 20 | 20 |
| U16720_ma1_s_at | Human interleukin 10 (IL10) "gene," complete cds | 26 | 25 | 98 | 33 | 87 | 38 |
| U16799_s_at | Human "Na, K-ATPase" beta-1 subunit "mRNA," complete cds | 223 | 163 | 256 | 334 | 20 | 20 |
| U16811_s_at | Human Bak "mRNA," complete cds | 20 | 30 | 20 | 20 | 76 | 20 |
| U16812_s_at | Human Bak-2 "gene," complete cds | 20 | 51 | 66 | 37 | 20 | 65 |
| U16861_at | Human inward rectifying potassium channel "mRNA," complete cds | 39 | 20 | 20 | 20 | 59 | 178 |
| U16954_at | Human (AF1q) "mRNA," complete cds | 20 | 20 | 20 | 20 | 20 | 20 |
| U16997_at | Human orphan receptor ROR gamma "mRNA," complete cds | 20 | 20 | 58 | 76 | 253 | 36 |
| U17032_at | Human p190-B (p190-B) "mRNA," complete cds | 26 | 20 | 20 | 20 | 20 | 20 |
| U17033_at | Human 180 kDa transmembrane PLA2 receptor "mRNA," complete cds | 20 | 20 | 20 | 20 | 113 | 20 |
| U17034_at | Human soluble PLA2 receptor "mRNA," complete cds | 23 | 56 | 20 | 20 | 20 | 20 |
| U17077_at | Human BENE "mRNA," partial cds | 841 | 119 | 47 | 35 | 38 | 20 |
| U17163_at | Human transcription factor ETV1 "mRNA," complete cds | 59 | 20 | 54 | 49 | 131 | 61 |
| U17195_at | Human A-kinase anchor protein (AKAP100) "mRNA," complete cds | 47 | 20 | 78 | 40 | 20 | 44 |
| U17280_at | Human steroidogenic acute regulatory protein (StAR) "mRNA," complete cds | 20 | 20 | 20 | 20 | 20 | 42 |
| U17327_at | Human neuronal nitric oxide synthase (NOS1) "mRNA," complete cds | 40 | 171 | 145 | 159 | 458 | 145 |
| U17418_at | Human parathyroid hormone/parathyroid hormone-related peptide receptor "mRNA," complete cds | 30 | 65 | 154 | 78 | 77 | 20 |
| U17566_at | Human 65 kDa hydrophobic protein "mRNA," complete cds | 20 | 20 | 20 | 20 | 20 | 20 |
| U17579_ma1_at | Human growth hormone-releasing hormone receptor gene, alternatively spliced forms a, b, and c, partial cds. | 20 | 20 | 48 | 20 | 20 | 52 |
| U17714_at | Human putative tumor suppressor (SNC6) "mRNA," complete cds | 20 | 20 | 21 | 20 | 20 | 20 |
| U17743_s_at | Human JNK activating kinase (JNKK1) "mRNA," complete cds | 41 | 20 | 20 | 36 | 74 | 20 |
| U17760_ma1_at | Human laminin S B3 chain (LAMB3) gene, exon 23, and complete cds | 20 | 20 | 460 | 143 | 20 | 52 |
| U17838_at | Human zinc finger protein RIZ "mRNA," complete cds | 20 | 20 | 20 | 20 | 20 | 56 |
| U17886_at | Human succinate dehydrogenase iron-protein subunit (sdhB) gene | 68 | 39 | 118 | 55 | 20 | 95 |
| U17894_at | Human "alpha(1,2)fucosyltransferase" (FUT2) "gene," complete cds | 131 | 127 | 20 | 105 | 135 | 200 |
| U17969_at | Human initiation factor eIF-5A "gene," complete cds | 20 | 38 | 20 | 20 | 71 | 57 |
| U17989_at | HSU17977 Homo sapiens cDNA | 20 | 65 | 20 | 20 | 20 | 20 |
| U18004_at | HSU18004 Homo sapiens cDNA | 44 | 39 | 30 | 32 | 20 | 53 |
| U18009_at | Human chromosome 17q21 mRNA clone LF113 | 163 | 62 | 83 | 20 | 23 | 98 |
| U18018_at | Human E1A enhancer binding protein (E1A-F) "mRNA," partial cds | 20 | 20 | 20 | 25 | 76 | 20 |
| U18062_at | Human TFIID subunit TAFII55 (TAFII55) "mRNA," complete cds | 50 | 27 | 130 | 110 | 20 | 72 |
| U18088_s_at | HUman "3′,5′-cyclic" AMP phosphodiesterase inactive splice variant HSPDE4A8A "mRNA," complete cds | 20 | 20 | 20 | 20 | 20 | 20 |
| U18235_at | Human ATP-binding cassette protein (ABC2) mRNA HFBCD04 "clone," partial cds | 20 | 39 | 20 | 20 | 79 | 91 |
| U18237_at | Human ATP-binding cassette protein mRNA 06B09 "clone," partial cds | 20 | 51 | 20 | 20 | 20 | 20 |
| U18242_at | Human calcium modulating cyclophilin ligand (CAMLG) "mRNA," complete cds | 70 | 21 | 20 | 32 | 20 | 20 |
| U18244_at | Human excitatory amino acid transporter 4 "mRNA," complete cds | 20 | 20 | 20 | 41 | 292 | 20 |
| U18259_at | Human clone CIITA-8 MHC class II transactivator CIITA "mRNA," complete cds | 20 | 20 | 20 | 20 | 20 | 22 |
| U18271_cds1_at | Human thymopoietin (TMPO) gene, partial exon 6, complete exon 7, partial exon 8, and partial cds for thymopoietin beta. | 23 | 20 | 20 | 20 | 20 | 22 |
| U18271_cds3_s_at | Human thymopoietin (TMPO) gene | 20 | 20 | 52 | 50 | 190 | 35 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U18288_at | Human clone CIITA-10 MHC class II transactivator CIITA "mRNA," complete cds | 27 | 20 | 20 | 20 | 20 | 20 |
| U18291_at | Human CDC 16Hs "mRNA," complete cds | 66 | 20 | 108 | 77 | 20 | 20 |
| U18297_s_at | Human MST1 (MST1) "mRNA," complete cds | 20 | 20 | 20 | 20 | 20 | 20 |
| U18300_at | Human damage-specific DNA binding protein p48 subunit (DDB2) "mRNA," complete cds | 80 | 20 | 183 | 62 | 66 | 44 |
| U18321_at | Human ionizing radiation resistance conferring protein "mRNA," complete cds | 38 | 48 | 39 | 57 | 20 | 58 |
| U18383_s_at | Human nuclear respiratory factor 1 (NRF-1) gene | 20 | 20 | 20 | 20 | 20 | 20 |
| U18422_at | Human DP2 (Humdp2) "mRNA," complete cds | 20 | 52 | 48 | 51 | 20 | 64 |
| U18467_at | Human pregnancy-specific beta 1-glycoprotein 7 (PSG7) "mRNA," complete cds | 46 | 64 | 139 | 115 | 98 | 40 |
| U18543_at | Human zinc-finger protein "mRNA," complete cds | 51 | 143 | 67 | 44 | 251 | 234 |
| U18548_at | Human GPR12 G protein coupled-receptor gene, complete cds. | 69 | 20 | 102 | 51 | 20 | 20 |
| U18549_at | Human GPR6 G protein-coupled receptor "gene," complete cds | 44 | 20 | 20 | 20 | 20 | 44 |
| U18550_at | Human GPR3 G protein-coupled receptor "gene," complete cds | 20 | 110 | 28 | 20 | 20 | 112 |
| U18671_ma1_at | Human Stat2 gene, complete cds. | 51 | 24 | 58 | 43 | 207 | 20 |
| U18914_at | Human 19.8 kDa protein "mRNA," complete cds | 71 | 20 | 20 | 20 | 20 | 20 |
| U18919_at | Human chromosome 17q12–21 "mRNA," clone "pOV-2," partial cds | 20 | 20 | 56 | 20 | 154 | 26 |
| U18932_at | Human heparan sulfate-N-deacetylase/N-sulfotransferase "mRNA," clone "HSST3", 3UTR | 20 | 132 | 20 | 31 | 20 | 20 |
| U18934_at | Human receptor tyrosine kinase (DTK) "mRNA," complete cds | 20 | 20 | 23 | 20 | 20 | 20 |
| U18937_at | Human histidyl-tRNA synthetase homolog (HO3) "mRNA," complete cds | 45 | 164 | 79 | 154 | 211 | 126 |
| U18965_at | Human triadin "mRNA," complete cds | 20 | 40 | 20 | 20 | 60 | 20 |
| U18991_at | Human retinal pigment epithelium-specific 61 kDa protein (RPE65) "mRNA," complete cds | 31 | 132 | 56 | 31 | 139 | 88 |
| U19107_ma1_at | Human ZNF127 (ANF127) gene, complete cds | 20 | 31 | 20 | 34 | 298 | 59 |
| U19142_at | Human GAGE-1 protein "mRNA," complete cds | 20 | 20 | 23 | 28 | 200 | 42 |
| U19147_s_at | Human GAGE-6 protein "mRNA," complete cds | 20 | 66 | 20 | 20 | 20 | 20 |
| U19180_at | Human B melanoma antigen (BAGE) "mRNA," complete cds | 26 | 60 | 26 | 20 | 20 | 85 |
| U19247_ma1_s_at | Human interferon-gamma receptor alpha chain gene | 72 | 76 | 239 | 196 | 20 | 39 |
| U19252_s_at | Human putative transmembrane protein "mRNA," complete cds | 29 | 63 | 121 | 98 | 20 | 20 |
| U19261_at | Human Epstein-Barr virus-induced protein "mRNA," complete cds | 20 | 20 | 47 | 20 | 63 | 20 |
| U19345_at | Human AR1 protein (AR) "mRNA," complete cds | 91 | 168 | 20 | 150 | 153 | 252 |
| U19487_at | Human microfibril-associated glycoprotein (MFAP2) "mRNA," complete cds | 20 | 87 | 29 | 49 | 20 | 20 |
| U19495_s_at | Human intercrine-alpha (hIRH) "mRNA," complete cds | 88 | 20 | 26 | 20 | 20 | 155 |
| U19517_at | Human (apoargC) long "mRNA," complete cds | 20 | 71 | 53 | 25 | 43 | 20 |
| U19523_at | Human GTP cyclohydrolase I "mRNA," complete cds | 20 | 20 | 65 | 85 | 20 | 249 |
| U19557_s_at | Human squamous cell carcinoma antigen 2 (SCCA2) "mRNA," complete cds | 43 | 271 | 20 | 156 | 234 | 20 |
| U19713_s_at | Human allograft-inflammatory factor-1 "mRNA," complete cds | 1195 | 62 | 46 | 20 | 20 | 76 |
| U19718_at | Human arginine vasopressin receptor 1 (AVPR1) "gene," complete cds | 67 | 100 | 47 | 20 | 83 | 25 |
| U19765_at | Human protein disulfide isomerase (PDIp) "mRNA," complete cds | 20 | 20 | 29 | 33 | 20 | 190 |
| U19796_at | Human preprocarboxypeptidase A2 (proCPA2) "mRNA," complete cds | 28 | 87 | 24 | 87 | 67 | 285 |
| U19878_at | Human 76 kDa tyrosine phosphoprotein SLP-76 "mRNA," complete cds | 32 | 31 | 65 | 20 | 78 | 79 |
| U19906_at | Human nucleic acid binding protein "gene," complete cds | 20 | 20 | 20 | 85 | 20 | 118 |
| U19948_at | Human melanoma antigen p15 "mRNA," complete cds | 160 | 271 | 65 | 156 | 199 | 49 |
| U19977_at | Human transmembrane protein "mRNA," complete cds | 32 | 20 | 20 | 20 | 234 | 249 |
| U20158_at | Human guanyl cyclase C "gene," partial cds. /gb=U20230 /ntype=DNA /annot=exon | 29 | 55 | 21 | 20 | 20 | 76 |
| U20230_at | Human C/EBP gamma "mRNA," complete cds | 115 | 62 | 20 | 104 | 67 | 25 |
| U20240_at | Human Gps1 (GPS1) "mRNA," complete cds | 74 | 26 | 24 | 87 | 78 | 46 |
| U20285_at | Human protein disulfide isomerase (PDIp) "mRNA," complete cds | 20 | 20 | 20 | 20 | 20 | 387 |
| U20325_at | Human cocaine and amphetamine regulated transcript CART (hCART) "gene," complete cds | 240 | 246 | 259 | 322 | 567 | 387 |
| | | 63 | 157 | 87 | 77 | 321 | 131 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U20350_at | Human G protein-coupled receptor V28 "mRNA," complete cds | 20 | 20 | 21 | 30 | 117 | 58 |
| U20362_at | Human Tg737 "mRNA," complete cds | 20 | 20 | 20 | 20 | 20 | 20 |
| U20391_ma6_at | Human folate receptor (FOLR1) gene, complete cds. | 94 | 20 | 139 | 20 | 20 | 20 |
| U20428_at | Human SNC19 mRNA sequence | 38 | 20 | 89 | 20 | 128 | 33 |
| U20499_at | Human thermolabile phenol sulfotransferase (stm) "gene," complete cds | 20 | 227 | 89 | 100 | 253 | 23 |
| U20530_at | Human bone phosphoprotein spp-24 precursor "mRNA," complete cds. /gb=U20530 /ntype=RNA | 56 | 36 | 126 | 71 | 353 | 73 |
| U20536_s_at | human cysteine protease Mch2 isoform alpha (Mch2) "mRNA," complete cds | 20 | 69 | 52 | 105 | 49 | 53 |
| U20582_at | Human actin-like peptide "mRNA," partial cds | 99 | 154 | 80 | 84 | 406 | 253 |
| U20647_at | Human zinc finger protein (ZNF151) "mRNA," partial cds | 62 | 22 | 48 | 48 | 134 | 122 |
| U20648_at | Human zinc finger protein (ZNF154) "mRNA," partial cds | 20 | 42 | 20 | 22 | 23 | 20 |
| U20657_at | Human ubiquitin protease (Unph) proto-oncogene "mRNA," complete cds | 21 | 134 | 20 | 20 | 20 | 20 |
| U20734_s_at | Human transcription factor junB (junB) "gene," 5' region and complete cds | 1069 | 58 | 824 | 1250 | 20 | 197 |
| U20758_ma1_at | Human osteopontin gene, complete cds. | 20 | 63 | 20 | 20 | 46 | 164 |
| U20759_s_at | Human parathyroid cell calcium-sensing receptor "mRNA," complete cds | 20 | 20 | 20 | 20 | 20 | 20 |
| U20760_at | Human extracellular calcium-sensing receptor "mRNA," complete cds | 20 | 20 | 20 | 20 | 109 | 45 |
| U20816_s_at | Human nuclear factor kappa-B2 (NF-KB2) "gene," partial cds. /gb=U20816 /ntype=DNA /annot=mRNA | 20 | 20 | 20 | 20 | 20 | 20 |
| U20860_at | Human angiotensin II type 2 receptor "gene," complete cds | 20 | 20 | 20 | 20 | 20 | 20 |
| U20908_at | Human clone 350/2 malanoma ubiquitous mutated protein (MUM-1) "gene," partial cds. /gb=U20908 /ntype=DNA /annot=CDS | 30 | 272 | 241 | 146 | 167 | 269 |
| U20938_at | Human lymphocyte dihydropyrimidine dehydrogenase "mRNA," complete cds. | 64 | 50 | 26 | 22 | 112 | 22 |
| U20979_at | Human chromatin assembly factor-I p150 subunit "mRNA," complete cds | 64 | 20 | 20 | 96 | 20 | 20 |
| U20980_at | Human chromatin assembly factor-I p60 subunit "mRNA," complete cds | 20 | 20 | 20 | 20 | 20 | 20 |
| U20998_at | Homo sapiens signal recognition particle subunit 9 (SRP9) "mRNA," complete cds | 196 | 115 | 584 | 277 | 120 | 230 |
| U21049_at | Human DD96 "mRNA," complete cds | 165 | 130 | 20 | 20 | 20 | 174 |
| U21051_ma1_at | Human G protein-coupled receptor (GPR4) gene, complete cds. | 20 | 20 | 20 | 20 | 20 | 20 |
| U21090_at | Human DNA polymerase delta small subunit "mRNA," complete cds | 48 | 20 | 20 | 20 | 20 | 20 |
| U21128_at | Human lumican "mRNA," complete cds. | 510 | 327 | 29 | 32 | 89 | 20 |
| U21551_at | Human ECA39 "mRNA," complete cds. /gb=U21551 /ntype=RNA | 20 | 20 | 20 | 40 | 20 | 20 |
| U21556_at | Human membrane protein-like protein "mRNA," partial cds. /gb=U21556 /ntype=RNA | 20 | 20 | 20 | 20 | 299 | 64 |
| U21689_at | Human glutathione S-transferase-P1c "gene," complete cds | 20 | 20 | 20 | 20 | 809 | 222 |
| U21858_at | Human transcriptional activation factor TAFII32 "mRNA," complete cds | 20 | 20 | 66 | 37 | 116 | 20 |
| U21931_at | Human 100 kDa coactivator "mRNA," complete cds | 55 | 115 | 20 | 112 | 155 | 20 |
| U21936_at | Human "fructose-1,6-biphosphatase" (FBP1) gene | 229 | 868 | 1283 | 1269 | 739 | 117 |
| U21943_at | Human peptide transporter (HPEPT1) "mRNA," complete cds | 20 | 44 | 75 | 84 | 34 | 900 |
| U22028_r_at | Human organic anion transporting polypeptide (OATP) "mRNA," complete cds | 20 | 20 | 43 | 20 | 20 | 92 |
| U22028_f_at | Human cytochrome P450 (CYP2A13) "gene," complete cds | 20 | 20 | 20 | 20 | 20 | 20 |
| U22029_f_at | Human cytochrome P450 (CYP2A13) "gene," complete cds | 20 | 20 | 136 | 20 | 20 | 222 |
| U22055_at | Human cytochrome P450 (CYP2A7) "mRNA," complete cds | 20 | 20 | 20 | 20 | 20 | 20 |
| U22178_s_at | Human prostatic secretory protein 57 "mRNA," complete cds. /gb=U22178 /ntype=RNA | 55 | 127 | 176 | 112 | 116 | 20 |
| U22233_at | Human methylthioadenosine phosphorylase (MTAP) "mRNA," complete cds | 20 | 34 | 20 | 89 | 29 | 27 |
| U22314_s_at | Human REST protein "mRNA," complete cds | 20 | 62 | 20 | 20 | 30 | 20 |
| U22322_s_at | Human nuclear tyrosine protein kinase Rak "mRNA," complete cds | 20 | 46 | 20 | 20 | 71 | 20 |
| U22376_cds2_s_at | c-myb gene extracted from Human (c-myb) "gene," complete primary "cds," and five complete alternatively spliced cds | 20 | 20 | 20 | 20 | 20 | 47 |
| U22377_at | Human Zn-15 related zinc finger protein (rlf) "mRNA," complete cds | 52 | 20 | 20 | 79 | 339 | 238 |
| U22398_at | Human Cdk-inhibitor p57KIP2 (KIP2) "mRNA," complet cds | 20 | 76 | 20 | 28 | 284 | 101 |
| U22431_s_at | Human hypoxia-inducible factor 1 alpha (HIF-1 alpha) "mRNA," complete cds | 98 | 135 | 113 | 87 | 153 | 24 |
| U22526_at | Human "2,3-oxidosqualene-lanosterol" cyclase "mRNA," complete cds | 20 | 94 | 20 | 46 | 20 | 124 |
| U22662_at | Human nuclear orphan receptor LXR-alpha "mRNA," complete cds | 83 | 169 | 30 | 123 | 121 | 328 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U22680_at | Human X2 box repressor "mRNA," complete cds | 20 | 20 | 20 | 20 | 20 | 20 |
| U22815_at | Human LAR-interacting protein 1a "mRNA," complete cds | 20 | 20 | 97 | 81 | 479 | 52 |
| U22816_at | Human LAR-interacting protein 1b "mRNA," complete cds | 20 | 28 | 20 | 20 | 20 | 20 |
| U22897_at | Homo sapiens nuclear domain 10 protein (ndp52) "mRNA," complete cds | 50 | 20 | 51 | 20 | 161 | 45 |
| U22961_s_at | Human mRNA clone with similarity to L-glycerol-3-phosphate:NAD oxidoreductase and albumin gene sequences | 22 | 52 | 61 | 24 | 20 | 60 |
| U22963_at | Human class I histocompatibility antigen-like protein mRNA, complete cds. | 73 | 184 | 89 | 145 | 97 | 118 |
| U22970_ma1_s_at | 16-Jun gene (interferon-inducible peptide precursor) extracted from Human interferon-inducible peptide (6–16) "gene," complete cds | 20 | 20 | 20 | 20 | 20 | 219 |
| U23028_at | Human eukaryotic initiation factor 2B-epsilon "mRNA," partial cds | 20 | 20 | 47 | 49 | 94 | 20 |
| U23070_at | Human putative transmembrane protein (nma) "mRNA," complete cds | 65 | 20 | 109 | 97 | 20 | 277 |
| U23143_at | Human mitochondrial serine hydroxymethyltransferase "gene," nuclear encoded mitochondrion "protein," complete cds | 66 | 87 | 86 | 185 | 45 | 186 |
| U23430_s_at | Human cholecystokinin type A receptor (CCK-A) gene | 20 | 26 | 20 | 20 | 266 | 121 |
| U23435_s_at | Human Abl interactor 2 (Abi-2) "mRNA," complete cds | 20 | 20 | 20 | 20 | 20 | 20 |
| U23736_s_at |  | 20 | 20 | 20 | 20 | 20 | 20 |
| U23752_at | Human SOX-11 "mRNA," complete cds | 29 | 20 | 20 | 20 | 39 | 20 |
| U23803_s_at | Human heterogeneous ribonucleoprotein A0 "mRNA," complete cds | 136 | 87 | 20 | 191 | 138 | 308 |
| U23850_s_at | Human inositol "1,4,5" trisphosphate receptor type 1 "mRNA," partial cds | 32 | 20 | 22 | 56 | 25 | 75 |
| U23852_s_at |  | 84 | 94 | 179 | 86 | 190 | 109 |
| U23942_at | Human lanosterol 14-demethylase cytochrome P450 (CYP51) "mRNA," complete cds | 56 | 20 | 61 | 20 | 117 | 78 |
| U23946_at | Human putative tumor suppressor (LUCA15) "mRNA," complete cds | 47 | 20 | 195 | 58 | 225 | 201 |
| U24056_s_at | Human inward rectifier K+ channel protein (hiri2) "mRNA," complete cds | 30 | 35 | 234 | 136 | 489 | 163 |
| U24105_at | Human coatomer protein (HEPCOP) "mRNA," complete cds | 212 | 257 | 422 | 196 | 376 | 372 |
| U24152_at | Human p21-activated protein kinase (Pak1) "gene," complete cds | 115 | 199 | 245 | 118 | 34 | 29 |
| U24153_at | Human p21-activated protein kinase (Pak2) "gene," complete cds | 20 | 20 | 20 | 20 | 151 | 209 |
| U24166_at | Human EB1 "mRNA," complete cds | 158 | 111 | 276 | 39 | 190 | 20 |
| U24169_at | Human JTV-1 (ITV-1) "mRNA," complete cds | 20 | 20 | 20 | 20 | 20 | 20 |
| U24183_s_at | Human phosphofructokinase (PFKM) "mRNA," complete cds | 20 | 20 | 20 | 20 | 20 | 30 |
| U24186_at | Human replication protein A complex subunit homolog Rpa4 "gene," complete cds | 20 | 27 | 20 | 65 | 162 | 160 |
| U24266_at | Human pyrroline-5-carboxylate dehydrogenase (P5CDh) "mRNA," long "form," complete cds | 80 | 169 | 117 | 115 | 401 | 246 |
| U24389_s_at | Human lysyl oxidase-like protein gene | 20 | 46 | 101 | 186 | 20 | 20 |
| U24488_s_at | Human tenascin-X (XA) "mRNA," complete cds | 20 | 20 | 20 | 20 | 20 | 20 |
| U24576_at | Human breast tumor autoantigen "mRNA," complete sequence. | 42 | 129 | 34 | 31 | 144 | 144 |
| U24577_at | Human LDL-phospholipase A2 "mRNA," complete cds | 20 | 20 | 20 | 20 | 56 | 81 |
| U24683_at | Human anti-B cell autoantibody IgM heavy chain variable V-D-J region (VH4) "gene," clone "A23;" VH4-55 non-productive rearrangement | 20 | 20 | 20 | 20 | 20 | 20 |
| U24685_at | Human anti-B cell autoantibody IgM heavy chain variable V-D-J region (VH4) "gene," clone "E11;" VH4-63 non-productive rearrangement | 20 | 20 | 20 | 20 | 321 | 89 |
| U24704_at | Human antisecretory factor-1 "mRNA," complete cds | 83 | 54 | 100 | 121 | 20 | 61 |
| U25029_at | Human glucocorticoid receptor alpha "mRNA," variant 3′ UTR | 20 | 20 | 20 | 20 | 20 | 68 |
| U25034_s_at | Human neuronatin beta "mRNA," complete cds | 36 | 57 | 704 | 70 | 152 | 105 |
| U25041_at | Human 5C5 "mRNA," putative complete cds | 20 | 20 | 20 | 20 | 489 | 20 |
| U25128_at | Human PTH2 parathyroid hormone receptor "mRNA," complete cds | 20 | 20 | 20 | 20 | 22 | 20 |
| U25138_at | Human MaxiK potassium channel beta subunit "mRNA," complete cds | 106 | 20 | 139 | 20 | 20 | 20 |
| U25165_at | Human fragile X mental retardation protein 1 homolog FXR1 "mRNA," complete cds | 42 | 33 | 68 | 92 | 111 | 87 |
| U25182_at | Human antioxidant enzyme AOE37-2 "mRNA," complete cds | 54 | 45 | 20 | 69 | 20 | 20 |
| U25265_at | Human MEK5 "mRNA," complete cds | 20 | 20 | 20 | 20 | 20 | 20 |
| U25433_at | Human protein associated with tumorigenic conversion (CATR1.3) "mRNA," complete cds | 20 | 49 | 33 | 20 | 91 | 58 |
| U25435_at | Human transcriptional repressor (CTCF) "mRNA," complete cds | 20 | 57 | 86 | 20 | 20 | 20 |
| U25750_at | Human chromosome 17q21 mRNA clone 1046:1-1 | 64 | 101 | 74 | 89 | 268 | 140 |
| U25771_at | Human ADP-ribosylation factor "mRNA," complete cds | 20 | 25 | 50 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U26789_at | Human ribosomal protein L21 "mRNA," complete cds | 1265 | 2092 | 2443 | 1148 | 191 | 982 |
| U25801_at | Human Tax1 binding protein "mRNA," partial cds | 20 | 20 | 20 | 20 | 189 | 119 |
| U25826_at | Human transcription factor (SC1) "gene," complete cds | 20 | 20 | 20 | 20 | 20 | 20 |
| U25849_at | Human red cell-type low molecular weight acid phosphatase (ACP1) "gene," 5' flanking region and | 20 | 20 | 113 | 66 | 105 | 167 |
| U25956_at | Human P-selectin glycoprotein ligand (SELPLG) gene | 20 | 20 | 20 | 20 | 20 | 20 |
| U25975_at | Human serine kinase (hPAK65) "mRNA," partial cds | 31 | 54 | 110 | 94 | 276 | 107 |
| U25988_at | Human pregnancy-specific glycoprotein 13 (PSG13) "mRNA," complete cds | 158 | 26 | 78 | 97 | 20 | 89 |
| U25997_at | Human stanniocalcin precursor (STC) "mRNA," complete cds | 20 | 20 | 20 | 20 | 20 | 20 |
| U26032_at | Human translation initiation factor eIF-2alpha "mRNA," 3'UTR | 70 | 20 | 25 | 44 | 20 | 71 |
| U26173_s_at | Human bZIP protein NF-IL3A (IL3BP1) "mRNA," complete cds | 114 | 55 | 29 | 47 | 131 | 52 |
| U26174_at | Human pre-granzyme 3 "mRNA," complete cds | 36 | 22 | 106 | 26 | 20 | 80 |
| U26266_s_at | Human deoxyhypusine synthase "mRNA," complete cds. /gb=U26266 /ntype=RNA | 20 | 20 | 20 | 20 | 20 | 20 |
| U26312_s_at | Human heterochromatin protein HP1Hs-gamma "mRNA," complete cds | 20 | 23 | 105 | 104 | 28 | 52 |
| U26398_at | Human inositol polyphosphate 4-phosphatase "mRNA," complete cds | 62 | 88 | 20 | 25 | 20 | 123 |
| U26403_at | Human receptor tyrosine kinase ligand LERK-7 precursor (EPLG7) "mRNA," complete cds | 67 | 34 | 80 | 55 | 131 | 59 |
| U26424_at | Human Ste20-like kinase (MST2) "mRNA," complete cds | 23 | 84 | 40 | 51 | 20 | 40 |
| U26591_at | Human clone IS10 diabetes mellitus type I autoantigen (ICAp69) "mRNA," complete cds | 27 | 82 | 20 | 30 | 20 | 49 |
| U26648_at | Human syntaxin 5 "mRNA," complete cds | 170 | 188 | 74 | 77 | 112 | 67 |
| U26710_at | Human cbl-b "mRNA," complete cds | 20 | 20 | 94 | 26 | 141 | 20 |
| U26712_at | Human cbl-b truncated from 2 lacking leucine zipper "mRNA," complete cds | 20 | 20 | 59 | 22 | 20 | 45 |
| U26726_s_at | Human 11-beta-hydroxysteroid dehydrogenase type 2 "mRNA," complete cds | 20 | 20 | 20 | 20 | 20 | 20 |
| U26727_at | Human p16INK4/MTS1 "mRNA," complete cds | 20 | 20 | 20 | 20 | 20 | 602 |
| U26914_at | Human ras-responsive element binding protein (RREB-1) "mRNA," complete cds | 28 | 20 | 26 | 28 | 91 | 20 |
| U27109_at | Human prepromultimerin "mRNA," complete cds | 20 | 43 | 20 | 20 | 96 | 33 |
| U27185_at | Human RAR-responsive (TIG1) "mRNA," complete cds | 27 | 152 | 27 | 27 | 256 | 86 |
| U27193_at | Human protein-tyrosine phosphatase "mRNA," complete cds | 20 | 20 | 20 | 20 | 45 | 20 |
| U27325_s_at | Human thromboxane A2 receptor "mRNA," complete cds | 20 | 47 | 138 | 200 | 399 | 165 |
| U27326_s_at | Human alpha "(1,3/1,4)" fucosyltransferase (FUT3) "mNE," major transcript "I," complete cds | 53 | 20 | 20 | 20 | 52 | 20 |
| U27330_at | Human alpha ("(1,3)" fucosyltransferase (FUT5) "mRNA," minor transcript "II," complete cds | 75 | 20 | 20 | 27 | 26 | 114 |
| U27333_s_at | | 20 | 20 | 20 | 20 | 36 | 179 |
| U27459_at | Human alpha "(1,3) fucosyltransferase (FUT6) "mRNA," major transcript "I," complete cds | 97 | 20 | 27 | 35 | 29 | 36 |
| U27460_at | Human origin recognition complex protein 2 homolog hORC2L "mRNA," complete cds | 20 | 20 | 40 | 38 | 20 | 56 |
| U27516_at | Human uridine diphosphoglucose pyrophosphorylase "mNRA," complete cds | 111 | 106 | 146 | 131 | 20 | 20 |
| U27655_at | Human recombination protein RAD52 "mRNA," complete cds | 20 | 20 | 20 | 20 | 20 | 20 |
| U27699_at | Human RGP3 "mRNA," complete cds | 61 | 123 | 20 | 39 | 536 | 393 |
| U27768_at | Human RGP4 "mRNA," complete cds | 20 | 156 | 90 | 20 | 61 | 128 |
| U27831_at | Human pephBGT-1 betaine-GAB transporter "mRNA" complete cds | 66 | 108 | 151 | 153 | 20 | 109 |
| U28014_at | Human striatum-enriched phosphatase (STEP) "mRNA," partial cds | 47 | 168 | 109 | 135 | 368 | 371 |
| U28015_at | Human cysteine protease (ICErel-II) "mRNA," complete cds | 94 | 20 | 20 | 105 | 20 | 63 |
| U28042_at | Human cysteine protease (ICErel-III) "mRNA," complete cds | 20 | 20 | 82 | 20 | 75 | 20 |
| U28043_at | Human DEAD box RNA helicase-like protein "mRNA," complete cds | 20 | 47 | 20 | 39 | 216 | 33 |
| U28049_at | Human plasma membrane Na+/H+ exchanger isoform 3 (NHE3) "mRNA," complete cds | 20 | 39 | 20 | 23 | 41 | 141 |
| U28055_at | Human TBX2 (TXB2) "mRNA," complete cds | 20 | 20 | 115 | 163 | 90 | 93 |
| U28131_at | Human hepatocyte growth factor-like protein homolog (D1F15S1A) "mRNA," partial cds | 35 | 20 | 20 | 20 | 20 | 20 |
| U28150_at | Human HMGI-C chimeric transcript mRNA, partial cds. /gb=U28150 /ntype=DNA /annot=CDS | 20 | 20 | 20 | 55 | 170 | 57 |
| U28249_at | Human adrenoleukodystrophy related protein (hALDR) "gene," partial cds | 20 | 114 | 29 | 20 | 20 | 26 |
| | Human 11kd protein "mRNA," complete cds | 20 | 115 | 108 | 165 | 20 | 97 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U28251_cds2_at | Human Krueppel-type zinc finger protein (ZNF169) gene, final exon, partial cds. | 20 | 20 | 20 | 20 | 20 | 20 |
| U28281_at | Human secretin receptor "mRNA," complete cds | 49 | 121 | 40 | 20 | 45 | 162 |
| U28368_at | Human Id-related helix-loop-helix protein Id4 "mRNA," complete cds | 20 | 35 | 45 | 20 | 20 | 20 |
| U28369_at | Human semaphorin V "mRNA," complete cds | 22 | 54 | 20 | 60 | 20 | 20 |
| U28413_at | Human nuclear localization sequence receptor hSRP1alpha "mRNA," complete cds | 89 | 69 | 125 | 138 | 186 | 136 |
| U28488_s_at | Human Cockayne syndrome complementation group A CSA protein (CSA) "mRNA," complete cds | 20 | 62 | 20 | 20 | 20 | 92 |
| U28686_at | Human putative G protein-coupled receptor (AZ3B) "mRNA," complete cds | 20 | 20 | 20 | 20 | 20 | 32 |
| U28687_at | Human putative RNA binding protein RNPL "mRNA," complete cds | 85 | 63 | 192 | 103 | 119 | 116 |
| U28727_at | Human zinc finger containing protein ZNF157 (ZNF157) "mRNA," complete cds | 20 | 89 | 114 | 48 | 20 | 20 |
| U28749_s_at | Human pregnancy-associated plasma protein-A preproform (PAPPA) "mRNA," complete cds | 20 | 20 | 20 | 20 | 20 | 20 |
| U28758_s_at | Human high-mobility group phosphoprotein isoform I-C (HMGIC) "mRNA," complete cds | 20 | 20 | 20 | 20 | 62 | 38 |
| U28811_at | Human NMDA receptor subtype 2B subunit (GRIN2B) "mRNA," particla cds | 20 | 54 | 36 | 25 | 20 | 20 |
| U28831_at | Human cysteine-rich fibroblast growth factor receptor (CFR-1) "mRNA," complete cds | 33 | 20 | 20 | 20 | 127 | 20 |
| U28833_at | Human protein immuno-reactive with anti-PTH polyclonal antibodies "mRNA," partial cds | 33 | 20 | 44 | 23 | 22 | 20 |
| U28963_at | Human Down syndrome critical region protein (DSCR1) "mRNA," complete cds | 69 | 81 | 20 | 87 | 32 | 20 |
| U29091_at | Human Gps2 (GPS2) "mRNA," complete cds | 55 | 63 | 20 | 44 | 111 | 183 |
| U29171_at | Human selenium-binding protein (hSBP) "mRNA," complete cds. /gb=U29091 /ntype=RNA | 104 | 137 | 20 | 190 | 105 | 233 |
| U29175_at | Human casein kinase I delta "mRNA," complete cds | 53 | 63 | 153 | 200 | 27 | 317 |
| U29295_at | Human neuronal pentraxin II (NPTX2) gene | 20 | 20 | 20 | 20 | 20 | 87 |
| U29343_s_at | Human hyaluronan receptor (RHAMM) "mRNA," complete cds | 20 | 109 | 20 | 20 | 128 | 57 |
| U29463_s_at | Human cytochrome b561 gene | 52 | 38 | 36 | 80 | 166 | 44 |
| U29589_at | Human m3 muscarinic acetylcholine receptor (CHRM3) "gene," complete cds | 44 | 41 | 20 | 26 | 127 | 62 |
| U29607_at | Human methionine aminopeptidase "mRNA," complete cds | 41 | 276 | 227 | 240 | 20 | 20 |
| U29615_at | Human chitotriosidase precursor "mRNA," complete cds | 33 | 101 | 20 | 20 | 20 | 241 |
| U29656_at | Human DR-nm23 "mRNA," complete cds | 158 | 412 | 387 | 174 | 176 | 209 |
| U29680_at | Human A1 protein "mRNA," complete cds | 43 | 139 | 20 | 44 | 325 | 251 |
| U29700_at | Human anti-mullerian hormone type II receptor precursor "gene," complete cds | 110 | 178 | 110 | 176 | 112 | 20 |
| U29725_at | Human BMK1 alpha kinase "mRNA," complete cds | 69 | 20 | 20 | 66 | 113 | 26 |
| U29943_s_at | Human ELAV-like neuronal protein-2 Hel-N2 "mRNA," complete cds | 20 | 20 | 20 | 20 | 20 | 25 |
| U29953_ma1_at | Human pigment epithelium-derived factor gene, complete cds. | 349 | 185 | 20 | 42 | 34 | 20 |
| U30185_at | Human orphan opioid receptor "mRNA," complete cds | 20 | 99 | 20 | 20 | 231 | 388 |
| U30245_at | Human myelomonocytic specific protein (MNDA) "gene," 5' flanking sequence and complete exon 1 /gb=U30245/ntype=DNA /annot=exon | 20 | 20 | 20 | 20 | 20 | 20 |
| U30246_at | Human bumetanide-sensitive Na-K-Cl cotransporter (NKCC1) "mRNA," complete cds | 20 | 77 | 49 | 42 | 26 | 40 |
| U30255_at | Human phosphogluconate dehydrogenase (hPGDH) "gene," complete cds | 503 | 115 | 20 | 119 | 50 | 20 |
| U30313_at | Human diadenosine tetraphosphate "mRNA," complete cds. /gb=U0313 /ntype=RNA | 20 | 20 | 20 | 20 | 20 | 209 |
| U30521_at | Human P311 HUM −3.1 "mRNA," complete cds | 23 | 70 | 20 | 20 | 60 | 20 |
| U30610_at | Human CD94 protein "mRNA," complete cds | 20 | 135 | 20 | 20 | 20 | 55 |
| U30825_at | Human splicing factor SRp30c "mRNA," complete cds | 206 | 355 | 918 | 439 | 206 | 137 |
| U30827_at | Human splicing factor SRp40-3 (SRp40) "mRNA," complete cds | 79 | 82 | 369 | 216 | 20 | 96 |
| U30828_at | Human splicing factor SRp55-2 (SRp55) "mRNA," complete cds | 37 | 37 | 93 | 20 | 112 | 151 |
| U30872_at | Human mitosin "mRNA," complete cds | 20 | 20 | 40 | 66 | 20 | 20 |
| U30888_at | Human tRNA-guanine transglyosylase "mRNA," complete cds | 138 | 266 | 128 | 23 | 193 | 221 |
| U30894_at | Human N-sulphoglucosamine sulphohydrolase "mRNA," complete cds | 20 | 145 | 164 | 167 | 317 | 390 |
| U30930_at | Human UDP-Galactose ceramide galactosyl transfease (CGT) "mRNA," complete cds | 45 | 75 | 28 | 45 | 59 | 147 |
| U30998_at | Human (nmd) "mRNA," 3'UTR. /gb=U30998 /ntype=RNA | 20 | 20 | 57 | 20 | 142 | 153 |
| U30999_at | Human (memc) "mRNA," 3'UTR. /gb=U30999 /ntype=RNA | 44 | 146 | 113 | 80 | 162 | 133 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| U31099_at | Human DP prostanoid receptor (PTGDR) mRNA, partial cds. | 20 | 20 | 20 | 20 | 20 | 20 | 20 |
| U31116_at | Human beta-sarcoglycan A3b "mRNA," complete cds | 21 | 67 | 20 | 20 | 20 | 20 | 20 |
| U31120_ma1_at | Human interleukin-13 (IL-13) precursor gene, complete cds. | 82 | 155 | 20 | 173 | 438 | 259 | 309 |
| U31176_at | Human hERV1 "mRNA," complete cds | 79 | 163 | 26 | 130 | 259 | 279 | 279 |
| U31201_cds1_at | Human laminin gamma2 chain gene (LAMC2), exon 23 and flanking sequences, and complete cds. | 20 | 20 | 20 | 20 | 44 | 22 | 22 |
| U31201_cds2_s_at | Human laminin gamma2 chain gene (LAMC2) | 20 | 20 | 20 | 20 | 20 | 20 | 20 |
| U31215_s_at | Human metabotropic glutamate receptor 1 alpha (mGluR1alpha) "mRNA," complete cds | 20 | 20 | 20 | 20 | 317 | 20 | 20 |
| U31216_s_at | Human metabotropic glutamate receptor 1 beta (mGluR1beta) "mRNA," complete cds | 63 | 38 | 40 | 65 | 367 | 20 | 123 |
| U31248_at | Human zinc finger protein (ZNF174) "mRNA," complete cds | 171 | 292 | 141 | 186 | 529 | 327 | 327 |
| U31342_at | Human nucleobindin gene | 114 | 20 | 26 | 102 | 163 | 111 | 111 |
| U31382_at | Human G protein gamma-4 subunit "mRNA," complete cds | 20 | 142 | 167 | 66 | 25 | 20 | 20 |
| U31383_at | Human G protein gamma-10 subunit "mRNA," complete cds | 139 | 161 | 25 | 59 | 138 | 81 | 81 |
| U31384_at | Human G protein gamma-11 subunit "mRNA," complete cds | 20 | 20 | 20 | 20 | 20 | 20 | 20 |
| U31449_at | Human intestinal and liver tetraspan membrane protein (il-TMP) "mRNA," complete cds | 147 | 217 | 20 | 129 | 182 | 406 | 406 |
| U31501_at | Human fragile X mental retardation syndrome related protein (FXR2) "mRNA," complete cds | 21 | 20 | 67 | 68 | 93 | 37 | 37 |
| U31556_at | Human transcription factor E2F-5 "mRNA," complete cds | 93 | 20 | 20 | 133 | 294 | 288 | 288 |
| U31628_at | Human interleukin-15 receptor alpha chain precursor (IL 15RA) "mRNA," complete cds | 20 | 20 | 20 | 20 | 101 | 60 | 60 |
| U31799_at | Human melanocyte protein Pmel 17 gene | 42 | 113 | 164 | 110 | 20 | 21 | 21 |
| U31814_at | Human transcriptional regulator homolog RPD3 "mRNA," complete cds. | 126 | 1358 | 2242 | 1444 | 822 | 1012 | 1012 |
| U31875_at | Human Hep27 protein mRNA, complete cds. | 97 | 144 | 311 | 176 | 610 | 209 | 209 |
| U31903_s_at | Human CREB-RP (creb-rp) "mRNA," complete cds | 67 | 117 | 149 | 66 | 368 | 135 | 135 |
| U31929_s_at | Human orphan nuclear receptor (DAX1) "mRNA," complete cds | 57 | 164 | 161 | 177 | 155 | 68 | 68 |
| U31930_at | Human deoxyuridine nucleotidohydrolase "mRNA," complete cds. | 20 | 20 | 20 | 20 | 128 | 20 | 20 |
| U31973_s_at | Human phosphodiesterase A' subunit (PDE6C) "mRNA," complete cds | 63 | 119 | 139 | 29 | 145 | 248 | 248 |
| U31986_at | Human cartilage-specific homeodomain protein Cart-1 "mRNA," complete cds | 49 | 20 | 31 | 41 | 163 | 37 | 37 |
| U32114_at | Human caveolin-2 "mRNA," complete cds | 43 | 20 | 36 | 55 | 80 | 82 | 82 |
| U32315_at | Human syntaxin 3 "mRNA," complete cds | 69 | 20 | 63 | 20 | 75 | 20 | 20 |
| U32324_at | Human interleukin-11 receptor alpha chain "mRNA," complete cds | 47 | 22 | 20 | 20 | 20 | 20 | 20 |
| U32331_at | Human RIG "mRNA," complete sequence | 20 | 33 | 20 | 20 | 20 | 20 | 20 |
| U32376_at | Human channel associated protein os synapse (chapsyn-110) "mRNA," complete cds | 22 | 20 | 20 | 20 | 191 | 102 | 102 |
| U32439_at | Human regulator of G-protein signaling similarity (RGS7) "mRNA," partial cds | 20 | 20 | 20 | 20 | 20 | 20 | 20 |
| U32499_s_at | Human d3 dopamine receptor "mRNA," complete cds. | 20 | 79 | 80 | 87 | 160 | 211 | 211 |
| U32519_at | Human GAP SH3 binding protein "mRNA," complete cds | 93 | 20 | 20 | 24 | 20 | 20 | 20 |
| U32576_ma1_at | Human apolipoprotein apoC-IV (APOC4) gene, complete cds. | 20 | 20 | 20 | 20 | 20 | 20 | 20 |
| U32581_at | Human lambda/iota-protein kinase C-interacting protein "mRNA," complete cds | 20 | 20 | 20 | 20 | 188 | 20 | 20 |
| U32645_at | Human myeloid elf-1 like factor (MDF) "mRNA," complete cds | 20 | 26 | 20 | 27 | 127 | 31 | 31 |
| U32659_at | Human IL-17 "mRNA," complete cds | 20 | 77 | 92 | 20 | 329 | 151 | 151 |
| U32674_s_at | Human orphan receptor GPR9 (GPR9) "gene," partial cds | 20 | 49 | 20 | 99 | 302 | 135 | 135 |
| U32680_at | Human CLN3 "mRNA," complete cds | 39 | 20 | 29 | 23 | 20 | 49 | 49 |
| U32849_at | Human Hou "mRNA," complete cds | 20 | 20 | 20 | 20 | 20 | 20 | 20 |
| U32907_at | Human p37NB "mRNA," complete cds | 743 | 290 | 526 | 524 | 329 | 189 | 189 |
| U32944_at | Human cytoplasmic dynein light chain 1 (hdlc1) "mRNA," complete cds | 110 | 218 | 298 | 231 | 302 | 90 | 90 |
| U32986_s_at | Human xeroderma pigmentosum group E UV-damaged DNA binding factor "mRNA," complete cds | 20 | 20 | 20 | 20 | 20 | 20 | 20 |
| U32989_at | Human tryptophan oxygenase (IDO) "mRNA," complete cds | 20 | 20 | 20 | 20 | 20 | 112 | 112 |
| U33017_at | Human signaling lymphocytic activation molecule (SLAM) "mRNA," complete cds | 59 | 41 | 190 | 117 | 169 | 95 | 95 |
| U33052_s_at | Human "lipid-activated," protein kinase PRK2 "mRNA," complete cds | 54 | 57 | 20 | 78 | 20 | 209 | 209 |
| U33053_s_at | Human lipid-activated protein kinase PRK1 "mRNA," complete cds | 54 | 57 | 20 | 78 | 20 | 209 | 209 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U33054_at | Human G protein-coupled receptor kinase GRK4 "mRNA," alpha splice "variant," complete cds | 20 | 20 | 20 | 20 | 20 | 20 |
| U33147_at | Human mammaglobin "mRNA," complete cds | 20 | 20 | 28 | 20 | 20 | 151 |
| U33202_s_at | Human mdm2-D (mdm2) "mRNA," complete cds. /gb=U33202 /ntype=RNA | 20 | 20 | 34 | 21 | 20 | 35 |
| U33203_s_at | Human mdm2-E (mdm2) "mRNA," complete cds. /gb=U33203 /ntype=RNA | 20 | 20 | 20 | 20 | 20 | 36 |
| U33267_at | Human glycine receptor beta subunit (GLRB) "mRNA," complete cds | 21 | 57 | 20 | 20 | 34 | 36 |
| U33286_at | Human chromosome segregation gene homolog CAS "mRNA," complete cds | 68 | 83 | 194 | 85 | 99 | 155 |
| U33317_ma1_at | Human defensin 6 (HD-6) gene, complete cds | 23 | 46 | 20 | 20 | 178 | 64 |
| U33429_at | human K+ channel beta 2 subunit "mRNA," complete cds | 20 | 20 | 20 | 46 | 48 | 39 |
| U33447_at | Human putative G-protein-coupled receptor (GPR17) "gene," complete cds | 20 | 20 | 20 | 20 | 20 | 20 |
| U33448_s_at | Human putative G-protein-coupled receptor (GPR16) "gene," complete cds | 20 | 20 | 20 | 71 | 20 | 20 |
| U33632_at | Human two P-domain K+ channel TWIK-1 "mRNA," complete cds | 52 | 53 | 114 | 71 | 57 | 64 |
| U33761_at | Human cyclin A/CDK2-associated p45 (Skp2) "mRNA," complete cds | 20 | 20 | 20 | 20 | 168 | 81 |
| U33818_at | Human inducible poly(A)-binding protein "mRNA," complete cds | 77 | 38 | 381 | 257 | 255 | 212 |
| U33821_at | Human tax1-binding protein TXBP151 "mRNA," complete cds | 346 | 336 | 367 | 268 | 294 | 319 |
| U33822_at | Human tax1-binding protein TXBP181 "mRNA," complete cds | 20 | 20 | 20 | 20 | 20 | 20 |
| U33837_at | Human glycoprotein receptor gp330 "precursor," "mRNA," complete cds | 20 | 20 | 20 | 20 | 20 | 20 |
| U33838_s_at | Human NF-kappa-B p65delta3 "mRNA," spliced transcript lacking exons 6 and "7," partial cds. /gb=U33838 /ntype=RNA | 57 | 20 | 20 | 20 | 478 | 24 |
| U33839_at | Human potassium channel "mRNA," complete cds. /gb=U33839 /ntype=RNA | 20 | 20 | 30 | 20 | 154 | 71 |
| U33841_at | Human beta 1 integrin isoform D (ITGB1) "gene," partial cds. /gb=U33880 /ntype=DNA /annot=exon | 20 | 20 | 55 | 20 | 20 | 20 |
| U33849_at | Human lymphoma proprotein convertase (LPC) "mRNA," complete cds | 20 | 20 | 20 | 79 | 136 | 20 |
| U33880_at | Human adenosine kinase "mRNA," complete cds. /gb=U33936 /ntype=RNA | 20 | 20 | 20 | 20 | 50 | 20 |
| U33920_at | Human clone lambda 5 semaphorin "mRNA," complete cds | 32 | 20 | 20 | 20 | 20 | 20 |
| U33921_at | HSU33921 Homo sapiens cDNA | 79 | 155 | 41 | 166 | 836 | 514 |
| U33936_s_at | Human CCAAT/enhancer binding protein alpha "gene," complete cds | 20 | 94 | 20 | 36 | 20 | 35 |
| U34038_at | Human proteinase-activated receptor-2 "mRNA," complete cds | 66 | 29 | 20 | 68 | 20 | 20 |
| U34044_at | Human selenium donor protein (selD) "mRNA," complete cds | 68 | 65 | 29 | 63 | 25 | 47 |
| U34070_s_at | Human nonmuscle myosin heavy chain IIB "gene," promoter region and exon 1 /gb=U34301 /ntype=DNA /annot=mRNA | 54 | 77 | 100 | 73 | 20 | 87 |
| U34252_at | Human gamma-aminobutyraldehyde dehydrogenase "mRNA," complete cds | 20 | 20 | 20 | 20 | 20 | 20 |
| U34301_r_at | | 113 | 148 | 130 | 49 | 20 | 43 |
| U34301_s_at | Human nonmuscle myosin heavy chain IIB "gene," promoter region and exon 1 /gb=U34301 /ntype=DNA /annot=mRNA | 20 | 20 | 20 | 20 | 20 | 84 |
| U34343_at | human 13kD differentiation-associated protein "mRNA," partial cds. /gb=U34343 /ntype=RNA | 135 | 152 | 398 | 223 | 220 | 230 |
| U34360_at | TEC gene extracted from Human protein tyrosine kinase TEC (tec) "gene," partial "cds," and tyrosine kinase TXK (txk) gene | 20 | 20 | 20 | 20 | 20 | 20 |
| U34587_at | Human corticotropin-releasing factor receptor 2 "mRNA," complete cds | 196 | 191 | 377 | 244 | 435 | 182 |
| U34605_at | Human retinoic acid- and interferon-inducible 58K protein R158 "mRNA," complete cds | 24 | 61 | 20 | 20 | 36 | 20 |
| U34683_at | Human glutathione synthetase "mRNA," complete cds | 49 | 20 | 20 | 35 | 20 | 57 |
| U34844_at | Human mercurial-insensitive water-channel "gene," "5' region and partial exon 1 /gb=U34844 /ntype=DNA /annot=exon | 44 | 122 | 20 | 28 | 20 | 33 |
| U34877_at | Human biliverdin-IXalpha reductase "mRNA," complete cds | 65 | 49 | 20 | 59 | 20 | 88 |
| U34879_ma1_at | Human 17-beta-hydroxysteroid dehydrogenase (EDH17B2) gene, complete cds. | 20 | 20 | 20 | 20 | 20 | 20 |
| U34880_at | Human DPH2L "mRNA," complete cds | 150 | 135 | 29 | 129 | 20 | 20 |
| U34962_at | Human transcription factor HCSX (hCsx) "mRNA," complete cds | 152 | 186 | 234 | 108 | 384 | 146 |
| U34976_at | Human gamma-sarcoglycan "mRNA," complete cds | 54 | 20 | 29 | 20 | 20 | 20 |
| U35005_s_at | Human JNK1 beta2 protein kinase (JNK1B2) "mRNA," complete cds | 76 | 32 | 20 | 20 | 20 | 20 |
| U35048_at | Human TSC-22 protein "mRNA," complete cds | 83 | 162 | 77 | 66 | 20 | 31 |
| U35100_at | Human complexin II mRNA, complete cds. | 20 | 20 | 20 | 20 | 20 | 20 |
| U35113_at | Human metastasis-associated mta1 "mRNA," complete cds | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U35139_at | Human NECDIN related protein "mRNA," complete cds | 20 | 20 | 20 | 20 | 31 | 20 |
| U35234_at | Human protein tyrosine phosphatase sigma "mRNA," complete cds | 20 | 56 | 299 | 67 | 967 | 55 |
| U35246_at | Human vacuolar protein sorting homolog h-vps45 "mRNA," complete cds | 20 | 20 | 20 | 33 | 20 | 20 |
| U35340_at | Human beta B1-crystallin "mRNA," complete cds | 62 | 130 | 20 | 122 | 307 | 232 |
| U35376_at | Human repressor transcriptional factor (ZNF85) "mRNA," complete cds | 20 | 20 | 21 | 20 | 42 | 33 |
| U35407_at | Human peroxisomal targeting signal import receptor (PXR1) "gene," allele "5," partial cds. /gb=U35407 /ntype=DNA /annot=mRNA | 62 | 54 | 20 | 20 | 20 | 21 |
| U35451_at | Human heterochromatin protein p25 "mRNA," complete cds | 20 | 20 | 67 | 49 | 51 | 20 |
| U35459_at | Human bomapin "mRNA," complete cds. /gb=U35459 /ntype=RNA | 10 | 108 | 20 | 42 | 69 | 120 |
| U35637_s_at | Human nebulin "mRNA," partial cds. /gb=U35637 /ntype=RNA | 20 | 20 | 20 | 20 | 20 | 20 |
| U35735_at | Human RACH1 (RACH1) "mRNA," complete cds | 20 | 65 | 119 | 35 | 30 | 20 |
| U35835_at | Human DNA-PK "mRNA,=, partial cds | 20 | 20 | 69 | 77 | 242 | 64 |
| U36221_at | Human pancreatic zymogen granule membrane protein GP-2 "mRNA," complete cds | 146 | 126 | 20 | 135 | 20 | 258 |
| U36341_ma1_at | SLC6A8 gene (creatine transporter) extracted from Human Xp28 "cosmid," creatine transporter (SLC6A8) "gene," complete "cds," and CD | 98 | 188 | 881 | 876 | 808 | 220 |
| U36448_at | Human Ca2+ dependent activator protein for secretion "mRNA," complete cds | 20 | 20 | 20 | 20 | 20 | 20 |
| U36500_at | Human lymphoid-specific SP100 homolog (LYSP100-B) "mRNA," complete cds | 20 | 62 | 20 | 20 | 37 | 20 |
| U36501_at | Human SP100-B (SP100-B) "mRNA," complete cds | 20 | 25 | 40 | 38 | 20 | 20 |
| U36601_at | Human heparan N-deactylase/N-sulfotransferase-2 "mRNA," complete cds | 20 | 75 | 20 | 54 | 122 | 265 |
| U36621_cds2_at | Human Y-chromosome RNA recognition motif protein (YRRM) gene, exon 12, partial cds, subclone 7S2. | 29 | 20 | 20 | 22 | 20 | 118 |
| U36759_at | Human pre-T cell receptor alpha-type chain "precursor," "mRNA," complete cds | 20 | 20 | 20 | 20 | 62 | 23 |
| U36764_at | Human TGF-beta receptor interacting protein 1 "mRNA," complete cds | 196 | 167 | 290 | 200 | 75 | 74 |
| U36787_at | Human putative holocytochrome c-type synthetase "mRNA," complete cds | 20 | 54 | 108 | 71 | 20 | 20 |
| U36798_at | Homo sapiens platelet cGI-PDE "mRNA," complete cds. | 67 | 173 | 59 | 20 | 20 | 20 |
| U36922_at | Human fork head domain protein (FKHR) "mRNA," 3' end. /gb=U36922 /ntype=RNA | 20 | 60 | 20 | 20 | 20 | 20 |
| U37012_at | Human cleavage and polyadenylation specificity factor "mRNA," complete cds | 145 | 248 | 221 | 299 | 756 | 713 |
| U37022_ma1_at | Human cyclin-dependent kinase 4 (CDK4) gene, complete cds. | 79 | 51 | 96 | 117 | 134 | 48 |
| U37055_ma1_s_at | Human hepatocyte growth factor-like protein "gene," complete cds | 20 | 20 | 20 | 20 | 20 | 20 |
| U37122_at | Human adducin gamma subunit "mRNA," complete cds | 282 | 188 | 379 | 191 | 30 | 196 |
| U37139_at | Human beta 3-endonexin "mRNA," long form and short "form," complete cds | 20 | 49 | 50 | 60 | 20 | 62 |
| U37143_at | Human cytochrome P450 monooxygenase CYP2J2 "mRNA," complete cds | 38 | 25 | 144 | 111 | 112 | 48 |
| U37146_at | Human silencing mediator of retinoid and thyroid hormone action (SMRT) "mRNA," complete cds | 76 | 127 | 123 | 142 | 20 | 20 |
| U37219_at | Human cyclophilin-like protein CyP-60 "mRNA," complete cds | 208 | 472 | 475 | 331 | 564 | 279 |
| U37221_at | Human cyclophilin-like protein "mRNA," partial cds | 20 | 20 | 20 | 20 | 20 | 20 |
| U37248_at | Human alpha-mannosidase (6A8) "mRNA," complete cds | 33 | 23 | 48 | 20 | 40 | 59 |
| U37251_at | Human CtBP "mRNA," complete cds | 58 | 60 | 20 | 65 | 20 | 20 |
| U37283_at | Human kinesin-like spindle protein HKSP (HKSP) "mRNA," complete cds | 20 | 20 | 20 | 30 | 20 | 20 |
| U37352_at | Human KRAB zinc finger protein (ZNF177) "mRNA," splicing "variant," complete cds | 92 | 91 | 79 | 51 | 276 | 24 |
| U37359_at | Human microfibril-associated glycoprotein-2 MAGP-2 "mRNA," complete cds | 22 | 20 | 20 | 20 | 89 | 66 |
| U37408_at | Human protein phosphatase 2A B'alpha1 regulatory subunit "mRNA," complete cds | 20 | 20 | 20 | 27 | 20 | 20 |
| U37426_at | Human MRE11 homolog hMRE11 "mRNA," complete cds | 20 | 20 | 28 | 58 | 20 | 20 |
| U37431_at | Human substance P beta-PPT-A "mRNA," complete cds | 20 | 20 | 20 | 20 | 20 | 20 |
| U37518_at | Human HOXA1 "mRNA," long transcript and alternatively spliced "forms," complete cds | 20 | 20 | 53 | 74 | 79 | 113 |
| U37519_at | Human TNF-related apoptosis inducing ligand TRAIL "mRNA," complete cds | 109 | 20 | 144 | 138 | 20 | 20 |
| U37529_at | Human aldehyde dehydrogenase (ALDH8) "mRNA," complete cds | 358 | 321 | 103 | 156 | 456 | 314 |
| U37546_s_at | Human IAP homolog C (MIHC) "mRNA," complete cds | 20 | 20 | 20 | 20 | 20 | 20 |
| U37547_at | Human IAP homolog B (MIHB) "mRNA," complete cds | 55 | 114 | 64 | 22 | 26 | 20 |
| U37673_at | Human neuron-specific vesicle coat protein and cerebellar degeneration antigen (beta-NAP) "mRNA," complete cds | 20 | 20 | 20 | 20 | 20 | 24 |
| U37689_at | Human RNA polymerase II subunit (hsRPB8) "mRNA," complete cds | 269 | 406 | 513 | 232 | 572 | 697 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U37690_at | Human RNA polymerase II subunit (hsRPB10) "mRNA," complete cds | 499 | 688 | 701 | 510 | 495 | 635 |
| U37707_at | Human dig3 "mRNA," complete cds | 46 | 56 | 20 | 27 | 295 | 131 |
| U38175_at | Human HuR RNA binding protein (HuR) "mRNA," complete cds | 20 | 26 | 20 | 20 | 20 | 20 |
| U38227_s_at | Human testis-specific hexokinase 1 (hHK1-tb) "mRNA," partial cds. /gb=U38227 /ntype=RNA | 20 | 20 | 20 | 20 | 141 | 20 |
| U38268_at | Human cytochrome b "pseudogene" partial cds. /gb=U38268 /ntype=DNA /annot=CDS | 28 | 40 | 74 | 27 | 20 | 104 |
| U38276_at | Human semaphorin III family homolog "mRNA," complete cds | 99 | 85 | 408 | 345 | 53 | 92 |
| U38291_ma1_at | Human microtubule-associated protein 1a (MAP1A) genomic sequence | 20 | 20 | 80 | 20 | 280 | 20 |
| U38372_at | Human huntingtin associated protein (hHAP1) "mRNA," partial cds. | 20 | 65 | 20 | 20 | 272 | 116 |
| U38480_at | human retinoid X receptor-gamma "mRNA," complete cds | 20 | 36 | 20 | 20 | 75 | 65 |
| U38545_at | Human ARF-activated phosphatidylcholine-specific phospholipase D1a (hPLD1) "mRNA," complete cds | 63 | 105 | 20 | 68 | 258 | 20 |
| U38810_at | Human mab-21 cell fate-determining protein homolog (CAGR1) "mRNA," complete cds | 40 | 20 | 20 | 20 | 20 | 188 |
| U38846_at | Human stimulator of TAR RNA binding (SRB) "mRNA," complete cds | 209 | 196 | 399 | 278 | 57 | 20 |
| U38847_at | Human TAR RNA loop binding protein (TRP-185) "mRNA," complete cds | 21 | 71 | 52 | 32 | 20 | 20 |
| U38864_at | Human zinc-finger protein C2H2-150 "mRNA," complete cds | 20 | 20 | 20 | 20 | 20 | 27 |
| U38896_at | Human zinc finger protein C2H2-171 "mRNA," complete cds | 20 | 20 | 20 | 20 | 20 | 20 |
| U38904_at | Human zinc finger protein C2H2-25 "mRNA," complete cds | 27 | 116 | 83 | 101 | 20 | 20 |
| U38964_s_at | Human PMS2 related (hPMSR2) "gene," complete cds | 37 | 20 | 87 | 79 | 20 | 27 |
| U38980_at | Human PMS2 related (hPMSR6) "mRNA," complete cds | 351 | 417 | 75 | 368 | 496 | 754 |
| U39196_at | Human clone hGIRK 1 G-protein coupled inwardly rectifying potassium channel "mRNA," complete cds | 20 | 20 | 20 | 20 | 20 | 30 |
| U39226_at | Human myosin VIIA (USH1B) "mRNA," complete cds | 45 | 82 | 20 | 35 | 20 | 26 |
| U39231_at | Human GiP Rreceptor (GIPR) "mRNA," complete cds | 20 | 50 | 20 | 20 | 184 | 20 |
| U39317_at | Human E2 ubiquitin conjugating enzyme UbcH5B (UBCH5B) "mRNA," complete cds | 132 | 50 | 201 | 97 | 56 | 20 |
| U39318_at | Human E2 ubiquitin conjugating enzyme UbcH5C (UBCH5C) "mRNA," complete cds | 134 | 162 | 233 | 219 | 117 | 213 |
| U39400_at | Human NOF1 "mRNA," compete cds | 95 | 103 | 162 | 129 | 20 | 20 |
| U39412_at | Human platelet alpha SNAP "mRNA," complete cds | 110 | 153 | 20 | 48 | 20 | 20 |
| U39447_at | Human placenta copper monoamine oxidase "mRNA," complete cds | 50 | 20 | 20 | 20 | 20 | 20 |
| U39487_at | Human xanthine dehydrogenase/oxidase "mRNA," complete cds | 29 | 20 | 20 | 22 | 20 | 754 |
| U39573_at | Human salivary peroxidase "mRNA," complete cds | 87 | 147 | 179 | 80 | 365 | 168 |
| U39576_at | Human butyrophilin precursor "mRNA," complete cds | 20 | 20 | 20 | 20 | 62 | 20 |
| U39617_at | Human MAP kinase kinase 6 (MKK6) "mRNA," complete cds | 20 | 20 | 20 | 20 | 20 | 41 |
| U39840_at | Human Bloom's syndrome protein (BLM) "mRNA," complete cds | 28 | 53 | 445 | 157 | 34 | 40 |
| U39905_at | Human hepatocyte nuclear factor-3 alpha (HNF-3 alpha) "mRNA," complete cds | 102 | 115 | 187 | 22 | 187 | 80 |
| U40002_s_at | Human vesicular monoamine transporter VMAT1 "mRNA," complete cds | 20 | 20 | 20 | 20 | 20 | 20 |
| U40038_at | Human hormone-sensitive lipase testicular isoform "mRNA," complete cds | 20 | 20 | 20 | 20 | 20 | 20 |
| U40152_s_at | Human GTP-binding protein alpha q subunit (GNAQ) "mRNA," complete cds | 20 | 20 | 20 | 76 | 20 | 20 |
| U40215_at | Human origin recognition complex 1 (HsORC1) "mRNA," complete cds | 38 | 20 | 39 | 20 | 35 | 20 |
| U40223_at | Human synapsin IIb "mRNA," complete cds | 119 | 185 | 20 | 102 | 418 | 341 |
| U40271_s_at | Human uridine nucleotide receptor (UNR) "gene," complete cds | 20 | 20 | 20 | 20 | 20 | 20 |
| U40279_at | Human transmembrane receptor precursor (PTK7) "mRNA," complete cds | 35 | 96 | 131 | 67 | 400 | 84 |
| U40282_at | Human beta-2 integrin alphaD subunit (ITGAD) "gene," exons "25–30," and partial cds. /gb=U40279 /ntype=DNA /annot=exon | 208 | 124 | 198 | 91 | 200 | 151 |
| U40343_at | Human integrin-linked kinase (ILK) "mRNA," complete cds | 20 | 20 | 20 | 20 | 20 | 62 |
| U40369_ma1_at | Human CDK inhibitor p19INK4d "mRNA," complete cds | 113 | 170 | 20 | 96 | 291 | 66 |
| U40370_at | Human spermidine/spermine N1-acetyltransferase (SSAT) gene, complete cds | 113 | 111 | 82 | 39 | 20 | 64 |
| U40371_at | Human "3',5'" cyclic nucleotide phosphodiesterase (HSPDE1A3A) "mRNA," complete cds | 78 | 22 | 20 | 20 | 211 | 20 |
| U40372_at | Human "3',5'" cyclic nucleotide phosphodiesterase (HSPDE1C1A) "mRNA," complete cds | 20 | 20 | 35 | 20 | 20 | 20 |
| | Human "3',5'" cyclic nucleotide phosphodiesterase (HSPDE1C3A) "mRNA," partial cds | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U40380_at | Human presenilin 1-374 (AD3-212) "mRNA," complete cds. | 20 | 39 | 20 | 20 | 111 | 348 |
| U40391_ma1_at | Human serotonin N-acetyltransferase gene, complete cds. | 237 | 254 | 326 | 224 | 464 | 510 |
| U40434_at | Human mesothelin or CAK1 antigen precursor "mRNA," complete cds. | 20 | 45 | 20 | 20 | 37 | 264 |
| U40462_at | Human Ikaros/LyF-1 homolog (hIk-1) "mRNA," complete cds | 20 | 20 | 20 | 20 | 93 | 20 |
| U40490_at | Human nicotinamide nucleotide transhydrogenase "mRNA," nuclear gene encoding mitochondrial "protein," complete cds | 25 | 50 | 28 | 226 | 388 | 99 |
| U40571_at | Human alpha1-syntrophin (SNT A1) "mRNA," complete cds | 27 | 20 | 20 | 20 | 284 | 56 |
| U40572_at | Human beta2-syntrophin (SNT B2) "mRNA," complet cds | 69 | 20 | 23 | 43 | 20 | 20 |
| U40622_at | Human XRCC4 "mRNA," complete cds | 20 | 20 | 20 | 20 | 20 | 20 |
| U40705_at | Homo sapiens telomeric repeat binding factor (TRF1) "mRNA," complete cds | 20 | 20 | 39 | 20 | 20 | 64 |
| U40714_at | Human tyrosyl-tRNA synthetase "mRNA," complete cds. /gb=U40714 /ntype=RNA | 30 | 20 | 101 | 58 | 20 | 59 |
| U40763_s_at | Human Clk-associated RS cyclohilin CARS-Cyp "mRNA," complete cds | 20 | 67 | 99 | 63 | 64 | 64 |
| U70846_s_at | Human alpha-N-acetylglucosaminidase (NAG) "mRNA," complete cds | 130 | 238 | 132 | 192 | 374 | 473 |
| U40990_at | Human nicotinamide voltage-gated potassium channel (KVLQT1) "mRNA," partial cds | 31 | 20 | 20 | 34 | 180 | 114 |
| U40992_at | Human heat shock protein hsp40 homolog "mRNA," complete cds | 190 | 221 | 81 | 251 | 859 | 625 |
| U40998_at | Human retinal protein (HRG4) "mRNA," complete cds | 24 | 92 | 279 | 94 | 20 | 60 |
| U41060_at | Human breast "cancer," estrogen regulated LIV-1 protein (LIV-1) "mRNA," partial cds | 20 | 20 | 20 | 20 | 174 | 72 |
| U41068_cds2_s_at | Human retinoid X receptor beta (RXRgeta) "gene," partial 3' "transcript," and collagen alpha2(XI) (COL11A2) gene | 20 | 20 | 174 | 275 | 72 | 70 |
| U41163_s_at | Human creatine transporter (SLC6A10) "gene," partial cds | 20 | 52 | 88 | 142 | 83 | 45 |
| U41315_ma1_s_at | Human ring zinc-finger protein (ZNF127-Xp) gene and 5' flanking sequence | 78 | 20 | 20 | 57 | 20 | 20 |
| U41344_at | Human prolargin (PRELP) "gene," 5' flanking sequence and | 88 | 310 | 302 | 180 | 421 | 334 |
| U41371_at | Human spliceosome associated protein (SAP 145) "mRNA," complete cds | 20 | 20 | 60 | 74 | 49 | 20 |
| U41387_at | Human Gu protein "mRNA," partial cds | 269 | 242 | 212 | 199 | 80 | 164 |
| U41515_at | Human deleted in split hand/split foot 1 (DSS1) "mRNA," complete cds | 90 | 69 | 84 | 86 | 20 | 20 |
| U41518_at | Human channel-like integral membrane protein (AQP-1) "mRNA," clone "AQP-12344," partial cds | 702 | 658 | 884 | 442 | 661 | 740 |
| U41635_at | Human OS-9 precurosor "mRNA," complete cds | 101 | 129 | 386 | 271 | 20 | 107 |
| U41654_at | Human adenovirus protein E3-14.7k interacting protein 1 (FIP-1) "mRNA," complete cds | 59 | 33 | 20 | 45 | 20 | 72 |
| U41668_at | Human deoxyguanosine kinase "mRNA," complete cds | 20 | 20 | 20 | 24 | 20 | 20 |
| U41737_at | Human pancreatic beta cell growth factor (INGAP) "mRNA," complete cds. /gb=U41737 /ntype=RNA | 59 | 111 | 175 | 130 | 92 | 44 |
| U41740_at | Human trans-Golgi p230 "mRNA," complete cds | 86 | 86 | 20 | 71 | 20 | 69 |
| U41745_at | Human PDGF associated protein "mRNA," complete cds | 35 | 68 | 20 | 20 | 20 | 20 |
| U41763_at | Human muscle specific slathrin heavy chain (CLITD) "mRNA," complete cds | 27 | 20 | 20 | 20 | 20 | 31 |
| U41766_s_at | Human metalloprotease/disintegrin/cysteine-rich protein precursor (MDC9) "mRNA," complete cds | 53 | 68 | 284 | 211 | 169 | 205 |
| U41767_s_at | Human metargidin precursor "mRNA," complete cds | 108 | 122 | 474 | 215 | 672 | 20 |
| U41804_at | Human putative TI/ST2 receptor binding protein precursor "mRNA," complete cds | 70 | 154 | 20 | 20 | 20 | 20 |
| U41813_at | Human class I homeoprotein (HOXA9) "mRNA," partial cds | 20 | 64 | 55 | 55 | 49 | 41 |
| U41815_at | Human nucleoporin 98 (NUP98) "mRNA," compelte cds | 20 | 20 | 20 | 20 | 42 | 20 |
| U41816_at | Human C-1 "mRNA," complete cds | 59 | 111 | 20 | 20 | 264 | 137 |
| U41898_at | Human sodium cotransporter RKST1 "mRNA," partial cds. /gb=U41898 /ntype=RNA | 20 | 20 | 20 | 20 | 20 | 114 |
| U42031_at | Human 54 kDa progesterone receptor-associated immunophilin FKBP54 "mRNA," partial cds | 20 | 24 | 20 | 20 | 20 | 152 |
| U42359_at | Human N33 protein form 1 (Nee) "gene," exon 10 and complete cds. /gb=U42359 /ntype=DNA /annot=exon | 45 | 83 | 284 | 128 | 178 | 20 |
| U42360_cds2_at | Human N33 protein form 2 (N33) gene, exon 11 and complete cds. | 20 | 36 | 79 | 98 | 48 | 20 |
| U42387_at | Human pancreatic polypeptide receptor "mRNA," complete cds | 20 | 49 | 55 | 20 | 20 | 41 |
| U42390_at | Human sapiens Trio "mRNA," complete cds | 22 | 61 | 20 | 20 | 20 | 20 |
| U42408_at | Human ladinin (LAD) "mRNA," complete cds | 216 | 101 | 103 | 253 | 264 | 185 |
| U42412_at | Human 5'-AMP-activated protein "kinase," gamma-1 subunit "mRNA," complete cds | 40 | 57 | 20 | 57 | 20 | 20 |
| U43030_at | Human cardiotrophin-1 (CTF1) "mRNA," complete cds | 113 | 70 | 20 | 146 | 388 | 204 |
| U43077_at | Human CDC37 homolog "mRNA," complete cds | 76 | 216 | 283 | 87 | 241 | 265 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U43083_at | Human G alpha-q (Gαq) "mRNA," complete cds | 49 | 34 | 20 | 83 | 211 | 142 |
| U43142_at | Human vascular endothelial growth factor related protein VRP "mRNA," complete cds | 20 | 20 | 20 | 20 | 20 | 20 |
| U43148_at | Human patched homolog (PTC) "mRNA," complete cds | 86 | 191 | 27 | 112 | 413 | 204 |
| U43177_at | Human urocortin "gene," complete cds | 20 | 20 | 20 | 54 | 153 | 218 |
| U43185_s_at | Human signaltransducer and activator of transcription Stat5A "mRNA," complete cds | 72 | 162 | 156 | 103 | 30 | 36 |
| U43189_s_at | Human Ets transcription factors NERF-1a and NERF-1b "(NERF-1a,b)" "mRNA," complete cds | 20 | 46 | 65 | 78 | 233 | 49 |
| U43203_s_at | Human thyroid transcription factor 1 (TTF-1) "mRNA," complete cds | 20 | 20 | 45 | 26 | 167 | 67 |
| U43279_at | Human nucleoporin nup 36 "mRNA," complete cds. /gb=U43279 /ntype=RNA | 32 | 23 | 20 | 33 | 20 | 20 |
| U43286_at | Human selenophosphate synthetase 2 (SPS2) "mRNA," complete cds | 143 | 246 | 118 | 102 | 196 | 172 |
| U43292_at | Human MDS1B (MDS1) "mRNA," complete cds | 76 | 107 | 20 | 48 | 129 | 189 |
| U43318_at | Human putative transmembrane receptor (frizzled 5) "mRNA," complete cds | 20 | 20 | 20 | 20 | 246 | 89 |
| U43328_at | Human link protein "mRNA," complete cds | 20 | 29 | 20 | 20 | 159 | 202 |
| U43374_at | Human normal keratinocyte mRNA | 20 | 20 | 92 | 32 | 26 | 20 |
| U43408_at | Human tyrosine kinase (Tnk1) "mRNA," complete cds | 77 | 91 | 20 | 20 | 20 | 79 |
| U43431_at | Human DNA topoisomerase III "mRNA," complete cds | 20 | 20 | 41 | 20 | 273 | 83 |
| U43519_at | Human dystrophin-related protein 2 (DRP2) "mRNA," complete cds | 97 | 64 | 61 | 98 | 93 | 196 |
| U43522_at | Human cell adhesion kinase beta (CAKbeta) "mRNA," complete cds | 71 | 197 | 41 | 124 | 28 | 63 |
| U43527_at | Human malignant melanoma metastasis-suppressor (KiSS-1) "gene," "mRNA," complete cds | 97 | 157 | 78 | 101 | 260 | 181 |
| U43586_at | Human kinase suppressor of ras-1 (KSR1) "mRNA," partial cds | 20 | 45 | 20 | 55 | 172 | 277 |
| U43653_at | Human obese protein (ob) "mRNA," complete cds | 20 | 20 | 20 | 20 | 72 | 20 |
| U43672_at | Human putative transmembrane receptor IL-1Rrp "mRNA," complete cds | 20 | 20 | 20 | 50 | 113 | 20 |
| U43747_s_at | Human frataxin (FRDA) "mRNA," complete cds | 20 | 43 | 91 | 71 | 44 | 20 |
| U43753_cds2_at | Human frataxin (FRDA) gene, exon 5b and complete cds. | 20 | 20 | 20 | 27 | 20 | 87 |
| U43843_at | Human h-neuro-d4 protein "mRNA," complete cds | 58 | 20 | 20 | 20 | 20 | 132 |
| U43885_at | Human Grb2-associated binder-1 "mRNA," complete cds | 20 | 20 | 20 | 20 | 98 | 40 |
| U43899_at | Human signal transducing adaptor molecule STAM "mRNA," complete cds | 35 | 87 | 20 | 53 | 89 | 44 |
| U43901_ma1_s_at | Human 37 kD alaminin receptor precursor/p40 ribosome associated protein "gene," complete cds | 2812 | 4088 | 6079 | 6070 | 963 | 2772 |
| U43916_s_at | Human tumor-associated membrane protein homolog (TMP) "mRNA," complete cds | 409 | 76 | 76 | 32 | 219 | 20 |
| U43923_at | Human transcription factor SUPT4H "mRNA," complete cds | 127 | 147 | 219 | 106 | 337 | 191 |
| U43944_at | Human breast cancer cytosolic NADP(+)-dependent malic enzyme "mRNA," partial cds | 84 | 20 | 20 | 20 | 20 | 20 |
| U43959_at | Human beta 4 adducin "mRNA," alternatively spliced partial cds | 121 | 94 | 20 | 77 | 20 | 20 |
| U43965_at | Human ankyrin G119 (ANK3) "mRNA," complete cds | 24 | 20 | 94 | 56 | 22 | 71 |
| U44059_at | Human thyrotroph embryonic factor (TEF) "mRNA," complete cds | 145 | 175 | 93 | 122 | 401 | 194 |
| U44060_at | Human homeodomain protein (Prox 1) "mRNA," complete cds | 20 | 20 | 20 | 20 | 20 | 38 |
| U44103_at | Human small GTP binding protein Rab9 "mRNA," complete cds | 59 | 20 | 20 | 41 | 20 | 37 |
| U44105_at | Human Rab9 expressed pseudogene "mRNA," complete cds | 20 | 20 | 20 | 20 | 20 | 20 |
| U44111_at | Human histamine N-methyltransferase (HNMT) gene | 20 | 41 | 68 | 105 | 287 | 20 |
| U44378_at | Human homozygous deletion target in pancreatic carcinoma (DPC4) "mRNA," complete cds | 24 | 22 | 80 | 52 | 55 | 99 |
| U44429_at | Human D53 (hD53) "mRNA," partial cds | 26 | 20 | 20 | 20 | 86 | 59 |
| U44754_at | Human PSE-binding factor PTF gamma subunit "mRNA," complete cds | 20 | 60 | 68 | 20 | 207 | 39 |
| U44755_at | Human PSE-binding factor PTF delta subunit "mRNA," complete cds | 250 | 242 | 112 | 183 | 579 | 491 |
| U44772_at | Human palmitoyl protein thioesterase "mRNA," complete cds | 88 | 78 | 118 | 88 | 20 | 97 |
| U44799_s_at | Human U1-snRNP binding protein homolog "mRNA," complete cds | 29 | 92 | 107 | 41 | 104 | 20 |
| U44839_at | Human putative ubiquitin C-terminal hydrolase (UHX1) "mRNA," complete cds | 566 | 805 | 795 | 545 | 946 | 830 |
| U44848_at | Human nuclear respiratory factor 1 (NRF1) "mRNA," 3' UTR. /gb=U44848 /ntype=RNA | 20 | 20 | 123 | 20 | 20 | 20 |
| U44975_at | Human DNA-binding protein CPBP (CPBP) "mRNA," partial cds | 153 | 20 | 115 | 48 | 20 | 76 |
| U45255_s_at | Human paired-box protein PAX2 (PAX2) gene | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| U45285_at | Human specific 116-kDa vacuolar proton pump subunit (OC-116kDa) "mRNA," complete cds | 20 | 224 | 98 | 95 | 72 | 20 | 20 |
| U45328_s_at | Human ubiquitin-conjugating enzyme (UBE2I) "mRNA," complete cds | 35 | 123 | 147 | 193 | 65 | 20 | 121 |
| U45448_at | Human P2x1 receptor "mRNA," complete cds | 81 | 20 | 20 | 71 | 323 | 20 | 116 |
| U45878_s_at | Human inhibitor of apoptosis protein 1 "mRNA," complete cds | 69 | 344 | 243 | 101 | 31 | 20 | 158 |
| U45880_at | Human X-linked inhibitor of apoptosis protein XIAP "mRNA," complete cds | 20 | 97 | 20 | 29 | 20 | 20 | 20 |
| U45955_at | Human neuronal membrane glycoprotein M6b "mRNA," partial cds | 20 | 44 | 20 | 20 | 20 | 20 | 20 |
| U45973_at | Human phosphatidylinositol "(4,5)bisphosphate" 5-phosphatase homolog "mRNA," partial cds | 227 | 342 | 34 | 183 | 299 | 332 | 332 |
| U45974_at | Human phosphatidylinositol "(4,5)" bisphosphate 5-phosphatase homolog "mRNA," partial cds | 114 | 209 | 207 | 67 | 55 | 55 | 134 |
| U45975_at | Human phosphatidylinositol "(4,5)bisphosphate" 5-phosphatase homolog "mRNA," partial cds | 266 | 485 | 425 | 321 | 553 | 505 | 505 |
| U45976_at | Human clathrin assembly protein lymphoid myeloid leukemia (CALM) "mRNA," complete cds | 80 | 45 | 36 | 46 | 157 | 20 | 20 |
| U45982_at | Human G protein-coupled receptor GRP-9-6 "gene," complete cds | 115 | 130 | 175 | 124 | 250 | 215 | 215 |
| U45983_at | Human G protein-coupled receptor GPR-CY6 "gene," complete cds | 20 | 20 | 20 | 26 | 111 | 20 | 20 |
| U46006_s_at | Hman smooth muscle LIM protein (h-SmLIM) "mRNA," complete cds. /gb=U46006 /ntype=RNA | 101 | 20 | 34 | 50 | 146 | 39 | 39 |
| U46023_at | Human Xq28 "mRNA," complete cds. | 20 | 20 | 20 | 20 | 20 | 39 | 39 |
| U46024_at | Human myotubularin (MRM1) "mRNA," partial cds | 20 | 28 | 42 | 20 | 55 | 20 | 20 |
| U46025_at | Human translation initiation factor eIF-3 p110 subunit "gene," complete cds | 349 | 463 | 837 | 506 | 373 | 581 | 581 |
| U46116_at | Human receptor tyrosine phosphatase gamma (PTPRG) gene | 20 | 20 | 20 | 20 | 41 | 20 | 20 |
| U46194_at | Human renal cell carcinoma antigen RAGe-4 "mRNA," complete cputative cds | 20 | 48 | 111 | 20 | 47 | 20 | 20 |
| U46461_at | Human dishevelled homolog (DVL) "mRNA," complete cds | 137 | 98 | 20 | 82 | 20 | 291 | 291 |
| U46499_at | Human microsomal glutathione transferase (GST12) "gene," 5' sequence | 437 | 484 | 1722 | 728 | 418 | 385 | 385 |
| U46569_at | Human aquaporin-5 (AQP5) gene | 31 | 20 | 20 | 81 | 70 | 51 | 51 |
| U46570_at | Human tetratricopeptide repeat protein (tpr1) "mRNA," complete cds | 347 | 550 | 348 | 301 | 651 | 433 | 433 |
| U46571_at | Human tetratricopeptide repeat protein (tpr2) "mRNA," complete cds | 92 | 84 | 67 | 50 | 138 | 101 | 101 |
| U46689_at | Human microsomal aldehyde dehydrogenase (ALD10) "mRNA," complete cds | 46 | 20 | 20 | 20 | 99 | 142 | 142 |
| U46892_ma1_at | Human cystatin B gene, complete cds. | 10030 | 746 | 1958 | 1434 | 1161 | 1076 | 1076 |
| U46744_at | Human dystrobrevin-alpha "mRNA," complete cds | 20 | 20 | 20 | 20 | 20 | 20 | 20 |
| U46746_s_at | Human dystrobrevin-epsilon "mRNA," complete cds | 20 | 21 | 20 | 20 | 20 | 20 | 20 |
| U46751_at | Human phosphotyrosine independent ligand p62 for the Lck SH2 domain "mRNA," complete cds | 619 | 644 | 757 | 723 | 324 | 515 | 515 |
| U46752_at | Human phosphotyrosine independent ligand p62B B-cell isoform for the Lck SH2 domain "mRNA," partial cds | 33 | 76 | 20 | 20 | 176 | 20 | 20 |
| U46767_at | Human monocyte chemoattractant protein-4 precursor (MCP-4) "mRNA," complete cds | 20 | 28 | 20 | 20 | 45 | 20 | 20 |
| U46901_at | Human NACP gene | 23 | 122 | 20 | 121 | 180 | 75 | 75 |
| U47007_at | Human transcriptional repressor (NAB1) NAB1 "mRNA," complete cds | 20 | 20 | 20 | 38 | 39 | 102 | 102 |
| U47011_cds1_at | Human fibroblast growth factor 8 (FGF8) gene, exon 3 and complete cds. | 20 | 20 | 20 | 20 | 20 | 23 | 23 |
| U47025_s_at | Human fetal brain glycogen phosphorylase B "mRNA," complete cds | 20 | 149 | 258 | 176 | 186 | 99 | 99 |
| U47050_at | Human putative calcium influx channel (htrp3) "mRNA," complete cds | 20 | 20 | 25 | 20 | 20 | 20 | 20 |
| U47054_at | Human putative mono-ADP-ribosyltransferase (htMART) "mRNA," complete cds | 20 | 78 | 67 | 20 | 20 | 80 | 80 |
| U47077_at | Human DNA-dependent protein kinase catalytic subunit (DNA-PKcs) "mRNA," complete cds | 47 | 20 | 69 | 20 | 45 | 20 | 20 |
| U47101_at | Human NitU-like protein (hNitU) "mRNA," partial cds | 138 | 56 | 334 | 83 | 45 | 69 | 69 |
| U47105_at | Human H105e3 "mRNA," complete cds | 142 | 298 | 65 | 67 | 140 | 181 | 181 |
| U47292_at | Human spasmolytic polypeptide (SP) "gene," 5' region and | 20 | 20 | 37 | 20 | 40 | 23 | 23 |
| U47334_at | Human gamma aminobutyric acid receptor beta4 subunit-like "mRNA," partial cds. /gb=U47334 /ntype=RNA | 20 | 90 | 20 | 20 | 91 | 64 | 64 |
| U47414_at | Human cyclin G2 "mRNA," complete cds | 55 | 87 | 153 | 51 | 74 | 20 | 20 |
| U47621_at | Human nucleolar autoantigen No55 "mRNA," complete cds | 99 | 73 | 20 | 46 | 20 | 20 | 20 |
| U47634_at | Human beta-tubulin class III isotype (beta-3) "mRNA," complete cds | 73 | 71 | 20 | 116 | 37 | 20 | 20 |
| U47635_at | Human D13S824E locus "mRNA," complete cds | 60 | 20 | 40 | 20 | 20 | 20 | 20 |
| U47677_at | Human transcription factor E2F1 (E2F1) "gene," promoter and | 20 | 20 | 20 | 20 | 20 | 20 | 20 |
| U47686_s_at | Human signal transducer and activator of transcription Stat5B "mRNA," complete cds | 20 | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U47742_at | Human monocytic leukaemia zinc finger protein (MOZ) "mRNA," complete cds | 108 | 149 | 156 | 82 | 317 | 196 |
| U47926_at | Human unknown protein B "mRNA," complete cds | 20 | 20 | 20 | 22 | 149 | 52 |
| U47927_at | Human isopeptidase T (ISOT) "mRNA," complete cds | 65 | 112 | 42 | 20 | 20 | 20 |
| U47928_at | Human protein A alternatively spliced from 2 (A-2) "mRNA," complete cds | 20 | 31 | 20 | 20 | 20 | 20 |
| U47931_at | Human G-protein beta-3 subunit alternatively spliced from mRNA sequence. /gb=U47931 /ntype=RNA | 203 | 328 | 168 | 249 | 489 | 356 |
| U48213_at | Human D-site binding protein "gene," promoter region and | 58 | 20 | 20 | 20 | 20 | 20 |
| U48231_at | Human bradykinin B1 receptor (BDKRB1) "gene," first | 80 | 98 | 20 | 20 | 57 | 20 |
| U48250_at | Human protein kinase C-binding protein RACK17 "mRNA," partial cds | 20 | 20 | 20 | 20 | 20 | 20 |
| U48251_at | Human protein kinase C-binding protein RACK7 "mRNA," partial cds | 20 | 20 | 43 | 20 | 20 | 122 |
| U48263_at | Human pre-pro-orphanin FQ (OFQ) "mRNA," complete cds | 97 | 132 | 201 | 126 | 590 | 226 |
| U48296_at | Human protein tyrosine phosphatase PTPCAAX1 (hPTPCAAX1) "mRNA," complete cds | 68 | 62 | 70 | 55 | 109 | 20 |
| U48405_at | Human G protein coupled receptor OGR1 "gene," complete cds | 124 | 179 | 20 | 168 | 194 | 357 |
| U48408_at | Human kidney wate channel (hKID) "mRNA," complete cds | 155 | 174 | 70 | 158 | 223 | 190 |
| U48436_s_at | Human fragile X mental retardation protein FMR2p (FMR2) "mRNA," complete cds | 24 | 20 | 59 | 26 | 159 | 32 |
| U48437_at | Human amyloid precursor-like element-containing "mRNA," clone pchMT2 | 93 | 153 | 97 | 84 | 157 | 173 |
| U48697_at | Human mariner-like element-containing "mRNA," clone pchMT2 | 20 | 20 | 20 | 20 | 20 | 20 |
| U48705_ma1_s_at | Human receptor tyrosine kinase DDR "gene," complete cds | 327 | 610 | 1344 | 1490 | 644 | 424 |
| U48707_at | Human protein phosphatase-1 inhibitor "mRNA," complete cds | 50 | 34 | 20 | 47 | 20 | 46 |
| U48730_at | Human transcription factor Stat5b (stat5b) "mRNA," complete cds | 20 | 20 | 20 | 20 | 20 | 20 |
| U48736_at | Human serine/threonine-protein kinase PRP4h (PRP4h) "mRNA," complete cds | 26 | 20 | 34 | 20 | 22 | 20 |
| U48807_at | Human MAP kinase phosphatase (MKP-2) "mRNA," complete cds | 60 | 52 | 41 | 20 | 20 | 126 |
| U48861_at | Human beta 4 nicotinic acetylcholine receptor subunit "mRNA," complete cds | 311 | 474 | 20 | 68 | 739 | 528 |
| U48865_s_at | Human C/EBP epsilon (CEBPE) "gene," complete cds | 20 | 20 | 20 | 20 | 20 | 20 |
| U48936_at | Human amiloride-sensitive epithelial sodium channel gamma subunit "mRNA," 5' "end," partial cds. /gb=U48936 /ntype=RNA | 368 | 198 | 20 | 144 | 432 | 546 |
| U48959_at | Human myosin light chain kinase (MLCK) "mRNA," complete cds | 621 | 131 | 20 | 20 | 20 | 20 |
| U49020_cds2_s_at | MEF2A gene (myocyte-specific enhancer factor "2A," C9 form) extracted from Human nyocyte-specific enhancer factor 2A (MEF2A) "ger | 24 | 46 | 33 | 45 | 20 | 20 |
| U49065_at | Human interleukin-1 receptor-related protein "mRNA," complete cds. /gb=U49065 /ntype=RNA | 81 | 20 | 20 | 55 | 37 | 126 |
| U49070_at | Human peptidyl-prolyl isomerase and essential mitotic regulator (PIN1) "mRNA," complete cds | 135 | 105 | 32 | 49 | 249 | 167 |
| U49082_at | Human transporter protein (g17) "mRNA," complete cds | 107 | 227 | 20 | 160 | 158 | 528 |
| U49089_at | Human neuroendocrine-dig (NE-dig) "mRNA," complete cds | 84 | 96 | 79 | 91 | 226 | 103 |
| U49114_at | Human prohormone convertase 5 precursor (PC5) "mRNA," partial cds | 25 | 96 | 20 | 35 | 20 | 91 |
| U49187_at | Human placenta (DIFF48) "mRNA," complete cds | 20 | 20 | 20 | 20 | 20 | 25 |
| U49188_at | Human placenta (DIFF33) "mRNA," complete cds | 163 | 105 | 210 | 146 | 181 | 65 |
| U49248_at | Human canalicular multispecific organic anion transporter "(cMOAT)," "gene," complete cds | 55 | 52 | 20 | 20 | 129 | 62 |
| U49250_at | Human putative cerebral cortex transcriptional regulator T-Brain-1 (Tbr-f) "mRNA," complete cds | 20 | 41 | 20 | 57 | 20 | 122 |
| U49260_at | Human mevalonate pyrophosphate decarboxylase (MPD) "mRNA," complete cds | 58 | 62 | 20 | 20 | 161 | 167 |
| U49278_at | Human putative DNA-binding protein "mRNA," partial cds | 115 | 81 | 20 | 170 | 251 | 127 |
| U49352_at | Human liver "2,4-dienoyl-CoA" reductase "mRNA," complete cds | 20 | 111 | 20 | 20 | 20 | 50 |
| U49379_at | Human diacylglycerol kinase epsilon DGK "mRNA," complete cds | 20 | 30 | 103 | 91 | 20 | 188 |
| U49395_at | Human ionotropic ATP receptor P2x5a "mRNA," complete cds | 210 | 212 | 144 | 126 | 503 | 551 |
| U49436_at | Human translation initiation factor 5 (eIF5) "mRNA," complete cds | 63 | 20 | 127 | 40 | 53 | 20 |
| U49441_at | Human serotonin 5-HT2c receptor "mRNA," complete cds | 25 | 20 | 91 | 31 | 336 | 71 |
| U49516_at | Human mitochondrial trifunctional protein beta subunit "mRNA," partial cds. /gb=U49441 /ntype=RNA | 20 | 20 | 20 | 20 | 20 | 25 |
| U49742_at | Human rhodopsin "gene," complete cds | 20 | 20 | 20 | 20 | 63 | 20 |
| U49785_at | Human D-dopachrome tautomerase "mRNA," complete cds | 178 | 256 | 278 | 237 | 169 | 225 |
| U49835_s_at | Human YKL-39 precursor "mRNA," complete cds | 49 | 257 | 285 | 171 | 153 | 138 |
| U49837_at | Human LIM protein MLP "mRNA," complete cds | 56 | 79 | 115 | 86 | 415 | 260 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U49844_at | Human FRAP-related protein (FRP1) "mRNA," complete cds | 20 | 29 | 75 | 20 | 20 | 20 |
| U49857_at | Human transcriptional activator "mRNA," complete cds | 41 | 71 | 41 | 44 | 80 | 20 |
| U49869_ma1_at | Human ubiquitin gene, complete cds. | 2053 | 3081 | 6193 | 2498 | 1653 | 2471 |
| U49928_at | Human TAK1 binding protein 1 (TAB1) "mRNA," complete cds | 20 | 20 | 20 | 26 | 20 | 20 |
| U49957_s_at | Human LIM protein (LPP) "mRNA," partial cds | 26 | 61 | 20 | 44 | 20 | 29 |
| U49973_xpt1_at | Human Tigger1 transposable element, complete consensus sequence. | 26 | 120 | 91 | 40 | 165 | 48 |
| U49973_xpt2_at | Human Tigger1 transposable element, complete consensus sequence. | 20 | 20 | 36 | 24 | 20 | 41 |
| U49974_f_at | Human mariner2 transposable "element," complete consensus sequence. /gb=U49974 /ntype=DNA /annot=CDS | 28 | 25 | 20 | 20 | 20 | 20 |
| U50062_at | Human RIP protein kinase "gene," compete cds | 20 | 29 | 63 | 105 | 259 | 162 |
| U50078_at | Human guanine nucleotide exchange factor p532 "mRNA," complete cds | 20 | 27 | 84 | 60 | 41 | 80 |
| U50079_s_at | Human histone deacetylase HD1 "mRNA," complete cds | 160 | 243 | 399 | 279 | 750 | 278 |
| U50136_ma1_at | Human leukotriene C4 synthase (LTC4S) gene, complete cds. | 193 | 338 | 153 | 181 | 384 | 326 |
| U50146_at | Human type 2 neuropeptide Y receptor (NPY Y2) "gene," partial | 20 | 20 | 20 | 20 | 20 | 20 |
| U50196_at | Human adenosine kinase "mRNA," complete cds | 106 | 97 | 90 | 117 | 181 | 43 |
| U50315_at | Human enhancer of zeste homolog 1 (EZH1) "mRNA," complete cds | 151 | 227 | 53 | 135 | 418 | 406 |
| U50327_s_at | Human protein kinase C substrate 80K-H gene (PRKCSH) | 20 | 71 | 89 | 190 | 507 | 58 |
| U50330_at | Human procollagen C-proteinase (pCP-2) "mRNA," complete cds | 163 | 59 | 20 | 68 | 124 | 238 |
| U50360_s_at | Human "calcium," calmodulin-dependent protein kinase II gamma "mRNA," partial cds. /gb=U50360 /ntype=RNA | 20 | 55 | 20 | 51 | 20 | 36 |
| U50361_s_at | Human "calcium," calmodulin-dependent protein kinase II delta "mRNA," partial cds. /gb=U50361 /ntype=RNA | 20 | 23 | 20 | 20 | 20 | 20 |
| U50383_at | Human retinoic acid-responsive protein (NN8-4AG) "mRNA," complete cds | 23 | 62 | 20 | 20 | 45 | 92 |
| U50523_at | Human BRCA2 "region," mRNA sequence CG037 | 510 | 946 | 613 | 369 | 129 | 346 |
| U50527_s_at | Human BRCA2 "region," mRNA sequence CG018 | 20 | 20 | 24 | 20 | 20 | 58 |
| U50531_s_at | Human BRCA2 "region," mRNA sequence CG030 | 37 | 41 | 20 | 20 | 182 | 137 |
| U50534_at | Human BRCA2 "region," mRNA sequence CG003 | 20 | 20 | 20 | 36 | 20 | 23 |
| U50535_at | Human BRCA2 "region," mRNA sequence CG006 | 37 | 304 | 129 | 96 | 161 | 92 |
| U50553_at | Human helicase like protein 2 "mRNA," complete cds | 108 | 72 | 72 | 72 | 137 | 20 |
| U50648_s_at | Human interferon-inducible RNA-dependent protein kinase (Pkr) gene | 20 | 228 | 154 | 143 | 29 | 41 |
| U50708_at | Human branched chain alpha-ketoacid dehydrogenase E1 beta subunit "mRNA," complete cds | 20 | 20 | 20 | 20 | 83 | 20 |
| U50733_at | Human dynamitin "mRNA," complete cds | 239 | 205 | 308 | 214 | 197 | 268 |
| U50743_at | Human "Na,K-ATPase" gamma subunit "mRNA," complete cds | 252 | 325 | 186 | 193 | 713 | 704 |
| U50822_ma1_s_at | Human neurogenic helix-loop-helix protein NEUROD (neurod) "gene," complete cds | 20 | 20 | 20 | 20 | 20 | 20 |
| U50839_at | Human g16 protein (g16) "mRNA," partial cds | 42 | 20 | 75 | 80 | 84 | 114 |
| U50928_at | Human autosomal dominant polycystic kidney disease type II (PKD2) "mRNA," complete cds | 33 | 98 | 36 | 23 | 20 | 20 |
| U50929_at | Human betaine:homocysteine methyltransferase "mRNA," complete cds | 20 | 35 | 85 | 121 | 20 | 259 |
| U50939_at | Human amyloid precursor protein-binding protein 1 "mRNA," complete cds | 46 | 42 | 118 | 54 | 20 | 73 |
| U50950_at | Human infant brain unknown product "mRNA," complete cds | 20 | 87 | 90 | 63 | 122 | 209 |
| U51003_s_at | Human DLX-2 (Dlx2) "mRNA," complete cds | 20 | 20 | 20 | 20 | 373 | 123 |
| U51004_at | Human putative protein kinase C inhibitor (PKCI-1) "mRNA," complete cds | 433 | 181 | 548 | 272 | 126 | 408 |
| U51010_s_at | Human nicotinamide N-methyltransferase "gene," exon 1 and 5' flanking region. /gb=U51010 /ntype=DNA /annot=exon | 20 | 20 | 20 | 20 | 20 | 77 |
| U51095_at | Human homeobox protein Cdx1 "mRNA," complete cds | 42 | 66 | 20 | 20 | 20 | 60 |
| U51096_at | Human homeobox protein Cdx2 "mRNA," complete cds | 54 | 64 | 20 | 31 | 20 | 20 |
| U51127_at | Human interferon regulatory factor 5 (Humirf5) "mRNA," complete cds | 177 | 285 | 136 | 162 | 100 | 204 |
| U51166_at | Human G/T mismatch-specific thymine DNA glycosylase "mRNA," complete cds | 20 | 41 | 58 | 25 | 20 | 35 |
| U51205_at | Human COP9 homolog (HCOP9) "mRNA," complete cds | 59 | 33 | 20 | 60 | 20 | 157 |
| U51240_s_at | Human lysosomal-associated multitransmembrane protein (LAPTm5) "mRNA," complete cds | 136 | 100 | 27 | 20 | 25 | 250 |
| U51241_at | Human eosinophil eotaxin receptor (CMKBR3) "gene," complete cds | 20 | 75 | 40 | 45 | 72 | 128 |
| U51269_at | Human armadillo repeat protein "mRNA," complete cds | 20 | 184 | 20 | 20 | 214 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U51333_s_at | Human hexokinase III (HK3) "mRNA," complete cds | 192 | 20 | 20 | 20 | 20 | 45 |
| U51334_at | Human putative RNA binding protein (RBP56) "mRNA," complete cds | 90 | 134 | 378 | 102 | 20 | 327 |
| U51336_at | Human inositol "1,3,4-trisphosphate" 5/6-kinase "mRNA," complete cds | 89 | 220 | 154 | 102 | 183 | 116 |
| U51432_at | Human nuclear protein Skip "mRNA," complete cds | 38 | 121 | 39 | 37 | 123 | 141 |
| U51477_at | Human diacylglycerol kinase zeta "mRNA," complete cds | 86 | 91 | 104 | 20 | 20 | 111 |
| U51478_at | Human sodium/potassium-transporting ATPase beta-3 subunit "mRNA," complete cds | 691 | 459 | 752 | 388 | 295 | 306 |
| U51561_at | Human cosmid "N79F2," complete sequence. | 20 | 20 | 28 | 20 | 65 | 20 |
| U51586_at | Human siah binding protein 1 (SiahBP1) "mRNA," partial cds. | 56 | 20 | 20 | 150 | 20 | 20 |
| U51587_at | Human Golgi complex autoantigen golgin-97 "mRNA," complete cds. | 86 | 95 | 20 | 20 | 20 | 55 |
| U51678_at | Human small acidic protein "mRNA," complete cds | 160 | 199 | 208 | 65 | 108 | 106 |
| U51711_at | Human desmocollin-2 "mRNA," 3' UTR | 146 | 20 | 20 | 20 | 44 | 32 |
| U51903_at | Human RasGAP-related protein (IQGAP2) "mRNA," complete cds | 62 | 52 | 33 | 46 | 161 | 98 |
| U51920_at | Human signal recognition particle (SRP54) "mRNA," complete cds | 22 | 20 | 101 | 78 | 28 | 112 |
| U51990_at | Human hPrp18 "mRNA," complete cds | 76 | 40 | 20 | 20 | 105 | 22 |
| U52077_s_at | Human mariner1 transposase "gene," complete consensus sequence. /gb=U52077 /ntype=DNA /annot=CDS | 24 | 29 | 64 | 91 | 155 | 74 |
| U52100_at | Human XMP "mRNA," complete cds | 192 | 224 | 268 | 208 | 75 | 163 |
| U52101_at | Human YMP "mRNA," complete cds | 174 | 20 | 20 | 23 | 20 | 164 |
| U52111_ma3_at | Homo sapiens Xq28 genomic DNA in the region of the ALD locus containing the genes for creatine transporter (SLC6A8), CDM, adrenole | 20 | 20 | 20 | 20 | 20 | 20 |
| U52111_ma4_at | Homo sapiens Xq28 genomic DNA in the region of the ALD locus containing the genes for creatine transporter (SLC6A8), CDM, adrenole | 20 | 20 | 20 | 20 | 20 | 20 |
| U52112_ma1_at | Homo sapiens Xq28 genomic DNA in the region of the L1CAM locus containing the genes for neural cell adhesion molecule L1 (L1CAM) | 146 | 210 | 55 | 141 | 287 | 199 |
| U52112_ma5_at | Homo sapiens Xq28 genomic DNA in the region of the L1CAM locus containing the genes for neural cell adhesion molecule L1 (L1CAM) | 205 | 201 | 103 | 176 | 228 | 317 |
| U52152_at | Human inwardly rectifying potassium channel Kir3.3 "mRNA," complete cds | 20 | 20 | 20 | 20 | 20 | 20 |
| U52153_at | Human inwardly rectifying potassium channel Kir3.2 "mRNA," complete cds | 28 | 28 | 66 | 33 | 77 | 20 |
| U52154_at | Human G protein-coupled inwardly rectifying potassium channel Kir3.4 "mRNA," complete cds | 82 | 97 | 20 | 20 | 472 | 364 |
| U52155_at | Human ATP-dependent inwardly rectifying potassium channel Kir4.1 "mRNA," complete cds | 20 | 72 | 20 | 20 | 139 | 20 |
| U52191_s_at | Human SMCY (H-Y) "mRNA," complete cds | 26 | 96 | 184 | 39 | 34 | 134 |
| U52373_s_at | Human serine/threonine kinase MNB (mnb) "mRNA," complete cds | 20 | 20 | 20 | 20 | 20 | 26 |
| U52426_at | Human GOK (GOK) "mRNA," complete cds | 129 | 91 | 65 | 84 | 20 | 146 |
| U52427_ma1_at | RNA polymerase II seventh subunit (rpb-7) gene, complete cds | 109 | 46 | 238 | 127 | 129 | 102 |
| U52513_at | Human RIG-G "mRNA," complete cds | 103 | 83 | 76 | 26 | 84 | 188 |
| U52518_at | Human Grb2-related adaptor protein (Grap) "mRNA," complete cds | 72 | 62 | 20 | 42 | 191 | 292 |
| U52521_at | Human arfaptin "1," putative target protein of ADP-ribosylation "factor," "mRNA," complete cds | 29 | 29 | 129 | 80 | 47 | 49 |
| U52522_at | Human arfaptin "2," putative target protein of ADP-ribosylation "factor," "mRNA," complete cds | 130 | 288 | 120 | 146 | 316 | 201 |
| U52682_at | Human lymphocyte specific interferon regulatory factor/interferon regulatory factor 4 (LSIRF/IRF4) "mRNA," complete cds | 37 | 20 | 21 | 20 | 164 | 20 |
| U52696_s_at | Human adrenal Creb-rp homolog "(Creb-rp)," RACE clone "N1," partial cds. /gb=U52696 /ntype=RNA | 135 | 852 | 1060 | 460 | 2808 | 637 |
| U52700_at | Human tenascin-X (XB) "mRNA," RACE clone "N1," partial cds. /gb=U52700 /ntype=RNA | 20 | 47 | 20 | 30 | 404 | 69 |
| U52827_at | Human Cri-du-chat region "mRNA," clone NIBB11 | 20 | 182 | 60 | 68 | 34 | 201 |
| U52828_s_at | Human Cri-du-chat region "mRNA," clone NIBA2 | 35 | 34 | 33 | 23 | 20 | 28 |
| U52830_at | Human Cri-du-chat region mRNA, clone CSC8. | 39 | 20 | 20 | 22 | 103 | 41 |
| U52840_at | Human Cri-du-chat region "mRNA," clone CSA1 | 20 | 20 | 20 | 20 | 20 | 20 |
| U52960_at | Human RNA polymerase II complex component SRB7 "mRNA," complete cds | 118 | 156 | 20 | 20 | 20 | 24 |
| U52969_at | Human PEP19 (PCP4) "mRNA," complete cds | 20 | 82 | 20 | 20 | 20 | 97 |
| U53003_at | Human GT335 "mRNA," complete cds | 20 | 20 | 20 | 53 | 20 | 150 |
| U53174_at | Human cell cycle checkpoint control protein "mRNA," complete cds | 20 | 62 | 20 | 103 | 202 | 182 |
| U53204_at | Human plectin (PLEC1) "mRNA," complete cds | 20 | 35 | 183 | 258 | 20 | 20 |
| U53209_at | Human transformer-2 alpha (htra-2 alpha) "mRNA," complete cds | 84 | 81 | 327 | 45 | 20 | 62 |
| U53225_at | Human sorting nexin 1 (SNX1) "mRNA," complete cds | 20 | 20 | 20 | 38 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| U53347_at | Human neutral amino acid transporter B "mRNA," complete cds | 228 | 364 | 367 | 337 | 380 | 446 | 20 |
| U53342_at | Human p38Beta MAP kinase "mRNA," complete cds | 20 | 20 | 20 | 20 | 20 | 20 | |
| U53445_at | Human ovarian cancer downregulated myosin heavy chain homolog (Doc1) "mRNA," complete cds | 143 | 145 | 20 | 21 | 20 | 20 | |
| U53446_at | Human mitogen-responsive phosphoprotein DDC-2 "mRNA," complete cds | 29 | 145 | 72 | 49 | 77 | 106 | |
| U53468_at | Human NADH:ubiquinone oxidoreductase subunit B13 (B13) "mRNA," complete cds | 20 | 20 | 20 | 20 | 20 | 119 | |
| U53476_at | Human proto-oncogene Wnt7a "mRNA," complete cds | 150 | 79 | 20 | 37 | 113 | 120 | |
| U53506_at | Human type II iodothyronine deiodinase "mRNA," complete cds. | 20 | 20 | 20 | 24 | 20 | 20 | |
| U53786_at | Human envoplakin (EVPL) "mRNA," complete cds | 336 | 229 | 231 | 269 | 251 | 501 | |
| U53830_at | Homo sapiens interferon regulatory factor 7A "mRNA," complete cds | 20 | 55 | 20 | 20 | 20 | 196 | |
| U54617_at | Human pyruvate dehydrogenase kinase isoform 4 "mRNA," complete cds | 20 | 20 | 29 | 57 | 65 | 81 | |
| U54644_s_at | Human tub homolog "mRNA," complete cds | 143 | 157 | 353 | 209 | 594 | 352 | |
| U54778_at | Human 14-3-3 epsilon "mRNA," complete cds | 195 | 159 | 382 | 165 | 250 | 101 | |
| U54804_at | Human Has2 "mRNA," complete cds | 20 | 21 | 60 | 20 | 20 | 41 | |
| U54999_at | Human LGN protein "mRNA," complete cds | 20 | 20 | 20 | 20 | 20 | 20 | |
| U55054_at | Human K-Cl cotransporter (hKCC1) "mRNA," complete cds | 72 | 55 | 20 | 23 | 140 | 285 | |
| U55206_at | Human gamma-glutamyl hydrolase (hGH) "mRNA," complete cds | 52 | 41 | 20 | 26 | 20 | 20 | |
| U55209_at | Human myosin VIIa transcript 2 "mRNA," complete cds | 20 | 20 | 20 | 20 | 161 | 20 | |
| U55258_at | Human hBRAVO/Nr-CAM precursor (hBRAVO/Nr-CAM) "gene," complete cds | 79 | 85 | 127 | 20 | 61 | 100 | |
| U55764_at | Human estrogen sulfotransferase "mRNA," partial cds | 20 | 20 | 20 | 20 | 20 | 20 | |
| U55766_at | Human Rev interacting protein Rip-1 "mRNA," complete cds | 20 | 69 | 63 | 20 | 20 | 77 | |
| U55853_at | Homo sapiens 130 kD Golgi-localized phosphoprotein (GPP130) "mRNA," complete cds | 20 | 47 | 20 | 20 | 20 | 89 | |
| U55936_at | Human SNAP-23 "mRNA," complete cds | 20 | 54 | 26 | 20 | 20 | 20 | |
| U56085_at | Human periodic tryptophan protein 2 (PWP2) "mRNA," complete cds | 20 | 20 | 20 | 20 | 20 | 53 | |
| U56102_at | Human adhesion molecule DNAM-1 "mRNA," complete cds | 20 | 37 | 20 | 40 | 20 | 20 | |
| U56244_at | Human HIG-1 "mRNA," complete cds | 48 | 31 | 190 | 44 | 354 | 191 | |
| U56402_s_at | Human chromatin structural protein homolog (SUPT5H) "mRNA," complete cds | 20 | 20 | 20 | 20 | 70 | 20 | |
| U56417_at | Human lysophosphatidic acid acyltransferase-alpha "mRNA," complete cds | 70 | 200 | 134 | 145 | 22 | 534 | |
| U56418_at | Human lysophosphatidic acid acyltransferase-beta "mRNA," complete cds | 115 | 248 | 208 | 195 | 20 | 30 | |
| U56637_at | Human capping protein alpha subunit isoform 1 "mRNA," complete cds | 442 | 240 | 959 | 339 | 288 | 381 | |
| U56814_at | Human DNAse I homologous protein (DHP2) "mRNA," complete cds | 59 | 172 | 51 | 103 | 152 | 79 | |
| U56816_at | Human kinase Myt1 (Myt1) "mRNA," complete cds | 137 | 368 | 20 | 160 | 483 | 175 | |
| U56833_at | Human VHL vinding protein-1 (VBP-1) "mRNA," partial cds | 20 | 20 | 37 | 20 | 20 | 20 | |
| U56976_at | Human calmodulin dependent phosphodiesterase PDE1B1 "mRNA," complete cds | 42 | 20 | 20 | 20 | 79 | 47 | |
| U56998_at | Human putative serine/threonine protein kinase PRK (prk) "mRNA," complete cds | 20 | 20 | 20 | 20 | 20 | 20 | |
| U57057_at | Human WD protein IR10 "mRNA," complete cds | 26 | 31 | 20 | 38 | 58 | 20 | |
| U57092_at | Human small GTP-binding protein rab30 | 85 | 123 | 20 | 76 | 44 | 256 | |
| U57093_at | Human small GTP-binding protein rab27b "mRNA," complete cds | 20 | 20 | 20 | 20 | 131 | 51 | |
| U57094_at | Human small GTP-binding protein "mRNA," complete cds | 73 | 86 | 20 | 20 | 20 | 83 | |
| U57099_at | Human APEG-1 "mRNA," complete cds | 105 | 20 | 20 | 20 | 77 | 60 | |
| U57316_at | Human GCN5 (hGCN5) "gene," complete cds | 126 | 162 | 103 | 179 | 374 | 234 | |
| U57317_at | Human p300/CBP-associated factor (P/CAF) "mRNA," complete cds | 20 | 20 | 20 | 20 | 20 | 20 | |
| U57341_at | Human neurofilament triplet L protein "mRNA," partial cds. /gb=U57341 /ntype=RNA | 20 | 124 | 131 | 50 | 455 | 236 | |
| U57341_r_at | Human neurofilament triplet L protein "mRNA," partial cds. /gb=U57341 /ntype=RNA | 941 | 1344 | 2685 | 1594 | 3223 | 1644 | |
| U57342_at | Human myelodysplaia/myeloid leukemia factor 2 (MLF2) "mRNA," complete cds | 281 | 387 | 480 | 333 | 621 | 536 | |
| U57352_at | Human sodium channel 1 (nGNaC1) "mRNA," complete cds | 147 | 20 | 20 | 36 | 21 | 20 | |
| U57450_at | Human EPC-1 gene | 206 | 365 | 60 | 176 | 320 | 277 | |
| U57452_at | Human SNF1-like protein kinase "mRNA," partial cds. /gb=U57452 /ntype=RNA | 29 | 20 | 20 | 20 | 20 | 20 | |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U57592_at | Human junonji putative protein (jumonji) "mRNA," complete cds | 30 | 20 | 63 | 81 | 66 | 174 |
| U57623_s_at | Human fatty acid binding protein FABP "gene," complete cds | 20 | 48 | 74 | 74 | 52 | 24 |
| U57627_at | Human fetal brain oculocerebrorenal syndrome (OCRL1) "mRNA," complete cds | 20 | 20 | 48 | 34 | 33 | 53 |
| U57629_at | Human retinitis pigmentosa GTPase regulator (RPGR) "mRNA," complete cds | 33 | 69 | 36 | 63 | 158 | 71 |
| U57650_at | Human SH2-containing inositol 5-phosphatase (hSHIP)"mRNA," complete cds | 70 | 66 | 118 | 97 | 20 | 141 |
| U57721_at | Human L-kynurenine hydrolase "mRNA," complete cds | 131 | 150 | 106 | 77 | 51 | 20 |
| U57796_at | Human zinc finger protein (LD5-1) "mRNA," complete cds | 20 | 20 | 20 | 20 | 31 | 20 |
| U57877_at | Human integral membrane protein CII-3 "mRNA," nuclear gene encoding mitochondrial "protein," complete cds | 169 | 170 | 164 | 161 | 291 | 345 |
| U57911_at | Human fetal brain (239FB) "mRNA," from the WAGR "region," complete cds | 20 | 25 | 59 | 20 | 20 | 20 |
| U57971_s_at | Human calcium ATPase isoform 3x/a "mRNA," complet cds | 20 | 23 | 38 | 20 | 95 | 119 |
| U58032_at | Human myotubularin related protein 1 (MTMR1) "gene," partial cds. /gb=U58032 /ntype=DNA /annot=CDS | 99 | 38 | 20 | 20 | 159 | 20 |
| U58033_at | Human myotubularin related protein 2 (MTMR2) "gene," partial cds. /gb=U58033 /ntype=RNA | 20 | 20 | 275 | 203 | 157 | 242 |
| U58034_at | Human myotubularin related protein 3 (MTMR3) "gene," partial cds. /gb=U58034 /ntype=RNA | 20 | 26 | 20 | 72 | 96 | 57 |
| U58046_s_at | Human p167 "mRNA," complete cds | 59 | 109 | 149 | 158 | 20 | 20 |
| U58048_at | Human metallopeptidase PRSM1 "mRNA," complete cds | 49 | 119 | 95 | 114 | 107 | 33 |
| U58087_at | Human Hs-cul-1 "mRNA," complete cds | 165 | 305 | 275 | 203 | 157 | 242 |
| U58089_at | Human Hs-cul-3 "mRNA," partial cds | 61 | 20 | 144 | 72 | 20 | 20 |
| U58090_at | Human Hs-cul-4A "mRNA," partial cds | 20 | 20 | 20 | 20 | 20 | 20 |
| U58091_at | Human Hs-cul-4B "mRNA," partial cds | 20 | 20 | 20 | 20 | 20 | 68 |
| U58096_at | Human testis-specific protein (TSPY) "mRNA," complete cds | 41 | 121 | 111 | 41 | 20 | 178 |
| U58130_at | Human bumetanide-sensitive Na-K-2Cl cotransporter (NKCC2) "mRNA," complete cds | 20 | 20 | 20 | 28 | 65 | 43 |
| U58331_at | Human placental delta sarcoglycan "mRNA," complete cds | 61 | 20 | 20 | 20 | 142 | 101 |
| U58334_at | Human "Bcl2," p53 binding protein Bbp/53BP2 (BBP/53BP2) "mRNA," complete cds | 125 | 119 | 214 | 133 | 149 | 20 |
| U58516_at | Human breast epithelial antigen BA46 "mRNA," complete cds | 20 | 102 | 20 | 20 | 20 | 75 |
| U58522_at | Human huntingtin interacting protein (HIP2) "mRNA," complete cds | 20 | 45 | 20 | 20 | 20 | 67 |
| U58658_at | Human unknown protein mRNA within the p53 intron "1," complete cds | 32 | 99 | 20 | 43 | 20 | 20 |
| U58675_cds1_at | OR17-40 gene extracted from Human olfactory receptor gene cluster on chromosome "17," OR17-228 and "OR17-40," complete "cds," an | 27 | 20 | 24 | 20 | 20 | 170 |
| U58675_cds2_at | OR17-40 gene extracted from Human olfactory receptor gene cluster on chromosome "17," OR17-228 and "OR17-40," complete "cds," an | 20 | 71 | 22 | 86 | 224 | 225 |
| U58681_at | Human neurogenic basic-helix-loop-helix protein (NeuroD2) "gene," complete cds. | 142 | 174 | 59 | 122 | 371 | 1581 |
| U58682_at | Human ribosomal protein S28 "mRNA," complete cds | 2129 | 3033 | 3263 | 2165 | 1008 | 20 |
| U58766_at | Human FX protein "mRNA," complete cds | 98 | 52 | 85 | 153 | 20 | 215 |
| U58837_s_at | Human cGMP-gated cation channel beta subunit (CNCG2) "mRNA," complete cds | 20 | 20 | 20 | 20 | 136 | 28 |
| U58970_at | Human putative outer mitochondrial membrane 34 kDa translocase hTOM34 "mRNA," complete cds | 201 | 276 | 131 | 234 | 292 | 60 |
| U59057_at | Human beta-A4 crystallin (CRYBA4) "mRNA," complete cds | 56 | 75 | 20 | 92 | 20 | 20 |
| U59058_s_at | Human beta-A3/A1 crystallin (CYRBA3/A1) "mRNA," partial cds | 43 | 20 | 28 | 71 | 214 | 20 |
| U59111_at | Human dermatan sulfate proteoglycan 3 (DSPG3) "mRNA," complete cds | 20 | 20 | 47 | 20 | 20 | 37 |
| U59228_at | Human ectodermal dysplasia protein (EDA) "mRNA," complete cds | 33 | 104 | 20 | 20 | 143 | 20 |
| U59286_at | Human beta-R1 "mRNA," partial cds. /gb=U59286 /ntype=RNA | 51 | 154 | 20 | 20 | 281 | 98 |
| U59289_at | Human H-cadherin "mRNA," complete cds | 20 | 71 | 43 | 53 | 174 | 120 |
| U59302_at | Human steroid receptor coactivator-1 F-SRC-1 "mRNA," complete cds | 153 | 146 | 177 | 125 | 309 | 143 |
| U59309_at | Human fumarase precursor (FH) "mRNA," nuclear gene encoding mitochondrial "protein," complete cds | 88 | 73 | 148 | 96 | 46 | 101 |
| U59321_at | Human DEAD-box protein p72 (P72) "mRNA," complete cds | 85 | 48 | 272 | 54 | 197 | 128 |
| U59325_at | Human cadherin-14 "mRNA," complete cds | 20 | 20 | 20 | 20 | 20 | 20 |
| U59423_at | Human Smad1 "mRNA," complete cds | 23 | 107 | 31 | 30 | 128 | 37 |
| U59632_s_at | Human H5 "mRNA," partial "cds," and platelet glycoprotein 1b beta chain "mRNA," complete cds | 20 | 20 | 20 | 20 | 20 | 20 |
| U59736_at | Human transcription factor (NFATc.b) "mRNA," complete cds | 56 | 149 | 90 | 71 | 243 | 282 |
| U59748_at | Human desert hedgehog (hDHH) "mRNA," partial cds. /gb=U59748 /ntype=RNA | 49 | 20 | 20 | 20 | 20 | 20 |

TABLE 8-continued

Expressed RNA in Suburothelial connective tissue, Normal urothelium and Transitional cell carcinomas.

| Gene name | Description | Connect. Tiss. | Norm. uroth. | Ta GrI | TaGrII | T2GrIII | T2GrIV |
|---|---|---|---|---|---|---|---|
| U59752_at | Human Sec7p-like protein "mRNA," partial cds | 224 | 167 | 234 | 188 | 370 | 332 |
| U59831_ma1_s_at | Human transcription "factor," forkhead related activator 4 (FREAC-4) "gene," complete cds | 42 | 39 | 71 | 20 | 116 | 57 |
| U59863_at | Human TRAF-interacting protein I-TRAF "mRNA," complete cds | 25 | 20 | 36 | 20 | 49 | 96 |
| U59877_s_at | Human low-Mr GTP-binding protein (RAB31) "mRNA," complete cds | 37 | 20 | 20 | 20 | 20 | 20 |
| U59878_at | Human low-Mr GTP-binding protein (RAB32) "mRNA," partial cds | 20 | 20 | 31 | 20 | 20 | 20 |
| U59913_at | Human chromosome 5 Mad homolog Smad5 "mRNA," complete cds | 20 | 33 | 60 | 20 | 142 | 62 |
| U59914_at | Human chromosome 15 Mad homolog Smad6 "mRNA," complete cds | 20 | 50 | 126 | 107 | 115 | 62 |
| U59919_at | Human Smg GDS-associated protein SMAP "mRNA," complete cds | 41 | 128 | 32 | 20 | 126 | 62 |
| U60060_at | Human FEZ1 "mRNA," complete cds | 20 | 42 | 36 | 20 | 20 | 20 |
| U60061_at | Human FEZ2 "mRNA," partial cds | 57 | 113 | 124 | 91 | 58 | 27 |
| U60062_at | Human FEZ1-T "mRNA," alternatively spliced "form," complete cds | 20 | 153 | 36 | 41 | 20 | 20 |
| U60115_at | Human skeletal muscle LIM-protein SLIM1 "mRNA," complete cds | 132 | 58 | 20 | 20 | 49 | 20 |
| U60116_at | Human skeletal muscle LIM-protein SLIM2 "mRNA," partial cds | 149 | 56 | 20 | 20 | 343 | 203 |
| U60205_at | Human methyl sterol oxidase (ERG25) "mRNA," complete cds | 73 | 63 | 43 | 20 | 20 | 104 |
| U60206_at | Human stress responsive serine/threonin protein kinase Krs-1 "mRNA," complete cds | 20 | 20 | 20 | 20 | 20 | 20 |
| U60269_cds1_at | Human endogenous retrovirus HERV-K(HML6) proviral clone HML6.17 putative polymerase and envelope genes, partial cds, and 3'LTR. | 20 | 25 | 20 | 33 | 57 | 114 |
| U60269_cds2_at | Human endogenous retrovirus HERV-K(HML6) proviral clone HML6.17 putative polymerase and envelope genes, partial cds, and 3'LTR. | 39 | 36 | 53 | 64 | 126 | 20 |
| U60269_cds3_at | Human endogenous retrovirus HERV-K(HML6) proviral clone HML6.17 putative polymerase and envelope genes, partial cds, and 3'LTR. | 35 | 79 | 23 | 110 | 318 | 100 |
| U60276_at | Human hASNA-I "mRNA," complete cds | 20 | 20 | 20 | 20 | 20 | 20 |
| U60319_at | Human hereditary haemochromatosis protein HLA-H "mRNA," complete cds | 20 | 25 | 20 | 33 | 20 | 43 |
| U60325_at | Human DNA polymerase gamma "mRNA," nuclear gene encoding mitochondrial "protein," complete cds | 57 | 20 | 20 | 68 | 138 | 263 |
| U60415_at | Human bHLH-PAS protein JAP3 "mRNA," complete cds | 20 | 33 | 21 | 21 | 20 | 90 |
| U60519_at | human apoptotic cysteine protease Mch4 (Mch4") "mRNA," complete cds | 20 | 20 | 20 | 20 | 64 | 159 |
| U60521_at | Human protease proMch6 (Mch5) "mRNA," complete cds | 77 | 53 | 20 | 20 | 502 | 20 |
| U60644_at | Human HU-K4 "mRNA," complete cds | 42 | 20 | 20 | 241 | 107 | 189 |
| U60665_at | Human testis specific baseic protein "(TSBP)," complete cds | 20 | 20 | 20 | 20 | 20 | 33 |
| U60666_at | Human testis specific leucine rich repeat protein "(TSLRP)," complete cds | 91 | 47 | 89 | 79 | 336 | 272 |
| U60800_at | Human semaphorin (CD100) "mRNA," complete cds | 20 | 20 | 20 | 20 | 20 | 68 |
| U608005_at | Human oncostatin-M specific receptor beta subunit (OSMRB) "mRNA," complete cds | 20 | 20 | 20 | 20 | 20 | 90 |
| U60808_s_at | Human CDP-diacylglycerol synthase (CDS) "mRNA," complete cds. | 20 | 20 | 20 | 21 | 20 | 20 |
| U60873_at | Human clone 137308 "mRNA," partial cds | 88 | 147 | 1803 | 415 | 141 | 127 |
| U60975_at | Human hybrid receptor gp250 precursor "mRNA," complete cds | 22 | 62 | 20 | 25 | 75 | 20 |
| U61145_at | Human enhancer of zeste homolog 2 (EZH2) "mRNA," complete cds | 27 | 166 | 29 | 20 | 72 | 148 |
| U61166_at | Human SH3 domain-containing protein SH3P17 "mRNA," complete cds | 20 | 20 | 20 | 20 | 38 | 20 |
| U61167_at | Human SH3 domain-containing protein SH3P18 "mRNA," complete cds | 20 | 45 | 20 | 119 | 20 | 100 |
| U61232_at | Human tubulin-folding cofactor E "mRNA," complete cds | 20 | 29 | 47 | 76 | 20 | 67 |
| U61234_at | Human bubulin-folding cofactor C "mRNA," complete cds | 20 | 20 | 20 | 20 | 164 | 20 |
| U61262_at | Human neogenin "mRNA," complete cds | 109 | 153 | 311 | 158 | 261 | 58 |
| U61263_at | Human acetolactate synthase homolog "mRNA," complete cds | 53 | 114 | 143 | 159 | 57 | 33 |
| U01276_s_at | Human transmembrane protein Jagged 1 (HJ1) "mRNA," complete cds | 132 | 47 | 54 | 58 | 76 | 20 |
| U61374_at | Human novel protein with short consensus repeats of six cysteines "mRNA," complete cds | 40 | 129 | 115 | 82 | 20 | 78 |
| U61397_s_at | Human ubiquitin-homology domain protein PIC1 "mRNA," complete cds | 20 | 20 | 64 | 52 | 150 | 22 |
| U61500_at | Human GT334 protein (GT334) gene "mRNA," complete cds | 82 | 20 | 24 | 20 | 49 | 100 |
| U61538_at | Human calcium-binding protein chp "mRNA," complete cds | 175 | 140 | 348 | 325 | 217 | 67 |
| U61734_s_at | Human protein trafficking protein (S31iii125) "mRNA," complete cds | 20 | 20 | 20 | 20 | 20 | 58 |
| U61741_at | Human clone 18 "(HL-18)," dynein heavy chain (Dnahc14) "mRNA," partial cds. /gb=U61741 /ntype=RNA | 20 | 20 | 20 | 158 | 20 | 331 |
| U61836_at | Human putative cyclin G1 interacting protein "mRNA," partial sequence | 44 | 110 | 20 | 291 | 291 | 121 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U61849_at | Human neuronal pentraxin 1 (NPTX1) "mRNA," complete cds | 43 | 20 | 20 | 20 | 20 | 62 |
| U61981_at | Human putative mismatch repair/binding protein hMSH3 (hMSH3) "mRNA," complete cds | 20 | 20 | 51 | 20 | 20 | 20 |
| U62015_at | Homo sapiens Cyr61 "mRNA," complete cds | 253 | 20 | 20 | 20 | 20 | 178 |
| U62136_at | Human putative enterocyte differentiation promoting factor "mRNA," partial cds | 75 | 20 | 20 | 41 | 20 | 20 |
| U62293_ma1_s_at | LMK1 gene (LIM-kinase1) extracted from Human LIM-kinase1 and alternatively spliced LIM-kinase1 (LIMK1) "gene," complete cds | 20 | 57 | 159 | 20 | 216 | 90 |
| U62317_ma3_at | Chromosome 22q13 BAC Clone CIT987SK-384D8 complete sequence. | 314 | 521 | 523 | 430 | 682 | 697 |
| U62317_ma6_at | Chromosome 22q13 BAC Clone CIT987SK-384D8 complete sequence. | 20 | 85 | 20 | 20 | 20 | 42 |
| U62317_ma7_at | Chromosome 22q13 BAC Clone CIT987SK-384D8 complete sequence. | 20 | 48 | 20 | 20 | 20 | 20 |
| U62325_at | Human FE65-like protein (hFE65L) "mRNA," partial cds | 54 | 49 | 20 | 20 | 23 | 85 |
| U62389_at | Human putative cytosolic NADP-dependent isocitrate dehydrogenase "mRNA," partial cds. /gb=U62389 /ntype=RNA | 63 | 93 | 311 | 206 | 20 | 430 |
| U62431_at | Human nicotinic acetylcholine receptor alpha2 subunit "precursor," "mRNA," complete cds | 20 | 20 | 20 | 20 | 20 | 55 |
| U62432_at | Human nicotinic acetylcholine receptor alpha3 subunit "precursor," "mRNA," complete cds | 20 | 20 | 20 | 20 | 33 | 20 |
| U62433_at | Human nicotinic acetylcholine receptor alpha4 subunit "precursor," "mRNA," complete cds | 117 | 44 | 20 | 106 | 77 | 215 |
| U62434_at | Human nicotinic acetylcholine receptor alpha5 subunit "precursor," "mRNA," complete cds | 20 | 20 | 20 | 20 | 34 | 20 |
| U62437_at | Human nicotinic acetylcholine receptor beta2 subunit "precursor," "mRNA," complete cds | 113 | 20 | 20 | 38 | 45 | 25 |
| U62438_at | Human nicotinic acetylcholine receptor beta3 subunit "precursor," "mRNA," complete cds | 20 | 20 | 20 | 20 | 20 | 20 |
| U62531_at | Human AE2 anion exchanger (SLC4A2) "mRNA," complete cds | 20 | 20 | 20 | 20 | 20 | 20 |
| U62739_at | Human branched-chain amino acid aminotransferase (ECA40) "mRNA," complete cds | 99 | 612 | 454 | 337 | 718 | 699 |
| U62800_at | Human cystatin M (CST6) "mRNA," complete cds | 153 | 200 | 20 | 52 | 20 | 20 |
| U62801_at | Human protease M "mRNA," complete cds | 75 | 155 | 20 | 56 | 20 | 140 |
| U62961_at | Human Int-6 "mRNA," complete cds | 37 | 595 | 688 | 473 | 139 | 31 |
| U62962_at | Human Na+/nucleoside cotransporter (hCNT1a) "mRNA," complete cds | 410 | 20 | 122 | 78 | 234 | 94 |
| U62966_at | Human Gal "beta-1,3" GalNAc "alpha-2,3" sialyltransferase (ST3Gal II) "mRNA," complete cds | 152 | 154 | 20 | 147 | 593 | 268 |
| U63090_at | Human Rad50 (Rad50) "mRNA," complete cds | 30 | 20 | 20 | 97 | 171 | 58 |
| U63139_at | Human RNA-binding protein CUG-BP/hNab50 (NAB50) "mRNA," complete cds | 20 | 20 | 20 | 64 | 377 | 117 |
| U63289_at | Human seven in absentia homolog "mRNA," complete cds | 20 | 20 | 20 | 56 | 97 | 32 |
| U63295_at | Human cosmid "LL12NC01-242E1, "ETv6 "gene," exons 1B and 3 and partial cds. /gb=U63312 /ntype=exon | 20 | 20 | 20 | 20 | 203 | 99 |
| U63312_at | Human mutY homolog (hMYH) "gene," complete cds. | 20 | 20 | 20 | 20 | 20 | 20 |
| U63329_at | Human super cysteine rich protein "mRNA," partial cds. | 20 | 20 | 20 | 24 | 20 | 20 |
| U63332_at | Human MHC Class I region proline rich protein "mRNA," complete cds | 45 | 26 | 20 | 20 | 28 | 20 |
| U63336_at | Human sulfonylurea receptor (SUR1) gene | 173 | 117 | 20 | 20 | 221 | 140 |
| U63455_at | Human mRNA expressed in HC/HCC livers and MolT-4 proliferating "cells," partial sequence | 213 | 40 | 20 | 62 | 20 | 31 |
| U63541_at | Human putative FAP protein "mRNA," partial cds | 137 | 20 | 20 | 20 | 20 | 91 |
| U63542_at | human osteoclast stimulating factor "mRNA," complete cds | 87 | 57 | 87 | 29 | 20 | 34 |
| U63717_at | Human mitotic centromere-associated kinesin "mRNA," complete cds | 43 | 63 | 20 | 20 | 20 | 268 |
| U63743_at | Human transcription factor RTEF-1 (RTEF1) "mRNA," complete cds | 20 | 36 | 25 | 57 | 20 | 58 |
| U63824_at | Human hepatitis delta antigen interacting protein A (dipA) "mRNA," complete cds | 144 | 20 | 20 | 20 | 20 | 20 |
| U63842_at | Human neurogenic basic-helix-loop-helix protein (neuroD3) "gene," complete cds | 20 | 20 | 20 | 20 | 20 | 20 |
| U64105_at | Human guanine nucleotide exchange factor p115-RhoGEF "mRNA," partial cds | 137 | 90 | 106 | 101 | 135 | 535 |
| U64197_at | Human chemokine exodus "mRNA," complete cds | 20 | 20 | 20 | 20 | 20 | 20 |
| U64198_at | Human Il-12 receptor beta2 "mRNA," complete cds | 20 | 20 | 20 | 20 | 20 | 20 |
| U64315_s_at | Human DNA repair endonuclease subunit (XPF) "mRNA," complete cds | 20 | 22 | 68 | 29 | 51 | 33 |
| U64444_at | Human ubiquitin fusion-degradation protein (UFD1L) "mRNA," complete cds | 138 | 54 | 244 | 107 | 112 | 102 |
| U64520_at | Human synaptobrevin-3 "mRNA," complete cds | 25 | 20 | 20 | 20 | 22 | 20 |
| U64573_s_at | Human connexin43 gap junction protein (connexin43) "gene," exon 1 and promoter region. /gb=U64573 /ntype=DNA /annot=exon | 26 | 20 | 51 | 57 | 50 | 20 |
| U64675_at | Human sperm membrane protein BS-63 "mRNA," complete cds | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| U64805_s_at | Human Brca1-delta11b (Brca1) "mRNA," complete cds. /gb=U64805 /ntype=RNA | 20 | 20 | 20 | 20 | 20 | 20 | 20 |
| U64863_at | Human hPD-1 (hPD-1) "mRNA," complete cds | 20 | 20 | 20 | 20 | 20 | 20 | 57 |
| U64871_at | Human putative G protein-coupled receptor (GPR19) "gene," complete cds | 20 | 20 | 20 | 20 | 20 | 20 | 20 |
| U64998_at | Human ribonuclease k5 precursor "gene," complete cds. /gb=U64998 /ntype=DNA /annot=CDS | 20 | 20 | 20 | 20 | 20 | 20 | 20 |
| U65002_at | Human zinc finger protein PLAG1 "mRNA," complete cds. | 20 | 51 | 20 | 20 | 20 | 20 | 20 |
| U65011_at | Human preferentially expressed antigen of melanoma (PRAME) "mRNA," complete cds | 20 | 20 | 20 | 20 | 20 | 20 | 20 |
| U65092_at | Human melanocyte-specific gene 1 (msg1) "mRNA," complete cds | 20 | 20 | 51 | 20 | 20 | 20 | 20 |
| U65093_at | Human msg1-related gene 1 (mrg1) "mRNA," complete cds | 89 | 102 | 320 | 20 | 20 | 20 | 20 |
| U65402_at | Human seven transmembrane G-coupled receptor (GPR31) "gene," complete cds. | 20 | 20 | 20 | 20 | 20 | 20 | 20 |
| U65404_at | Human erythroid-specific transcription factor EKLF "mRNA," complete cds. | 20 | 62 | 20 | 20 | 20 | 20 | 20 |
| U65406_ma4_at | Human alternatively spliced potassium channels ROM-K1, ROM-K2, ROM-K3, ROM-K4, ROM-K5, and ROM-K6 (KCNJ1) gene, complete | 20 | 20 | 20 | 20 | 20 | 20 | 20 |
| U65410_at | Human Mad2 (hsMAD2) "mRNA," complete cds | 20 | 20 | 20 | 20 | 20 | 20 | 20 |
| U65416.ma1_s_at | Human MHC class I molecule (MICB) "gene," complete cds | 118 | 233 | 447 | 139 | 489 | 256 | 256 |
| U65437_ma1_at | Human homeodomain-containing protein (HANF) gene, partial cds. | 20 | 20 | 20 | 20 | 20 | 20 | 20 |
| U65533_s_at | Human regulator of nonsense transcript stability (RENT1) "mRNA," complete cds | 33 | 20 | 20 | 20 | 140 | 69 | 69 |
| U65579_at | Human mitochondrial NADH dehydrogenase-ubiquinone Fe-S protein "8," 23 kDa subunit precursor (NDUFS8) nuclear mRNA encoding r | 20 | 20 | 20 | 20 | 20 | 20 | 20 |
| U65581_at | Human ribosomal protein L3-like "mRNA," complete cds. | 20 | 25 | 527 | 20 | 20 | 20 | 108 |
| U65676_at | Human Hemansky-Pudiak syndrome protein (HPS) "mRNA," complete cds | 20 | 20 | 20 | 20 | 20 | 20 | 20 |
| U65785_at | human 150 kDa oxygen-regulated protein ORP150 "mRNA," complete cds | 249 | 153 | 194 | 143 | 215 | 336 | 336 |
| U65918_f_at | Human putative RNA biding protein (DAZH) "mRNA," complete cds | 20 | 20 | 20 | 20 | 20 | 20 | 20 |
| U65928_at | Human Jun activation domain binding protein "mRNA," complete cds | 69 | 44 | 76 | 96 | 98 | 82 | 82 |
| U65932_at | Human extracellular matrix protein 1 (ECM1) "mRNA," complete cds | 853 | 95 | 84 | 41 | 27 | 57 | 57 |
| U66033_at | Human glypican-5 (GPC5) "mRNA," complete cds | 20 | 20 | 20 | 20 | 20 | 20 | 20 |
| U66036_at | Human sulfotransferase "mRNA," complete cds | 20 | 20 | 22 | 20 | 56 | 20 | 20 |
| U66048_at | Human clone 161566-2-3 B cell expressed mRNA from chromosome X | 78 | 27 | 42 | 21 | 115 | 133 | 133 |
| U66052_at | Human clone W2-6 mRNA from chromosome X. /gb=U66052 /ntype=RNA | 29 | 20 | 28 | 29 | 165 | 108 | 108 |
| U66059_cds7_at | Human germline T-cell receptor geta chain Dopamine-beta-hydroxylase-like, TRY1, TRY2, TRY3, TCRBV27S1P, TCRBV22S1A2N1T, T0 | 220 | 154 | 138 | 117 | 271 | 257 | 257 |
| U66061_cds3_at | TCRBC1 from Human germline T-cell receptor beta chain "TCRBV17S1A1T;" "TCRBV2S1," "TCRBV10S1P," "TCRBV29S1P," "TCRBV1 | 43 | 83 | 103 | 120 | 20 | 35 | 35 |
| U66075_at | Human transcription factor hGATA-6 "mRNA," complete cds | 30 | 20 | 20 | 20 | 20 | 20 | 22 |
| U66077_at | Human DAZ "mRNA," 3'UTR | 20 | 20 | 38 | 20 | 351 | 46 | 46 |
| U66083_at | Human contig of two cosmids from LLNL X chromosome library "(U83F1," "U109H10)," including MAGE-9 antigen (MAGE9) "gene," com | 20 | 20 | 20 | 41 | 35 | 20 | 20 |
| U66088_at | Human sodium iodide symporter "mRNA," comlete cds. | 57 | 22 | 28 | 28 | 20 | 62 | 62 |
| U66198_at | Human fibroblast growth factor homologous factor 2 (FGF-2) "mRNA," complete cds. /gb=U66198 /ntype=RNA | 20 | 40 | 20 | 20 | 84 | 20 | 20 |
| U66359_at | Human T54 protein (T54) "mRNA," complete cds | 20 | 20 | 20 | 20 | 123 | 46 | 46 |
| U66406_at | Human putative EPH-related PTK receptor ligand LERK-8 (Epig8) "mRNA," complete cds | 64 | 56 | 76 | 93 | 20 | 20 | 20 |
| U66464_at | Human hematopoietic progenitor kinas (HPK1) "mRNA," complete cds | 20 | 47 | 20 | 20 | 102 | 145 | 145 |
| U66468_at | Human cell growth regulator CGR11 "mRNA," complete cds | 187 | 235 | 64 | 167 | 505 | 130 | 130 |
| U66469_at | Human cell growth regulator CGR19 "mRNA," complete cds | 68 | 55 | 53 | 29 | 59 | 38 | 38 |
| U66497_at | Human leptin receptor splice variant form 13.2 "mRNA," complete cds. | 20 | 20 | 20 | 20 | 66 | 20 | 20 |
| U66559_at | Human anaplastic lymphoma kinase receptor "mRNA," cpomplete cds | 20 | 159 | 38 | 46 | 165 | 371 | 371 |
| U66561_at | Human kruppel-related zinc finger protein (ZNF184) "mRNA," partial cds | 23 | 20 | 20 | 20 | 20 | 43 | 43 |
| U66578_at | Human putative G protein-coupled receptor (GPR23) "gene," complete cds | 57 | 23 | 67 | 61 | 104 | 109 | 109 |
| U66580_at | Human putative G protein-coupled receptor (GPR21) "gene," complete cds | 20 | 20 | 20 | 20 | 46 | 20 | 20 |
| U66581_at | Human putative G protein-coupled receptor (GPR22) "gene," complete cds | 20 | 20 | 20 | 20 | 43 | 30 | 30 |
| U66615_at | Human SWI/SNF complex 155 KDa subunit (BAF155) "mRNA," complete cds | 193 | 135 | 164 | 154 | 261 | 237 | 237 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U66616_at | Human SWI/SNF complex 170 KDa subunit (BAF170) "mRNA," complete cds | 113 | 113 | 150 | 117 | 390 | 553 |
| U66617_at | Human SWI/SNF complex 60 KDa subunit (BAF60a) "mRNA," alternatively "spliced," complete cds | 89 | 183 | 125 | 112 | 195 | 206 |
| U66618_at | Human SWI/SNF complex 60 KDa subunit (BAF60b) "mRNA," complete cds | 89 | 68 | 92 | 109 | 77 | 155 |
| U66619_at | Human SI/SNF complex 60 KDa subunit (BAF60c) "mRNA," complete cds | 20 | 20 | 20 | 20 | 20 | 20 |
| U66661_at | Human GABA-A receptor epsilon subunit "mRNA," complete cds | 20 | 56 | 49 | 38 | 52 | 43 |
| U66669_at | Human 3-hydroxyisobutyryl-coenzyme A hydrolase "mRNA," complete cds | 48 | 40 | 28 | 31 | 34 | 32 |
| U66702_at | Human phogrin "mRNA," complete cds. | 30 | 22 | 67 | 23 | 20 | 20 |
| U66711_ma1_s_at | Human Ly-6-related protein −9804 "gene," complete cds | 137 | 297 | 534 | 407 | 365 | 366 |
| U66726_at | | 20 | 20 | 20 | 20 | 20 | 20 |
| U66726_s_at | Human testis specific RNA binding protein (SPGYLA) "mRNA," complete cds | 20 | 31 | 20 | 20 | 141 | 38 |
| U66828_s_at | Human carnitine palmitoyltransferase I (CPIT) "mRNA," complete cds | 20 | 75 | 20 | 20 | 20 | 20 |
| U66838_at | Human cyclin A1 "mRNA," complete cds | 72 | 39 | 43 | 36 | 94 | 101 |
| U66879_at | Human Bcl-2 binding component 6 (bbc6) "mRNA," complete cds | 221 | 246 | 192 | 153 | 288 | 324 |
| U67092_at | | 20 | 20 | 20 | 20 | 20 | 20 |
| U67092_s_at | Human ataxia-telangiectasia locus protein (ATM) "gene," exons "1a," "1b," "2," 3 and "4," partial cds. /gb=U67092 /ntype=DNA /annot=ex | 227 | 173 | 593 | 368 | 311 | 362 |
| U67122_s_at | Human ubiquitin-related protein SUMO-1 "mRNA," complete cds. | 94 | 20 | 112 | 177 | 35 | 136 |
| U67156_at | Human mitogen-activated kinase kinase 5 (MAPKKK5) "mRNA," complete cds | 20 | 20 | 71 | 55 | 20 | 20 |
| U67171_at | Human selenoprotein W (selW) "mRNA," complete cds. /gb=U67171 /ntype=RNA | 440 | 575 | 530 | 620 | 279 | 621 |
| U67191_at | Human multiple exostosis-like protein (EXTL) "mRNA," complete cds | 20 | 20 | 20 | 22 | 20 | 20 |
| U67319_at | Human Lice2 beta cysteine protease "mRNA," complete cds. | 41 | 33 | 35 | 28 | 20 | 54 |
| U67368_s_at | Human multiple exostosis 2 (EXT2) gene | 20 | 20 | 45 | 21 | 20 | 48 |
| U67611_at | Human growth factor independence-1 (Gfi-1) "mRNA," complete cds | 65 | 50 | 68 | 57 | 94 | 111 |
| U67369_at | Mouse transaldolase gene "mRNA," complete cds. /gb=U67611 /ntype=RNA | 20 | 20 | 20 | 20 | 42 | 24 |
| U67614_at | Human sinusoidal reduced glutathione transporter-associated protein (HsGshT) "mRNA," complete cds. /gb=U67614 /ntype=RNA | 37 | 25 | 23 | 20 | 68 | 20 |
| U67615_at | Human beige protein homolog (chs) "mRNA," complete cds | 20 | 34 | 20 | 21 | 171 | 20 |
| U67674_at | Human ileal sodium dependent bile acid transporter | 82 | 77 | 72 | 51 | 287 | 265 |
| U67733_at | Human cGMP-stimulated "3',5'-cyclic" nucleotide phosphodiesterase PDE2A3 (PDE2A) "mRNA," complete cds | 43 | 20 | 20 | 20 | 35 | 20 |
| U67784_at | Human orphan G protein-coupled receptor (RDC1) "mRNA," partial cds | 120 | 36 | 47 | 46 | 135 | 69 |
| U67849_at | Human beta-galactoside "alpha2,6-sialyltransferase" (SIAT1) "mRNA," exon W. /gb=U67849 /ntype=RNA | 69 | 73 | 68 | 20 | 20 | 20 |
| U67932_s_at | Human cAMP phosphodiesterase (Pde7A2) "mRNA," complete cds. /gb=U67932 /ntype=RNA | 20 | 20 | 20 | 20 | 205 | 20 |
| U67934_at | Human 44.9 kDa protein C18811 homolog "gene," partial cds | 74 | 71 | 117 | 68 | 223 | 179 |
| U67963_at | Human lysophospholipase homolog (HU-K5) "mRNA," complete cds | 206 | 87 | 45 | 47 | 57 | 106 |
| U67988_at | Human guanylate kinase associated protein (GKAP) "mRNA," complete cds | 20 | 20 | 20 | 20 | 47 | 41 |
| U68018_at | Human mad protein homolog (hMAD-2) "mRNA," complete cds | 41 | 25 | 54 | 42 | 20 | 68 |
| U68019_at | Human mad protein homolog (hMAD-3) "mRNA," complete cds | 54 | 68 | 127 | 97 | 82 | 136 |
| U68030_at | Human G protein-coupled receptor (STRL22) "mRNA," complete cds | 20 | 36 | 20 | 20 | 20 | 61 |
| U68031_at | Human G protein-coupled receptor (STRL22) "mRNA," alternatively spliced 5UTR sequence. /gb=U68031 /ntype=RNA | 20 | 25 | 20 | 20 | 59 | 23 |
| U68063_at | Human transformer-2 beta (htra-2 beta) "(PABP)" "gene," promoter region and | 137 | 123 | 190 | 136 | 106 | 185 |
| U68105_s_at | Human poly(A)-binding protein (PABP) "gene," promoter region and | 1173 | 2639 | 2985 | 3231 | 1336 | 2123 |
| U68111_at | Human protein phosphatase inhibitor 2 (PPP1R2) gene | 45 | 21 | 20 | 20 | 20 | 34 |
| U68133_at | Human SCC-S4 mRNA expressed in primary and relatively radiosensitive squamous cell "carcinoma," partial 3' sequence. /gb=U68133 /r | 20 | 20 | 20 | 20 | 20 | 20 |
| U68135_s_at | Human SCC-S1c mRNA expressed in metastatic and relatively radioresistant squamous cell "carcinoma," partial 3' sequence. /gb=U6813 | 20 | 20 | 20 | 20 | 144 | 68 |
| U68142_at | Human RalGDS-like 2 (RGS2) "mRNA," partial cds | 74 | 193 | 252 | 191 | 241 | 205 |
| U68162_cds1_s_at | MPL gene (thrombopoietin receptor) extracted from Human thrombopoietin receptor (MPL) gene | 20 | 23 | 20 | 20 | 20 | 61 |
| U68233_at | Human farnesol eceptor HRR-1 (HRR-1) "mRNA," complete cds | 49 | 144 | 103 | 56 | 31 | 23 |
| U68385_at | Human Meis1-related protein 2 "(MRG2)," "mRNA," partial cds. | 23 | 56 | 36 | 31 | 151 | 76 |
| U68485_at | Human Box-dependent MYC-interacting protein-1 (BIN1) "mRNA," complete cds | 111 | 41 | 53 | 20 | 25 | 21 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | TaGrIII | T2GrIII | T2GrIV |
|---|---|---|---|---|---|---|---|---|
| U68488_at | Human 5-hydroxytryptamine7 receptor isoform d "mRNA," complete cds | 130 | 113 | 105 | 102 | 169 | 186 |
| U68494_at | Human hbc647 mRNA sequence | 20 | 23 | 37 | 46 | 25 | 41 |
| U68536_at | Human zinc finger protein "mRNA," complete cds | 28 | 203 | 20 | 23 | 112 | 33 |
| U68566_at | Human HS1 binding protein HAX-1 "mRNA," nuclear gene encoding mitochondrial "protein," complete cds | 204 | 203 | 212 | 198 | 231 | 168 |
| U68723_at | Human checkpoint suppressor 1 "mRNA," complete cds. | 20 | 20 | 20 | 20 | 20 | 20 |
| U68727_at | Human homeobox-containing protein "mRNA," complete cds. | 20 | 20 | 20 | 20 | 48 | 20 |
| U69108_at | Homo sapiens TNF receptor associated factor 5 "mRNA," partial cds | 20 | 70 | 20 | 20 | 20 | 20 |
| U69126_s_at | Human FUSE binding protein 2 (FBP2) "mRNA," partial cds | 20 | 30 | 36 | 72 | 20 | 20 |
| U69127_at | Human FUSE binding protein 3 (FBP3) "mRNA," partial cds | 35 | 20 | 69 | 55 | 27 | 28 |
| U69140_s_at | Human zyginII "mRNA," partial cds | 44 | 20 | 20 | 42 | 256 | 31 |
| U69141_at | Human glutaryl-CoA dehydrogenase "mRNA," complete cds | 53 | 65 | 42 | 116 | 48 | 113 |
| U69263_at | Human matrilin-2 precursor "mRNA," partial cds | 152 | 20 | 20 | 20 | 89 | 20 |
| U69546_at | Human RNA binding protein Etr-3 "mRNA," complete cds | 22 | 20 | 20 | 20 | 20 | 32 |
| U69611_at | Human TNF-alpha converting enzyme "mRNA," complete cds | 23 | 20 | 47 | 52 | 85 | 20 |
| U69645_at | Human zinc finger protein "mRNA," complete cds | 44 | 76 | 74 | 66 | 43 | 58 |
| U69961_at | Human solurshin (RGS) "mRNA," complete cds | 20 | 51 | 20 | 61 | 20 | 20 |
| U70063_at | Human acid ceramidase "mRNA," complete cds | 176 | 229 | 313 | 267 | 83 | 197 |
| U70064_s_at | Human lysosomal trafficking regulator (LYST) "mRNA," partial cds | 75 | 89 | 242 | 126 | 429 | 160 |
| U70136_at | Human megakaryocyte stimulating factor "mRNA," complete cds | 20 | 20 | 20 | 20 | 20 | 23 |
| U70321_at | Human herpesvirus entry mediator "mRNA," complete cds | 109 | 162 | 190 | 174 | 132 | 133 |
| U70322_at | Human copper transport protein HAH1 (HAH1) "mRNA," complete cds | 151 | 116 | 101 | 88 | 77 | 90 |
| U70323_at | Human transportin (TRN) "mRNA," complete cds | 56 | 51 | 66 | 61 | 44 | 20 |
| U70370_at | Human ataxin-2 (SCA2) "mRNA," complete cds | 20 | 20 | 20 | 20 | 20 | 20 |
| U70426_at | Human ataxin-2 related protein "mRNA," partial cds | 361 | 20 | 20 | 20 | 256 | 255 |
| U70439_s_at | Human hindlimb expressed homeobox protein backfoot (Bft) "mRNA," complete cds | 69 | 113 | 125 | 113 | 226 | 241 |
| U70451_at | Human A28-RGS14p "mRNA," complete cds | 288 | 766 | 387 | 387 | 135 | 297 |
| U70660_at | Human silver-stainable protein SSP29 "mRNA," complete cds | 139 | 54 | 111 | 108 | 188 | 267 |
| U70663_at | Human myeloid differentiation primary response protein MyD88 "mRNA," complete cds. | 160 | 160 | 130 | 91 | 160 | 164 |
| U70671_at | Human zinc finger transcription factor hEZF (EZF) "mRNA," complete cds | 187 | 20 | 20 | 20 | 20 | 125 |
| U70732_ma1_at | Human glutamate pyruvate transaminase (GPT) gene, complete cds. | 177 | 181 | 225 | 207 | 256 | 33 |
| U70735_at | Human 34 kDa mov34 isologue "mRNA," complete cds. /gb=U70735 /ntype=RNA | 240 | 90 | 117 | 131 | 147 | 59 |
| U70862_at | Human nuclear factor I B3 "mRNA," complete cds | 298 | 143 | 209 | 188 | 206 | 267 |
| U70867_at | Human prostaglandin transporter hPGT "mRNA," complete cds | 20 | 20 | 20 | 20 | 24 | 20 |
| U70981_at | Human interleukin-13 receptor "mRNA," complete cds | 212 | 167 | 121 | 131 | 443 | 378 |
| U71087_at | Human GAP binding protein p62dok (DOK) "mRNA," complete cds | 34 | 20 | 20 | 20 | 20 | 20 |
| U71088_at | Human MAP kinase kinase MEK5b "mRNA," complete cds. | 20 | 27 | 20 | 20 | 52 | 22 |
| U71092_at | Human MAP kinase kinase MEK5c "mRNA," complete cds. | 56 | 38 | 45 | 63 | 62 | 70 |
| U71203_s_at | Human somatostatin receptor-like protein (SLC1) "gene," complete cds | 20 | 20 | 20 | 20 | 83 | 20 |
| U71207_at | Human rit "mRNA," complete cds. | 56 | 87 | 83 | 70 | 134 | 48 |
| U71300_at | Human eyes absent homolog (Eab1) "mRNA," complete cds. | 53 | 20 | 20 | 20 | 47 | 20 |
| U71364_at | Human snRNA activating protein complex 50kD subunit (SNAP60) "mRNA," complete cds | 29 | 26 | 28 | 26 | 73 | 45 |
| U71374_at | Human serine proteinase inhibitor (P19) "mRNA," complete cds. /gb=U71374 /ntype=RNA | 20 | 27 | 20 | 20 | 20 | 20 |
| U71598_at | Human HsPex13p "mRNA," complete cds. /gb=U71374 /ntype=RNA | 28 | 42 | 40 | 42 | 20 | 60 |
| U71601_at | Human zinc finger protein zfp2 (zf2) "mRNA," partial cds | 50 | 54 | 68 | 47 | 76 | 74 |
| U72066_at | Human zinc finger protein zfp47 (zf47) "mRNA," partial cds | 22 | 30 | 20 | 20 | 20 | 20 |
| U72206_at | Human CtBP interacting protein CtIP "mRNA," complete cds | 162 | 137 | 130 | 105 | 177 | 236 |
| U72206_at | Human guanine nucleotide regulatory factor (LFP40) "mRNA," complete cds | 114 | 108 | 125 | 123 | 312 | 114 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| U72209_at | Human YY1-associated factor 2 (YAF2) "mRNA," complete cds | 87 | 62 | 49 | 62 | 96 | 84 | |
| U72263_s_at | Human multiple exostoses type II protein EXT2.1 "mRNA," complete cds. /gb=U72263 /ntype=RNA | 20 | 29 | 20 | 28 | 20 | 20 | |
| U72342_at | Human platelet activating factor "acetylhydrolase," brain "isoform," 45 kDa subunit (LIS1) gene | 48 | 20 | 68 | 47 | 20 | 20 | |
| U72507_at | Human 40871 mRNA partial sequence | 20 | 20 | 20 | 27 | 20 | 20 | |
| U72508_at | Human B7 "mRNA," complete cds | 58 | 79 | 71 | 71 | 212 | 177 | |
| U72509_s_at | Human alternatively spliced B8 (B7) "mRNA," partial sequence. /gb=U72509 /ntype=RNA | 82 | 179 | 149 | 116 | 207 | 111 | |
| U72511_at | Human B-cell receptor associated protein (hBAP) "mRNA," partial cds | 383 | 357 | 640 | 655 | 283 | 434 | |
| U72512_at | Human B-cell receptor associated protein (hBAP) alternatively spliced "mRNA," partial 3UTR. /gb=U72512 /ntype=RNA | 272 | 251 | 396 | 350 | 284 | 227 | |
| U72514_at | Human C2f "mRNA," complete cds | 20 | 81 | 21 | 42 | 20 | 20 | |
| U72515_at | Human C3f "mRNA," complete cds | 65 | 166 | 134 | 142 | 191 | 139 | |
| U72517_at | Human alternatively spliced variant C7f (C3f) "mRNA," partial 3UTR. /gb=U72517 /ntype=RNA | 175 | 144 | 120 | 97 | 266 | 184 | |
| U72621_at | Human LOT1 "mRNA," complete cds | 20 | 28 | 20 | 20 | 20 | 20 | |
| U72648_s_at | Human alpha2-C4-adrenergic receptor "gene," complete cds | 20 | 20 | 20 | 20 | 20 | 20 | |
| U72649_at | Human BTG2 (BTG2) "mRNA," complete cds | 244 | 412 | 802 | 886 | 464 | 289 | |
| U72661_at | Human ninjurin1 "mRNA," complete cds. | 20 | 20 | 20 | 20 | 20 | 20 | |
| U72671_at | Human telencephalin precursor "mRNA," complete cds | 20 | 20 | 20 | 44 | 46 | 20 | |
| U72761_at | Human karyopherin beta 3 "mRNA," complete cds. /gb=U72761 /ntype=RNA | 30 | 20 | 33 | 20 | 20 | 20 | |
| U72882_s_at | Human interferon-induced leucine zipper protein (IFP35) "mRNA," partial cds | 20 | 20 | 20 | 20 | 49 | 157 | |
| U72935_cds3_s_at | ATRX gene (putative DNA dependent ATPase and helicase) extracted from Human putative DNA dependent ATPase and helicase (ATRX | 20 | 24 | 61 | 41 | 80 | 39 | |
| U72936_s_at | Human putative DNA dependent ATPase and helicase (ATRX) "mRNA," alternatively spliced product "1," complete cds | 25 | 45 | 69 | 43 | 20 | 36 | |
| U73167_cds3_at | H_LUCA 14.6 gene extracted from Human cosmid LUCA14 | 20 | 20 | 20 | 20 | 20 | 20 | |
| U73167_cds4_at | | 20 | 47 | 20 | 20 | 20 | 20 | |
| U73167_cds5_at | | 46 | 20 | 20 | 20 | 114 | 20 | |
| U73167_cds7_at | | 20 | 20 | 20 | 20 | 20 | 20 | |
| U73191_at | Human inward rectifier potassium channel '(Kir1.3)," complete cds | 28 | 20 | 29 | 25 | 62 | 127 | |
| U73304_ma1_at | Human CB1 cannabinoid receptor (CNR1) "mRNA," complete cds. | 36 | 37 | 48 | 59 | 20 | 20 | |
| U73328_at | Human DLX7 (dlx7) "mRNA," complete cds | 20 | 20 | 20 | 20 | 20 | 288 | |
| U73330_at | Human PAC "85D2," complete sequence. /gb=U73330 /ntype=DNA /annot=exon | 79 | 71 | 122 | 108 | 244 | 20 | |
| U73338_at | Human methionine synthase "mRNA," complete cds. | 20 | 20 | 20 | 20 | 20 | 20 | |
| U73377_at | Human p66shc (SHC) "mRNA," complete cds | 22 | 79 | 63 | 45 | 98 | 84 | |
| U73379_at | Human cyclin-selective ubiquitin carrier protein "mRNA," complete cds | 73 | 105 | 188 | 156 | 36 | 726 | |
| U73477_s_at | Human acidic nuclear phosphoprotein pp32 "mRNA," complete cds | 191 | 181 | 169 | 204 | 604 | 28 | |
| U73499_at | Human hepatic nuclear factor 1-alpha (TCF-1-alpha) "gene," promoter region and partial cds. /gb=U73499 /ntype=DNA /annot=mRNA | 20 | 20 | 43 | 155 | 142 | 20 | |
| U73514_at | Human short-chain alcohol dehydrogenase (XH98G2) "mRNA," complete cds. | 20 | 20 | 20 | 20 | 60 | 20 | |
| U73524_at | Human putative ATP/GTP-binding protein (HEAB) "mRNA," complete cds | 26 | 20 | 20 | 32 | 20 | 20 | |
| U73682_at | Human meningioma-expressed antigen 11 (MEA11) "mRNA," partial cds | 58 | 31 | 29 | 21 | 20 | 26 | |
| U73704_at | Homo sapiens 48 kDa FKBP-associated protein FAP48 "mRNA," complete cds | 20 | 20 | 20 | 20 | 20 | 20 | |
| U73737_at | Human hMSH5 "gene," 5' UTR and | 20 | 20 | 20 | 20 | 20 | 20 | |
| U73738_at | Human calcium/calmodulin-dependent protein kinase II delta E "mRNA," partial cds. /gb=U73738 /ntype=RNA | 20 | 20 | 20 | 20 | 20 | 20 | |
| U73799_at | Human dynactin "mRNA," partial cds. /gb=U73799 /ntype=RNA | 76 | 55 | 20 | 20 | 20 | 20 | |
| U73824_at | Human p97 "mRNA," complete cds | 586 | 268 | 722 | 715 | 134 | 324 | |
| U73843_at | Human epithelial-specific transcription factor ESE-1b (ESE-1) "mRNA," complete cds | 356 | 411 | 756 | 652 | 734 | 862 | |
| U73936_at | Human Jagged 1 (HJ1) "mRNA," complete cds | 42 | 90 | 136 | 106 | 61 | 92 | |
| U73960_at | Human ADP-ribosylation factor-like protein 4 "mRNA," complete cds | 30 | 20 | 20 | 22 | 30 | 20 | |
| U74324_at | Human guanine nucleotide exchange factor mss4 "mRNA," complete cds. | 20 | 20 | 20 | 20 | 89 | 20 | |
| U74382_s_at | Human telomeric repeat DNA-binding protein (PIN2) "mRNA," complete cds. | 20 | 20 | 20 | 20 | 20 | 20 | |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U74612_at | Human hepatocyte nuclear factor-3/fork head homolog 11A (HFH-11A) mRNA complete cds. | 20 | 20 | 20 | 20 | 46 | 20 |
| U74667_at | Human tat interactive protein (TIP60) "mRNA," complete cds. | 69 | 86 | 79 | 97 | 205 | 141 |
| U75272_s_at | Human gastricsin "mRNA," complete cds | 20 | 20 | 20 | 20 | 32 | 20 |
| U75276_s_at | Human TFIIIB related factor hBRF (HBRF) "mRNA," complete cds. | 20 | 20 | 20 | 20 | 298 | 45 |
| U75308_at | Human TBP-associated factor (hTAFII130) "mRNA," partial cds | 20 | 20 | 20 | 20 | 20 | 20 |
| U75309_s_at | human TBP-associated factor (hTAFII100) "mRNA," partial cd | 20 | 20 | 20 | 20 | 52 | 20 |
| U75362_at | Human isopeptidase T-3 (ISOT-3) "mRNA," complete cds | 43 | 24 | 34 | 27 | 24 | 20 |
| U75370_at | Human mitochondrial RNA polymerase "mRNA," nuclear gene encoding mitochondrial "protein," complete cds | 20 | 20 | 77 | 40 | 20 | 20 |
| U75679_at | Human histone stem-loop binding protein (SLBP) "mRNA," complete cds | 29 | 24 | 48 | 49 | 41 | 53 |
| U75968_at | Human clone C3 CHL1 protein (CHL1) "mRNA," alternatively "spliced," complete cds | 60 | 132 | 94 | 90 | 148 | 281 |
| U76010_at | Human putative zinc transporter ZnT-3 (ZnT-3) "mRNA," complete cds. | 128 | 155 | 128 | 164 | 218 | 104 |
| U76189_at | Human EXTL3 "mRNA," partial cds. /gb=U76189 /ntype=RNA | 20 | 28 | 20 | 20 | 20 | 20 |
| U76272_at | Human diadenosine triphosphate (Ap3A) hydrolase (FHIT) "gene," 5′ of | 20 | 20 | 20 | 20 | 20 | 20 |
| U76366_s_at | Human Treacher Collins syndrome (TCOF1) "mRNA," complete cds | 20 | 20 | 51 | 22 | 20 | 20 |
| U76369_at | Human cationic amino acid transporter-2B (ATRC2) "mRNA," partial cds. /gb=U76369 /ntype=RNA | 62 | 27 | 20 | 39 | 23 | 46 |
| U76388_at | Human steroidogenic factor 1 "mRNA," complete cds | 20 | 20 | 20 | 20 | 164 | 86 |
| U76421_at | Human dsRNA aenosine deaminase DRADA2b (DRADA2b) "mRNA," complete cds | 20 | 35 | 21 | 20 | 20 | 39 |
| U76456_at | Human tissue inhibitor of metalloproteinase 4 "mRNA," complete cds | 20 | 20 | 20 | 20 | 20 | 20 |
| U76638_at | Human BRCA1-associated RING domain protein (BARD1) "mRNA," complete cds | 32 | 20 | 20 | 20 | 29 | 20 |
| U76764_at | Human CD97 "mRNA," complete cds | 20 | 20 | 20 | 20 | 20 | 20 |
| U76992_at | Human Tat-SF1 "mRNA," complete cds | 68 | 39 | 98 | 84 | 20 | 84 |
| U77129_at | Human SPS1/STE20 homolog KHS1 "mRNA," complete cds | 37 | 40 | 39 | 33 | 20 | 35 |
| U77180_at | Human macrophage inflammatory protein 3 beta (MIP-3beta) "mRNA," complete cds | 78 | 20 | 20 | 20 | 20 | 20 |
| U77396_at | Human TNF-alpha inducible responsive element "mRNA," complete cds | 201 | 180 | 93 | 125 | 91 | 123 |
| U77413_at | Human O-linked GlcNAc transferase "mRNA," complete cds. /gb=U77413 /ntype=RNA | 20 | 20 | 74 | 61 | 20 | 51 |
| U77456_at | Human nucleosome assembly protein 2 "mRNA," complete cds | 35 | 56 | 67 | 53 | 20 | 44 |
| U77594_at | Human tazarotene-induced gene 2 (TIG2) "mRNA," complete cds | 262 | 197 | 22 | 20 | 20 | 549 |
| U77604_at | Human microsomal glutathione S-tranferase (GST-II) "mRNA," complete cds | 286 | 374 | 506 | 560 | 544 | 63 |
| U77643_at | Human K12 protein precursor "mRNA," complete cds | 94 | 71 | 33 | 21 | 99 | 20 |
| U77664_at | Human RNaseP protein p38 (RPP38) "mRNA," complete cds. | 20 | 20 | 25 | 37 | 71 | 145 |
| U77665_at | Human RNaseP protein p30 (RPP30) "mRNA," complete cds | 63 | 73 | 55 | 64 | 94 | 31 |
| U77718_at | Human desmosome associated protein pinin "mRNA," complete cds | 31 | 31 | 71 | 39 | 20 | 20 |
| U77735_at | Human pim-2 protooncogene homolog pim-2h "mRNA," complete cds | 20 | 20 | 20 | 53 | 20 | 51 |
| U77827_at | Human orphan G protein-coupled receptor (CEPTR) "gene," complete cds. | 209 | 78 | 82 | 84 | 137 | 141 |
| U77845_at | Human hepatocyte nuclear factor 6 (HNF-6) "mRNA," partial cds | 20 | 24 | 20 | 24 | 20 | 20 |
| U77975_at | Human hTRIP (hTRIP) "mRNA," complete cds | 33 | 68 | 65 | 41 | 20 | 55 |
| U77846_ma1_at | | | | | | | |
| U77846_ma1_s_at | Human elastin "gene," partial cds and partial 3UTR | 61 | 151 | 41 | 36 | 20 | 119 |
| U77948_at | Human Bruton's tyrosine kinase-associated protein-135 "mRNA," complete cds. | 137 | 215 | 465 | 448 | 783 | 193 |
| U77949_at | Human Cdc6-related protein (HsCDC6) "mRNA," complete cds. | 20 | 20 | 20 | 20 | 91 | 20 |
| U77968_at | Human neuronal PAS1 (NPAS1) "mRNA," complete cds. | 20 | 20 | 20 | 20 | 20 | 20 |
| U77970_at | Human neuronal PAS2 (NPAS2) "mRNA," complete cds. | 20 | 20 | 20 | 20 | 88 | 20 |
| U77975_at | Human pim-2 protooncogene homolog pim-2h "mRNA," partial cds | 31 | 45 | 30 | 37 | 47 | 57 |
| U78027_ma3_at | Homo sapiens Bruton's tyrosine kinase (BTK), alpha-D-galactosidase A (GLA), L44-like ribosomal protein (L44L) and FTP3 (FTP3) genes | 2156 | 2430 | 2098 | 2838 | 757 | 1616 |
| U78027_ma4_at | Homo sapiens Bruton's tyrosine kinase (BTK), alpha-D-galactosidase A (GLA), L44-like ribosomal protein (L44L) and FTP3 (FTP3) genes | 34 | 51 | 20 | 20 | 24 | 20 |
| U78095_at | Human Placental bikunin "mRNA," complete cds | 435 | 433 | 870 | 1149 | 493 | 288 |
| U78107_at | Human gamma SNAP "mRNA," complete cds. | 20 | 20 | 29 | 25 | 20 | 20 |
| U78180_at | Human sodium channel 2 (hBNaC2) "mRNA," alternatively "spliced," complete cds | 20 | 20 | 20 | 20 | 42 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U78190_ma1_at | Human GTP cyclohydrolase I feedback regulatory protein gene, complete cds. | 20 | 24 | 20 | 20 | 147 | 107 |
| U78313_at | Human myogenic repressor I-mf (MDFI) "mRNA," complete cds | 37 | 54 | 80 | 87 | 85 | 20 |
| U78521_at | Homo sapiens immunophilin homolog ARA9 "mRNA," complete cds | 296 | 294 | 313 | 290 | 412 | 472 |
| U78524_at | Human Gu binding protein "mRNA," partial cds. | 147 | 143 | 129 | 152 | 31 | 229 |
| U78525_at | Human eukaryotic translation initiation factor (eIF3) "mRNA," complete cds | 74 | 172 | 162 | 146 | 176 | 215 |
| U78551_at | Homo sapiens gallbladder mucin MUC5B "mRNA," partial cds | 35 | 20 | 20 | 20 | 20 | 20 |
| U78556_at | Human cisplatin resistance associated alpha protein (hCRA alpha) "mRNA," complete cds | 104 | 104 | 112 | 112 | 239 | 178 |
| U78575_at | Human 68 kDa type I phosphatidylinositol-4-phosphate 5-kinase alpha "mRNA," clone "PIP5KIa1," complete cds | 92 | 44 | 117 | 74 | 189 | 132 |
| U78628_at | Human leukemia inhibitory factor receptor "mRNA," 5' untranslated region. /gb=U78628 /ntype=RNA | 28 | 51 | 39 | 40 | 62 | 54 |
| U78678_at | Human thioredoxin "mRNA," nuclear gene encoding mitochondrial "protein," complete cds | 215 | 319 | 217 | 236 | 521 | 546 |
| U78722_at | Homo sapiens zinc finger protein 165 (Zpf165) "mRNA," complete cds. | 20 | 20 | 20 | 20 | 91 | 58 |
| U78735_at | Human ABC3 "mRNA," complete cds. | 39 | 40 | 29 | 34 | 97 | 53 |
| U78793_at | Human folate receptor alpha (hFR) "mRNA," partial cds. /gb=U78793 /ntype=RNA | 118 | 115 | 90 | 75 | 147 | 30 |
| U78798_at | Human TNF receptor associated factor 6 (TRAF6) "mRNA," complete cds. | 148 | 96 | 52 | 91 | 152 | 61 |
| U78876_at | Human MEK kinase 3 "mRNA," complet cds | 20 | 20 | 20 | 20 | 20 | 20 |
| U79115_s_at | Human death adaptor molecule RAIDD (RAIDD) "mRNA," complete cds. | 20 | 97 | 20 | 20 | 41 | 46 |
| U79241_at | Human clone 23759 "mRNA," partial cds. | 20 | 20 | 20 | 20 | 20 | 53 |
| U79242_at | Human clone 23560 mRNA sequence | 20 | 45 | 20 | 20 | 51 | 42 |
| U79245_at | Human clone 23586 mRNA sequence | 25 | 20 | 20 | 20 | 20 | 20 |
| U79246_at | Human clone 23799 mRNA sequence | 20 | 20 | 20 | 20 | 20 | 20 |
| U79247_at | Human clone 23599 mRNA sequence | 20 | 20 | 20 | 20 | 20 | 20 |
| U79248_at | Human clone 23826 mRNA sequence | 20 | 20 | 20 | 20 | 20 | 20 |
| U79249_at | Human clone 23839 mRNA sequence | 20 | 20 | 20 | 20 | 20 | 20 |
| U79251_at | Human clone 23878 mRNA sequence | 34 | 20 | 31 | 21 | 20 | 20 |
| U79252_at | Human clone 23679 "mRNA," complete cds. | 82 | 76 | 82 | 78 | 143 | 151 |
| U79253_at | Human clone 23893 "mRNA," complete cds. | 20 | 20 | 20 | 26 | 99 | 25 |
| U79254_at | Human clone 23693 mRNA sequence | 165 | 188 | 269 | 298 | 82 | 87 |
| U79255_at | Human X11 protein "mRNA," partial cds. | 67 | 25 | 20 | 20 | 225 | 21 |
| U79256_at | Human clone 23719 mRNA sequence | 35 | 20 | 20 | 26 | 68 | 74 |
| U79257_at | Human clone 23932 mRNA sequence | 20 | 20 | 21 | 20 | 20 | 40 |
| U79258_at | Human clone 23732 "mRNA," partial cds. | 27 | 20 | 34 | 20 | 70 | 20 |
| U79259_at | Human clone 23945 "mRNA," complete cds. | 89 | 29 | 138 | 117 | 20 | 20 |
| U79260_at | Human clone 23745 "mRNA," complete cds. | 112 | 84 | 135 | 86 | 143 | 163 |
| U79261_s_at | Human clone 23959 "mRNA," partial cds. | 20 | 20 | 20 | 20 | 25 | 20 |
| U79262_at | Human deoxyhypusine synthase "mRNA," complete cds. | 106 | 87 | 151 | 141 | 83 | 212 |
| U79263_at | Human clone 23760 "mRNA," complete cds. | 20 | 24 | 20 | 20 | 20 | 20 |
| U79265_at | Human clone 23614 mRNA sequence | 20 | 57 | 20 | 28 | 20 | 20 |
| U79266_at | Human clone 23627 "mRNA," complete cds. | 178 | 148 | 104 | 98 | 150 | 224 |
| U79267_at | Human clone 23840 "mRNA," partial cds. | 110 | 70 | 66 | 90 | 72 | 39 |
| U79270_at | Human clone 23707 "mRNA," partial cds. | 20 | 20 | 29 | 30 | 20 | 20 |
| U79271_at | Human clones 23920 and 23921 mRNA sequence | 20 | 32 | 20 | 20 | 20 | 53 |
| U79273_at | Human clone 23720 mRNA sequence | 20 | 26 | 20 | 20 | 20 | 20 |
| U79274_at | Human clone 23933 mRNA sequence | 22 | 45 | 30 | 20 | 20 | 20 |
| U79275_at | Human clone 23733 "mRNA," complete cds. | 51 | 62 | 36 | 27 | 93 | 76 |
| U79277_at | Human clone 23947 "mRNA," partial cds. | 194 | 138 | 132 | 103 | 165 | 61 |
| U79278_at | Human clone 23548 mRNA sequence | 20 | 20 | 20 | 20 | 20 | 37 |
| U79280_at | Human clone 23575 "mNA," partial cds. | 93 | 39 | 42 | 56 | 226 | 105 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U79282_at | Human clone 23801 mRNA sequence | 20 | 20 | 22 | 30 | 20 | 48 |
| U79285_at | Human clone 23828 mRNA sequence | 39 | 56 | 20 | 42 | 99 | 157 |
| U79286_at | Human arginine methyltransferase "mRNA," complete cds. | 20 | 20 | 20 | 20 | 20 | 20 |
| U79287_at | Human clone 23867 mRNA sequence | 88 | 135 | 177 | 233 | 98 | 147 |
| U79288_at | Human clone 23682 mRNA sequence | 73 | 27 | 47 | 20 | 39 | 20 |
| U79289_at | Human clone 23695 mRNA sequence | 20 | 20 | 20 | 20 | 20 | 52 |
| U79290_at | Human clone 23908 mRNA sequence | 20 | 20 | 37 | 21 | 20 | 24 |
| U79291_at | Human clone 23721 mRNA sequence | 50 | 20 | 31 | 25 | 20 | 48 |
| U79293_at | Human clone 23948 mRNA sequence | 20 | 20 | 20 | 20 | 24 | 20 |
| U79294_at | Human clone 23748 "mRNA," complete cds. | 370 | 417 | 294 | 256 | 286 | 241 |
| U79295_at | Human clone 23961 mRNA sequence | 44 | 20 | 20 | 20 | 164 | 20 |
| U79296_at | Human dihydrolipoamide acetyl transferase "mRNA," partial cds. | 31 | 20 | 31 | 23 | 141 | 60 |
| U79297_at | Human clone 23589 mRNA sequence | 60 | 38 | 55 | 61 | 20 | 20 |
| U79298_at | Human clone 23803 "mRNA," partial cds. | 72 | 20 | 28 | 21 | 57 | 20 |
| U79299_at | Human neuronal olfactomedin-related ER localized protein "mRNA," partial cds. | 20 | 35 | 20 | 20 | 117 | 232 |
| U79300_at | Human clone 23629 mRNA sequence | 20 | 20 | 20 | 20 | 102 | 24 |
| U79301_at | Human A33 antigen precursor "mRNA," complete cds | 20 | 20 | 20 | 20 | 42 | 20 |
| U79302_at | Human clone 23855 "mRNA," partial cds. | 20 | 48 | 20 | 20 | 63 | 28 |
| U79303_at | Human clone 23882 "mRNA," complete cds. | 158 | 20 | 163 | 177 | 55 | 175 |
| U79304_at | Human clone 23909 "mRNA," partial cds. | 20 | 20 | 20 | 20 | 99 | 20 |
| U79526_at | Human orphan G-protein coupled receptor Dez isoform a "mRNA," complete cds. | 20 | 20 | 20 | 20 | 20 | 20 |
| U79528_s_at | Human SR31747 binding protein 1 "mRNA," complete cds | 160 | 195 | 494 | 308 | 399 | 319 |
| U79667_s_at | Human alpha1A-voltage-dependent calcium channel "mRNA," splice form "VI-1-V2-GGCAG," partial cds | 20 | 20 | 20 | 20 | 20 | 20 |
| U79716_at | Human reelin (RELN) "mRNA," complete cds | 43 | 20 | 20 | 28 | 58 | 20 |
| U79718_at | Human endonuclease III homolog 1 (OCTS3) "mRNA," complete cds. | 20 | 20 | 24 | 22 | 35 | 20 |
| U79734_at | Human huntingtin interacting protein (HIP1) "mRNA," complete cds. | 20 | 48 | 42 | 32 | 112 | 49 |
| U79751_at | Human basic-leucine zipper nuclear factor (JEM-1) "mRNA," complete cds. /gb=U79751 /ntype=RNA | 20 | 20 | 20 | 20 | 20 | 20 |
| U80017_ma1_at | Human basic transcription factor 2 prr (btf2p44) gene, partial cds, neuronal apoptosis inhibitory protein (naip) and survival motor neuron | 120 | 95 | 212 | 200 | 168 | 184 |
| U80017_ma2_at | Human basic transcription factor 2 p44 (btf2p44) gene, partial cds, neuronal apoptosis inhibitory protein (naip) and survival motor neuron | 37 | 20 | 96 | 84 | 20 | 85 |
| U80017_ma3_at | Human basic transcription factor 2 prr (btf2p44) gene, partial cds, neuronal apoptosis inhibitory protein (naip) and survival motor neuron | 71 | 34 | 82 | 73 | 41 | 39 |
| U80034_at | Human mitochondrial intermediate peptidase precursor (MIPEP) "mRNA," mitochondrial gene encoding mitochondrial "protein," complete | 20 | 20 | 20 | 20 | 20 | 20 |
| U80040_at | Human nuclear aconitase "mRNA," encoding mitochondrial "protein," complete cds | 87 | 45 | 63 | 157 | 20 | 20 |
| U80073_at | Human tip associating protein (TAP) "mRNA," complete cds. /gb=U80073 /ntype=RNA | 34 | 103 | 117 | 27 | 222 | 51 |
| U80184_ma1_at | Homo sapiens FLII gene, complete cds | 20 | 20 | 20 | 20 | 20 | 20 |
| U80226_s_at | Human gamma-aminobutyric acid transaminase "mRNA," partial cds. /gb=U80226 /ntype=RNA | 20 | 20 | 20 | 20 | 20 | 20 |
| U80456_at | Human transcription factor SIM2 long form "mRNA," complete cds | 20 | 29 | 24 | 20 | 20 | 39 |
| U80457_at | Human transcription factor SIM2 short for m"mRNA," complete cds. | 20 | 20 | 20 | 20 | 20 | 20 |
| U80628_at | Human thymidine kinase 2 isoform B (TK2) "mRNA," alternatively "spliced," partial cds | 20 | 28 | 20 | 20 | 20 | 20 |
| U80669_at | Human androgen regulated homeobox protein (NIKX3.1) "mRNA," complete cds | 20 | 20 | 20 | 20 | 20 | 20 |
| U80811_at | Human lysophosphatidic acid receptor homolog "mRNA," complete cds | 38 | 116 | 73 | 39 | 246 | 94 |
| U80987_s_at | Human transcription factor TBX5 "mRNA," complete cds. /gb=U80987 /ntype=RNA | 76 | 35 | 191 | 193 | 137 | 20 |
| U81001_at | Human SNRPN "mRNA," 3' "UTR," partial sequence | 20 | 20 | 20 | 20 | 72 | 20 |
| U81006_at | Human p76 "mRNA," complete cds | 43 | 73 | 57 | 143 | 182 | 162 |
| U81262_at | Human lerk-5 (Lerk-5) "mRNA," complete cds. | 20 | 71 | 73 | 20 | 135 | 20 |
| U81375_at | Human placental equilibrative nucleoside transporter 1 (hENT1) "mRNA," complete cds | | | | | | |
| U81523_at | Human endometrial bleeding associated factor "mRNA," comlete cds. | | | | | | |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| U81554_at | Human CaM kinase II isoform "mRNA," complete cds. /gb=U81554 /ntype=RNA | 28 | 45 | 40 | 31 | 20 | 20 | 20 |
| U81556_at | Human hypothetical protein A4 "mRNA," complete cds | 207 | 124 | 254 | 208 | 235 | 170 |
| U81599_at | Human homeodomain protein HOXB13 "mRNA," complete cds. | 98 | 71 | 93 | 89 | 261 | 193 |
| U81600_at | Human paired-like homeodomain protein PRX-2 "mRNA," partial cds. | 199 | 237 | 146 | 163 | 242 | 319 |
| U81607_at | Human gravin "mRNA," complete cds | 76 | 27 | 20 | 20 | 20 | 60 |
| U81787_at | Human Wnt10B "mRNA," complete cds. | 45 | 39 | 20 | 20 | 20 | 83 |
| U81802_at | Human Ptdins 4-kinase (PI4Kb) "mRNA," complete cds. | 90 | 80 | 89 | 94 | 123 | 139 |
| U81984_at | Human endothelial PAS domain protein 1 (EPAS1) "mRNA," complete cds | 139 | 20 | 91 | 87 | 173 | 20 |
| U82010_ma1_at | Homo sapiens heme A: farnesyltransferase (COX10) gene, exon 7 and complete cds. | 141 | 156 | 143 | 105 | 20 | 227 |
| U82108_s_at | Human SIP-1 "mRNA," complete cds | 20 | 23 | 20 | 20 | 217 | 20 |
| U82130_at | Human tumor susceptibility protein (TSG101) "mRNA," complete cds | 82 | 42 | 84 | 70 | 20 | 77 |
| U82169_at | Human frizzled homolog (FZD3) "mRNA," complete cds. | 29 | 31 | 45 | 20 | 315 | 169 |
| U82256_at | Human arginase type II "mRNA," complete cds | 45 | 20 | 21 | 20 | 27 | 57 |
| U82275_at | Human immunoglobulin-like transcript 1 "mRNA," complete cds | 28 | 20 | 33 | 20 | 20 | 20 |
| U82279_at | Human immunoglobulin-like transcript 2 "mRNA," complete cds | 20 | 34 | 45 | 25 | 185 | 81 |
| U82303_at | Human unknown protein "mRNA," partial cds. /gb=U82303 /ntype=RNA | 20 | 20 | 20 | 20 | 20 | 70 |
| U82306_at | Human unknown protein "mRNA," partial cds. /gb=U82306 /ntype=RNA | 20 | 20 | 20 | 26 | 61 | 78 |
| U82310_at | Human unknown protein "mRNA," partial cds. /gb=U82310 /ntype=RNA | 20 | 20 | 20 | 20 | 70 | 80 |
| U82311_at | Human unknown protein "mRNA," partial cds. /gb=U82311 /ntype=RNA | 111 | 93 | 160 | 93 | 176 | 20 |
| U82313_at | Human unknown protein "mRNA," partial cds. /gb=U82313 /ntype=RNA | 20 | 20 | 20 | 20 | 20 | 20 |
| U82319_at | Human clone YDD19 mRNA sequence | 20 | 20 | 20 | 20 | 20 | 20 |
| U82320_at | Human unknown protein "mRNA," partial cds. /gb=U82320 /ntype=RNA | 20 | 21 | 20 | 20 | 20 | 20 |
| U82321_at | Human clone 14.9B mRNA sequence | 42 | 20 | 20 | 20 | 57 | 77 |
| U82467_at | Human tub homolog (TUB) "mRNA," complete cds. | 133 | 20 | 20 | 20 | 20 | 20 |
| U82468_at | Human tubby related protein 1 (TULP1) "mRNA," complete cds. | 20 | 20 | 20 | 20 | 20 | 20 |
| U82532_at | Human GDI-dissociation inhibitor RhoGDIgammma "mRNA," complete cds | 20 | 36 | 71 | 76 | 89 | 112 |
| U82535_at | Human fatty acid amide hydrolase "mRNA," complete cds. | 26 | 77 | 20 | 28 | 107 | 117 |
| U82613_at | Human DNA-binding protein ABP/ZF "mRNA," complete cds | 20 | 20 | 20 | 20 | 20 | 20 |
| U82668_ma1_at | Homo sapiens shox gene, alternatively spliced products, complete cds. | 109 | 47 | 29 | 20 | 54 | 20 |
| U82671_cds2_at | Homo sapiens cosmids Qc14E2, Qc12H12, Qc11F9, Qc10G9, LA1733 and Qc17B8 from Xq28, complete sequence. | 20 | 20 | 20 | 20 | 20 | 20 |
| U82759_at | Human homeodomain protine HoxA9 "mRNA," complete cds. | 33 | 20 | 20 | 45 | 157 | 152 |
| U82818_at | Homo sapiens UCP3S "mRNA," complete cds. /gb=U82818 /ntype=RNA | 27 | 29 | 20 | 20 | 137 | 20 |
| U82970_at | Human metalloendopeptidase homolog (PEX) "mRNA," complete sequence. | 20 | 20 | 20 | 48 | 20 | 94 |
| U82987_at | Human immunoglobulin-like transcript-3 "mRNA," complete cds | 20 | 20 | 20 | 20 | 58 | 20 |
| U83115_at | Human Bcl-2 binding component 3 (bbc3) "mRNA," partial cds | 239 | 228 | 184 | 138 | 76 | 179 |
| U83117_at | Human non-lens beta gamma-crystallin like protein (AIM1) "mRNA," partial cds | 20 | 20 | 20 | 20 | 20 | 20 |
| U83171_at | Human sentrin "mRNA," complete cds. | 145 | 216 | 350 | 244 | 382 | 256 |
| U83192_at | Human macrophage-derived chemokine precursor (MDC) "mRNA," complet ecds | 20 | 20 | 40 | 37 | 40 | 20 |
| U83239_s_at | Homo sapiens post-synaptic density protein 95 (PSD95) "mRNA," complete cds | 202 | 238 | 512 | 402 | 669 | 282 |
| U83246_at | Human CC chemokine STCP-1 "mRNA," complete cds | 84 | 152 | 291 | 259 | 333 | 391 |
| U83303_cds_at | Human copine I "mRNA," complete cds | 20 | 32 | 20 | 20 | 20 | 20 |
| U83326_s_at | Human line-1 reverse transcriptase gene, partial cds, and granulocyte chemotactic protein-2 (GCP-2) gene, complete cds. | 20 | 20 | 20 | 20 | 20 | 20 |
| U83410_at | Human CUL-2 (cul-2) "mRNA," complete cds. | 20 | 20 | 32 | 40 | 63 | 60 |
| U83411_at | Homo sapiens carboxypeptidase Z "precursor," "mRNA," complete cds. | 20 | 20 | 20 | 20 | 20 | 20 |
| U83461_at | Homo sapiens putative copper uptake protein (hCTR2) "mRNA," complete cds. /gb=U83461 /ntype=RNA | 34 | 65 | 23 | 25 | 110 | 66 |
| U83463_at | Human scaffold protein Pbp 1 "mRNA," complete cds. | 95 | 69 | 61 | 70 | 97 | 97 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U83598_at | Human death domain receptor 3 soluble form (DDR3) "mRNA," partial cds | 114 | 191 | 198 | 69 | 20 | 20 |
| U83598_s_at | Human death domain receptor 3 (DDR3) "mRNA," alternatively spliced form "2," partial cds. /gb=U83600 /ntype=RNA | 20 | 20 | 20 | 20 | 197 | 78 |
| U83600_at | Human calpastatin "gene," exons 14 and "15," partial cds /gb=U83601 /ntype=DNA /annot=mRNA | 43 | 20 | 20 | 20 | 20 | 20 |
| U83601_at | Human HIV-1 Nef interacting protein (Nip7-1) "mRNA," partial cds. /gb=U83843 /ntype=RNA | 20 | 21 | 107 | 118 | 55 | 62 |
| U83843_at | Human nuclear antigen H731 "mRNA," complete cds | 74 | 20 | 20 | 24 | 20 | 20 |
| U83908_at | Human glycogen debranching enzyme isoform 6 (AGL) "mRNA," alternatively spliced "isoform," complete cds | 48 | 41 | 35 | 60 | 20 | 48 |
| U84011_s_at | Human death domain containing protein CRADD "mRNA," complete cds | 20 | 55 | 20 | 62 | 20 | 37 |
| U84388_at | Human CX3C chemokine "precursor," "mRNA," alternatively "apliced," complete cds | 45 | 20 | 20 | 20 | 20 | 20 |
| U84487_at | Human dystrobrevin isoform DTN-3 (DTN) "gene," exon 11B and complete cds. /gb=U84540 /ntype=DNA /annot=mRNA | 20 | 20 | 20 | 20 | 20 | 20 |
| U84450_at | Human dystrobrevin isoform DTN-1 (DTN) gene, exon 21 and complete cds. | 20 | 20 | 20 | 20 | 20 | 20 |
| U84551_cds2_at | Human YF5 "mRNA," complete cds | 241 | 270 | 247 | 256 | 494 | 691 |
| U84569_at | Human sapiens lysyl hydroxylase isoform 2 (PLOD2) "mRNA," complete cds | 46 | 22 | 20 | 20 | 72 | 29 |
| U84573_at | Human mRNA export protein Rae1 (RAE1) "mRNA," complete cds. | 20 | 20 | 20 | 20 | 20 | 20 |
| U84720_at | Human nuclear factor I-B2 (NFIB2) "mRNA," complete cds. | 51 | 126 | 48 | 42 | 78 | 139 |
| U85193_at | Human phosphatidylinositol-4-phosphate 5-kinase type II beta "mRNA," complete cds. | 20 | 20 | 20 | 32 | 49 | 67 |
| U85245_at | Human down syndrome crigical region 1 (DSCR1) "gene," alternative exon 1 /gb=U85265 /ntype=RNA | 20 | 34 | 20 | 20 | 62 | 20 |
| U85265_at | Human down syndrome critical region 1 (DSCR1) "gene," alternative exon "1," partial cds. /gb=U85267 /ntype=RNA | 20 | 20 | 20 | 20 | 20 | 20 |
| U85267_at | Human transcription factor NFATx4 "mRNA," complete cds. | 20 | 26 | 20 | 20 | 20 | 20 |
| U85430_at | Human DNA-PK interaction protein (KIP) "mRNA," complete cds | 192 | 342 | 377 | 376 | 197 | 329 |
| U85611_at | Human transcription factor ERF-1 "mRNA," complete cds | 61 | 37 | 45 | 46 | 30 | 20 |
| U85658_at | Human leukemogenic homolog protein (MEIS1) "mRNA," complete cds | 33 | 20 | 31 | 20 | 20 | 20 |
| U85707_at | Human myeloid progenitor inhibitory factor-1 MPIF-1 "mRNA," complete cds | 88 | 106 | 105 | 106 | 174 | 251 |
| U85767_at | Human mRNA-associated protein mmp41 "mRNA," complete cds. /gb=U85943 /ntype=RNA | 20 | 20 | 20 | 39 | 86 | 103 |
| U85943_at | Human brain secretory protein hSec10p (HSEC10) "mRNA," complete cds | 20 | 30 | 22 | 20 | 35 | 53 |
| U85946_at | Human clone IMAGE:35527 unknown protein "mRNA," partial cds | 52 | 54 | 76 | 22 | 94 | 48 |
| U85267_at | Human phosphomannomutase "mRNA," complete cds | 128 | 111 | 135 | 116 | 339 | 265 |
| U86070_at | Human telomerase-associated protein TP-1 "mRNA," complete cds | 20 | 20 | 22 | 20 | 20 | 49 |
| U86136_at | Human Fas-associated death domain protein interleukin-1b-converting enzyme 2 "mRNA," complete cds. | 20 | 20 | 20 | 20 | 20 | 20 |
| U86214_at | Human chemokine (TECK) "mRNA," complete cds. /gb=U86358 /ntype=RNA | 20 | 20 | 20 | 20 | 83 | 26 |
| U86358_at | Human hyaluronan synthase 3 (HAS3) "gene," partial cds. /gb=U86409 /ntype=DNA /annot=CDS | 130 | 152 | 125 | 133 | 364 | 254 |
| U86409_at | Human glutathione transferase Zeta 1 (GSTZ1) "mRNA," complete cds. /gb=U86529 /ntype=RNA | 189 | 252 | 207 | 189 | 185 | 329 |
| U86529_at | Human nucleolar protein p40 "mRNA," complete cds | 88 | 91 | 78 | 86 | 55 | 97 |
| U86602_at | Human TNF-alpha converting enzyme "mRNA," complete cds | 20 | 20 | 20 | 20 | 20 | 20 |
| U86755_s_at | Human netrin-2 like protein (NTN2I) "mRNA," complete cds | 20 | 38 | 70 | 20 | 375 | 193 |
| U86759_s_at | Human 26S proteasome-associated pad1 homolog (POH1) "mRNA," complete cds. /gb=U86782 /ntype=RNA | 93 | 21 | 55 | 66 | 20 | 90 |
| U86782_at | Human contactin associated protein (Caspr) "mRNA," complete cds | 36 | 38 | 20 | 20 | 48 | 20 |
| U87223_at | Human 120E4F transcription factor "mRNA," complete cds. | 44 | 20 | 20 | 20 | 20 | 20 |
| U87269_at | Human hVps41p (HVPS41) "mRNA," complete cds. | 20 | 20 | 20 | 20 | 20 | 20 |
| U87309_at | Human clone IMAGE:74593 unknown protein "mRNA," partial cds | 68 | 49 | 83 | 51 | 20 | 162 |
| U87408_at | Human autoimmunogenic cancer/testis antigen NY-ESO-1 "mRNA," complete cds | 93 | 137 | 107 | 111 | 129 | 220 |
| U87459_at | Human putative endothelin receptor type B-like protein "mRNA," complete cds. | 20 | 20 | 20 | 20 | 20 | 20 |
| U87460_at | Human endogenous retrovirus clone P1.8 polymerase "mRNA," partial cds. /gb=U87593 /ntype=RNA | 20 | 20 | 20 | 20 | 20 | 20 |
| U87593_f_at | Human putative G-protein (GP-1) "mRNA," complete cds. | 20 | 20 | 20 | 20 | 51 | 111 |
| U87964_at | Human NAD+-isocitrate dehydrogenase "mRNA," partial cds. /gb=U87972 /ntype=RNA | 34 | 33 | 45 | 37 | 305 | 100 |
| U87972_at | Human DNA binding protein homolog (DRX) "mRNA," partial cds | 63 | 68 | 81 | 55 | 94 | 74 |
| U88047_at | Human RNA polymerase II elongation factor "ELL2," complete cds. /gb=U88629 /ntype=DNA /annot=CDS | 199 | 84 | 102 | 79 | 256 | 219 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U88666_at | Human serine kinase SRPK2 "mRNA," complete cds | 37 | 27 | 69 | 41 | 20 | 54 |
| U88667_at | Human ATP binding cassette transporter (ABCR) "mRNA," complete cds | 20 | 20 | 20 | 20 | 20 | 34 |
| U88726_at | Human symptekin "mRNA," partial cds. /gb=U88726 /ntype=RNA | 20 | 38 | 20 | 25 | 20 | 20 |
| U88871_at | Human HsPex7p (HsPEX7) "mRNA," complete cds. | 20 | 20 | 20 | 20 | 20 | 20 |
| U88892_at | Human tenascin-C "mRNA," splice variant "TNCfn-ad2," partial cds. /gb=U88892 /ntype=RNA | 20 | 20 | 20 | 20 | 35 | 20 |
| U88898_at | Human endogenous retroviral H protease/integrase-derived ORF1 "mRNA," complete "cds," and putative envelope protein "mRNA," parti | 65 | 20 | 54 | 20 | 20 | 20 |
| U88898_r_at | Human endogenous retroviral H protease/integrase-derived ORF1 "mRNA," complete "cds," and putative envelope protein "mRNA," parti | 176 | 422 | 721 | 449 | 1296 | 494 |
| U88902_cds1_f_at | integrase gene extracted from Human endogenous retrovirus H clone g10.34 integrase and putative envelope protein "genes," partial cds | 20 | 20 | 74 | 20 | 131 | 101 |
| U88964_at | Human HEM45 "mRNA," complete cds. | 161 | 229 | 89 | 92 | 163 | 442 |
| U89012_at | Homo sapiens dentin matrix acidic phosphoprotein 1 (DMP1) "mRNA," complete cds | 20 | 20 | 20 | 20 | 20 | 30 |
| U89278_at | Human polyhomeotic 2 homolog (HPH2) "mRNA," complete cds. | 91 | 105 | 147 | 103 | 227 | 339 |
| U89326_at | Human bone morphogenetic protein receptor type I ALK-6 "mRNA," complete cds. | 20 | 20 | 20 | 21 | 184 | 44 |
| U89335_cds2_at | Human HLA class III region containing notch4 (NOTCH) gene, partial sequence, complet ecds, complete sequence | 76 | 68 | 70 | 82 | 33 | 102 |
| U89336_cds1_at | Human HLA class III region containing NOTCH4 gene, partial sequence, homeobox PBX2 (HPBX) gene, receptor for advanced glycosyla | 112 | 130 | 110 | 88 | 101 | 262 |
| U89336_cds3_at | Human HLA class III region containing NOTCH4 gene, partial sequence, homeobox PBX2 (HPBX) gene, receptor for advanced glycosyla | 134 | 104 | 142 | 120 | 305 | 263 |
| U89336_cds4_at | Human HLA class III region containing NOTCH4 gene, partial sequence, homeobox PBX2 (HPBX) gene, receptor for advanced glycosyla | 20 | 20 | 36 | 61 | 48 | 20 |
| U89336_cds6_at | Human HLA class III region containing NOTCH4 gene, partial sequence, homeobox PBX2 (HPBX) gene, receptor for advanced glycolyla | 26 | 36 | 29 | 42 | 115 | 79 |
| U89336_cds7_at | Human HLA class III region containing NOTCH4 gene, partial sequence, homeobox PBX2 (HPBX) gene, receptor for advanced glycosyla | 20 | 20 | 20 | 20 | 20 | 20 |
| U89336_cds8_at | Human HLA class III region containing NOTCH4 gene, partial sequence, homeobox PBX2 (HPBX) gene, receptor for advanced glycosyla | 44 | 53 | 31 | 50 | 87 | 65 |
| U89355_at | Homo sapiens clone cRT16 CREB-binding protein "mRNA," partial cds. | 20 | 27 | 40 | 22 | 20 | 45 |
| U89268_at | Human Hlark "mRNA," complete cds. | 47 | 91 | 173 | 134 | 104 | 31 |
| U89606_at | Human pyridoxal kinase "mRNA," complete cds. | 20 | 20 | 20 | 37 | 20 | 57 |
| U89717_at | Human 9-cis-retinolspecific dehydrogenase "mRNA," complete cds. | 20 | 20 | 20 | 20 | 20 | 20 |
| U89896_at | Human casein kinase I gamma 2 "mRNA," complete cs | 29 | 20 | 37 | 63 | 79 | 33 |
| U89916_at | Homo sapiens putative OSP like protein "mRNA," partial cds. | 20 | 25 | 20 | 20 | 20 | 20 |
| U89922_at | Human lymphotoxin beta isoform "variant," alternatively spliced "mRNA," complete cds | 20 | 20 | 20 | 20 | 20 | 49 |
| U89942_at | Human lysyl oxidase-related protein (WS9-14) "mRNA," complete cds | 28 | 61 | 29 | 20 | 59 | 38 |
| U89995_at | Human DNA binding protein FKHL15 (FKHL15) "mRNA," complete cds | 20 | 20 | 20 | 20 | 20 | 20 |
| U9065_s_at | Human potassium channel KCNO1 "mRNA," complete cds | 20 | 20 | 20 | 20 | 20 | 20 |
| U90268_at | Human Krit1 "mRNA," complete cds. | 20 | 20 | 20 | 20 | 20 | 20 |
| U90304_at | Human iroquois-class homeodomain protein IRX-2a "mRNA," complete cds. | 20 | 42 | 20 | 20 | 20 | 51 |
| U90306_at | Human iroquois-class homeodomain protein IRX-4 "mRNA," partial cds. /gb=U90306 /ntype=RNA | 53 | 20 | 56 | 36 | 47 | 80 |
| U90313_at | Human glutathione-S-transferase homolog "mRNA," complete cds. | 270 | 295 | 398 | 334 | 212 | 412 |
| U90336_at | Human PEG3 "mRNA," partial cds. | 20 | 20 | 20 | 20 | 20 | 20 |
| U90426_at | Human nuclear RNA "helicase," complete cds | 113 | 93 | 122 | 127 | 169 | 383 |
| U90437_at | Human RP1 homolog "mRNA," 3′UTR region. /gb=U90437 /ntype=RNA | 20 | 27 | 20 | 20 | 47 | 20 |
| U90543_at | | 20 | 20 | 20 | 20 | 20 | 20 |
| U90543_s_at | Human butyrophilin (BTF1) "mRNA," complete cds. | 20 | 20 | 120 | 20 | 20 | 51 |
| U90544_at | Human sodium phosphate transporter (NPT3) "mRNA," complete cds. | 20 | 20 | 20 | 20 | 20 | 20 |
| U90546_at | Human butyrophilin (BTF4) "mRNA," complete cds. | 20 | 20 | 20 | 20 | 47 | 45 |
| U90546_r_at | Human butyrophilin (BTF4) "mRNA," complete cds. | 20 | 20 | 20 | 20 | 535 | 20 |
| U90547_at | Human Ro/SSA ribonucleoprotein homolog (RoRet) "mRNA," complete cds | 80 | 148 | 87 | 98 | 160 | 233 |
| U90549_at | Human non-histone hcromosomal protein (NHC) "mRNA," complete cds | 58 | 20 | 93 | 82 | 20 | 69 |
| U90550_at | Human butyrophilin (BTF2) "mRNA," complete cds | 79 | 107 | 93 | 100 | 174 | 138 |
| U90551_at | Human histone 2A-like protein (HsA/l) "mRNA," complete cds | 22 | 20 | 20 | 20 | 20 | 20 |
| U90552_s_at | Human butyrophilin (BTF5) "mRNA," complete cds | 54 | 347 | 225 | 141 | 20 | 123 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U90651_at | Human embryonic ectoderm development protein homolog (eed) "mRNA," partial cds. | 25 | 54 | 74 | 56 | 55 | 64 |
| U90716_at | Human cell surface protein HCAR "mRNA," complete cds | 81 | 203 | 386 | 269 | 161 | 266 |
| U90878_at | Human LIM domain protein CLP-36 "mRNA," complete cds. | 335 | 220 | 414 | 320 | 237 | 176 |
| U90902_at | Human clone 23612 mRNA sequence | 63 | 32 | 90 | 67 | 87 | 34 |
| U90904_at | Human clone 23773 mRNA sequence | 30 | 41 | 84 | 65 | 20 | 25 |
| U90905_at | Human clone 23574 mRNA sequence | 20 | 20 | 20 | 20 | 20 | 20 |
| U90907_at | Human clone 23907 mRNA sequence | 66 | 130 | 56 | 39 | 68 | 149 |
| U90908_at | Human clones 23549 and 23762 "mRNA," complete cds | 20 | 20 | 20 | 20 | 20 | 20 |
| U90909_at | Human clone 23722 mRNA sequence | 82 | 57 | 80 | 68 | 20 | 73 |
| U90910_at | Human clone 23564 mRNA sequence | 20 | 20 | 20 | 20 | 20 | 20 |
| U90911_at | Human clone 23652 mRNA sequence | 76 | 45 | 142 | 134 | 48 | 64 |
| U90912_at | Human clone 23865 mRNA sequence | 40 | 25 | 28 | 23 | 33 | 20 |
| U90913_at | Human clone 23665 mRNA sequence | 98 | 44 | 167 | 130 | 48 | 74 |
| U90914_at | Human clone 23587 mRNA sequence | 20 | 20 | 24 | 25 | 20 | 20 |
| U90915_at | Human clone 23600 cytochrome c oxidase subunit IV "mRNA," complete cds | 684 | 988 | 952 | 1036 | 261 | 513 |
| U90916_at | Human clone 23815 mRNA sequence | 31 | 79 | 496 | 250 | 20 | 48 |
| U90918_at | Human clone 23654 mRNA sequence | 20 | 31 | 31 | 22 | 20 | 74 |
| U90919_at | Human lcones 23667 and 23775 zinc finger protein "mRNA," complete cds | 86 | 71 | 54 | 68 | 20 | 72 |
| U91316_at | Human acyl-CoA thioester hydrolase "mRNA," complete cds | 49 | 23 | 20 | 20 | 20 | 20 |
| U91327_at | Human chromosome 12p15 BAC clone CIT987SK-99D8 complet esequence. /gb=U91327 /ntype=DNA /annot=mRNA | 64 | 34 | 100 | 110 | 20 | 41 |
| U91521_at | Human peroxin 12 (HsPEX12) "mRNA," complete cds. | 20 | 20 | 82 | 20 | 20 | 20 |
| U91616_3at | Human I kappa B epsilon (IkB3) "mRNA," complete cds | 26 | 20 | 25 | 36 | 38 | 20 |
| U91618_at | Human proneurotensin/proneuromedin N "mRNA," complete cds. | 20 | 26 | 20 | 56 | 20 | 20 |
| U91903_at | Human Fritz "mRNA," complete cds | 27 | 20 | 20 | 20 | 20 | 33 |
| U91930_at | Human AP-3 complex delta subunit "mRNA," complete cds | 62 | 100 | 198 | 159 | 20 | 80 |
| U91931_at | Human Ap-3 complex beta3A subunit "mRNA," complete cds | 37 | 20 | 41 | 39 | 33 | 20 |
| U91932_at | Human AP-3 complex sigma3A subunit "mRNA," complete cds | 113 | 103 | 142 | 129 | 135 | 218 |
| U91985_at | Human DNA fragmentation factor-45 "mRNA," complete cds | 20 | 20 | 20 | 20 | 20 | 20 |
| U92014_at | Human clone 121711 detective mariner transposon Hsmar2 mRNA sequence | 20 | 20 | 82 | 49 | 20 | 45 |
| U92015_at | Human clone 143789 detective mariner transposon Hsmar2 mRNA sequence | 26 | 20 | 25 | 36 | 132 | 82 |
| U92027_at | Human lcone 61501 detective mariner transposon Hsmar2 mRNA sequence | 20 | 26 | 20 | 56 | 20 | 33 |
| U92314_s_at | Homo sapiens hydroxysteroid sulfotransferase SULT2B1a (HSST2) "mRNA," complete cds. | 311 | 105 | 120 | 102 | 287 | 345 |
| U92436_at | Human mutated in multiple advanced cancers protein (MMAC1) "mRNA," complete cds | 30 | 27 | 20 | 20 | 20 | 20 |
| U92457_s_at | Human metabotropic glutamate receptor 4 "mRNA," complete cds. | 20 | 24 | 20 | 20 | 20 | 20 |
| U92458_at | Human metabotropic glutamate receptor 7 "mRNA," complete cds. | 20 | 20 | 39 | 32 | 62 | 87 |
| U92459_at | Human metabotropic glutamate receptor 8 "mRNA," complete cds | 20 | 20 | 20 | 20 | 20 | 20 |
| U92971_at | Human protease-activated receptor 3 (PAR3) "mRNA," complete cds. | 20 | 20 | 20 | 20 | 20 | 40 |
| U93049_at | Human SLP-76 associated protein "mRNA," complete cds | 107 | 105 | 120 | 102 | 287 | 345 |
| U93091_at | Human Toll protein homolog "mRNA," complete cds and LINE-1 reverse transcriptase "homolog," pseudogene. | 20 | 27 | 20 | 20 | 20 | 20 |
| U93205_at | Human nuclear chloride ion channel protein (NCC27) "mRNA," complete cds | 570 | 818 | 754 | 825 | 323 | 1262 |
| U93237_ma2_at | Human menin (MEN1) gene, complete cds. | 132 | 146 | 145 | 133 | 299 | 292 |
| U93553_at | Human alpha1-fetoprotein transcription factor (hFTF) "mRNA," complete cds. | 20 | 20 | 23 | 20 | 95 | 49 |
| U93867_at | Human RNA polymerase III subunit (RPC62) "mRNA," comlete cds. /gb=U93867 /ntype=RNA | 69 | 48 | 48 | 42 | 100 | 48 |
| U94319_at | Human autoantigen DFS70 "mRNA," partial cds. | 39 | 20 | 41 | 23 | 20 | 30 |
| U94320_at | Human neuropeptide Y5 receptor (NPYY5) "mRNA," complete cds. | 20 | 20 | 20 | 20 | 20 | 345 |
| U94332_at | Human osteoprotegerin (OPG) "mRNA," complete cds. | 45 | 20 | 58 | 28 | 57 | 37 |
| U94333_at | Human C1q/MBL/SPA receptor C1qR(p) "mRNA," complete cds. | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| U94585_at | Human sapiens requlem homolog (hsReq) "mRNA," complete cds. | 163 | 131 | 214 | 187 | 261 | 286 |
| U94586_at | Human NADH:ubiquinone oxidoreductase:MLRQ subunit "mRNA," complete cds. | 876 | 559 | 584 | 599 | 377 | 638 |
| U94592_at | Human uncoupling protein homolog (UCPH) "mRNA," complete cds. | 27 | 158 | 136 | 186 | 224 | 251 |
| U94747_at | Human WD repeat protein HAN11 "mRNA," complete cds. /gb=U94747 /ntype=RNA | 44 | 20 | 20 | 20 | 65 | 140 |
| U94831_at | Human multispanning membrane protein "mRNA," complete cds. /gb=U94831 /ntype=RNA | 71 | 55 | 136 | 146 | 198 | 144 |
| U94832_at | Human KH type splicing regulatory protein KSRP "mRNA," complete cds. | 39 | 115 | 141 | 152 | 67 | 49 |
| U94836_at | Human ERPROT 213-21 "mRNA," complete cds. | 20 | 20 | 20 | 20 | 20 | 20 |
| U94855_at | Human translation initiation factor 3 47 kDa subunit "mRNA," complete cds. | 293 | 259 | 540 | 420 | 100 | 246 |
| U95006_at | Human D9 splice variant A "mRNA," complete cds. | 20 | 42 | 100 | 68 | 97 | 102 |
| U95019_s_at | Human voltage-dependent calcium channel beta-2c subunit "mRNA," complete cds. | 20 | 20 | 20 | 20 | 20 | 20 |
| U95020_at | Human voltage-dependent calcium channel beta-4 subunit "mRNA," complete cds | 20 | 20 | 20 | 20 | 20 | 20 |
| U95040_at | Human transcriptional corepressor hKAP1/TIF1B "mRNA," complete cds. | 189 | 219 | 460 | 565 | 439 | 552 |
| U95090_at | Human chromosome 19 cosmid "F19541," complete sequence. | 20 | 20 | 20 | 20 | 20 | 20 |
| U95626_ma1_at | Homo sapiens ccr2b (ccr2), ccr2a (ccr2), ccr5 (ccr5) and ccr6 (ccr6) genes, complete cds, and lactoferrin (lactoferrin) gene, partial cds, c | 20 | 20 | 20 | 20 | 20 | 20 |
| U95626_ma3_at | ccr5 gene extracted from Homo sapiens ccr2b "(ccr2)," (ccr2)," ccr2a "(ccr2)," (ccr2)," ccr5 (ccr5) and ccr6 (ccr6) "genes," complete "cds," and lactoferrin | 20 | 20 | 20 | 20 | 20 | 20 |
| U95740_ma1_at | Human chromosome 16p13.1 BAC clone CIT987SK-362G6 complete sequence. | 54 | 23 | 97 | 53 | 20 | 20 |
| U95740_ma2_at | Human chromosome 16p13.1 BAC clone CIT987SK-362G6 complete sequence. | 29 | 66 | 50 | 20 | 20 | 20 |
| U96094_at | Human sarcolipin (SLN) "mRNA," complete cds. | 62 | 34 | 60 | 75 | 20 | 92 |
| U96113_at | Homo sapiens Nedd-4-like ubiquitin-protein ligase WWP1 "mRNA," partial cds. /gb=U96113 /ntype=RNA | 78 | 20 | 84 | 103 | 30 | 107 |
| U96114_at | Homo sapiens Nedd-4-like ubiquitin-protein ligase WWP2 "mRNA," complete cds. | 72 | 84 | 87 | 80 | 43 | 59 |
| U96115_at | Homo sapiens WW domain-containing protein WWP3 "mRNA," partial cds. /gb=U96115 /ntype=RNA | 33 | 20 | 20 | 22 | 20 | 49 |
| U96131_at | Homo sapiens HPV15 E1 protein binding protein "mRNA," complete cds. /gb=U96131 /ntype=RNA | 60 | 74 | 114 | 73 | 56 | 20 |
| U96136_at | Human delta-catenin "mRNA," complete cds | 23 | 36 | 20 | 20 | 308 | 20 |
| U96191_at | Human trophoblast hypoxia-regulated factor-5 (HRF-5) "mRNA," 3' end. /gb=U96191 /ntype=RNA | 20 | 20 | 20 | 20 | 20 | 20 |
| U96629_ma1_at | Homo sapiens sin3 associated polypeptide p18 (SAP18) "mRNA," complete cds. | 27 | 20 | 23 | 63 | 20 | 36 |
| U96629_ma2_at | Human chromosome 8 BAC clone CIT987SK-2A8 complete sequence. | 49 | 61 | 74 | 50 | 20 | 20 |
| U96769_ma1_at | Homo sapiens chondroadherin gene, exon 3, and complete cds. | 37 | 25 | 20 | 20 | 20 | 29 |
| U96781_ma1_cds1_at | Human Ca2+ ATPase of fast-twitch skeletal muscle sarcoplasmic reticulum adult and neonatla isoforms (ATP2A1) gene, exons 16 to 23 | 88 | 87 | 76 | 89 | 113 | 169 |
| U96915_at | Homo sapiens sin3 associated polypeptide p18 (SAP18) "mRNA," complete cds. | 126 | 44 | 200 | 185 | 57 | 140 |
| U96922_at | Homo sapiens inositol polyphosphate 4-phosphatase type II-alpha "mRNA," complete cds. /gb=U96922 /ntype=RNA | 20 | 20 | 20 | 20 | 20 | 20 |
| U97018_at | Homo sapiens echinoderm microtubule-associated protein homolog HuEMAP "mRNA," complete cds. | 22 | 20 | 22 | 26 | 20 | 31 |
| U97105_at | Homo sapiens N2A3 "mRNA," complete cds. | 111 | 49 | 25 | 30 | 20 | 35 |
| U97188_at | Homo sapiens putative RNA binding protein KOC (koc) "mRNA," complete cds. | 20 | 25 | 20 | 20 | 20 | 20 |
| U97502_ma1_at | Homo sapiens butyrophilin (BT3.3) gene, exon 10, and complete cds. | 20 | 23 | 20 | 20 | 20 | 20 |
| V00503_at | Human mRNA encoding Pro-alpha-2 chain of type I procollagen. (major part) | 20 | 83 | 59 | 37 | 87 | 315 |
| V00532_ma1_f_at | IFNA gene (interferon alpha-i) extracted from Human gene for leukocyte (alpha) interferon C | 150 | 393 | 59 | 37 | 87 | 315 |
| V00533_ma1_f_at | IFNA gene (interferon alph-h2) extracted from Human gene for leukocyte (alpha) interferon H | 20 | 20 | 20 | 20 | 20 | 20 |
| V00535_ma2_s_at | interferon beta 1 gene extracted from Gene for humna fibroblast interferon beta 1 | 26 | 20 | 21 | 20 | 20 | 20 |
| V00536_ma1_at | IFNG gene extracted from Human immunie interferon (IFN-gamma) gene | 20 | 33 | 20 | 20 | 20 | 20 |
| V00542_f_at | Messenger RNA for human leukocyte (alpha) interferon | 32 | 31 | 20 | 20 | 20 | 29 |
| V00551_f_at | Messenger RNA for human leukocyte (alpha) interferon | 20 | 30 | 20 | 26 | 67 | 20 |
| V00563_at | Human gene for immunoglobulin mu, parto f exon 8. | 20 | 49 | 52 | 32 | 107 | 20 |
| V00565_s_at | Human gene for "preproinsulin," from chromosome 11 includes a highly polymorphic region upstream from the insulin gene containing tan | 20 | 20 | 20 | 20 | 20 | 20 |
| V00571_ma1_at | Human gene encoding prepro form of corticotropin releasing factor. | 20 | 83 | 59 | 37 | 87 | 315 |
| V00572_at | Human mRNA encoding phosphoglycerate kinase | 758 | 447 | 846 | 1246 | 478 | 867 |
| V00574_s_at | Human germ line gene homologous to bladder carcinoma oncogene T24 (Gene code c-Ha-ras-1) with four exons | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| V00594_at | Human mRNA for metallothionein from cadmium-treated cells | 715 | 20 | 20 | 20 | 20 | 119 |
| V00594_s_at | | 2805 | 2716 | 524 | 325 | 1302 | 1844 |
| V00599_s_at | Human mRNA fragment encoding beta-tubulin. (from clone D-beta-1) | 278 | 528 | 1083 | 1165 | 491 | 1107 |
| V01510_ma1_at | H. sapiens gene coding for ACTH and beta-LPH precursors. Gene codes for the common precursor of the pituitary hormones corticotropin | 20 | 100 | 20 | 20 | 20 | 20 |
| V01512_ma1_at | Human cellular oncogene c-fos (complete sequence). | 574 | 164 | 164 | 125 | 20 | 124 |
| V01514_at | Human mRNA encoding alpha-fetoprotein (AFP). AFP is a major serum protein (MG: 70000) synthesized during fetal life | 20 | 20 | 20 | 20 | 26 | 20 |
| V01515_cds1_at | Human gene encoding preproglucagon. Glucagon is a 29-amino acid pancreatic hormone which counteracts the blood glucose-lowering a | 20 | 20 | 20 | 20 | 20 | 210 |
| V01516_f_at | Human messenger fragment encoding cytoskeletal keratin (type II). mRNA from cultured epidermal cells from human foreskin | 4779 | 162 | 395 | 200 | 325 | 210 |
| X00038_at | Human H4 histone gene | 20 | 20 | 20 | 20 | 20 | 20 |
| X00088_at | Human histone H2b gene | 20 | 20 | 20 | 20 | 20 | 20 |
| X00090_f_at | | 20 | 25 | 20 | 20 | 78 | 20 |
| X00129_at | Human mRNA for retinol binding protein (RBP) | 20 | 25 | 20 | 20 | 33 | 20 |
| X00237_at | Human F variable segment 5' to antithrombin III gene (AT III) | 34 | 20 | 20 | 20 | 64 | 63 |
| X00274_at | Human gene for HLA-DR alpha heavy chain a class II antigen (immune response gene) of the major histocompatibility complex (MHC) | 2780 | 2334 | 423 | 259 | 1196 | 5040 |
| X00351_f_at | Human mRNA for beta-actin. | 4186 | 1737 | 3505 | 3753 | 514 | 328 |
| X00363_xpt2_at | Human protactin gene 5' region. | 20 | 31 | 20 | 20 | 66 | 29 |
| X00371_ma1_at | Human myoglobin gene (exon 1) (and joined CDS). | 37 | 47 | 65 | 32 | 142 | 35 |
| X00437_s_at | Human mRNA for T-cell specific protein | 34 | 41 | 20 | 20 | 20 | 144 |
| X00540_at | H. sapiens gene encoding "prolactin," exon 2 and joined CDS | 20 | 20 | 20 | 20 | 216 | 20 |
| X00588_at | Human mRNA for precursor of epidermal growth factor receptor | 20 | 20 | 20 | 20 | 66 | 20 |
| X00695_s_at | Human interleukin-2 (IL-2) gene and 5'-glanking region | 20 | 22 | 67 | 20 | 235 | 73 |
| X00734_at | Human beta-tubulin gene (5-beta) with ten Alu family membets | 20 | 20 | 20 | 20 | 20 | 27 |
| X00948_at | Human mRNA for prepro-relaxin H2. /gb=X00948 /ntype=RNA | 20 | 20 | 20 | 20 | 20 | 20 |
| X00949_at | Human mRNA for prepro-relaxin H1. /gb=X00949 /ntype=RNA | 20 | 20 | 20 | 46 | 802 | 206 |
| X01038_ma1_s_at | Human fetal gene for apolipoprotein AI precursor | 20 | 20 | 20 | 20 | 20 | 20 |
| X01057_at | Human mRNA for interleukin-2 receptor | 20 | 31 | 20 | 26 | 92 | 68 |
| X01059_at | Human placenta mRNA for luetinizing hormone releasing hormone pecursor (LHRH) | 130 | 96 | 216 | 84 | 339 | 313 |
| X01060_at | Human mRNA for transferrin receptor | 182 | 149 | 163 | 135 | 202 | 278 |
| X01388_at | Human mRNA for pre-apolipoprotein CIII | 114 | 645 | 198 | 154 | 1254 | 1874 |
| X01630_at | Human mRNA for argininosuccinate synthetase | 3234 | 2281 | 5525 | 6843 | 34 | 171 |
| X01677_f_at | Human liver mRNA for glyceraldehyde-3-phosphate dehydrogenase "(G3PD," EC 1.2.1.12) | 218 | 267 | 102 | 71 | 140 | 151 |
| X01703_at | Human gene for alpha-tubulin (b alpha 1) | 44 | 50 | 30 | 24 | 334 | 1227 |
| X01715_at | H. sapiens gene fragment for the acetylcholine receptor gamma subunit precursor (exons 1 and 2) | 1432 | 374 | 899 | 1495 | 20 | 20 |
| X02152_at | Human mRNA for lactate dehydrogenase-A "(LDH-A," EC 1.1.1.27) | 20 | 20 | 20 | 20 | 20 | 20 |
| X02158_ma1_at | Human gene for erthropoietin. | 20 | 20 | 20 | 20 | 20 | 20 |
| X02160_at | Human mRNA for insulin receptor precursor | 509 | 428 | 526 | 465 | 218 | 471 |
| X02176_s_at | Human mRNA fragment for complement component C9 | 20 | 28 | 20 | 20 | 40 | 31 |
| X02317_at | Human mRNA for Cu/Zn superoxide dismutase (SOD) | 35 | 44 | 30 | 74 | 30 | 20 |
| X02404_at | Human mRNA fragment for second calcitonin gene related peptide (CGRP) from medullary thyroid carcinoma (MTC) | 99 | 71 | 55 | 20 | 20 | 184 |
| X02419_ma1_s_at | H. sapiens uPA gene | 20 | 20 | 20 | 20 | 20 | 20 |
| X02530_at | Human mRNA for gamma-interferon inducible early response gene (with homology to platelet proteins) | 49 | 43 | 108 | 74 | 27 | 20 |
| X02544_at | Human mRNA for alpha1-acid glycoprotein (orosomucoid) | 199 | 57 | 99 | 20 | 20 | 20 |
| X02596_at | Human mRNA for BCR (breakpoint cluster region) gene in Philadelphia chromosome | 87 | 60 | 74 | 81 | 162 | 156 |
| X02612_at | Human gene for cytochrome P(1)-450 | 20 | 20 | 20 | 20 | 20 | 20 |
| X02750_at | Human liver mRNA for protein C | 397 | 119 | 20 | 33 | 93 | 66 |
| X02751_at | Human N-ras mRNA and flanking regions | | | | | | |
| X02761_s_at | Human mRNA for fibronectin (FN precursor) | | | | | | |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X02874_at | Human mRNA for (2′-5′) oligo A synthetase E (1,6 kb RNA). | 21 | 80 | 84 | 164 | 62 | 165 |
| X02875_s_at | Human mRNA (3′-fragment) for (2′-5′) oligo A synthetase E″(1.8″ kb RNA) | 62 | 95 | 414 | 230 | 178 | 331 |
| X02883_at | Human gene for T-cell receptor alpha chain C region. /gb=X02883 /ntype=DNA /annot=exon | 20 | 20 | 20 | 20 | 179 | 20 |
| X02910_at | Human gene for tumor necrosis factor (TNF-alpha) | 20 | 50 | 20 | 22 | 39 | 71 |
| X02956_at | Human interferon alpha gene IFN-alpha 5 | 20 | 20 | 20 | 20 | 103 | 20 |
| X02958_at | Human interferon alpha gene IFN-alpha 6 | 20 | 45 | 20 | 20 | 166 | 20 |
| X03066_at | Human mRNA for HLA-D class II antigen DO beta chain | 51 | 72 | 53 | 54 | 65 | 135 |
| X03068_f_at | Human mRNA for HLA-D class II antigen DQw1.1 beta chain | 194 | 606 | 148 | 92 | 294 | 673 |
| X03072_at | Human int-1 mammary oncogene | 20 | 20 | 20 | 20 | 83 | 58 |
| X03100_cds2_at | Human HLA-SB(DP) alpha gene. | 457 | 403 | 111 | 87 | 259 | 1023 |
| X03168_at | Human mRNA for S-protein | 44 | 20 | 20 | 20 | 20 | 20 |
| X03342_at | Human mRNA for ribosomal protein L32 | 3818 | 5147 | 4534 | 4491 | 2059 | 2854 |
| X03350_at | Human mRNA for alcohol dehydrogenase beta-1-subunit (ADH1-2 allele) | 112 | 52 | 48 | 20 | 20 | 20 |
| X03363_s_at | Human c-erb-B-2 mRNA | 86 | 109 | 386 | 417 | 961 | 158 |
| X03473_at | Human gene for histone H1(0) | 20 | 20 | 20 | 20 | 20 | 20 |
| X03484_at | Human mRNA for ref oncogene | 56 | 62 | 105 | 98 | 167 | 167 |
| X03635_at | Human mRNA for oestrogen receptor | 63 | 20 | 20 | 20 | 20 | 20 |
| X03656_ma1_at | Human gene for granulocyte colony-stimulating factor (G-CSF). | 124 | 20 | 20 | 20 | 59 | 20 |
| X03663_at | Human mRNA for c-fms proto-oncogene | 84 | 75 | 81 | 64 | 20 | 188 |
| X03689_s_at | Human mRNA fragment for elongation factor TU (N-terminus). /gb=X03689 /ntype=RNA | 4233 | 2419 | 8197 | 7590 | 83 | 2092 |
| X03794_s_at | Human embryonic mRNA 3′ end with homoeo box (clone HHOc10) | 20 | 20 | 20 | 20 | 109 | 20 |
| X03934_at | Human T-cell antigen receptor gene T3-delta | 111 | 144 | 88 | 80 | 47 | 244 |
| X04011_at | Human mRNA of X-CGD gene involved in chronic granulomatous disease located on chromosome X | 43 | 32 | 35 | 20 | 67 | 116 |
| X04085_ma1_at | Human gene for catalase (EC 1.11.1.6) 5′flank and exon 1 mapping to chromosome 11, band p13 (and joined CDS). | 60 | 246 | 233 | 175 | 135 | 180 |
| X04106_at | Human mRNA for calcium dependent protease (small subunit) | 383 | 139 | 490 | 519 | 173 | 248 |
| X04143_at | Human mRNA for bone gla protein (BGP) | 20 | 20 | 20 | 20 | 20 | 20 |
| X04145_at | Human mRNA for T-cell receptor T3 gamma polypeptide | 20 | 39 | 20 | 20 | 20 | 20 |
| X04201_at | Human skeletal muscle 1.3 kb mRNA for tropomyosin | 20 | 20 | 20 | 51 | 20 | 25 |
| X04297_at | Human mRNA for "Na,K-ATPase" alpha-subunit | 29 | 63 | 23 | 26 | 20 | 31 |
| X04325_at | Human liver mRNA for gap junction protein | 20 | 20 | 43 | 46 | 20 | 20 |
| X04327_at | Human erythrocyte "2,3-bisphosphoglycerate" mutase mRNA EC 2.7.5.4 | 20 | 20 | 20 | 29 | 74 | 20 |
| X04347_s_at | Human liver mRNA fragment DNA binding protein UPI homologue (C-terminus) | 911 | 1076 | 2975 | 2460 | 195 | 836 |
| X04366_at | Human mRNA for calcium activated neutral protease large subunit "(muCANP," "calpain," EC 3.4.22.17) | 188 | 137 | 301 | 460 | 260 | 118 |
| X04412_at | Human mRNA for lymphocyte glycoprotein T1/Leu-1 | 20 | 20 | 49 | 24 | 60 | 73 |
| X04434_at | Human mRNA for plasma gelsolin | 746 | 246 | 81 | 68 | 20 | 62 |
| X04445_ma1_s_at | Human mRNA for insulin-like growth factor I receptor | 20 | 20 | 55 | 53 | 20 | 20 |
| X04500_at | H. sapiens inhA gene exon 1 (and joined CDS) | 20 | 20 | 20 | 62 | 20 | 20 |
| X04470_s_at | Human mRNA for antileuioprotease (ALP) from cervix uterus | 1525 | 396 | 57 | 20 | 171 | 100 |
| X04500_at | Human gene for prointerleukin 1 beta | 147 | 20 | 46 | 43 | 20 | 30 |
| X04526_at | Human live mRNA for beta-subunit signal transducing proteins Gs/Gi (beta-G) | 185 | 305 | 657 | 499 | 334 | 296 |
| X04571_at | Human mRNA for kidney epidermal growth factor (EGF) precursor | 23 | 20 | 20 | 20 | 20 | 41 |
| X04602_s_at | Human mRNA for interleukin BSF-2 (B-cell differentiation factor) | 141 | 20 | 20 | 20 | 260 | 118 |
| X04654_s_at | Human mRNA for U1 RNA-associated 70K protein | 68 | 488 | 523 | 471 | 393 | 551 |
| X04688_at | Human mRNA for T-cell replacing factor (interleukin-5) | 20 | 20 | 81 | 68 | 20 | 40 |
| X04706_s_at | Human homeobox gene (clone HHO.c13) | 20 | 20 | 55 | 53 | 20 | 20 |
| X04707_at | Human c-erb-A mRNA for thyroid hormone receptor | 20 | 48 | 37 | 20 | 35 | 42 |
| X04729_s_at | Human mRNA for plasminogen activator inhibitor type 1 N-terminus. /gb=X04729 /ntype=RNA | 23 | 20 | 112 | 21 | 229 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| X04741_at | Human mRNA for protein gene product (PGP) 9.5 | 20 | 20 | 20 | 20 | 20 | 20 | 20 |
| X04828_at | Human mRNA for G(i) protein alpha-subunit (adenylate cyclase inhibiting GTP-binding protein) | 57 | 84 | 184 | 130 | 20 | 20 | 265 |
| X04898_ma1_at | Human gene for apolipoprotein AII. | 20 | 20 | 20 | 20 | 20 | 20 | 20 |
| X05130_s_at | Human mRNA for prolyl 4-hydroxylase beta subunit (EC 1.13.11.2) "(procollagen-L-proline," "2-oxoglutarate:oxygen" "oxidoreductase," 4-hy | 484 | 247 | 802 | 1147 | 20 | 20 | 420 |
| X05153_ma1_at | Human alpha-lactalbumin gene. | 20 | 45 | 20 | 20 | 20 | 20 | 20 |
| X05196_at | Human aldolase C gene | 107 | 100 | 157 | 210 | 148 | 20 | 157 |
| X05232_at | Human mRNA for stromelysin | 20 | 20 | 20 | 20 | 20 | 20 | 20 |
| X05246_at | Human testis-specific PGK-2 gene for phosphoglycerate kinase (ATP:3-phospho-D-glycerate "1-phosphotransferase," EC 2.7.2.3) | 20 | 30 | 20 | 20 | 20 | 20 | 20 |
| X05276_at | Human mRNA for fibroblast tropomyosin TM30 (pI) | 842 | 71 | 200 | 285 | 75 | 20 | 351 |
| X05299_at | Human mRNA (~95%) for major centromere autoantigen CENP-B | 20 | 20 | 20 | 20 | 20 | 20 | 20 |
| X05309_at |  | 20 | 20 | 20 | 20 | 20 | 20 | 20 |
| X05323_at | Human MRC OX-2 gene signal sequence | 24 | 25 | 26 | 20 | 100 | 20 | 38 |
| X05345_at | Human mRNA for histidyl-tRNA synthetase (HRS) | 32 | 48 | 20 | 40 | 57 | 20 | 20 |
| X05360_at | Human CDC2 gene involved in cell cycle control | 20 | 23 | 27 | 37 | 102 | 20 | 91 |
| X05409_at | Human RNA for mitochondrial aldehyde dehydrogenase I ALDH I (EC 1.2.1.3) | 112 | 133 | 37 | 20 | 20 | 20 | 66 |
| X05608_at | Human gene for neurofilament subunit NF-L | 20 | 26 | 20 | 21 | 62 | 20 | 27 |
| X05610_at | Human mRNA for type IV collagen alpha-2 chain | 104 | 126 | 60 | 20 | 61 | 20 | 63 |
| X05615_at | Human mRNA for thyroglobulin | 20 | 20 | 20 | 20 | 20 | 20 | 20 |
| X05839_ma1_s_at | transforming growth factor beta 1 precursor gene extracted from Human transforming growth factor-beta precursor gene exon 1 and 5'flan | 20 | 20 | 20 | 20 | 90 | 20 | 20 |
| X05855_at | Human histone H3.3 gene exon 2 | 148 | 143 | 352 | 437 | 465 | 20 | 184 |
| X05855_s_at | Human mRNA for lipocortin | 3217 | 44 | 34 | 36 | 20 | 20 | 60 |
| X05908_at | Human mRNA for gastric lipase | 20 | 28 | 22 | 20 | 52 | 20 | 61 |
| X05997_at | Human c-kit proto-oncogene mRNA | 38 | 35 | 29 | 78 | 20 | 20 | 73 |
| X06182_s_at | Human mRNA for fibronectin receptor alpha subunit | 66 | 20 | 20 | 20 | 20 | 20 | 20 |
| X06256_at | Human mRNA for pro-alpha 1 (II) collagen 3'end C-term. triple helical and C-terminal non-helical domain | 20 | 20 | 94 | 53 | 353 | 20 | 73 |
| X06268_at | Human mRNA for docking protein (signal recognition particle receptor) | 36 | 58 | 85 | 43 | 20 | 20 | 20 |
| X06272_at | Human mRNA for apolipoprotein(a) | 20 | 34 | 20 | 20 | 20 | 20 | 20 |
| X06290_at | Human mRNA for protein kinase C (PKC) type beta I | 20 | 20 | 20 | 20 | 20 | 20 | 20 |
| X06318_at | Human MRL3 mRNA for ribosomal protein L3 homologue (MRL3 = mammalian ribosome L3) | 96 | 34 | 129 | 108 | 51 | 20 | 108 |
| X06323_at | Human mRNA for synaptophysin (p38) | 20 | 20 | 20 | 20 | 81 | 20 | 20 |
| X06389_at | Human theta 1-globin gene | 20 | 20 | 20 | 20 | 20 | 20 | 20 |
| X06482_at | Human mRNA for growth hormone receptor | 31 | 20 | 65 | 20 | 41 | 20 | 38 |
| X06562_at | Human mRNA for receptor of retinoic acid | 45 | 80 | 65 | 58 | 24 | 20 | 20 |
| X06614_at | Human mRNA for ribosomal protein S11 | 3387 | 5392 | 4444 | 3982 | 2540 | 4027 | 20 |
| X06617_at | Human mRNA for 27-kDa calbindin | 20 | 20 | 21 | 20 | 30 | 31 | 20 |
| X06661_at | Human mRNA 3' region for pro-alpha1(III) collagen | 226 | 124 | 81 | 20 | 56 | 20 | 20 |
| X06700_s_at | Human mRNA for DNA polymerase alpha-subunit | 20 | 20 | 27 | 20 | 46 | 20 | 20 |
| X06745_at | Human mRNA for skeletal beta-tropomyosin | 20 | 20 | 20 | 20 | 20 | 20 | 20 |
| X06825_at | Human mRNA for high affinity IgE receptor alpha-subunit (FcERI) | 40 | 34 | 20 | 20 | 27 | 20 | 63 |
| X06948_at | Human HALPHA44 gene for "alpha-tubulin," exons 3-Jan | 35 | 20 | 20 | 106 | 20 | 20 | 20 |
| X06956_at | Human mRNA for heme oxygenase | 257 | 77 | 100 | 66 | 309 | 20 | 358 |
| X06985_at | Human X chromosome mRNA for CCG1 protein Inv. in cell proliferation | 41 | 78 | 69 | 49 | 63 | 20 | 71 |
| X07024_at | Human mRNA for protein kinase C (PKC) type beta II | 20 | 26 | 48 | 20 | 20 | 20 | 53 |
| X07109_at | Human mRNA for second protein of inter-alpha-trypsin inhibitor complex | 20 | 29 | 36 | 20 | 60 | 20 | 64 |
| X07173_at | Human mRNA for CD20 receptor (S7) | 20 | 105 | 20 | 20 | 20 | 20 | 20 |
| X07203_at | Human HF.12 gene mRNA | 48 | 39 | 102 | 78 | 114 | 20 | 131 |
| X07290_at |  |  |  |  |  |  |  |  |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X07315_at | Human gene for PP15 (placental protein 15) | 38 | 48 | 63 | 79 | 108 | 45 |
| X07384_at | Human mRNA for G1i protein | 20 | 20 | 20 | 23 | 48 | 20 |
| X07438_s_at | Human DNA for cellular retinol binding protein (CRBP) exons 3 and 4 /gb=X07438 /ntype=DNA /annot=exon | 88 | 159 | 60 | 20 | 71 | 87 |
| X07495_at | Human mRNA for cp19 homeobox from HOX-3 locus. | 20 | 20 | 20 | 20 | 20 | 96 |
| X07496_at | Human Tangler apoA-I gene | 20 | 20 | 20 | 20 | 20 | 30 |
| X07618_s_at | Human mRNA for cytochrome P450 db1 variant a | 45 | 72 | 20 | 27 | 377 | 95 |
| X07619_s_at | Human mRNA for cytochrome P450 db1 variant b | 20 | 20 | 20 | 20 | 784 | 147 |
| X07695_at | Human mRNA for cytokeratin 4 C-terminal region | 7458 | 28 | 72 | 34 | 20 | 20 |
| X07696_at | Human mRNA for cytokeratin 15 | 777 | 20 | 492 | 328 | 20 | 20 |
| X07730_at | Human mRNA for prostate specific antigen | 62 | 60 | 20 | 20 | 1221 | 347 |
| X07732_at | Human hepatoma mRNA for serine protease hepsin | 20 | 20 | 20 | 20 | 20 | 20 |
| X07743_at | Human mRNA for pleckstrin (P47) | 68 | 20 | 65 | 46 | 41 | 77 |
| X07767_at | Human mRNA for cAMP-dependent protein kinase catalytic subunit type alpha (EC 2.7.1.37) | 20 | 20 | 73 | 21 | 98 | 56 |
| X07820_at | Human mRNA for metalloproteinase stromelysin-2 | 30 | 24 | 20 | 20 | 81 | 61 |
| X07834_at | Human mRNA for manganese superoxide dismutase (EC 1.15.1.1) | 24 | 20 | 20 | 20 | 20 | 20 |
| X07876_at | Human mRNA for irp protein (int-1 related protein) | 23 | 56 | 71 | 50 | 28 | 20 |
| X07948_at | Human mRNA for transition protein 1 (TP1) | 44 | 20 | 20 | 20 | 81 | 28 |
| X07979_at | Human mRNA for fibronectin receptor beta subunit | 543 | 484 | 832 | 591 | 253 | 275 |
| X07994_at | Human mRNA for lactase-phlorizin hydrolase LPH (EC 3.2.1.23–62) | 20 | 20 | 20 | 20 | 20 | 20 |
| X12433_at | Human pHS1-2 mRNA with ORF homologous to membrane receptor proteins | 70 | 75 | 101 | 85 | 126 | 119 |
| X12447_at | Human aldolase A gene (EC 4.1.2.13) | 1127 | 797 | 1863 | 2864 | 1801 | 1119 |
| X12451_at | Human mRNA for pro-cathepsin L (major excreted protein MEP) | 118 | 135 | 93 | 74 | 194 | 299 |
| X12453_at | Human mRNA for retinal S-antigen (48 KDa protein) | 20 | 20 | 20 | 20 | 20 | 20 |
| X12458_ma1_at | Human P3 gene. | 66 | 65 | 85 | 112 | 217 | 252 |
| X12492_at | Human mRNA for CAAT-box binding transcription factor CTF-1 (syn. CTF/NFI or CTF or NF-I or NF-1) | 150 | 162 | 149 | 131 | 167 | 276 |
| X12517_at | Human mRNA for U1 small nuclear RNP-specific C protein | 20 | 20 | 20 | 20 | 20 | 20 |
| X12530_s_at | Human mRNA for B lymphocyte antigen CD20 "(BI," Bp35) | 23 | 86 | 20 | 20 | 20 | 70 |
| X12556_at | Human mRNA for dbl proto-oncogene | 20 | 20 | 20 | 20 | 20 | 23 |
| X12662_ma1_at | H. sapiens arginase gene exon 1 and flanking regions (EC 3.5.3.1) (and joined CDS). | 20 | 20 | 20 | 20 | 32 | 30 |
| X12671_ma1_at | hnmp a1 protein gene extracted from Human gene for heterogeneous nuclear ribonucleoprotein (hnRNP) core protein A1 | 594 | 917 | 1762 | 1593 | 112 | 384 |
| X12791_at | Human mRNA for 19kD protein of signal recognition particle (SRP) | 146 | 92 | 134 | 110 | 33 | 149 |
| X12794_at | Human v-erbA related ear-2 gene | 157 | 197 | 298 | 395 | 502 | 380 |
| X12876_s_at | | 385 | 745 | 2078 | 2384 | 1014 | 310 |
| X12901_at | Human mRNA for villin | 20 | 20 | 20 | 20 | 38 | 20 |
| X12953_at | Human rab2 "mRNA," YPT1-related and member of ras family | 108 | 69 | 29 | 132 | 20 | 63 |
| X13100_s_at | Human mRNA fragment for myosin heavy chain | 20 | 20 | 20 | 20 | 20 | 20 |
| X13227_at | Human mRNA for D-amino acid oxidase (EC 1.4.3.3) | 41 | 20 | 51 | 36 | 20 | 157 |
| X13238_at | Human mRNA for cytochrome c oxidase subunit VIc | 563 | 339 | 399 | 560 | 286 | 494 |
| X13255_at | Human mRNA for dopamine beta-hydroxylase type a (EC 1.1.4.17.1) | 20 | 20 | 20 | 20 | 42 | 20 |
| X13293_at | Human mRNA for B-myb gene | 20 | 20 | 20 | 20 | 20 | 20 |
| X13334_at | Human CD14 mRNA for myeloid cell-specific leucine-rich glycoprotein | 20 | 20 | 20 | 20 | 20 | 407 |
| X13444_at | Human mRNA for CD8 beta-chain glycoprotein (CD8 beta 1) | 241 | 152 | 223 | 151 | 246 | 268 |
| X13451_s_at | | 20 | 20 | 20 | 20 | 20 | 20 |
| X13461_s_at | H. sapiens intronless calmodulin-like gene (CLP gene) for mcalmodulin-like protein | 296 | 41 | 74 | 71 | 20 | 68 |
| X13482_at | Human mRNA for U2 snRNP-specific A' protein | 54 | 216 | 271 | 89 | 45 | 38 |
| X13546_ma1_at | Human HMG-17 gene for non-histone chromosomal protein HMG-17. | 222 | 20 | 20 | 254 | 208 | 1126 |
| X13589_at | Human mRNA for aromatase (estrogen synthetase) | 20 | 20 | 20 | 20 | 31 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X13766_s_at | Human beta-casein mRNA 3′-terminal fragment | 20 | 20 | 20 | 20 | 20 | 20 |
| X13794_ma1_at | H. sapiens lactate dehydrogenase B gene exon 1 and 2 (EC 1.1.1.27) (and joined CDS). | 300 | 508 | 961 | 947 | 160 | 232 |
| X13810_s_at | Human OTF-2 mRNA for lymphoid-specific transcription factor | 20 | 273 | 201 | 74 | 1568 | 517 |
| X13839_at | Human mRNA for vascular smooth muscle alpha-actin | 1405 | 801 | 20 | 20 | 43 | 20 |
| X13916_at | Human mRNA for LDL-receptor related protein | 29 | 38 | 35 | 57 | 20 | 20 |
| X13930_f_at | Human CYP2A4 mRNA for P-450 IIA4 protein | 94 | 113 | 253 | 127 | 204 | 158 |
| X13955_s_at | Human mRNA for myosin alkali light chain | 20 | 20 | 20 | 20 | 20 | 20 |
| X13956_at | Human 12S RNA induced by "poly(rI)," poly(rC) and Newcastle disease virus | 26 | 67 | 104 | 41 | 55 | 119 |
| X13967_at | Human mRNA for leukaemia inhibitory factor (LIF/HILDA) | 145 | 80 | 94 | 62 | 268 | 236 |
| X13973_at | Human mRNA for ribonuclease/angiogenin inhibitor (RAI) | 153 | 131 | 173 | 176 | 156 | 204 |
| X14008_ma1_f_at | Human lysozyme gene (EC 3.2.1.17) | 602 | 1072 | 336 | 481 | 553 | 986 |
| X14046_at | Human mRNA for leukocyte antigen CD37 | 43 | 63 | 31 | 20 | 42 | 159 |
| X14085_s_at | H. sapiens mRNA for "beta-1,4-galactosyltransferase" (EC 2.4.1.22) | 112 | 141 | 275 | 192 | 215 | 124 |
| X14253_s_at | Human mRNA for cripto protein | 51 | 33 | 20 | 20 | 175 | 22 |
| X14329_at | Human mRNA for carobxypepidase N small subunit (EC 3.4.17.3) | 20 | 61 | 20 | 20 | 81 | 72 |
| X14346_at | Human mRNA for eoisinophil peroxidase | 20 | 20 | 20 | 20 | 20 | 32 |
| X14362_at | Human CR1 mRNA for C3b/C4b receptor secreted form | 20 | 20 | 20 | 20 | 20 | 20 |
| X14445_at | Human int-2 proto-oncogene | 98 | 21 | 20 | 20 | 140 | 83 |
| X14448_at | Human GLA gene for alpha-D-galactosidase A (EC 3.2.1.22) | 123 | 115 | 109 | 97 | 178 | 228 |
| X14474_at | Human mRNA for microtubule-associated tau protein | 20 | 22 | 95 | 20 | 143 | 31 |
| X14675_at | Human bcr-abl mRNA 5′ fragment (clone 3c). /gb=X14675 /ntype=RNA | 130 | 60 | 116 | 85 | 20 | 189 |
| X14684_s_at | H. sapiens mRNA for La protein C-terminal region | 136 | 258 | 469 | 379 | 244 | 172 |
| X14690_s_at | Human mRNA for plasma inter-alpha-trypsin inhibitor heavy chain H(3) | 20 | 20 | 20 | 20 | 20 | 20 |
| X14766_at | Human mRNA for GABA-A "receptor," alpha 1 subunit | 115 | 91 | 226 | 123 | 20 | 56 |
| X14767_at | Human mRNA for GABA-A "mreceptor," beta 1 subunit | 30 | 20 | 20 | 20 | 180 | 20 |
| X14787_at | Human mRNA for thrombospondin | 155 | 20 | 23 | 20 | 20 | 23 |
| X14789_at | H. sapiens alpha-A crystallin gene exon "1,2" and pseudoexon | 30 | 20 | 44 | 20 | 20 | 20 |
| X14813_at | Human liver mRNA for 3-oxoacyl-CoA thiolase | 60 | 32 | 91 | 114 | 61 | 219 |
| X14830_at | Human mRNA for muscle acetylcholine receptor beta-subunit | 58 | 45 | 46 | 24 | 75 | 161 |
| X14850_at | Human H2A.X mRNA encoding histone H2A.X | 54 | 44 | 87 | 99 | 47 | 165 |
| X14885_ma1_s_at | H. sapiens gene for transforming growth factor-beta 3 (TGF-beta 3) exon 1 (and joined CDS) | 20 | 20 | 20 | 20 | 20 | 20 |
| X14894_at | Human mRNA for myogenic factor Myf-5 | 20 | 20 | 20 | 20 | 20 | 20 |
| X14968_at | Human testis mRNA for the RII-alpha subunit of cAMP dependent protein kinase | 20 | 20 | 20 | 20 | 20 | 20 |
| X14975_at | Human CDI R2 gene for MHC-related antigen | 20 | 21 | 20 | 20 | 20 | 27 |
| X15088_at | Human GNAT1 mRNA for transducin alpha-chain | 20 | 20 | 20 | 20 | 20 | 20 |
| X15183_at | Human mRNA for 90-kDa heat-shock protein | 919 | 1273 | 1901 | 1791 | 586 | 1790 |
| X15187_at | Human tra1 mRNA for human homologue of murine tumor rejection antigen gp96 | 199 | 106 | 307 | 246 | 139 | 172 |
| X15217_at | Human sno oncogene mRNA for snoA "protein," ski-related | 20 | 20 | 20 | 20 | 20 | 20 |
| X15218_at | Human ski oncogene mRNA | 20 | 20 | 20 | 20 | 20 | 20 |
| X15306_ma1_at | H. sapiens NF-H gene, exon 1 (and joined CDS) | 20 | 25 | 28 | 23 | 38 | 20 |
| X15331_s_at | Human mRNA for phosphoribosylpyrophosphate synthetase subunit one | 20 | 20 | 20 | 20 | 70 | 112 |
| X15341_at | Human COX VIa-L mRNA for cytochrome c oxidase liver-specific subunit VIa (EC 1.9.3.1) | 1338 | 1071 | 1351 | 1611 | 109 | 1377 |
| X15357_at | Human mNA for natriuretic peptide receptor (ANP-A receptor) | 20 | 20 | 38 | 52 | 944 | 108 |
| X15376_at | Human mRNA for GABA-A "receptor," gamma 2 subunit | 90 | 83 | 92 | 73 | 31 | 104 |
| X15393_ma1_at | H. sapiens motilin gene exon 2 (and joined CDS). | 93 | 98 | 138 | 116 | 91 | 223 |
| X15414_at | Human mRNA for aldose reductase (EC 1.1.1.2) | 110 | 174 | 93 | 249 | 254 | 254 |
| X15422_at | Human mRNA for mannose-binding protein C | 20 | 20 | 20 | 20 | 383 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X15525_ma1_at | H. sapiens lyosomal acid phosphatase gene (EC 3.1.3.2) Exon 1 (and joined CDS) | 25 | 54 | 59 | 22 | 31 | 53 |
| X15573_at | Human liver-type 1-phosphofructokinase (PFKL) "mRNA," complete cds | 20 | 20 | 20 | 31 | 20 | 20 |
| X15673_s_at | Human pTR2 mRNA for repetitive sequence. /gb=X15673 /ntype=RNA | 66 | 108 | 246 | 124 | 262 | 137 |
| X15675_at | Human pTR7 mRNA for repetitive sequence. /gb=X15675 /ntype=RNA | 20 | 20 | 20 | 20 | 136 | 20 |
| X15722_at | Human mRNA for glutathione reductase (EC 1.6.4.2) | 20 | 20 | 20 | 20 | 20 | 20 |
| X15729_s_at | Human mRNA for nuclear p68 protein | 305 | 295 | 511 | 489 | 201 | 262 |
| X15822_at | Human COX VIIa-L mRNA for liver-specific cytochrome c oxidase (EC 1.9.3.1.) | 760 | 830 | 710 | 834 | 439 | 1003 |
| X15875_at | Human mRNA for cAMP response element (CRE-BP1) binding protein | 62 | 35 | 64 | 58 | 123 | 78 |
| X15880_at | Human mRNA for collagen VI alpha-1 C-terminal globular domain | 429 | 267 | 136 | 92 | 221 | 181 |
| X15882_at | Human mRNA for collagen VI alpha-2 C-terminal globular domain | 314 | 68 | 31 | 20 | 52 | 30 |
| X15940_at | Human mRNA form ribsosomal protein L31 | 3375 | 5994 | 4331 | 4748 | 2189 | 4097 |
| X15943_at | Human calcitonin/alpha-C GRP gene | 20 | 20 | 20 | 60 | 20 | 20 |
| X15949_at | Human mRNA for interferon regulatory factor-2 (IRF-2) | 21 | 33 | 52 | 20 | 22 | 49 |
| X15954_ma1_s_at | H. sapiens MBP1 "gene," exon 1 (and joined CDS) | 20 | 20 | 20 | 20 | 20 | 20 |
| X16064_at | Human mRNA for translationally controlled tumor protein | 4572 | 3795 | 3961 | 4448 | 1971 | 2255 |
| X16105_at | Human mRNA for RD "protein," RNA-binding | 81 | 99 | 118 | 108 | 20 | 54 |
| X16135_at | Human mRNA for novel heterogeneous nuclear RNP "protein," L protein | 242 | 326 | 388 | 317 | 481 | 477 |
| X16260_s_at | Human mRNA for inter-alpha-trypsin inhibitor subunit 3 | 20 | 20 | 20 | 20 | 20 | 20 |
| X16281_at | Human mRNA for zinc finger protein (clone 431) | 20 | 20 | 20 | 20 | 73 | 20 |
| X16282_at | Human mRNA for zinc finger protein (clone 647) | 20 | 20 | 20 | 20 | 35 | 20 |
| X16316_at | Human mRNA for vav oncogene | 153 | 111 | 179 | 127 | 215 | 315 |
| X16323_at | Human mRNA for hepatocyte growth factor (HGF) | 23 | 20 | 38 | 20 | 159 | 20 |
| X16354_at | Human mRNA for transmembrane carcinoembryonic antigen BGPa (formerly TM1-CEA) | 60 | 29 | 34 | 41 | 21 | 84 |
| X16396_at | Human mRNA for NAD-dependent methylene tetrahydrofolate dehydrogenase cyclohydrolase (EC 1.5.1.15) | 49 | 20 | 20 | 20 | 20 | 26 |
| X16416_at | Human c-abl mRNA encoding p150 protein | 102 | 51 | 96 | 66 | 106 | 163 |
| X16504_s_at |  | 20 | 20 | 20 | 20 | 20 | 20 |
| X16546_at | Human DNA for eosinophil derived neurotoxin | 20 | 20 | 20 | 20 | 37 | 20 |
| X16560_at | Human COX VIIc gene for subunit VIIc of cytochrome c oxidase (EC 1.9.3.1) | 858 | 983 | 844 | 956 | 497 | 737 |
| X16609_s_at | Human mRNA for ankyrin (variant 2.1) | 20 | 20 | 20 | 20 | 154 | 22 |
| X16660_cds1_s_at | open reading frame p15 (AA 1–138) gene extracted from Human HTlV-I related endogenous retroviral sequence (HRES-1/1) | 20 | 20 | 20 | 20 | 20 | 20 |
| X16662_at | Human mRNA for vascular anticoagulant-beta (VAC-beta) | 355 | 285 | 317 | 243 | 118 | 545 |
| X16663_at | Human HS1 gene for heamatopoietic lineage cell specific protein | 38 | 46 | 71 | 23 | 25 | 53 |
| X16665_at | Human HOX2H mRNA from the Hox2 locus | 22 | 71 | 120 | 94 | 140 | 141 |
| X16666_s_at |  | 20 | 20 | 20 | 20 | 20 | 20 |
| X16687_at | Human HOX2G mRNA from the Hox2 locus | 77 | 86 | 136 | 104 | 141 | 230 |
| X16699_at | HumanmRNA for cytochrome P-450HP | 20 | 20 | 20 | 20 | 20 | 20 |
| X16706_at | Human fra-2 mRNA | 20 | 20 | 55 | 70 | 20 | 20 |
| X16707_at | Human fra-1 mRNA | 20 | 20 | 20 | 20 | 20 | 20 |
| X16832_at | Human mRNA for cathepsin H (EC 3.4.22.16) | 661 | 971 | 1219 | 1555 | 596 | 566 |
| X16866_at | Human mRNA for cytochrome P-450IID (clone pMP33) | 20 | 20 | 20 | 20 | 20 | 20 |
| X16901_at | Human mRNA for RAP30 subunit of transcription initiation factor RAP 30/74 | 20 | 20 | 20 | 20 | 20 | 48 |
| X16983_at | Human mRNA for integrin alpha-4 subunit | 20 | 20 | 20 | 20 | 20 | 20 |
| X17025_at | Human homolog of yeast IPP isomerase | 35 | 71 | 317 | 23 | 118 | 545 |
| X17042_at | Human mRNA for hematopoetic proteglycan core protein | 314 | 280 | 111 | 35 | 114 | 386 |
| X17059_s_at | Human NAT1 gene for arylamine N-acetyltransferase | 20 | 29 | 20 | 24 | 54 | 20 |
| X17093_at | Human HLA-F gene for human leukocyte antigen F | 435 | 2844 | 1104 | 565 | 338 | 963 |
| X17094_at | Human fur mRNA for furin | 20 | 20 | 41 | 52 | 31 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X17098_at | Human PSG10 mRNA for pregnancy specific glycoprotein 10 | 20 | 20 | 20 | 20 | 74 | 20 |
| X17206_at | Human mRNA for LLRep3 | 4928 | 4634 | 6071 | 5895 | 2199 | 4017 |
| X17254_at | Human mRNA for the transcription factor Eryf1 | 20 | 20 | 20 | 24 | 20 | 20 |
| X17360_ma1_at | Human HOX 5.1 gene for HOX 5.1 protein | 20 | 20 | 20 | 20 | 20 | 20 |
| X17567_s_at | H. sapiens RNA for snRNP protein B | 206 | 261 | 636 | 558 | 467 | 391 |
| X17576_at | Human melanoma mRNA for nck "protein," showing homology to src | 49 | 20 | 25 | 20 | 20 | 26 |
| X17620_at | Human mRNA for Nm23 "protein," involved in developmental regulation (homolog to Drosophila Awd protein) | 139 | 178 | 195 | 200 | 248 | 269 |
| X17622_at | Human HBK2 mRNA for potassium channel protein | 36 | 20 | 37 | 27 | 80 | 20 |
| X17644_s_at | Human GST1-Hs mRNA for GTP-binding protein | 22 | 20 | 20 | 91 | 20 | 27 |
| X17648_at | Human mRNA for granulocyte-macrophage colony-stimulating factor receptor (hGM-CSF-R) | 33 | 25 | 36 | 20 | 98 | 67 |
| X17651_at | Human Myf-4 mRNA for myogenic determination factor | 61 | 35 | 54 | 55 | 128 | 113 |
| X17345_at | Human jun-B mRNA for Jun-B protein | 1446 | 1817 | 1394 | 1497 | 502 | 609 |
| X51362_s_at | Human mRNA for dopamine D2 receptor | 40 | 123 | 186 | 115 | 218 | 103 |
| X51405_at | Human mRNA for carboxypeptidase E (EC 3.4.17.10) | 28 | 20 | 20 | 20 | 20 | 20 |
| X51408_at | Human mRNA for n-chimaerin | 24 | 32 | 37 | 20 | 26 | 80 |
| X51417_at | Human mRNA for steroid hormone receptor hERR2 | 20 | 20 | 20 | 20 | 31 | 20 |
| X51420_at | Human mRNA for tyrosinase-related protein | 20 | 20 | 20 | 20 | 20 | 20 |
| X51435_s_at | Human pRDII-BF1 gene for a DNA-binding protein | 30 | 53 | 73 | 26 | 32 | 22 |
| X51441_at | | 31 | 71 | 34 | 25 | 237 | 20 |
| X51441_s_at | Human mRNA for serum amyloid A (SAA) protein "partial," clone pAS3-alpha | 20 | 50 | 20 | 20 | 20 | 33 |
| X51466_at | Human mRNA for elongation factor 2 | 1116 | 758 | 1732 | 1754 | 354 | 608 |
| X51521_at | Human mRNA for ezrin | 376 | 485 | 621 | 425 | 337 | 501 |
| X51602_at | Human fit mRNA for receptor-related tyrosine kinase | 20 | 20 | 20 | 20 | 20 | 20 |
| X51630_at | Human Wilms tumor WT1 mRNA for zinc finger "protein," Krueppel-like | 20 | 20 | 22 | 20 | 20 | 20 |
| X51688_at | Human mRNA for cyclin A | 30 | 20 | 20 | 20 | 30 | 20 |
| X51698_s_at | H. sapiens spasmoytic polypeptide (SP) mRNA | 20 | 20 | 87 | 66 | 50 | 39 |
| X51730_at | Human mRNA and promoter DNA for prostesterone receptor | 20 | 20 | 20 | 20 | 20 | 20 |
| X51755_cds5_s_at | Ig "light-chain," partial Ke-Oz- polypeptide; Author-given protein sequence is in conflict with the conceptual translation gene extracted from | 20 | 20 | 20 | 20 | 59 | 33 |
| X51757_at | Human teat-shock protein HSP70B' gene | 20 | 20 | 20 | 20 | 116 | 26 |
| X51801_at | Human OP-1 mRNA for osteogenic protein | 20 | 68 | 20 | 52 | 20 | 20 |
| X51804_at | Human PMI gene for a putative receptor protein | 42 | 20 | 37 | 24 | 49 | 26 |
| X51823_at | | 20 | 20 | 32 | 20 | 20 | 66 |
| X51823_s_at | Human mRNA for B-subunit of coagulation factor XIII (VXIIIB) (partial). /gb=X51823 /ntype=RNA | 20 | 20 | 20 | 20 | 20 | 20 |
| X51952_xpt1_at | Human UCP gene for uncoupling protein exons 1 and 2. | 139 | 20 | 20 | 20 | 20 | 20 |
| X51953_at | Human UCP gene for uncoupling protein exons 3 and 4 /gb=X51953 /ntype=DNA /annot=exon | 20 | 20 | 20 | 20 | 20 | 20 |
| X51954_at | Human UCP gene for uncoupling protein exon 5 /gb=X51954 /ntype=DNA /annot=exon | 20 | 20 | 24 | 20 | 20 | 20 |
| X51956_ma1_at | Human ENO2 gene for neuron specific (gamma) encolase. | 20 | 23 | 54 | 66 | 50 | 39 |
| X51985_at | Human LAG-3 mRNA for CD4-related protein involved in lymphocyte activation | 20 | 20 | 20 | 20 | 20 | 20 |
| X52001_at | H. sapiens endothelin 3 mRNA | 20 | 20 | 20 | 20 | 20 | 38 |
| X52003_at | H. sapiens pS2 protein gene | 321 | 63 | 1845 | 71 | 20 | 46 |
| X52005_at | H. sapiens skeletal embryonic myosin light chain 1 (MLC1) mRNA | 20 | 20 | 30 | 20 | 34 | 20 |
| X52008_at | H. sapiens alpha-2 strychine binding subunit of inhibitory glycine receptor mRNA | 41 | 20 | 20 | 34 | 20 | 20 |
| X52009_s_at | | 20 | 20 | 20 | 20 | 88 | 39 |
| X52011_at | H. sapiens MYF6 gene encoding a muscle determination factor | 24 | 23 | 54 | 20 | 86 | 20 |
| X52022_at | H. sapiens RNA for type VI collagen alpha3 chain | 231 | 138 | 20 | 20 | 20 | 20 |
| X52056_at | Human mRNA for spi-1 proto-oncogene | 20 | 20 | 20 | 20 | 20 | 20 |
| X52075_ma1_at | Human gene for sialophorin (CD43) | 20 | 20 | 20 | 20 | 44 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| X52142_at | Human mRNA for CTP synthetase (EC 6.3.4.2) | 20 | 20 | 20 | 23 | 20 | 20 | 33 |
| X52151_at | Homo sapiens arylsulphatase A "mRNA," complete cds | 96 | 27 | 90 | 84 | 117 | 135 | 135 |
| X52192_at | H. sapiens RNA for c-fes | 101 | 104 | 164 | 115 | 219 | 210 | 210 |
| X52213_s_at | H. sapiens ltk mRNA | 20 | 20 | 20 | 20 | 20 | 20 | 20 |
| X52221_at | H. sapiens ERCC2 "gene," exons 1 & 2 (partial) | 20 | 20 | 20 | 30 | 37 | 62 | 62 |
| X52228_at | Human mRNA for secreted epithelial tumour mucin antigen | 20 | 20 | 20 | 20 | 20 | 20 | 20 |
| X52282_s_at | Human mRNA for atrial natriuretic peptide clearance receptor (ANP-C receptor) | 20 | 20 | 20 | 20 | 20 | 20 | 179 |
| X52425_at | Human IL-4-R mRNA for the interleukin 4 receptor | 91 | 73 | 124 | 103 | 255 | 179 | 179 |
| X52426_s_at | H. sapiens mRNA for cytokeratin 13 | 13355 | 5075 | 5448 | 3230 | 340 | 850 | 850 |
| X52479_at | Human PKC alpha mRNA for protein kinase C alpha | 48 | 31 | 59 | 39 | 20 | 52 | 52 |
| X52520_at | Human mRNA for tyrosine aminotransferase (TAT) (EC 2.6.1.5) | 41 | 20 | 31 | 20 | 29 | 20 | 20 |
| X52541_at | Human mRNA for early growth response protein 1 (hEGR1) | 160 | 39 | 20 | 20 | 20 | 50 | 50 |
| X52599_at | Human mRNA for beta nerve growth factor | 20 | 20 | 20 | 20 | 20 | 20 | 20 |
| X52611_s_at | Human mRNA for transcription factor AP-2 | 20 | 25 | 20 | 20 | 20 | 41 | 41 |
| X52638_at | Human mRNA for "6-phosphofructo-2-kinase/fructose-2,6-bisphosphatase" (EC "2.7.1.105," EC 3.1.46) | 26 | 51 | 65 | 49 | 20 | 20 | 20 |
| X52730_ma1_at | Human gene for phenylethanolamine N-methylase (PNMT) (EC 2.1.1.28). | 222 | 192 | 242 | 196 | 157 | 257 | 257 |
| X52773_at | Human mRNA for retinoic acid receptor-like protein | 20 | 20 | 20 | 20 | 20 | 20 | 20 |
| X52851_ma1_at | Human cyclophilin gene for cyclophilin (EC 5.2.1.8). | 1727 | 1384 | 1492 | 1802 | 1382 | 1695 | 1695 |
| X52882_at | Human t-complex polypeptide 1 gene | 127 | 66 | 204 | 258 | 68 | 241 | 241 |
| X52889_at | Human gene for cardiac beta myosin heavy chain | 20 | 77 | 132 | 24 | 678 | 217 | 217 |
| X52896_s_at | H. sapiens RNA for dermal fibroblast elastin | 21 | 20 | 20 | 20 | 263 | 142 | 142 |
| X52943_at | Human mRNA for ATF-a transcription factor | 43 | 73 | 71 | 57 | 136 | 89 | 89 |
| X52947_at | Human mRNA for cardiac gap junction protein | 188 | 39 | 50 | 79 | 113 | 31 | 31 |
| X52966_at | Human mRNA for ribosomal protein L35a | 1361 | 1485 | 1662 | 1388 | 359 | 1319 | 1319 |
| X52979_ma1_s_at | SmB protein gene extracted from Human gene for small nuclear ribonucleoproteins SmB and SmB' | 209 | 218 | 528 | 408 | 379 | 410 | 410 |
| X53002_s_at | Human mRNA for integrin beta-5 subunit | 59 | 20 | 102 | 52 | 56 | 59 | 59 |
| X53065_f_at | Human SPR2-1 gene for small proline rich protein (exon 2) | 4285 | 20 | 55 | 59 | 145 | 109 | 109 |
| X53296_s_at | H. sapiens mRNA for IRAP 1652 | 217 | 219 | 237 | 20 | 144 | 20 | 20 |
| X53331_at | Human mRNA for matrix Gla protein | 1079 | 293 | 82 | 72 | 375 | 179 | 179 |
| X53390_s_at | Human mRNA for upstream binding factor (hUBF) | 20 | 143 | 167 | 140 | 265 | 144 | 144 |
| X53414_at | Human mRNA for peroxisomal L-alanine: glyoxylate aminotransferase | 221 | 100 | 52 | 38 | 75 | 20 | 20 |
| X53416_at | Human mRNA for actin-binding protein (filamin) (ABP-280) | 158 | 90 | 55 | 33 | 20 | 60 | 60 |
| X53586_ma1_at | Human mRNA for integrin alpha 6. | 57 | 43 | 153 | 97 | 20 | 28 | 28 |
| X53587_at | Human mRNA for integrin beta 4 | 20 | 30 | 274 | 329 | 40 | 34 | 34 |
| X53595_s_at | Human mRNA for beta-2-glycoprotein I (apolipoprotein H) | 20 | 73 | 75 | 20 | 20 | 48 | 48 |
| X53683_at | Human LAG-1 mRNA | 20 | 20 | 20 | 20 | 31 | 48 | 48 |
| X53742_at | H. sapiens mRNA for fibulin-1 B | 20 | 20 | 20 | 20 | 20 | 20 | 20 |
| X53777_at | Human L23 mRNA for putative ribosomal protein | 1915 | 2851 | 2260 | 2066 | 302 | 1098 | 1098 |
| X53793_at | H. sapiens ADE2H1 mRNA showing homologies to SAICAR synthetse and AIR carboxylase of the purine pathway (EC "6.3.2.6," EC 4.1. | 39 | 34 | 61 | 41 | 64 | 75 | 75 |
| X53795_at | Human R2 mRNA for an inducible membrane protein | 20 | 85 | 21 | 24 | 96 | 20 | 20 |
| X53800_s_at | Human mRNA for macrophage inflammatory protein-2beta (MIP2beta) | 20 | 20 | 20 | 20 | 20 | 21 | 21 |
| X53961_at | Human mRNA for lactoferrin | 20 | 20 | 20 | 20 | 20 | 20 | 20 |
| X54131_s_at | Human HPTP beta mRNA for protein tyrosine phosphatase beta | 20 | 20 | 20 | 20 | 20 | 20 | 20 |
| X54150_at | Human mRNA for Fc receptor | 20 | 20 | 20 | 20 | 20 | 20 | 20 |
| X54162_s_at | Human mRNA for a 64 Kd autoantigen expressed in thyroid and extra-ocular muscle | 47 | 24 | 20 | 20 | 20 | 34 | 34 |
| X54199_s_at | Human mRNA for GARS-AIRS-GART | 20 | 20 | 20 | 20 | 20 | 20 | 20 |
| X54232_at | Human mRNA for heparan sulfate proteaglycan (glypican) | 131 | 118 | 245 | 235 | 50 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X54304_at | Human mRNA for myosin regulatory light chain | 350 | 187 | 315 | 301 | 132 | 357 |
| X54326_at | H. sapiens mRNA for glutaminyl-tRNA synthetase | 39 | 20 | 31 | 35 | 33 | 20 |
| X54380_at | Human mRNA for pregnancy zine protein | 20 | 20 | 20 | 20 | 20 | 20 |
| X54457_s_at | | 20 | 20 | 20 | 20 | 20 | 20 |
| X54489_ma1_at | Human gene for melanoma growth stimulatory activity (MGSA) | 43 | 85 | 20 | 20 | 20 | 23 |
| X54637_at | Human tyk2 mRNA for non-receptor protein tyrosine kinase | 20 | 20 | 53 | 55 | 98 | 91 |
| X54667_at | | 27 | 29 | 204 | 75 | 20 | 20 |
| X54667_s_at | H. sapiens mRNA for cystatin S | 110 | 129 | 299 | 153 | 320 | 135 |
| X54673_at | H. sapiens GAT1 mRNA for GABA transporter | 20 | 20 | 20 | 20 | 20 | 20 |
| X54741_at | Human CYPXIB2 gene for aldosterone synthase | 20 | 20 | 20 | 20 | 20 | 20 |
| X54816_at | Human gene for "alpha-1-microblobulin-bikunin," exns 5-Jan (encoding "alpha-1-microglobulin," N-terminus.) | 20 | 20 | 20 | 20 | 45 | 20 |
| X54867_s_at | Human mRNA for NKG2-A gene | 56 | 34 | 34 | 29 | 20 | 42 |
| X54870_at | Human mRNA for NKG2-D gene | 20 | 20 | 26 | 20 | 20 | 20 |
| X54871_at | H. sapiens mRNA for ras-related protein Rab5b | 20 | 33 | 23 | 131 | 20 | 33 |
| X54925_at | H. sapiens mRNA for type I interstitial collagenase | 20 | 20 | 25 | 34 | 90 | 51 |
| X54936_at | H. sapiens mRNA for placenta growth factor (PlGF) | 45 | 29 | 59 | 50 | 122 | 70 |
| X54938_at | Human mRNA for inositol "1,4,5-triphosphate" 3-kinase | 46 | 55 | 51 | 74 | 77 | 87 |
| X54941_at | H. sapiens ckshs1 mRNA for Cks1 protein homologue | 89 | 26 | 68 | 94 | 135 | 328 |
| X54942_at | H. sapiens ckshs2 mRNA for Cks1 protein homologue | 40 | 34 | 55 | 20 | 144 | 33 |
| X54993_s_at | H. sapiens TFIID mRNA | 80 | 116 | 231 | 147 | 36 | 56 |
| X55005_ma1_at | Human c-erbA-1 mRNA for thyroid hormone receptor alpha | 77 | 89 | 226 | 192 | 296 | 145 |
| X55019_at | | 21 | 201 | 578 | 577 | 619 | 535 |
| X55037_s_at | H. sapiens GATA-3 mRNA | 20 | 68 | 153 | 143 | 48 | 171 |
| X55079_ma1_at | Human lysosomal alpha-glucosidase gene exon 1. | 20 | 20 | 20 | 20 | 29 | 21 |
| X55330_at | H. sapiens mRNA for aspartylglucosaminidase | 70 | 167 | 300 | 274 | 114 | 245 |
| X55448_cds1_s_at | 19-Feb gene (1–19 protein) extracted from H. sapiens G6PD gene for glucose-6-phosphate dehydrogenase | 26 | 20 | 49 | 53 | 50 | 142 |
| X55448_cds2_at | H. sapiens G6PD gene for glucose-6-phosphate dehydrogenase. | 59 | 36 | 33 | 25 | 101 | 66 |
| X55544_at | H. sapiens cDNA for TREB protein | 64 | 72 | 130 | 86 | 96 | 112 |
| X55666_at | Human mRNA for proteinase 3 | 20 | 20 | 20 | 20 | 20 | 20 |
| X55715_at | Human Hums3 mRNA for 40S ribosomal protein s3 | 1744 | 1884 | 2479 | 2409 | 1018 | 1040 |
| X55733_at | H. sapiens initiation factor 4B cDNA | 272 | 487 | 392 | 343 | 88 | 156 |
| X55740_at | Human placental cDNA coding for 5'nucleotidase (EC 3.1.3.5) | 20 | 47 | 20 | 20 | 20 | 20 |
| X55777_cds2_at | H. sapiens Mahlavu hepatocellular carcinoma hhc(M) DNA. | 20 | 20 | 20 | 20 | 20 | 20 |
| X55885_at | Human mRNA for a presumptive KDEL receptor | 84 | 129 | 236 | 238 | 286 | 266 |
| X55889_at | Human gene for ciliary neurotrophic "factor;" exon 1 | 21 | 29 | 32 | 27 | 172 | 20 |
| X55954_at | Human mRNA for HI.23 ribosomal protein homologue | 2495 | 3744 | 3023 | 2713 | 1374 | 2177 |
| X55990_ma1_at | Human ECRP gene for eosinophil cationic related protein | 20 | 117 | 308 | 117 | 500 | 20 |
| X55990_ma1_at | Human ECP gene for eosinophil cationic protein | 46 | 20 | 20 | 20 | 249 | 109 |
| X56088_s_at | Human mRNA for cholesterol 7-alpha-hydroxylase | 20 | 20 | 20 | 20 | 20 | 20 |
| X56199_at | Human "XIST," coding sequence a mRNA (locus DXS399E) | 20 | 20 | 20 | 24 | 20 | 21 |
| X56253_ma1_at | Human MPR46 gene for 46kd mannose 6-phosphate receptor. | 191 | 263 | 309 | 295 | 268 | 337 |
| X56411_ma1_at | H. sapiens ADH4 gene for class II alcohol dehydrogenase (pi subunit), exon 1. | 20 | 33 | 20 | 20 | 20 | 20 |
| X56465_at | Human znf6 mRNA for zinc finger transcription factor | 20 | 20 | 20 | 20 | 36 | 20 |
| X56468_at | Human mRNA for 14,3,3 "protein," a protein kinase regulator | 462 | 83 | 278 | 314 | 181 | 315 |
| X56494_at | H. sapiens M gene fro M1-type and M2-type pyruvate kinase | 563 | 527 | 888 | 1290 | 390 | 295 |
| X56654_at | Human DSG1 mRNA for desmoglein type 1 | 20 | 20 | 20 | 20 | 20 | 20 |

TABLE 8-continued

Expressed RNA in Suburothelial connective tissue, Normal urothelium and Transitional cell carcinomas

Figure 2:
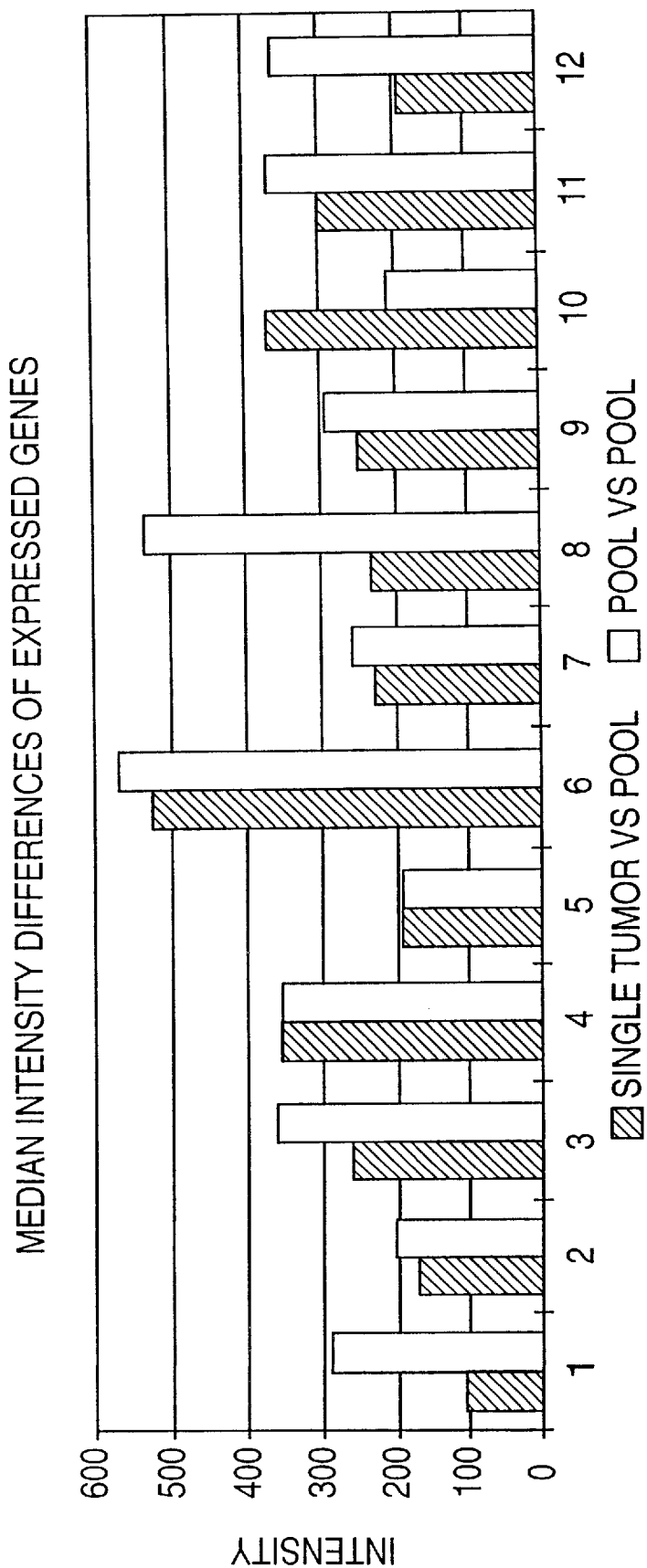
FIG. 2 shows a comparison of intensity differences between a tumor and a pool of tumors of the same stage and grade, and two pools of different stages and grades. The difference is larger between the pools, demonstrating the validity of using expression patterns to determine stage, grade, prognosis, and treatment regimen.

| Gene name | Description | Connect. Tiss. | Norm. uroth. | Ta GrI | TaGrII | T2GrII | T2GrIII | T2GrIV |
|---|---|---|---|---|---|---|---|---|
| X56667_at | Human mRNA for calretinin | 59 | 58 | 44 | 35 | 84 | — | 94 |
| X56677_at | Human MyoD mRNA | 20 | 33 | 25 | 20 | 91 | — | 20 |
| X56681_s_at | Human junD mRNA | 1204 | 766 | 293 | 330 | 285 | — | 287 |
| X56687_s_at | H. sapiens mRNA for autoantigen NOR-90 | 20 | 140 | 20 | 20 | 20 | — | 97 |
| X56692_at | H. sapiens mRNA for C-reactive protein | 20 | 20 | 20 | 20 | 22 | — | 40 |
| X56741_at | H. sapiens mRNA for rab8 gene | 38 | 20 | 50 | 20 | 58 | — | 38 |
| X56807_at | Human DSC2 mRNA for desmocollins type 2a and 2b | 76 | 540 | 371 | 292 | 49 | — | 315 |
| X56841_at | H. sapiens HLA-E gene | 154 | 8427 | 5476 | 5082 | 2195 | — | 4088 |
| X56932_at | H. sapiens mRNA for 23 kD highly basic protein | 4210 | 2279 | 1646 | 1549 | 1034 | — | 1322 |
| X56997_ma1_at | Human UbA52 gene coding for ubiquitin-52 amino acid fusion protein. | 1308 | 20 | 20 | 20 | 20 | — | 20 |
| X57025_at | Human IGF-I mRNA for insuln-like growth factor I | 30 | 103 | 152 | 66 | 329 | — | 116 |
| X57110_s_at | | 32 | 20 | 20 | 20 | 20 | — | 20 |
| X57129_at | H. sapiens H1.2 gene for histone H1 | 20 | 160 | 475 | 414 | 594 | — | 492 |
| X57152_ma1_s_at | Human gene for casecin kinase II subunit beta (EC 2.7.1.37) | 223 | 24 | 30 | 35 | 20 | — | 20 |
| X57206_at | H. sapiens mRNA for 1D-myo-inositol-trisphosphate 3-kinase B isoenzyme | 35 | 20 | 20 | 20 | 26 | — | 277 |
| X57303_at | H. sapiens REC1L mRNA | 34 | 191 | 277 | 259 | 246 | — | 319 |
| X57346_at | H. sapiens mRNA for HS1 protein | 230 | 183 | 109 | 283 | 20 | — | 336 |
| X57348_s_at | H. sapiens mRNA (clone 9112) | 3031 | 369 | 20 | 20 | 395 | — | 2554 |
| X57351_at | | 816 | 4215 | 1088 | 293 | 986 | — | 71 |
| X57351_s_at | Human 1-8D gene from interferon-inducible gene family | 1945 | 138 | 192 | 171 | 165 | — | 170 |
| X57398_at | Human mRNA for pM5 protein | 65 | 85 | 66 | 59 | 20 | — | 20 |
| X57522_at | H. sapiens RING4 cDNA | 65 | 20 | 100 | 81 | 133 | — | 167 |
| X57579_s_at | H. sapiens activin beta-A subunit (exon 2) | 22 | 125 | 105 | 88 | 191 | — | 1889 |
| X57766_at | Human stromelysin-3 mRNA | 88 | 84 | 27 | 20 | 20 | — | 20 |
| X57809_at | | 25 | 629 | 144 | 93 | 240 | — | 476 |
| X57809_s_at | Human rearranged immunoglobulin lambda light chain mRNA | 737 | 20 | 20 | 20 | 34 | — | 63 |
| X57830_at | H. sapiens serotonin 5-HT2 receptor mRNA | 20 | 1125 | 1288 | 1615 | 287 | — | 205 |
| X57959_at | H. sapiens mRNA for ribosomal protein L7 | 1426 | 20 | 20 | 30 | 20 | — | 20 |
| X57985_ma2_at | GL105 gene (histone H2B) extracted from H. sapiens genes for histones H2B.1 and H2A | 21 | 20 | 20 | 20 | 20 | — | 20 |
| X58022_at | Human mRNA for corticotropin-releasing factor binding protein (CRF-BP) | 20 | 373 | 1167 | 676 | 20 | — | 130 |
| X58072_at | Human hGATA3 mRNA for trans-acting T-cell specific transcription factor | 20 | 32 | 22 | 24 | 20 | — | 20 |
| X58079_at | Human mRNA for S100 alpha protein | 42 | 81 | 193 | 121 | 839 | — | 82 |
| X58199_s_at | Human mRNA for beta adducin | 43 | 20 | 20 | 20 | 25 | — | 20 |
| X58234_at | Human mRNA for anti-lectin antibody epitope (clone p36/8-5) | 20 | 69 | 33 | 20 | 116 | — | 20 |
| X58255_at | H. sapiens FIG. 2 gene for fibroblast growth factor receptor | 20 | 20 | 50 | 30 | 78 | — | 20 |
| X58288_at | H. sapiens hR-PRPu gene for protein tyrosine phosphatase | 20 | 20 | 20 | 20 | 77 | — | 20 |
| X58298_s_at | Human mRNA for interleukin-6-receptor | 20 | 35 | 20 | 20 | 26 | — | 20 |
| X58377_at | Human mRNA for adipogenesis inhibitory factor | 20 | 20 | 20 | 20 | 116 | — | 20 |
| X58399_at | | 20 | 20 | 20 | 20 | 20 | — | 190 |
| X58401_at | HOX 2.2 gene extracted from Human Hox2.2 gene for a homeobox protein | 50 | 124 | 174 | 190 | 251 | — | 128 |
| X58431_ma2_s_at | Human mRNA for p62 nucleoporin | 68 | 86 | 57 | 63 | 307 | — | 83 |
| X58521_at | Human PMP70 mRNA for a peroxisomal membrane protein | 99 | 54 | 94 | 184 | 84 | — | 20 |
| X58528_s_at | Human rearranged immunoglobulin mRNA for mu heavy chain enhancer and constant region | 20 | 56 | 20 | 20 | 20 | — | 20 |
| X58529_at | Human MDR1 (multidrug resistance) gene for P-glycoprotein | 27 | 24 | 24 | 20 | 20 | — | 62 |
| X58723_at | Human IFN-omega 1 gene for interferon-omega 1 | 20 | 37 | 20 | 20 | 147 | — | 21 |
| X58822_ma1_s_at | H. sapiens gene for MHC class II regulatory factor RFX | 20 | 20 | 20 | 20 | 20 | — | 20 |
| X58964_at | | | | | | | | |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X58987_at | Human mRNA for D-1 dopamine receptor | 20 | 20 | 20 | 20 | 20 | 20 |
| X59065_at | H. sapiens FGF "gene," exone 3 | 20 | 20 | 20 | 20 | 20 | 20 |
| X59131_at | H. sapiens D13S106 mRNA for a highly charged amino acid sequence | 20 | 20 | 20 | 20 | 20 | 20 |
| X59244_f_at | Human ZNF43 mRNA | 39 | 47 | 133 | 86 | 148 | 86 |
| X59303_s_at | Human G7a mRNA for valyl-tRNA synthetase | 20 | 20 | 124 | 56 | 20 | 20 |
| X59350_s_at | H. sapiens mRNA for B cell membrane protein CD22 | 20 | 20 | 28 | 20 | 39 | 20 |
| X59372_at | Human HOX4C mRNA for a homeobox protein | 20 | 46 | 20 | 20 | 20 | 20 |
| X59373_at | Human HOX4D mRNA for a homeobox protein | 44 | 20 | 29 | 40 | 109 | 79 |
| X59405_at | H. sapiens, gene for Membrane cofactor protein | 61 | 109 | 332 | 263 | 45 | 82 |
| X59417_at | H. sapiens PROS-27 mRNA | 231 | 327 | 285 | 295 | 96 | 296 |
| X59434_at | Human rohu mRNA for rhodanese | 100 | 172 | 119 | 130 | 96 | 59 |
| X59543_at | Human mRNA for M1 subunit of ribonucleotide reductase | 42 | 29 | 37 | 30 | 20 | 20 |
| X59618_at | H. sapiens RR2 mRNA for small subunit ribonucleotide reductase | 20 | 20 | 20 | 20 | 20 | 20 |
| X59656_at | H. sapiens crk-like gene CRKL | 20 | 20 | 20 | 20 | 20 | 20 |
| X59710_at | H. sapiens mRNA for CAAT-box DNA binding protein subunit B (NF-YB) | 20 | 20 | 20 | 20 | 21 | 21 |
| X59711_at | H. sapiens mRNA for CAAT-box DNA binding protein subunit A | 20 | 20 | 20 | 34 | 34 | 60 |
| X59727_at | H. sapiens 63 kDa protein kinase related to rat ERK3 | 20 | 23 | 20 | 20 | 33 | 44 |
| X59739_at | Human ZFX mRNA for put. transcription "activator," isoform 2 | 20 | 20 | 76 | 30 | 84 | 44 |
| X59766_at | H. sapiens mRNA for Zn-alpha2-glycoprotein | 20 | 47 | 72 | 47 | 110 | 69 |
| X59770_at | H. sapiens IL-1R2 mRNA for type II interleukin-1 "receptor," (cell line CB23) | 68 | 44 | 30 | 30 | 126 | 145 |
| X59798_at | Human PRAD1 mRNA for cyclin | 63 | 37 | 324 | 436 | 20 | 22 |
| X59812_at | H. sapiens CYP 27 mRNA for vitamin D3 25-hydroxylase | 20 | 20 | 76 | 20 | 20 | 20 |
| X59834_at | Human rearranged mRNA for glutamine synthase | 482 | 128 | 263 | 252 | 86 | 275 |
| X59841_at | Human PBX3 mRNA | 42 | 208 | 68 | 37 | 30 | 146 |
| X59842_ma1_s_at | Human PBX2 mRNA | 20 | 48 | 262 | 85 | 238 | 171 |
| X59871_at | Human TCF-1 mRNA for T cell factor 1 (splice form C) | 20 | 87 | 20 | 20 | 20 | 26 |
| X59892_at | H. sapiens mRNA for IFN-inducible gamma2 protein | 366 | 20 | 293 | 174 | 324 | 445 |
| X59932_s_at | Human mRNA for C-SRC-kinase | 20 | 338 | 201 | 32 | 110 | 203 |
| X60003_s_at | Human delta CREB mRNA for cAMP-responsive element (CRE) binding protein | 72 | 109 | 105 | 78 | 211 | 134 |
| X60036_at | H. sapiens mRNA for mitochondrial phosphate carrier protein | 376 | 74 | 584 | 539 | 115 | 243 |
| X60104_s_at | H. sapiens mRNA for zinc finger protein | 20 | 196 | 20 | 20 | 175 | 99 |
| X60188_at | Human ERK1 mRNA for protein serine/threonine kinase | 158 | 20 | 109 | 83 | 20 | 20 |
| X60221_at | H. sapiens mRNA for H+-ATP synthase subunit b | 329 | 94 | 333 | 307 | 309 | 328 |
| X60299_s_at | H. sapiens KALIG-1 mRNA for neural cell adhesion and axonal path-finding molecule homologue | 34 | 278 | 72 | 37 | 241 | 20 |
| X60382_ma1_at | H. sapiens COL10A1 gene for collagen (alpha-1 type X). | 34 | 31 | 20 | 20 | 43 | 20 |
| X60483_at | H. sapiens H4/d gene for H4 histone | 20 | 20 | 20 | 20 | 20 | 20 |
| X60484_at | H. sapiens H4/e gene for H4 histone | 20 | 20 | 20 | 20 | 20 | 20 |
| X60486_at | H. sapiens H4/g gene for H4 histone | 20 | 20 | 20 | 20 | 20 | 20 |
| X60487_at | H. sapiens H4/h gene for H4 histone | 20 | 20 | 20 | 20 | 163 | 23 |
| X60489_at | Human mRNA for elongation factor-1-beta | 1169 | 996 | 1042 | 949 | 285 | 503 |
| X60592_at | Human CD240 mRNA for nerve growth factor receptor -related B-lymphocyte activation molecule | 119 | 179 | 111 | 114 | 189 | 177 |
| X60655_at | H. sapiens EVX1 mRNA. | 46 | 87 | 75 | 79 | 140 | 116 |
| X60673_ma1_at | Human AK3 mRNA for adenylate kinase 3. | 49 | 49 | 35 | 20 | 20 | 88 |
| X60708_at | Human pcHDP7 mRNA for liver dipeptidyl peptidase IV | 20 | 20 | 20 | 20 | 20 | 20 |
| X60787_s_at | Human mRNA for transcription factor ILF | 20 | 20 | 20 | 31 | 20 | 20 |
| X60955_s_at | Human TYRRP gene for tyrosinase-related protein (TRP-1) (partial) | 20 | 20 | 20 | 20 | 20 | 20 |
| X60957_at | Human tie mRNA for putative receptor tyrosine kinase | 80 | 138 | 71 | 65 | 129 | 77 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X60992_at | H. sapiens CD6 mRNA for T cell glycoprotein CD6 | 20 | 20 | 31 | 22 | 20 | 29 |
| X61070_at | Human mRNA for T cell receptor, clone IGRA15. | 20 | 20 | 20 | 20 | 20 | 20 |
| X61072_at | Human mRNA for T cell receptor, clone IGRA17. | 30 | 20 | 25 | 22 | 40 | 40 |
| X61079_at | Human mRNA for T cell receptor, clone IGRA24. | 28 | 20 | 20 | 20 | 25 | 26 |
| X61100_ma1_at | Human mRNA for mitochondrial 75 kDa iron sulphur protein. | 74 | 84 | 46 | 66 | 84 | 72 |
| X61118_ma1_at | Human TTG-2 mRNA for a cysteine rich protein with LIM motif. | 40 | 48 | 20 | 20 | 60 | 20 |
| X61123_at | Human BTG1 mRNA | 111 | 94 | 107 | 123 | 103 | 123 |
| X61177_at | Human HSIL5R2 gene for interleukin-5 receptor type 2 | 20 | 34 | 20 | 20 | 20 | 20 |
| X61373_at | H. sapiens alternatively spliced tau "gene," exons 13 and 14 /gb=X61373 /ntype=DNA /annot=exon | 76 | 47 | 28 | 20 | 69 | 37 |
| X61587_at | H. sapiens rhoG mRNA for GTPase | 20 | 20 | 29 | 56 | 56 | 62 |
| X61615_at | H. sapiens mRNA for leukemia inhibitory factor (LIF) receptor | 47 | 86 | 68 | 47 | 57 | 194 |
| X61755_ma1_s_at | Human HOX3D gene for homeoprotein HOX3D | 20 | 20 | 20 | 20 | 20 | 20 |
| X61970_at | H. sapiens mRNA for macropain subunit zeta | 157 | 159 | 174 | 161 | 256 | 211 |
| X62025_ma1_at | H. sapiens rod cP-PDe G gene for 3',5'-cyclic nucleotide phosphodiesterase. | 90 | 63 | 112 | 92 | 258 | 120 |
| X62048_at | H. sapiens Wee1 hu gene | 44 | 20 | 45 | 46 | 41 | 20 |
| X62055_at | H. sapiens PTP1C mRNA for protein-tyrosine phosphatase 1C | 107 | 105 | 110 | 132 | 166 | 117 |
| X62078_at | H. sapiens mRNA for GM2 activator protein | 165 | 157 | 84 | 70 | 43 | 130 |
| X62083_s_at | H. sapiens mRNA for Drosophila female sterile homeotic (FSH) homologue | 84 | 177 | 180 | 212 | 20 | 58 |
| X62153_s_at | H. sapiens mRNA for P1 protein (P1.h) | 56 | 94 | 235 | 240 | 211 | 267 |
| X62320_at | H. sapiens mRNA for epithelin 1 and 2 | 327 | 231 | 428 | 483 | 563 | 485 |
| X62429_s_at | H. sapiens mRNA for transcription factor Pit-1 | 20 | 36 | 20 | 20 | 48 | 20 |
| X62466_at | H. sapiens mRNA for CAMPATH-1 (CD252) antigen | 89 | 224 | 108 | 86 | 273 | 517 |
| X62515_s_at | H. sapiens mRNA for basement membrane heparan sulfate proteoglycan | 20 | 20 | 20 | 20 | 20 | 20 |
| X62534_s_at | H. sapiens HMG-2 mRNA | 83 | 92 | 111 | 92 | 20 | 145 |
| X62535_at | H. sapiens mRNA for diacylglycerol kinase | 155 | 182 | 367 | 315 | 313 | 405 |
| X62573_at | H. sapiens RNA for Fc "receptor," TC9 | 79 | 68 | 98 | 71 | 139 | 120 |
| X62654_ma1_at | H. sapiens gene for Me491/CD63 antigen. | 404 | 637 | 1017 | 913 | 428 | 381 |
| X62691_at | H. sapiens mRNA for ribosomal protein (homologuous to yeast S24) | 2885 | 4105 | 3367 | 3004 | 1242 | 2296 |
| X62744_at | Human RING6 mRNA for HLA class II alpha chain-like product | 100 | 131 | 31 | 23 | 20 | 305 |
| X62822_at | H. sapiens gene encoding beta-galactoside "alpha-2,6-sialyltransferase" | 20 | 20 | 20 | 20 | 20 | 20 |
| X62891_s_at | H. sapiens mRNA for rhesus polypeptide (RhXIII) | 33 | 20 | 33 | 20 | 20 | 20 |
| X63097_at | H. sapiens My1 (PML) mRNA | 145 | 49 | 20 | 20 | 79 | 36 |
| X63131_s_at | H. sapiens mRNA for hst-2 (GFG-6) mRNA | 20 | 20 | 20 | 26 | 56 | 20 |
| X63187_at | H. sapiens mRNA for HE4 mRNA for extracellular proteinase inhibitor homologue | 32 | 87 | 65 | 27 | 179 | 20 |
| X63337_at | H. sapiens HB2A gene for high sulfur keratin | 50 | 40 | 55 | 36 | 94 | 48 |
| X63359_at | H. sapiens mRNA for UGT2BIO mRNA for udp glucuronosyltransferase | 122 | 63 | 87 | 48 | 217 | 207 |
| X63380_at | H. sapiens mRNA for RSRFR2 | 20 | 20 | 20 | 20 | 122 | 122 |
| X63417_at | H. sapiens irfB mRNA | 33 | 20 | 33 | 20 | 23 | 47 |
| X63422_at | H. sapiens mRNA for tre oncogene (clone 210) | 145 | 156 | 123 | 96 | 21 | 40 |
| X63454_at | H. sapiens mRNA for delta-subunit of mitochondrial F1F0 ATP-synthase (clone #1) | 20 | 20 | 20 | 20 | 20 | 20 |
| X63468_at | H. sapiens mRNA for transcription factor TFIIE alpha | 32 | 46 | 59 | 23 | 292 | 21 |
| X63469_at | H. sapiens mRNA for transcription factor TFIIE beta | 54 | 75 | 69 | 40 | 68 | 25 |
| X63622_s_at | H. sapiens mRNA DAUDI6 for retinoic acid X receptor b | 20 | 20 | 20 | 20 | 20 | 207 |
| X63527_at | H. sapiens mRNA for ribosomal protein L19 | 3282 | 3755 | 4097 | 4339 | 9432 | 3589 |
| X63546_at | H. sapiens mRNA for tre oncogene (clone 210) | 20 | 28 | 20 | 20 | 20 | 20 |
| X63563_s_at | H. sapiens mRNA for RNA polymerase II 140 kDa subunit | 68 | 45 | 127 | 95 | 122 | 100 |
| X63575_s_at | H. sapiens mRNA for plasma membrane calcium ATPase | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X63578_ma1_at | H. sapiens gene for parvalbumin. | 20 | 20 | 20 | 176 | 57 | 20 |
| X63597_at | H. sapiens si mRNA for sucrase-isomaltase | 20 | 20 | 20 | 20 | 20 | 20 |
| X63629_at | H. sapiens mRNA for p cadherin | 59 | 26 | 104 | 65 | 27 | 20 |
| X63657_at | H. sapiens fvt1 mRNA | 20 | 53 | 35 | 28 | 67 | 44 |
| X63679_at | H. sapiens mRNA for TRAMP protein | 74 | 47 | 81 | 124 | 84 | 42 |
| X63692_at | H. sapiens mRNA for DNA (cytosin-5)-methyltransferase | 20 | 23 | 28 | 20 | 20 | 36 |
| X63717_at | H. sapiens mRNA for APO-1 cell surface antigen | 51 | 45 | 130 | 33 | 20 | 40 |
| X63741_s_at | H. sapiens pilot mRNA | 38 | 28 | 20 | 20 | 20 | 20 |
| X63753_at | H. sapiens son-a mRNA | 70 | 63 | 142 | 101 | 78 | 94 |
| X63755_at | H. sapiens mRNA for high-sulphur keratin | 20 | 33 | 28 | 20 | 20 | 31 |
| X63759_at | H. sapiens hTNP2 gene for transition protein 2 | 20 | 20 | 20 | 20 | 20 | 20 |
| X64037_at | H. sapiens mRNA for RNA polymerase II associated protein RAP74 | 51 | 20 | 87 | 70 | 84 | 81 |
| X64044_at | H. sapiens mmRNA for large subunit of splicing factor U2AF | 39 | 20 | 32 | 42 | 20 | 81 |
| X64072_s_at | H. sapiens CD18 exon 2 | 20 | 20 | 20 | 20 | 20 | 203 |
| X64177_f_at | H. sapiens mRNA for metallothionein | 225 | 103 | 20 | 20 | 20 | 81 |
| X64229_at | H. sapiens dek mRNA | 50 | 33 | 30 | 42 | 34 | 268 |
| X64269_at | H. sapiens gene MtTF1 for mitochondrial transcription factor 1 | 63 | 55 | 51 | 50 | 131 | 130 |
| X64330_at | H. sapiens mRNA for ATP-citrate lyase | 70 | 66 | 97 | 158 | 147 | 221 |
| X64364_at | H. sapiens mRN for M6 antigen | 126 | 132 | 323 | 780 | 47 | 125 |
| X64559_at | H. sapiens mRNA for tetranectin | 190 | 39 | 20 | 20 | 20 | 20 |
| X64594_at | H. sapiens mRNA for 50 kDa erythrocyte plasma membrane glycoprotein | 20 | 20 | 20 | 20 | 33 | 20 |
| X64624_s_at | H. sapiens mRN for RDC-1 POU domain containing protein | 20 | 20 | 20 | 32 | 208 | 20 |
| X64643_at | H. sapiens c6.1A mRNA | 20 | 20 | 20 | 20 | 26 | 51 |
| X64707_at | H. sapiens BBC1 mRNA | 2268 | 4230 | 3091 | 2867 | 823 | 1895 |
| X64728_at | H. sapiens CHML mRNA | 20 | 20 | 20 | 20 | 20 | 20 |
| X64810_at | H. sapiens encoding PC2/PC3 | 28 | 33 | 20 | 20 | 43 | 20 |
| X64838_at | H. sapiens mRNA for restin | 84 | 20 | 20 | 38 | 20 | 88 |
| X64877_at | | 25 | 20 | 20 | 20 | 20 | 20 |
| X64878_at | H. sapiens mRNA for serum protein | 20 | 20 | 20 | 20 | 24 | 20 |
| X64994_at | H. sapiens mRNA for oxytocin receptor | 39 | 61 | 35 | 90 | 20 | 32 |
| X65233_at | H. sapiens HGMPO7I gene for olfactory receptor | 20 | 27 | 20 | 20 | 39 | 20 |
| X65293_at | H. sapiens mRNA for Zinc-finger protein (ZNFpT17) | 20 | 20 | 68 | 20 | 20 | 20 |
| X65463_at | H. sapiens mRNA for protein kinase C-Epsilon | 40 | 20 | 20 | 20 | 20 | 21 |
| X65488_at | H. sapiens mRNA for MHC class I promoter binding protein | 81 | 94 | 414 | 307 | 129 | 79 |
| X65550_at | H. sapiens U21.1 mRNA | 20 | 25 | 20 | 20 | 30 | 102 |
| X65614_at | H. sapiens mki67a mRNA (long type) for antigen of monoclonal antibody Ki-67 | 687 | 4027 | 3566 | 3068 | 3376 | 55 |
| X65633_at | H. sapiens mRNA for calcium-binding protein S100P | 62 | 78 | 27 | 32 | 22 | 2249 |
| X65644_at | H. sapiens ACTH-R gene for adrenocorticotropic hormone receptor | 42 | 20 | 68 | 56 | 20 | 61 |
| X65663_at | H. sapiens mRNA MBP-2 for MHC binding protein 2 | 20 | 24 | 20 | 20 | 20 | 20 |
| X65724_at | H. sapiens Sox-6 mRNA. /gb=X65663 /ntype=RNA | 20 | 33 | 20 | 20 | 52 | 21 |
| X65727_cds2_s_at | H. sapiens DNA for ORF1 and ORF2 from chromosome X | 20 | 27 | 34 | 22 | 30 | 79 |
| X65784_s_at | GSTalpha locus gene (glutathione S-transferase) extracted from H. sapiens GSTalpha gene for glutathione S-transferase exon 2 | 21 | 87 | 47 | 46 | 110 | 85 |
| X65857_at | H. sapiens CAR gene | 28 | 20 | 74 | 20 | 20 | 54 |
| X65867_at | H. sapiens HGMP07E gene for olfactory receptor | 62 | 20 | 25 | 30 | 173 | 44 |
| X65873_at | H. sapiens mRNA for adenylosuccinate lyase | 100 | 52 | 56 | 71 | 20 | 24 |
| X65962_s_at | H. sapiens mRNA for kinesin (heavy chain) | 28 | 66 | 99 | 84 | 70 | 115 |
| | H. sapiens mRNA for cytochrom P-450 | | | | | 181 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| X65965_s_at | H. sapiens gene for manganese superoxide dismutase. /gb=X65965 /ntype=DNA /annot=exon | 112 | 209 | 45 | 115 | 104 | 123 |
| X65977_at | H. sapiens mRNA for corticostatin HP-4 precursor | 20 | 20 | 20 | 20 | 20 | 20 | 20 |
| X66079_at | H. sapiens Spi-B mRNA | 128 | 70 | 108 | 78 | 47 | 103 |
| X66087_at | H. sapiens a-myb mRNA | 23 | 41 | 20 | 21 | 293 | 20 |
| X66113_s_at | H. sapiens mRNA for PM/Sci 100kD nucleolar protein | 20 | 49 | 63 | 44 | 20 | 65 |
| X66114_ma1_at | H. sapiens gene for 2-oxoglutarate carrier protein. | 20 | 34 | 31 | 20 | 20 | 84 |
| X66141_at | H. sapiens mRNA for cardiac ventricular myosin light chain-2 | 54 | 79 | 82 | 42 | 34 | 127 |
| X66142_s_at | H. sapiens mRNA for rod cGMP phosphodiesterase | 64 | 117 | 214 | 108 | 20 | 44 |
| X66171_at | H. sapiens CMRF35 "mRNA," complete CDS | 20 | 38 | 20 | 20 | 20 | 20 |
| X66276_s_at | H. sapiens mRNA for skeletal muscle C-protein | 20 | 38 | 76 | 37 | 20 | 45 |
| X66358_at | H. sapiens mRN KKIALRE for serine/threonine protein kinase | 20 | 20 | 20 | 20 | 22 | 20 |
| X66360_at | H. sapiens mRNA PCTAIRE-2 for serine/threonine protein kinase | 50 | 53 | 54 | 20 | 20 | 20 |
| X66362_at | H. sapiens mRNA PCTAIRE-3 for serine/threonine protein kinase | 20 | 20 | 20 | 20 | 20 | 20 |
| X66363_at | H. sapiens mRNA PCTAIRE-1 for serine/threonine protein kinase | 84 | 138 | 26 | 47 | 164 | 254 |
| X66364_at | H. sapiens mRNA PSSALRE for serine/threonine protein kinase | 80 | 91 | 98 | 69 | 311 | 198 |
| X66365_at | H. sapiens mRNA PLSTIRE for serin/threonine protein kinase | 25 | 20 | 45 | 112 | 150 | 26 |
| X66397_at | H. sapiens trp mRNA | 62 | 92 | 130 | 31 | 20 | 99 |
| X66401_cds1_at | H. sapiens genes TAP1, TAP2, LMP2, LMP7 and DOB. | 90 | 188 | 70 | 111 | 98 | 205 |
| X66403_at | H. sapiens mRNA for acetylcholine receptor (epsilon subunit) | 41 | 52 | 25 | 38 | 73 | 20 |
| X66417_at | H. sapiens casK mRNA for kappe-casein | 66 | 57 | 79 | 32 | 25 | 200 |
| X66436_at | H. sapiens hsr1 mRNA (partial) | 51 | 128 | 159 | 45 | 86 | 243 |
| X66503_at | Human adenylosuccinate synthetase mRNA | 20 | 42 | 56 | 76 | 138 | 31 |
| X66533_at | H. sapiens mRNA soluble guanylate cyclase small subunit mRNA | 20 | 45 | 20 | 52 | 20 | 42 |
| X66534_at | H. sapiens mRNA soluble guanylate cyclase large subunit mRNA | 59 | 33 | 20 | 20 | 20 | 20 |
| X66610_at | H. sapiens mRNA for enolase | 20 | 20 | 20 | 20 | 20 | 20 |
| X66785_at | H. sapiens mRNA for transactylase (DBT) | 20 | 27 | 20 | 20 | 51 | 38 |
| X66839_at | H. sapiens MaTu MN mRNA for p54/58N protein | 105 | 408 | 588 | 266 | 926 | 274 |
| X66867_cds1_at | H. sapiens max gene | 32 | 89 | 101 | 140 | 163 | 161 |
| X66894_s_at | H. sapiens FACC mRNA from complementatin group C (FA(C)) | 40 | 20 | 26 | 24 | 28 | 20 |
| X66899_at | H. sapiens EWS mRNA | 20 | 76 | 84 | 48 | 112 | 54 |
| X66922_at | H. sapiens mRNA for myo-insositol monophosphatase | 35 | 20 | 164 | 77 | 20 | 51 |
| X66945_at | H. sapiens mRNA for N-sam mRNA for fibroblast growth factor receptor | 20 | 20 | 20 | 20 | 20 | 20 |
| X67081_at | H. sapiens histone H4 gene | 59 | 33 | 20 | 20 | 20 | 20 |
| X67098_at | H. sapiens rfTS alpha mRNA containing four open reading frames | 20 | 20 | 51 | 27 | 23 | 20 |
| X67155_at | H. sapiens mRNA for mitotic kinesin-like protein-1 | 34 | 71 | 23 | 23 | 41 | 20 |
| X67235_s_at | H. sapiens mRNA for proline rich homeobox (Prh) protein | 20 | 35 | 20 | 20 | 20 | 20 |
| X67247_ma1_at | H. sapiens rpS8 gene for ribosomal protein S8. | 3725 | 3402 | 3977 | 3818 | 1511 | 2083 |
| X67318_at | H. sapiens mRNA for procarboxypeptidase A1 | 20 | 20 | 20 | 20 | 20 | 20 |
| X67325_at | H. sapiens p27 mRNA | 102 | 194 | 64 | 20 | 20 | 893 |
| X67337_at | H. sapiens HPBRII-4 mRNA | 20 | 25 | 20 | 61 | 20 | 20 |
| X67491_f_at | H. sapiens gene for glutamate dehydrogenase | 27 | 20 | 20 | 20 | 20 | 20 |
| X67594_at | H. sapiens mRNA for MSH receptor | 20 | 20 | 20 | 20 | 20 | 20 |
| X67683_at | H. sapiens mRNA for keratin 4 /gb=X67683 /ntype=RNA | 2126 | 161 | 114 | 106 | 268 | 189 |
| X67697_at | H. sapiens HE2 mRNA | 87 | 36 | 56 | 46 | 172 | 57 |
| X67698_at | H. sapiens tissue specific mRNA | 401 | 372 | 388 | 322 | 265 | 472 |
| X67734_at | H. sapiens mRNA for transient axonal glycoprotein (tag-1) | 20 | 20 | 20 | 33 | 56 | 20 |
| X67951_at | H. sapiens mRNA for proliferation-associated gene (pag) | 1472 | 608 | 647 | 646 | 543 | 814 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X68090_s_at | H. sapiens Fc-gamma-RIIA gene for IgG Fc receptor class IIA (5'flank). /gb=X58090 /ntype=DNA /annot=CDS | 20 | 20 | 20 | 20 | 133 | 20 |
| X68149_at | H. sapiens BLR1 gene for Burkitt's lymphoma receptor 1 | 20 | 20 | 20 | 20 | 20 | 20 |
| X68194_at | H. sapiens h-Sp1 mRNA | 42 | 31 | 124 | 101 | 20 | 21 |
| X68242_at | H. sapiens mRNA for Hin-1 | 20 | 20 | 20 | 20 | 20 | 20 |
| X68264_ma1_at | H. sapiens MGF gene exons 1&2. | 20 | 20 | 20 | 20 | 20 | 198 |
| X68277_at | H. sapiens CL 100 mRNA for protein tyrosine phosphatase | 1972 | 105 | 44 | 42 | 74 | 20 |
| X68285_s_at | H. sapiens mRNA for glycerol kinase | 20 | 20 | 32 | 20 | 20 | 20 |
| X68314_at | H. sapiens mRNA for glutathione peroxidase-GI | 380 | 739 | 734 | 1019 | 386 | 293 |
| X68486_at | H. sapiens mRNA for A2a adenosine receptor | 134 | 121 | 145 | 117 | 41 | 77 |
| X68487_at | H. sapiens mRNA for A2b adenosine receptor | 22 | 20 | 34 | 20 | 20 | 20 |
| X68505_s_at | | 27 | 31 | 20 | 25 | 20 | 20 |
| X68560_at | H. sapiens SPR-2 mRNA for GT box binding protein | 78 | 55 | 51 | 44 | 40 | 94 |
| X68561_at | H. sapiens SPR-1 mRNA for FT box binding protein | 20 | 20 | 20 | 22 | 20 | 20 |
| X68688_ma1_s_at | H. sapiens ZNF33B gene | 20 | 20 | 48 | 20 | 262 | 227 |
| X68733_ma1_at | H. sapiens gene for alpha1-antichymotrypsin, exon 1. | 142 | 185 | 98 | 97 | 92 | 174 |
| X68742_at | H. sapiens mRNA for "integrin," alpha subunit | 20 | 49 | 20 | 20 | 42 | 35 |
| X68836_at | H. sapiens mRNA for S-adenosylmethionine synthetase | 27 | 20 | 24 | 21 | 21 | 21 |
| X68985_s_at | H. sapiens mRNA for hepatic leukemia factor | 20 | 20 | 152 | 71 | 97 | 20 |
| X68994_at | H. sapiens CREB gene, exon Y. | 20 | 20 | 34 | 20 | 20 | 57 |
| X69089_at | H. sapiens mRNA for skeletal muscle 165kD protein | 20 | 20 | 20 | 20 | 20 | 20 |
| X69090_at | H. sapiens mRNA for skeletal muscle 190kD protein | 20 | 20 | 20 | 20 | 20 | 20 |
| X69111_at | H. sapiens HLH 1R21 mRNA for helix-loop-helix protein | 160 | 284 | 558 | 534 | 172 | 190 |
| X69115_at | H. sapiens ZNF37A mRNA for zinc finger protein | 20 | 50 | 98 | 71 | 154 | 32 |
| X69116_s_at | H. sapiens ZNF37A gene for zinc finger protein | 20 | 20 | 32 | 20 | 20 | 20 |
| X69141_at | H. sapiens mRNA for squalene synthase | 76 | 104 | 89 | 135 | 28 | 85 |
| X69150_at | L06432 H. sapiens mRNA for ribosomal protein S18. | 6256 | 6897 | 6075 | 6095 | 2300 | 4190 |
| X69391_at | H. sapiens mRNA for ribosomal protein L6 | 2094 | 2656 | 2081 | 1912 | 891 | 1054 |
| X69398_at | H. sapiens mRNA for OA3 antigenic surface determinant | 20 | 20 | 45 | 40 | 20 | 20 |
| X69433_at | H. sapiens mRNA for mitochondrial isocitrate dehydrogense (NADP+) | 212 | 133 | 105 | 160 | 121 | 236 |
| X69550_at | H. sapiens gene for mitochondrial ATP synthase c subunit (P2 form). | 420 | 362 | 411 | 412 | 629 | 576 |
| X69636_at | H. sapiens p63 mRNA for transmembrane protein | 28 | 51 | 58 | 43 | 81 | 60 |
| X69654_at | H. sapiens mRNA for ribosomal protein S26 | 1050 | 3615 | 1712 | 2534 | 2672 | 1457 |
| X69699_at | H. sapiens mRNA sequence (15q11–13) | 183 | 221 | 134 | 125 | 233 | 246 |
| X69819_at | H. sapiens Pax8 mRNA | 20 | 58 | 20 | 20 | 20 | 20 |
| X69838_at | H. sapiens ICAM-3 mRNA | 37 | 41 | 40 | 28 | 20 | 52 |
| X69878_at | H. sapiens mRNA for G9a | 45 | 41 | 65 | 46 | 124 | 20 |
| X69886_s_at | H. sapiens Flt4 mRNA for transmembrane tyrosine kinase | 20 | 20 | 20 | 20 | 20 | 20 |
| X69908_ma1_at | H. sapiens mRNA for glycerol kinase | 209 | 292 | 437 | 473 | 158 | 253 |
| X69910_at | H. sapiens gene for mitochondrial ATP synthase c subunit (P2 form). | 217 | 176 | 213 | 138 | 184 | 63 |
| X69920_s_at | H. sapiens p63 mRNA for transmembrane protein | 59 | 100 | 140 | 92 | 109 | 24 |
| X69950_s_at | H. sapiens mRNA for calcitonin receptor | 20 | 20 | 20 | 20 | 20 | 29 |
| X69962_s_at | H. sapiens DNA sequence for Wilms' tumor gene | 23 | 20 | 28 | 22 | 20 | 20 |
| X69978_at | H. sapiens FMR-1 mRNA | 37 | 34 | 29 | 25 | 136 | 61 |
| X70040_at | H. sapiens mRNA for XP-G factor | 109 | 181 | 273 | 160 | 20 | 230 |
| X70070_at | H. sapiens RON mRNA for tyrosine kinase | 20 | 20 | 20 | 20 | 20 | 20 |
| X70083_at | H. sapiens mRNA for neurotensin receptor | 20 | 20 | 20 | 20 | 31 | 20 |
| X70218_at | H. sapiens ABP-280-like mRNA for filamin (695 bps). /gb=X70083 /ntype=RNA | 41 | 72 | 121 | 177 | 83 | 90 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X70297_at | H. sapiens mRNA for neuronal nicotinic acetylcholine receptor alpha-7 subunit | 61 | 68 | 54 | 38 | 37 | 126 |
| X70340_at | H. sapiens mRNA for transforming growth factor alpha | 101 | 20 | 20 | 29 | 20 | 26 |
| X70394_at | H. sapiens OZF mRNA | 34 | 32 | 89 | 69 | 72 | 40 |
| X70476_at | H. sapiens subunit of coatomer complex | 131 | 186 | 115 | 135 | 90 | 250 |
| X70649_at | H. sapiens cl. 1042 mRNA of DEAD box protein family | 44 | 20 | 57 | 56 | 30 | 24 |
| X70683_at | H. sapiens mRNA for SOX-4 protein | 58 | 107 | 399 | 403 | 358 | 478 |
| X70811_at | H. sapiens mRNA for beta 3 adrenergic receptor | 30 | 25 | 69 | 43 | 20 | 36 |
| X70940_s_at | H. sapiens mRNA for elongation factor 1 alpha-2 | 37 | 20 | 470 | 596 | 244 | 90 |
| X70944_s_at | H. sapiens mRNA for PTB-associated splicing factor | 46 | 53 | 65 | 54 | 20 | 49 |
| X70991_at | H. sapiens MADER mRNA | 20 | 28 | 28 | 45 | 20 | 23 |
| X71125_at | H. sapiens mRNA for glutamine cyclotransferase | 20 | 20 | 20 | 37 | 20 | 20 |
| X71129_at | H. sapiens mRNA for electron transfer flavoprotein beta subunit | 159 | 127 | 127 | 132 | 125 | 124 |
| X71135_at | H. sapiens sox3 gene | 86 | 43 | 20 | 20 | 20 | 20 |
| X71345_f_at | H. sapiens mRNA for trypsinogen IV b-form | 166 | 67 | 20 | 40 | 43 | 22 |
| X71348_at | H. sapiens vHNF-1-C mRNA | 20 | 230 | 459 | 272 | 320 | 190 |
| X71428_at | H. sapiens fus mRNA | 240 | 52 | 29 | 29 | 21 | 20 |
| X71490_at | H. sapiens mRNA for vacuolar proton "ATPase," subunit D | 46 | 20 | 35 | 210 | 79 | 20 |
| X71661_at | H. sapiens ERGIC-53 mRNA | 20 | 57 | 20 | 20 | 20 | 20 |
| X71874_cds1_at | H. sapiens genes for proteasome-like subunit (MECL-1), chymotrypsin-like protease (CTRL-1) and protein serine kinase (PSK-H1) last ex | 99 | 488 | 228 | 175 | 86 | 209 |
| X71877_at | H. sapiens mRNA for chymotrypsin-like protease CTRL-1 | 20 | 20 | 20 | 20 | 20 | 20 |
| X71973_at | H. sapiens GPx-4 mRNA for phospholipid hydroperoxide glutathione peroxidase | 297 | 499 | 490 | 571 | 385 | 453 |
| X72012_at | H. sapiens end mRNA for endoglin | 20 | 20 | 20 | 20 | 20 | 20 |
| X72177_ma1_at | H. sapiens C6 gene, exon 1. | 71 | 50 | 59 | 57 | 233 | 108 |
| X72304_at | H. sapiens mRNA for corticotrophin releasing factor receptor | 20 | 20 | 20 | 20 | 20 | 20 |
| X72308_at | H. sapiens MCP-3 mRNA for monocyte chemotactic protein-3 | 25 | 20 | 29 | 26 | 20 | 20 |
| X72475_at | H. sapiens mRNA for rearranged Ig kappa light chain variable region (I.114) | 38 | 36 | 20 | 61 | 182 | 51 |
| X72632_s_at | | 20 | 20 | 20 | 20 | 51 | 27 |
| X72727_at | H. sapiens tunp mRNA for transformation upregulated nuclear protein | 183 | 204 | 577 | 527 | 93 | 162 |
| X72755_at | H. sapiens Humig mRNA | 120 | 88 | 46 | 27 | 153 | 281 |
| X72790_at | Human endogenous retrovirus mRNA for ORF. /gb=X72790 /ntype=RNA | 20 | 20 | 20 | 20 | 20 | 20 |
| X72841_at | H. sapiens IEF 7442 mRNA | 63 | 43 | 83 | 76 | 60 | 49 |
| X72879_at | H. sapiens 14A2AK DNA sequence | 26 | 45 | 20 | 20 | 184 | 111 |
| X72882_at | H. sapiens 14A6CK DNA sequence | 20 | 20 | 20 | 20 | 20 | 20 |
| X72889_at | H. sapiens hbrm mRNA | 35 | 103 | 170 | 143 | 20 | 84 |
| X72925_at | H. sapiens mRNA for desmocollin type 1 | 20 | 20 | 20 | 20 | 20 | 20 |
| X72964_at | H. sapiens mRN for caltractin | 192 | 153 | 160 | 115 | 129 | 204 |
| X73079_at | Homo sapiens encoding Polymeric immunoglobulin receptor | 23 | 68 | 27 | 20 | 29 | 61 |
| X73113_at | H. sapiens mRNA for fast MyBP-C | 111 | 104 | 84 | 72 | 174 | 254 |
| X73358_s_at | H. sapiens hAES-1 mRNA | 159 | 153 | 768 | 737 | 292 | 214 |
| X73460_at | H. sapiens mRNA for ribosomal protein L3 | 2949 | 3009 | 3953 | 3688 | 617 | 1838 |
| X73478_at | H. sapiens hPTPA mRNA | 52 | 154 | 258 | 101 | 20 | 32 |
| X73501_at | H. sapiens gene for cytokeratin 20 | 20 | 20 | 42 | 20 | 20 | 102 |
| X73608_at | H. sapiens mRNA for testican | 37 | 20 | 77 | 20 | 20 | 85 |
| X73874_at | H. sapiens PHKA 1 mRNA | 20 | 20 | 20 | 20 | 63 | 20 |
| X73881_at | H. sapiens E-MAP-115 mRNA | 26 | 20 | 33 | 40 | 20 | 32 |
| X74008_at | H. sapiens mRNA for protein phosphatase 1 gamma | 145 | 105 | 176 | 136 | 23 | 107 |
| X74039_at | H. sapiens mRNA for uokinase plasminogen activator receptor | 20 | 20 | 22 | 20 | 64 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X74104_at | H. sapiens mRNA for TRAP beta subunit | 222 | 249 | 324 | 321 | 227 | 296 |
| X74142_at | H. sapiens HBG-1 mRNA for transcription factor | 20 | 38 | 53 | 20 | 151 | 20 |
| X74262_at | H. sapiens RbAP48 mRNA encoding retinoblastoma binding protein | 42 | 120 | 97 | 80 | 107 | 39 |
| X74295_at | H. sapiens mRNA for alpha 7B integrin | 94 | 145 | 40 | 50 | 149 | 135 |
| X74301_s_at | H. sapiens mRNA for MHC class II transactivator | 20 | 20 | 20 | 20 | 20 | 20 |
| X74328_ma1_at | H. sapiens mRNA for CB2 (peripheral) cannabinoid receptor. | 50 | 20 | 20 | 20 | 41 | 20 |
| X74330_at | H. sapiens mRNA for DNA primase (subunit p48) | 29 | 20 | 20 | 20 | 98 | 41 |
| X74331_at | H. sapiens mRNA for DNA primase (subunit p58) | 20 | 35 | 20 | 20 | 20 | 61 |
| X74496_at | H. sapiens mRNA for prolyl oligpeptidase | 48 | 88 | 82 | 71 | 84 | 97 |
| X74570_at | H. sapiens mRNA for Gal-beta(1–3/1–4)GlcNAc alpha-2,3-sialyltransferase | 20 | 36 | 91 | 107 | 393 | 44 |
| X74614_at | H. sapiens mRNA for ODF2 (allele 2) gene for outer dense fiber protein | 112 | 127 | 137 | 89 | 205 | 220 |
| X74764_at | H. sapiens mRNA for receptor protein tyrosine kinase | 103 | 117 | 113 | 71 | 20 | 30 |
| X74794_at | H. sapiens P1-Cdc21 mRNA | 20 | 20 | 20 | 23 | 20 | 20 |
| X74795_at | H. sapiens P1-Cdc46 mRNA | 143 | 190 | 159 | 126 | 286 | 269 |
| X74801_at | H. sapiens Cdg mRNA for chaperonin | 152 | 211 | 219 | 298 | 195 | 310 |
| X74819_at | H. sapiens mRNA for cardiac troponin T | 41 | 81 | 49 | 48 | 238 | 259 |
| X74837_at | H. sapiens HUMM9 mRNA | 20 | 20 | 20 | 20 | 20 | 20 |
| X74874_ma1_s_at | RNA polymerase II largest subunit gene extracted from H. sapiens gene for RNA pol II largest "subunit," exon 1 | 36 | 203 | 217 | 213 | 119 | 40 |
| X74929_s_at | H. sapiens KRT8 mRNA for keratin 8 | 20 | 869 | 2744 | 2232 | 2204 | 912 |
| X74987_s_at | H. sapiens mRNA for 2′-5′ oligoadenylate binding protein | 20 | 27 | 55 | 20 | 20 | 41 |
| X75042_at | H. sapiens rel proto-oncogene mRNA | 26 | 20 | 28 | 20 | 72 | 37 |
| X75091_s_at | H. sapiens mRNA for HLA-DR associated protein II (PHAPII) | 38 | 20 | 116 | 49 | 30 | 45 |
| X75208_at | H. sapiens HEK2 mRN for protein tyrosine kinase receptor | 99 | 75 | 50 | 45 | 101 | 20 |
| X75252_at | H. sapiens phosphatidylethanolamine binding protein mRNA | 247 | 307 | 214 | 264 | 390 | 220 |
| X75304_at | H. sapiens giantin mRNA | 24 | 95 | 123 | 114 | 48 | 79 |
| X75308_at | H. sapiens mRNA for collagenase 3 | 20 | 20 | 20 | 20 | 20 | 36 |
| X75315_at | H. sapiens seb4B mRNA | 31 | 20 | 20 | 20 | 22 | 20 |
| X75342_at | H. sapiens SHB mRNA | 117 | 132 | 113 | 105 | 142 | 117 |
| X75346_s_at | H. sapiens mRN for MAP kinase activated protein kinase | 20 | 20 | 20 | 20 | 20 | 20 |
| X75535_at | H. sapiens mRNA for PxF protein | 20 | 20 | 40 | 47 | 415 | 20 |
| X75546_at | H. sapiens mRNA for fibromodulin | 48 | 20 | 20 | 35 | 160 | 174 |
| X75593_at | H. sapiens mRNA for rab 13 | 65 | 63 | 56 | 235 | 242 | 153 |
| X75755_ma1_s_at | H. sapiens PR264 gene | 260 | 359 | 297 | 110 | 193 | 62 |
| X75756_at | H. sapiens mRN for protein kinase C mu | 23 | 20 | 132 | 20 | 85 | 36 |
| X75861_at | H. sapiens TEGT gene | 26 | 32 | 22 | 21 | 277 | 218 |
| X75917_at | H. sapiens mRNA for fetal beta-MHC binding factor | 290 | 290 | 502 | 459 | 23 | 20 |
| X75918_at | H. sapiens mRNA for NOT | 20 | 20 | 20 | 20 | 20 | 20 |
| X75958_at | H. sapiens trkB mRNA for protein-tyrosine kinase | 48 | 20 | 40 | 20 | 20 | 20 |
| X75962_at | H. sapiens mRNA for OX40 homologue | 20 | 63 | 56 | 35 | 39 | 174 |
| X76013_at | H. sapiens QRSHs mRNA for glutaminyl-tRNA synthetase | 31 | 98 | 72 | 50 | 70 | 63 |
| X76029_at | H. sapiens mRNA for neuromedin U | 215 | 342 | 451 | 417 | 154 | 285 |
| X76040_at | H. sapiens mRNA for Ion protease-like protein | 150 | 20 | 20 | 20 | 20 | 20 |
| X76057_at | H. sapiens PMI1 mRNA for phosphomannose isomerase | 20 | 22 | 50 | 32 | 60 | 20 |
| X76059_at | H. sapiens mRNA for YRRM1 | 46 | 75 | 85 | 70 | 180 | 55 |
| X76061_at | H. sapiens p130 mRNA for 130K protein | 20 | 20 | 20 | 20 | 20 | 52 |
| X76092_at | H. sapiens HRFX3 mRNA | 35 | 20 | 49 | 35 | 20 | 81 |
| X76104_at | H. sapiens DAP-kinase mRNA | 89 | 65 | 72 | 51 | 108 | 100 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X76105_at | H. sapiens DAP-1 mRNA | 20 | 36 | 78 | 76 | 71 | 54 |
| X76132_at | H. sapiens DCC mRNA | 67 | 32 | 55 | 45 | 33 | 111 |
| X76180_at | H. sapiens mRNA for lung amiloride sensitive Na+ channel protein | 255 | 104 | 353 | 253 | 20 | 20 |
| X76223_s_at | | 3490 | 20 | 20 | 111 | 20 | 49 |
| X76228_at | H. sapiens mRNA for vacuolar H+ ATPase E subunit | 175 | 153 | 135 | 124 | 70 | 123 |
| X76302_at | H. sapiens RY-1 mRNA for putative nucleic acid binding protein | 85 | 89 | 71 | 48 | 97 | 174 |
| X76342_at | H. sapiens ADH7 mRNA | 132 | 20 | 20 | 20 | 20 | 20 |
| X76383_at | H. sapiens mRNA for HE3(alpha) | 20 | 20 | 20 | 20 | 20 | 20 |
| X76498_at | H. sapiens gene for uterine bombesin receptor | 20 | 20 | 20 | 20 | 65 | 20 |
| X76534_at | H. sapiens NMB mRNA | 142 | 125 | 31 | 142 | 324 | 437 |
| X76538_at | H. sapiens Mpv17 mRNA | 62 | 82 | 65 | 75 | 67 | 64 |
| X76648_at | H. sapiens mRNA for glutaredoxin | 47 | 107 | 20 | 20 | 34 | 73 |
| X76717_at | H. sapiens mT-1I mRNA | 251 | 68 | 72 | 73 | 100 | 62 |
| X76732_at | H. sapiens NEFA protein "mRNA," complete cds (DNA-binding leucine zipper "protein," calcium-binding EF-hand "protein," from acute lym | 91 | 46 | 20 | 20 | 20 | 20 |
| X76770_at | H. sapiens PAP mRNA | 139 | 109 | 107 | 98 | 197 | 178 |
| X76942_s_at | | 57 | 109 | 190 | 84 | 221 | 72 |
| X77094_at | H. sapiens mRNA for p40phox | 21 | 20 | 26 | 20 | 77 | 42 |
| X77166_at | H. sapiens gene for kunitz-type protease "inhibitor," HKIB9 | 20 | 20 | 20 | 20 | 20 | 33 |
| X77197_at | H. sapiens mRNA for chloride channel | 20 | 20 | 20 | 20 | 40 | 36 |
| X77307_at | H. sapiens mRNA for 5-HT2B serotonin receptor | 27 | 20 | 20 | 20 | 57 | 20 |
| X77366_at | H. sapiens HBZ17 mRNA | 59 | 43 | 102 | 86 | 25 | 20 |
| X77383_at | H. sapiens mRNA for cathepsin-O | 20 | 20 | 20 | 20 | 20 | 20 |
| X77533_at | H. sapiens mRNA for activin type II receptor | 20 | 20 | 20 | 20 | 20 | 20 |
| X77548_at | H. sapiens cDNA for RFG | 67 | 39 | 69 | 75 | 25 | 79 |
| X77567_s_at | H. sapiens mRNA for InsP3 5-phosphatase | 20 | 20 | 20 | 23 | 20 | 20 |
| X77584_at | H. sapiens mRNA for ATL-derived factor/thiredoxin | 1470 | 400 | 375 | 522 | 317 | 507 |
| X77588_s_at | | 108 | 184 | 163 | 60 | 20 | 49 |
| X77737_at | H. sapiens mRNA for red cell anion exchange "(EPB3," "AE1," Band 3) 3' non-coding region | 43 | 33 | 36 | 24 | 26 | 32 |
| X77744_at | H. sapiens F11 mRNA | 20 | 20 | 20 | 20 | 31 | 20 |
| X77748_at | H. sapiens mRNA for metabotropic glutamate receptor type 3 | 20 | 20 | 20 | 20 | 20 | 20 |
| X77753_at | H. sapiens TROP-2 gene | 20 | 30 | 79 | 20 | 49 | 20 |
| X77777_s_at | H. sapiens intestinal VIP receptor related protein mRNA | 20 | 20 | 79 | 76 | 53 | 20 |
| X77794_at | H. sapiens mRNA for cyclin G1 | 93 | 119 | 251 | 176 | 20 | 71 |
| X77909_at | H. sapiens IKBL mRNA | 58 | 20 | 20 | 34 | 20 | 20 |
| X77922_s_at | H. sapiens GD3 synthase mRNA | 20 | 20 | 38 | 20 | 120 | 26 |
| X78031_at | H. sapiens mRNA for "alpha-1," 3-fucosyltransferase mRAN | 94 | 65 | 67 | 50 | 147 | 97 |
| X78121_at | H. sapiens mRNA for choroideremia | 20 | 20 | 20 | 20 | 20 | 20 |
| X78136_at | H. sapiens hnRNP-E2 mRNA | 309 | 240 | 604 | 464 | 304 | 473 |
| X78338_at | Synthetic adenovirus transformed human retina cell "line," MRP mRNA | 41 | 42 | 170 | 77 | 355 | 117 |
| X78342_at | H. sapiens PISSLRE mRNA | 20 | 23 | 36 | 31 | 20 | 20 |
| X78416_s_at | H. sapiens alpha-s1-casein mRNA | 35 | 22 | 38 | 20 | 20 | 20 |
| X78520_at | H. sapiens RNA for CLCN3 | 79 | 20 | 97 | 79 | 27 | 20 |
| X78549_at | H. sapiens brk mRNA for tyrosine kinase | 175 | 80 | 138 | 105 | 120 | 28 |
| X78565_at | H. sapiens mRNA for "tenascin-C," 7560bp | 81 | 53 | 20 | 20 | 133 | 138 |
| X78578_at | H. sapiens PPP1R3 mRNA for protein phosphatase "1," glycogen-binding regulatory subunit | 20 | 20 | 20 | 20 | 73 | 20 |
| X78627_at | H. sapiens mRNA for translin | 60 | 43 | 63 | 48 | 28 | 41 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X78669_at | H. sapiens ERC-55 mRNA | 20 | 20 | 61 | 59 | 26 | 36 |
| X78678_at | H. sapiens KHK mRNA for "ketohexokinase," clone pHKHK3a | 20 | 20 | 20 | 20 | 88 | 20 |
| X78686_at | H. sapiens ENA-78 mRNA | 20 | 26 | 21 | 32 | 21 | 29 |
| X78687_at | H. sapiens G9 gene encoding sialidase | 29 | 60 | 68 | 59 | 280 | 118 |
| X78706_at | H. sapiens mRNA for carnitine acetyltransferase | 20 | 20 | 20 | 25 | 38 | 20 |
| X78710_at | H. sapiens MTF-1 mRNA for metal-retulatory transcription factor | 20 | 20 | 20 | 22 | 20 | 20 |
| X78711_at | H. sapiens mRNA for glycerol kinase testis specific 1 | 20 | 20 | 20 | 20 | 20 | 20 |
| X78712_at | H. sapiens mRNA for glycerol kinase testis specific 2 | 76 | 20 | 20 | 20 | 164 | 118 |
| X78817_at | H. sapiens partial C1 mRNA | 44 | 66 | 87 | 66 | 41 | 49 |
| X78924_at | H. sapiens HZF1 mRNA for zinc finger protein | 82 | 28 | 51 | 23 | 20 | 96 |
| X78925_at | H. sapiens HZF2 mRNA for zinc finger protein | 20 | 23 | 57 | 36 | 32 | 35 |
| X78926_at | H. sapiens HZF3 mRNA for zinc finger protein | 20 | 22 | 20 | 20 | 20 | 20 |
| X78932_at | H. sapiens HZF9 mRNA for zinc finger protein | 20 | 20 | 20 | 20 | 28 | 57 |
| X78933_at | H. sapiens HZF10 mRNA for zinc finger protein | 20 | 25 | 20 | 20 | 20 | 28 57 |
| X78992_at | H. sapiens ERG-2 mRNA | 134 | 20 | 20 | 52 | 20 | 20 |
| X79066_at | H. sapiens ERFG-1 mRNA 5' end | 22 | 20 | 26 | 20 | 20 | 20 |
| X79067_at | H. sapiens ERF-1 mRNA 3' end | 56 | 52 | 62 | 62 | 158 | 190 |
| X79200_at | H. sapiens mRNA for "SYT-SSX," synovial sarcoma translocation junction. /gb=X79200 /ntype=RNA | 39 | 20 | 179 | 62 | 844 | 139 |
| X79200_s_at |  | 20 | 20 | 20 | 20 | 20 | 20 |
| X79201_at | H. sapiens mRNA for SYT | 27 | 20 | 34 | 20 | 20 | 56 |
| X79204_at | H. sapiens SCA1 mRNA for ataxin | 33 | 27 | 35 | 20 | 21 | 31 |
| X79234_at | H. sapiens mRNA for ribosomal protein L11 | 2602 | 2843 | 2247 | 1939 | 795 | 1287 |
| X79353_at | H. sapiens XAP-4 mRNA for GDP-dissociation inhibitor | 69 | 48 | 115 | 80 | 55 | 81 |
| X79439_at | H. sapeins Notch 3 DNA sequence. /gb=X79439 /ntype=DNA /annot=CDS | 94 | 93 | 72 | 83 | 412 | 190 |
| X79440_at | H. sapiens mRNA for NADP+-dependent malic enzyme | 20 | 34 | 49 | 25 | 20 | 20 |
| X79483_at | H. sapiens ERK6 mRNA for extracellular signal regulated kinase | 68 | 43 | 24 | 20 | 20 | 20 |
| X79510_at | H. sapiens mRNA for protein-tyrosine-phosphatase D1 | 20 | 35 | 20 | 20 | 20 | 76 |
| X79536_at | H. sapiens mRNA for hnRNP core protein A1. | 24 | 90 | 114 | 70 | 30 | 42 |
| X79568_at | H. sapiens BDP1 mRNA for ptoein-tyrosine-phosphatase | 20 | 20 | 20 | 20 | 20 | 20 |
| X79683_s_at |  | 37 | 75 | 20 | 20 | 20 | 20 |
| X79780_at | H. sapiens YPT3 mRNA | 20 | 20 | 36 | 33 | 64 | 56 |
| X79781_at | H. sapiens ray mRNA | 21 | 96 | 33 | 29 | 33 | 57 |
| X79865_at | H. sapiens Mrp17 mRNA | 103 | 51 | 82 | 156 | 54 | 69 |
| X79882_at | H. sapiens lrp mRNA | 62 | 195 | 196 | 222 | 106 | 104 |
| X79888_at | H. sapiens AUH mRNA | 25 | 41 | 20 | 20 | 92 | 27 |
| X79981_at | H. sapiens VE-cadherin mRNA | 35 | 41 | 25 | 23 | 61 | 52 |
| X79984_at | H. sapiens AA1 mRNA. /gb=X79984 /ntype=RNA | 20 | 20 | 20 | 20 | 94 | 48 |
| X80026_at | H. sapiens B-cam mRNA | 68 | 43 | 49 | 34 | 148 | 74 |
| X80062_at | H. sapiens SA mRNA | 61 | 30 | 20 | 30 | 136 | 99 |
| X80198_at | H. sapiens MLN64 mRNA | 51 | 67 | 97 | 96 | 559 | 136 |
| X80199_at | H. sapiens MLN51 mRNA | 146 | 209 | 212 | 177 | 312 | 300 |
| X80200_at | H. sapiens MLN62 mRNA | 208 | 409 | 415 | 373 | 970 | 592 |
| X80230_at | H. sapiens mRNA (clone C02k) mRNA for serine/threonine protein kinase | 71 | 62 | 51 | 48 | 20 | 20 |
| X80343_at | H. sapiens p35 mRNA for regulatory subunit of cdk5 kinase | 20 | 20 | 20 | 20 | 20 | 27 |
| X80497_at | H. sapiens PHKLA mRNA | 45 | 72 | 55 | 68 | 143 | 79 |
| X80507_at | H. sapiens YAP65 mRNA | 50 | 50 | 20 | 20 | 65 | 20 |
| X80590_at | H. sapiens PHDG1 mRNA | 43 | 62 | 60 | 57 | 123 | 66 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| X80692_at | H. sapiens ERK3 mRNA | 276 | 115 | 129 | 154 | 57 | 57 | 94 |
| X80695_at | H. sapiens OXA1Hs mRNA | 94 | 44 | 120 | 106 | 55 | 55 | 29 |
| X80754_at | H. sapiens mRNA for GTP-binding protein | 123 | 196 | 164 | 130 | 206 | 206 | 152 |
| X80763_s_at | H. sapiens gene for 5-HT2c receptor | 124 | 115 | 459 | 148 | 689 | 689 | 134 |
| X80818_at | H. sapiens mRNA for metabotropic glutamate receptor type 4 | 84 | 180 | 472 | 250 | 542 | 542 | 277 |
| X80822_at | H. sapiens mRNA for ORF | 3963 | 3471 | 4092 | 3897 | 2279 | 2279 | 2840 |
| X80878_at | H. sapiens R kappa B mRNA | 20 | 20 | 20 | 20 | 20 | 20 | 20 |
| X80907_at | H. sapiens mRNA for p85 beta subunit of phosphatidyl-inositol-3-kinase | 62 | 46 | 79 | 83 | 213 | 213 | 169 |
| X80909_at | H. sapiens mRNA alpha NAC mRNA | 1203 | 939 | 1180 | 1144 | 352 | 352 | 666 |
| X80910_at | H. sapiens PPP1CB mRNA | 91 | 66 | 80 | 44 | 20 | 20 | 33 |
| X80915_ma1_at | H. sapiens Gd5 gene. | 101 | 95 | 88 | 70 | 140 | 140 | 174 |
| X80923_at | H. sapiens nov gene. /gb=X80923 /ntype=DNA /annot=mRNA | 48 | 32 | 52 | 41 | 54 | 54 | 69 |
| X81003_at | H. sapiens HCG V mRNA | 89 | 64 | 103 | 96 | 20 | 20 | 20 |
| X81198_at | H. sapiens mRNA (clone p5) for archain | 70 | 33 | 98 | 59 | 87 | 87 | 53 |
| X81333_at | H. sapiens mRNA for PPH beta subunit protein | 20 | 20 | 22 | 20 | 20 | 20 | 41 |
| X81372_at | H. sapiens mRNA for biphenyl hydrolase-related protein | 20 | 25 | 27 | 21 | 20 | 20 | 20 |
| X81420_at | H. sapiens smRNA for hHKb1 protein | 38 | 40 | 20 | 26 | 177 | 177 | 49 |
| X81438_at | H. sapiens mRNA for amphiphysin | 20 | 20 | 20 | 20 | 20 | 20 | 20 |
| X81479_at | H. sapiens mRNA for EMR1 hormone receptor | 20 | 20 | 20 | 20 | 20 | 20 | 20 |
| X81625_at | H. sapiens mRNA for Cl1 protein | 54 | 48 | 68 | 104 | 20 | 20 | 90 |
| X81636_at | H. sapiens mRNA for clathrin light chain a gene | 20 | 20 | 20 | 20 | 20 | 20 | 20 |
| X81637_at | H. sapiens mRNA for clathrin light chain b gene | 20 | 20 | 20 | 20 | 147 | 147 | 20 |
| X81788_at | H. sapiens DS-1 mRNA | 40 | 50 | 44 | 56 | 20 | 20 | 46 |
| X81817_at | H. sapiens BAP31 mRNA | 266 | 395 | 828 | 944 | 385 | 385 | 371 |
| X81832_s_at | H. sapiens mRNA for glucose-dependant insulinotropic polypeptide receptor gene | 20 | 20 | 20 | 20 | 20 | 20 | 20 |
| X81836_s_at | H. sapiens mRNA for Dents Disease candidate gene | 20 | 20 | 20 | 20 | 57 | 57 | 20 |
| X81851_s_at | H. sapiens IL-4 gene splice variant. /gb=X81851 /ntype=RNA | 36 | 24 | 25 | 24 | 81 | 81 | 24 |
| X81882_at | H. sapiens mRNA for vasopressin activated calcium mobilizing receptor-like protein | 20 | 20 | 20 | 20 | 20 | 20 | 20 |
| X81889_at | H. sapiens mRNA for p0071 protein | 20 | 32 | 20 | 20 | 42 | 42 | 24 |
| X81892_at | H. sapiens mRNA for HE6 Tm7 receptor | 20 | 20 | 20 | 20 | 20 | 20 | 20 |
| X81895_at | H. sapiens mRNA GENX-5624 "mRNA," 3' UTR. /gb=X81895 /ntype=RNA | 20 | 20 | 20 | 20 | 20 | 20 | 20 |
| X82018_at | H. sapiens mRNA for ZID protein | 20 | 20 | 20 | 20 | 20 | 20 | 20 |
| X82068_at | H. sapiens mRNA for glutamate receptor subunit GluRC | 66 | 82 | 87 | 98 | 111 | 111 | 76 |
| X82103_at | H. sapiens mRNA for beta-COP | 20 | 24 | 20 | 20 | 20 | 20 | 20 |
| X82125_at | H. sapiens HOK-2 mRNA for zinc finger protein | 114 | 81 | 20 | 20 | 20 | 20 | 63 |
| X82153_at | H. sapiens mRNA for cathepsin O | 97 | 129 | 131 | 20 | 60 | 60 | 154 |
| X82200_at | H. sapiens Stat50 mRNA | 20 | 20 | 20 | 20 | 20 | 20 | 38 |
| X82206_s_at | H. sapiens mRNA for alpha-centractin | 20 | 36 | 65 | 42 | 20 | 20 | 20 |
| X82207_at | H. sapiens mRNA for beta-cetractin (PC3) | 27 | 20 | 20 | 48 | 23 | 23 | 34 |
| X82209_at | H. sapiens MN1 mRNA | 20 | 20 | 20 | 20 | 20 | 20 | 20 |
| X82224_at | H. sapiens mRNA for glutamine transaminase K | 20 | 20 | 20 | 20 | 20 | 20 | 20 |
| X82240_ma1_at | H. sapiens mRNA for Tcell leukemia/lymphoma 1. | 20 | 20 | 20 | 20 | 20 | 20 | 20 |
| X82279_s_at | H. sapiens "Fas," Apo-1 gene (promoter and exon I). /gb=X82279 /ntype=DNA /annot=EXON | 20 | 24 | 20 | 20 | 20 | 20 | 20 |
| X82324_at | H. sapiens Brain 4 mRNA | 237 | 130 | 137 | 153 | 111 | 111 | 369 |
| X82434_at | H. sapiens mRNA for emerin | 142 | 190 | 389 | 315 | 657 | 657 | 186 |
| X82456_at | H. sapiens MLN50 mRNA | 59 | 20 | 20 | 20 | 20 | 20 | 20 |
| X82494_at | H. sapiens mRNA for fibulin-2 | 59 | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrII | T2GrIII | T2GrIV |
|---|---|---|---|---|---|---|---|---|
| X82539_at | H. sapiens mRNA for MAGE-Xp | 20 | 20 | 20 | 20 | 20 | 20 | 20 |
| X82554_ma1_at | H. sapiens SPHAR gene for cyclin-related protein. | 27 | 39 | 21 | 20 | 20 | 71 | 20 |
| X82629_at | H. sapiens mRNA for Mox-2 | 20 | 20 | 20 | 20 | 20 | 20 | 20 |
| X82634_at | H. sapiens partial mRNA for hair keratin acidic 3-II | 25 | 20 | 20 | 20 | 20 | 42 | 48 |
| X82676_at | H. sapiens mRNA for tyrosine phosphatase | 20 | 20 | 20 | 20 | 20 | 20 | 20 |
| X82693_at | H. sapiens mRNA for E48 antigen | 1046 | 492 | 831 | 1292 | 20 | 287 | 20 |
| X82835_at | H. sapiens mRNA for voltage-activated sodium channel | 20 | 20 | 20 | 20 | 20 | 20 | 20 |
| X82850_s_at | H. sapiens mRNA for thyroid transcript factor 1 | 20 | 20 | 36 | 20 | 20 | 20 | 20 |
| X82877_at | H. sapiens Na+D-glucose cotransport regulator gene | 26 | 41 | 55 | 43 | 20 | 51 | 22 |
| X82895_at | H. sapiens mRNA for DLG2 | 124 | 123 | 128 | 106 | 20 | 364 | 155 |
| X83107_at | H. sapiens Bmx mRNA for cytoplasmic tyrosine kinase | 20 | 20 | 20 | 20 | 20 | 20 | 20 |
| X83127_at | H. sapiens mRNA for voltage gated potassium "channels," beta subunit | 20 | 58 | 72 | 46 | 20 | 38 | 20 |
| X83218_at | H. sapiens mNRA for ATP synthase | 322 | 190 | 288 | 240 | 20 | 97 | 187 |
| X83228_at | H. sapiens mRNA for Ll-cadherin | 20 | 20 | 20 | 20 | 20 | 20 | 20 |
| X83301_s_at | | 20 | 20 | 20 | 20 | 20 | 29 | 20 |
| X83368_at | H. sapiens mRNA for phosphatidylinositol 3 kinase gamma | 34 | 60 | 20 | 20 | 20 | 31 | 20 |
| X83378_at | H. sapiens mRNA for putative chloride channel | 70 | 58 | 72 | 46 | 20 | 38 | 58 |
| X83412_at | H. sapiens B1 mRNA for mucin. | 20 | 20 | 20 | 20 | 20 | 25 | 20 |
| X83416_s_at | H. sapiens PrP "gene," exon 2 | 128 | 139 | 124 | 159 | 20 | 67 | 255 |
| X83425_at | H. sapiens LU gene for Lutheran blood group glycoprotein | 246 | 201 | 351 | 204 | 20 | 324 | 44 |
| X83441_at | H. sapiens mRNA for DNA ligase IV | 20 | 20 | 20 | 20 | 20 | 20 | 20 |
| X83490_s_at | H. sapiens mRNA for Fas/Apo-1 (clone "pCRTM11-Fasdelta(3,4)."/gb=X83490 /ntype=RNA | 31 | 38 | 37 | 20 | 20 | 20 | 367 |
| X83492_at | H. sapiens mRNA for Fas/Apo-1 (clone "pCRTM11-Fasdelta(4,7)."/gb=X83492 /ntype=RNA | 29 | 28 | 22 | 61 | 20 | 935 | 20 |
| X83535_s_at | H. sapiens mRNA for membrane-type matrix metalloproteinase | 20 | 20 | 20 | 20 | 20 | 20 | 20 |
| X83543_at | H. sapiens APXL mRNA | 20 | 26 | 63 | 43 | 20 | 20 | 20 |
| X83572_at | H. sapiens ARSD mRNA | 31 | 51 | 24 | 28 | 20 | 112 | 112 |
| X83573_s_at | H. sapiens ARSE mRNA | 67 | 69 | 60 | 68 | 20 | 60 | 43 |
| X83618_at | H. sapiens mRNA for 3-hydroxy-3-methylglutaryl coenzyme A synthase | 20 | 202 | 384 | 895 | 20 | 194 | 393 |
| X83703_at | H. sapiens mRNA for cytokine inducible nuclear protein | 20 | 20 | 20 | 20 | 20 | 20 | 20 |
| X83705_s_at | | 68 | 20 | 98 | 50 | 20 | 293 | 68 |
| X83857_at | H. sapiens mRNA for prostaglandin E receptor (EP3a1) | 20 | 20 | 20 | 20 | 20 | 20 | 20 |
| X83863_at | H. sapiens mRNA for prostaglandin E receptor (EP3f) | 20 | 20 | 28 | 20 | 20 | 20 | 73 |
| X83928_at | H. sapiens mRNA for transcription factor TFIID subunit TAFII28 | 20 | 20 | 20 | 20 | 20 | 20 | 20 |
| X83929_s_at | H. sapiens mRNA for type 3 desmocollin | 72 | 31 | 42 | 37 | 20 | 169 | 20 |
| X83973_at | H. sapiens mRNA for TTF-I | 37 | 20 | 30 | 20 | 20 | 73 | 64 |
| X84002_at | H. sapiens TAFII20 mRNA for transcription factor TFIID | 20 | 20 | 20 | 20 | 20 | 38 | 20 |
| X84003_at | H. sapiens TAFII18 mRNA for transcription factor TFIID | 20 | 20 | 20 | 20 | 20 | 20 | 20 |
| X84194_at | H. sapiens mRNA for "acylphosphatase," erythrocyte (CT) isoenzyme | 20 | 39 | 20 | 20 | 20 | 20 | 38 |
| X84195_at | H. sapiens mRNA for "acylphosphatase," muscle type (MT) isoenzyme | 29 | 20 | 20 | 20 | 20 | 44 | 20 |
| X84213_s_at | H. sapiens BAK mRNA for BCI-2 homologue | 20 | 20 | 342 | 239 | 20 | 480 | 246 |
| X84373_at | H. sapiens mRNA for nuclear factor RIP140 | 72 | 40 | 49 | 47 | 20 | 26 | 20 |
| X84707_ma1_at | H. sapiens MIA gene. | 28 | 28 | 35 | 20 | 20 | 124 | 80 |
| X84709_at | H. sapiens mRNA for mediator of receptor-induced toxicity | 20 | 67 | 65 | 87 | 20 | 20 | 20 |
| X84740_at | H. sapiens mRNA for DNA ligase III | 48 | 98 | 56 | 54 | 20 | 142 | 125 |
| X84746_at | H. sapiens Histo-blood group AB0 "gene," exon 1 | 20 | 51 | 20 | 20 | 20 | 80 | 34 |
| X84908_at | H. sapiens mRNA for "phosphorylase-kinase," beta subunit | 20 | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X85106_at | H. sapiens mRNA for ribosomal S6 kinase | 20 | 20 | 20 | 20 | 126 | 20 |
| X85116_ma1_s_at | H. sapiens epb72 gene exon 1 | 149 | 331 | 77 | 30 | 20 | 140 |
| X85133_at | H. sapiens RBQ-1 mRNA | 20 | 20 | 20 | 20 | 20 | 20 |
| X85134_ma1_at | H. sapiens RBQ-3 mRNA. | 20 | 20 | 20 | 20 | 20 | 20 |
| X85137_s_at | H. sapiens mRNA for kinesin-related protein | 28 | 90 | 117 | 80 | 326 | 88 |
| X85178_at | H. sapiens SURF-5 mRNA | 20 | 20 | 20 | 20 | 20 | 20 |
| X85237_at | H. sapiens mRNA for splicing factor SF3a120 | 20 | 20 | 20 | 20 | 41 | 20 |
| X85372_at | H. sapiens mRNA for Sm protein F | 87 | 47 | 118 | 113 | 56 | 26 |
| X85373-3at | H. sapiens mRNA for Sm protein G | 155 | 129 | 136 | 113 | 56 | 26 |
| X85545_at | H. sapiens mRN for protein "kinase," PKX1 | 20 | 20 | 20 | 20 | 20 | 20 |
| X85740_at | H. sapiens mRNA for C-C chemokine receptor-4 | 40 | 20 | 20 | 20 | 20 | 100 |
| X85750_at | H. sapiens mRNA for transcript associated with monocyte to macrophage differentiation | 26 | 20 | 20 | 20 | 27 | 20 |
| X85753_at | H. sapiens mRNA for CDK8 protein kinase | 20 | 20 | 20 | 20 | 20 | 20 |
| X85781_s_at | H. sapiens NOS2 "gene," exon 27 /gb=X85781 /ntype=DNA /annot=exon | 20 | 44 | 20 | 20 | 160 | 33 |
| X85785_ma1_at | H. sapiens DARC gene. | 229 | 207 | 80 | 99 | 238 | 306 |
| X85786_at | H. sapiens mRNA for DNA binding regulatory factor | 79 | 34 | 45 | 76 | 57 | 118 |
| X86012_at | Human DNA sequence from intron 22 of the factor VIII "gene," Xq28. Contains the end of a 9.5kb repeated "region," "int22h-1," involved in | 20 | 20 | 40 | 22 | 20 | 20 |
| X86018_at | H. sapiens mRNA for MUF1 protein | 20 | 20 | 63 | 77 | 20 | 81 |
| X86019_at | H. sapiens mRNA for PRPL-2 protein | 20 | 27 | 20 | 20 | 20 | 20 |
| X86098_at | H. sapiens mRNA for BS69 protein | 23 | 25 | 26 | 27 | 27 | 20 |
| X86163_at | H. sapiens mRNA for B2-bradykinin "receptor," 3' | 111 | 55 | 20 | 20 | 20 | 20 |
| X86371_s_at | H. sapiens mRNA for tumour suppressor "protein," HUGL | 20 | 112 | 89 | 134 | 351 | 92 |
| X86400_at | H. sapiens mRNA for gamma subunit of sodium potassium ATPase | 20 | 20 | 20 | 20 | 59 | 20 |
| X86401_s_at | H. sapiens mRNA for L-arginine:glycine amidinotransferase | 20 | 20 | 20 | 20 | 20 | 20 |
| X86428_s_at | H. sapiens gene for phosphotyrosyl phosphatase activator (exon 1) | 20 | 20 | 20 | 20 | 20 | 20 |
| X86564_at | H. sapiens FHR-2 "gene," exon 1 | 20 | 20 | 20 | 20 | 32 | 20 |
| X86570_at | H. sapiens mRNA for acidic hair keratin 1 | 76 | 79 | 55 | 42 | 106 | 71 |
| X86681_at | H. sapiens mRNA for nucleolar "protein," HNP36 | 20 | 20 | 84 | 20 | 20 | 20 |
| X86691_at | H. sapiens mRNA for 218kD mi-2 protein | 142 | 77 | 156 | 115 | 39 | 20 |
| X86693_at | H. sapiens mRNA for hexin like protein | 533 | 212 | 20 | 20 | 22 | 20 |
| X86779_at | H. sapiens mRNA for FAST kinase | 125 | 236 | 185 | 123 | 241 | 325 |
| X86809_at | H. sapiens mRNA for major astrocytic phosphoprotein PEA-15 | 283 | 295 | 93 | 134 | 247 | 326 |
| X86816_at | H. sapiens estrogen receptor "cDNA," 5' splice variant. /gb=X86816 /ntype=RNA | 20 | 20 | 20 | 20 | 20 | 20 |
| X87159_at | H. sapiens mRNA for beta subunit of epithelial amiloride-sensitive sodium channel | 20 | 50 | 143 | 188 | 162 | 25 |
| X87160_at | H. sapiens mRNA for gamma subunit of epithelial amiloride-sensitive sodium channel | 23 | 20 | 29 | 22 | 20 | 60 |
| X87176_at | H. sapiens mRNA for 17-beta-hydroxysteroid dehydrogenase | 75 | 82 | 150 | 104 | 78 | 66 |
| X87211_at | H. sapiens mRNA for anion exchange protein. /gb=X87211 /ntype=RNA | 20 | 20 | 20 | 20 | 61 | 20 |
| X87212_at | H. sapiens mRNA for cathepsin C | 55 | 47 | 49 | 20 | 77 | 320 |
| X87237_at | H. sapiens mRNA for processing α-glucosidase I | 56 | 146 | 144 | 228 | 224 | 244 |
| X87241_at | H. sapiens mRNA for hFat protein | 44 | 28 | 242 | 138 | 20 | 30 |
| X87342_at | H. sapiens mRNA for human giant larvae homolog | 20 | 20 | 21 | 185 | 20 | 20 |
| X87344_cds10_at | DMA gene extracted from H. sapien "DMA," "DMB," "DMB," "HLA-Z1," "IPP2," "LMP2," "TAP1," "LMP7," "TAP2," "DOB," DQB2 and "RING8," "9, | 20 | 20 | 20 | 20 | 108 | 20 |
| X87344_cds10_r_at | DMA gene extracted from H. sapiens "DMA," "DMB," "DMB," "HLA-Z1," "IPP2," "LMP2," "TAP1," "LMP7," "TAP2," "DOB," DQB2 and "RING8," "9, | 227 | 327 | 651 | 351 | 1571 | 683 |
| X87613_at | H. sapiens mRNA for skeletal muscle abundant protein | 20 | 34 | 39 | 41 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X87767_at | H. sapiens CD89 "gene," exon S1. /gb=X87767 /ntype=DNA /annot=exon | 20 | 46 | 30 | 20 | 114 | 77 |
| X87838_at | H. sapiens mRNA for beta-catenin | 248 | 255 | 371 | 278 | 155 | 160 |
| X87843_at | H. sapiens mRNA for cyclin H assembly factor | 20 | 20 | 20 | 20 | 20 | 20 |
| X87852_at | H. sapiens mRNA for SEX gene | 20 | 20 | 20 | 20 | 20 | 20 |
| X87870_at | H. sapiens mRNA for hepatocyte nuclear factor 4a | 33 | 20 | 31 | 20 | 47 | 64 |
| X87871_s_at | H. sapiens mRNA for hepatocyte nuclear factor 4b | 20 | 25 | 83 | 20 | 713 | 161 |
| X87904_at | H. sapiens mRNA for SEP protein | 20 | 25 | 50 | 71 | 71 | 61 |
| X89059_at | H. sapiens mRNA for unknown protein expressed in macrophages | 46 | 42 | 25 | 40 | 97 | 43 |
| X89066_at | H. sapiens mRNA for TRPC1 protein | 20 | 27 | 20 | 20 | 42 | 24 |
| X89067_at | H. sapiens mRNA for trpc2 transcript (possible pseudogene) | 20 | 20 | 20 | 20 | 20 | 20 |
| X89101_s_at | H. sapiens mRNA for Fas "(Apo-1," CD95). /gb=X89101 /ntype=RNA | 20 | 20 | 20 | 20 | 282 | 75 |
| X89109_s_at | H. sapiens mRNA for coronin | 20 | 41 | 44 | 28 | 20 | 140 |
| X89211_at | h. sapiens DNA for endogenous retroviral like element. /gb=X89211 /ntype=DNA /annot=CDS | 38 | 207 | 333 | 249 | 77 | 90 |
| X89267_at | H. sapiens DNA for uroporphyrinogen decarboxylase gene. /gb=X89267 /ntype=DNA /annot=exon | 306 | 20 | 53 | 25 | 172 | 224 |
| X89398_cds2_at | H. sapiens ung gene for uracil DNA-glycosylase. | 20 | 20 | 20 | 20 | 24 | 20 |
| X89399_s_at | H. sapiens mRNA for "Ins(1,3,4,5)P4-binding" protein | 31 | 118 | 49 | 148 | 83 | 193 |
| X89416_at | H. sapiens mRNA for protein phosphatase 5 | 20 | 23 | 20 | 47 | 85 | 265 |
| X89426_at | H. sapiens mRNA for ESM-1 protein | 20 | 20 | 20 | 20 | 31 | 20 |
| X89430_at | H. sapiens mRNA for methyl CpG binding protein 2 | 20 | 35 | 20 | 20 | 144 | 26 |
| X89576_at | H. sapiens mRNA for putative MT4-MMP protein | 20 | 20 | 20 | 20 | 20 | 20 |
| X89750_at | H. sapiens mRNA for TGIF protein | 186 | 145 | 194 | 154 | 182 | 233 |
| X89894_at | H. sapiens mRNA for nuclear receptor | 20 | 40 | 22 | 20 | 47 | 20 |
| X89960_at | H. sapiens mRNA for mitochondrial capsule selenoprotein | 130 | 172 | 99 | 98 | 163 | 82 |
| X89984_at | H. sapiens mRNA for BCL7A protein | 20 | 44 | 20 | 20 | 28 | 20 |
| X89885_at | H. sapiens mRNA for BCL7B protein | 36 | 20 | 40 | 20 | 20 | 91 |
| X89986_s_at | H. sapiens mRNA for NBK apoptotic inducer protein | 25 | 20 | 20 | 20 | 240 | 43 |
| X90392_at | H. sapiens mRNA for DNase X gene | 20 | 20 | 72 | 70 | 30 | 20 |
| X90530_at | H. sapiens mRNA for ragB protein | 46 | 88 | 98 | 78 | 226 | 79 |
| X90568_at | H. sapiens mRNA for titin protein (clone hh1-hh54) | 20 | 20 | 20 | 20 | 20 | 20 |
| X90761_at | H. sapiens hHa2 gene | 72 | 89 | 92 | 66 | 228 | 251 |
| X90863_at | H. sapiens mRNA for type I "keratin," hHa5 | 57 | 65 | 42 | 53 | 151 | 80 |
| X90780_ma1_at | H. sapiens cardiac troponin I gene, exons 1 to 5. | 20 | 20 | 20 | 20 | 20 | 20 |
| X90824_s_at | H. sapiens mRNA for USF2a & "USF2b," clone P9DH | 20 | 218 | 82 | 127 | 193 | 121 |
| X90828_at | H. sapiens mRNA for transcription "factor," Lbx1 | 27 | 27 | 20 | 20 | 64 | 20 |
| X90840_at | H. sapiens mRNA for axonal transporter of synaptic vesicles | 40 | 20 | 20 | 24 | 52 | 75 |
| X90846_at | H. sapiens mRNA for mixed lineage kinase 2 | 123 | 214 | 457 | 276 | 2099 | 604 |
| X90846_s_at | H. sapiens mRNA for −14 "gene," containing globin regulatory element | 20 | 20 | 20 | 20 | 20 | 20 |
| X90857_at | H. sapiens mRNA for uridine phosphorylase | 285 | 42 | 81 | 58 | 38 | 58 |
| X90858_at | H. sapiens mRNA for gp25L2 protein | 148 | 113 | 241 | 210 | 74 | 143 |
| X90872_at | H. sapiens mRNA for 1-15P (I-BABP) protein | 20 | 63 | 94 | 75 | 135 | 150 |
| X90908_at | H. sapiens mRNA for an acute myeloid leukaemia protein (3917bp) | 20 | 20 | 20 | 20 | 20 | 77 |
| X90976_s_at | H. sapiens mRNA for an acute myeloid leukaemia protein (1793bp) | 75 | 40 | 60 | 40 | 211 | 144 |
| X90978_at | H. sapiens mRNA for Glyoxalase II | 20 | 27 | 28 | 51 | 22 | 20 |
| X90999_at | H. sapiens mRNA for Hr44 protein. /gb=X91103 /ntype=RNA | 20 | 32 | 20 | 20 | 109 | 74 |
| X91103_at | H. sapiens HG NF7 gene exon 1. | 41 | 59 | 33 | 25 | 62 | 105 |
| X91117_ma1_at | H. sapiens mRNA for RABAPTIN-5 protein | 20 | 20 | 20 | 20 | 20 | 27 |
| X91141_at | | | | | | | |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X91148_at | H. sapiens mRNA for microsomal triglyceride transfer protein | 20 | 20 | 20 | 20 | 20 | 20 |
| X91196_s_at | H. sapiens mRNA for E14 and A–T proteins. /gb=X91196 /ntype=RNA | 20 | 22 | 27 | 27 | 81 | 24 |
| X91220_at | H. sapiens mRNA for Na—Cl electroneutral thiazide-sensitive cotransporter | 20 | 20 | 20 | 20 | 20 | 34 |
| X91247_at | H. sapiens mRNA for thioredoxin reductase | 258 | 84 | 81 | 57 | 202 | 131 |
| X91249_at | H. sapiens mRNA for white gene protein | 20 | 31 | 71 | 43 | 66 | 39 |
| X91257_at | H. sapiens mRNA for seryl-tRNA synthetase | 249 | 266 | 289 | 234 | 251 | 334 |
| X91348_at | H. sapiens predicted non coding cDNA (DGCR5) | 20 | 20 | 20 | 20 | 20 | 20 |
| X91504_at | H. sapiens mRNA for ARP1 protein | 360 | 256 | 369 | 310 | 428 | 273 |
| X91648_at | H. sapiens mRNA for pur alphae extended 3′untranslated region | 20 | 20 | 20 | 20 | 31 | 20 |
| X91653_s_at | H. sapiens DNA for exon encoding for N-acetylglucosaminyltransferase V (340 bp). /gb=X91653 /ntype=DNA /annot=exon | 20 | 20 | 20 | 20 | 20 | 20 |
| X91788_at | H. sapiens mRNA for icin protein | 65 | 60 | 84 | 62 | 65 | 20 |
| X91809_at | H. sapiens mRNA for GAIP protein | 127 | 140 | 99 | 90 | 197 | 263 |
| X91868_at | H. sapeins mRNA for SIX1protein | 20 | 20 | 20 | 21 | 97 | 20 |
| X91911_s_at | H. sapiens mRNA for RTVP-1 protein | 20 | 20 | 20 | 20 | 20 | 20 |
| X91992_at | H. sapiens mRNA for alkB protein homolog | 20 | 20 | 20 | 20 | 79 | 20 |
| X92098_at | H. sapiens mRNA for transmembrane protein mp24 | 113 | 51 | 136 | 136 | 20 | 90 |
| X92106_at | H. sapiens mRNA for bleomycin hydrolase | 32 | 20 | 33 | 30 | 51 | 90 |
| X92110_at | H. sapiens mRNA for hcgVIII protein | 27 | 20 | 31 | 24 | 20 | 20 |
| X92368_at | H. sapiens ncx1 gene (exon 1). /gb=X92368 /ntype=DNA /annot=mRNA | 24 | 88 | 80 | 20 | 74 | 20 |
| X92396_at | H. sapiens mRNA for novel gene in Xq28 region | 48 | 49 | 31 | 35 | 20 | 241 |
| X92475_at | H. sapiens mRNA for ITBA1 protein | 75 | 113 | 80 | 64 | 253 | 20 |
| X92493_s_at | H. sapiens mRNA for STM-7 protein | 33 | 47 | 20 | 21 | 20 | 121 |
| X92518_s_at | H. sapiens mRNA for HMGI-C protein | 61 | 105 | 151 | 78 | 323 | 47 |
| X92521_at | H. sapiens mRNA for MMP-19 protein | 39 | 50 | 40 | 41 | 84 | 87 |
| X92689_at | H. sapiens mRNA for UDP-GalNAc:polypeptide N-acetylgalactosaminyl transferase. /gb=X92689 /ntype=RNA | 26 | 20 | 24 | 41 | 20 | 53 |
| X92715_at | H. sapiens mRNA for ZNF74 protein | 21 | 20 | 35 | 20 | 69 | 20 |
| X92720_at | H. sapiens mRNA for phosphoenolpyruvate carboxykinase | 65 | 80 | 79 | 20 | 111 | 60 |
| X92744_at | H. sapiens mRNA for hBD-1 protein | 94 | 60 | 20 | 20 | 34 | 241 |
| X92762_at | H. sapiensm mRNA for tafazzins protein | 39 | 62 | 50 | 50 | 197 | 20 |
| X92814_at | H. sapiens mRNA for rat HREV107-like protein | 79 | 102 | 62 | 61 | 120 | 116 |
| X92896_at | H. sapiens mRNA for ITBA2 protein | 53 | 108 | 62 | 41 | 20 | 124 |
| X92972_at | H. sapiens mRNA for protein phosphatase 6 | 37 | 20 | 22 | 26 | 20 | 192 |
| X93017_at | H. sapiens ncx2 gene (exon 2). /gb=X93017 /ntype=DNA /annot=exon | 20 | 20 | 20 | 20 | 99 | 38 |
| X93036_at | H. sapiens mRNA for MAT8 protein | 730 | 1232 | 2161 | 3762 | 1307 | 55 |
| X93498_at | H. sapiens mRNA for 21-Glutamic Acid-Rich Protein (21-GARP) | 20 | 23 | 20 | 20 | 20 | 851 |
| X93499_at | H. sapiens mRNA for RAB7 protein | 95 | 20 | 44 | 61 | 113 | 20 |
| X93510_at | H. sapiens mRNA for 37 kDa LIM domain protein | 43 | 54 | 103 | 56 | 20 | 20 |
| X93511_s_at | H. sapiens mRNA for telomeric DNA binding protein (orf1) | 37 | 20 | 20 | 91 | 91 | 37 |
| X93512_at | H. sapiens mRNA for telomeric DNA binding protein (orf2) | 20 | 20 | 20 | 66 | 20 | 20 |
| X93920_at | H. sapiens mRNA for protein-tyrosine-phosphatase (tissue type: foreskin) | 59 | 61 | 77 | 59 | 33 | 65 |
| X93921_at | H. sapiens mRNA for protein-tyrosine-phosphatase (tissue type: testis) | 76 | 20 | 43 | 20 | 20 | 20 |
| X93996_ma1_at | H. sapiens mRNA for AFX protein | 201 | 211 | 219 | 211 | 517 | 199 |
| X94232_at | H. sapiens mRNA for novel T-cell activation protein | 44 | 51 | 20 | 50 | 20 | 69 |
| X94333_at | H. sapiens mRNA for TGN46 protein | 20 | 20 | 20 | 20 | 20 | 20 |
| X94453_at | H. sapiens mRNA for pyrroline 5-carboxylate synthetase | 20 | 24 | 20 | 39 | 20 | 20 |
| X94563_xpt2_r_at | exon 1b; used only in type 2 transcripts from H. sapiens dbi/acbp gene exon 1 & 2 /gb=X94563 /ntype=DNA /annot=exon | 171 | 255 | 576 | 600 | 3021 | 1445 |
| X94612_at | H. sapiens mRNA for type II cGMP-dependent protein kinase | 20 | 111 | 20 | 23 | 35 | 45 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X94628_ma1_s_at | H. sapiens MeCP-2 gene | 20 | 20 | 20 | 20 | 20 | 20 |
| X94629_at | H. sapiens mRNA for metaphase chromosmal protein | 20 | 20 | 20 | 20 | 20 | 20 |
| X94703_at | H. sapiens rab28 mRNA | 20 | 20 | 20 | 20 | 38 | 20 |
| X94754_at | h. sapiens mRNA for yeast methionyl-tRNA synthetase homologue | 59 | 93 | 96 | 101 | 142 | 228 |
| X94910_at | H. sapiens mRNA for ERp31 protein | 32 | 20 | 155 | 129 | 20 | 20 |
| X95073_at | H. sapiens mRNA for translin associated protein X | 20 | 20 | 20 | 20 | 139 | 23 |
| X95095_at | H. sapiens mRNA for PDGFRalpha protein. /gb=X95095 /ntype=RNA | 20 | 23 | 94 | 20 | 20 | 20 |
| X95097_ma1_s_at | H. sapiens mRNA for VIP2 receptor | 20 | 38 | 20 | 20 | 20 | 38 |
| X95152_ma1_at | H. sapiens brca2 gene exon 2 (and joined coding region). | 20 | 20 | 20 | 20 | 20 | 20 |
| X95190_at | H. sapiens mRNA for Brached chain Aceyl-CoA Oxidase | 20 | 20 | 20 | 20 | 20 | 20 |
| X95191_at | H. sapiens mRNA for delta-sarcoglycan. /gb=X95191 /ntype=RNA | 20 | 20 | 20 | 20 | 26 | 20 |
| X95237_at | H. sapiens mRNA for cysteine-rich secretory protein-1 | 20 | 20 | 20 | 20 | 20 | 20 |
| X95239_at | H. sapiens mRNA for cystein-rich secretory protein-2/type I | 20 | 20 | 20 | 20 | 20 | 20 |
| X95240_s_at | H. sapiens mRNA for cysteine-rich secretory protein-3 | 626 | 20 | 20 | 20 | 20 | 20 |
| X95289_at | H. sapiens mRNA for HCGIX protein | 20 | 20 | 20 | 20 | 20 | 20 |
| X95325_s_at | H. sapiens mRNA for DNA binding protein A variant | 340 | 60 | 362 | 293 | 116 | 177 |
| X95384_at | H. sapiens mRNA for unknown 14kDa protein | 20 | 23 | 20 | 20 | 20 | 20 |
| X95404_at | H. sapiens mRNA for non-muscle type cofillin | 960 | 1170 | 1079 | 1298 | 1655 | 1534 |
| X95406_at | H. sapiens cyclin E gene. | 76 | 119 | 51 | 45 | 20 | 26 |
| X95425_s_at | H. sapiens mRNA for EHK-1 receptor tyrosine kinase | 20 | 20 | 20 | 20 | 128 | 20 |
| X95463_s_at | H. sapiens mRNA for ox19 protein | 20 | 20 | 20 | 20 | 20 | 20 |
| X95525_at | H. sapiens mRNA for TAFII100 protein | 22 | 20 | 32 | 20 | 20 | 20 |
| X95586_at | H. sapiens MB1 gene | 160 | 187 | 195 | 189 | 153 | 220 |
| X95592_at | H. sapiens mRNA for C1D protein | 25 | 20 | 20 | 20 | 20 | 64 |
| X95632_s_at | H. sapiens mRNA for Arg protein tyrosine kinase-binding protein | 20 | 35 | 20 | 20 | 261 | 20 |
| X95648_at | H. sapiens mRNA for elF-28 alpha subunit | 20 | 20 | 25 | 20 | 56 | 20 |
| X95654_at | H. sapiens mRNA for SCP1 protein | 20 | 20 | 20 | 20 | 55 | 20 |
| X95677_at | H. sapiens mRNA for ArgBPIB protein. /gb=X95677 /ntype=RNA | 20 | 20 | 20 | 20 | 20 | 20 |
| X95715_at | H. sapiens mRNA for anthracycline resistance associated protein | 20 | 20 | 20 | 20 | 20 | 20 |
| X95735_at | H. sapiens mRN for zyxin 2 | 112 | 20 | 36 | 43 | 119 | 91 |
| X95808_s_at | H. sapiens mRN for protein encoded by a candidate "gene," "DXS6673E," for mental retardation | 28 | 159 | 206 | 171 | 20 | 39 |
| X95826_at | H. sapiens ART4 gene. /gb=X95826 /ntype=DNA /annot=CDS | 20 | 20 | 20 | 20 | 20 | 20 |
| X95876_at | H. sapiens mRNA for G-protein couled receptor | 20 | 20 | 20 | 20 | 20 | 20 |
| X96381_ma1_at | H. sapiens erm gene, exon 2,3,4,5 (and joined CDS). | 27 | 20 | 23 | 20 | 20 | 20 |
| X96401_at | H. sapiens mRNA for ROX protein | 121 | 32 | 38 | 34 | 389 | 283 |
| X96484_at | H. sapiens mRNA for DGCR6 protein | 154 | 163 | 163 | 107 | 71 | 206 |
| X96506_s_at | H. sapiens mRNA for NC2 alpha subunit | 190 | 245 | 1315 | 254 | 778 | 380 |
| X96584_at | H. sapiens mRNA for NOV protein | 20 | 20 | 20 | 20 | 20 | 20 |
| X96586_at | H. sapiens mRN for FAN protein | 42 | 56 | 56 | 58 | 20 | 35 |
| X96698_at | H. sapiens mRNA for D1075-like gene | 52 | 39 | 32 | 30 | 49 | 49 |
| X96719_at | H. sapiens mRNA for AICL (activation-induced C-type lectin) | 120 | 104 | 20 | 20 | 66 | 56 |
| X96752_at | H. sapiens mRNA for L-3-hydroxyacyl-CoA dehydrogenase | 20 | 36 | 47 | 50 | 20 | 79 |
| X96753_at | H. sapiens mRNA for melanoma-associated chondroitin sulfate proteoglycan (MCSP) | 20 | 20 | 20 | 20 | 31 | 20 |
| X96754_at | H. sapiens gene encoding kappa light chain constant regin. | 20 | 20 | 20 | 20 | 20 | 20 |
| X96783_ma1_at | H. saiens Syt V gene (genomic and cDNA sequence). | 20 | 69 | 54 | 51 | 20 | 175 |
| X96849_at | H. sapiens 5' mRNA of PECAM-1 molecule. /gb=X96849 /ntype=RNA | 20 | 104 | 347 | 309 | 20 | 245 |
| X96924_ma1_at | H. sapiens gene encoding mitochondrial citrate transport protein. | 212 | 104 | 347 | 309 | 113 | 245 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X96969_at | H. sapiens mRNA for urea transporter | 56 | 21 | 67 | 44 | 94 | 104 |
| X97058_at | H. sapiens mRNA for P2Y6 receptor | 23 | 42 | 20 | 26 | 34 | 77 |
| X97064_at | H. sapiens mRNA for Sec23A "isoform," 2748bp | 20 | 20 | 20 | 20 | 28 | 20 |
| X97065_at | H. sapiens mRNA for Sec23B "isoform," 2450bp | 63 | 20 | 51 | 58 | 20 | 84 |
| X97074_at | H. sapiens mRNA for clathrin-associated protein | 247 | 148 | 113 | 128 | 140 | 231 |
| X97160_ma1_at | H. sapiens TFE3 gene, exons 1,2,3 (and joined CDS). | 101 | 91 | 69 | 75 | 121 | 140 |
| X97198_at | H. sapiens mRNA for receptor phosphate PCP-2 | 24 | 43 | 80 | 84 | 140 | 53 |
| X97230_f_at | H. sapiens mRNA for NK "receptor," clone library 4M1#6 | 46 | 29 | 96 | 20 | 152 | 67 |
| X97249_at | H. sapiens mRNA for leucine-rich primary response protein 1 | 41 | 40 | 43 | 26 | 20 | 68 |
| X97261_at | H. sapiens mRNA for metallothionein isoform 1R | 40 | 20 | 20 | 27 | 55 | 45 |
| X97261_r_at | H. sapiens mRNA for metallothionein isoform 1R | 20 | 20 | 20 | 20 | 20 | 20 |
| X97267_ma1_s_at | H. sapiens LPAP gene | 20 | 20 | 20 | 20 | 20 | 199 |
| X97301_at | H. sapiens mRNA for Ptg-11 protein. /gb=X97301 /ntype=RNA | 20 | 20 | 20 | 30 | 20 | 20 |
| X97302_at | H. sapiens mRNA for Ptg-1 protein. /gb=X97302 /ntype=RNA | 90 | 100 | 108 | 79 | 217 | 145 |
| X97303_at | H. sapiens mRNA for Ptg-12 protein. /gb=X97303 /ntype=RNA | 20 | 20 | 20 | 20 | 20 | 55 |
| X97324_at | H. sapiens mRNA for adipophilin. /gb=X97324 /ntype=RNA | 20 | 20 | 141 | 65 | 20 | 186 |
| X97335_at | H. sapiens mRNA for kinase A anchor protein | 20 | 20 | 25 | 45 | 20 | 20 |
| X97444_f_at | H. sapiens mRNA for transmembrane protein Tmp21-Ilex. /gb=X97444 /ntype=RNA | 50 | 20 | 93 | 80 | 20 | 40 |
| X97544_at | H. sapiens mRNA for TIM17 preprotein transfocase | 24 | 36 | 50 | 49 | 46 | 28 |
| X97630_at | H. sapiens mRNA for serine/threonine protein kinase EMK | 20 | 21 | 21 | 20 | 62 | 20 |
| X97671_at | H. sapiens mRNA for erythropoietin receptor | 20 | 20 | 20 | 20 | 32 | 20 |
| X97674_at | H. sapiens mRNA for transcriptional intermediary factor 2 | 20 | 20 | 20 | 20 | 20 | 20 |
| X97675_ma1_at | H. sapiens mRNA for pfakophilin 2a and b. | 20 | 20 | 20 | 20 | 31 | 20 |
| X97748_s_at | H. sapiens PTX3 gene promotor region. /gb=X97748 /ntype=DNA /annot=mRNA | 20 | 20 | 20 | 20 | 20 | 20 |
| X97795_at | H. sapiens mRNA homologous to S. cerevisiae RAD54 | 20 | 20 | 48 | 20 | 20 | 20 |
| X98001_at | H. sapiens mRNA for geranylgeranyl transferase II | 70 | 45 | 20 | 42 | 20 | 20 |
| X98085_at | H. sapiens mRNA for tenascin-R | 225 | 202 | 186 | 215 | 173 | 226 |
| X98172_at | H. sapiens mRNA for MACH-alpha-1 protein | 45 | 42 | 65 | 43 | 64 | 45 |
| X98176_at | H. sapiens mRNA for MACH-beta-1 protein. /gb=X98176 /ntype=RNA | 24 | 30 | 22 | 35 | 20 | 20 |
| X98178_s_at | H. sapiens mRNA for MACH-beta-4 protein. /gb=X98178 /ntype=RNA | 20 | 20 | 31 | 25 | 20 | 20 |
| X98206_at | H. sapiens mRNA for UV-B repressed "sequence," HUR 8 /gb=X98206 /ntype=RNA | 43 | 35 | 67 | 42 | 20 | 41 |
| X98225_at | H. sapiens mRNA for gastrin-binding protein. /gb=X98225 /ntype=RNA | 81 | 55 | 91 | 79 | 80 | 118 |
| X98248_ma1_at | H. sapiens mRNA for sortilin. | 89 | 56 | 103 | 64 | 170 | 77 |
| X98253_at | H. sapiens ZNF183 gene. /gb=X98253 /ntype=RNA | 20 | 20 | 20 | 20 | 20 | 20 |
| X98258_at | H. sapiens mRNA for M-phase "phoaphoprotein," mpp9 | 23 | 62 | 114 | 87 | 85 | 84 |
| X98260_at | H. sapiens mRNA for M-phase "phosphoprotein," mpp11 | 84 | 169 | 143 | 170 | 176 | 51 |
| X98261_at | H. sapiens mRNA for M-phase "phosphoprotein," mpp5 | 43 | 20 | 21 | 20 | 104 | 20 |
| X98263_at | H. sapiens mRNA for M-phase "phosphoprotein," mpp6 | 154 | 113 | 20 | 20 | 20 | 20 |
| X98266_cds2_at | H. sapiens mRNA for ligase like protein, X-1. | 20 | 20 | 20 | 20 | 20 | 20 |
| X98296_at | H. sapiens mRNA for ubiquitin hydrolase | 39 | 26 | 46 | 33 | 59 | 23 |
| X98307_at | H. sapiens mRNA for UV-B repressed "sequence," HUR 7 | 105 | 97 | 63 | 76 | 97 | 20 |
| X98311_at | H. sapiens mRNA for carcinoembryonic "antigen," CGM2 | 20 | 20 | 20 | 20 | 90 | 80 |
| X98330_at | H. sapiens mRNA for ryanodine receptor 2 | 20 | 20 | 20 | 20 | 181 | 38 |
| X98337_s_at | H. sapiens mRNA for complement factor H-related protein 4 | 20 | 20 | 20 | 20 | 20 | 20 |
| X98411_at | H. sapiens mRNA for myosin-IE | 20 | 20 | 20 | 20 | 20 | 20 |
| X98482_at | H. sapiens TNNT2 gene exon 11 /gb=X98482 /ntype=DNA /annot=mRNA | 20 | 20 | 20 | 20 | 20 | 20 |
| X98482_r_at | H. sapiens TNNT2 gene exon 11 /gb=X98482 /ntype=DNA /annot=mRNA | 3885 | 2448 | 5047 | 2490 | | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| X98507_at | H. sapiens mRNA for myosin-I beta | 23 | 45 | 38 | 37 | 123 | 72 |
| X98534_s_at | H. sapiens VASP "gene," exons 4 to 13 | 48 | 180 | 126 | 156 | 20 | 75 |
| X98743_at | H. sapiens mRNA for RNA helicase (Myc-regulated dead box protein) | 84 | 58 | 105 | 82 | 58 | 106 |
| X98801_at | H. sapiens mRNA for dynactin | 69 | 87 | 90 | 81 | 248 | 133 |
| X98833_ma1_at | H. sapiens mRNA for zinc finger protein, Hsal1 | 20 | 20 | 20 | 20 | 63 | 20 |
| X98834_ma1_at | H. sapiens mRNA for zinc finger protein, Hsal2 | 20 | 20 | 34 | 20 | 62 | 20 |
| X99050_ma1_at | H. sapiens mRNA; UV Radiation Resistance Associated Gene | 37 | 53 | 24 | 29 | 48 | 74 |
| X99076_ma1_at | H. sapiens NRGN gene, exons 2,3 & 4 (joined CDS). | 20 | 20 | 20 | 31 | 20 | 20 |
| X99101_at | H. sapiens mRNA for estrogen receptor. | 30 | 38 | 31 | 22 | 20 | 20 |
| X99133_at | H. sapiens NGAL gene | 384 | 1351 | 20 | 20 | 50 | 78 |
| X99140_at | H. sapiens mRNA for hair "keratin," hHb5 | 20 | 22 | 20 | 20 | 420 | 20 |
| X99141_at | H. sapiens mRNA for hair "keratin," hHb3 | 105 | 124 | 85 | 65 | 68 | 224 |
| X99142_at | H. sapiens mRNA for hair "keratin," hHb6 | 135 | 20 | 75 | 65 | 283 | 82 |
| X99209_at | H. sapiens mRNA for arginine methyltransferase | 82 | 170 | 226 | 110 | 35 | 156 |
| X99226_at | H. sapiens mRNA for FAA protein | 20 | 51 | 20 | 28 | 201 | 40 |
| X99268_at | H. sapiens mRNA for B-HLH DNA binding protein | 20 | 20 | 20 | 20 | 20 | 20 |
| X99296_xpt1_at | H. sapiens RD gene (5' partial) and G11a gene (5' partial). | 20 | 20 | 20 | 20 | 73 | 20 |
| X99325_at | H. sapiens mRNA for Ste20-like kinase | 63 | 50 | 145 | 100 | 100 | 77 |
| X99350_ma1_at | H. sapiens HFH4 gene, exon 1 and joined CDS. | 20 | 20 | 20 | 20 | 122 | 20 |
| X99374_s_at | H. sapiens mRNA for fertilin beta | 20 | 20 | 20 | 20 | 20 | 40 |
| X99393_s_at | H. sapiens CMKBR5 "gene," non-functional mutant | 20 | 20 | 34 | 20 | 89 | 33 |
| X99459_at | H. sapiens mRNA for sigma 3B protein | 141 | 176 | 148 | 155 | 199 | 215 |
| X99479_f_at | H. sapiens mRNA for NK "receptor," clone 12.11C | 20 | 20 | 20 | 20 | 73 | 72 |
| X99584_at | H. sapiens mRNA for SMT3A protein | 27 | 28 | 28 | 27 | 49 | 20 |
| X99585_at | H. sapiens mRNA for SMT3B protein | 206 | 93 | 185 | 210 | 115 | 288 |
| X99586_at | H. sapiens mRNA for SMT3C protein | 20 | 20 | 20 | 20 | 20 | 20 |
| X99656_at | H. sapiens mRNA for protein containing SH3 "domain," SH3GL1 | 21 | 20 | 20 | 20 | 30 | 28 |
| X99657_at | H. sapiens mRNA for protein containing SH3 "domain," SH3GL2 | 20 | 20 | 20 | 20 | 20 | 20 |
| X99664_at | H. sapiens mRNA for protein containing SH3 "domain," SH3GL3 | 31 | 20 | 39 | 29 | 20 | 71 |
| X99687_at | H. sapiens mRNA for methyl-CpG-binding protein "2," intron 2 /gb=X99687 /ntype=RNA | 51 | 23 | 46 | 31 | 85 | 38 |
| X99688_at | H. sapiens mRNA from TYL gene | 242 | 355 | 283 | 213 | 543 | 447 |
| X99699_at | H. sapiens mRNA for XIAP associated factor-1 | 24 | 38 | 40 | 20 | 23 | 43 |
| X99720_ma1_at | H. sapiens TPRC gene. | 20 | 20 | 20 | 42 | 71 | 40 |
| X99728_at | H. sapiens NDUFV3 "gene," exon 3 /gb=X99726 /ntype=DNA /annot=exon | 109 | 110 | 87 | 116 | 165 | 210 |
| X99802_at | H. sapiens mRNA for ZYG homologue | 20 | 20 | 20 | 20 | 20 | 20 |
| X99886_s_at | H. sapiens MCP-2 gene | 40 | 20 | 20 | 20 | 75 | 20 |
| X99894_at | H. sapiens mRNA coding for insulin promoter factor 1 | 20 | 20 | 20 | 20 | 20 | 20 |
| X99897_s_at | H. sapiens mRNA for P/Q-type calcium channel alpha1 subunit | 20 | 20 | 20 | 20 | 20 | 51 |
| X99920_at | H. sapiens mRNA for S100 calcium-binding protein A13 | 145 | 176 | 108 | 131 | 20 | 20 |
| X99947_at | H. sapiens mRNA dynein-related protein | 32 | 20 | 20 | 20 | 58 | 38 |
| X99961_at | H. sapiens mRNA for novel protein. /gb=X99961 /ntype=RNA | 20 | 20 | 20 | 20 | 20 | 20 |
| X99975_at | H. sapiens mRNA for hRTR/hGCNG protein | 20 | 88 | 88 | 63 | 244 | 65 |
| Y00062_at | Human mRNA for T200 leukocyte common antigen "(CD45)," LC-A) | 44 | 46 | 20 | 20 | 21 | 118 |
| Y00064_at | Human mRNA for secretogranin I (chromogranin B) | 20 | 20 | 25 | 20 | 58 | 46 |
| Y00067_ma1_at | Human gene for neurofilament subunit M (NF-M). | 20 | 20 | 20 | 20 | 32 | 20 |
| Y00081_s_at | Human (BSF-2/IL6) gene for B cell stimulatory factor-2 | 99 | 20 | 20 | 20 | 20 | 20 |
| Y00083_s_at | Human mRNA for glioblastoma-derived T-cell suppressor factor G-TsF (transforming growth "factor-beta2," TGF-beta2) | 27 | 20 | 20 | 20 | 34 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| Y00097_s_at | Human mRNA for protein p68 | 82 | 123 | 88 | 81 | 20 | 66 |
| Y00264_at | Human mRNA for amyloid A4 precursor of Alzheimer's disease | 183 | 302 | 547 | 295 | 161 | 83 |
| Y00281_at | Human mRNA for ribophorin I | 272 | 244 | 398 | 291 | 343 | 295 |
| Y00282_at | Human mRNA for ribophorin II | 199 | 435 | 408 | 353 | 333 | 234 |
| Y00285_s_at | Human mRNA for insuline-like growth factor II receptor | 20 | 20 | 45 | 34 | 20 | 20 |
| Y00291_at | Human hep mRNA encoding a DNA-binding hormone receptor | 20 | 20 | 20 | 20 | 20 | 20 |
| Y00317_at | Human mRNA for liver microsomal UDP-glucuronosyltransferase (UDPGT) | 20 | 20 | 20 | 22 | 20 | 20 |
| Y00318_at | Human mRNA for complement control protein factor I | 20 | 20 | 22 | 22 | 20 | 67 |
| Y00339_s_at | Human mRNA for carbonic anhydrase II (EC 4.2.1.1) | 20 | 31 | 22 | 22 | 20 | 20 |
| Y00414_s_at | Human mRNA mRNA for tyrosine hydroxylase type 3 | 20 | 70 | 164 | 235 | 569 | 103 |
| Y00433_at | Human mRNA for glutathione peroxidase (EC 1.11.1.9.) | 708 | 1027 | 928 | 1119 | 603 | 1281 |
| Y00451_s_at | Human mRNA for 5-aminolevulnate synthase | 73 | 125 | 178 | 274 | 187 | 155 |
| Y00477_at | Human bone marrow serine protease gene (medullasin) (leukocyte neutrophil elastase gene) | 50 | 61 | 113 | 68 | 20 | 32 |
| Y00486_ma1_at | Human APRT gene for adenine phosphoribosyltransferase. | 307 | 278 | 341 | 332 | 491 | 354 |
| Y00503_at | Human mRNA for keratin 19 | 452 | 772 | 1649 | 2051 | 645 | 660 |
| Y00636_at | Human mRNA for lymphocyte function associated antigen-3 (LFA-3) | 20 | 20 | 20 | 32 | 20 | 20 |
| Y00705_at | Homo sapiens psti mRNA for pancreatic secretory inhibitor (expressed in neoplastic tissue). | 20 | 2124 | 2217 | 2756 | 822 | 2168 |
| Y00757_at | Human mRNA for polypeptide 7B2 | 20 | 20 | 20 | 20 | 20 | 20 |
| Y00764_at | Human mRNA for mitochondrial hinge protein | 347 | 335 | 443 | 451 | 221 | 336 |
| Y00787_s_at | Human mRNA for MDNCF (monocyte-derived neutrophil chemotactic factor) | 224 | 127 | 20 | 38 | 855 | 393 |
| Y00796_at | Human mRNA for leukocyte-associated molecule-1 alpha subunit (LFA-1 alpha subunit) | 33 | 25 | 31 | 24 | 127 | 70 |
| Y00815_at | Human mRNA for LCA-homolog, LAR protein (leukocyte antigen related) | 101 | 137 | 326 | 337 | 189 | 167 |
| Y07512_at | Human mRNA for type I beta cGMP-dependent protein kinase (EC 2.7.1.37) | 20 | 20 | 20 | 23 | 20 | 20 |
| Y07565_s_at | H. sapiens mRNA for RIN protein | 20 | 20 | 35 | 29 | 31 | 20 |
| Y07566_at | H. sapiens mRNA for RIT protein | 23 | 20 | 20 | 20 | 20 | 31 |
| Y07595_at | H. sapiens mRNA for 52 kD subunit of transcription factor TFIIH | 24 | 20 | 20 | 20 | 20 | 31 |
| Y07596_at | H. sapiens mRNA for GPI8 protein | 33 | 20 | 20 | 25 | 20 | 37 |
| Y07604_at | H. sapiens mRNA for nucleoside-diphosphate kinase | 53 | 55 | 60 | 59 | 20 | 54 |
| Y07683_at | H. sapiens mRNA for P2X3 purinoceptor. /gb=Y07683 /ntype=RNA | 20 | 20 | 20 | 20 | 20 | 20 |
| Y07701_at | H. sapiens mRNA for aminopeptidase | 88 | 39 | 20 | 64 | 77 | 48 |
| Y07707_at | H. sapiens mRNA for ITBA4 gene. /gb=Y07707 /ntype=RNA | 28 | 12 | 180 | 152 | 123 | 37 |
| Y07755_at | H. sapiens S100A2 "gene," exon "1," 2 and 3 | 20 | 20 | 20 | 27 | 39 | 20 |
| Y07759_at | H. sapiens mRNA for myosin heavy chain 12 | 20 | 38 | 20 | 28 | 20 | 20 |
| Y07827_s_at | H. sapiens mRNA for put. "B7.3" molecule of CD80-CD60 protein family | 2378 | 1877 | 1159 | 596 | 415 | 107 |
| Y07828_at | H. sapiens mRNA for RING protein | 20 | 20 | 20 | 20 | 20 | 38 |
| Y07829_xpt3_at | H. sapiens gene encoding RING finger protein. | 20 | 20 | 20 | 20 | 20 | 44 |
| Y07829_xpt4_at | H. sapiens gene encoding RING finger protein. | 20 | 21 | 20 | 21 | 20 | 20 |
| Y07846_at | H. sapiens mRNA for GAR22 protein | 51 | 89 | 76 | 69 | 175 | 80 |
| Y07847_at | H. sapiens mRNA for RRP22 protein | 46 | 70 | 86 | 58 | 85 | 20 |
| Y07867_at | H. sapiens mRNA for "Pirin," isolate 1 | 68 | 84 | 87 | 89 | 57 | 155 |
| Y07909_at | H. sapiens mRNA for Preogression Associated Protein | 1399 | 24 | 33 | 22 | 20 | 128 |
| Y08134_at | H. sapiens mRNA for ASM-like phosphodiesterase 3b | 113 | 64 | 60 | 71 | 119 | 83 |
| Y08136_at | H. sapiens mRNA for ASM-like phosphodiesterase 3a | 29 | 27 | 22 | 35 | 49 | 20 |
| Y08200_at | H. sapiens mRNA for rab geranylgeranyl "transferase," alpha-subunit | 209 | 175 | 185 | 158 | 249 | 298 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| Y08223_at | H. sapiens MFH-1 gene | 50 | 20 | 47 | 20 | 110 | 127 |
| Y08263_at | H. sapiens mRNA for AAD14 "protein," partial | 30 | 20 | 25 | 36 | 39 | 40 |
| Y08265_s_at | H. sapiens mRNA for DAN26 "protein," partial | 349 | 133 | 291 | 192 | 359 | 104 |
| Y08302_at | H. sapiens mRNA for MAP kinase phosphatase 4 | 58 | 82 | 45 | 77 | 127 | 98 |
| Y08319_at | H. sapiens mRNA for kinesin-2 | 20 | 23 | 20 | 20 | 20 | 24 |
| Y08374_ma1_at | H. sapiens gene encoding cartilage GP-39 protein, exon 1 and 2 (and joined CDS). | 25 | 34 | 20 | 20 | 73 | 20 |
| Y08409_at | H. sapiens spot14 gene | 20 | 20 | 20 | 20 | 20 | 20 |
| Y08417_s_at | H. sapiens mRNA for nicotinic acetylcholine receptor beta3 subunit precursor | 20 | 30 | 20 | 20 | 120 | 20 |
| Y08564_at | H. sapiens GalNAc-T4 gene. /gb=Y08564 /ntype=DNA /annot=CDS | 20 | 20 | 20 | 20 | 20 | 20 |
| Y08612_at | H. sapiens mRNA for Nup88 protein | 37 | 33 | 39 | 40 | 20 | 94 |
| Y08613_at | H. sapiens mRNA alternative 3' UTR of Nup88 mRNA. /gb=Y08613 /ntype=RNA | 20 | 63 | 20 | 20 | 30 | 31 |
| U08614_at | H. sapiens mRNA for DRM1 protein | 72 | 107 | 127 | 73 | 20 | 135 |
| Y08639_at | H. sapiens mRNA for transcription factor RZRbeta | 20 | 49 | 20 | 20 | 24 | 77 |
| Y08682_ma1_s_at | H. sapiens mRNA for carnitine palmitoyltransferase I typeI | 42 | 74 | 145 | 107 | 20 | 59 |
| Y08765_s_at | H. sapiens mRNA for splicing "factor," SF1-HL1 isoform | 42 | 71 | 152 | 119 | 158 | 62 |
| Y08766_s_at | H. sapiens mRNA for splicing "factor," SF1-Bo isoform | 20 | 20 | 20 | 20 | 20 | 92 |
| Y08836_at | H. sapiens mRNA for HRX-like protein. /gb=Y08836 /ntype=RNA | 42 | 53 | 54 | 43 | 165 | 20 |
| Y08337_at | H. sapiens mRNA for RAD51-like protein. /gb=Y08837 /ntype=RNA | 20 | 20 | 20 | 20 | 33 | 20 |
| Y08915_at | H. sapiens mRNA for alpha 4 protein | 87 | 85 | 178 | 160 | 62 | 91 |
| Y08976_at | H. sapiens mRNA for FEV protein | 185 | 147 | 221 | 181 | 438 | 417 |
| Y08991_at | H. sapiens mRNA for adaptor protein p150 | 33 | 22 | 41 | 20 | 73 | 98 |
| Y08999_at | H. sapiens mRNA for Sop2p-like protein | 88 | 20 | 112 | 111 | 20 | 32 |
| Y09022_at | H. sapiens mRNA for Not56-like protein | 66 | 101 | 141 | 96 | 110 | 220 |
| Y09216_at | H. sapiens mRNA for protein "kinase," Dyrk2 | 84 | 48 | 103 | 85 | 107 | 106 |
| Y09267_at | H. sapiens mRNA for flavin-containing monooxygenase 2 /gb=Y09267 /ntype=RNA | 20 | 58 | 52 | 20 | 43 | 20 |
| Y09305_at | H. sapiens mRNA for protein "kinase, "Dyrk4," partial | 20 | 20 | 20 | 20 | 26 | 26 |
| Y09306_at | H. sapiens mRNA for protein "kinase," "Dyrk6," partial. /gb=Y09306 /ntype=RNA | 20 | 20 | 20 | 20 | 54 | 20 |
| Y09321_at | H. sapiens TAFII105 "mRNA," partial | 20 | 20 | 20 | 20 | 20 | 20 |
| Y09392_s_at | H. sapiens mRNA for "WSL-LR," WSL-S1 and WSL-S2 proteins | 59 | 42 | 141 | 20 | 20 | 38 |
| Y09443_s_at | H.sapiens mRNA for alkyl-dihydroxyacetonephosphate synthase precursor | 20 | 20 | 22 | 27 | 27 | 36 |
| Y09980_ma4_at | H. sapiens mRNA for transcription factor TBX5 | 20 | 20 | 20 | 20 | 20 | 20 |
| Y09561_at | H. sapiens mRNA for P2X7 receptor | 27 | 20 | 20 | 20 | 20 | 20 |
| Y09615_at | H. sapiens mRNA for mitochondrial transcription termination factor | 20 | 25 | 20 | 20 | 20 | 20 |
| Y09616_at | H. sapiens mRNA for putative carboxylesterase | 121 | 92 | 143 | 96 | 135 | 159 |
| Y09836_at | H. sapiens mRNA for CD77 protein. /gb=Y09306 /ntype=RNA | 62 | 35 | 20 | 20 | 64 | 20 |
| Y09858_at | H. sapiens mRN for unknown protein | 20 | 30 | 27 | 24 | 52 | 38 |
| Y09912_ma1_at | H. sapiens AP-2 beta gene. | 20 | 20 | 20 | 20 | 20 | 20 |
| Y09943_s_at | H. sapiens mRNA for NGF-inducible PC3 anti-proliferative protein | 20 | 27 | 27 | 20 | 20 | 20 |
| Y09980_ma4_at | H. sapiens HOXD3 gene. | 130 | 28 | 20 | 26 | 56 | 20 |
| Y10032_at | H. sapiens mRNA for putative serine/threonine protein kinase | 20 | 20 | 20 | 20 | 76 | 107 |
| Y10055_at | H. sapiens mRNA for phosphoinositide 3-kinase | 20 | 92 | 133 | 96 | 149 | 85 |
| Y10141_s_at | H. sapiens DAT1 "gene," "partial," VNTR. /gb=Y10141 /ntype=DNA /annot=CDS | 20 | 20 | 20 | 24 | 231 | 143 |
| Y10202_at | H. sapiens mRNA for CD207 protein. /gb=Y10202 /ntype=RNA | 20 | 20 | 20 | 20 | 20 | 24 |
| Y10204_at | H. sapiens mRNA for CD77 protein. /gb=Y10204 /ntype=RNA | 20 | 24 | 20 | 20 | 20 | 20 |
| Y10205_at | H. sapiens mRNA for CD88 protein. /gb=Y10205 /ntype=RNA | 20 | 20 | 20 | 20 | 20 | 20 |
| Y10207_at | H. sapiens mRNA for CD171 protein. /gb=Y10207 /ntype=RNA | 57 | 90 | 27 | 20 | 135 | 211 |
| Y10209_at | H. sapiens mRNA for CD30L protein. /gb=&10209 /ntype=RNA | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| Y10210_at | Y. sapiens mRNA for CD22 protein. /gb=Y10210 /ntype=RNA | 20 | 20 | 20 | 20 | 20 | 20 |
| Y10256_at | H. sapiens mRNA for serine/threonine protein "kinase," NIK | 20 | 20 | 20 | 20 | 53 | 20 |
| Y10260_at | H.sapiens EYA1 gene | 20 | 40 | 20 | 20 | 125 | 21 |
| Y10262_s_at | H. sapiens EYA3 gene. /gb=Y10262 /ntype=DNA /annot=CDS | 20 | 20 | 66 | 20 | 112 | 29 |
| Y10275_at | H. sapiens mRNA for L-3-phosphoserine phosphatase | 20 | 20 | 20 | 20 | 30 | 29 |
| Y10313_at | H. sapiens mRNA for nerve growth factor-inducible PC4 homologue | 34 | 26 | 26 | 20 | 95 | 51 |
| Y10375_s_at | H. sapiens mRNA for SIRP-alpha1 | 20 | 20 | 20 | 20 | 467 | 139 |
| Y10376_at | H. sapiens mRNA for SIRP-beta1 | 106 | 20 | 33 | 30 | 20 | 147 |
| Y10505_at | H. sapiens mRNA for CD104 protein. /gb=Y10505 /ntype=RNA | 20 | 20 | 20 | 20 | 20 | 20 |
| Y10506_at | H. sapiens mRNA for CD110 protein. /gb=Y10506 /ntype=RNA | 24 | 65 | 20 | 20 | 59 | 20 |
| Y10508_s_at | H. sapiens mRNA for CD190 protein. /gb=Y10508 /ntype=RNA | 20 | 20 | 20 | 20 | 20 | 20 |
| Y10510_at | H. sapiens mRNA for CD67S protein. /gb=Y10510 /ntype=RNA | 20 | 20 | 20 | 20 | 47 | 20 |
| Y10511_at | H. sapiens mRNA for CD176 protein. /gb=Y10511 /ntype=RNA | 23 | 20 | 20 | 20 | 20 | 20 |
| Y10512_at | H. sapiens mRNA for CD282 protein. /gb=Y10512 /ntype=RNA | 20 | 20 | 20 | 20 | 20 | 20 |
| Y10514_s_at | mNRA for CD152 protein. /gb=Y10514 /ntype=RNA | 20 | 26 | 20 | 31 | 166 | 55 |
| Y10515_at | H. sapiens mRNA for CD58 T7 protein. /gb=Y10515 /ntype=RNA | 20 | 20 | 20 | 20 | 45 | 20 |
| Y10517_at | H.sapiens mRNA for CD108 protein. /gb=Y10517 /ntype=RNA | 20 | 20 | 20 | 20 | 28 | 20 |
| Y10518_at | H. sapiens mRNA for CD202 protein. /gb=Y10518 /ntype=RNA | 20 | 20 | 20 | 20 | 59 | 25 |
| Y10571_at | H. sapiens mRNA for dinG gen | 20 | 20 | 20 | 20 | 20 | 22 |
| Y10615_at | H. sapiens CYRN2 gene. /gb=Y10615 /ntype=DNA /annot=CDS | 34 | 20 | 53 | 34 | 110 | 63 |
| Y10659_at | H. sapiens IL-13Ra mRNA | 20 | 20 | 20 | 20 | 20 | 24 |
| Y10807_s_at | H. sapiens mRNA for arginine "methyltransferase," splice "variant," 1262 bp | 87 | 101 | 558 | 442 | 456 | 407 |
| Y10812_at | H. sapiens mRNA for fructose-bisphosphatase | 20 | 20 | 20 | 20 | 20 | 20 |
| Y10871_at | H. sapiens twist gene | 110 | 154 | 116 | 97 | 279 | 284 |
| Y10936_at | H. sapiens mRNA for hypothetical protein downstream of DMPK and DMAHP 41 | 20 | 61 | 35 | 58 | 40 | |
| Y11174_at | H. sapiens mRNA for RP3 gene. /gb=Y11174 /ntype=RNA | 20 | 20 | 20 | 20 | 20 | 20 |
| Y11180_at | H. sapiens mRNA for twist "protein," partial. /gb=Y11180 /ntype=RNA | 20 | 29 | 20 | 20 | 20 | 20 |
| Y11215_at | H. sapiens mRNA for SKAP55 protein. /gb=Y11215 /ntype=RNA | 34 | 58 | 55 | 50 | 20 | 66 |
| Y11251_at | H. sapiens mRNA for novel member of serine-arginine domain "protein," SRrp129 | 20 | 20 | 40 | 22 | 41 | 20 |
| Y11306_ma1_at | Homo sapiens mRNA for hTCF-4. | 67 | 58 | 63 | 53 | 20 | 96 |
| Y11416_at | H. sapiens mRNA for P73. | 20 | 43 | 20 | 20 | 125 | 64 |
| Y11651_at | H. sapiens mRNA for phosphate cyclase | 20 | 20 | 24 | 30 | 20 | 20 |
| Y11681_at | Homo sapiens mRNA for mitochondrial ribosomal protein S12. /gb=Y11681 /ntype=RNA | 112 | 172 | 137 | 114 | 40 | 154 |
| Y11709_at | H. sapiens mRNA for extracellular matrix protein collagen type "XIV;" N-terminus. /gb=Y11709 /ntype=RNA | 20 | 20 | 20 | 20 | 20 | 20 |
| Y11710_ma1_at | H. sapiens mRNA for extracellular matrix protein collagen type XIV, C-terminus. | 21 | 73 | 43 | 52 | 127 | 131 |
| Y11897_at | H. sapiens Brx gene 3'UTR. /gb=Y11897 /ntype=RNA | 66 | 40 | 57 | 56 | 159 | 98 |
| Y11999_at | H. sapiens mRNA for inositol "1,4,5-trisphosphate" 3-kinase. /gb=Y11999 /ntype=RNA | 20 | 20 | 20 | 20 | 20 | 20 |
| Y12393_s_at | H. sapiens mRNA for SRP1-like "protein," partial | 20 | 20 | 88 | 40 | 20 | 39 |
| Y12394_at | H. sapiens mRNA for SRP1-like protein | 20 | 20 | 27 | 20 | 20 | 20 |
| Y12478_at | H. sapiens mRNA for CHD5 protein | 20 | 20 | 20 | 20 | 20 | 20 |
| Y12556_at | H. sapiens mRNA for AMP-activated protein kinase beta-1. /gb=Y12556 /ntype=RNA | 20 | 20 | 20 | 20 | 20 | 20 |
| Y12670_at | H. sapiens OB-RGRP gene. /gb=Y12670 /ntype=RNA | 20 | 71 | 165 | 133 | 20 | 20 |
| Y12711_at | H. sapiens mRNA for putative proteseterone binding protein | 73 | 48 | 133 | 153 | 91 | 65 |
| Y12812_at | H. sapiens RFXAP mRNA | 20 | 20 | 20 | 20 | 20 | 20 |
| Y12856_at | H. sapiens mRNA for AMp-activated protein kinase "alpha-1," partial. /gb=Y12856 /ntype=RNA | 41 | 20 | 22 | 48 | 105 | 39 |
| Y13115_at | Homo sapiens mRNA for serin/threonine protein kinase SAK | 55 | 78 | 26 | 48 | 117 | 92 |
| Y13153_at | Homo sapiens mRNA for kynurenin 3-monooxygenase. /gb=Y13153 /ntype=RNA | 32 | 26 | 24 | 26 | 133 | 99 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| Y13247_at | Homo sapiens fb19 mRNA | 81 | 49 | 91 | 123 | 328 | 171 |
| Y13618_at | Homo sapiens mRNA for DFFRY "protein," abundant transcript | 20 | 20 | 20 | 22 | 20 | 20 |
| Y13620_at | Homo sapiens mRNA for BCL9 gene. /gb=Y13620 /ntype=RNA | 20 | 20 | 20 | 20 | 20 | 60 |
| Y13896_at | Homo sapiens skeletal muscle alternate 5'end of gene Kir4.2 5'UTR. /gb=Y13896 /ntype=RNA | 20 | 20 | 20 | 20 | 143 | 35 |
| Y14140_at | Homo sapiens G protein gene encoding beta 3 subunit exon 1 and promoter. /gb=Y14140 /ntype=DNA /annot=exon | 88 | 57 | 121 | 88 | 128 | 120 |
| Z00010_at |  | 20 | 20 | 20 | 20 | 38 | 31 |
| Z11502_at | H. sapiens mRNA for intestine-specific annexin | 20 | 20 | 20 | 20 | 66 | 45 |
| Z11518_s_at | H. sapiens mRN for histidyl-tRNA synthetase | 20 | 20 | 98 | 38 | 216 | 57 |
| Z11559_at | H. sapiens mRNA for iron regulatory factor | 38 | 24 | 28 | 20 | 20 | 60 |
| Z11685_s_at | H. sapiens mRNA for RNA helicase | 20 | 20 | 20 | 33 | 32 | 20 |
| Z11695_at | H. sapiens 40 kDa protein kinase related to rat ERK2 | 20 | 20 | 20 | 20 | 20 | 20 |
| Z11697_at | Homo sapiens mRNA for HB15 | 27 | 20 | 25 | 20 | 87 | 54 |
| Z11737_at | H. sapiens mRNA for flavin-containing monooxygenase 4 | 20 | 20 | 37 | 20 | 44 | 20 |
| Z11793_at | H. sapiens mRNA for selenoprotein P | 208 | 92 | 40 | 28 | 20 | 20 |
| Z11850_at | H. sapiens mRNA for somatotropin receptor 5' upstream region. /gb=Z11850 /ntype=RNA | 20 | 20 | 20 | 20 | 20 | 139 |
| Z11899_s_at | H. sapiens OTF3 mRNA encoding octamer binding protein 3B | 68 | 154 | 191 | 235 | 94 | 20 |
| Z11933_at | H. sapiens mRNA for N-Oct "3," "N-Oct5a," and N-Oct 5b proteins | 20 | 20 | 20 | 20 | 275 | 243 |
| Z12173_at | H. sapiens GNS mRNA encoding glucosamine-6-sulphatase | 20 | 20 | 20 | 20 | 20 | 43 |
| Z12830_at | H. sapiens mRNA for SSR alpha subunit | 20 | 20 | 23 | 36 | 20 | 29 |
| Z12962_at | H. sapiens mRNA for homologue to yeast ribosomal protein L41 | 7468 | 11237 | 7087 | 7602 | 8100 | 7623 |
| Z14000_at | H. sapiens RING1 gene | 174 | 135 | 205 | 149 | 223 | 249 |
| Z14093_at | H. sapiens mRNA for branched chain decarboxylase alpha subunit | 20 | 20 | 20 | 34 | 20 | 20 |
| Z14244_at | H. sapiens coxVIIb mRNA for cytochrome c oxidase subunit VIIb | 260 | 146 | 181 | 194 | 52 | 243 |
| Z14978_at | H. sapiens mRNA for acint-related protein | 20 | 20 | 20 | 20 | 327 | 162 |
| Z14982_ma1_at | H. sapiens gene for major histocompatibility complex encoded proteasome subunit LMP7. | 45 | 105 | 90 | 37 | 20 | 42 |
| Z15005_at | H. sapiens CENP-E mRNA | 20 | 20 | 21 | 20 | 52 | 47 |
| Z15108_at | H. sapiens mRNA for protein kinase C zeta | 20 | 30 | 59 | 28 | 29 | 84 |
| Z15114_at | H. sapiens mRNA for protein kinase C gamma (partial) | 88 | 87 | 92 | 73 | 119 | 188 |
| Z15115_at | H. sapiens TOP2 mRNA for DNA topoisomerase II (partial) | 184 | 543 | 893 | 869 | 296 | 448 |
| Z16411_s_at | H. sapiens mRNA encoding phospholipase c | 20 | 20 | 20 | 20 | 133 | 38 |
| Z17227_at | H. sapiens mRNA for transmembrane receptor protein | 57 | 48 | 65 | 55 | 88 | 20 |
| Z17240_at | H. sapiens mRNA encoding HMG2B | 20 | 20 | 20 | 20 | 20 | 20 |
| Z18859_ma1_at | H. sapiens gene for cone transducin alpha subunit. | 20 | 34 | 34 | 20 | 48 | 49 |
| Z18948_at | H. sapiens mRNA for S100E calcium binding protein | 23 | 20 | 35 | 20 | 20 | 20 |
| Z18951_at | H. sapiens mRNA for caveolin | 20 | 20 | 20 | 20 | 20 | 20 |
| Z18954_at | H. sapiens mRNA for S100D calcium binding protein | 53 | 92 | 85 | 64 | 112 | 193 |
| Z18956_at | H. sapiens mRNA for taurine transporter | 20 | 52 | 128 | 86 | 288 | 116 |
| Z19002_at | H. sapeins of PLZF gene encoding kruppel-like zinc finger protein | 20 | 20 | 20 | 20 | 44 | 20 |
| Z19574_s_at | H. sapiens vimentin gene | 1186 | 827 | 111 | 28 | 258 | 891 |
| Z19574_ma1_at | H. sapiens vimentin gene | 1069 | 173 | 644 | 638 | 67 | 350 |
| Z19585_at | H. sapiens mRNA for thrombospondin-4 | 36 | 20 | 20 | 20 | 20 | 20 |
| Z20656_ma1_s_at | Homo sapiens of cardiac alpha-myosin heavy chain gene | 20 | 20 | 20 | 20 | 96 | 48 |
| Z21488_at | H. sapiens contactin mRNA | 39 | 37 | 20 | 29 | 144 | 178 |
| Z21507_at | H. sapiens EF-1 delta gene encoding human elongation factor-1-delta | 335 | 395 | 391 | 517 | 54 | 26 |
| Z21707_at | H. sapiens p18 mRNA | 20 | 20 | 20 | 20 | 20 | 20 |
| Z21966_at | H. sapiens mPOU homeobox protein mRNA | 20 | 20 | 20 | 20 | 20 | 20 |
| Z22534_at | H. sapiens ALK-2 mRNA | 40 | 25 | 29 | 21 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| Z22535_at | H. sapiens ALK-3 mRNA | 27 | 20 | 25 | 27 | 80 | 56 |
| Z22536_at | Homo sapiens ALK-4 "mRNA," complete CDS | 25 | 20 | 66 | 61 | 50 | 37 |
| Z22548_at | H. sapiens thiol-specific antioxidant protein mRNA | 80 | 111 | 193 | 276 | 146 | 73 |
| Z22551_at | H. sapiens kinectin gene | 20 | 72 | 81 | 71 | 20 | 30 |
| Z22780_at | H. sapiens encoding CLA-1 mRNA | 86 | 102 | 80 | 70 | 115 | 135 |
| Z22865_at | H. sapiens cylicin mRNA | 20 | 20 | 20 | 20 | 47 | 42 |
| Z22951_ma1_s_at | H. sapiens dermatopontin "mRNA," complete cds | 67 | 20 | 20 | 20 | 20 | 20 |
| Z22970_at | Homo sapiens of p65 gene encoding p65 subunit of transcription factor NF-kappaB | 93 | 154 | 286 | 149 | 194 | 136 |
| Z23064_at | H. sapiens mRNA for M130 antigen cytoplasmic variant 2 | 20 | 20 | 20 | 20 | 20 | 20 |
| Z23090_at | H. sapiens mRN gene for hnRNP G protein | 75 | 37 | 143 | 122 | 20 | 93 |
| Z23091_ma1_at | H. sapiens mRNA for 28 kDa heat shock protein | 9609 | 4116 | 3734 | 3610 | 4076 | 3491 |
| Z23115_at | H. sapiens GPV gene encoding platelet glycoprotein V precursor | 20 | 20 | 20 | 20 | 20 | 20 |
| Z24459_xpt5_at | H. sapiens bcl-xL mRNA | 62 | 37 | 46 | 48 | 20 | 101 |
| Z24680_at | H. sapiens mTCP1 gene, exons 2A to 7 (and joined mRNA). | 20 | 20 | 20 | 20 | 20 | 20 |
| Z24724_at | H. sapiens garp gene "mRNA," complete CDS | 51 | 48 | 20 | 20 | 138 | 53 |
| Z24725_at | H. sapiens polyA site DNA | 46 | 38 | 74 | 84 | 30 | 20 |
| Z24727_at | H. sapiens mitogen inducible gene "mig-2," complete CDS | 128 | 68 | 20 | 20 | 22 | 36 |
| Z25521_s_at | H. sapiens tropomyosin isoform "mRNA," complete CDS | 464 | 366 | 48 | 55 | 20 | 80 |
| Z25535_at | H. sapiens mRNA for nuclear pore complex protein hnup 153 | 127 | 140 | 119 | 143 | 20 | 86 |
| Z25749_ma1_at | H. sapiens gene for ribosomal protein S7. | 33 | 20 | 26 | 28 | 20 | 97 |
| Z25884_at | H. sapiens mRNA for ClC-1 muscle chloride channel protein | 1122 | 2348 | 1493 | 1385 | 426 | 1036 |
| Z26248_s_at | H. sapiens mRNA for eosinophil granule major basic protein | 57 | 101 | 81 | 54 | 345 | 267 |
| Z26256_at | H. sapiens isoform 1 gene for L-type calcium "channe," exon 1 /gb=Z26256 /ntype=DNA /annot=exon | 20 | 20 | 20 | 20 | 151 | 20 |
| Z26317_at | H. sapiens mRNA for desmoglein 2 | 20 | 20 | 20 | 20 | 20 | 20 |
| Z26491_s_at | H. sapiens gene for catechol O-methyltransferase | 66 | 361 | 563 | 642 | 287 | 280 |
| Z26634_at | H. sapiens mRNA for ankyrin B (440 kDa) | 20 | 20 | 20 | 20 | 44 | 20 |
| Z26653_at | H. sapiens mRNA for laminin M chain (merosin) | 42 | 46 | 20 | 31 | 68 | 100 |
| Z26876_at | H. sapiens gene for ribosomal protein L38 | 2490 | 3163 | 3071 | 2971 | 1944 | 3365 |
| Z27113_at | H. sapiens gene for RNA polymerase II subunit 14.4 kD | 221 | 241 | 202 | 189 | 339 | 409 |
| Z28339_at | H. sapiens mRNA for delta 4-3-oxosteroid 5 beta-reductase | 20 | 20 | 20 | 20 | 20 | 20 |
| Z28407_at | H. sapiens mRNA for ribosomal protein L8 | 2386 | 2557 | 2990 | 3446 | 517 | 539 |
| Z29064_at | H. sapiens AF-1p mRNA | 72 | 44 | 38 | 49 | 37 | 39 |
| Z29066_s_at | H. sapiens nek2 mRNA for protein kinase | 20 | 20 | 20 | 25 | 144 | 46 |
| Z29067_at | H. sapiens nek3 mRN for protein kinase | 20 | 20 | 20 | 20 | 34 | 20 |
| Z29074_at | H. sapiens mRNA for cytokeratin 9 | 20 | 20 | 20 | 20 | 20 | 20 |
| Z29077_xpt1_at | H. sapiens cdc25 gene promoter region. | 55 | 20 | 20 | 20 | 46 | 20 |
| Z29083_at | H. sapiens 5T4 gene for 5T4 Oncofetal antigen | 20 | 73 | 112 | 83 | 103 | 3365 |
| Z29090_at | H. sapiens mRN for phosphatidylinositol 3-kinase | 20 | 20 | 20 | 20 | 20 | 20 |
| Z29331_at | H. sapiens (23k/3) mRNA for ubiquitin-conjugating enzyme UbcH2 | 50 | 20 | 37 | 20 | 20 | 20 |
| Z29481_at | H. sapiens mRNA for 3-hydroxyanthranilic acid dioxygenase | 86 | 67 | 89 | 54 | 169 | 297 |
| Z29505_at | H. sapiens mRNA for nucleic acid binding protein sub2.3 | 345 | 174 | 285 | 284 | 127 | 221 |
| Z29572_at | H. sapiens antisense mRNA for BCMA peptide | 20 | 20 | 20 | 20 | 33 | 20 |
| Z29574_at | Homo sapiens gene for BCMA peptide | 20 | 20 | 20 | 20 | 20 | 20 |
| Z29678_at | H. sapiens mIF mRNA | 49 | 83 | 43 | 35 | 229 | 125 |
| Z30425_at | H. sapiens mRNA for orphan nuclear hormone receptor | 31 | 49 | 20 | 26 | 20 | 20 |
| Z30426_at | H. sapiens gene for early lymphocyte activation antigen "CD69," exon 1 | 20 | 20 | 20 | 20 | 20 | 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| Z30643_at | H. sapiens mRNA for chloride channel (putative) 2139bp | 640 | 152 | 925 | 623 | 248 | 477 |
| Z30644_at | H. sapiens mRNA for chloride channel (putative) 2163bp | 86 | 227 | 366 | 193 | 908 | 375 |
| Z31357_at | H. sapiens mRNA for cysteine dioxygenase type1 | 20 | 20 | 20 | 20 | 20 | 20 |
| Z31560_s_at | H. sapiens sox-2 mRNA (partial) | 59 | 125 | 237 | 110 | 188 | 101 |
| Z31690_s_at | H. sapiens (HepG2) LAL mRNA for lysosomal acid lipase | 37 | 20 | 20 | 22 | 20 | 91 |
| Z31695_at |  | 20 | 20 | 20 | 20 | 20 | 20 |
| Z32684_at | H. sapiens XK mRNA for membrane transport protein | 20 | 20 | 20 | 20 | 20 | 34 |
| Z32765_at | H. sapiens CD36 gene exon 15 /gb=Z32765 /ntype=DNA /annot=exon | 330 | 294 | 309 | 228 | 752 | 655 |
| Z33642_at | H. sapiens V7 mRNA for leukocyte surface protein | 20 | 20 | 20 | 20 | 20 | 20 |
| Z33905_at | H. sapiens gene for 43kD acetylcholine receptor-associated protein (Rapsyn) | 20 | 20 | 20 | 20 | 20 | 20 |
| Z34822_f_at | H. sapiens (HLCC85) mRNA for voltage-dependent L-type Ca channel alpha 1 subunit (splice variant) | 20 | 46 | 39 | 34 | 20 | 27 |
| Z34897_at | H. sapiens mRNA for H1 histamine receptor | 35 | 20 | 37 | 32 | 118 | 30 |
| Z34918_at | H. sapiens mRNA for translation initiation factor eIF-4gamma (partial) | 20 | 20 | 20 | 20 | 20 | 20 |
| Z34974_s_at | H. sapiens mRNA for plakophilin (partial) | 20 | 20 | 20 | 20 | 20 | 20 |
| Z34975_at | H. sapiens LDLC mRNA | 20 | 20 | 20 | 20 | 20 | 20 |
| Z35085_s_at | H. sapiens mRNA for unknown antigen | 90 | 93 | 221 | 179 | 95 | 43 |
| Z35093_at | H. sapiens mRNA for SURF-1 | 98 | 188 | 190 | 134 | 241 | 285 |
| Z35102_at | H. sapiens mRNA for Ndr protein kinase | 20 | 21 | 59 | 45 | 20 | 20 |
| Z35227_at | H. sapiens TTF mRNA for small G protein | 38 | 28 | 30 | 24 | 23 | 21 |
| Z35278_at | H. sapiens mRNA for PEBP2aC1 acute myeloid leukaemia mRNA | 20 | 20 | 20 | 44 | 20 | 20 |
| Z35307_at | H. sapiens mRNA for endothelin-converting-enzyme 1 | 20 | 20 | 24 | 20 | 118 | 109 |
| Z35309_at | H. sapiens mRNA for adenylyl cyclase | 20 | 20 | 20 | 20 | 46 | 20 |
| Z35402_ma1_s_at | H. sapiens gene encoding "E-cadherin," exon 3 and joined CDS | 159 | 305 | 704 | 762 | 63 | 242 |
| Z35491_at | H. sapiens mRNA for novel glucocorticoid receptor-associated protein | 50 | 65 | 149 | 64 | 87 | 85 |
| Z36531_at | H. sapiens mRNA for fibrinogen-like protein (pT49 protein) | 98 | 68 | 37 | 20 | 72 | 100 |
| Z36714_at | H. sapiens mRNA for cyclin F | 112 | 20 | 62 | 79 | 58 | 20 |
| Z36715_at | H. sapiens mRNA for Net transcription factor | 20 | 49 | 46 | 35 | 43 | 46 |
| Z37166_at | H. sapiens BAT1 mRNA for nuclear RNA helicase (DEAD family) | 78 | 95 | 371 | 369 | 199 | 531 |
| Z37976_at | H. sapiens mRNA for latent transforming growth factor-beta binding protein (LTBP-2) | 35 | 24 | 29 | 23 | 115 | 22 |
| Z37986_at | H. sapiens mRNA for phenylalkylamine binding protein | 157 | 174 | 102 | 111 | 237 | 258 |
| Z37987_s_at | H. sapiens mRNA for MXR7 | 39 | 39 | 46 | 82 | 20 | 36 |
| Z38026_at | H. sapiens mRNA for FALL-39 peptide antibiotic | 20 | 20 | 20 | 20 | 20 | 20 |
| Z38133_s_at | H. sapiens mRNA for myosin | 20 | 20 | 20 | 20 | 70 | 20 |
| Z46261_at | H. sapiens DNA for histone H3a | 20 | 20 | 20 | 26 | 20 | 20 |
| Z46376_ma1_at | H. sapiens HK2 mRNA for hexokinase II. | 20 | 20 | 20 | 20 | 20 | 20 |
| Z46629_at | Homo sapiens SOX9 mRNA | 20 | 20 | 20 | 20 | 20 | 20 |
| Z46632_r_at | H. sapiens HSPDE4C1 gene for "3,5'-cyclic" AMP phosphodiesterase | 20 | 20 | 20 | 20 | 127 | 20 |
| Z46788_at | H. sapiens HSPDE4XC1 gene for "3,5'-cyclic" AMP phosphodiesterase | 79 | 219 | 298 | 96 | 985 | 288 |
| Z46967_at | H. sapiens mRNA for cylicin II | 20 | 20 | 20 | 20 | 21 | 20 |
| Z46973_at | H. sapiens mRN for calicin (partial) | 20 | 20 | 20 | 20 | 20 | 20 |
| Z47038_s_at | H. sapiens mRNA for phosphatidylinositol 3-kinase | 28 | 20 | 32 | 23 | 142 | 20 |
| Z47043_s_at | Human partial cDNA "sequence," clone "x101," putative microtubule-associated; protein 1A (MAP1A). /gb=Z47038 /ntype=DNA /annot=C | 77 | 120 | 309 | 193 | 467 | 209 |
| Z57043_at | Human partial cDNA "sequence," clone "x529," unknown open reading frame;./gb=Z47043 /ntype=DNA /annot=CDS | 20 | 20 | 20 | 20 | 20 | 20 |
| Z47055_s_at | Human partial cDNA "sequence," farnesyl pyrophosphate synthetase like-4. /gb=Z470555 /ntype=DNA /annot=CDS | 124 | 120 | 166 | 258 | 129 | 260 |
| Z47087_at | H. sapiens mRNA for RNA polymerase II elongation factor-like protein | 94 | 89 | 136 | 96 | 20 | 78 |
| Z47553_at | h. sapiens mRNA for flavin-conatining monooxygenase 5 (FMO5) | 20 | 20 | 20 | 25 | 45 | 20 |
| Z47556_ma2_at | semenogelin II gene extracted from H. sapiens genes for semenogelin I and semenogelin II | 20 | 20 | 20 | 20 | 20 | 43 20 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| Z47727_at | H. sapiens mRNA for RNA fpolymerase II subunit | 142 | 129 | 151 | 141 | 210 | 407 |
| Z48042_at | H. sapiens mRNA encoding GPI-anchored protein p137 | 98 | 99 | 200 | 192 | 37 | 170 |
| Z48051_ma1_at | H. sapiens fene for myelin oligodendrocyte glycoprotein (MOG) | 20 | 20 | 20 | 20 | 22 | 20 |
| Z48054_at | H. sapiens mRNA for peroxisomal targeting signal 1 (SKL type) receptor | 29 | 20 | 36 | 24 | 47 | 64 |
| Z48199_at | H. sapeins syndecan-1 gene (exons 2–5) | 263 | 294 | 795 | 937 | 678 | 438 |
| Z48314_s_at | H.s apiens mRNA for apomucin | 20 | 20 | 20 | 20 | 20 | 20 |
| Z48475_at | H. sapiens GCKR mRNA for glucokinase regulator | 20 | 53 | 116 | 84 | 20 | 20 |
| Z48481_at | H. sapiens mRNA for membrane-type matrix metalloproteinase 1 | 27 | 20 | 20 | 20 | 149 | 189 |
| Z48482_at | H. sapiens mRNA for membrane-type matrix metalloproteinase 2 | 20 | 20 | 20 | 20 | 20 | 20 |
| Z48501_s_at | H. sapiens mRNA for polyadenylate binding protein II. /gb=Z48501 /ntype=RNA | 1263 | 748 | 3197 | 3945 | 560 | 2533 |
| Z48510_at | H. sapiens XG mRNA (clone FB1). /gb=Z48510 /ntype=RNA | 20 | 20 | 20 | 20 | 20 | 20 |
| Z48511_at | H. sapiens XG mRNA (clone PEP11) | 32 | 22 | 33 | 24 | 47 | 32 |
| Z48512_at | H. sapiens XGmRNA (clone PEP6). /gb=Z48512 /ntype=RNA | 44 | 43 | 25 | 26 | 33 | 44 |
| Z48519_s_at | H. sapiens XG gene (clone RACE5). /gb=Z48519 /ntype=RNA | 20 | 20 | 20 | 20 | 113 | 46 |
| Z48520_at | H. sapiens XG mRNA (clone RACE6). /gb=Z48520 /ntype=RNA | 20 | 20 | 20 | 20 | 20 | 20 |
| Z48541_at | H. sapiens mRNA for protein tyrosine phosphatase | 20 | 20 | 20 | 20 | 20 | 26 |
| Z48570_at | H. sapiens Sp17 gene | 20 | 20 | 20 | 64 | 50 | 20 |
| Z48579_at | H. sapiens mRNA for disintegrin-metalloprotease (partial) | 20 | 20 | 62 | 20 | 20 | 20 |
| Z48605_at | H. sapiens partial mRNA for pyrophosphatase. /gb=Z48605 /ntype=RNA | 20 | 58 | 20 | 20 | 20 | 32 |
| Z48633_at | H. sapiens mRNA for retrotransposon | 20 | 20 | 20 | 20 | 20 | 20 |
| Z48804_at | H. sapiens mRNA (ocular albinism type 1 related) | 20 | 48 | 53 | 46 | 97 | 37 |
| Z48923_at | H. sapiens mRNA for BMPR-II | 52 | 308 | 481 | 641 | 243 | 672 |
| Z48950_at | H. sapiens hH3.3B gene for histone H3.3 | 527 | 134 | 143 | 133 | 154 | 211 |
| Z49099_at | H. sapiens mRNA for spermine synthase | 116 | 20 | 143 | 87 | 323 | 70 |
| Z49105_at | H. sapiens HD21 mRNA | 87 | 623 | 1517 | 413 | 1393 | 696 |
| Z49107_s_at | H. sapiens gene for galectin | 369 | 2957 | 6221 | 5964 | 616 | 1801 |
| Z49148_s_at | H. sapiens mRNA for ribosomal protein L29 | 2303 | 49 | 52 | 49 | 194 | 111 |
| Z49155_at | Human DNA from cosmi "L83d3;" Huntington's Disease "Region," chromosome 4p16.3 | 42 | 30 | 20 | 20 | 20 | 56 |
| Z49194_at | H. sapiens mRNA for oct-binding factor | 20 | 20 | 20 | 20 | 76 | 20 |
| Z49205_at | H. sapiens mRNA for purinergic receptor | 20 | 26 | 20 | 20 | 20 | 20 |
| Z49208_at | Human DNA from cosmid "L161A8;" Huntington's Disease "Region," chromosome 4p16.3 | 20 | 20 | 20 | 20 | 20 | 22 |
| Z49254_at | H. sapiens L23-related mRNA | 105 | 216 | 123 | 92 | 20 | 121 |
| Z49269_at | H. sapiens gene for chemokine HCC-1 | 62 | 20 | 20 | 20 | 72 | 20 |
| Z49825_s_at | H. sapiens mRNA for hepatocyte nuclear factor 4 alpha | 20 | 20 | 20 | 20 | 203 | 20 |
| Z49835_s_at | H. sapiens mRNA for protein disulfide isomerase | 349 | 195 | 1098 | 989 | 321 | 277 |
| Z49878_at | H. sapiens mRNA for guanidinoacetate N-methyltransferase | 50 | 116 | 50 | 65 | 52 | 126 |
| Z49989_at | H. sapiens mRNA for smoothelin | 43 | 26 | 20 | 20 | 21 | 20 |
| Z49995_at | H. sapiens mRNA (non-coding; clone h2A) | 20 | 20 | 20 | 20 | 20 | 20 |
| Z50022_at | H. sapiens mRNA for surface glycoprotein | 145 | 237 | 344 | 251 | 31 | 85 |
| Z50053_at | H. sapiens mRNA for alpha2i-subunit of soluble guanylyl cyclase | 20 | 20 | 20 | 20 | 20 | 20 |
| Z50115_s_at | H. sapiens mRNA for thimet oligopeptidase (metalloproteinase) | 20 | 20 | 20 | 20 | 113 | 37 |
| Z50194_at | H. sapiens mRNA for PQ-rich protein | 103 | 20 | 20 | 20 | 20 | 20 |
| Z50749_at | H. sapiens sds22-like mRNA | 41 | 25 | 54 | 45 | 20 | 68 |
| Z50781_at | H. sapiens mRNA for leucine zipper protein | 67 | 113 | 84 | 121 | 64 | 218 |
| Z50853_at | H. sapiens mRNA for CLPP | 80 | 59 | 107 | 88 | 30 | 134 |
| Z54367_s_at | H. sapiens gene for plectin | 44 | 20 | 200 | 176 | 349 | 93 |
| Z56281_at | H. sapiens mRNA for interferon regulatory factor 3 | 20 | 120 | 102 | 104 | 135 | 235 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| Z67743_at | H. sapiens mRNA for CLC-7 chloride channel protein | 33 | 20 | 43 | 43 | 84 | 72 |
| Z68129_cds1_at | H. sapiens IDH gamma gene and TRAP delta gene. | 47 | 20 | 62 | 60 | 22 | 85 |
| Z68193_at | Human DNA sequence from cosmid "QC8B6," on chromosome "Xq28," containing red opsin gene | 38 | 20 | 20 | 20 | 102 | 30 |
| Z68204_at | H. sapiens mRNA for succinyl CA synthetase. /gb=Z68204 /ntype=RNA | 61 | 20 | 38 | 44 | 20 | 61 |
| Z68228_s_at | H. sapiens mRNA for plakoglobin | 779 | 199 | 772 | 1008 | 660 | 342 |
| Z68274_at | HUman DNA sequence from cosmid "L129H7," Huntington's Disease "Region," chromosome 4p16.3 contains Pseudogene and CpG islan | 20 | 20 | 20 | 20 | 20 | 20 |
| Z68280_cds2_s_at | Erythrocyte adducin alpha subunit gene extracted from Human DNA sequence from cosmid "L25A3," Huntington'Disease "Region," chro | 35 | 20 | 154 | 123 | 207 | 110 |
| Z68747_at | H. sapiens mRNA for imogen 38 /gb=Z68747 /ntype=RNA | 20 | 80 | 24 | 20 | 20 | 20 |
| Z69030_s_at | H. sapiens mRNA for gamma 1 isoform of 61kDa regulatory subunit of PP2A | 78 | 99 | 164 | 143 | 251 | 114 |
| Z69043_s_at | H. sapiens mRNA translocon-associated protein delta subunit precursor | 342 | 722 | 863 | 876 | 325 | 357 |
| Z69720_at | Human DNA sequence from cosmid RA36 from a contig from the tip of the short arm of chromosome "16," spanning 2Mb of 16p13.3 Con | 83 | 101 | 64 | 57 | 133 | 99 |
| Z69881_at | H. sapiens mRNA for adenosine "triphosphatase," calcium | 20 | 20 | 20 | 20 | 20 | 20 |
| Z69915_at | H. sapiens mRNA (clone ICRFp507L1876). /gb=Z69915 /ntype=RNA | 31 | 20 | 52 | 44 | 49 | 85 |
| Z69923_at | Human DNA sequence from cosmid "L219F9," Huntington's Disease "Region," chromosome 4p16.3 contains hepatocyte growth factor (H | 20 | 20 | 20 | 20 | 39 | 20 |
| Z70218_s_at | H. sapiens mRNA for MN1 protein (clone ICRFp507I0498) | 20 | 20 | 20 | 20 | 20 | 20 |
| Z70219_at | H. sapiens mRNA for 5UTR for unknown protein (clone iCRFp507C0696). /gb=Z70219 /ntype=RNA | 49 | 69 | 43 | 39 | 75 | 62 |
| Z70220_at | H. sapiens mRNA for 5UTR for unknown protein (clone iCRFp507O0882). /gb=Z70220 /ntype=RNA | 20 | 20 | 20 | 20 | 20 | 20 |
| Z70222_at | H. sapiens mRNA for ORF (clone ICRFp507G2490). /gb=270222 /ntype=RNA | 20 | 20 | 20 | 20 | 20 | 20 |
| Z70276_s_at | H. sapiens mRNA for fibroblast growth factor 12 (partial). /gb=Z70276 /ntype=RNA | 20 | 20 | 20 | 21 | 49 | 20 |
| Z70295_at | H. sapiens GCAP-II gene | 20 | 20 | 20 | 20 | 25 | 20 |
| Z70723_at | H. sapiens mRNA for serum aryldiakylphosphatase | 20 | 20 | 20 | 20 | 20 | 20 |
| Z70759_at | H. sapiens mRNA mitochondrial 16S rRNA gene (partial). /gb=Z70759 /ntype=RNA | 7648 | 8169 | 5750 | 6666 | 18718 | 15856 |
| Z71389_at | H. sapiens mRNA for skin-antimicrobial-peptide 1 (SAP1). /gb=Z71389 /ntype=RNA | 20 | 20 | 20 | 20 | 20 | 20 |
| Z71460_at | H. sapiens mRNA for vacuolar-type H(+)-ATPase 115 kDa subunit | 122 | 125 | 144 | 102 | 163 | 188 |
| Z72499_at | H. sapiens mRNA for herpesvirus associated ubiquitin-specific protease (HAUSP) | 73 | 42 | 90 | 79 | 20 | 20 |
| Z73497_at | Human DNA sequence from cosmid "U240C2," between markers DXS366 and DXS87 on chromosome X. Contains Histone "H2B," "ESTs | 20 | 20 | 20 | 20 | 20 | 20 |
| Z73677_at | H. sapiens gene encoding plakophilin 1b. /gb=Z73677 /ntype=DNA /annot=mRNA | 20 | 20 | 20 | 20 | 20 | 20 |
| Z73903_at | H. sapiens mRNA for TRPC1A | 20 | 20 | 20 | 20 | 20 | 20 |
| Z74615_at | H. sapiens mRNA for prepro-alpha1(I) collagen | 90 | 137 | 314 | 295 | 537 | 347 |
| Z74616_s_at | H. sapiens mRNA for prepro-alpha2(I) collagen | 153 | 90 | 20 | 20 | 20 | 20 |
| Z74792_s_at | H. sapiens mRNA for CCAAT transcription binding factor subunit gamma | 21 | 32 | 72 | 58 | 20 | 20 |
| Z75190_s_at | H. sapiens mRNA for apolipoprotein E receptor 2 | 20 | 20 | 20 | 20 | 20 | 20 |
| Z75330_at | H. sapiens mRNA for nuclear protein SA-1. /gb=Z75330 /ntype=RNA | 20 | 20 | 20 | 20 | 20 | 20 |
| Z78285_f_at | H. sapiens mRNA (clone 1A7). /gb=Z78285 /ntype=DNA /annot=mRNA | 20 | 20 | 20 | 20 | 20 | 20 |
| Z78289_at | H. sapiens mRNA (clone 1D2). /gb=Z78289 /ntype=DNA /annot=mRNA | 82 | 68 | 48 | 42 | 54 | 110 |
| Z78290_at | H. sapiens mRNA (clone 1D7). /gb=Z78290 /ntype=DNA /annot=mRNA | 20 | 20 | 20 | 20 | 20 | 20 |
| Z78291_at | H. sapiens mRNA (clone 1D8). /gb=Z78291 /ntype=DNA /annot=mRNA | 20 | 20 | 20 | 20 | 20 | 20 |
| Z79581_at | H. sapiens LAZ3/BCL6 "gene," first non coding exon. /gb=Z79581 /ntype=DNA /annot=exon | 20 | 99 | 20 | 196 | 201 | 38 |
| Z79693_s_at | H. sapiens mRNA for protein-tyrosine phosphatase NC-PTPCOM1 | 20 | 20 | 20 | 20 | 20 | 20 |
| Z80345_ma1_s_at | H. sapiens SCAD "gene," exon 1 and joining features | 20 | 20 | 20 | 20 | 67 | 50 |
| Z80776_at | H. sapiens H2A/g gene | 20 | 20 | 20 | 20 | 61 | 20 |
| Z80779_at | H. sapiens H2A/k gene | 20 | 20 | 27 | 31 | 71 | 20 |
| Z80780_f_at | H. sapiens H2B/g gene. /gb=Z80780 /ntype=DNA /annot=CDS | 20 | 20 | 20 | 20 | 20 | 20 |
| Z80781_at | H. sapiens H2B/h gene | 20 | 20 | 20 | 20 | 20 | 20 |
| Z80783_at | H. sapiens H2B/j gene | 329 | 185 | 289 | 203 | 1044 | 468 |
| Z80787_at | H. sapiens H4/j gene | 20 | 24 | 107 | 22 | 762 | 99 |

TABLE 8-continued

Expressed RNA in Suburothelial connective tissue, Normal urothelium and Transitional cell carcinomas

| Gene name | Description | Connect. Tiss. | Norm. uroth. | Ta GrI | TaGrII | T2GrIII | T2GrIV |
|---|---|---|---|---|---|---|---|
| Z80788_at | H. sapiens H4/l gene | 20 | 20 | 20 | 20 | 24 | 20 |
| Z81326_at | H. sapiens mRNA for protease inhibitor 12 (PI12; neuroserpin) | 20 | 20 | 20 | 20 | 20 | 20 |
| Z83336_at | H. sapiens hH2B/d gene | 41 | 79 | 98 | 58 | 555 | 178 |
| Z83735_at | H. sapiens hH3/k gene | 20 | 20 | 20 | 20 | 20 | 20 |
| Z83741_at | H. sapiens hH2A/m gene | 20 | 20 | 20 | 20 | 20 | 20 |
| Z83742_at | H. sapiens hH2A/c gene | 28 | 20 | 21 | 20 | 27 | 27 |
| Z83745_at | Human DNA sequence from PAC 453A3 contains EST and STS. /gb=Z83745 /ntype=DNA /annot=exon | 20 | 35 | 20 | 23 | 90 | 20 |
| Z83799_at | H. sapiens mRNA for axonemal dynein heavy chain "(partial," ID hdhc1). /gb=Z83799 /ntype=DNA /annot=CDS | 20 | 20 | 20 | 20 | 20 | 20 |
| Z83800_at | H. sapiens mRNA for cytoplasmic dynein heavy chain "(partial," ID hdhc11). /gb=Z83800 /ntype=DNA /annot=CDS | 20 | 41 | 20 | 20 | 21 | 20 |
| Z83802_at | H. sapiens mRNA for axonemal dynein heavy chain "(partial," ID hdhc3). /gb=Z83802 /ntype=DNA /annot=CDS | 20 | 20 | 20 | 20 | 29 | 20 |
| Z83803_at | H. sapiens mRNA for axonemal dynein heavy chain "(partial," ID hdhc4). /gb=Z83803 /ntype=DNA /annot=CDS | 20 | 20 | 20 | 20 | 20 | 20 |
| Z83804_at | H. sapiens mRNA for axonemal dynein heavy chain "(partial," ID hdhc7). /gb=Z83804 /ntype=DNA /annot=CDS | 20 | 20 | 20 | 20 | 63 | 60 |
| Z83805_at | H. sapiens mRNA for axonemal dynein heavy chain "(partial," ID hdhc8). /gb=Z83805 /ntype=DNA /annot=CDS | 20 | 20 | 20 | 20 | 74 | 55 |
| Z83806_at | H. sapiens mRNA for axonemal dynein heavy chain "(partial," ID hdhc9). /gb=Z83806 /ntype=DNA /annot=CDS | 20 | 20 | 20 | 20 | 20 | 20 |
| Z83821_cds2_at | Human DNA sequence from PAC 296K21 on chromosome X contains cytokeratin exon, delta-aminolevulinate synthase (erythroid); 5-ami | 20 | 20 | 20 | 20 | 20 | 20 |
| Z84483_at | Human DNA sequence from PAC "46H23," BRCA2 gene region chromosome 13q12–13 contains lactase phlorizin hydrolase "(LCT)," EST | 20 | 111 | 390 | 240 | 345 | 201 |
| Z84497_s_at | Human DNA sequence from cosmid O14 on hcromosome 6 contains RIN3. CpG Island | 131 | 20 | 20 | 20 | 20 | 20 |
| Z84718_cds1_at | Human DNA sequence from BAC 322B1 on chromosome 22q11.2-ater contains GSTT1, GSTT2 glutathione transferases 4E-binding prot | 20 | 20 | 20 | 26 | 20 | 99 |
| Z84721_cds1_at | Human DNA sequnce form cosmid GG1 from a contig from the tip of the short arm of chromosome 16, spanning 2Mb of 16p13.3 Contain | 20 | 27 | 20 | 30 | 20 | 2470 |
| Z84721_cds2_at | Human DNA sequnce from cosmid GG1 from a contig from the tip of the short arm of chromosome 16, spanning 2Mb of 16p13.3 | 125 | 604 | 189 | 116 | 1155 | 2470 |
| Z84722_at | Human DNA sequnce from cosmid GG4 from a contig from the tip of the sort arm of chromosome "16," spanning 2Mb of 16p13.3 | 20 | 20 | 20 | 20 | 20 | 20 |
| Z86000_at | Human DNA sequence from PAC 151B14 on chromosome 22q12-qter contains somatostatin receptor subtype 3 "(SSTR3)," "tRNA," "EST | 48 | 59 | 127 | 115 | 135 | 88 |
| Z93784_at | Homo sapiens DNA sequence from PAC 398C22 on chromosome 22q11.2-qter. Contains mouse Brain Protein E46 like "sequences," EST | 31 | 20 | 76 | 76 | 20 | 20 |
| Z94753_s_at | Human DNA sequence from PAC465G10 on chromosome X contains Menkes Disease (ATP7A) putative Cu++tansporting P-type ATPa | 20 | 77 | 20 | 29 | 106 | 34 |
| Z95624_at | Human DNA sequence from cosmid U237H1 contains Ras like GTPase and ESTs | 44 | 39 | 31 | 21 | 50 | 70 |
| Z96810_at | Human DNA sequence from PAC452H17 on chromosome X contains sodium-and chloride-dependent glycine transporter 1 (GIYT-1) "lik | 20 | 20 | 20 | 20 | 73 | 20 |
| Z97054_xpt2_at | Human DNA sequence from PAC 339A18 on chromosome Xp11.2. Contains KIAA0178 gene, similar to mitosis-specific chromosome seg | 26 | 20 | 47 | 80 | 143 | 89 |
| Z97074_at | Homo sapiens mRNA for Rab9 effector "p40," comlete cds. /gb=Z97074 /ntype=RNA | 20 | 57 | 20 | 20 | 20 | 22 |

TABLE 9

| Genbank | Gene ID | Gene name | covariance |
|---|---|---|---|
| AB000584_at | AB000584 | TGF-beta superfamily protein, | av dif neg |
| AB002533_at | KPNA4 | Qip1, :karyopherin alpha 4 | av dif neg |
| AB002559_at | AB002559 | hunc18b2, | av dif neg |
| AB003102_at | AB003102 | 26S proteasome subunit p44.5, | av dif neg |
| AB006782_at | AB006782 | galectin-9 isoform, | av dif neg |
| AC002045_xpt2_s_at | AC002045 | Chromosome 16 BAC clone CIT987 | av dif neg |
| AC002073_cdst_at | AC002073 | PAC clone DJ515N1 from 22q11.2 | av dif neg |
| AC0O2115_cds1_at | AC002115 | DNA from overlapping chromosom | av dif neg |
| AC002115_cds4_at | AC002115 | DNA from overlapping chromosom | av dif neg |
| A0000092_cds1_at | CH19HHR23 | DNA from chromosome 19p13.2 co | av dif neg |
| AF000562_at | AF000562 | uroplakin II mRNA, | av dif neg |
| AF001359_f_at | AF001359 | DNA mismatch repair protein Ü | av dif neg |
| AF009368_at | AF009368 | Luman mRNA, :Luman "mRNA," / | av dif neg |
| AF015913_at | SKB1 | SKB1Hs mRNA, :skb1 ÜS. pombe | av dif neg |
| D00017 at | HUMLIC | lipocortin II, :annexin II | av dif neg |
| D00408_s_at | HUMXYPFLA | fetal liver cytochrome P-450 | av dif neg |
| D00596_at | HUMTS1 | gene for thymidylate synthase, | av dif neg |
| D00654_at | HUMACTSG7 | gene for enteric smooth muscle | av dif neg |
| D10523_at | HUM20GDH | 2-oxoglutarate dehydrogenase, | av dif neg |
| D11086_at | HUMIL2RG | interleukin 2 receptor gamma | av dif neg |
| D11086_at | HUMIL2RG | interleukin 2 receptor gamma | av dif neg |
| D11094_at | HUMMSS1 | MSS1, :proteasome Üprosome, | av dif neg |
| D11327_s_at | HUMLCPTP | protein-tyrosine phosphatase, | av dif neg |
| D13118_at | HUMATPSCP1 | P1 ATP synthase subunit c, : | av dif neg |
| D13413_ma1_s_at | HUMTA120 | tumor-associated 120 kDa nucl | av dif neg |
| D13643_at | HUMRSC390 | KIAA0018 gene, :KIAA0018 gen | av dif neg |
| D13705_s_at | HUMOMHY | fatty acids omega-hydroxylase | av dif neg |
| D13748_at | HUM4AI | eukaryotic initiation factor | av dif neg |
| D14043_at | HUMMGC24 | MGC-24, : "MGC-24", complete | av dif neg |
| D14530_at | HUMRSPT | homolog of yeast ribosomal pro | av dif neg |
| D14710_at | HUMIPASAS2 | ATP synthase alpha subunit, | av dif neg |
| D16294_at | HUMDSAEC | mitochondrial 3-oxoacyl-COA t | av dif neg |
| D16562_at | HUMATPSGL | ATP synthase gamma-subunit Ü | av dif neg |
| D16581_at | HUM8ODGTP | 8-oxo-dGTPase, : "8-oxo-dGTP | av dif neg |
| D17516_at | HUMPACAPR | PACAP receptor, :adenylate c | av dif neg |
| D17516_at | HUMPACAPR | PACAP receptor, :adenylate c | av dif neg |
| D17525_at | D17525 | precursor of P100 serine prot | av dif neg |
| D21063_at | HUMORFAAA | KIAA0030 gene, | av dif neg |
| D21261_at | HUMORFFA | KIAA0120 gene, :transgelin 2 | av dif neg |
| D23860_at | HUMRSP | ribosomal protein, : ribosom | av dif neg |
| D25218_at | HUMORFN | KIAA0112 gene, | av dif neg |
| D25218_at | HUMORFN | KIAA0112 gene, | av dif neg |
| D25248_at | HUMRES44 | mRNA, clone:RES4-4. | av dif neg |
| D25248_at | HUMRES44 | mRNA, clone:RES4-4. | av dif neg |
| D25278_at | HUMORFO | KIAA0036 gene, :KIM0036 gen | av dif neg |
| D25303_at | HUMIAS | integrin alpha subunit, | av dif neg |
| D26129_at | HUMRNASA | ribonuclease A ÜRNase Aü, | av dif neg |
| D26528_at | HUMRNA | RNA helicase, :DEAD/H ÜAsp- | av dif neg |
| D26535_s_at | HUMDS | gene for dihydrolipoamide succ | av dif neg |
| D26599_at | HUMPSH2 | proteasome subunit HsC7-1, : | av dif neg |
| D28383_at | HUMASB42 | ATP synthase B chain, 5'UTR | av dif neg |
| D28589_at | HUMKG1E | mRNA ÜKIAA00167ü, partial se | av dif neg |
| D28915_at | HUMHCAMAP8 | gene for hepatitis C-associate | av dif neg |
| D29012_at | HUMPSY | proteasome subunit Y, : prot | av dif neg |
| D29841_at | HUMORFA02 | KIAA0052 gene, | av dif neg |
| D29958_at | HUMORFA10 | KIAA0116 gene, | av dif neg |
| D30655_at | HUMELF4A11 | eukaryotic initiation factor | av dif neg |
| D31764_at | HUMORFKG1C | KIAA0064 gene, :KIAA0064 gen | av dif neg |
| D31764_at | HUMORFKG1C | KIAA0064 gene, :KIAA0064 gen | av dif neg |
| D31883_at | HUMORFKG1L | KIAA0059 gene, :KIAA0059 "g | av dif neg |
| D31884_at | HUMORFKG1M | KIAA0063 gene, :KIAA0063 gen | av dif neg |
| D31884_at | HUMORFKG1M | KIAA0063 gene, :KIAA0063 gen | av dif neg |
| D31891_at | HUMORFKG1T | KIAA0067 gene, :SET domain, | av dif neg |
| D32129_f_at | HUMHLAAD | HLA class-I ÜHLA-A26ü heavy | av dif neg |
| D38047_at | HUMPSP31 | 26S proteasome subunit p31, | av dif neg |
| D38555_at | HUMORF008 | KIAA0079 gene, :Sec24p, S. C | av dif neg |
| D38583_at | HUMCOLO | calgizzarin, : "calgizzarin, | av dif neg |
| D42046_at | HUMKIAAJ | KIAA0083 gene, :DNA2 ÜDNA r | av dif neg |
| D42046_at | HUMKIAAJ | KIAA0083 gene, :DNA2 ÜDNA r | av dif neg |
| D42047_at | HUMKIAAK | KIAA0089 gene, : KIAA0089 "g | av dif neg |
| D43882_s_at | HUMVLCAD | very-long-chain acyl-COA dehy | av dif neg |
| D45370_at | HUMUPST1 | apM2 G82374 Üunknown product | av dif neg |
| D49396_at | HUMAOP1 | Apo1_ÜMER5ÜAop1-Mouseü-lik | av dif neg |
| D49488_at | HUMHTTP | alpha-tocopherol transfer pro | av dif neg |
| D49728_at | HUMNAK1 | NAK1 DNA binding protein, | av dif neg |
| D49824_s_at | HUMHLABAA | HLA-B null allele mRNA. :HLA-B | av dif neg |
| D50640_at | D50625S16 | DNA for phosphodiesterase 3B, | av dif neg |

TABLE 9-continued

| Genbank | Gene ID | Gene name | covariance |
|---|---|---|---|
| D63478_at | KIAA0144 | KIAA0144 gene, :KIAA0144 gen | av dif neg |
| D63479_s_at | D63479 | KIAA0145 gene, | av dif neg |
| D63485_at | KIAA0151 | KIAA0151 gene, :KIAA0151 gen | av dif neg |
| D63486_at | KIAA0152 | KIAA0152 gene, :KIAA0152 gen | av dif neg |
| D63851_at | D63851 | unc-18 homologue, | av dif neg |
| D78129_at | HUMHL1115B | squalene epoxidase, | av dif neg |
| D78275_at | PSMC6 | proteasome subunit p42, :pro | av dif neg |
| D79205_at | D79205 | ribosomal protein L39, | av dif neg |
| D79984_s_at | D79984 | KIAA0182 gene, | av dif neg |
| D79984_s_at | D79984 | KIAA0162 gene, | av dif neg |
| D80002_at | D80002 | KIAA0180 gene, | av dif neg |
| D82345_at | D82345 | NB thymosin beta, | av dif neg |
| D88425_at | D86425 | osteonidogen, | av dif neg |
| D86974_at | D86974 | KIAA0220 gene, :"KIAA0220" | av dif neg |
| D86985_at | KIAA0232 | KIAA0232 gene, :KIAA0232 gen | av dif neg |
| D87258_at | D87258 | serin protease with IGF-bindi | av dif neg |
| D87735_at | RPL14 | ribosomal protein L14, :ribo | av dif neg |
| D87953_at | D87953 | RTP, : "RTP," complete cds | av dif neg |
| D89052_at | ATP6F | proton-ATPase-like protein, | av dif neg |
| HG1034-HT1034_f_at | <empty> | <empty> | av dif neg |
| HG1400-HT1400_s_at | <empty> | <empty> | av dif neg |
| HG1428-HT1428_s_at | HG1428-HT1428 | :""Globin,"" Beta" | av dif neg |
| HG1428-HT1428_s_at | HG1428-HT1428 | :""Globin,"" Beta" | av dif neg |
| HG1515-HT1515_f_at | HG1515-HT1515 | :Transcription Factor Btf3b | av dif neg |
| HG1515-HT1515_f_at | HG1515-HT1515 | :Transcription Factor Btf3b | av dif neg |
| HG1614-HT1614_at | HG1614-HT1614 | :Protein Phosphatase "1," Alp | av dif neg |
| HG1614-HT1614_at | HG16I4-HT1614 | :Protein Phosphatase "1," Alp | av dif neg |
| HG1800-HT1823_at | <empty> | <empty> | av dif neg |
| HG1872-HT1907_at | <empty> | <empty> | av dif neg |
| HG1872-HT1907_f_at | <empty> | <empty> | av dif neg |
| HG1980-HT2023_f_at | <empty> | <empty> | av dif neg |
| HG2147-HT2217_r_at | <empty> | <empty> | av dif neg |
| HG2147-HT2217_r_at | <empty> | <empty> | av dif neg |
| HG2149-HT2219_at | <empty> | <empty> | av dif neg |
| HG2167-HT2237_at | <empty> | <empty> | av dif neg |
| HG2197-HT2267_s_at | HG2197-HT2267 | :""Collage,"" Type ""V111""" | av dif neg |
| HG2238-HT2321_s_at | HG2238-HT2321 | :""Nuclear Mitotic Apparatus P | av dif neg |
| HG2239-HT2324_r_at | <empty> | <empty> | av dif neg |
| HG2239-HT2324_r_at | <empty> | <empty> | av dif neg |
| HG2264-HT2360_at | <empty> | <empty> | av dif neg |
| HG2279-HT2375_at | HG2279-HT2375 | :Triosephosphate Isomerase | av dif neg |
| HG2588-HT4867_at | HG2566-HT4867 | :Microtubule-Associated Prote | av dif neg |
| HG2788-HT2896_at | HG2788-HT2896 | :Calcyclin | av dif neg |
| HG2815-HT2931_at | <empty> | <empty> | av dif neg |
| HG2815-HT2931_s_at | <empty> | <empty> | av dif neg |
| HG2815-HT4023_s_at | <empty> | <empty> | av dif neg |
| HG2873-HT3017_at | <empty> | <empty> | av dif neg |
| HG2917-HT3061_f_at | HG2917-HT3061 | :"Major Histocompatibility""" | av dif neg |
| HG2917-HT3061_f_at | HG2917-HT3061 | :"Major Histocompatibility """ | av dif neg |
| HG2981-HT3127_s_at | <empty> | <empty> | av dif.neg |
| HG2994-HT4850_s_at | <empty> | <empty> | av dif neg |
| HG3039-HT3200_at | <empty> | <empty> | av dif neg |
| HG3076-HT3238_s_at | HG3076-HT3238 | :"Heterogeneous Nuclear Ribon | av dif neg |
| HG3107-HT3283_s_at | <empty> | <empty> | av dif neg |
| HG3107-HT3283_s_at | <empty> | <empty> | av dif neg |
| HG311-HT311_at | <empty> | <empty> | av dif neg |
| HG3214-HT3391_at | <empty> | <empty> | av dif neg |
| HG3236-HT3413_f_at | <empty> | <empty> | av dif neg |
| HG3254-HT3431_at | <empty> | <empty> | av dif neg |
| HG3342-HT3519_s_at | HG3342-HT3519 | :Id1 | av dif neg |
| HG3364-HT3541_at | HG3364-HT3541 | :Ribosomal Protein L37 | av dif neg |
| HG33-HT33_at | HG33-HT33 | <empty> | av dif neg |
| HG3484-HT3678_s_at | <empty> | <empty> | av dif neg |
| HG3514-HT3708_at | HG3514-HT3708 | :Tropomyosin "Tm30nm1" Cytosk | av dif neg |
| HG3543-HT3739_at | HG3543-HT3739 | :Insulin-Like Growth Factor 2 | av dif neg |
| HG3543-HT3739_at | HG3543-HT3739 | :Insulin-Like Growth Factor 2 | av dif neg |
| HG3549-HT3751_at | HG3549-HT3751 | :Wilm's Tumor-Related Protein | av dif neg |
| HG3570-HT3773_at | HG3570-HT3773 | :Protein Phosphatase Inhibito | av dif neg |
| HG3576-HT3779_f_at | <empty> | <empty> | av dif neg |
| HG3576-HT3779_f_at | <empty> | <empty> | av dif neg |
| HG3731-HT4001_at | <empty> | <empty> | av dif neg |
| HG384-HT384_at | HG384-HT384 | :Ribosomal Protein L26 | av dif neg |
| HG384-HT384_at | HG384-HT384 | :Ribosomal Protein L26 | av dif neg |
| HG394-HT4215_at | <empty> | <empty> | av dif neg |
| HG3991-HT4261_r_at | <empty> | <empty> | av dif neg |
| HG4020-HT4290_s_at | HG4020-HT4290 | :Transglutaminase | av dif neg |
| HG4258-HT4528_at | <empty> | <empty> | av dif neg |

TABLE 9-continued

| Genbank | Gene ID | Gene name | covariance |
|---|---|---|---|
| HG4319-HT4589_at | HG4319-HT4589 | :Ribosomal Protein L5 | av dif neg |
| HG4336-HT4606_at | <empty> | <empty> | av dif neg |
| HG4533-HT4938_at | <empty> | <empty> | av dif neg |
| HG4542-HT4947_at | HG4542-HT4947 | :Ribosomal Protein L10 | av dif neg |
| HG4557-HT4962_r_at | <empty> | <empty> | av dif neg |
| HG4668-HT5083_s_at | <empty> | <empty> | av dif neg |
| HG4668-HT5083_s_at | <empty> | <empty> | av dif neg |
| HG4749-HT5197_at | <empty> | <empty> | av dif neg |
| HG613-HT613_at | HG613-HT613 | :Ribosomal Protein S12 | av dif neg |
| HG613-HT613_at | HG613-HT613 | :Ribosomal Protein S12 | av dif neg |
| HG821-HT821_at | <empty> | <empty> | av dif neg |
| HG880-HT880_at | <empty> | <empty> | av dif neg |
| HG880-HT880_at | <empty> | <empty> | av dif neg |
| HG987-HT987_at | HG987-HT987 | :Mac25 :Mac25 | av dif neg |
| J00105_s_at | HSMGLO | messenger RNA fragment for the | av dif neg |
| J02611_at | HUMAPOD | apolipoprotein D mRNA, :apoli | av dif neg |
| J02611_at | HUMAPOD | apolipoprotein D mRNA, :apoli | av dif neg |
| J02683_s_at | HUMATPC | ADP/ATP carrier protein mRNA, | av dif neg |
| J02783_at | HUMTHBP | thyroid hormone binding protei | av dif neg |
| J02874_at | HUMALBP | adipocyte lipid-binding protei | av dif neg |
| J02874_at | HUMALBP | adipocyte lipid-binding protei | av dif neg |
| J02902_at | HUMP2A | pmtein phosphatase 2A regulat | av dif neg |
| J02906_at | HUMCYPIIF | cytochrome P450IIF1 proteinÜ | av dif neg |
| J03077_s_at | HUMGLBA | co-beta glucosidase Üproactiv | av dif neg |
| J03242_s_at | HUMGFIL2 | insulin-like growth factor II m | av dif neg |
| J03242_s_at | HUMGFIL2 | insulin-like growth factor II m | av dif neg |
| J03592_at | HUMTLCA | ADP/ATP translocase mRNA, 3' e | av dif neg |
| J03756_at | HUMGHVA | growth hormone-variant ÜGH1ü | av dif neg |
| J03801_f_at | HUMLSZ | lysozyme mRNA, complete cds wi | av dif neg |
| J03909_at | HUMIIP | gamma-interferon-inducible pm | av dif neg |
| J03909_at | HUMIIP | gamma-interferon-inducible pro | av dif neg |
| J03934_s_at | HUMNMOR | Human, NADÜPüH:menadione oxi | av dif neg |
| J04093_s_at | HUMUGT1FA | phenol UDP-glucuronosyitransfe | av dif neg |
| J04093_s_at | HUMUGT1FA | phenol UDP-glucuronosyitransfe | av dif neg |
| J04152_ma1_s_at | HUMGA733A | gastrointestinal tumor-associa | av dif neg |
| J04164_at | HUM927A | interferon-inducible protein 9 | av dif neg |
| J04164_at | HUM927A | interferon-inducible protein 9 | av dif neg |
| J04173_at | HUMPGAM | phosphoglycerate mutase ÜPGAM | av dif neg |
| J04611_at | HUMANP70 | lupus p70 ÜKuü autoantigen p | av dif neg |
| J04615_at | HUMSNRAA | lupus autoantigen Üsmall nucl | av dif neg |
| J04617_s_at | HUMEF1A | elongation factor EF-1-alpha g | av dif neg |
| J04973_at | HUMCOR2M | cytochrome bc-1 complex core p | av dif neg |
| J05036_s_at | HUMCTSE | cathepsin E mRNA, :cathepsin | av dif neg |
| J05036_s_at | HUMCTSE | cathepsin E mRNA, :cathepsin | av dif neg |
| J05272_at | HUMIMPH | IMP dehydregenase type 1 mRNA | av dif neg |
| K02405_f_at | HUMMHDC3B | MHC class II HLA-DC-3-beta gen | av dif neg |
| K03189_f_at | HUMCGBEL03 | chorionic gonadotropin beta su | av dif pos |
| K03430_at | HUMC1QB2 | complement C1q B-chain gene, e | av dif pos |
| K03430_at | HUMCIQB2 | complement C1q B-chain gene, e | av dif pos |
| L00634_s_at | HUMFPTA | famesyl-protein transferase a | av dif pos |
| L02326_f_at | HUMPREBLYM | Üclone Hu lambda-17ü lambda- | av dif pos |
| L04270_at | HUMTNFRRP | Üclone CD18ü tumor necrosis | av dif pos |
| L04483_s_at | HUMRPS21X | ribosomal protein S21 ÜRPS21 | av dif pos |
| L04490_at | HUMNADH | Üclone CC6ü NADH-ubiquinone | av dif pos |
| L05072_s_at | HUMIFNRF1A | interferon regulatory factor 1 | av dif pos |
| L05188_f_at | HUMSPRR2B | small proline-rich protein 2 | av dif pos |
| L06499_at | HUMRPL37A | ribosomal protein L37a ÜRPL37 | av dif pos |
| L06505_at | HUML12A | ribosomal protein L12 mRNA, : | av dif pos |
| L06797_s_at | HUMGPCR | Üclone L5ü orphan G protein- | av dif pos |
| L08797_s_at | HUMGPCR | Üclone L5ü orphan G protein- | av dif pos |
| L07044_at | HUMCCDPKB | calcium/calmodulin-dependent p | av dif pos |
| L08866_at | HUMPORIN | porin Üporü mRNA, complete c | av dif pos |
| L09209_s_at | HUMAMYLOID | amyloid protein homologue mRNA | av dif pos |
| L10413_at | HUMFTA | famesyltransferase alpha-subu | av dif pos |
| L11566_at | HUMRPL18A | ribosomal protein L18 ÜRPL18 | av dif pos |
| L11672_at | HUMKRUPZN | Kruppel related zinc finger pr | av dif pos |
| L11708_at | HUMB17HSD | 17 beta hydroxysteroid dehydro | av dif pos |
| L11708_at | HUMB17HSD | 17 beta hydroxysteroid dehydro | av dif pos |
| L12711_s_at | HUMTRANSKE | transketolase Ütkü mRNA, :" | av dif pos |
| L12711_s_at | HUMTRANSKE | transketolase Ütkü mRNA, :" | av dif pos |
| L19493_s_at | HUMFMR1R | FMR1 gene, 3'end. | av dif pos |
| L19527_at | HUMRPL27 | ribosomal protein L27 ÜRPL27 | av dif pos |
| L19686_ma1_at | HUMMIF | macrophage migration inhibitor | av dif pos |
| L19686_ma1_at | HUMMIF | macrophage migration inhibitor | av dif pos |
| L19779_at | HUMH2A2A | histone H2A.2 mRNA, :H2A hist | av dif pos |
| L20688_at | HUMLYGDI | GDP-dissociation inhibitor pro | av dif pos |
| L20941_at | HUMFERRITH | ferritin heavy chain mRNA, :f | av dif pos |

TABLE 9-continued

| Genbank | Gene ID | Gene name | covariance |
| --- | --- | --- | --- |
| L21954_at | HSPBR4 | peripheral benzodiazepine rece | av dif pos |
| L21954_at | HSPBR4 | peripheral benzodiazepine rece | av dif pos |
| L26247_at | HUMSUIISO | sui1iso1 mRNA, | av dif pos |
| L27943_at | HUMCYDE | cytidine deaminase ÜCDAü mRN | av dif pos |
| L32868_at | HUMEPR1NP | effector cell protease recepto | av dif pos |
| L32976_at | HUMMLK3A | protein kinase ÜMLK-3ü mRNA, | av dif pos |
| L33075_at | HUMIQGA | ras GTPase-activating-like pro | av dif pos |
| L33243_at | HUMPKD1A | polycystic kidney disease 1 pr | av dif pos |
| L33842_ma1_at | HUMIMPDH | Üclone FFE-7ü type II inosin | av dif pos |
| L33842_ma1_at | HUMIMPDH | Üclone FFE-7ü type II inosin | av dif pos |
| L33930_s_at | HUMCD24B | CD24 signal transducer mRNA, c | av dif pos |
| L37127_at | HUMRPIA | RNA polymerase II mRNA, :poly | av dif pos |
| L38490_s_at | HUMADPRF | ADP-ribosylation factor mRNA, | av dif pos |
| L38928_at | HUMMETSYN | 5,10-methenyltetrahydrofolate | av dif pos |
| L38941_at | HUMRPL34A | ribosomal protein L34 ÜRPL34 | av dif pos |
| L39059_at | HUMTFSL1A | transcription factor SL1 mRNA, | av dif pos |
| L40357_at | HUMTRIP7M | thyroid receptor interactor Ü | av dif pos |
| L40379_at | HUMTRIP10M | thyroid receptor interactor Ü | av dif pos |
| L40387_at | HUMTRIP14G | thyroid receptor interactor Ü | av dif pos |
| L40392_at | HUMORFB | Üclone S164ü mRNA, 3' end of | av dif pos |
| L40904_at | HUMPPARGB | H. sapiens peroxisome prolifer | av dif pos |
| L41870_at | HUMRB1MRNA | retinoblastoma susceptibility | av dif pos |
| L42176_at | HUMDRAL | Üclone 35.3ü DRAL mRNA, :Ü | av dif pos |
| L42373_at | HUMPP2A | phosphatase 2A B56-alpha ÜPP2 | av dif pos |
| L42542_at | HUMRIP1R | RLIP76 protein mRNA, :RLIP76 | av dif pos |
| L76159_at | HUMFRG1R | FRG1 mRNA, :FSHD region gene | av dif pos |
| L76485_at | HUMPGDHB | NAD+-dependent 15 hydroxyprost | av dif pos |
| L77886_at | HUMPTPC | protein tyrosine phosphatase m | av dif pos |
| M10612_at | HUMAPOCII | apolipoprotein C-II gene, | av dif pos |
| M11119_at | HUMERRNA | endogenous retrovirus envelope | av dif pos |
| M11147_at | HUMFERL | ferritin L chain mRNA, :ferri | av dif pos |
| M11313_s_at | HUMA2M | alpha-2-macroglobulin mRNA, : | av dif pos |
| M11353_at | HUMHISH3C | H3.3 histone dass C mRNA, | av dif pos |
| M12529_at | HUMAPOE | apolipoprotein E mRNA, :apoli | av dif pos |
| M12529_at | HUMAPOE | apolipoprotein E mRNA, :apoli | av dif pos |
| M12886_at | HUMTCBYY | T-cell receptor active beta-ch | av dif pos |
| M12886_at | HUMTCBYY | T-cell receptor active beta-ch | av dif pos |
| M13207_at | HUMCSFGMA | granulocyte-macrophage colony- | av dif pos |
| M13560_s_at | HUMIAIG8 | Ia-associated invariant gamma- | av dif pos |
| M13666_at | HUMCMYBB | c-myb mRNA, 34 end. | av dif pos |
| M13755_at | HUMIFN15K | interferon-induced 17-kDa/15-k | av dif pos |
| M13829_s_at | HUMPKS | putative raf related protein | av dif pos |
| M13829_s_at | HUMPKS | putative raf related protein | av dif pos |
| M13903_at | HUMINV2 | involucrin gene, exon 2. :invo | av dif pos |
| M13929_s_at | HUMMYCPOA | c-myc-P64 mRNA, initiating fro | av dif pos |
| M13929_s_at | HUMMYCPOA | c-myc-P64 mRNA, initiating fro | av dif pos |
| M13934_cds2_at | HUMRPS14 | ribosomal protein S14 gene, | av dif pos |
| M13955_at | HUMKERMII | mesothelial keratin K7 Ütype | av dif pos |
| M14199_s_at | HUMLAMR | laminin receptor Ü2H5 epitope | av dif pos |
| M14199_s_at | HUMLAMR | laminin receptor Ü2H5 epitope | av dif pos |
| M14328_s_at | HUMENOA | alpha enolase mRNA, :enolase | av dif pos |
| M14483_ma1_s_at | HUMTHYMAA | prothymosin alpha mRNA, | av dif pos |
| M14676_at | HUMSLK | src-like kinase Üslkü mRNA, | av dif pos |
| M14676_at | HUMSLK | src-like kinase Üslkü mRNA, | av dif pos |
| M15395_at | HUMLAP | leukocyte adhesion protein ÜL | av dif pos |
| M15661_at | HUMRPZH21 | ribosomal protein mRNA, :ribo | av dif pos |
| M15661_at | HUMRPZH21 | ribosomal protein mRNA, :ribo | av dif pos |
| M16038_at | HUMLYN | lyn mRNA encoding a tyrosine k | av dif pos |
| M17733_at | HUMTHYB4 | thymosin beta-4 mRNA, :thymos | av dif pos |
| M17863_s_at | HUMFF12B | preproinsulin-like growth fact | av dif pos |
| M17863_s_at | HUMFF12B | preproinsulin-like growth fact | av dif pos |
| M17885_at | HUMPPARP0 | acidic ribosomal phosphoprotei | av dif pos |
| M17886_at | HUMPPARP1 | acidic ribosomal phosphoprotei | av dif pos |
| M18000_at | HUMRPS17A | ribosomal protein S17 gene, : | av dif pos |
| M18737_ma1_at | HUMHFSP | Hanukah factor serine protease | av dif pos |
| M19045_f_at | HUMLSZH | lysozyme mRNA, :"lysozyme ""m | av dif pos |
| M19159_at | HUMALPPD | placental heat-stable alkaline | av dif pos |
| M19159_at | HUMALPPD | placental heat-stable alkaline | av dif pos |
| M19301_at | HUMKAD | branched-chain alpha-keto acid | av dif pos |
| M19878_s_at | HUMCALB01 | calbindin 27 gene, exons 1 and | av dif pos |
| M20902_at | HUMAPOCIA | apolipoprotein C-I ÜVLDLü ge | av dif pos |
| M20902_at | HUMAPOCIA | apolipoprotein C-I ÜVLDLü ge | av dif pos |
| M21142_cds2_s_at | HUMGNAS6 | guanine nucleotide-binding pro | av dif pos |
| M21142_cds2_s_at | HUMGNAS6 | guanine nucleotide-binding pro | av dif pos |
| M21186_at | HUMNCBLCA | neutrophil cytochrome b light | av dif pos |
| M21186_at | HUMNCBLCA | neutrophil cytochrome b light | av dif pos |
| M21302_at | HUMSPR2B | small proline rich protein Üs | av dif pos |

TABLE 9-continued

| Genbank | Gene ID | Gene name | covariance |
|---|---|---|---|
| M21984_at | HUMTRT | Üclone PWHTnT16ü skeletal mu | av dif pos |
| M22490_at | HUMBMP2B | bone morphogenetic protein-2B | av dif pos |
| M22960_at | HUMPPR | protective protein mRNA, :pro | av dif pos |
| M23178_s_at | HUMG0S19A | homologue-1 of gene encoding a | av dif pos |
| M23813_at | HUMNPM | nudeophosmin mRNA, :nucleoph | av dif pos |
| M24194_at | HUMMHBA123 | MHC protein homologous to chic | av dif pos |
| M24194_at | HUMMHBA123 | MHC protein homologous to chic | av dif pos |
| M24485_s_at | HUMGSTP1G | Üclone PHGST-piü glutathione | av dif pos |
| M24488_s_at | HUMPYHBASA | prolyl 4-hydroxylase alpha sub | av dif pos |
| M25079_s_at | HUMBETGLA | sickle cell beta-globin mRNA, | av dif pos |
| M25079_s_at | HUMBETGLA | sickle ceII beta-globin mRNA, | av dif pos |
| M25280_at | HUMLNHR | Iymph node homing receptor mRN | av dif pos |
| M26311_s_at | HUMCFA | cystic fibrosis antigen mRNA, | av dif pos |
| M26311_s_at | HUMCFA | cystic fibrosis antigen mRNA, | av dif pos |
| M28685_s_at | HUMH1S2X | histatin 2 ÜHIS2ü mRNA, :hi | av dif pos |
| M28708_s_at | HUMPTAA | prothymosin alpha mRNA ÜProT- | av dif pos |
| M28730_s_at | HUMQBPC8 | mitochondrial ubiquinone-bindi | av dif pos |
| M27281_at | HUMVPF | vascular permeability factor m | av dif pos |
| M27749_r_at | HUMIGLR141 | immunoglobulin-related 14.1 pr | av dif pos |
| M27749_r_at | HUMIGLR141 | immunoglobulin-related 14.1 pr | av dif pos |
| M27826_at | HUMRTVLH3 | endogenous retroviral protease | av dif pos |
| M27891_at | HUMCYS3A3 | cystatin C ÜCST3ü gene, exon | av dif pos |
| M28212_at | HUMRAB6A | GTP-binding protein ÜRAB6ü m | av dif pos |
| M28882_s_at | HUMMUC18B | MUC18 glycoprotein mRNA, :mel | av dif pos |
| M28882_s_at | HUMMUC18B | MUC18 glycoprotein mRNA, :mel | av dif pos |
| M29335_at | HUMMHDOA | MHC class II DO-alpha mRNA, | av dif pos |
| M29335_at | HUMMHDOA | MHC class II DO-alpha mRNA, | av dif pos |
| M29610_s_at | HUMGLYE | glycophorin E mRNA, :glycopho | av dif pos |
| M30818_at | HUMMXB | interferon-induced cellular re | av dif pos |
| M30938_at | HUMKUP | Ku Üp70/p80ü subunit mRNA, | av dif pos |
| M31303_ma1_at | HUMOP18A | oncoprotein 18 ÜOp18ü gene, | av dif pos |
| M31303_ma1_at | HUMOP18A | oncoprotein 18 ÜOp18ü gene, | av dif pos |
| M31520_at | HUMRPS24A | ribosomal protein S24 mRNA. | av dif pos |
| M31520_ma1_s_at | HUMRPS24A | ribosomal protein S24 mRNA. :r | av dif pos |
| M31627_at | HUMHXBP1 | X box binding protein-1 ÜXBP- | av dif pos |
| M31994_at | HUMALDC13 | aldehyde dehydrogenase ÜALDH1 | av dif pos |
| M32053_at | HUMH19 | H19 RNA gene, | av dif pos |
| M32304_s_at | HUMMET | metalloproteinase inhibitor mR | av dif pos |
| M32405_at | HUMRIGA | homologue of rat insulinoma ge | av dif pos |
| M32886_at | HUMSRICPA | sorcin CP-22 mRNA, :sorcin :s | av dif pos |
| M33600_f_at | HUMMHDRA1C | MHC class II HLA-DR-beta-1 ÜH | av dif pos |
| M33680_at | HUMTAPA1 | 26-kDa cell surface protein TA | av dif pos |
| M33684_s_at | HUMPPPB1A5 | Üclone lambda-16-1ü non-rece | av dif pos |
| M34041_at | HUMADRA2RA | alpha-2-adrenergic receptor Ü | av dif pos |
| M34182_at | HUMPRKACG | testis-specific protein kinase | av dif pos |
| M34516_at | HUMIGL122 | omega light chain protein 14.1 | av dif pos |
| M34516_r_at | HUMIGL122 | omega light chain protein 14.1 | av dif pos |
| M34516_r_at | HUMIGL122 | omega light chain protein 14.1 | av dif pos |
| M34715_at | HUMPSBGAA | pregnancy-specific beta-1-glc | av dif pos |
| M34996_s_at | HUMDQA1A | MHC cell surface glycoprotein | av dif pos |
| M34996_s_at | HUMDQA1A | MHC cell surface glycoprotein | av dif pos |
| M35198_at | HUMINTB6A | integrin B-6 mRNA, :integrin, | av dif pos |
| M35252_at | HUMCOOTAA | CO-029. :transmembrane 4 super | av dif pos |
| M35878_at | HUMIBP3 | insulin-like growth factor-bin | av dif pos |
| M36072_at | HUMRPL7A | ribosomal protein L7a Üsurf 3 | av dif pos |
| M37238_s_at | HUMPLC | phospholipase C mRNA, :phosph | av dif pos |
| M37245_at | HUMIGCTL3 | Ig superfamily cytotoxic T-lym | av dif pos |
| M37245_at | HUMIGCTL3 | Ig superfamily cytotoxic T-lym | av dif pos |
| M37435_at | HUMCSDF1 | macrophage-specific colony-sti | av dif pos |
| M37583_at | HUMHIS2AZ | histone ÜH2A.Zü mRNA, :hist | av dif pos |
| M37815_cds1_at | HUMCD284 | T-cell membrane glycoprotein C | av dif pos |
| M38449_s_at | HUMTGFBA | transforming growth factor-bet | av dif pos |
| M38890_at | HUMANTCD9 | CD9 antigen mRNA, :CD9 antige | av dif pos |
| M38690_at | HUMANTCD9 | CD9 antigen mRNA, :CD9 antige | av dif pos |
| M54995_at | HUMCTAP3 | connective tissue activation p | av dif pos |
| M55409_s_at | HUMPANCAN | pancreatic tumor-related prote | av dif pos |
| M55409_s_at | HUMPANCAN | pancreatic tumor-related prote | av dif pos |
| M57293_at | HUMPTHRPA | parathyroid hormone-related pe | av dif pos |
| M57399_at | HUMHBNF1 | nerve growth factorÜHBNF-1ü | av dif pos |
| M57399_at | HUMHBNF1 | nerve growth factor ÜHBNF-1ü | av dif pos |
| M57466_s_at | HUMMHDPL | MHC class II HLA-DP light chai | av dif pos |
| M57466_s_at, | HUMMHDPL | MHC class II HLA-DP light chai | av dif pos |
| M57710_at | HUMBPIGE | IgE-binding protein Üepsilon- | av dif pos |
| M58378_cds1_at | HUMSYN1E13 | synapsin I ÜSYN1ü gene, exon | av dif pos |
| M58525_s_at | HUMCOMTC | catechol-O-methyltransferase | av dif pos |
| M58525_s_at | HUMCOMTC | catechol-O-methyltransferase | av dif pos |
| M59216_s_at | UMGABRB1S5 | gamma-aminobutyric acid-A ÜGA | av dif pos |

TABLE 9-continued

| Genbank | Gene ID | Gene name | covariance |
|---|---|---|---|
| M59371_at | HUMECK | protein tyrosine kinase mRNA, | av dif pos |
| M59807_at | HUMNK4 | NK4 mRNA, :natural killer cel | av dif pos |
| M59830_at | HUMMHHSP2 | MHC class III HSP70-2 gene ÜH | av dif pos |
| M59911_at | HUMINTA3A | integrin alpha-3 chain mRNA, | av dif pos |
| M80483_ma1_s_at | HUMPP2AA | protein phosphatase 2A catalyst | av dif pos |
| M60854_at | HUMSRAA | ribosomal protein S16 mRNA, : | av dif pos |
| M61916_at | HUMLAM101 | laminin B1 chain mRNA, :lamin | av dif pos |
| M62403_s_at | HUMIGFBP5 | insulin-like growth factor bin | av dif pos |
| M62403_s_at | HUMIGFBP5 | insulin-like growth factor bin | av dif pos |
| M62486_at | UMPRPC4SI2 | C4b-binding protein gene, exon | av dif pos |
| M63256_at | HUMCDR2AA | major Yo paraneoplastic antige | av dif pos |
| M63379_at | HUMTRPM2A4 | TRPM-2 protein gene, exons 7,8 | av dif pos |
| M63438_s_at | HUMIGGK | Ig rearranged gamma chain mRNA | av dif pos |
| M63438_s_at | HUMIGGK | Ig rearranged gamma chain mRNA | av dif pos |
| M63573_at | HUMSCYLP | secreted cyclophilin-like prot | av dif pos |
| M63589_at | HUMSCL7 | stem cell leukemia gene produc | log neg |
| M64347_at | HUMFGFLR | novel growth factor receptor m | log neg |
| M64347_at | HUMFGFLR | novel growth factor receptor m | log neg |
| M64673_at | HUMHSF1 | heat shock factor 1 ™CF5ü m | log neg |
| M64716_at | HUMRPS25 | ribosomal protein S25 mRNA, : | log neg |
| M64992_at | HUMPRO530 | prosomal protein P30-33K Üpro | log neg |
| M65292_s_at | HUMHAAA | factor H homologue mRNA, :"fa | log neg |
| M65292_s_at | HUMHAAA | factor H homologue mRNA, :"fa | log neg |
| M69023_at | HUMGGEFERA | globin gene. | log neg |
| M69068_at | HUMMOESIN | moesin mRNA, :moesin :moesin | log neg |
| M69238_at | HUMARNTA | aryl hydrocarbon receptor nucl | log neg |
| M73077_at | HUMGRF1A | glucocorticoid receptor repres | log neg |
| M73239_s_at | HUMSCFA1 | Üclone SF1ü hepatocyte growt | log neg |
| M73547_at | HUMPOLLA | polyposis locus ÜDP1 geneü m | log neg |
| M74093_at | HUMCLNC | cyvclin mRNA. :cyclin E1 | log neg |
| M74297_at | HUMHOX14 | homeobox 1.4 protein mRNA, :h | log neg |
| M74715_s_at | HUMIDNAL | alpha-L-iduronidas ÜIDUAü mR | log neg |
| M77232_ma1_at | HUMRPS6B | ribosomal protein S6 gene, com | log neg |
| M77836_at | HUMP5CR | pyrroline 5-carboxylate reduct | log neg |
| M80244_at | HUME16GEN | E16 mRNA, | log neg |
| M80254_at | HUMCYP | cydophilin isoform ÜhCyP3ü | log neg |
| M80359_at | HUMP78A | protein p78 mRNA, :MAP/microt | log neg |
| M80563_at | HUMCAPL | CAPL protein mRNA, :S100 calc | log neg |
| M80563 at | HUMCAPL | CAPL protein mRNA, :S100 calc | log neg |
| M80899_at | HUMAHNAKA | novel protein AHNAK mRNA, part | log neg |
| M81750_at | HUMMCNDA | myeloid cell nuclear different | log neg |
| M81757_at | HUMS19RP | S19 ribosomal protein mRNA, | log neg |
| M81883_at | HUMGAD67A | glutamate decarboxylase ÜGAD6 | log neg |
| M83181_at | HUMHTRB | serotonin receptor gene, :5-h | log neg |
| M84424_at | HUMCTSE09 | cathepsin E ÜCTSEü gene, exo | log neg |
| M84711_at | HUMFTE1A | v-fos transfonnation effector | log neg |
| M85289_at | HUMHSPG2B | heparan sulfate proteoglycan | log neg |
| M86400_at | HUMPHPLA2 | phospholipase A2 mRNA, :tyros | log neg |
| M86699_at | HUMTTK | kinase ™TKü mRNA, :TTK pro | log neg |
| M86737_at | HUMHMGBP | high mobility group box ÜSSRP | log neg |
| M87789_s_at | HUMIGHEPAH | Ühybridoma H210ü anti-hepati | log neg |
| M87789_s_at | HUMIGHEPAH | Ühybridoma H210ü anti-hepati | log neg |
| M90356_f_at | HUMBTFD | BTF3 protein homologue gene, | log neg |
| M90856_at | HUMGCSH | gamma-glutamylcysteine synthet | log neg |
| M91670_at | HUME2EP1 | ubiquitin carrier protein ÜE2 | log neg |
| M94856_at | HUMFABPHA | fatty acid binding protein hom | log neg |
| M94856_at | HUMFABPHA | fatty acid binding protein hom | log neg |
| M94880_f_at | HUMHLAAX | MHC class I ÜHLA-A*8001ü mRN | log neg |
| M96233_s_at | HUMGSTM4A | glutathione transferase class | log neg |
| M96233_s_at | HUMGSTM4A | glutathione transferase class | log neg |
| M96326_ma1_at | HUMAZCDI | azurocidin gene, | log neg |
| M96958_at | HUMTDGF3A | Üclone CR-3ü teratocarcinoma | log neg |
| M97796_s_at | HUMID2X | helix-loop-helix protein ÜId- | log neg |
| M97815_at | HUMCRABP02 | retinoic acid-binding protein | log neg |
| S34389_at | HMOX2 | heme oxygenase-2 (human, kidne | log neg |
| S58544_at | SPAG1 | 75 kda infertility-related spe | log neg |
| S69115_at | S69115 | granulocyte colony-stimulating | log neg |
| S69115_at | S69115 | granulocyte colony-stimulating | log neg |
| S71043_ma1_s_at | S71043 | Ig alpha 2=immunoglobulin A he | log neg |
| S71043_ma1_s_at | S71043 | Ig alpha 2=immunoglobulin A he | log neg |
| S73591_at | VDUP1 | brain-expressed HHCPA78 homolo | log neg |
| S73591_at | VDUP1 | brain-expressed HHCPA78 homolo | log neg |
| S75463_at | S75463 | P43=mitochondrial elongation f | log neg |
| S77356_at | S77356 | transcript ch21 =oligomycin sen | log neg |
| S77582_at | S77582 | HERVK10/HUMMTV reverse transcr | log neg |
| S78234_at | S78234 | nuc2 homolog [human, fibroblas | log neg |
| S78771_s_at | S78771 | NAT=CpG island-associated gene | log neg |

TABLE 9-continued

| Genbank | Gene ID | Gene name | covariance |
|---|---|---|---|
| 579219_s_at | S79219 | metastasis-associated gene (hu | log neg |
| S79522_at | S79522 | ubiquitin carboxyl extension p | log neg |
| 580562_at | CNN3 | acidic calponin [human, kidney | log neg |
| 582297_at | S82297 | beta 2-microglobulin (11bp del | log neg |
| S82597_ma1_s_at | S82597 | UDP-GaINAc:polypeptide | log neg |
| S90469_at | POR | cytochrorme P450 reductase [hum | log neg |
| U00947_s_at | U00947 | clone C4E 3.2 ÜCACün/ÜGTGü | log neg |
| U03397_s_at | U03397 | receptor protein 4-1BB mRNA, | log neg |
| U03398_at | TNFSF9 | receptor 4-1BB ligand mRNA, | log neg |
| U04241_at | U04241 | homolog of Drosophila enhancer | log neg |
| U04313_at | P15 | maspin mRNA, :protease inhibi | log neg |
| U05340_at | CDC20 | p55CDC mRNA, :cell division c | log neg |
| U06155_s_at | U06155 | chromosome iq subtelomeric seq | log neg |
| U06863_at | U06863 | follistatin-related protein pr | log neg |
| U06863_at | U06863 | follistatin-related protein pr | log neg |
| UO9117_at | PLCD1 | phospholipase c delta 1 mRNA, | log neg |
| U09303_at | EFNB1 | T cell leukemia LERK-2 ÜEPLG2 | log neg |
| U09813_at | ATP5G3 | mitochondrial ATP synthase sub | log neg |
| U09953_at | U09953 | ribosomal protein L9 mRNA, :r | log neg |
| U10362_at | U10362 | GP36b glycoprotein mRNA, : | log neg |
| U10492_at | HSMOX1 | Mox1 protein ÜMOX1ü mRNA, : | log neg |
| U12404_at | U12404 | Csa-19 mRNA, | log neg |
| U12404_at | U12404 | Csa-19 mRNA, | log neg |
| U12485_at | U12465 | ribosomal protein L35 mRNA, | log neg |
| U12779_at | U12779 | MAP kinase activated protein k | log neg |
| U14391_at | MYO1C | myosin-IC mRNA, :myosin 1C | log neg |
| U14588_at | PXN | paxillin mRNA, :paxillin :pax | log neg |
| U14968_at | U14968 | ribosomal protein L27a mRNA, | log neg |
| U14969_at | U14969 | ribosomal protein L28 mRNA, : | log neg |
| U14970_at | U14970 | ribosomal protein 55 mRNA, :r | log neg |
| U14971_at | U14971 | ribosomal protein S9 mRNA, :r | log neg |
| U14971_at | U14971 | ribosomal protein S9 mRNA, :r | log neg |
| U14972_at | U14972 | ribosomal protein S10 mRNA, | log neg |
| U14973_at | U14973 | ribosomal protein S29 mRNA, : | log neg |
| U15177_at | U15177 | cosmid CRI-JC2015 at D108289 i | log neg |
| U16660_at | ECH1 | peroxisomal enoyl-CoA hydratas | log neg |
| U16799_s_at | U16799 | Na,K-ATPase beta-1 subunit mRN | log neg |
| U16861_at | KCNJ2 | inward rectifying potassium ch | log neg |
| U17077_at | BENE | BENE mRNA, :BENE protein | log neg |
| U17760_ma1_at | HSLAMB3SI7 | laminin S B3 chain ÜLAMB3ü g | log neg |
| U19247_ma1_s_at | HSINFGRA7 | interferon-gamma receptor alph | log neg |
| U19251_s_at | NAIP | neuronal apoptosis inhibitory | log neg |
| U20857_at | USP4 | ubiquitin pmtease ÜUnphü pr | log neg |
| U20734_s_at | U20734 | transcription factor junB Üju | log neg |
| U20734_s_at | U20734 | transcription factor junB Üju | log neg |
| U20758_ma1_at | U20758 | osteopontin gene, | log neg |
| U22376_cds2_s_at | MYB | Üc-mybü gene, complete prima | log neg |
| U22431_s_at | U22431 | hypoxia-inducible factor 1 alp | log neg |
| U22970_ma1_s_at | U22970 | interferon-inducible peptide | log neg |
| U22970_ma1_s_at | U22970 | interferon-inducible peptide | log neg |
| U24183_at | U24183 | phosphofructokinase ÜPFKMü m | log neg |
| U24389_s_at | H8LYOXL7 | lysyl oxidase-like protein gen | log neg |
| U25789_at | U25789 | ribosomal protein L21 mRNA, | log neg |
| U27333_at | U27333 | alpha Ü1,3ü fucosyltransfera | log neg |
| U27333_at | U27333 | alpha Ü1,3ü fucosyltransfera | log neg |
| U27831_at | U27831 | striatum-enriched phosphatase | log neg |
| U29175_at | U29175 | transcriptional activator ÜBR | log neg |
| U29953_ma1_at | PEDF | pigment epithelium-derived fac | log neg |
| U30827_s_at | U30827 | splicing factor SRp40-3ÜSRp4 | log neg |
| U30888_at | USP14 | tRNA-guanine transglycosylase | log neg |
| U30888_at | USP14 | tRNA-guanine transglycosylase | log neg |
| U31814_at | HDAC2 | transcriptional regulator homo | log neg |
| U31875_at | HEP27 | Hep27 protein mRNA, :short-ch | log neg |
| U32944_at | PIN | cytoplasmic dynein light chain | log neg |
| U34880_at | U34880 | DPH2L mRNA; :DPH2L "mRNA," co | log neg |
| U38341_ma1_at | U36341 | Xq28 cosmid, creatine transpor | log neg |
| U38764_at | U38764 | TGF-beta receptor interacting | log neg |
| U37012_at | U37012 | cleavage and polyadenylation s | log neg |
| U37146_at | U37146 | silencing mediator of retinoid | log neg |
| U37408_at | CTBP1 | phosphoprotein CtBP mRNA, :C- | log neg |
| U37689_at | POLR2H | RNA polymerase II subunit Ühs | log neg |
| U38276_at | SEMA3F | semaphorin III family homolog | log neg |
| U38276_at | SEMA3F | semaphorin III family homolog | log neg |
| U39400_at | C11orf4 | NOF1 mRNA, :chromosome 11 op | log neg |
| U40998_at | U40998 | retinal protein ÜHRG4ü mRNA, | log neg |
| U41060_at | U41060 | breast cancer, estrogen regula | log neg |
| U41768_s_at | ADAM9 | metalloprotease/disintegrin/cy | log neg |

TABLE 9-continued

| Genbank | Gene ID | Gene name | covariance |
|---|---|---|---|
| U42359_at | HUMN33S10 | N33 protein form 1ÜN33ü gen | log neg |
| U43328_at | U43328 | link protein mRNA, | log neg |
| U43901_ma1_s_at | U43901 | 37 kD laminin receptor precurs | log neg |
| U43901_ma1_s_at | U43901 | 37 kD laminin receptor precurs | log neg |
| U45448_s_at | U45448 | P2x1 receptor mRNA, | log neg |
| U48705_ma1_s_at | U48705 | receptor tyrosine kinase DDR g | log neg |
| U48938_at | U48936 | amiloride-sensitive epithelial | log neg |
| U48938_at | U48936 | amiloride-sensitive epithelial | log neg |
| U49395_at | U49395 | ionotropic ATP receptor P2x5a | log neg |
| U49889_ma1_at | UBB | ubiquitin gene, :ubiquitin B | log neg |
| U50523_at | U50523 | BRCA2 region, mRNA sequence CG | log neg |
| U50929_at | BHMT | betaine:homocysteine methyltra | log neg |
| U52154_at | KCNJ5 | G protein-coupled inwardly rec | log neg |
| U52154_at | KCNJ5 | G protein-coupled inwardly rec | log neg |
| U52696_s_at | U52696 | adrenal Creb-rp homolog ÜCreb | log neg |
| U53786_at | U53786 | envoplakin ÜEVPLü mRNA, :en | log neg |
| U55054_at | HSKCC | K-Cl cotransporter ÜhKCC1ü m | log neg |
| U55054_at | HSKCC | K-Cl cotransporter ÜhKCC1ü m | log neg |
| U57341_r_at | U57341 | neurofilament triplet L protei | log neg |
| U57342_at | MLF2 | myelodysplasia/myeloid leukemi | log neg |
| U57629_at | RPGR | retinitis pigmentosa GTPase re | log neg |
| U58882_at | U58682 | ribosomal protein S28 mRNA, : | log neg |
| U80975_at | U60975 | hybrid receptor gp250 precurso | log neg |
| U60975_at | U60975 | hybrid receptor gp250 precurso | log neg |
| U62739_at | BCAT2 | branched-chain amino acid amin | log neg |
| U62962_at | E1F356 | Int-6 mRNA, :eukaryotic trans | log neg |
| U63541_at | U63541 | mRNA expressed in HC/HCC liver | log neg |
| U64863_at | PDCD1 | hPD-1 ÜhPD-1ü mRNA, :progra | log neg |
| U66061_cds3_at | U66061 | germline T-cell receptor beta | log neg |
| U66406_at | EFNB3 | putative EPH-related PTK recep | log neg |
| U66616_at | SMARCC2 | SWI/SNF complex 170 KDa subuni | log neg |
| U68616_at | SMARCC2 | SWI/SNF complex 170 KDa subuni | log neg |
| U87092_s_at | U67092 | ataxia-telangiectasia locus pr | log neg |
| U67156_at | MEKK5 | mitogen-activated kinase kinas | log neg |
| U68105_s_at | HSPABPS13 | polyÜAü-binding protein ÜPA | log neg |
| U70732_ma1_at | GPT | glutamate pyruvate transaminas | log neg |
| U70867_at | SLC21A2 | prostaglandin transporter hPGT | log neg |
| U73379_at | U73379 | cyclin-selective ubiquitin car | log neg |
| U73379_at | U73379 | cyclin-selective ubiquitin car | log neg |
| U73824_at | EIF4G2 | p97 mRNA, :eukaryotic transla | log neg |
| U73843_at | U73843 | epithelial-specific transcript | log neg |
| U77456_at | NAP1L4 | nucleosome assembly protein 2 | log neg |
| U77848_ma1_at | U77846 | elastin gene, partial cds and | log neg |
| U77846_ma1_s_at | U77846 | elastin gene, partial cds and | log neg |
| U77848_ma1_s_at | U77846 | elastin gene, partial cds and | log neg |
| U78021_ma3_at | U78027 | Bruton's tyrosine kinase ÜBTK | log neg |
| U78095_at | U78095 | placental bikunin mRNA, :Plac | log neg |
| U78678_at | U78678 | thioredoxin mRNA, nuclear gene | log neg |
| U78722_at | U78722 | zinc finger protein 165 ÜZpf1 | log neg |
| U78735_at | U78735 | ABC3 mRNA, | log neg |
| U79256_at | U79256 | clone 23719 mRNA sequence. | log neg |
| U79280_at | U79280 | clone 23575 mRNA, | log neg |
| U79299_at | U79299 | neuronal olfactomedin-related | log neg |
| U80184_ma1_at | FUI | FLII gene, :flightless I ÜDr | log neg |
| U81984_at | EPAS1 | endothelial PAS domain protein | log neg |
| U82169_at | FZD9 | frizzled homolog ÜFZD3ü mRNA | log neg |
| U82169_at | FZD9 | frizzled homolog ÜFZD3ü mRNA | log neg |
| U82818_at | U82818 | UCP3S mRNA, | log neg |
| U83246_at | CPNE1 | copine I mRNA, :copine I :cop | log neg |
| U83598_at | U83598 | death domain receptor 3 solubl | log neg |
| U86136_at | U86136 | telomerase-associated protein | log neg |
| U87972_at | U87972 | NAD+-isocitrate dehydrogenase | log pos |
| U88964_at | ISG20 | HEM45 mRNA, :interferon stimu | log pos |
| U89326_at | U89326 | bone morphogenetic protein rec | log pos |
| U90426_at | DDXL | nudear RNA helicase, :nucla | log pos |
| U90552_s_at | U90552 | butyrophilin ÜBTF5ü mRNA, : | log pos |
| U90913_at | U90913 | clone 23665 mRNA sequence. :cl | log pos |
| U90916_at | U90916 | clone 23815 mRNA sequence. :cl | log pos |
| U94747_at | HAN11 | WD repeat protein HAN1 1 mRNA, | log pos |
| U95740_ma1_at | U95740 | Chromosome 16 BAC clone CIT987 | log pos |
| V00571_ma1_at | HSPCRF | gene encoding prepro form of c | log pos |
| V00572_at | HSPGK1 | mRNA encoding phosphoglycerate | log pos |
| V00594_s_at | HSTHIO | metallothionein from cadmium- | log pos |
| V01512_ma1_at | HSCFOS | cellular oncogene c-fos Ücomp | log pos |
| X00274_at | HSHL07 | gene for HLA-DR alpha heavy ch | log pos |
| X00274_at | HSHL07 | gene for HLA-DR alpha heavy ch | log pos |
| X00351_f_at | HSAC07 | beta-actin. | log pos |

TABLE 9-continued

| Genbank | Gene ID | Gene name | covariance |
|---|---|---|---|
| X00368__xpt2__at | HSPROL1 | prolactin gene 5' region. | log pos |
| X01677__f__at | HSGAPDR | liver glyceraldehyde-3-phosph | log pos |
| X02152__at | HSLDHAR | lactate dehydrogenase-A ÜLDH | log pos |
| X02596__at | HSBCRR | bcr ▪reakpoint cluster regi | log pos |
| X03068__f__at | HSHLDQWB | HLA-D class II antigen DQw1.1 | log pos |
| X03100__cds2__at | HSHLASBA | HLA-SBÜDPü alpha gene. :HLA- | log pos |
| X03100__cds2__at | HSHLASBA | HLA-SBÜDPü alpha gene. :HLA- | log pos |
| X03342__at | HSRPL32 | ribosomal protein L32. :ribos | log pos |
| X03689__s__at | HSEFTUR5 | mRNA fragment for elongation f | log pos |
| X03689__s__at | HSEFTUR5 | mRNA fragment for elongation f | log pos |
| X04347__s__at | HSUPIR1 | liver mRNA fragment DNA bindin | log pos |
| X04347__s__at | HSUPIR1 | liver mRNA fragment DNA bindin | log pos |
| X06814__at | HSRRA | receptor of retinoic acid. :r | log pos |
| X06617__at | HSRPS11 | ribosomal protein S11. : ribo | log pos |
| X06985__at | HSOXYGR | heme oxygenase. :heme oxygena | log pos |
| X06985__at | HSOXYGR | heme oxygenase. :heme oxygena | log pos |
| X07696__at | HSKERC15 | cytokeratin 15. :keratin 15: | log pos |
| X07730__at | HSPSA | prostate specific antigen.: | log pos |
| X07730__at | HSPSA | prostate specific antigen.: | log pos |
| X12447__at | HSALDOA | aldolase A gene ÜEC 4.1.2.13 | log pos |
| X12671__ma1__at | HSHNRNPA | gene for heterogeneous nuclear | log pos |
| X12671__ma1__at | HSHNRNPA | gene for heterogeneous nuclear | log pos |
| X12876__s__at | HSKER18A | mRNA fragment for cytokeratin | log pos |
| X12876__s__at | HSKER18A | mRNA fragment for cytokeratin | log pos |
| X13334__at | HSCD14R | CD14 myelid cell-specific leu | log pos |
| X13546__ma1__at | HSHMG17G | HMG-17 gene for non-histone cn | log pos |
| X13794__ma1__at | HSLDHB1 | lactate dehydrogenase B gene e | log pos |
| X13794__ma1__at | HSLDHB1 | lactate dehydrogenase B gene e | log pos |
| X14008__ma1__f__at | HSLYSOZY | lysozyme gene ÜEC 3.2.1.17ü. | log pos |
| X15940__at | HSRPL31 | ribosomal protein L31. :ribos | log pos |
| X16084__at | HSTUMP | translationally controlled tu | log pos |
| X16832__at | HSCATHH | cathepsin H ÜEC 3.4.22.16ü. | log pos |
| X17042__at | HSHPCP | hematopoetic proteoglycan cor | log pos |
| X17206__at | HSLLREP3 | LLRep3. : LLRep3 | log pos |
| X51345__at | HSJUNB | jun-B JUN-B protein. :jun B p | log pos |
| X51466__at | HSEF2 | elongation factor 2. : elonga | log pos |
| X51688__at | HSCYCLINA | cyclin A. | log pos |
| X52003__at | HSPS2MKN | p52 protein gene. :trefoil fac | log pos |
| X52003__at | HSPS2MKN | P52 protein gene. :trefoil fac | log pos |
| X52426__s__at | HSCYTK | cytokeratin 13. : cytokeratin | log pos |
| X52426__s__at | HSCYTK | cytokeratin 13. : cytokeratin | log pos |
| X52851__ma1__at | HSCPH70 | cyclophilin gene for cyclophil | log pos |
| X52966__at | HSL35A | ribosomal protein L35a. :ribo | log pos |
| X53588__ma1__at | HSINTA6R | integrin alpha 8. :integrin, | log pos |
| X53587__at | HSINTB4R | integrin beta 4. : integrin b | log pos |
| X53777__at | HSL23MR | L23 putative ribosomal protei | log pos |
| X54232__at | HSGLYPIC | heparan sulfate proteaglycan | log pos |
| X54867__at | HSCYSTATS | cystatin S. | log pos |
| X54942__at | HSCKSHS2 | ckshs2 Cks1 protein homologue | log pos |
| X54942__at | HSCKSHS2 | ckshs2 Cks1 protein homologue | log pos |
| X55005__ma1__at | HSCERBAR | c-erbA-1 thyroid hormone rece | log pos |
| XS5715__at | HSHUMS3 | Hums3 40S ribosomal protein s | log pos |
| X55954__at | HSL17ARP | HL23 ribosomal protein homolo | log pos |
| X56494__at | HSPKM12 | M gene for M1-type and M2-type | log pos |
| X56887__s__at | HSAUTNOR | autoantigen NOR-90. | log pos |
| X56807__at | HSDGII | DSC2 desmocollins type 2a and | log pos |
| X58841__at | HSHLAE | HLA-E gene. :major histocompat | log pos |
| X56932__at | HS23KDHBP | 23 kD highly basic protein. | log pos |
| X57351__at | HS18D | 1-8D gene from interferon-indu | log pos |
| X57351__at | HS18D | 1-8D gene from interferon-indu | log pos |
| X57351__s__at | HS18D | 1-8D gene from interferon-indu | log pos |
| X57809__s__at | HSIGVL009 | rearranged immunoglobulin lamb | log pos |
| X57809__s__at | HSIGVL009 | rearranged immunoglobulin lamb | log pos |
| X57959__at | HSRBPRL7A | ribosomal protein L7. :riboso | log pos |
| X58072__at | HSGATA3R | hGATA3 trans-acting T-cell sp | log pos |
| X59373__at | HSHOX4D | HOX4D a homeobox protein. :ho | log pos |
| X59798__at | HSPRAD1CY | PRAD1 cyclin. :PRAD1 cyclin | log pos |
| X80489__at | HSEF1B | elongation factor-1-beta. | log pos |
| X61587__at | HSRHOG | rhoG GTPase. :ras homolog gen | log pos |
| X82320__at | HSEPIT1 | epithelin 1 and 2. : epitheli | log pos |
| X82468__at | HSCAMPAT1 | CAMPATH-1 ÜCDw52ü antigen. | log pos |
| X62468__at | HSCAMPAT1 | CAMPATH-1 ÜCDw52ü antigen. | log pos |
| X62854__ma1__at | HSMECDAG | gene for Me491/CD63 antigen.: | log pos |
| X62891__at | HSRPRNA | ribosomal protein Ühomologuo | log pos |
| X63359__at | HSUGT2BIO | UGT2BIO udp glucuronosyltrans | log pos |
| X83527__at | HSRPL19 | ribosomal protein L19. :ribos | log pos |
| X83629__at | HSPCAD | p cadherin. :cadherin 3, P-ca | log pos |

TABLE 9-continued

| Genbank | Gene ID | Gene name | covariance |
|---|---|---|---|
| X84229_at | HSDEK9 | dek mRNA. :DEK gene | log pos |
| X64707_at | HSBBC1 | BBC1 mRNA. | log pos |
| X65814_at | HSS100PCB | calcium-binding protein S100P | log pos |
| X68114_ma1_at | HS2OXOC | gene for 2-oxoglutarate carrie | log pos |
| X88383_at | HSSTHPKD | mRNA PCTAIRE-1 for serine/thre | log pos |
| X66363_at | HSSTHPKD | mRNA PCTAIRE-1 for serine/thre | log pos |
| X88899_at | HSEWS | EWS mRNA. :Ewing sarcoma break | log pos |
| X87247_ma1_at | HSRPS8 | rpS8 gene for ribosomal protei | log pos |
| X87325_at | H5P27 | p27 mRNA. :interferon, alpha-1 | log pos |
| X87951_at | HSPAG | proliferation-associated gene | log pos |
| X68314_at | HSGPGI | glutathione peroxidase-GI. :g | log pos |
| X68314_at | HSGPGI | glutathione peroxidase-GI. :g | log pos |
| X68688_ma1_s_at | HSZNB | ZNF33B gene. | log pos |
| X89150_at | HSRPS18 | ribosomal protein S18. :ribos | log pos |
| X69391_at | HSRPL6AA | ribosomal protein L6. :riboso | log pos |
| X89550_at | HSRHO1 | rho GDP-dissociation Inhibito | log pos |
| X69854_at | H5S26 | ribosomal protein S26. | log pos |
| X70940_s_at | HSEFAC1A2 | elongation factor 1 alpha-2. | log pos |
| X70940_s_at | HSEFAC1A2 | elongation factor 1 alpha-2. | log pos |
| X73079_at | HSPIR | encoding Polymeric immunoglobu | log pos |
| X73358_s_at | HSAES1 | hAES-1 mRNA. :amino-terminal e | log pos |
| X73460_at | HSRPL3A | ribosomal protein L3. | log pos |
| X73478_at | HSPTPAA | hPTPA mRNA. :hPTPA mRNA | log pos |
| X74819_at | HSCARTROT | cardiac troponin T. | log pos |
| X74819_at | HSCARTROT | cardiac troponin T. | log pos |
| X74929_s_at | HSKRT8 | KRT8 keratin 8. :keratin 8 :K | log pos |
| X75252_at | HSPEABP | phosphatidylethanolamine bindi | log pos |
| X76534_at | HSNMB | NMB mRNA. :transmembrane glyco | log pos |
| X76534_at | HSNMB | NMB mRNA. :transmembrane glyco | log pos |
| X77794_at | HSCYCG1 | cyclin G1. : cyclin G1 | log pos |
| X78992_at | HSERF2 | ERF-2 mRNA. | log pos |
| X79234_at | HSRPL11 | ribosomal protein L11. | log pos |
| X79439_at | HSNOTCH3 | Notch 3 DNA sequence. :Notch | log pos |
| X80062_at | HSSAMRNA | SA mRNA. | log pos |
| X80198_at | HSMLN64 | MLN64 mRNA. | log pos |
| X80200_at | HSMLN62 | MLN62 mRNA. :TNF receptor-asso | log pos |
| X80822_at | HSPLORF | ORF. | log pos |
| X80909_at | HSANAC | alpha NAC mRNA. :nascent-polyp | log pos |
| X82893_at | HSE48 | E48 antigen. : E48 antigen | log pos |
| X82693_at | HSE48 | E48 antigen. : E48 antigen | log pos |
| X83418_s_at | HSPRP2 | PrP gene, exon 2. :"Prp "gene | log pos |
| X83492_at | HSFAS47 | Fas/Apo-1 Üclone pCRTM11-Fas | log pos |
| X83492_at | HSFAS47 | Fas/Apo-1 Üclone pCRTM11-Fas | log pos |
| X83572_at | HSARSD | ARSD gene, complete CDS. :aryl | log pos |
| X88809_at | HSPEA15 | major astrocytic phosphoprote | log pos |
| X87159_at | HSSCNN1B | beta subunit of epithelial am | log pos |
| X87241_at | HSHFATPRO | hFat protein. :FAT tumor supp | log pos |
| X89418_at | HSRNAPPP5 | protein phosphatase 5. :prote | log pos |
| X89416_at | HSRNAPPP5 | protein phosphatase 5. :prote | log pos |
| X90848_at | HARNAMLK2 | mixed lineage kinase 2. | log pos |
| X91103_at | HSRNAHR44 | Hr44 protein. | log pos |
| X93038_at | HSMAT82 | MAT8 protein. : phospholemman- | log pos |
| X94563_xpt2_r_at | HSDBIEX12 | dbi/acbp gene exon 1 & 2. | log pos |
| X94612_at | HS2CGMPPK | type ‖ cGMP-dependent protei | log pos |
| X95404_at | HSNMCFL1 | non-muscle type cofilin. :cof | log pos |
| X95735_at | HSZYXIN2R | zyxin. :zyxin | log pos |
| X95808_s_at | HSDXS | protein encoded by a candidat | log pos |
| X98482_at | HS.TNNTX11 | TNNT2 gene exon 11. | log pos |
| X98482_r_at | HSTNNTX11 | TNNT2 gene exon 11. | log pos |
| X98482_r_at | HSTNNTX11 | TNNT2 gene exon 11. | log pos |
| X98534_s_at | HSVASP413 | VASP gene1 exons 4 to 13. :"VA | log pos |
| X99133_at | HSNGALGEN | NGAL gene. :lipocalin 2 Üonco | log pos |
| X99688_at | HSTYL | mRNA from TYL gene. :pleckstri | log pos |
| Y00062_at | HSLCA | T200 leukocyte common antigen | log pos |
| Y00503_at | HSKER19 | keratin 19. :keratin 19 : ker | log pos |
| Y00705_at | HSPSTI | pstl pancreatic secretory inh | log pos |
| Y00787_s_at | HSMDNCF | MDNCF Ümonocyte-derived neut | log pos |
| Y00787_s_at | HSMDNCF | MDNCF Ümonocyte-derived neut | log pos |
| Y00796_at | HSFLA1A | leukocyte-associated molecule | log pos |
| Y07755_at | HSS100A2 | S100A2 gene, exon 1, 2 and 3. | log pos |
| Y07755_at | HSS100A2 | S100A2 gene, exon 1, 2 and 3. | log pos |
| Y08374_ma1_at | Y08374 | gene encoding cartilage GP-39 | log pos |
| Y08839_at | HSTFAC | nuclear orphan receptor ROR-b | log pos |
| Y08976_at | HSRNAFEV | FEV protein. | log pos |
| Y10207_at | HSCD171 | CD171 protein. | log pos |
| Y10871_at | HSTWISTGE | twist gene. :twist ÜDrosophil | log pos |
| Y12670_at | HSOBRGRP | leptin receptor gene-related | log pos |

TABLE 9-continued

| Genbank | Gene ID | Gene name | covariance |
|---|---|---|---|
| Z12982_at | HSRPL41 | homologue to yeast ribosomal | log pos |
| Z19554_s_at | HSVIMENTA | vimentin gene. :vimentin gene | log pos |
| Z19574_ma1_at | HSCYTOK17 | gene for cytokeratin 17. :gene | log pos |
| Z22551_at | HSKINEC | kinectin gene. | log pos |
| Z25749_ma1_at | HSRPS7 | gene for ribosomal protein 57. | log pos |
| Z25884_at | HSCLC1MR | ClC-1 muscle chloride channel | log pos |
| Z25884_at | HSCLC1MR | ClC-1 muscle chloride channel | log pos |
| Z28491_s_at | HSCOMT2 | gene for catechol O-methyltran | log pos |
| Z28407_at | HSRBPL8 | ribosomal protein L8. :riboso | log pos |
| Z28407_at | HSRBPL8 | ribosomal protein L8. :riboso | log pos |
| Z30843_at | HSCLCHPRA | chloride channel Üputativeü | log pos |
| Z32765_at | HSCD38G15 | CD38 gene exon 15. | log pos |
| Z35402_ma1_s_at | HSECAD3 | gene encoding E-cadherin, exon | log pos |
| Z35402_ma1_s_at | HSECAD3 | gene encoding E-cadherin, exon | log pos |
| Z48501_s_at | HSPABPII | polyadenylate binding protein | log pos |
| Z48950_at | HSHH3X3B | hH3.3B gene for histone H3.3. | log pos |
| Z49107_s_at | Z49107 | galectin. | log pos |
| Z49148_s_at | HSRPL29 | ribosomal protein L29. | log pos |
| Z49148_s_at | HSRPL29 | ribosomal protein L29. | log pos |
| Z49835_s_at | HSP2SISOM | protein disulfide isomerase. | log pos |
| Z50022_at | HSSGP1N15 | surface glycoprotein. :chromo | log pos |
| Z69043_s_at | HSTRAPRNA | mRNA translocon-associated pm | log pos |
| Z70759_at | H5M243 | mitochondrial 16S rRNA gene Ü | log pos |
| Z80783_at | HSH2BL | H2B/l gene. :H2B histone famil | log pos |
| Z80787_at | HSH4J | H4/j gene. :H4 histone family, | log pos |
| Z80787_at | HSH4J | H4/j gene. :H4 histone family, | log pos |
| Z83804_at | HSHDHC7 | axonemal dynein heavy chain | log pos |
| Z84721_cds2_at | HSGG1 | DNA sequence from cosmid GG1 f | log pos |
| Z84721_cds2_at | HSGG1 | DNA sequence from cosmid GG1 f | log pos |
| Z93784_at | H5398C22 | DNA sequence from PAC 398C22 o | log pos |

TABLE 10

| | Urothelium | | | Other cell types | | |
|---|---|---|---|---|---|---|
| Protein | Normal | pTa | pT2+ | Leukocytes | Endothelium | Histiocytes |
| Keratin 8 | + | + | + | − | − | − |
| Cystatin C | + | + | + | + | | + |
| Vimentin | + | − | + | | + | |
| E-cadherin | + | (+) | (+) | ? | | |
| CD59 | + | (+) | − | + | + | + |
| Cathepsin E | − | + | − | + | + | + |
| junB | − | + | − | − | − | + |
| IGF | + | + | − | − | − | − |
| Beta-2-microglob. | + | + | + | + | + | − |
| ApoE | + | − | + | − | − | − |

What is claimed is:

1. A method of determining an expression pattern of a cell sample independent of the proportion of submucosal, smooth muscle, or connective tissue cells present, comprising:
    determining expression of two or more genes in a sample comprising cells, wherein the two or more genes exclude genes which are expressed in the submucosal, smooth muscle, or connective tissue,
    forming a pattern of expression of the two or more genes for the sample which is independent of the proportion of submucosal, smooth muscle, or connective tissue cells in the sample.

2. The method of claim 1 wherein the sample comprises epithelial or carcinoma cells.

3. The method of claim 2 wherein the sample comprises urothelial or bladder cancer cells.

4. A method of determining an expression pattern of a cell sample, comprising:
    determining expression of one or more genes in a sample comprising cells, whereby a first pattern of expression is formed for the sample;
    removing expression of genes which are expressed in submucosal, smooth muscle, or connective tissue cells from the first pattern of expression, whereby a second pattern of expression is formed, wherein the second pattern is independent of the proportion of submucosal, smooth muscle, or connective tissue cells in the sample.

5. The method of claim 4 wherein the cell sample is an epithelium or carcinoma sample.

6. The method of claim 5 wherein the cell sample is a urothelium or bladder cancer sample.

7. A method for determining an expression pattern of a urothelium or bladder cancer cell, comprising:
    determining expression of one or more genes in a sample comprising urothelium or bladder cancer cells, whereby a first pattern of expression is formed;
    subtracting from the first pattern of expression a second pattern of expression, wherein the second pattern was formed using the one or more genes and a sample comprising predominantly submucosal, smooth muscle, or connective tissue cells, said step of subtracting forming a third pattern of expression which reflects expression of the urothelium or bladder cancer cells independent of the proportion of submucosal, smooth muscle, or connective tissue cells present in the sample.

8. The method of any of claims 1–7 wherein expression of the genes is determined by assaying for an mRNA transcribed from the genes or proteins translated from an mRNA transcribed from the genes.

9. The method of any of claims 1–7 wherein expression of three or more genes is determined and used to form the pattern of expression.

10. The method of claim 1 wherein expression of five or more genes is determined and used to form the pattern of expression.

11. The method of claim 4 mRNA levels for the one or more genes is measured to determine gene expression.

12. The method of claim 7 mRNA levels for the one or more genes is measured to determine gene expression.

13. The method of claim 10 wherein RT-PCR is employed to measure.

14. The method of claim 11 wherein RT-PCR is employed to measure.

15. The method of claim 12 wherein RT-PCR is employed to measure.

16. The method of claim 10 wherein northern blotting is employed to measure.

17. The method of claim 11 wherein northern blotting is employed to measure.

18. The method of claim 12 wherein northern blotting is employed to measure.

19. The method of claim 10 wherein a high density expression array is employed to measure.

20. The method of claim 11 wherein a high density expression array is employed to measure.

21. The method of claim 12 wherein a high density expression array is employed to measure.

* * * * *